US010035853B2

(12) United States Patent
Arathoon et al.

(10) Patent No.: US 10,035,853 B2
(45) Date of Patent: Jul. 31, 2018

(54) SITE-SPECIFIC ANTIBODY CONJUGATION METHODS AND COMPOSITIONS

(71) Applicant: ABBVIE STEMCENTRX LLC, North Chicago, IL (US)

(72) Inventors: William Robert Arathoon, Los Altos Hills, CA (US); Ishai Padawer, San Francisco, CA (US); Luis Antonio Cano, Oakland, CA (US); Vikram Natwarsinhji Sisodiya, San Francisco, CA (US); Karthik Narayan Mani, San Francisco, CA (US); David Liu, San Francisco, CA (US)

(73) Assignee: AbbVie Stemcentrx LLC, North Chicago, IL (US)

( * ) Notice: Subject to any disclaimer, the term of this patent is extended or adjusted under 35 U.S.C. 154(b) by 0 days.

(21) Appl. No.: 15/056,490

(22) Filed: Feb. 29, 2016

(65) Prior Publication Data
US 2016/0176964 A1    Jun. 23, 2016

Related U.S. Application Data

(63) Continuation of application No. PCT/US2014/053310, filed on Aug. 28, 2014, which is a continuation-in-part of application No. PCT/US2014/053014, filed on Aug. 27, 2014.

(60) Provisional application No. 61/871,289, filed on Aug. 28, 2013, provisional application No. 61/871,173, filed on Aug. 28, 2013.

(51) Int. Cl.
| | |
|---|---|
| C07K 16/28 | (2006.01) |
| C07K 16/30 | (2006.01) |
| A61K 47/48 | (2006.01) |
| A61K 39/395 | (2006.01) |
| C07K 16/18 | (2006.01) |
| A61K 39/00 | (2006.01) |

(52) U.S. Cl.
CPC ........ *C07K 16/28* (2013.01); *A61K 47/48384* (2013.01); *A61K 47/48415* (2013.01); *A61K 47/48538* (2013.01); *A61K 47/48561* (2013.01); *C07K 16/18* (2013.01); *C07K 16/2896* (2013.01); *C07K 16/30* (2013.01); *A61K 2039/505* (2013.01); *C07K 2317/24* (2013.01); *C07K 2317/53* (2013.01); *C07K 2317/73* (2013.01)

(58) Field of Classification Search
None
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 5,112,946 A | 5/1992 | Maione |
| 5,122,368 A | 6/1992 | Greenfield et al. |
| 5,191,066 A | 3/1993 | Bieniarz et al. |
| 5,223,409 A | 6/1993 | Ladner et al. |
| 5,336,603 A | 8/1994 | Capon et al. |
| 5,349,053 A | 9/1994 | Landolfi |
| 5,359,046 A | 10/1994 | Capon et al. |
| 5,447,851 A | 9/1995 | Beutler et al. |
| 5,530,101 A | 6/1996 | Queen |
| 5,545,806 A | 8/1996 | Lonberg et al. |
| 5,545,807 A | 8/1996 | Surani et al. |
| 5,569,825 A | 10/1996 | Lonberg et al. |
| 5,622,929 A | 4/1997 | Willner et al. |
| 5,625,126 A | 4/1997 | Lonberg et al. |
| 5,633,425 A | 5/1997 | Lonberg et al. |
| 5,648,237 A | 7/1997 | Carter |
| 5,661,016 A | 8/1997 | Lonberg et al. |
| 5,693,762 A | 12/1997 | Queen et al. |
| 5,750,373 A | 5/1998 | Garrard et al. |
| 5,824,805 A | 10/1998 | King et al. |
| 6,075,181 A | 6/2000 | Kucherlapati et al. |
| 6,150,584 A | 11/2000 | Kucherlapati et al. |
| 6,180,370 B1 | 1/2001 | Queen et al. |
| 6,214,345 B1 | 4/2001 | Firestone et al. |
| 6,300,064 B1 | 10/2001 | Knappik et al. |
| 6,362,331 B1 | 3/2002 | Kamal et al. |
| 6,376,217 B1 | 4/2002 | Better |
| 6,753,165 B1 | 6/2004 | Cox |
| 6,982,321 B2 | 1/2006 | Winter |
| 7,049,311 B1 | 5/2006 | Thurston et al. |
| 7,087,409 B2 | 8/2006 | Barbas, III et al. |
| 7,189,710 B2 | 3/2007 | Kamal et al. |
| 7,279,554 B2 | 10/2007 | Chan et al. |
| 7,279,558 B2 | 10/2007 | Ota et al. |
| 7,407,951 B2 | 8/2008 | Thurston et al. |
| 7,422,739 B2 | 9/2008 | Anderson et al. |
| 7,429,658 B2 | 9/2008 | Howard et al. |
| 7,521,541 B2 | 4/2009 | Eigenbrot et al. |
| 7,557,099 B2 | 7/2009 | Howard et al. |
| 7,608,429 B2 | 10/2009 | Reilly |
| 7,619,068 B2 | 11/2009 | Pilkington et al. |
| 7,632,678 B2 | 12/2009 | Hansford et al. |
| 7,659,241 B2 | 2/2010 | Senter et al. |
| 7,700,302 B2 | 4/2010 | Hua et al. |
| 7,723,485 B2 | 5/2010 | Junutula |
| 7,741,319 B2 | 6/2010 | Howard et al. |
| 7,825,267 B2 | 11/2010 | Koide et al. |
| 7,837,980 B2 | 11/2010 | Alley |
| 7,855,275 B2 | 12/2010 | Eigenbrot |

(Continued)

FOREIGN PATENT DOCUMENTS

| | | |
|---|---|---|
| EP | 0307434 | 3/1989 |
| EP | 0367166 | 5/1990 |

(Continued)

OTHER PUBLICATIONS

Accession No. NM_016941; "Homo sapiens delta-like 3 (Drosophila) (DLL3), transcript variant 1, mRNA".

(Continued)

*Primary Examiner* — Julie Wu
(74) *Attorney, Agent, or Firm* — Womble Bond Dickinson (US) LLP

(57) ABSTRACT

Provided are novel antibody drug conjugates (ADCs), and methods of using such ADCs to treat proliferative disorders.

42 Claims, 19 Drawing Sheets

(56) References Cited

U.S. PATENT DOCUMENTS

| | | |
|---|---|---|
| 8,008,443 B2 | 8/2011 | Dall'Acqua |
| 8,029,984 B2 | 10/2011 | Alitalo et al. |
| 8,034,808 B2 | 10/2011 | Delavault et al. |
| 8,053,562 B2 | 11/2011 | Humphreys |
| 8,133,857 B2 | 3/2012 | Aikawa |
| 8,163,736 B2 | 4/2012 | Gauzy et al. |
| 8,226,945 B2 | 7/2012 | Ebens |
| 8,507,654 B2 | 8/2013 | Baker |
| 8,557,965 B2 | 10/2013 | Saunders et al. |
| 8,788,213 B2 | 7/2014 | Bright et al. |
| 8,865,875 B2 | 10/2014 | Liu |
| 8,986,972 B2 | 3/2015 | Stull et al. |
| 9,089,615 B2 | 7/2015 | Stull et al. |
| 9,089,616 B2 | 7/2015 | Stull et al. |
| 9,089,617 B2 | 7/2015 | Stull et al. |
| 9,090,683 B2 | 7/2015 | Stull et al. |
| 9,107,961 B2 | 8/2015 | Stull et al. |
| 9,133,271 B1 | 9/2015 | Stull et al. |
| 9,150,664 B2 | 10/2015 | Kufer et al. |
| 9,155,803 B1 | 10/2015 | Stull et al. |
| 9,173,959 B1 | 11/2015 | Stull et al. |
| 9,334,318 B1 | 5/2016 | Stull et al. |
| 9,345,784 B1 | 5/2016 | Stull et al. |
| 9,352,051 B1 | 5/2016 | Stull et al. |
| 9,353,182 B2 | 5/2016 | Stull et al. |
| 9,358,304 B1 | 6/2016 | Stull et al. |
| 9,676,850 B2* | 6/2017 | Saunders ............... C07K 16/28 |
| 2003/0180784 A1 | 9/2003 | McCarthy et al. |
| 2003/0211991 A1 | 11/2003 | Su |
| 2004/0067490 A1 | 4/2004 | Zhong et al. |
| 2004/0101920 A1 | 5/2004 | Radziejewski et al. |
| 2005/0008625 A1 | 1/2005 | Balint et al. |
| 2005/0152894 A1 | 7/2005 | Krummen |
| 2005/0238649 A1 | 10/2005 | Doronina et al. |
| 2006/0120959 A1 | 6/2006 | De Haen et al. |
| 2007/0141066 A1 | 6/2007 | Phillips et al. |
| 2007/0154889 A1 | 7/2007 | Wang |
| 2007/0292414 A1 | 12/2007 | Duntsch et al. |
| 2008/0138313 A1 | 6/2008 | Frankel |
| 2008/0175870 A1 | 7/2008 | Mather et al. |
| 2008/0220448 A1 | 9/2008 | Blincko et al. |
| 2008/0305044 A1 | 12/2008 | McDonagh et al. |
| 2009/0010945 A1 | 1/2009 | Alley et al. |
| 2009/0130105 A1 | 5/2009 | Glaser et al. |
| 2009/0155255 A1 | 6/2009 | Glaser et al. |
| 2009/0324614 A1* | 12/2009 | TenHoor ............... G01N 33/68 424/172.1 |
| 2010/0162416 A1 | 6/2010 | Krtolica et al. |
| 2010/0184021 A1 | 7/2010 | Sella-Tavor et al. |
| 2010/0184119 A1 | 7/2010 | Bright et al. |
| 2010/0184125 A1 | 7/2010 | Huang et al. |
| 2010/0273160 A1 | 10/2010 | Donahoe et al. |
| 2010/0275280 A1 | 10/2010 | Clevers et al. |
| 2011/0020221 A1 | 1/2011 | Berman et al. |
| 2011/0033378 A1* | 2/2011 | Dimasi ............ A61K 47/48215 424/1.49 |
| 2011/0256157 A1 | 10/2011 | Howard et al. |
| 2011/0301334 A1* | 12/2011 | Bhakta ............... A61K 51/1051 530/387.3 |
| 2012/0071634 A1 | 3/2012 | Igawa et al. |
| 2012/0078028 A1 | 3/2012 | Satpayev et al. |
| 2012/0178634 A1 | 7/2012 | Sakai et al. |
| 2012/0244171 A1 | 9/2012 | Li et al. |
| 2012/0328624 A1 | 12/2012 | Yoshida et al. |
| 2013/0028919 A1 | 1/2013 | Howard et al. |
| 2013/0040362 A1 | 2/2013 | Vogel et al. |
| 2013/0058947 A1 | 3/2013 | Stull et al. |
| 2013/0061340 A1 | 3/2013 | Dylla et al. |
| 2013/0061342 A1 | 3/2013 | Dylla et al. |
| 2013/0101581 A1 | 4/2013 | Kuramochi et al. |
| 2013/0136718 A1 | 5/2013 | Chang et al. |
| 2013/0144041 A1 | 6/2013 | Dillon et al. |
| 2013/0171170 A1 | 7/2013 | Ebens, Jr. et al. |
| 2013/0259806 A1 | 10/2013 | Light |
| 2013/0260385 A1 | 10/2013 | Dylla et al. |
| 2013/0330350 A1 | 12/2013 | DiMasi |
| 2014/0106449 A1 | 4/2014 | June et al. |
| 2014/0120581 A1 | 5/2014 | Niwa |
| 2014/0127239 A1 | 5/2014 | Howard |
| 2014/0348839 A1 | 11/2014 | Chowdhury et al. |
| 2014/0363455 A1 | 12/2014 | Stull et al. |
| 2014/0363826 A1 | 12/2014 | Stull et al. |
| 2014/0363887 A1 | 12/2014 | Stull et al. |
| 2014/0364590 A1 | 12/2014 | Stull et al. |
| 2014/0364593 A1 | 12/2014 | Stull et al. |
| 2014/0370037 A1 | 12/2014 | Stull et al. |
| 2015/0005477 A1 | 1/2015 | Lowman |
| 2015/0018531 A1* | 1/2015 | Saunders ............... C07K 16/28 530/388.2 |
| 2015/0030636 A1 | 1/2015 | Dylla et al. |
| 2015/0265724 A1 | 9/2015 | Stull et al. |
| 2015/0320879 A1 | 11/2015 | Lyon |
| 2015/0328332 A1 | 11/2015 | Stull et al. |
| 2015/0337048 A1 | 11/2015 | Stull et al. |
| 2016/0015828 A1 | 1/2016 | Torgov et al. |
| 2016/0075779 A1 | 3/2016 | Stull et al. |
| 2016/0130331 A1 | 5/2016 | Stull et al. |
| 2016/0136296 A1 | 5/2016 | Stull et al. |
| 2016/0151513 A1 | 6/2016 | Stull et al. |
| 2016/0158379 A1 | 6/2016 | Stull et al. |
| 2016/0175460 A1* | 6/2016 | Arathoon ............. A61K 47/481 424/181.1 |
| 2016/0176964 A1 | 6/2016 | Arathoon et al. |
| 2016/0228571 A1 | 8/2016 | Stull et al. |
| 2017/0369571 A1* | 12/2017 | Saunders ............... C07K 16/28 |

FOREIGN PATENT DOCUMENTS

| | | |
|---|---|---|
| EP | 2530091 A1 | 12/2012 |
| JP | 58-180487 | 10/1983 |
| JP | 2009-523709 A | 6/2009 |
| JP | 2011-516520 A | 5/2011 |
| JP | 2016-030269 | 5/2016 |
| WO | WO 91/00360 | 1/1991 |
| WO | WO 91/06570 | 5/1991 |
| WO | WO 91/17271 | 11/1991 |
| WO | WO 92/00373 | 1/1992 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 94/04690 | 3/1994 |
| WO | WO 96/04388 | 2/1996 |
| WO | WO 96/07754 | 3/1996 |
| WO | WO 96/27011 | 9/1996 |
| WO | WO 97/33899 | 9/1997 |
| WO | WO 97/34911 | 9/1997 |
| WO | WO 98/52976 | 11/1998 |
| WO | WO 99/37779 | 1/1999 |
| WO | WO 99/23105 | 5/1999 |
| WO | WO 00/34317 | 6/2000 |
| WO | WO 01/12664 | 2/2001 |
| WO | WO 01/83552 | 11/2001 |
| WO | WO 02/14358 | 2/2002 |
| WO | WO 03/048731 | 6/2003 |
| WO | WO 03/075957 | 9/2003 |
| WO | WO 2004/035537 | 4/2004 |
| WO | WO 2005/003171 A2 | 7/2004 |
| WO | WO 2006/034488 A2 | 9/2005 |
| WO | WO 2006/065533 A2 | 6/2006 |
| WO | WO 2006/119062 A2 | 11/2006 |
| WO | WO 2006/134173 | 12/2006 |
| WO | WO 2007/080597 A2 | 7/2007 |
| WO | WO 2007/085930 | 8/2007 |
| WO | WO 2007/111733 A2 | 10/2007 |
| WO | WO 2008/047925 A1 | 4/2008 |
| WO | WO 2009/052249 A1 | 4/2009 |
| WO | WO 2009/079587 | 6/2009 |
| WO | WO 2009/124931 A2 | 10/2009 |
| WO | WO 2010/056337 | 5/2010 |
| WO | WO 2010/096574 | 8/2010 |
| WO | WO 2011/093097 A1 | 8/2011 |

(56) References Cited

FOREIGN PATENT DOCUMENTS

| | | |
|---|---|---|
| WO | WO 2011/128650 | 10/2011 |
| WO | WO 2011/130598 | 10/2011 |
| WO | WO 2011/130613 | 10/2011 |
| WO | WO 2011/130616 | 10/2011 |
| WO | WO 2012/064733 A2 | 11/2011 |
| WO | WO 2012/012801 | 1/2012 |
| WO | WO 2012/031280 A2 | 3/2012 |
| WO | WO 2012/078761 | 6/2012 |
| WO | WO 2012/103455 | 8/2012 |
| WO | WO 2012/128801 | 9/2012 |
| WO | WO 2013/093809 A1 | 12/2012 |
| WO | WO 2013/006495 | 1/2013 |
| WO | WO 2013/041606 | 3/2013 |
| WO | WO 2013/053873 A1 | 4/2013 |
| WO | WO 2013/055987 | 4/2013 |
| WO | WO 2013/119960 A2 | 8/2013 |
| WO | WO 2013/119964 A2 | 8/2013 |
| WO | WO 2013/126746 A2 | 8/2013 |
| WO | WO 2013/126810 | 8/2013 |
| WO | WO 2013/134658 | 9/2013 |
| WO | WO 2014/057072 | 4/2014 |
| WO | WO 2014/057074 | 4/2014 |
| WO | WO 2014/124316 A2 | 7/2014 |
| WO | WO 2014/125273 | 8/2014 |
| WO | WO 2014/130879 | 8/2014 |
| WO | WO 2015/123265 A1 | 2/2015 |
| WO | WO 2015/031541 A1 | 3/2015 |
| WO | WO 2015/031693 | 3/2015 |
| WO | WO 2015/031698 A1 | 3/2015 |
| WO | WO 2015/052532 | 4/2015 |
| WO | WO 2015/052533 | 4/2015 |
| WO | WO 2015/052534 | 4/2015 |
| WO | WO 2015/052535 | 4/2015 |
| WO | WO 2015/127407 | 8/2015 |
| WO | WO 2016/064749 | 4/2016 |

OTHER PUBLICATIONS

Accession No. NM_203486; "*Homo sapiens* delta-like 3 (*Drosophila*) (DLL3), transcript variant 2, mRNA".
Accession No. NP_031892; "Delta-like protein 3 precursor [Mus musculus]".
Accession No. NP_058637; "Delta-like protein 3 isoform 1 precursor [*Homo sapiens*]".
Accession No. NP_446118; "Delta-like protein 3 precursor [Rattus norvegicus]".
Accession No. NP_982353; "Delta-like protein 3 isoform 2 precursor [*Homo sapiens*]".
Accession No. XP_003316395; "Predicted: delta-like protein 3 isoform X2 [Pan troglodytes]".
Ashkenazi et al.,"Protection against endotoxic shock by a tumor necrosis factor receptor immunoadhesin," *Proc Natl Acad Sci USA* (Dec. 1, 1991) 88(23):10535-10539.
Bjellqvist et al., Electrophoresis (1993) 14:1023-1031.
Bork et al., "The CUB domain. A widespread module in developmentally regulated proteins," *J Mol Biol.* (1993) 231(2):539-45.
Boswell, C. A., et al., "An Integrated Approach to Identify Normal Tissue Expression of Targets for Antibody-drug Conjugates: Case Study of TENB2," *British Journal of Pharmacology* (2013) 168:445-457.
Capel et al., "Heterogeneity of human IgG Fc receptors," *Immunomethods* (Feb. 1994) 4(1):25-34.
Carrodus, N.L., et al., "Seizure-Related Gene 6: A Modulator of Excitatory Synapse Development," Australian Neuroscience Society Annual Meeting, Auckland (Jan. 31-Feb. 3, 2011) p. 87.
Chothia et al.,"Canonical Structures for Hypervariable Regions of Immunoglobulins," *J. Mol. Biol.* (1987) 196:901-917.
Chothia et al., "Conformations of immunoglobulin hypervariable regions," *Nature* (1989) 342:877-883.
Chumsae et al., "Identification and Localization of Unpaired Cysteine Residues in Monocolonal Antibodies by Fluorescence Labeling and Mass Spectrometry," *Anal. Chem.* (2009) 81:6449-6457.

Cochran et al., "Domain-level antibody epitope mapping through yeast surface display of epidermal growth factor receptor fragments," *J Immunol Methods* (2004) 287(1-2):147-58.
Denardo et al., "Comparison of 1,4,7,10-tetraazacyclododecane-N,N',N",N"'-tetraacetic acid (DOTA)-peptide-ChL6, a novel immunoconjugate with catabolizable linker, to 2-iminothiolane-2[p-(bromoacetamido)benzyl]-DOTA-ChL6 in breast cancer xenografts," *Clin Cancer Res* (1998) 4:2483-2490.
Dubowchik et al.,"Cathepsin B-labile dipeptide linkers for lysosomal release of doxorubicin from internalizing immunoconjugates: model studies of enzymatic drug release and antigen-specific in vitro anticancer activity," *Bioconjug Chem.* (Jul.-Aug. 2002) 13(4):855-69.
Dylla et al., "Colorectal Cancer Stem Cells are Enriched in Xenogeneic Tumors Following Chemotherapy," PLoS One (2008) 3(6):e2428.
Fuhrmann, S., et al., "Abstract 5625: In vitro and in vivo pharmacology of MEDI-565 (MT111), a novel CEA/CD3-bispecific single-chain BiTE antibody in development for the treatment of gastrointestinal adenocarcinomas," *Cancer Research* (Apr. 15, 2010) 70(8), Supplement 1.
Galluzzo et al., "Notch signaling in lung cancer," *Expert Rev Anticancer Ther.* (Apr. 2011) 11(4):533-40 PMID: 21504320.
Garnett, "Targeted drug conjugates: principles and progress," *Advanced Drug Delivery Reviews* 53 (2001) 171-216.
Gene Cards, "SEZ6 Gene" definition; pp. 1-14(Jan. 15, 2016).
Gunnersen et al., "Sez-6 proteins affect dendritic arborization patterns and excitability of cortical pyramidal neurons," *Neuron.* Nov. 21, 2007; 56(4):621-39.PMID: 18031681.
Gunnersen, Jenny M., et al., "Seizure-related gene 6 (Sez-6) in amacrine cells of the rodent retina and the consequence of gene deletion," PLOS ONE, 2009, vol. 4, No. 8, p. e6546.
Harris et al., "Targeting embryonic signaling pathways in cancer therapy," *Expert Opin Ther Targets* (Jan. 2012) 16(1):131-45.
Herbst et al., "SEZ-6: promoter selectivity, genomic structure and localized expression in the brain," *Brain Res Mol Brain Res.* (Mar. 1997) 44(2):309-22 PMID: 9073173.
Hochleitner et al., "Characterization of a discontinuous epitope of the human immunodeficiency virus (HIV) core protein p24 by epitope excision and differential chemical modification followed by mass spectrometric peptide mapping analysis," *Protein Sci.* (Mar. 2000) 9(3):487-96 PMID: 10752610.
Hoey et al., "DLL4 blockade inhibits tumor growth and reduces tumor-initiating cell frequency," *Cell Stem Cell.* (Aug. 7, 2009) 5(2):168-77 PMID: 19664991.
Ishikawa et al., "Characterization of SEZ6L2 cell-surface protein as a novel prognostic marker for lung cancer," *Cancer Sci.* (Aug. 2006) 97(8):737-45.
Jones et al., "Replacing the complementarity-determining regions in a human antibody with those from a mouse," *Nature* (1986) 321:522-525—Abstract.
Klimstra et al., "The pathologic classification of neuroendocrine tumors: a review of nomenclature, grading, and staging systems," *Pancreas.* (Aug. 2010) 39(6):707-12 PMID: 20664470.
Klöppel, "Classification and pathology of gastroenteropancreatic neuroendocrine neoplasms," *Endocr Relat Cancer* (Oct. 17, 2011) 18 Suppl 1:S1-16 PMID: 22005112.
MacCallum et al., "Antibody-antigen interactions: contact analysis and binding site topography," *J. Mol. Biol.* (1996) 262:732-745.
Mulley et al., "The Role of Seizure-Related SEZ6 as a Susceptibility Gene in Febrile Seizures," *Neurol Res Int.* (2011) 2011:917565 PMID: 21785725.
NCBI protein database search ("human seizure related 6 homologue" or "SEZ6") and (*Homo sapiens*)) (pp. 1-2, Jun. 3, 2016).
NM_001098635—*Homo sapiens* seizure related 6 homolog (SEZ6), transcript variant 2, mRNA.
NM_178860—*Homo sapiens* seizure related 6 homolog (SEZ6), transcript variant 1, mRNA.
NP_067261—seizure protein 6 isoform 1 precursor [Mus musculus].
NP_849191.3—seizure protein 6 homolog isoform 1 precursor [*Homo sapiens*].

(56) References Cited

OTHER PUBLICATIONS

NP_001092105—seizure protein 6 homolog isoform 2 precursor [*Homo sapiens*].
NP_001099224—seizure protein 6 homolog precursor [Rattus norvegicus].
NP_001139913—synaptojanin-1 [Salmo salar].
Osaki et al., "The distribution of the seizure-related gene 6 (Sez-6) protein during postnatal development of the mouse forebrain suggests multiple functions for this protein: An analysis using a new antibody," *Brain Research* (Feb. 10, 2011), 1386:58-69, XP028186555.
Panowski, S., et al., "Site-specific Antibody Drug Conjugates for Cancer Therapy," *MAbs* (Jan.-Feb. 2014) 6(1):34-35.
Perez-Moreno et al., "Sticky business: Orchestrating Cellular Signals at Adherens Junctions," *Cell* (Feb. 21, 2003) 112:535-548.
Peterson et al., "Enzymatic Cleavage of Peptide-Linked Radiolabels from Immunoconjugates," *Bioconjugate Chem*. (1999) (10)4:553-557.
Ravetch et al., "Fc receptors," *Annu Rev Immunol*. (1991) 9:457-92.
Reineke, "Antibody Epitope Mapping Using Arrays of Synthetic Peptides," *Methods Mol Biol*. (2004) 2 48:443-63.
Rodrigues, M. L., et al., "Engineering Fab' Fragments for Efficient F(ab)2 Formation in *Escherichia coli* and for Improved In Vivo Stability," *The Journal of Immunology* (Dec. 15, 1993) 151(12):6954-6961.
Schulenburg et al., "Neoplastic stem cells: current concepts and clinical perspectives," Crit Rev Oncol Hematol. (Nov. 2010) 76(2):79-98 PMID: 20185329.
Shimizu-Nishikawa, K., et al., "Cloning and expression of SEZ-6, a brain-specific and seizure-related cDNA," *Brain Res Mol Brain Res*. (Feb. 1995) 28(2):201-10 PMID 7723619.
Strop, P., et al., "Location Matters: Site of Conjugation Modulates Stability and Pharmacokinetics of Antibody Drug Conjugates," *Chemistry & Biology* 20 (Feb. 21, 2013) pp. 161-167.
Sun, M., et al., "Reduction-Alkylation Strategies for the Modification of Specific Monoclonal Antibody Disulfides," *Bioconug. Chem*. (2005) 16(5):1282-1290.
Sussman, D., et al., "Abstract 4634: Engineered Cysteine Drug Conjugates Show Potency and Improved Safety," *Cancer Research* (Apr. 15, 2012) vol. 72, Issue 8, Supp. 1.
Umetsu, M., et al., "How Additives Influence the Refolding of Immunoglobulin-folded Proteins in a Stepwise Dialysis System: Spectroscopic Evidence for Highly Efficient Refolding of a Single-chain Fv Fragment," *J. Biol. Chem*. (Mar. 14, 2003) 278(11):8979-8987.
Vermeer et al., "The thermal stability of immunoglobulin: unfolding and aggregation of a multi-domain protein," *Biophys J*. (Jan. 2000) 78(1):394-404.
Vermeer et al., "The unfolding/denaturation of immunogammaglobulin of isotype 2b and its F(ab) and F(c) fragments," *Biophys. J*. (2000) 79(4): 2150-2154 PMID: 11023918.
Vié et al., Human fusion proteins between interleukin 2 and IgM heavy chain are cytotoxic for cells expressing the interleukin 2 receptor, *Proc Natl Acad Sci USA* (Dec. 1, 1992) 89(23):11337-11341.
Visvader et al., "Cancer stem cells in solid tumours: accumulating evidence and unresolved questions," *Nat Rev Cancer* (Oct. 2008) 8(10):755-68 PMID: 18784658.
Waldmann et al., "Microarray analysis reveals differential expression of benign and malignant pheochromocytoma," *Endocr. Relat. Cancer* (2010) 17(3):743-56.
Xiong et al., "Development of tumor targeting anti-MUC-1 multimer: effects of di-scFv unpaired cysteine location on PEGylation and tumor binding," *Prot. Eng*., (2006) 19(8):359-367.
XP_511368—Predicted: seizure protein 6 homolog isoform X2 [Pan troglodytes].
Yao, J.C., et al., "One hundred years after "carcinoid": epidemiology of and prognostic factors for neuroendocrine tumors in 35,825 cases in the United States," *J Clin Oncol*. (2008) 26:3063-72 PMID: 18565894.
Yu, Z.L., et al., "Febrile seizures are associated with mutation of seizure-related (SEZ) 6, a brain-specific gene," *J Neurosci Res*. (2007) 85:166-72 PMID: 17086543.
Zheng et al., "Administration of noncytolytic IL-10/Fc in murine models of lipopolysaccharide-induced septic shock and allogeneic islet transplantation," *J Immunol*. (May 15, 1995) 154(10):5590-600 PMID: 7730658.
Zimmerman et al., "A triglycine linker improves tumor uptake and biodistributions of 67-Cu-labeled anti-neuroblastoma MAb chCE7 F(ab')2 fragments," *Nucl Med Biol*. (1999) 26(8):943-50 PMID: 10708309.
Official action dated May 3, 2016, issued in Colombian application (No. 16-068.176).
Official action dated Jul. 26, 2016, issued in Saudi Arabian application (No. 516370637).
Official action dated Jul. 6, 2016, issued in Vietnamese application (No. 1-2016-01076).
International Search Report dated Feb. 4, 2015, issued in PCT application (No. PCT/US2014/053310).
Written Opinion dated Feb. 4, 2015, issued in PCT application (No. PCT/US2014/053310).
IPRP dated Mar. 1, 2016, issued in PCT application (No. PCT/US2014/053310).
International Search Report dated Apr. 16, 2013, issued in PCT application (No. PCT/US2013/027476).
Written Opinion dated Apr. 16, 2013, issued in PCT application (No. PCT/US2013/027476).
IPRP dated May 29, 2014, issued in PCT application (No. PCT/US2013/027476).
International Search Report and Written Opinion dated Dec. 24, 2014, issued in PCT application (No. PCT/US2014/053304).
IPRP dated Mar. 1, 2016, issued in PCT application (No. PCT/US2014/053304).
International Search Report dated Dec. 12, 2014, issued in PCT application (No. PCT/US2014/053014).
Written Opinion dated Dec. 12, 2014, issued in PCT application (No. PCT/US2014/053014).
IPRP dated Mar. 1, 2016, issued in PCT application (No. PCT/US2014/053014).
Accession No. Q9NYJ7; RecName: Full=Delta-like protein 3; AltName: Full=*Drosophila* Delta homolog 3; Short=Delta3; Flags: Precursor [*Homo sapiens*].
ADC Review: "Rovalpituzumab tesirine / Rova-T / SC16LD6.5 Drug Description" (Feb. 27, 2016).
Antonow and Thurston, "Synthesis of DNA-interactive pyrrolo[2,1-c][1,4]benzodiazepines (PBDs)," *Chem. Rev*. (2011) 111(4):2815-2864.
Apelqvist, A., et al., "Notch signalling controls pancreatic cell differentiation," *Nature* (1999) 400(6747):877-81.
Arima et al., "Studies on tomaymycin, a new antibiotic. I. Isolation and properties of tomaymycin," *J Antibiot* (Tokyo) (1972) 25(8):437-44.
Ayyanan, A., et al., "Increased Wnt signaling triggers oncogenic conversion of human breast epithelial cells by Notch-dependent mechanism," Proceedings of theNational Academy of Sciences of USA, 2006, vol. 103, No. 10, pp. 3799-3804.
Ball, "Achaete-scute homolog-1 and Notch in lung neuroendocrine development and cancer," Cancer Letters, 2004, 204(2): 159-69.
Barabas et al., "Assembly of combinatorial antibody libraries on phage surfaces: the gene III site," *Proc. Natl. Acad. Sci. USA* 88:7978-7982 (1991).
Bertolotto C., "Melanoma: From melanocyte to genetic alterations and clinical options," *Scientifica*. (2013) 2013:1-22.
Bigas A and Espinosa L, "Hematopoietic stem cells: to be or Notch to be," Blood (Apr. 5, 2012) 119(14):3226-35.
Boerner et al.,"Production of antigen-specific human monoclonal antibodies from in vitro-primed human splenocytes," *J Immunol*. (Jul. 1, 1991) 147(1):86-95—Abstract.
Bose et al., "New approaches to pyrrolo[2,1-c][1,4]benzodiazepines: synthesis, DNA-binding and cytotoxicity of DC-81," *Tetrahedron*, (1992) 48:751-58.
Carter, P., "Potent antibody therapeutics by design," *Nat Rev Immunol*. (2006) 6(5):343-57.

(56) References Cited

OTHER PUBLICATIONS

Chao et al., "Isolating and engineering human antibodies using yeast surface display," *Nat Protoc.* (2007) 1(2):755-68 PMID: 17406305.

Chapman, G., et al., "Notch inhibition by the ligand Delta-Like 3 defines the mechanism of abnormal vertebral segmentation in spondylocostal dysostosis," *Hum Mol Genet.* (Mar. 1, 2011) 20(5):905-16.

Chen H et al., "Conservation of the *Drosophila* lateral inhibition pathway in human lung cancer: a hairy-related protein (HES-1) directly represses achaete-scute homolog-1 expression," *Proc Natl Acad Sci USA* (1997) 94:5355-60, PMID: 9144241.

Chothia D et al., "Structural repertoire of the human VH segments," *J Mol Biol.* (Oct. 5, 1992) 227(3):799-817—Abstract.

Cook M et al., "Notch in the development of thyroid C-cells and the treatment of medullary thyroid cancer," *Am J Transl Res.* (Feb. 10, 2010) 2(1):119-25.

Cook, G. P., et al., "The human immunoglobulin VH repertoire," *Immunol Today* (May 16, 1995) (5):237-42—Abstract.

Davies et al., "Mutations of the BRAF gene in human cancer," *Nature* (2002) 417:949-54.

De La Pompa JL et al., "Conservation of the Notch signaling pathway in mammalian neurogenesis," *Development* (Mar. 1997) 124(6):1139-48.

DLL3 Aptamer Presentation, "Aptamer Technology for Cell-Specific Cancer Therapy," *Academia Sinica* (Jul. 7, 2010).

Dornan et al., "Therapeutic potential of an anti-CD79b antibody-drug conjugate, anti-CD79b-vc-MMAE, for the treatment of non-Hodgkin lymphoma," *Blood* (2009) 114(13):2721-9.

Doronina et al., "Enhanced activity of monomethylauristatin F through monoclonal antibody delivery: effects of linker technology on efficacy and toxicity," *Bioconjug Chem.* (2006) 17(1):114-24.

D'Souza Brendan et al., "Canonical and non-canonical Notch ligands," *Curr Top Dev Biol.* (2010) 92:73-129.

Dunwoodie et al., "Mouse DLL3: a novel divergent Delta gene which may complement the function of other Delta homologues during early pattern formation in the mouse embryo," *Development* (Aug. 1997) 124(16):3065-76.

Dunwoodie, S.L., "The role of Notch in patterning the human vertebral column," *Curr Opin Genet Dev.* (2009) 19(4):329-37.

Dutta S et al., "Notch signaling regulates endocrine cell specification in the zebrafish anterior pituitary," *Dev Biol.* (Jul. 15, 2008) 319(2):248-57.

Edlundh-Rose et al., "NRAS and BRAF mutations in melanoma tumours in relation to clinical characteristics: a study based on mutation screening by pyrosequencing," *Melanoma Res.* (2006) 16(6):471-8 PMID: 17119447.

Erickson et al., "Antibody-maytansinoid conjugates are activated in targeted cancer cells by lysosomal degradation and linker-dependent intracellular processing," *Cancer Res.* (2006) 66(8):4426-33.

Fre, S., et al., "Notch signals control the fate of immature progenitor cells in the intestine," *Nature* (Jun. 16, 2005) 435(7044):964-8.

Fre, S., et al., "Notch and Wnt signals cooperatively control cell proliferation and tumorigenesis in the intestine," *Proc Natl Acad Sci USA* (Apr. 14, 2009) 106(15):6309-14.

Geffers, I., et al., "Divergent functions and distinct localization of the Notch ligands DLL1 and DLL3 in vivo," *J Cell Biol.* (Jul. 30, 2007) 178(3):465-76.

Glittenberg M, et al., "Role of conserved intracellular motifs in Serrate signalling, cis-inhibition and endocytosis," *EMBO J.* (Oct. 18, 2006) 25(20):4697-706, Epub Sep. 28, 2006.

Goldbeter A, and Pourquié O, "Modeling the segmentation clock as a network of coupled oscillations in the Notch, Wnt and FGF signaling pathways," *J Theor Biol.* (Jun. 7, 2008) 252(3):574-85.

Gregson et al., "Synthesis of a novel C2/C2'-exo unsaturated pyrrolobenzodiazepine cross-linking agent with remarkable DNA binding affinity and cytotoxicity," *Chem. Commun.* (1999) 9:797-798.

Gregson et al., "Design, synthesis, and evaluation of a novel pyrrolobenzodiazepine DNA-interactive agent with highly efficient cross-linking ability and potent cytotoxicity," *J Med Chem.* (2001) 44(5):737-48.

Habener, J.F., et al., "Minireview: transcriptional regulation in pancreatic development," *Endocrinology* (2005) 146(3):1025-34, Epub Dec. 16, 2004.

Hamann, P., "Monoclonal antibody—drug conjugates," *Expert Opin Ther Patents*, (2005) 15(9):1087-1103.

Hamblett et al., "Effects of drug loading on the antitumor activity of a monoclonal antibody drug conjugate," *Clin Cancer Res.* (2004) 10(20):7063-70.

Hara et al., "DC 102, a new glycosidic pyrrolo(1,4)benzodiazepine antibiotic produced by *Streptomyces* sp," *J Antibiot* (Tokyo) (1988) 41(5):702-4.

Henke, R.M., et al., "Ascl1 and Neurog2 form novel complexes and regulate Delta-like3 (DLL3) expression in the neural tube," *Dev. Biol.* (2009) 328(2):529-40.

Hochlowski et al., "Abbeymycin, a new anthramycin-type antibiotic produced by a streptomycete," *J Antibiot* (Tokyo). (1987) 40(2):145-8.

Hoyne G.F., et al., "A cell autonomous role for the Notch ligand Delta-like 3 in αβ T-cell development," *Immunol Cell Biol.* (2011) 89(6):696-705.

Huber K et al., "Development of chromaffin cells depends on MASH1 function," *Development* (2002) 129(20):4729-38.

Huff, Carol Ann et al., "Strategies to eliminate cancer stem cells: Clinical implications," *European Journal of Cancer*, 42 (2006) 1293-1297.

Hurley and Needham-Vandevanter, "Covalent binding of antitumor antibiotics in the minor groove of DNA. Mechanism of action of CC-1065 and the pyrrolo(1,4)benzodiazepines," *Acc. Chem. Res.* (1986) 19 (8): 230-237.

Ito, T., et al., "Basic helix-loop-helix transcription factors regulate the neuroendocrine differentiation of fetal mouse pulmonary epithelium," *Development* (Sep. 2000) 127(18):3913-21.

Itoh et al., "Sibanomicin, a new pyrrolo[1,4]benzodiazepine antitumor antibiotic produced by a *Micromonospora* sp," *J Antibiot* (Tokyo) (1988) 41(9):1281-4.

Ivan and Prieto, "Use of immunohistochemistry in the diagnosis of melanocytic lesions: applications and pitfalls," *Future Oncol.* (2010) 6(7):1163-75 PMID: 20624128.

Jeffrey et al., "Design, synthesis, and in vitro evaluation of dipeptide-based antibody minor groove binder conjugates," *J Med Chem.* (2005) 48(5):1344-58.

Jensen, J., et al., "Control of endodermal endocrine development by Hes-1," *Nat Genet.* (2000) 24(1):36-44.

Junutula et al., "Site-specific conjugation of a cytotoxic drug to an antibody improves the therapeutic index," *Nat Biotechnol.* (2008) 26(8):925-32.

Kageyama, R., et al., "Oscillator mechanism of Notch pathway in the segmentation clock," *Dev Dyn.* (2007) 236(6):1403-9.

Kameda, Y., et al., "Mash1 regulates the development of C cells in mouse thyroid glands," *Dev Dyn.* (Jan. 2007), 236(1):262-70.

Klein, T., et al., "An intrinsic dominant negative activity of serrate that is modulated during wing development in *Drosophila*," *Dev Biol.* (Sep. 1, 1997) 189(1):123-34.

Koch, U., and Radtke, F., "Notch signaling in solid tumors," *Curr Top Dev Biol.* (2010) 92:411-55.

Kohn, "Anthramycin," In Antibiotics III. Springer-Verlag, New York, (1975) pp. 3-11.

Konishi et al., "Chicamycin, a new antitumor antibiotic. II. Structure determination of chicamycins A and B," *J Antibiot* (Tokyo) (1984) 37(3):200-6.

Kovtun et al., "Antibody-drug conjugates designed to eradicate tumors with homogeneous and heterogeneous expression of the target antigen," *Cancer Res.* (2006) 66(6):3214-21.

Kroesen, B.J., et al., "Approaches to lung cancer treatment using the CD3 × EGP-2-directed bispecific monoclonal antibody BIS-1," *Cancer Immunol Immunother* (1997) 45(3-4):203-6.

Kudchadkar et al., "New Targeted Therapies for Melanoma," *Cancer Control* (2013) 20(4):282-288.

(56) References Cited

OTHER PUBLICATIONS

Kunimoto et al., "Mazethramycin, a new member of anthramycin group antibiotics," *J Antibiot* (Tokyo) (1980) 33(6):665-7.

Kusumi, K., et al., "The mouse pudgy mutation disrupts Delta homologue DLL3 and initiation of early somite boundaries," *Nat Genet.* (1988) 19(3):274-8.

Ladi, E. et al., "The divergent DSL ligand Dll3 does not activate Notch signaling but cell autonomously attenuates signaling induced by other DSL ligands," *J Cell Biol.* (2005) 170(6):983-92.

Lambert, J., et al., "Drug-conjugated monoclonal antibodies for the treatment of cancer," *Curr Opin Pharmacol.* (2005) 5(5):543-9.

Langley and Thurston, "A versatile and efficient synthesis of carbinolamine-containing pyrrolo[1,4]benzodiazepines via the cyclization of N-(2-aminobenzoyl)pyrrolidine-2-carboxaldehyde diethyl thioacetals: total synthesis of prothracarcin," *J Org Chem.* (1987) 52,91-97.

Law et al., "Lymphocyte activation antigen CD70 expressed by renal cell carcinoma is a potential therapeutic target for anti-CD70 antibody-drug conjugates," *Cancer Res.* (2006) 66(4):2328-37.

Leber et al., "A revised structure of sibiromycin," *J. Am. Chem. Soc.*, (1988) 110 (9):2992-2993.

Leimgruber et al., "Isolation and characterization of anthramycin, a new antitumor antibiotic," *J. Am. Chem. Soc.* (1965) 87(24): 5791-93.

Leimgruber et al., "The structure of anthramycin," *J. Am. Chem. Soc.* (1965) 87(24):5793-95.

Linos et al., "Melanoma update: diagnostic and prognostic factors that can effectively shape and personalize management," (2011) *Biomark Med.* 5(3):333-60 PMID: 21657842.

Liu, J., et al., "Notch signaling in the regulation of stem cell self-renewal and differentiation," *Curr Top Dev Biol.* (2010) 92:367-409.

Lonberg et al., "Human antibodies from transgenic mice," *Int Rev Immunol.* (1995) 13(1):65-93—Abstract.

Maemura, Kentaro, et al., "Delta-like 3 is silenced by methylation and induces apoptosisin human hepatocellular carcinoma," *Int J Oncol.* (2013) 42(3): 817-822.

Marks et al., "By-passing immunization: building high affinity human antibodies by chain shuffling," *Biotechnology* (NY) (1992) 10(7):779-783—Abstract.

McDonagh et al., "Engineered Antibody-Drug Conjugates with Defined Sites and Stoichiometries of Drug Attachment" (2006) *Protein Engineering, Design & Selection*, vol. 19, No. 7, pp. 299-307 XP003013764.

Millipore, "Anti-Delta3, clone 1E7.2," (Jul. 15, 2008) pp. 1-3 (XP002697359).

Milstein et al., "Hybridomas and their use in immunohistochemistry," *Nature*, (1983) 305:537-539—Abstract.

Morrison et al., "Chimeric human antibody molecules: mouse antigen-binding domains with human constant region domains," *Proc Natl Acad Sci USA* (1984) 81(21):6851-5.

Nagase, H., et al., "γ-Secretase-regulated signaling pathways, such as notch signaling, mediate the differentiation of hematopoietic stem cells, development of the immune system, and peripheral immune responses," *Curr Stem Cell Res Ther.* (2011) 6(2):131-41.

Payne, G., "Progress in immunoconjugate cancer therapeutics," *Cancer Cell.* (2003) 3(3):207-12.

Press News Release, AbbVie and Bristol-Myers Squibb Oncology Clincal Collaboration with Rova-T (Jul. 25, 2016).

Prunotto et al., "Proteomic analysis of podocyte exosome-enriched fraction from normal human urine," *J Proteomics.* (2013) 82:193-229.

R&D Systems: "Human DLL3 Antibody Monoclonal Mouse IgG2B Clone #378703, Catalog No. MA4315" (May 5, 2010) pp. 1-1, (XP002697358).

Raetzman, L.T., et al., "Developmental regulation of Notch signaling genes in the embryonic pituitary: Prop1 deficiency affects Notch2 expression," *Dev Biol.* (2004) 265(2):329-40.

Rebay I, et al., "Specific EGF repeats of Notch mediate interactions with Delta and Serrate: implications for Notch as a multifunctional receptor," *Cell.* (Nov. 15, 1991) 67(4):687-99.

Retter et al., "VBASE2, an integrative V gene database," *Nucleic Acids Res.* (Jan. 1, 2005) 33 (Database issue):D671-4.

Robine, S., et al., "Notch signals control the fate of immature progenitor cells in the intestine," *Med Sci* (Paris) (Aug.-Sep. 2005) 21(8-9):780-2.

Roitt I., et al., Immunology, Moscow, Mir (2000) 592 pages, pp. 110-111.

Rothberg et al., "Tissue biomarkers for prognosis in cutaneous melanoma: A systematic review and meta-analysis," *J Natl Cancer Inst* (2009) 101:452-74.

Sakamoto, K., et al., "Intracellular cell-autonomous association of Notch and its ligands: a novel mechanism of Notch signal modification," *Dev Biol.* (Jan. 15, 2002) 241(2):313-26, PMID: 11784114.

Sanderson et al., "In vivo drug-linker stability of an anti-CD30 dipeptide-linked auristatin immunoconjugate," *Clin Cancer Res.* (2005) 11(2 Pt 1):843-52.

Saunders et al., "A DLL3-targeted antibody-drug conjugate eradicates high-grade pulmonary neuroendocrine tumor-initiating cells in vivo," *Sci Transl Med.* (Aug. 26, 2015) 7(302):302ra136. doi: 10.1126/scitranslmed.aac9459.

Schalper et al., "Programmed death-1/programmed death-1 ligand axis as a therapeutic target in oncology: current insights," Journal of Receptor, Ligand and Channel Research ePub (Dec. 23, 2014) 8: 1-7.

Schildbach, J.F., et al., "Modulation of antibody affinity by a non-contact residue," *Protein Sci* (1993) 2:206-214.

Schonhoff, S.E., et al., "Minireview: Development and differentiation of gut endocrine cells," *Endocrinology* (Jun. 2004) 145(6):2639-44.

Sebastian, Martin, et al., "Treatment of non-small cell lung cancer patients with the trifunctional monoclonal antibody catumaxomab (anti-EpCAM × anti-CD3): a phase I study," *Cancer Immunol Immunother.* (2007) 56(10):1637-44. Epub (Apr. 5, 2007).

Sheets et al., "Efficient construction of a large nonimmune phage antibody library: the production of high-affinity human single-chain antibodies to protein antigens," *Proc Natl Acad Sci USA* (1998) 95(11):6157-62.

Shimizu et al., "Prothracarcin, a novel antitumor antibiotic," *J Antibiotics*, (1982) 29:2492-2503.

Shimizu K et al., "Mouse jagged1 physically interacts with notch2 and other notch receptors. Assessment by quantitative methods," *J Biol Chem.* (Nov. 12, 1999) 274(46):32961-9.

Shinkai Y et al., "New mutant mouse with skeletal deformities caused by mutation in delta like 3 (DLL3) gene," *Exp Anim.* (Apr. 2004) 53(2):129-36.

Spigel et al., "Rationale for chemotherapy, immunotherapy, and checkpoint blockade in SCLC: beyond traditional treatment approaches," *J Thorac Oncol.* (May 2013) 8(5):587-98. doi: 10.1097/JTO.0b013e318286cf88.

Sprinzak, D., et al., "Cis-interactions between Notch and Delta generate mutually exclusive signalling states," *Nature* (May 6, 2010) 465(7294):86-90.

Sriuranpong, V., et al., "Notch signaling induces rapid degradation of achaete-scute homolog 1," *Mol. Cell Biol.* (2002) 22(9):3129-39.

Sternberg, P.W., "Lateral inhibition during vulval induction in Caenorhabditis elegans," *Nature* (1988) 335(6190):551-4.

Syrigos and Epenetos, "Antibody directed enzyme prodrug therapy (ADEPT): a review of the experimental and clinical considerations," *Anticancer Res.* (1999) 19(1A):605-13.

Takahashi et al., "Human Fas ligand: gene structure, chromosomal location and species specificity," *International Immunology*, (1994) vol. 6, No. 10, pp. 1567-1574; PMID 7826947.

Takeuchi et al., "Neothramycins A and B, new antitumor antibiotics," *J Antibiot* (Tokyo) (1976) 29(1):93-6.

Thomas et al., "Number of nevi and early-life ambient UV exposure are associated with BRAF-mutant melanoma," *Cancer Epidemiol Biomarkers Prev.* (2007) 16(5):991-7.

Thomas et al., "Tandem BRAF Mutations in Primary Invasive Melanomas," *J Invest Dermatol.* (2004) 122:1245-50.

(56) References Cited

OTHER PUBLICATIONS

Thurston et al., "The Molecular Recognition of DNA," *Chem. Brit.* (1990) 26:767-772.
Thurston et al., "Synthesis of DNA-Interactive Pyrrolo[2,1-c][1,4]benzodiazepines," *Chem. Rev.* (1994) 94(2):433-465.
Tomlinson et al., "The repertoire of human germline VH sequences reveals about fifty groups of VH segments with different hypervariable loops," Mol Biol. (Oct. 5, 1992) 227(3):776-98—Abstract.
Tomlinson et al., "The structural repertoire of the human V kappa domain," *EMBO J.* (Sep. 15, 1995) 14(18):4628-38.
Trail et al., "Monoclonal antibody drug immunoconjugates for targeted treatment of cancer," *Cancer Immunol Immunother.* (2003) 52(5):328-37.
Tsunakawa et al., "Porothramycin, a new antibiotic of the anthramycin group: production, isolation, structure and biological activity," *J Antibiot* (Tokyo) (1988) 41(10):1366-73.
Turnpenny, P.D., et al., "A gene for autosomal recessive spondylocostal dysostosis maps to 19q13.1-q13.3," *Am J Hum Genet.* (Jul. 1999) 65(1):175-82.
Vaughan et al., "Human antibodies with sub-nanomolar affinities isolated from a large non-immunized phage display library," *Nature Biotechnol.* (Mar. 1996) 14(3):309-14—Abstract.
Wharton, K.A., et al., "Nucleotide sequence from the neurogenic locus notch implies a gene product that shares homology with proteins containing EGF-like repeats," *Cell.* (Dec. 1985) 43(3 Pt 2):567-81.
Wu et al., "Arming antibodies: prospects and challenges for immunoconjugates," *Nat Biotechnol.* (2005) 23(9):1137-46.

Wu et al., "Adoptive T-cell Therapy Using Autologous Tumor-infiltrating Lymphocytes for Metastatic Melanoma: Current Status and Future Outlook," *Cancer J.* (2012) 18(2):160-175.
Xie et al., "In vivo behaviour of antibody-drug conjugates for the targeted treatment of cancer," *Expert Opin Biol Ther.* (2006) 6(3):281-91.
XP002767506, "Phase I/II Open Label Dose Escalation Study of the Safety, Pharmacokinetics, and Preliminary Efficacy of SC16LD6.5 as a Single Agent in Patients With Recurrent Small Cell Lung Cancer," Clinical Trials.gov archive, URL:https://clinicaltrials.gov/archive/NCT01901653/2013_08_20, Aug. 20, 2013.
Zarebczan, B., Chen H., "Signaling mechanisms in neuroendocrine tumors as targets for therapy," *Endocrinol Metab Clin North Am.* (2010) 39(4):801-10.
Zeng et al., "hOLF44, a secreted glycoprotein with distinct expression pattern, belongs to an uncharacterized olfactomedin-like subfamily newly identified by phylogenetic analysis," *FEBS Letters.* (2004) 571:74-80.
Zhou, Bin-Bing S., et al., "Tumour-initiating cells: challenges and opportunities for anticancer drug discovery," *Nat Rev Drug Disco.* (Oct. 2009) 8(10):806-23.
Partial supplementary search report dated Mar. 1, 2017, in European application (No. 14839285.5).
Extended search report dated Jun. 26, 2017, in European application (No. 14839261.6).
Official action / opposition demand dated Jun. 22, 2017, in Chilean application (No. 00465-2016).
Official action dated Sep. 11, 2017, issued in Colombian application (No. 16-068.176).
Extended search report dated Jul. 28, 2017, in European application (No. 14839285.5).

\* cited by examiner

Amino Acid Sequences of Exemplary Humanized anti-DLL3 Antibody Light Chain Variable Regions

| mAb | FR1 | CDRL1 | FR2 | CDRL2 | FR3 | CDRL3 | FR4 | SEQ ID NO. |
|---|---|---|---|---|---|---|---|---|
| hSC16.13 | DIQMTQSPSSLSASVGDRVTITC | SASSSVSYMY | WYQQKPGKAPKLLIY | LTSNLAS | GVPSRFSGSGSGTDFTLTISSLQPEDFATYYC | QQWRSNPFT | FGQGTKLEIK | 519 |
| hSC16.15 | AIQLTQSPSSLSASVGDRVTITC | RASENIYYNLA | WYQQKPGKAPKLLIY | TANSLED | GVPSRFSGSGSGTDFTLTISSLQPEDFATYFC | KQAYDVPPT | FGGGTKLEIK | 520 |
| hSC16.25 | EIVLTQSPDFQSVTPKEKVTITC | SASSSVSYMH | WYQQKPDQSPKLLIK | DSSKLAS | GVPSRFSGSGSGTDFTLTINSLEAEDAATYYC | QQWSSNPLT | FGQGTKLEIK | 521 |
| hSC16.34 | DIQMTQSPSSLSASVGDRVTITC | KASQSVSNDVA | WYQQKPGKVPKLLIY | YASNRYS | GVPSRFSGSGSGTDFTLTISSLQPEDVATYFC | QQDYSSPWT | FGGGTKVEIK | 522 |
| hSC16.56 | EIVMTQSPATLSVSPGERATLSC | KASQSVSNDVV | WYQQKPGQAPRLLIY | YASNRYT | GIPARFSGSGSGTEFTLTISSLQSEDFAVYYC | QQDYTSPWT | FGQGTKLEIK | 523 |

FIG. 2A

Amino Acid Sequences of Exemplary Humanized anti-DLL3 Antibody Heavy Chain Variable Regions

| mAb | FR1 | CDRH1 | FR2 | CDRH2 | FR3 | CDRH3 | FR4 | SEQ ID NO. |
|---|---|---|---|---|---|---|---|---|
| hSC16.13 | QITLKESGPTLVKPTQTLTLTCTFSGFSLS | TSGMGVG | WIRQPPGKALEWLA | HIWWDDVKRYSPSLKS | RLTITKDTSKNQVVLTMTNMDPVDTATYYCAR | IVSFDNDVVSAMDY | WGQGTLVTVSS | 524 |
| hSC16.15 | QVQLVQSGAEVKKPGASVKVSCKASGYTFT | RYWIH | WIRQAPGQGLEWMG | YINPTTVYTEFNQNFKD | RVTMTRDTSTSTVYMELSSLRSEDTAVYYCAR | GGSNFFDY | WGQGTTVTVSS | 525 |
| hSC16.25 | QITLKESGPTLVKPTQTLTLTCTFSGFSLS | TSGMGVG | WIRQPPGKALEWLT | DIWWDDNKYYNPSLKS | RLTITKDTSKNQVVLTMTNMDPVDTATYYCAR | RVNYYDPYYAMDY | WGQGTLVTVSS | 526 |
| hSC16.34 | QVQLVQSGAEVKKPGASVKVSCKASGYTFT | NYGMN | WVRQAPGQRLEWMG | WINTYTGDPTYADDFKG | RVTITRDTSASTAYMELSSLRSEDTAVYYCAR | IGGNSPSDY | WGQGTTVTVSS | 527 |
| hSC16.56 | QVQLVQSGAEVKKPGASVKVSCKASGYTFT | NYGMN | WVRQAPGQGLEWMG | WINTYTGEPTYADDFKG | RVTMTTDTSTSTAYMELRSLRSDDTAVYYCAR | IGDSSPSDY | WGQGTLVTVSS | 528 |

FIG. 2B

Amino Acid Sequences of Exemplary Humanized SEZ6 Modulator Light Chain Variable Regions

| Name | FR1 | CDR1 | FR2 | CDR2 | FR3 | CDR3 | FR4 | SEQ ID NO |
|---|---|---|---|---|---|---|---|---|
| hSC17.16 | DIQMTQSPSSLSASVGDRVTITC | RASANINSNLV | WYQQKPGKAPKLLIY | AATNLAD | GVPSRFSGSGSGTDFTLTISSLQPEDFATYYC | QHFWGTPRT | FGGGTKLEIK | 170 |
| hSC17.17 | EIVLTQSPATLSLSPGERATLSC | SASSSVSYMH | WYQQKPGQAPRLLIY | DTSKLPS | GIPARFSGSGSGTDFTLTISSLEPEDFAVYYC | QQWSSTPPT | FGGQTKLEIK | 172 |
| hSC17.24 | DIVMTQSPDSLAVSLGERATINC | KSSQSLLYSSNQKSYLA | WYQQKPGQPPKLLIY | WASTRES | GVPDRFSGSGSGTDFTLTISSLQAEDVAVYYC | KQSYNLRT | FGGGTKVEIK | 174 |
| hSC17.28 | EIVLTQSPDFQSVTPKEKVTITC | RASQSIGTSIH | WYQQKPDQSPKLLIK | YASESIS | GVPSRFSGSGSGTDFTLTINSLEAEDAATYYC | QQSNSWPLT | FGGQTKLEIK | 176 |
| hSC17.34 | DIQMTQSPSSLSASVGDRVTITC | KASQDINSYLS | WFQQKPGKAPKSLIY | RANRLVD | GVPSRFSGSGSGTDYTLTISSLQPEDFATYYC | LQYDEFPPT | FGQGTKLEIK | 178 |
| hSC17.46 | AIQMTQSPSSLSASVGDRVTITC | KASQSVNNDVA | WYQQKPGKAPKLLIY | YASNRYT | GVPSRFSGSGSGTDFTLTISSLQPEDFATYFC | QQDYSSPRT | FGGQTKLEIK | 180 |
| hSC17.151 | EIVLTQSPATLSLSPGERATLSC | RASESVDSYGNSFMH | WYQQKPGQAPRLLIY | RASNLES | GIPARFSGSGSGTDFTLTISSLEPEDFAVYYC | QQSHEDPYT | FGQGTKLEIK | 182 |
| hSC17.155 | DIVMTQSPDSLAVSLGERATINC | KSSQSLLYSSNQKNYLA | WYQQKPGQPPKLLIY | WASTRKS | GVPDRFSGSGSGTDFTLTISSLQAEDVAVYYC | HQYYSYPLT | FGGQTKLEIK | 184 |
| hSC17.156 | DIVMTQTPLSLPVTPGEPASISC | RSSQSIVHSNGNTYLE | WYLQKPGQSPQLLIY | KVSNRFS | GVPDRFSGSGSGTDFTLKISRVEAEDVGVYYC | FQGSHVPPT | FGGGTKLEIK | 186 |
| hSC17.161 | DIVMTQSPDSLAVSLGERATINC | ESSQSLLYNSNQKNYLA | WYQQKPGQPPKLLIY | WASTRES | GVPDRFSGSGSGTDFTLTISSLQAEDVAVYYC | QQYFNYPLT | FGQGTKLEIK | 188 |
| hSC17.200 | EIVLTQSPATLSLSPGERATLSC | RASQSVDYNGISYMH | WYQQKPGQAPRLLIY | AASNVQS | GIPARFSGSGSGTDFTLTISSLEPEDFAVYYC | QQSIEDPPT | FGGGTKVEIK | 190 |
| | | | | | | | | |
| hSC17.200vL1 | EIVLTQSPATLSLSPGERATLSC | RASQSVDYGISYMH | WYQQKPGQAPRLLIY | AASNVQS | GIPARFSGSGSGTDFTLTISSLEPEDFAVYYC | QQSIEDPPT | FGGGTKVEIK | 192 |

FIG. 3A

Amino Acid Sequences of Exemplary Humanized SEZ6 Modulator Heavy Chain Variable Regions

| Name | FR1 | CDR1 | FR2 | CDR2 | FR3 | CDR3 | FR4 | SEQ ID NO |
|---|---|---|---|---|---|---|---|---|
| hSC17.16 | QVQLVQSGAEVKKPGASVKVSCKASGYTFT | DYNMY | WVRQAPGQGLEWMG | EINPNNGGTAYNQKFRG | KVTMTRDTSISTAYMELSRLRSDDTAVYYCAR | YDKGFDY | WGQGTTVTVSS | 171 |
| hSC17.17 | QVQLVQSGAEVKKPGASVKVSCKASGYTFT | DYNMH | WVRQAPGQGLEWMG | EINPNIGGTGYNQKFKG | RVTMTRDTSISTAYMELSRLRSDDTAVYYCAR | TYSYSYEFAY | WGQGTLVTVSS | 173 |
| hSC17.24 | EVQLVQSGAEVKKPGATVKISCKVSGYTFT | DHTIH | WVRQAPGKGLEWIG | YIYPRDGSTKYNEEFKG | RVTITADTSTDTAYMELSSLRSEDTAVYYCAR | SYSNYFDY | WGQGTTVTVSS | 175 |
| hSC17.28 | QVQLVQSGAEVKKPGASVKVSCKASGYTFT | RSYIH | WVRQAPGQGLEWMG | YISSGSGGTTYNQKFKG | RVTSTRDTSISTAYMELSRLRSDDTAVYYCAR | GGVRYFDV | WGQGTTVTVSS | 177 |
| hSC17.34 | QVQLVQSGAEVKKPGASVKVSCKASGYTFT | DYNMD | WVRQAPGQRLEWIG | YIYPDNGGAGYNQKFKG | RVTITVDTSASTAYMELSSLRSEDTAVYYCSR | SITTAWFAY | WGQGTLVTVSS | 179 |
| hSC17.46 | QVQLVQSGAEVKKPGASVKVSCKASGYTFT | SYWIN | WVRQAPGQGLEWIG | NIFPDTTTNYNEKFKG | RVTLTRDTSISTAYMELSRLRSDDTAVYYCAR | EYDGTYDAMDY | WGQGTLVTVSS | 181 |
| hSC17.151 | QVQLVQSGAEVKKPGASVKVSCKASGYTFT | SYWMH | WVRQAPGQGLEWMG | AIYPGKSDTTYNQKFKG | RVTMTRDTSTSTVYMELSSLRSEDTAVYYCAR | SGKGYFAY | WGQGTLVTVSS | 183 |
| hSC17.155 | QVQLVQSGAEVKKPGASVKVSCKASGYTFN | SYWMH | WVRQAPGQGLEWMG | EIHPNNGSTNYNEKFKG | RVTMTRDTSTSTVYMELSSLRSEDTAVYYCAR | WTLFTY | WGQGTLVTV | 185 |
| hSC17.156 | QVTLKESGPVLVKPTETLTLTCTVSGFSLS | TSGMGVS | WIRQPPGKALEWLA | HIFWDDDKWYNPSLKS | RLTISKDTSKSQVVLTMTNMDPVDTATYYCAT | FYGLYFAY | WGQGTLVTVSS | 187 |
| hSC17.161 | QVQLVQSGAEVKKPGASVKVSCKASGFTFS | DAWMD | WVRQAPGQRLEWMG | EIRSKPNNHATYYAESVKG | RVTITRDTSASTAYMELSSLRSEDTAVYYCAR | TGTSY | WGQGTLVTVSS | 189 |
| hSC17.200 | EVQLVQSGAEVKKPGESLKISCKGSGYSFT | SSWIN | WVRQMPGKGLEWMG | RIYPGEGDTNYSGNFEG | QVTISADKSISTAYLQWSSLKASDTAMYYCTR | GLVMDY | WGQGTLVTVSS | 191 |
| hSC17.155vH1 | QVQLVQSGAEVKKPGASVKVSCKASGYTFD | SYWMH | WVRQAPGQGLEWMG | EIHPNNGSTNYNEKFKG | RVTMTRDTSTSTVYMELSSLRSEDTAVYYCAR | WTLFTY | WGQGTLVTV | 193 |
| hSC17.155vH2 | QVQLVQSGAEVKKPGASVKVSCKASGYTFT | SYWMH | WVRQAPGQGLEWMG | EIHPNNGSTNYNEKFKG | RVTMTRDTSTSTVYMELSSLRSEDTAVYYCAR | WTLFTY | WGQGTLVTV | 194 |
| hSC17.155vH3 | QVQLVQSGAEVKKPGASVKVSCKASGYTFN | YYWMH | WVRQAPGQGLEWMG | EIHPNNGSTNYNEKFKG | RVTMTRDTSTSTVYMELSSLRSEDTAVYYCAR | WTLFTY | WGQGTLVTV | 195 |
| hSC17.155vH4 | QVQLVQSGAEVKKPGASVKVSCKASGYTFN | SYWMH | WVRQAPGQGLEWMG | EIHPNDGSTNYNEKFKG | RVTMTRDTSTSTVYMELSSLRSEDTAVYYCAR | WTLFTY | WGQGTLVTV | 196 |
| hSC17.155vH5 | QVQLVQSGAEVKKPGASVKVSCKASGYTFN | SYWMH | WVRQAPGQGLEWMG | EIHPNGGSTNYNEKFKG | RVTMTRDTSTSTVYMELSSLRSEDTAVYYCAR | WTLFTY | WGQGTLVTV | 197 |
| hSC17.155vH6 | QVQLVQSGAEVKKPGASVKVSCKASGYTFN | SYWMH | WVRQAPGQGLEWMG | EIHPNSGSTNYNEKFKG | RVTMTRDTSTSTVYMELSSLRSEDTAVYYCAR | WTLFTY | WGQGTLVTV | 198 |
| hSC17.161vH1 | EVQLVESGGGLVQPGGSLRLSCAASGFTFS | DAWMD | WVRQAPGKGLEWVG | EIRSKPNNHATYYAESVKG | RFTISRDDSKNSLYLQMNSLKTEDTAVYYCAR | TGTSY | WGQGTLVTVSS | 199 |

FIG. 3B

Amino Acid Sequences of Exemplary Humanized CD324 Modulator Heavy and Light Chain Variable Regions

| mAb | Chain | FW1 | CDR1 | FW2 | CDR2 | FW3 | CDR3 | FW4 | SEQ ID NO. |
|---|---|---|---|---|---|---|---|---|---|
| SC10.17 | light | DVLMTQTPLSLPVSLGDQASISC | RSSQSIVHSDGNTYLE | WYLRKPGQSPRLLIY | KVSNRFS | GVPDRFSGSGSGTDFTLKISRVEAEDLGVYYC | FQGSHAPWT | FGGGTKLEIK | 529 |
| SC10.17 | heavy | DVQLVESGGGLVQPGGSRKLSCAASGFTFS | SYGMH | WVRQAPETGLEWVA | YITTRSSTIYYAATVKG | RFTISRDNARNTLFLQMTSLRSEDTAMYYCTR | EPLTGYYAMDY | WGQGTSVTVSS | 530 |
| hSC10.17 | light | DVVMTQSPLSLPVTLGQPASISC | RSSQSIVHSDGNTYLE | WYQQRPGQSPRRLIY | KVSNRFS | GVPDRFSGSGSGTDFTLKISRVEAEDVGVYYC | FQGSHAPWT | FGGGTKVEIK | 531 |
| hSC10.17 | heavy | EVQLVESGGGLVQPGGSLRLSCAASGFTFS | SYGMH | WVRQAPGKGLEWVA | YITTRSSTIYYADSVKG | RFTISRDNAKNSLYLQMNSLRAEDTAVYYCTR | EPLTGYYAMDY | WGQGTSVTVSS | 532 |

FIG. 4

Amino Acid Sequences of Light and Heavy anti-DLL3 Engineered Antibody Chains

HSC16.56SS1– HC

SEQ ID NO: 509

QVQLVQSGAEVKKPGASVKVSCKASGYTFTNYGMNWVRQAPGQGLEWMGWINTYTGEPTYADDFKGRVTMTTDTSTSTAYMELRSRDDTAVYYCARIGDSSPSDYWGQGTLVTVSS
ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSSDKTHTCPPCPAPELLGGPSVFLFP
PKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHEALHNHYTQKSLSLSPG

HSC16.56SS1– LC

SEQ ID NO: 507

EIVMTQSPATLSVSPGERATLSCKASQSVSNDVVWYQQKPGQAPRLLIYYASNRYTGIPARFSGSGSGTEFTLTISSLQSEDFAVYYCQQDYTSPWTFGQGTKLEIKRTVAAPSVFIFPPSDEQL
KSGTASVVCLLNNFYPREAKVQWKVDNALQSGNSQESVTEQDSKDSTYSLSSTLTLSKADYEKHKVYACEVTHQGLSSPVTKSFNRGEC

HSC16.56SS2– HC

SEQ ID NO: 510

QVQLVQSGAEVKKPGASVKVSCKASGYTFTNYGMNWVRQAPGQGLEWMGWINTYTGEPTYADDFKGRVTMTTDTSTSTAYMELRSRDDTAVYYCARIGDSSPSDYWGQGTLVTVSS
ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSDKTHTCPPCPAPELLGGPSVFLFPP
KPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLV
KGFYPSDIAVEWESNGQPENNYKTTPPVLDSDGSFFLYSKLTVDKSRWQQGNVFSCSVMHEALHNHYTQKSLSLSPG

HSC16.56SS2– LC

SEQ ID NO: 507

EIVMTQSPATLSVSPGERATLSCKASQSVSNDVVWYQQKPGQAPRLLIYYASNRYTGIPARFSGSGSGTEFTLTISSLQSEDFAVYYCQQDYTSPWTFGQGTKLEIKRTVAAPSVFIFPPSDEQL
KSGTASVVCLLNNFYPREAKVQWKVDNALQSGNSQESVTEQDSKDSTYSLSSTLTLSKADYEKHKVYACEVTHQGLSSPVTKSFNRGEC

FIG. 5A

Amino Acid Sequences of Light and Heavy anti-DLL3 Engineered Antibody Chains

HSC16.56SS3– HC
SEQ ID NO: 508
QVQLVQSGAEVKKPGASVKVSCKASGYTFTNYGMNWVRQAPGQGLEWMGWINTYTGEPTYADDFKGRVTMTTDTSTSTAYMELRSRSDDTAVYYCARIGDSSPSDYWGQGTLVTVSS
ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHEALHNHYTQKSLSLSPG

HSC16.56SS3– LC
SEQ ID NO: 511
EIVMTQSPATLSVSPGERATLSCKASQSVSNDVVWYQQKPGQAPRLLIYYASNRYTGIPARFSGSGSGTEFTLTISSLQSEDFAVYYCQQDYTSPWTFGQGTKLEIKRTVAAPSVFIFPPSDEQL
KSGTASVVCLLNNFYPREAKVQWKVDNALQSGNSQESVTEQDSKDSTYSLSSTLTLSKADYEKHKVYACEVTHQGLSSPVTKSFNRGE

HSC16.56SS4– HC
SEQ ID NO: 508
QVQLVQSGAEVKKPGASVKVSCKASGYTFTNYGMNWVRQAPGQGLEWMGWINTYTGEPTYADDFKGRVTMTTDTSTSTAYMELRSRSDDTAVYYCARIGDSSPSDYWGQGTLVTVSS
ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHEALHNHYTQKSLSLSPG

HSC16.56SS4– LC
SEQ ID NO: 512
EIVMTQSPATLSVSPGERATLSCKASQSVSNDVVWYQQKPGQAPRLLIYYASNRYTGIPARFSGSGSGTEFTLTISSLQSEDFAVYYCQQDYTSPWTFGQGTKLEIKRTVAAPSVFIFPPSDEQL
KSGTASVVCLLNNFYPREAKVQWKVDNALQSGNSQESVTEQDSKDSTYSLSSTLTLSKADYEKHKVYACEVTHQGLSSPVTKSFNRGES

FIG. 5B

Amino Acid Sequences of Light and Heavy anti-SEZ6 Engineered Antibody Chains

HSC17.200S1 – HC

SEQ ID NO: 515

EVQLVQSGAEVKKPGESLKISCKGSGYSFTSSWINWVRQMPGKGLEWMGRIYPGEGDTNYSGNFEGQVTISADKSISTAYLQWSSLKASDTAMYYCTRGLVMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG

HSC17.200S1 – LC

SEQ ID NO: 513

EIVLTQSPATLSLSPGERATLSCRASQSVDYNGISYMHWYQQKPGQAPRLLIYAASNVQSGIPARFSGSGSGTDFTLTISSLEPEDFAVYYCQQSIEDPPTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

HSC17.200S2 – HC

SEQ ID NO: 516

EVQLVQSGAEVKKPGESLKISCKGSGYSFTSSWINWVRQMPGKGLEWMGRIYPGEGDTNYSGNFEGQVTISADKSISTAYLQWSSLKASDTAMYYCTRGLVMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG

HSC17.200S2 – LC

SEQ ID NO: 513

EIVLTQSPATLSLSPGERATLSCRASQSVDYNGISYMHWYQQKPGQAPRLLIYAASNVQSGIPARFSGSGSGTDFTLTISSLEPEDFAVYYCQQSIEDPPTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIG. 6A

Amino Acid Sequences of Light and Heavy anti-SEZ6 Engineered Antibody Chains

HSC17.200SS3 – HC

SEQ ID NO: 514

EVQLVQSGAEVKKPGESLKISCKGSGYSFTSSWINWVRQMPGKGLEWMGRIYPGEGDTNYSGNFEGQVTISADKSISTAYLQWSSLKASDTAMYYCTRGLVMDYWGQGTLVTVSSASTK GPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVFSCSVMHEALHNHYTQKSLSLSPG

HSC17.200SS3 – LC

SEQ ID NO: 517

EIVLTQSPATLSLSPGERATLSCRASQSVDYNGISYMHWYQQKPGQAPRLLIYAASNVQSGIPARFSGSGSGTDFTLTISSLEPEDFAVYYCQQSIEDPPTFGGGTKVEIKRTVAAPSVFIFPPSD EQLKSGTASVVCLLNNFYPREAKVQWKVDNALQSGNSQESVTEQDSKDSTYSLSSTLTLSKADYEKHKVYACEVTHQGLSSPVTKSFNRGE

HSC17.200SS4 – HC

SEQ ID NO: 514

EVQLVQSGAEVKKPGESLKISCKGSGYSFTSSWINWVRQMPGKGLEWMGRIYPGEGDTNYSGNFEGQVTISADKSISTAYLQWSSLKASDTAMYYCTRGLVMDYWGQGTLVTVSSASTK GPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVFSCSVMHEALHNHYTQKSLSLSPG

HSC17.200SS4 – LC

SEQ ID NO: 518

EIVLTQSPATLSLSPGERATLSCRASQSVDYNGISYMHWYQQKPGQAPRLLIYAASNVQSGIPARFSGSGSGTDFTLTISSLEPEDFAVYYCQQSIEDPPTFGGGTKVEIKRTVAAPSVFIFPPSD EQLKSGTASVVCLLNNFYPREAKVQWKVDNALQSGNSQESVTEQDSKDSTYSLSSTLTLSKADYEKHKVYACEVTHQGLSSPVTKSFNRGES

FIG. 6B

Amino Acid Sequences of Heavy and Light anti-CD324 Engineered Antibody Chains hSC10.17ss3 Heavy Chain

```
1
EVQLVESGGG LVQPGGSLRL SCAASGFTFS SYGMHWVRQA PGKGLEWVAY
51
ITTRSSTIYY ADSVKGRFTI SRDNAKNSLY LQMNSLRAED TAVYYCTREP
101
LTGYYAMDYW GQGTSVTVSS ASTKGPSVFP LAPSSKSTSG GTAALGCLVK
151
DYFPEPVTVS WNSGALTSGV HTFPAVLQSS GLYSLSSVVT VPSSSLGTQT
201                       *
YICNVNHKPS NTKVDKKVEP KSCDKTHTCP PCPAPELLGG PSVFLFPPKP
251
KDTLMISRTP EVTCVVVDVS HEDPEVKFNW YVDGVEVHNA KTKPREEQYN
301
STYRVVSVLT VLHQDWLNGK EYKCKVSNKA LPAPIEKTIS KAKGQPREPQ
351
VYTLPPSRDE LTKNQVSLTC LVKGFYPSDI AVEWESNGQP ENNYKTTPPV
401
LDSDGSFFLY SKLTVDKSRW QQGNVFSCSV MHEALHNHYT QKSLSLSPG

SEQ ID NO: 543
``` hSC10.17ss3 Light Chain

```
1
DVVMTQSPLS LPVTLGQPAS ISCRSSQSIV HSDGNTYLEW YQQRPGQSPR
51
RLIYKVSNRF SGVPDRFSGS GSGTDFTLKI SRVEAEDVGV YYCFQGSHAP
101
WTFGGGTKVE IKRTVAAPSV FIFPPSDEQL KSGTASVVCL LNNFYPREAK
151
VQWKVDNALQ SGNSQESVTE QDSKDSTYSL SSTLTLSKAD YEKHKVYACE
201                                    *
VTHQGLSSPV TKSFNRGES

SEQ ID NO: 544
```

FIG. 7

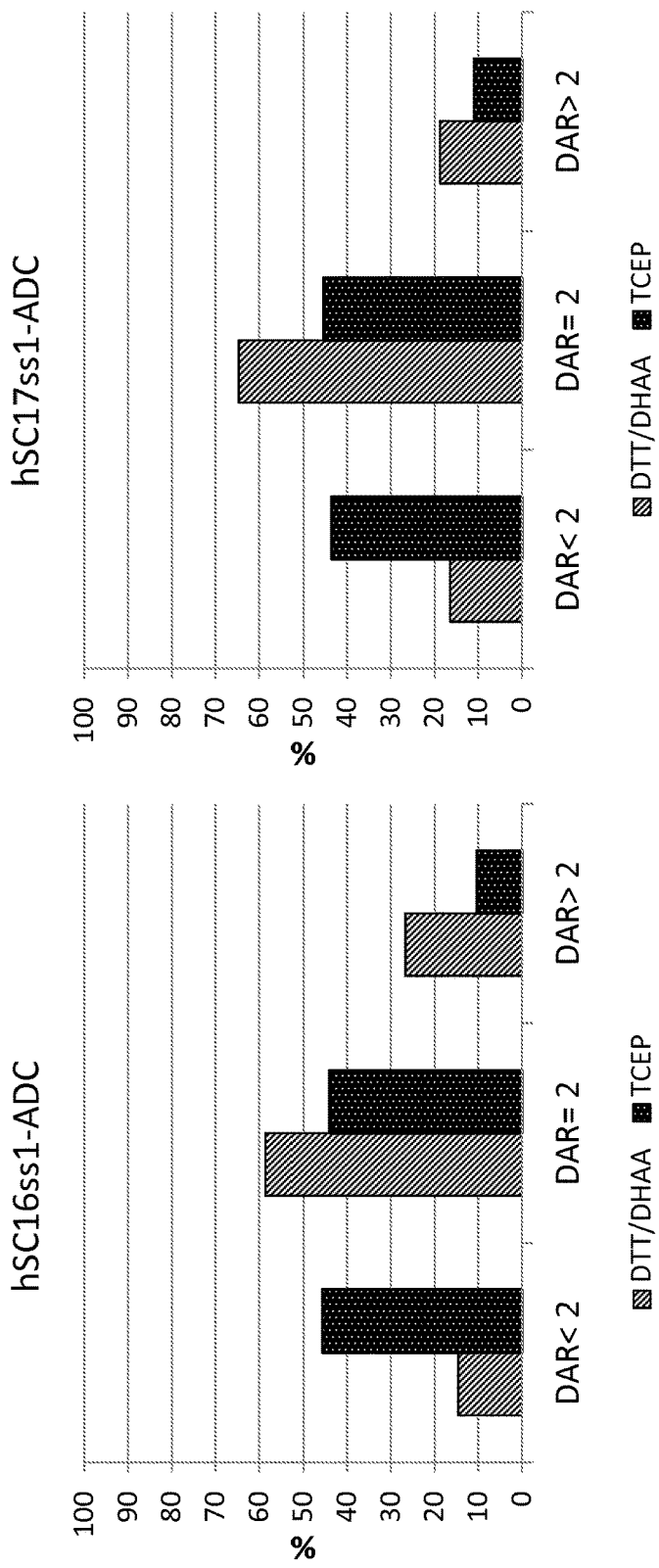

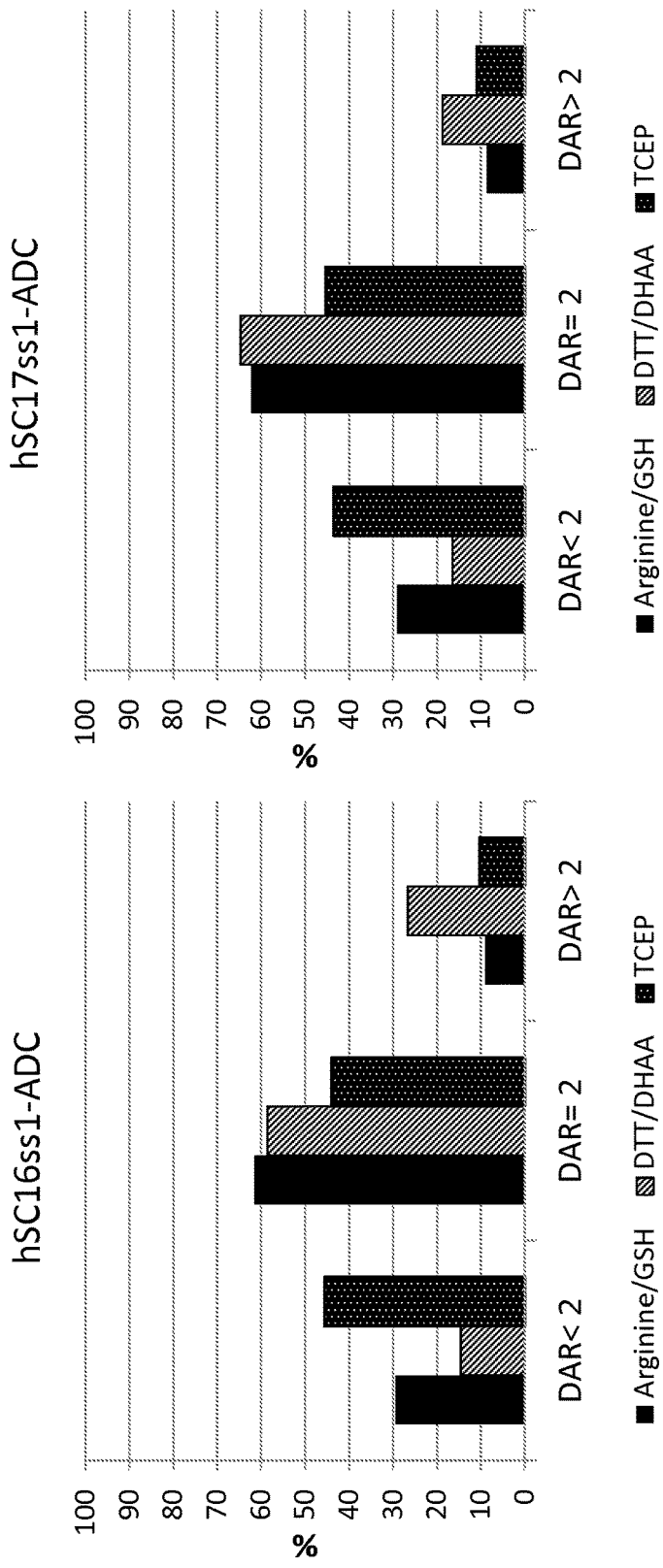

SITE-SPECIFIC ANTIBODY CONJUGATION METHODS AND COMPOSITIONS

CROSS REFERENCED APPLICATIONS

This application claims the benefit of U.S. Provisional Application No. 61/871,173 filed on Aug. 28, 2013, U.S. Provisional Application No. 61/871,289 filed on Aug. 28, 2013, and PCT International Application No. PCT/US2014/053014 filed on Aug. 27, 2014, each of which is incorporated herein by reference in its entirety.

SEQUENCE LISTING

The instant application contains a sequence listing which has been submitted in ASCII format via EFS-Web and is hereby incorporated by reference in its entirety. Said ASCII copy, created on Aug. 28, 2014, is named "sc0003pct_S69697_1190WO_SEQL_082814.txt" and is 538 KB (551,262 bytes) in size.

FIELD OF THE INVENTION

This application generally relates to novel compounds comprising site-specific antibodies or immunoreactive fragments thereof having one or more unpaired cysteine residues conjugated to cytotoxins and use of the same for the treatment or prophylaxis of cancer and any recurrence or metastasis thereof.

BACKGROUND OF THE INVENTION

Many commonly employed cancer therapeutics tend to induce substantial toxicity due to their inability to selectively target proliferating tumor cells. Rather, these traditional chemotherapeutic agents act non-specifically and often damage or eliminate normally proliferating healthy tissue along with the tumor cells. Quite often this unintended cytotoxicity limits the dosage or regimen that the patient can endure, thereby effectively limiting the therapeutic index of the agent. As a result, numerous attempts have made to target cytotoxic therapeutic agents to the tumor site with varying degrees of success. One promising area of research has involved the use of antibodies to direct cytotoxic agents to the tumor so as to provide therapeutically effective localized drug concentrations.

In this regard it has long been recognized that the use of targeting monoclonal antibodies ("mAbs") conjugated to selected cytotoxic agents provides for the delivery of relatively high levels of such cytotoxic payloads directly to the tumor site while reducing the exposure of normal tissue to the same. While the use of such antibody drug conjugates ("ADCs") has been extensively explored in a laboratory or preclinical setting, their practical use in the clinic is much more limited. In certain cases these limitations were the result of combining weak or ineffective toxins with tumor targeting molecules that were not sufficiently selective or failed to effectively associate with the tumor. In other instances the molecular constructs proved to be unstable upon administration or were cleared from the bloodstream too quickly to accumulate at the tumor site in therapeutically significant concentrations. While such instability may be the result of linker selection or conjugation procedures, it may also be the result of overloading the targeting antibody with toxic payloads (i.e., the drug to antibody ratio or "DAR" is too high) thereby creating an unstable conjugate species in the drug preparation. In some instances construct instability, whether from design or from unstable DAR species, has resulted in unacceptable non-specific toxicity as the potent cytotoxic payload is prematurely leached from the drug conjugate and accumulates at the site of injection or in critical organs as the body attempts to clear the untargeted payload. As such, relatively few ADCs have been approved by the Federal Drug Administration to date though several such compounds are presently in clinical trials. Accordingly, there remains a need for stable, relatively homogeneous antibody drug conjugate preparations that exhibit a favorable therapeutic index.

SUMMARY OF THE INVENTION

These and other objectives are provided for by the present invention which, in a broad sense, is directed to novel methods, compounds, compositions and articles of manufacture that provide improved site-specific antibodies and conjugates which exhibit a favorable pharmacokinetic and pharmacodynamic properties. The benefits provided by the present invention are broadly applicable in the field of antibody therapeutics and diagnostics and may be used in conjunction with antibodies that react with a variety of targets. As will be discussed in detail below, the disclosed site-specific conjugates comprise engineered antibody constructs having one or more unpaired cysteines which may be preferentially conjugated to therapeutic or diagnostic payloads using novel selective reduction techniques. Such site-specific conjugate preparations are relatively stable when compared with conventional conjugated preparations and substantially homogenous as to average DAR distribution and payload position. As shown in the appended Examples the stability and homogeneity of disclosed anti-DLL3 site-specific conjugate preparations (regarding both average DAR distribution and payload positioning) provide for a favorable toxicity profile that contributes to an improved therapeutic index.

In one embodiment the invention is directed to site-specific engineered antibodies comprising one or more unpaired cysteine residues. Those of skill in the art will appreciate that the unpaired cysteine residues provide site(s) for the selective and controlled conjugation of pharmaceutically active moieties to produce engineered conjugates in accordance with the teachings herein.

Accordingly, in one embodiment the present invention is directed to an engineered antibody comprising one or more unpaired cysteine residues wherein the engineered antibody immunospecifically reacts with a determinant selected from the group of DLL3, SEZ6 and CD324.

In a related embodiment site-specific antibodies are used to fabricate engineered conjugates wherein the free cysteine(s) are conjugated to a therapeutic or diagnostic agent. In this regard the invention comprises an antibody drug conjugate of the formula:

or a pharmaceutically acceptable salt thereof wherein
    Ab comprises an antibody comprising one or more unpaired cysteines;
    L comprises an optional linker;
    D comprises a drug; and
    n is an integer from about 1 to about 8.

In addition to the foregoing antibody drug conjugates the invention further provides pharmaceutical compositions generally comprising the disclosed ADCs and methods of using such ADCs to diagnose or treat disorders, including cancer, in a patient. In particularly preferred embodiments the engineered antibodies or conjugates will associate with a determinant selected from the group consisting of DLL3, SEZ6 and CD324.

In another embodiment the invention is directed to a site-specific engineered IgG1 isotype antibody comprising at least one unpaired cysteine residue. In some embodiments the unpaired cysteine residue(s) will comprise heavy/light chain interchain residues as opposed to heavy/heavy chain interchain residues. In other embodiments the unpaired cysteine residue will be generated from an intrachain disulfide bridge.

In another embodiment the invention provides an engineered antibody wherein the C214 residue (numbered according to the EU index of Kabat) of the light chain comprising said site-specific engineered antibody is substituted with another residue or deleted. In a further embodiment the invention provides an engineered antibody wherein the C220 residue (numbered according to the EU index of Kabat) of the heavy chain comprising the engineered antibody is substituted with another residue or deleted.

In a related embodiment the invention is directed to a method of killing, reducing the frequency or inhibiting the proliferation of tumor cells or tumorigenic cells comprising treating said tumor cells or tumorigenic cells with a site-specific ADC of the instant invention. In a related embodiment the invention provides a method of treating cancer comprising administering to a subject a pharmaceutical composition comprising a site-specific conjugate of the instant invention.

In another embodiment the present invention comprises a method of preparing an antibody drug conjugate of the invention comprising the steps of:
  a) providing an engineered antibody comprising an unpaired cysteine;
  b) selectively reducing the engineered antibody; and
  c) conjugating the selectively reduced engineered antibody to a drug.

In a related preferred embodiment the step of selectively reducing the antibody comprises the step of contacting the antibody with a stabilizing agent. In yet another embodiment the process may further comprise the step of contacting the antibody with a mild reducing agent.

As indicated such conjugates may be used for the treatment, management, amelioration or prophylaxis of proliferative disorders or recurrence or progression thereof. Selected embodiments of the present invention provide for the use of such site-specific conjugates, for the immunotherapeutic treatment of malignancies preferably comprising a reduction in tumor initiating cell frequency. The disclosed ADCs may be used alone or in conjunction with a wide variety of anti-cancer compounds such as chemotherapeutic or immunotherapeutic agents (e.g., therapeutic antibodies) or biological response modifiers. In other selected embodiments, two or more discrete site-specific antibody drug conjugates may be used in combination to provide enhanced anti-neoplastic effects.

Beyond the therapeutic uses discussed above it will also be appreciated that the engineered conjugates of the instant invention may be used to detect, diagnose or classify disorders and, in particular, proliferative disorders. They may also be used in the prognosis and/or theragnosis of such disorders. In some embodiments the site-specific conjugates may be administered to the subject and detected or monitored in vivo. Those of skill in the art will appreciate that such modulators may be labeled or associated with effectors, markers or reporters as disclosed below and detected using any one of a number of standard techniques (e.g., MRI, CAT scan, PET scan, etc.).

Thus, in some embodiments the invention will comprise a method of diagnosing, detecting or monitoring a proliferative disorder in vivo in a subject in need thereof comprising the step of administering an engineered conjugate.

In other instances the conjugates may be used in an in vitro diagnostic setting using art-recognized procedures (e.g., immunohistochemistry or IHC). As such, a preferred embodiment comprises a method of diagnosing a proliferative disorder in a subject in need thereof comprising the steps of:
  a. obtaining a tissue sample from said subject;
  b. contacting the tissue sample with at least one site-specific conjugate; and
  c. detecting or quantifying the site-specific conjugate associated with the sample.

Such methods may be easily discerned in conjunction with the instant application and may be readily performed using generally available commercial technology such as automatic plate readers, dedicated reporter systems, etc. In selected embodiments the engineered conjugate will be associated with tumor perpetuating cells (i.e., cancer stem cells) present in the sample. In other preferred embodiments the detecting or quantifying step will comprise a reduction of cancer stem cell frequency which may be monitored as described herein.

The present invention also provides kits or devices and associated methods that employ the site-specific conjugates disclosed herein, and pharmaceutical compositions of engineered conjugates as disclosed herein, which are useful for the treatment of proliferative disorders such as cancer. To this end the present invention preferably provides an article of manufacture useful for treating such disorders comprising a receptacle containing an site-specific antibody drug conjugate and instructional materials for using the conjugates to treat, ameliorate or prevent a proliferative disorder or progression or recurrence thereof. In selected embodiments the devices and associated methods will comprise the step of contacting at least one circulating tumor cell.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

FIGS. 2A and 2B provide, in a tabular form, contiguous amino acid sequences (SEQ ID NOS: 519-528) of light and heavy chain variable regions of a number of humanized exemplary DLL3 antibodies compatible with the disclosed antibody drug conjugates isolated, cloned and engineered as described in the Examples herein.

FIGS. 3A and 3B provide, in a tabular form, contiguous amino acid sequences (SEQ ID NOS: 170-199) of light and heavy chain variable regions of a number of humanized exemplary SEZ6 antibodies compatible with the disclosed antibody drug conjugates isolated, cloned and engineered as described in the Examples herein.

FIG. 4 depicts, in a tabular form, contiguous amino acid sequences (SEQ ID NOS: 529-532) of light and heavy chain variable regions of murine and humanized exemplary CD324 antibodies compatible with the disclosed antibody drug conjugates isolated, cloned and engineered as described in the Examples herein.

FIGS. 5A and 5B provide amino acid sequences of light and heavy chains (SEQ ID NOS: 507-512) of exemplary site-specific anti-DLL3 antibodies produced in accordance with the instant teachings.

FIGS. 6A and 6B provide amino acid sequences of light and heavy chains (SEQ ID NOS: 513-518) of exemplary site-specific anti-SEZ6 antibodies produced in accordance with the instant teachings.

FIG. 7 depicts the amino acid sequences of the light and heavy chains (SEQ ID NOS: 543-544) of an exemplary CD324ss3 site-specific antibody produced in accordance with the instant teachings.

FIGS. 11A and 11B are graphical representations showing the DAR distribution of site-specific antibody constructs conjugated using reducing agents as determined using HIC.

FIGS. 13A and 13B are graphical representations showing the DAR distribution of site-specific antibody constructs conjugated using stabilization or reducing agents as determined using HIC.

DETAILED DESCRIPTION OF THE INVENTION

I. Introduction

Figure 1:
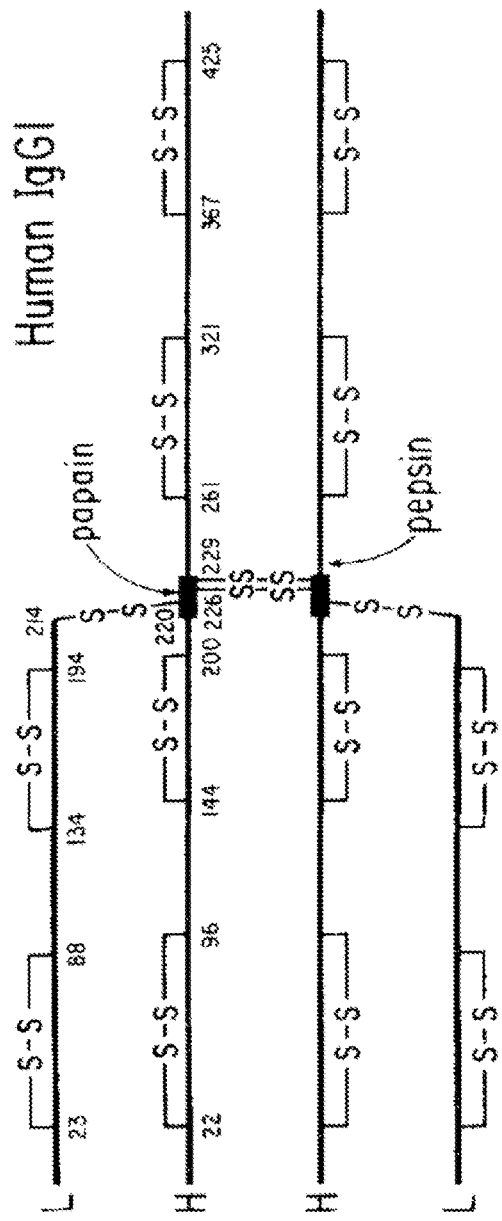
FIG. 1 is a depiction of the structure of the human IgG1 antibody showing the intrachain and interchain disulfide bonds.

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes only and are not to be construed as limiting the subject matter described. Finally, for the purposes of the instant disclosure all identifying sequence Accession numbers may be found in the NCBI Reference Sequence (RefSeq) database and/or the NCBI GenBank archival sequence database unless otherwise noted.

Initially it is important to note that the site-specific antibodies and site-specific conjugates of the instant invention are not limited to any particular target or antigen. Rather, as any existing antibody or any antibody that may be generated as described herein may be converted to a site-specific antibody, the advantages conferred by the present invention are broadly applicable and may be used in conjunction with any target antigen (or determinant). More specifically, the beneficial properties imparted by the use of unpaired cysteine conjugation sites and selective reduction of the same (e.g., enhanced conjugate stability and reduced non-specific toxicity) are broadly applicable to therapeutic and diagnostic antibodies irrespective of the particular target. Accordingly, while certain non-limiting determinants have been used for the purposes of explanation and demonstration of the benefits of the instant invention, they are in no way restrictive as to the scope of the same.

In any event the site-specific antibody conjugates of the instant invention have been found to exhibit favorable characteristics that make them particularly suitable for use as therapeutic compounds and compositions. In this regard the conjugates immunospecifically react with determinants that have been found to be associated with various proliferative disorders and shown to be a good therapeutic targets. Additionally, the constructs of the instant invention provide for selective conjugation at specific cysteine positions derived from disrupted native disulfide bond(s) obtained through molecular engineering techniques. This engineering of the antibodies provides for regulated stoichiometric conjugation that allows the drug to antibody ratio ("DAR") to largely be fixed with precision resulting in the generation of substantially DAR homogeneous preparations. Moreover the disclosed site-specific constructs further provide preparations that are substantially homogeneous with regard to the position of the payload on the antibody. Selective conjugation of the engineered constructs using stabilization agents as described herein increases the desired DAR species percentage and, along with the fabricated unpaired cysteine site, imparts conjugate stability and homogeneity that reduces non-specific toxicity caused by the inadvertent leaching of cytotoxin. This reduction in toxicity provided by selective conjugation of unpaired cysteines and the relative homogeneity (both in conjugation positions and DAR) of the preparations also provides for an enhanced therapeutic index that allows for increased cytotoxin payload levels at the tumor site. Additionally, the resulting site-specific conjugates may optionally be purified using various chromatographic methodology to provide highly homogeneous site-specific conjugate preparations comprising desired DAR species (e.g., DAR=2) of greater than 75%, 80%, 85%, 90% or even 95%. Such conjugate homogeneity may further increase the therapeutic index of the disclosed preparations by limiting unwanted higher DAR conjugate impurities (which may be relatively unstable) that could increase toxicity.

It will be appreciated that the favorable properties exhibited by the disclosed engineered conjugate preparations is predicated, at least in part, on the ability to specifically direct the conjugation and largely limit the fabricated conjugates in terms of conjugation position and absolute DAR. Unlike most conventional ADC preparations the present invention does not rely entirely on partial or total reduction of the antibody to provide random conjugation sites and relatively uncontrolled generation of DAR species. Rather, the present invention provides one or more predetermined unpaired (or free) cysteine sites by engineering the targeting antibody to disrupt one or more of the naturally occurring (i.e., "native")

interchain or intrachain disulfide bridges. Thus, as used herein, the terms "free cysteine" or "unpaired cysteine" may be used interchangeably unless otherwise dictated by context and shall mean any cysteine constituent of an antibody whose native disulfide bridge partner has been substituted, eliminated or otherwise altered to disrupt the naturally occurring disulfide bride under physiological conditions thereby rendering the unpaired cysteine suitable for site-specific conjugation. It will be appreciated that, prior to conjugation, free or unpaired cysteines may be present as a thiol (reduced cysteine), as a capped cysteine (oxidized) or as a non-natural intramolecular disulfide bond (oxidized) with another free cysteine on the same antibody depending on the oxidation state of the system. As discussed in more detail below, mild reduction of this antibody construct will provide thiols available for site-specific conjugation.

More specifically the resulting free cysteines may then be selectively reduced using the novel techniques disclosed herein without substantially disrupting intact native disulfide bridges, to provide reactive thiols predominantly at the selected sites. These manufactured thiols are then subject to directed conjugation with the disclosed drug-linker compounds without substantial non-specific conjugation. That is, the engineered constructs and, optionally, the selective reduction techniques disclosed herein largely eliminate non-specific, random conjugation of the toxin payloads. Significantly this provides preparations that are substantially homogeneous in both DAR species distribution and conjugate position on the targeting antibody. As discussed below the elimination of relatively high DAR contaminants can, in and of itself, reduce non-specific toxicity and expand the therapeutic index of the preparation. Moreover, such selectivity allows the payloads to largely be placed in particularly advantageous predetermined positions (such as the terminal region of the light chain constant region) where the payload is somewhat protected until it reaches the tumor but is suitably presented and processed once it reaches the target. Thus, design of the engineered antibody to facilitate specific payload positioning may also be used to reduce the non-specific toxicity of the disclosed preparations.

As discussed below and shown in the Examples, creation of these predetermined free cysteine sites may be achieved using art-recognized molecular engineering techniques to remove, alter or replace one of the constituent cysteine residues of the disulfide bond. Using these techniques one skilled in the art will appreciate that any antibody class or isotype may be engineered to selectively exhibit one or more free cysteine(s) capable of being selectively conjugated in accordance with the instant invention. Moreover, the selected antibody maybe engineered to specifically exhibit 1, 2, 3, 4, 5, 6, 7 or even 8 free cysteines depending on the desired DAR. More preferably the selected antibody will be engineered to contain 2 or 4 free cysteines and even more preferably to contain 2 free cysteines. It will also be appreciated that the free cysteines may be positioned in engineered antibody to facilitate delivery of the selected cytotoxin to the target while reducing non-specific toxicity. In this respect selected embodiments of the invention comprising IgG1 antibodies will position the payload on the $C_H1$ domain and more preferably on the C-terminal end of the domain. In other preferred embodiments the constructs will be engineered to position the payload on the light chain constant region and more preferably at the C-terminal end of the constant region.

Limiting payload positioning to the engineered free cysteines may also be facilitated by selective reduction of the construct using novel stabilization agents a set forth below. "Selective reduction" as used herein will mean exposure of the engineered constructs to reducing conditions that reduce the free cysteines (thereby providing reactive thiols) without substantially disrupting intact native disulfide bonds. In general selective reduction may be effected using any reducing agents, or combinations thereof that provide the desired thiols without disrupting the intact disulfide bonds. In certain preferred embodiments, and as set forth in the Examples below, selective reduction may be effected using a stabilizing agent and mild reducing conditions to prepare the engineered construct for conjugation. As discussed in more detail below compatible stabilizing agents will generally facilitate reduction of the free cysteines and allow the desired conjugation to proceed under less stringent reducing conditions. This allows a substantial majority of the native disulfide bonds to remain intact and markedly reduces the amount of non-specific conjugation thereby limiting unwanted contaminants and potential toxicity. The relatively mild reducing conditions may be attained through the use of a number of systems but preferably comprises the use of thiol containing compounds. One skilled in the art could readily derive compatible reducing systems in view of the instant disclosure.

II. Determinants

Those skilled in the art will appreciate that the engineered antibodies or conjugates may be generated from any antibody that specifically recognizes or associates with any relevant determinant. As used herein "determinant" means any detectable trait, property, marker or factor that is identifiably associated with, or specifically found in or on a particular cell, cell population or tissue. Determinants may be morphological, functional or biochemical in nature and are generally phenotypic. In certain preferred embodiments the determinant is a protein that is differentially modified with regard to its physical structure and/or chemical composition or a protein that is differentially expressed (up- or down-regulated) by specific cell types or by cells under certain conditions (e.g., during specific points of the cell cycle or cells in a particular niche). For the purposes of the instant invention the determinant preferably comprises a cell surface antigen, or a protein(s) which is differentially expressed by aberrant cells as evidenced by chemical modification, form of presentation (e.g., splice variants), timing or amount. In certain embodiments a determinant may comprise a SEZ6, DLL3 or CD324 protein, or any of their variants, isoforms or family members, and specific domains, regions or epitopes thereof. An "immunogenic determinant" or "antigenic determinant" or "immunogen" or "antigen" means any fragment, region or domain of a polypeptide that can stimulate an immune response when introduced into an immunocompetent animal and is recognized by the antibodies produced from the immune response. Determinants contemplated herein may identify a cell, cell subpopulation or tissue (e.g., tumors) by their presence (positive determinant) or absence (negative determinant).

As discussed herein and set forth in the Examples below, selected embodiments of the invention may comprise complete or partial variable regions from murine antibodies that immunospecifically bind to a selected determinant and which can be considered "source" antibodies. In such embodiments, antibodies contemplated by the invention may be derived from such "source" antibodies through optional modification of the constant region or the epitope-binding amino acid sequences of the source antibody. In one embodiment an antibody is "derived" from a source antibody if selected amino acids in the source antibody are altered through deletion, mutation, substitution, integration or combination. In another embodiment, a "derived" antibody is one in which fragments of the source antibody (e.g., one or more CDRs or the entire variable region) are combined with or incorporated into an acceptor antibody sequence to provide the derivative antibody (e.g. chimeric, CDR grafted or humanized antibodies). Significantly, these derivative antibodies may comprise the site-specific antibodies of the instant invention wherein, for example, the antigen binding region of a donor antibody is associated with an constant region comprising one or more unpaired cysteines. These "derived" (e.g. chimeric, humanized or site-specific constructs) antibodies can be generated using standard molecular biology techniques for various reasons such as, for example, to provide a free cysteine; to improve affinity for the determinant; to improve production and yield in cell culture; to reduce immunogenicity in vivo; to reduce toxicity; to facilitate conjugation of an active moiety; or to create a multispecific antibody. Such antibodies may also be derived from source antibodies through modification of the mature molecule (e.g., glycosylation patterns or pegylation) by chemical means or post-translational modification. Of course, it will be appreciated that the source antibodies (e.g., murine antibodies) may be engineered to provide the desired conjugation sites without undergoing further modifications to the antibody structure.

Again it must be emphasized that the site-specific conjugation technology set forth herein is generally applicable in the field of antibody therapeutics or diagnostics and may work with any existing antibody or any antibody that may be generated regardless of the antibody target. In this context certain non-limiting determinants used to demonstrate the benefits provided by the instant invention are set forth below:

CD324 (also known as E-cadherin, epithelial cadherin or CDH1) is a member of the classical subfamily of cadherins, and as such is a calcium-dependent cell-cell adhesion glycoprotein that mediates homotypic (i.e., epithelial-epithelial) cell-cell adhesion. The intracellular portions of CD324 interact with various proteins inside the cell, including α-catenin, β-catenin and p120, which themselves interact with the actin filaments of the cytoskeleton (Perez-Moreno et al, 2003). CD324 is thought to act as a bridge between the cell-adhesion machinery and the cytoskeleton, and provide cells with a compass that orients them in tissues such as stratified epithelia. With respect to the development of cancer, disturbance of the expression of CD324 is one of the main events in the early and late steps of tumorigenesis and metastasis. Inactivating germline mutations of CDH1 that result in structurally altered CD324 proteins or complete loss of CD324 expression have been correlated with gastric, breast, colorectal, thyroid, and ovarian cancers. Well-differentiated tumors have long been known to exhibit a strong staining pattern of CD324/catenin compared to poorly differentiated ones. Accordingly CD324 has been used by pathologists as a significant prognostic marker to diagnose different kinds of cancer by immunohistochemistry. Reports about the functional role of CD324 in providing mechanical support for cells, regulating cell localization and motility phenotypes, and its links to differentiation status of the cell make CD324 a very intriguing target for the development of anti-cancer therapeutics. The CD324 gene is transcribed and spliced into a 4815 bp mature mRNA transcript which has an open reading frame encoding a pre-proprotein of 882 amino acids including a signal peptide. CD324 orthologs are well conserved between different species and the sequence homology among the various members of the cadherin family is generally high. The CD324 protein is composed of four extracellular cadherin repeats (EC1-EC4) of approximately 110 amino acids, a membrane-proximal extracellular domain (EC5) that is less closely related to the other cadherin repeats, a transmembrane domain, and a highly conserved intracellular domain that can be further subdivided into the juxtamembrane domain (JMD) and a highly-phosphorylated β-catenin binding domain (CBD). Calcium ions bind at sites between the EC repeats of cadherins, conferring a rigid rod-like structure to the extracellular portion of these proteins.

SEZ6 (also known as seizure related 6 homolog) is a type I transmembrane protein originally cloned from mouse cerebrum cortex-derived cells treated with the convulsant pentylentetrazole (Shimizu-Nishikawa, 1995, PMID: 7723619). SEZ6 has two isoforms, one of approximately 4210 bases (NM_178860) encoding a 994 amino acid protein (NP_849191), and one of approximately 4194 bases (NM_001098635) encoding a 993 amino acid protein (NP_001092105). These differ only in the final ten amino acid residues in their ECDs. SEZ6 has two other family members: SEZ6L and SEZ6L2. The term "SEZ6 family", refers to SEZ6, SEZ6L, SEZ6L2 and their various isoforms. The mature SEZ6 protein is composed of a series of structural domains: a cytoplasmic domain, a transmembrane domain and an extracellular domain comprising a unique N-terminal domain, followed by two alternating Sushi and CUB-like domains, and three additional tandem Sushi domain repeats. Mutations in the human SEZ6 gene have been linked to febrile seizures, a convulsion associated with a rise in body temperature and the most common type of seizure in childhood (Yu et al., 2007, PMID:17086543). Analysis of the structural modules of the SEZ6 protein identified by homology and sequence analysis suggest a possible role in signaling, cell-cell communication, and neural development. Anti-SEZ6 humanized antibodies were generated, as described below, from antibodies that had been isolated from mice immunized with a SEZ6 antigen.

As set forth in the Examples below particularly preferred determinants for the engineered conjugates of the instant invention comprise SEZ6, CD324 and DLL3. DLL3 (also known as Delta-like Ligand 3 or SCDO1) is a member of the Delta-like family of Notch DSL ligands. Representative DLL3 protein orthologs include, but are not limited to, human (Accession Nos. NP_058637 and NP_982353), chimpanzee (Accession No. XP_003316395), mouse (Accession No. NP_031892), and rat (Accession No. NP_446118). In humans, the DLL3 gene consists of 8 exons spanning 9.5 kBp located on chromosome 19q13. Alternate splicing within the last exon gives rise to two processed transcripts, one of 2389 bases (Accession No. NM_016941) and one of 2052 bases (Accession No. NM_203486). The former transcript encodes a 618 amino acid protein (Accession No. NP_058637), whereas the latter encodes a 587 amino acid protein (Accession No. NP_982353). These two protein isoforms of DLL3 share overall 100% identity across their extracellular domains and their transmembrane domains, differing only in that the longer isoform contains an extended cytoplasmic tail containing 32 additional residues at the carboxy terminus of the protein.

In general, DSL ligands are composed of a series of structural domains: a unique N-terminal domain, followed by a conserved DSL domain, multiple tandem epidermal growth factor (EGF)-like repeats, a transmembrane domain, and a cytoplasmic domain not highly conserved across ligands but one which contains multiple lysine residues that are potential sites for ubiquitination by unique E3 ubiquitin ligases. The DSL domain is a degenerate EGF-domain that is necessary but not sufficient for interactions with Notch receptors. Additionally, the first two EGF-like repeats of most DSL ligands contain a smaller protein sequence motif known as a DOS domain that co-operatively interacts with the DSL domain when activating Notch signaling.

The extracellular region of the DLL3 protein comprises six EGF-like domains, a single DSL domain and the N-terminal domain. Generally, the EGF domains are recognized as occurring at about amino acid residues 216-249 (domain 1), 274-310 (domain 2), 312-351 (domain 3), 353-389 (domain 4), 391-427 (domain 5) and 429-465 (domain 6), with the DSL domain at about amino acid residues 176-215 and the N-terminal domain at about amino acid residues 27-175 of hDLL3. The DSL domain and the N-terminal domain comprise part of the DLL3 protein as defined by a distinct amino acid sequence. Note that for the purposes of the instant disclosure the respective EGF-like domains may be termed EGF1 to EGF6 with EGF1 being closest to the N-terminal portion of the protein. In regard to the structural composition of the protein one significant aspect of the instant invention is that the disclosed DLL3 antibodies may be generated, fabricated, engineered or selected so as to react with a selected domain, motif or epitope. In certain cases such site specific antibodies may provide enhanced reactivity and/or efficacy depending on their primary mode of action.

DLL3 antibodies compatible with the instant invention and that may be used as source antibodies are disclosed in PCT Application No. US2013/0027391 which is incorporated herein by reference as to the disclosed antibodies.

More generally engineered antibodies contemplated by the invention can be derived from "source" antibodies through optional modification of the epitope-binding amino acid sequences of the source antibody and the introduction of site-specific free cysteine residues. In one embodiment an engineered antibody is "derived" from a source antibody if selected amino acids in the source antibody are altered through deletion, mutation, substitution, integration or combination to produce the engineered antibody comprising at least one free cysteine residue. In another embodiment, a "derived" antibody is one in which fragments of the source antibody (e.g., one or more CDRs) are combined with or incorporated into an acceptor antibody sequence comprising one or more free cysteine residues to provide the derivative antibody (e.g. chimeric or humanized antibodies). These "derived" antibodies can be generated for various reasons such as, for example, to improve affinity for the target; to improve production and yield in cell culture; to reduce immunogenicity in vivo; to reduce toxicity; to facilitate conjugation of an active moiety; or to create a multispecific antibody. Most importantly they provide for the site-specific conjugation of one or more pharmaceutically active moieties. Such antibodies may be derived from source antibodies through modification of the mature molecule (e.g., glycosylation patterns or pegylation) by chemical means or post-translational modification, or through alteration of amino acid sequence.

While the invention is directed generally to any engineered antibody capable of specifically binding to a determinant, engineered anti-SEZ6, engineered anti-DLL3 and engineered anti-CD324 antibodies shall be used as illustrative examples of embodiments of the invention.

III. Cell Binding Agents

1. Antibody Structure

As alluded to above, particularly preferred embodiments of the instant invention comprise the disclosed conjugates with a cell binding agent in the form of a site-specific antibody, or immunoreactive fragment thereof, that preferentially associates with one or more epitopes on a selected determinant. In this regard antibodies, and site-specific variants and derivatives thereof, including accepted nomenclature and numbering systems, have been extensively described, for example, in Abbas et al. (2010), *Cellular and Molecular Immunology* ($6^{th}$ Ed.), W.B. Saunders Company; or Murphey et al. (2011), *Janeway's Immunobiology* ($8^{th}$ Ed.), Garland Science.

Note that, for the purposes of the instant application it will be appreciated that the terms "modulator" and "antibody" may be used interchangeably unless otherwise dictated by context. Similarly, for discussion purposes the embodiments of the invention may be couched in terms of one determinant or the other. However, unless otherwise specified or required by context. such designations are merely for the purpose of explanation and not limiting as to the general concepts being described or the scope of the invention. Accordingly, the terms "anti-DLL3 conjugate" and "DLL3 conjugate", or simply "conjugate", all refer to the site-specific conjugates set forth herein and may be used interchangeably unless otherwise dictated by context.

An "antibody" or "intact antibody" typically refers to a Y-shaped tetrameric protein comprising two heavy (H) and two light (L) polypeptide chains held together by covalent disulfide bonds and non-covalent interactions. Human light chains comprise a variable domain ($V_L$) and a constant domain (CO wherein the constant domain may be readily classified as kappa or lambda based on amino acid sequence and gene loci. Each heavy chain comprises one variable domain ($V_H$) and a constant region, which in the case of IgG, IgA, and IgD, comprises three domains termed $C_H1$, $C_H2$, and $C_H3$ (IgM and IgE have a fourth domain, $C_H4$). In IgG, IgA, and IgD classes the $C_H1$ and $C_H2$ domains are separated by a flexible hinge region, which is a proline and cysteine rich segment of variable length (generally from about 10 to about 60 amino acids in IgG). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues.

There are two types of native disulfide bridges or bonds in immunoglobulin molecules: interchain and intrachain disulfide bonds. The location and number of interchain disulfide bonds vary according to the immunoglobulin class and species. While the invention is not limited to any particular class or subclass of antibody, the IgG1 immunoglobulin shall be used for illustrative purposes only. Interchain disulfide bonds are located on the surface of the immunoglobulin, are accessible to solvent and are usually relatively easily reduced. In the human IgG1 isotype there are four interchain disulfide bonds, one from each heavy chain to the light chain and two between the heavy chains. The interchain disulfide bonds are not required for chain association. The cysteine rich IgG1 hinge region of the heavy chain has generally been held to consist of three parts: an upper hinge (Ser-Cys-Asp-Lys-Thr-His-Thr), a core hinge (Cys-Pro-Pro-Cys), and a lower hinge (Pro-Ala-Glu-Leu-Leu-Gly-Gly). Those skilled in the art will appreciate that that the IgG1 hinge region contain the cysteines in the heavy chain that comprise the interchain disulfide bonds (two heavy/heavy, two heavy/light), which provide structural flexibility that facilitates Fab movements.

The interchain disulfide bond between the light and heavy chain of IgG1 are formed between C214 of the kappa or lambda light chain and C220 in the upper hinge region of the heavy chain (FIG. 1). The interchain disulfide bonds between the heavy chains are at positions C226 and C229. (all numbered per the EU index according to Kabat, et al., infra.)

As used herein the term "antibody" may be construed broadly and includes polyclonal antibodies, multiclonal antibodies, monoclonal antibodies, chimeric antibodies, humanized and primatized antibodies, CDR grafted antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof, immunospecific antibody fragments such as Fd, Fab, F(ab')$_2$, F(ab') fragments, single-chain fragments (e.g. ScFv and ScFvFc); and derivatives thereof including Fc fusions and other modifications, and any other immunoreactive molecule so long as it exhibits preferential association or binding with a DLL3 determinant. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). Heavy-chain constant domains that correspond to the different classes of antibodies are typically denoted by the corresponding lower case Greek letter α, δ, ε, γ, and μ, respectively. Light chains of the antibodies from any vertebrate species can be assigned to one of two clearly distinct types, called kappa (κ) and lambda (λ), based on the amino acid sequences of their constant domains.

In selected embodiments and as discussed in more detail below, the $C_L$ domain may comprise a kappa $C_L$ domain exhibiting a free cysteine. In other embodiments the source antibody may comprise a lambda $C_L$ domain exhibiting a free cysteine. As the sequences of all human IgG $C_L$ domains are well known, one skilled in the art may easily analyze both lambda and kappa sequences in accordance with the instant disclosure and employ the same to provide compatible antibody constructs. Similarly, for the purposes of explanation and demonstration the following discussion and appended Examples will primarily feature the IgG1 type antibodies. As with the light chain constant region, heavy chain constant domain sequences from different isotypes (IgM, IgD, IgE, IgA) and subclasses (IgG1, IgG2, IgG3, IgG4, IgA1, IgA2) are well known and characterized. Accordingly, one skilled in the art may readily exploit anti-DLL3 (or anti-SEZ6) antibodies comprising any isotype or subclass and conjugate each with the disclosed drugs as taught herein to provide the site-specific antibody drug conjugates of the present invention.

The variable domains of antibodies show considerable variation in amino acid composition from one antibody to another and are primarily responsible for antigen recognition and binding. Variable regions of each light/heavy chain pair form the antibody binding site such that an intact IgG antibody has two binding sites (i.e. it is bivalent). $V_H$ and $V_L$ domains comprise three regions of extreme variability, which are termed hypervariable regions, or more commonly, complementarity-determining regions (CDRs), framed and separated by four less variable regions known as framework regions (FRs). The non-covalent association between the $V_H$ and the $V_L$ region forms the Fv fragment (for "fragment variable") which contains one of the two antigen-binding sites of the antibody. ScFv fragments (for single chain fragment variable), which can be obtained by genetic engineering, associates in a single polypeptide chain, the $V_H$ and the $V_L$ region of an antibody, separated by a peptide linker.

As used herein, the assignment of amino acids to each domain, framework region and CDR may be in accordance with one of the numbering schemes provided by Kabat et al. (1991) *Sequences of Proteins of Immunological Interest* (5$^{th}$ Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) *Handbook of Therapeutic Antibodies*, 3$^{rd}$ Ed., Wily-VCH Verlag GmbH and Co. unless otherwise noted. Amino acid residues which comprise CDRs as defined by Kabat, Chothia and MacCallum as obtained from the Abysis website database (infra)) are set out below

TABLE 1

|  | Kabat | Chothia | MacCallum |
| --- | --- | --- | --- |
| $V_H$ CDR1 | 31-35 | 26-32 | 30-35 |
| $V_H$ CDR2 | 50-65 | 52-56 | 47-58 |
| $V_H$ CDR3 | 95-102 | 95-102 | 93-101 |
| $V_L$ CDR1 | 24-34 | 24-34 | 30-36 |
| $V_L$ CDR2 | 50-56 | 50-56 | 46-55 |
| $V_L$ CDR3 | 89-97 | 89-97 | 89-96 |

Variable regions and CDRs in an antibody sequence can be identified according to general rules that have been developed in the art (as set out above, such as, for example, the Kabat numbering system) or by aligning the sequences against a database of known variable regions. Methods for identifying these regions are described in Kontermann and Dubel, eds., Antibody Engineering, Springer, New York, N.Y., 2001 and Dinarello et al., Current Protocols in Immunology, John Wiley and Sons Inc., Hoboken, N. J., 2000. Exemplary databases of antibody sequences are described in, and can be accessed through, the "Abysis" website at www.bioinf.org.uk/abs (maintained by A. C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably sequences are analyzed using the Abysis database, which integrates sequence data from Kabat, IMGT and the Protein Data Bank (PDB) with structural data from the PDB. See Dr. Andrew C. R. Martin's book chapter *Protein Sequence and Structure Analysis of Antibody Variable Domains*. In: *Antibody Engineering Lab Manual* (Ed.: Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein. Unless otherwise indicated, all CDRs set forth herein are derived according to the Abysis database website as per Kabat.

For heavy chain constant region amino acid positions discussed in the invention, numbering is according to the Eu index first described in Edelman et al., 1969, Proc, Natl. Acad. Sci. USA 63(1): 78-85 describing the amino acid sequence of myeloma protein Eu, which reportedly was the first human IgG1 sequenced. The Eu index of Edelman is also set forth in Kabat et al., 1991 (supra.). Thus, the terms "EU index as set forth in Kabat" or "EU index of Kabat" or "EU index according to Kabat" in the context of the heavy chain refers to the residue numbering system based on the human IgG1 Eu antibody of Edelman et al. as set forth in Kabat et al., 1991 (supra.). The numbering system used for the light chain constant region amino acid sequence is similarly set forth in Kabat et al., 1991.

Exemplary kappa $C_L$ and IgG1 heavy chain constant region amino acid sequences compatible with the instant invention are set forth as SEQ ID NOS: 403 and 404 in the appended sequence listing. Similarly, an exemplary lambda $C_L$ light chain constant region is set forth as SEQ ID NO: 504 in the appended sequence listing. Those of skill in the art will appreciate that such light chain constant region sequences, engineered as disclosed herein to provide unpaired cysteines (e.g., see SEQ ID NOS: 502, 503, 505 and 506), may be joined with the disclosed heavy and light chain variable regions using standard molecular biology techniques to provide full-length antibodies (e.g., see SEQ ID NOS: 513-518) that may be incorporated in the SEZ6 conjugates of the instant invention.

The site-specific antibodies or immunoglobulins of the invention may comprise, or be derived from, any antibody that specifically recognizes or immunospecifically associates with any determinant. As used herein "determinant" or "target" means any detectable trait, property, marker or factor that is identifiably associated with, or specifically found in or on a particular cell, cell population or tissue. Determinants or targets may be morphological, functional or biochemical in nature and are preferably phenotypic. In certain preferred embodiments a determinant is a protein that is differentially expressed (over- or under-expressed) by specific cell types or by cells under certain conditions (e.g., during specific points of the cell cycle or cells in a particular niche). For the purposes of the instant invention a determinant preferably is differentially expressed on aberrant cancer cells and may comprise a particular protein (e.g., CD324, SEZ6 or DLL3) or any of its splice variants, isoforms or family members, or specific domains, regions or epitopes thereof. An "antigen", "immunogenic determinant", "antigenic determinant" or "immunogen" means any protein or any fragment, region, domain or epitope thereof that can stimulate an immune response when introduced into an immunocompetent animal and is recognized by antibodies produced from the immune response of the animal. The presence or absence of the determinants contemplated herein may be used to identify a cell, cell subpopulation or tissue (e.g., tumors, tumorigenic cells or CSCs).

As set forth below in the Examples, selected embodiments of the invention comprise murine antibodies that immunospecifically bind to SEZ6, which can be considered "source" antibodies. In other embodiments, antibodies contemplated by the invention may be derived from such "source" antibodies through optional modification of the constant region (i.e., to provide site-specific antibodies) or the epitope-binding amino acid sequences of the source antibody. In one embodiment an antibody is "derived" from a source antibody if selected amino acids in the source antibody are altered through deletion, mutation, substitution, integration or combination. In another embodiment, a "derived" antibody is one in which fragments of the source antibody (e.g., one or more CDRs or the entire variable region) are combined with or incorporated into an acceptor antibody sequence to provide the derivative antibody (e.g. chimeric, CDR grafted or humanized antibodies). These "derived" (e.g. humanized or CDR-grafted) antibodies can be generated using standard molecular biology techniques for various reasons such as, for example, to improve affinity for the determinant; to improve production and yield in cell culture; to reduce immunogenicity in vivo; to reduce toxicity; to facilitate conjugation of an active moiety; or to create a multispecific antibody. Such antibodies may also be derived from source antibodies through modification of the mature molecule (e.g., glycosylation patterns or pegylation) by chemical means or post-translational modification. Of course, as discussed extensively herein these derived antibodies may be further engineered to provide the desired site-specific antibodies comprising one or more free cysteines.

In the context of the instant invention it will be appreciated that any of the disclosed light and heavy chain CDRs derived from the murine variable region amino acid sequences set forth in the appended sequence listing (anti-SEZ6 antibodies) may be combined with acceptor antibodies or rearranged to provide optimized anti-human SEZ6 (e.g. humanized or chimeric anti-hSEZ6) site-specific antibodies in accordance with the instant teachings. That is, one or more of the CDRs derived or obtained from the contiguous light chain variable region amino acid sequences set forth in the appended sequence listing (together SEQ ID NOS: 20-169) may be incorporated in a site-specific construct and, in particularly preferred embodiments, in a CDR grafted or humanized site-specific antibody that immunospecifically associates with one or more SEZ6 isoforms or family members. Examples of "derived" light and heavy chain variable region amino acid sequences of such humanized modulators are also set forth in FIGS. 2A and 2B for anti-DLL3 antibodies (SEQ ID NOS: 519-528), FIGS. 3A and 3B for anti-SEZ6 antibodies (SEQ ID NOS: 170-199) and FIG. 4 for an anti-CD324 antibodies (SEQ ID NOS: 531 and 532).

In FIGS. 2A and 2B, 3A and 3B and 4 the annotated CDRs and framework sequences are defined as per Kabat using a proprietary Abysis database. However, as discussed herein one skilled in the art could readily define, identify, derive and/or enumerate the CDRs as defined by Kabat et al., Chothia et al. or MacCallum et al. for each respective heavy and light chain sequence set forth in the appended sequence listing. Accordingly, each of the subject CDRs and antibodies comprising CDRs defined by all such nomenclature are expressly included within the scope of the instant invention. More broadly, the terms "variable region CDR amino acid residue" or more simply "CDR" includes amino acids in a CDR as identified using any sequence or structure based method as set forth above. Within this context Kabat CDRs for the exemplary humanized antibodies in FIGS. 3A and 3B are provided in the appended sequence listing as SEQ ID NOS: 405-470.

Another aspect of the invention comprises site-specific anti-SEZ6 antibodies obtained or derived from SC17.1, SC17.2, SC17.3, SC17.4, SC17.8, SC17.9, SC17.10, SC17.11, SC17.14, SC17.15, SC17.16, SC17.17, SC17.18, SC17.19, SC17.22, SC17.24, SC17.27, SC17.28, SC17.29, SC17.30, SC17.32, SC17.34, SC17.35, SC17.36, SC17.38, SC17.39, SC17.40, SC17.41, SC17.42, SC17.45, SC17.46, SC17.47, SC17.49, SC17.50, SC17.53, SC17.54, SC17.56, SC17.57, SC17.59, SC17.61, SC17.63, SC17.71, SC17.72, SC17.74, SC17.76, SC17.77, SC17.79, SC17.81, SC17.82, SC17.84, SC17.85, SC17.87, SC17.89, SC17.90, SC17.91, SC17.93, SC17.95, SC17.97, SC17.99, SC17.102, SC17.114, SC17.115, SC17.120, SC17121, SC17.122, SC17.140, SC17.151, SC17.156, SC17.161, SC17.166, SC17.187, SC17.191, SC17.193, SC17.199 and SC17.200; or any of the above-identified antibodies, or chimeric or humanized versions thereof. In other embodiments the ADCs of the invention will comprise a SEZ6 antibody having one or more CDRs, for example, one, two, three, four, five, or six CDRs, from any of the aforementioned modulators. The annotated sequence listing provides the individual SEQ ID NOS for the heavy and light chain variable regions for each of the aforementioned anti-SEZ6 antibodies.

2. Site-Specific Antibodies

Based on the instant disclosure one skilled in the art could readily fabricate engineered constructs as described herein. As used herein, "engineered antibody" "engineered construct" or "site-specific antibody" means an antibody, or immunoreactive fragment thereof, wherein at least one amino acid in either the heavy or light chain is deleted, altered or substituted (preferably with another amino acid) to provide at least one free cysteine. Similarly, an "engineered conjugate" or "site-specific conjugate" shall be held to mean an antibody drug conjugate comprising an engineered antibody and at least one cytotoxin conjugated to the unpaired cysteine(s). In certain embodiments the unpaired cysteine residue will comprise an unpaired intrachain residue. In other preferred embodiments the free cysteine residue will comprise an unpaired interchain cysteine residue. The engineered antibody can be of various isotypes, for example, IgG, IgE, IgA or IgD; and within those classes the antibody can be of various subclasses, for example, IgG1, IgG2, IgG3 or IgG4. With regard to such IgG constructs the light chain of the antibody can comprise either a kappa or lambda isotype each incorporating a C214 that, in preferred embodiments, may be unpaired due to a lack of a C220 residue in the IgG1 heavy chain.

In one embodiment the engineered antibody comprises at least one amino acid deletion or substitution of an intrachain or interchain cysteine residue. As used herein "interchain cysteine residue" means a cysteine residue that is involved in a native disulfide bond either between the light and heavy chain of an antibody or between the two heavy chains of an antibody while an intrachain cysteine residue is one naturally paired with another cysteine in the same heavy or light chain. In one embodiment the deleted or substituted interchain cysteine residue is in involved in the formation of a disulfide bond between the light and heavy chain. In another embodiment the deleted or substituted cysteine residue is involved in a disulfide bond between the two heavy chains. In a typical embodiment, due to the complementary structure of an antibody, in which the light chain is paired with the $V_H$ and $C_H1$ domains of the heavy chain and wherein the $C_H2$ and $C_H3$ domains of one heavy chain are paired with the $C_H2$ and $C_H3$ domains of the complementary heavy chain, a mutation or deletion of a single cysteine in either the light chain or in the heavy chain would result in two unpaired cysteine residues in the engineered antibody.

In some embodiments an interchain cysteine residue is deleted. In other embodiments an interchain cysteine is substituted for another amino acid (e.g., a naturally occurring amino acid). For example, the amino acid substitution can result in the replacement of an interchain cysteine with a neutral (e.g. serine, threonine or glycine) or hydrophilic (e.g. methionine, alanine, valine, leucine or isoleucine) residue. In one particularly preferred embodiment an interchain cysteine is replaced with a serine.

Figure 9:
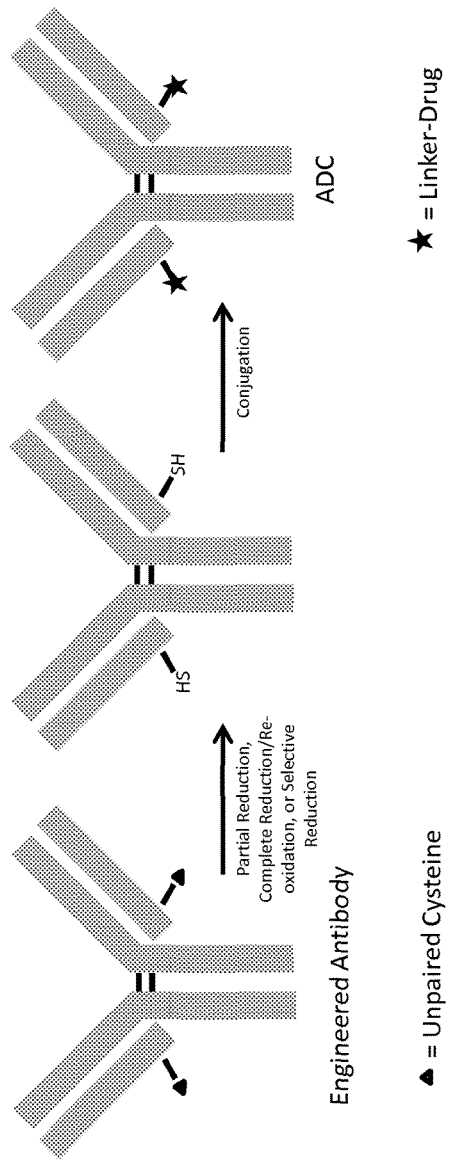
FIG. 9 is a schematic representation depicting the process of conjugating an engineered antibody to a cytotoxin.

In some embodiments contemplated by the invention the deleted or substituted cysteine residue is on the light chain (either kappa or lambda) thereby leaving a free cysteine on the heavy chain. In other embodiments the deleted or substituted cysteine residue is on the heavy chain leaving the free cysteine on the light chain constant region. FIG. 1 depicts the cysteines involved in the interchain disulfide bonds in an exemplary IgG1/kappa antibody. As previously indicated in each case the amino acid residues of the constant regions are numbered based on the EU index according to Kabat. As shown in FIG. 9, deletion or substitution of a single cysteine in either the light or heavy chain of an intact antibody results in an engineered antibody having two unpaired cysteine residues.

In one particularly preferred embodiment the cysteine at position 214 (C214) of the IgG light chain (kappa or lambda) is deleted or substituted. In another preferred embodiment the cysteine at position 220 (C220) on the IgG heavy chain is deleted or substituted. In further embodiments the cysteine at position 226 or position 229 on the heavy chain is deleted or substituted. In one embodiment C220 on the heavy chain is substituted with serine (C220S) to provide the desired free cysteine in the light chain. In another embodiment C214 in the light chain is substituted with serine (C214S) to provide the desired free cysteine in the heavy chain. Such site-engineered constructs provided as per Examples 6-8 respectively are shown in FIGS. 5A and 5B using the exemplary anti-DLL3 antibody SC16.56, FIGS. 6A and 6B using the exemplary anti-SEZ6 antibody SC17.200 and FIG. 7 for the exemplary anti-CD324 antibody SC10.17. Additional examples are also provided for the exemplary anti-SEZ6 antibody SC17.17 in the appended sequence listing (SEQ ID NOS: 537-542). A summary of these preferred constructs is shown in Table 2 immediately below where all numbering is according to the EU index as set forth in Kabat and WT stands for "wild-type" or native constant region sequences without alterations. Note that, while the referenced sequences are kappa light chains, exemplary lambda light chains comprising C214 may also be used as set forth herein. Also, as used herein delta (Δ) shall designate the deletion of an amino acid residue (e.g., C214Δ indicates that the cysteine at position 214 has been deleted).

TABLE 2

| Designation | Antibody Component | Alteration | Const. Reg. SEQ ID NO: |
|---|---|---|---|
| ss1 | Heavy Chain | C220S | 500 |
|  | Light Chain | WT | 403 |
| ss2 | Heavy Chain | C220Δ | 501 |
|  | Light Chain | WT | 403 |
| ss3 | Heavy Chain | WT | 404 |
|  | Light Chain | C214Δ | 502 |
| ss4 | Heavy Chain | WT | 404 |
|  | Light Chain | C214S | 503 |

The strategy for generating antibody-drug conjugates with defined sites and stoichiometries of drug loading, as disclosed herein, is broadly applicable to other antibodies as it primarily involves engineering of the conserved constant domains of the antibody. As the amino acid sequences and native disulfide bridges of each class and subclass of antibody are well documented, one skilled in the art could readily fabricate engineered constructs of various antibodies without undue experimentation and, accordingly, such constructs are expressly contemplated as being within the scope of the instant invention.

3. Antibody Generation a. Polyclonal Antibodies

The production of polyclonal antibodies in various host animals, including rabbits, mice, rats, etc. is well known in the art. In some embodiments, polyclonal antibody-containing serum is obtained by bleeding or sacrificing the animal. The serum may be used for research purposes in the form obtained from the animal or, in the alternative, the antibodies may be partially or fully purified to provide immunoglobulin fractions or homogeneous antibody preparations.

Briefly the selected animal is immunized with an immunogen (e.g., soluble DLL3 or sDLL3) which may, for example, comprise selected isoforms, domains and/or peptides, or live cells or cell preparations expressing DLL3 or immunoreactive fragments thereof. Art known adjuvants that may be used to increase the immunological response, depending on the inoculated species include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants may protect the antigen from rapid dispersal by sequestering it in a local deposit, or they may contain substances that stimulate the host to secrete factors that are chemotactic for macrophages and other components of the immune system. Preferably the immunization schedule will involve two or more administrations of the selected immunogen spread out over a predetermined period of time.

By way of example the amino acid sequence of a DLL3 protein can be analyzed to select specific regions of the DLL3 protein for generating antibodies. For instance, hydrophobicity and hydrophilicity analyses of a DLL3 amino acid sequence are used to identify hydrophilic regions in the DLL3 structure. Regions of a DLL3 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each DLL3 region, domain or motif identified by any of these programs or methods is within the scope of the present invention and may be isolated or engineered to provide immunogens giving rise to modulators comprising desired properties. Preferred methods for the generation of DLL3 antibodies are further illustrated by way of the Examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents are effective. Administration of a DLL3 immunogen is often conducted by injection over a suitable time period and with use of a suitable adjuvant, as is understood in the art. During the immunization schedule, titers of antibodies can be taken as described in the Examples below to determine adequacy of antibody formation.

b. Monoclonal Antibodies

In addition, the invention contemplates use of monoclonal antibodies. As known in the art, the term "monoclonal antibody" (or mAb) refers to an antibody obtained from a population of substantially homogeneous antibodies, i.e., the individual antibodies comprising the population are identical except for possible mutations (e.g., naturally occurring mutations) that may be present in minor amounts. In certain embodiments, such a monoclonal antibody includes an antibody comprising a polypeptide sequence that binds or associates with an antigen wherein the antigen-binding polypeptide sequence was obtained by a process that includes the selection of a single target binding polypeptide sequence from a plurality of polypeptide sequences.

More generally, and as set forth in the Examples herein, monoclonal antibodies can be prepared using a wide variety of techniques known in the art including hybridoma techniques, recombinant techniques, phage display technologies, transgenic animals (e.g., a XenoMouse®) or some combination thereof. For example, monoclonal antibodies can be produced using hybridoma and art-recognized biochemical and genetic engineering techniques such as described in more detail in An, Zhigiang (ed.) *Therapeutic Monoclonal Antibodies: From Bench to Clinic*, John Wiley and Sons, 1$^{st}$ ed. 2009; Shire et. al. (eds.) *Current Trends in Monoclonal Antibody Development and Manufacturing*, Springer Science+Business Media LLC, 1$^{st}$ ed. 2010; Harlow et al., *Antibodies: A Laboratory Manual*, Cold Spring Harbor Laboratory Press, 2nd ed. 1988; Hammerling, et al., in: *Monoclonal Antibodies and T-Cell Hybridomas* 563-681 (Elsevier, N. Y., 1981) each of which is incorporated herein in its entirety by reference. It should be understood that a selected binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also an antibody of this invention. Murine monoclonal antibodies compatible with the instant invention are provided as set forth in Example 1 below.

c. Chimeric and Humanized Antibodies

In another embodiment, the antibodies of the invention may comprise chimeric antibodies derived from covalently joined protein segments from at least two different species or class of antibodies. The term "chimeric" antibodies is directed to constructs in which a portion of the heavy and/or light chain is identical or homologous to corresponding sequences in antibodies derived from a particular species or belonging to a particular antibody class or subclass, while the remainder of the chain(s) is identical or homologous to corresponding sequences in antibodies derived from another species or belonging to another antibody class or subclass, as well as fragments of such antibodies (U.S. Pat. No. 4,816,567; Morrison et al., 1984, PMID: 6436822).

In one embodiment, a chimeric antibody may comprise murine $V_H$ and $V_L$ amino acid sequences and constant regions derived from human sources, for example, humanized antibodies as described below. In some embodiments, the antibodies can be "CDR-grafted", where the antibody comprises one or more CDRs from a particular species or belonging to a particular antibody class or subclass, while the remainder of the antibody chain(s) is/are identical with or homologous to a corresponding sequence in antibodies derived from another species or belonging to another antibody class or subclass. For use in humans, selected rodent CDRs, e.g., mouse CDRs may be grafted into a human antibody, replacing one or more of the naturally occurring CDRs of the human antibody. These constructs generally have the advantages of providing full strength antibody functions, e.g., complement dependent cytotoxicity (CDC) and antibody-dependent cell-mediated cytotoxicity (ADCC) while reducing unwanted immune responses to the antibody by the subject.

Similar to the CDR-grafted antibody is a "humanized" antibody. As used herein, "humanized" forms of non-human (e.g., murine) antibodies are chimeric antibodies that comprise amino acids sequences derived from one or more non-human immunoglobulins. In one embodiment, a humanized antibody is a human immunoglobulin (recipient or acceptor antibody) in which residues from one or more CDRs of the recipient are replaced by residues from one or more CDRs of a non-human species (donor antibody) such as mouse, rat, rabbit, or non-human primate. In certain preferred embodiments, residues in one or more FRs in the variable domain of the human immunoglobulin are replaced by corresponding non-human residues from the donor antibody to help maintain the appropriate three-dimensional configuration of the grafted CDR(s) and thereby improve affinity. This can be referred to as the introduction of "back mutations". Furthermore, humanized antibodies may comprise residues that are not found in the recipient antibody or in the donor antibody to, for example, further refine antibody performance. Humanized anti-DLL3 antibodies compatible with the instant invention are provided in Example 3 below with resulting humanized light and heavy chain amino acid sequences shown in FIGS. 2A and 2B. Humanized anti-SEZ6 antibodies are provided as per Example 4 with resulting humanized light and heavy chain amino acid sequences shown in FIGS. 3A and 3B while a humanized anti-CD324 antibody was provided as per Example 5 with corresponding sequences shown in FIG. 4. FIGS. 5A and 5B, 6A and 6B and 7 show, respectively, site-specific exemplary humanized antibody heavy and light chain annotated amino acid sequences for the three antigens.

Various sources can be used to determine which human sequences to use in the humanized antibodies. Such sources include human germline sequences that are disclosed, for example, in Tomlinson, I. A. et al. (1992) *J. Mol. Biol.* 227:776-798; Cook, G. P. et al. (1995) *Immunol. Today* 16: 237-242; Chothia, D. et al. (1992) *J. Mol. Biol.* 227:799-817; and Tomlinson et al. (1995) *EMBO J* 14:4628-4638; the V-BASE directory (VBASE2—Retter et al., Nucleic Acid Res. 33; 671-674, 2005) which provides a comprehensive directory of human immunoglobulin variable region sequences (compiled by Tomlinson, I. A. et al. MRC Centre for Protein Engineering, Cambridge, UK); or consensus human FRs described, for example, in U.S. Pat. No. 6,300, 064.

CDR grafting and humanized antibodies are described, for example, in U.S. Pat. Nos. 6,180,370 and 5,693,762. For further details, see, e.g., Jones et al., 1986, PMID: 3713831); and U.S. Pat. Nos. 6,982,321 and 7,087,409.

Another method is termed "humaneering" which is described, for example, in U.S.P.N. 2005/0008625. In another embodiment a non-human antibody may be modified by specific deletion of human T-cell epitopes or "deimmunization" by the methods disclosed in WO 98/52976 and WO 00/34317.

As discussed above in selected embodiments at least 60%, 65%, 70%, 75%, or 80% of the humanized or CDR grafted antibody heavy or light chain variable region amino acid residues will correspond to those of the recipient human sequences. In other embodiments at least 83%, 85%, 87% or 90% of the humanized antibody variable region residues will correspond to those of the recipient human sequences. In a further preferred embodiment, greater than 95% of each of the humanized antibody variable regions will correspond to those of the recipient human sequences.

The sequence identity or homology of the humanized antibody variable region to the human acceptor variable region may be determined as previously discussed and, when measured as such, will preferably share at least 60% or 65% sequence identity, more preferably at least 70%, 75%, 80%, 85%, or 90% sequence identity, even more preferably at least 93%, 95%, 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution.

d. Human Antibodies

In another embodiment, the antibodies may comprise fully human antibodies. The term "human antibody" refers to an antibody which possesses an amino acid sequence that corresponds to that of an antibody produced by a human and/or has been made using any of the techniques for making human antibodies.

Human antibodies can be produced using various techniques known in the art. One technique is phage display in which a library of (preferably human) antibodies is synthesized on phages, the library is screened with the antigen of interest or an antibody-binding portion thereof, and the phage that binds the antigen is isolated, from which one may obtain the immunoreactive fragments. Methods for preparing and screening such libraries are well known in the art and kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; and Barbas et al., Proc. Natl. Acad. Sci. USA 88:7978-7982 (1991)).

In one embodiment, recombinant human antibodies may be isolated by screening a recombinant combinatorial antibody library prepared as above. In one embodiment, the library is a scFv phage display library, generated using human $V_L$ and $V_H$ cDNAs prepared from mRNA isolated from B-cells.

The antibodies produced by naive libraries (either natural or synthetic) can be of moderate affinity ($K_a$ of about $10^6$ to $10^7$ M$^{-1}$), but affinity maturation can also be mimicked in vitro by constructing and reselecting from secondary libraries as described in the art. For example, mutation can be introduced at random in vitro by using error-prone polymerase (reported in Leung et al., *Technique*, 1: 11-15 (1989)). Additionally, affinity maturation can be performed by randomly mutating one or more CDRs, e.g. using PCR with primers carrying random sequence spanning the CDR of interest, in selected individual Fv clones and screening for higher-affinity clones. WO 9607754 described a method for inducing mutagenesis in a CDR of an immunoglobulin light chain to create a library of light chain genes. Another effective approach is to recombine the $V_H$ or $V_L$ domains selected by phage display with repertoires of naturally occurring V domain variants obtained from unimmunized donors and to screen for higher affinity in several rounds of chain reshuffling as described in Marks et al., *Biotechnol.*, 10: 779-783 (1992). This technique allows the production of antibodies and antibody fragments with a dissociation constant $K_D$ ($k_{off}/k_{on}$) of about $10^{-9}$ M or less.

In other embodiments, similar procedures may be employed using libraries comprising eukaryotic cells (e.g., yeast) that express binding pairs on their surface. See, for example, U.S. Pat. No. 7,700,302 and U.S. Ser. No. 12/404, 059. In one embodiment, the human antibody is selected from a phage library, where that phage library expresses human antibodies (Vaughan et al. Nature *Biotechnology* 14:309-314 (1996): Sheets et al. *Proc. Natl. Acad. Sci. USA* 95:6157-6162 (1998). In other embodiments, human binding pairs may be isolated from combinatorial antibody libraries generated in eukaryotic cells such as yeast. See e.g., U.S. Pat. No. 7,700,302. Such techniques advantageously allow for the screening of large numbers of candidate modulators and provide for relatively easy manipulation of candidate sequences (e.g., by affinity maturation or recombinant shuffling).

Human antibodies can also be made by introducing human immunoglobulin loci into transgenic animals, e.g., mice in which the endogenous immunoglobulin genes have been partially or completely inactivated and human immunoglobulin genes have been introduced. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and U.S. Pat. Nos. 6,075,181 and 6,150,584 regarding XenoMouse® technology; and Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual suffering from a neoplastic disorder or may have been immunized in vitro). See, e.g., Cole et al., *Monoclonal Antibodies and Cancer Therapy*, Alan R. Liss, p. 77 (1985); Boerner et al., *J. Immunol,* 147 (1):86-95 (1991); and U.S. Pat. No. 5,750,373.

4. Recombinant Production of Antibodies

The site-specific antibodies and fragments thereof may be produced or modified using genetic material obtained from antibody producing cells and recombinant technology (see, for example, Berger and Kimmel, Guide to Molecular Cloning Techniques, *Methods in Enzymology* vol. 152 Academic Press, Inc., San Diego, Calif.; Sambrook and Russell (Eds.) (2000) *Molecular Cloning: A Laboratory Manual* ($3^{rd}$ Ed.), NY, Cold Spring Harbor Laboratory Press; Ausubel et al. (2002) *Short Protocols in Molecular Biology: A Compendium of Methods from Current Protocols in Molecular Biology*, Wiley, John & Sons, Inc. (supplemented through 2006); and U.S. Pat. No. 7,709,611).

More particularly, another aspect of the invention pertains to engineered nucleic acid molecules that encode the site-specific antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. A nucleic acid of the invention can be, for example, DNA or RNA and may or may not contain intronic sequences. More generally the term "nucleic acid", as used herein, includes genomic DNA, cDNA, RNA and artificial variants thereof (e.g., peptide nucleic acids), whether single-stranded or double-stranded. In a preferred embodiment, the nucleic acid is a cDNA molecule.

Nucleic acids of the invention can be obtained and manipulated using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques (e.g., see Example 1). For antibodies obtained from an immunoglobulin gene library (e.g., using phage display techniques), nucleic acid encoding the antibody can be recovered from the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_H1$, $C_H2$ and $C_H3$) which may or may not be engineered as described herein. The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. As discussed in more detail below an exemplary IgG1 constant region that is compatible with the teachings herein is set forth as SEQ ID NO: 404 in the appended sequence listing with compatible engineered IgG1 constant regions set forth in SEQ ID NOS: 500 and 501. For a Fab fragment heavy chain gene, the VH-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region. In this respect an exemplary compatible kappa light chain constant region is set forth as SEQ ID NO: 403 in the appended sequence listing while a compatible lambda light chain constant region is set forth in SEQ ID NO: 504. Compatible engineered versions of the kappa and lambda light chain regions are shown in SEQ ID NOS: 502, 503 and 505,506 respectively.

The instant invention also provides vectors comprising such nucleic acids described above, which may be operably linked to a promoter (see, e.g., WO 86/05807; WO 89/01036; and U.S. Pat. No. 5,122,464); and other transcriptional regulatory and processing control elements of the eukaryotic secretory pathway. The invention also provides host cells harboring those vectors and host-expression systems.

As used herein, the term "host-expression system" includes any kind of cellular system which can be engineered to generate either the nucleic acids or the polypeptides and antibodies of the invention. Such host-expression systems include, but are not limited to microorganisms (e.g., *E. coli* or *B. subtilis*) transformed or transfected with recombinant bacteriophage DNA or plasmid DNA; yeast (e.g., *Saccharomyces*) transfected with recombinant yeast expression vectors; or mammalian cells (e.g., COS, CHO-S, HEK-293T, 3T3 cells) harboring recombinant expression constructs containing promoters derived from the genome of mammalian cells or viruses (e.g., the adenovirus late promoter). The host cell may be co-transfected with two expression vectors, for example, the first vector encoding a heavy chain derived polypeptide and the second vector encoding a light chain derived polypeptide.

Methods of transforming mammalian cells are well known in the art. See, for example, U.S. Pat. Nos. 4,399,216, 4,912,040, 4,740,461, and 4,959,455. The host cell may also be engineered to allow the production of an antigen binding molecule with various characteristics (e.g. modified glycoforms or proteins having GnTIII activity).

For long-term, high-yield production of recombinant proteins stable expression is preferred. Accordingly, cell lines that stably express the selected antibody may be engineered using standard art recognized techniques and form part of the invention. Rather than using expression vectors that contain viral origins of replication, host cells can be transformed with DNA controlled by appropriate expression control elements (e.g., promoter or enhancer sequences, transcription terminators, polyadenylation sites, etc.), and a selectable marker. Any of the selection systems well known in the art may be used, including the glutamine synthetase gene expression system (the GS system) which provides an efficient approach for enhancing expression under certain conditions. The GS system is discussed in whole or part in connection with U.S. Pat. Nos. 5,591,639 and 5,879,936. Another preferred expression system for the development of stable cell lines is the Freedom™ CHO-S Kit (Life Technologies).

Once an antibody of the invention has been produced by recombinant expression or any other of the disclosed techniques, it may be purified or isolated by methods known in the art, meaning that it is identified and separated and/or recovered from its natural environment and separated from contaminants that would interfere with conjugation or diagnostic or therapeutic uses for the antibody. Isolated antibodies include antibodies in situ within recombinant cells.

These isolated preparations may be purified using various art recognized techniques, such as, for example, ion exchange and size exclusion chromatography, dialysis, diafiltration, and affinity chromatography, particularly Protein A or Protein G affinity chromatography.

5. Antibody Fragments and Derivatives a. Fragments

Regardless of which form of site-specific antibody (e.g. chimeric, humanized, etc.) is selected to practice the invention it will be appreciated that immunoreactive fragments of the same may be used in accordance with the teachings herein. An "antibody fragment" comprises at least a portion of an intact antibody. As used herein, the term "fragment" of an antibody molecule includes antigen-binding fragments of antibodies, and the term "antigen-binding fragment" refers to a polypeptide fragment of an immunoglobulin or antibody comprising at least one free cysteine that immunospecifically binds or reacts with a selected antigen or immunogenic determinant thereof or competes with the intact antibody from which the fragments were derived for specific antigen binding.

Exemplary site-specific fragments include: $V_L$, $V_H$, scFv, F(ab')2 fragment, Fab fragment, Fd fragment, Fv fragment, single domain antibody fragments, diabodies, linear antibodies, single-chain antibody molecules and multispecific antibodies formed from antibody fragments. In addition, an active site-specific fragment comprises a portion of the antibody that retains its ability to interact with the antigen/substrates or receptors and modify them in a manner similar to that of an intact antibody (though maybe with somewhat less efficiency).

In other embodiments, a site-specific antibody fragment is one that comprises the Fc region and that retains at least one of the biological functions normally associated with the Fc region when present in an intact antibody, such as FcRn binding, antibody half-life modulation, ADCC function and complement binding. In one embodiment, a site-specific antibody fragment is a monovalent antibody that has an in vivo half-life substantially similar to an intact antibody. For example, such an antibody fragment may comprise an antigen binding arm linked to an Fc sequence comprising at least one free cysteine capable of conferring in vivo stability to the fragment.

As would be well recognized by those skilled in the art, fragments can be obtained by molecular engineering or via chemical or enzymatic treatment (such as papain or pepsin) of an intact or complete antibody or antibody chain or by recombinant means. See, e.g., Fundamental Immunology, W. E. Paul, ed., Raven Press, N.Y. (1999), for a more detailed description of antibody fragments.

b. Multivalent Antibodies

In one embodiment, the site-specific conjugates of the invention may be monovalent or multivalent (e.g., bivalent, trivalent, etc.). As used herein, the term "valency" refers to the number of potential target binding sites associated with an antibody. Each target binding site specifically binds one target molecule or specific position or locus on a target molecule. When an antibody is monovalent, each binding site of the molecule will specifically bind to a single antigen position or epitope. When an antibody comprises more than one target binding site (multivalent), each target binding site may specifically bind the same or different molecules (e.g., may bind to different ligands or different antigens, or different epitopes or positions on the same antigen). See, for example, U.S.P.N. 2009/0130105. In each case at least one of the binding sites will comprise an epitope, motif or domain associated with a DLL3 isoform.

In one embodiment, the modulators are bispecific antibodies in which the two chains have different specificities, as described in Millstein et al., 1983, *Nature*, 305:537-539. Other embodiments include antibodies with additional specificities such as trispecific antibodies. Other more sophisticated compatible multispecific constructs and methods of their fabrication are set forth in U.S.P.N. 2009/0155255, as well as WO 94/04690; Suresh et al., 1986, *Methods in Enzymology,* 121:210; and WO96/27011.

As alluded to above, multivalent antibodies may immunospecifically bind to different epitopes of the desired target molecule or may immunospecifically bind to both the target molecule as well as a heterologous epitope, such as a heterologous polypeptide or solid support material. While preferred embodiments of the anti-DLL3 antibodies only bind two antigens (i.e. bispecific antibodies), antibodies with additional specificities such as trispecific antibodies are also encompassed by the instant invention. Bispecific antibodies also include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

In yet other embodiments, antibody variable domains with the desired binding specificities (antibody-antigen combining sites) are fused to immunoglobulin constant domain sequences, such as an immunoglobulin heavy chain constant domain comprising at least part of the hinge, $C_H2$, and/or $C_H3$ regions, using methods well known to those of ordinary skill in the art.

c. Fc Region Modifications

In addition to the various modifications, substitutions, additions or deletions to the variable or binding region of the disclosed site-specific conjugates set forth above, including those generating a free cysteine, those skilled in the art will appreciate that selected embodiments of the present invention may also comprise substitutions or modifications of the constant region (i.e. the Fc region). More particularly, it is contemplated that the site-specific antibodies of the invention may contain inter alia one or more additional amino acid residue substitutions, mutations and/or modifications which result in a compound with preferred characteristics including, but not limited to: altered pharmacokinetics, increased serum half life, increase binding affinity, reduced immunogenicity, increased production, altered Fc ligand binding to an Fc receptor (FcR), enhanced or reduced "ADCC" (antibody-dependent cell mediated cytotoxicity) or "CDC" (complement-dependent cytotoxicity) activity, altered glycosylation and/or disulfide bonds and modified binding specificity. In this regard it will be appreciated that these Fc variants may advantageously be used to enhance the effective anti-neoplastic properties of the disclosed modulators.

To this end certain embodiments of the invention may comprise substitutions or modifications of the Fc region beyond those required to generate a free cysteine, for example the addition of one or more amino acid residue, substitutions, mutations and/or modifications to produce a compound with enhanced or preferred Fc effector functions. For example, changes in amino acid residues involved in the interaction between the Fc domain and an Fc receptor (e.g., FcγRI, FcγRIIA and B, FcγRIII and FcRn) may lead to increased cytotoxicity and/or altered pharmacokinetics, such as increased serum half-life (see, for example, Ravetch and Kinet, Annu Rev. Immunol 9:457-92 (1991); Capel et al., Immunomethods 4:25-34 (1994); and de Haas et al., J. Lab. Clin. Med. 126:330-41 (1995) each of which is incorporated herein by reference).

In selected embodiments, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S.P.N. 2003/0190311. With regard to such embodiments, Fc variants may provide half-lives in a mammal, preferably a human, of greater than 5 days, greater than 10 days, greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-life results in a higher serum titer which thus reduces the frequency of the administration of the antibodies and/or reduces the concentration of the antibodies to be administered. Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 describes antibody variants with improved or diminished binding to FcRns. See also, e.g., Shields et al. J. Biol. Chem. 9(2):6591-6604 (2001).

In other embodiments, Fc alterations may lead to enhanced or reduced ADCC or CDC activity. As in known in the art, CDC refers to the lysing of a target cell in the presence of complement, and ADCC refers to a form of cytotoxicity in which secreted Ig bound onto FcRs present on certain cytotoxic cells (e.g., Natural Killer cells, neutrophils, and macrophages) enables these cytotoxic effector cells to bind specifically to an antigen-bearing target cell and subsequently kill the target cell with cytotoxins. In the context of the instant invention antibody variants are provided with "altered" FcR binding affinity, which is either enhanced or diminished binding as compared to a parent or unmodified antibody or to an antibody comprising a native sequence FcR. Such variants which display decreased binding may possess little or no appreciable binding, e.g., 0-20% binding to the FcR compared to a native sequence, e.g. as determined by techniques well known in the art. In other embodiments the variant will exhibit enhanced binding as compared to the native immunoglobulin Fc domain. It will be appreciated that these types of Fc variants may advantageously be used to enhance the effective anti-neoplastic properties of the disclosed antibodies. In yet other embodiments, such alterations lead to increased binding affinity, reduced immunogenicity, increased production, altered glycosylation and/or disulfide bonds (e.g., for conjugation sites), modified binding specificity, increased phagocytosis; and/or down regulation of cell surface receptors (e.g. B cell receptor; BCR), etc.

d. Altered Glycosylation

Still other embodiments comprise one or more engineered glycoforms, i.e., a DLL3 site-specific antibody comprising an altered glycosylation pattern or altered carbohydrate composition that is covalently attached to the protein (e.g., in the Fc domain). See, for example, Shields, R. L. et al. (2002) J. Biol. Chem. 277:26733-26740. Engineered glycoforms may be useful for a variety of purposes, including but not limited to enhancing or reducing effector function, increasing the affinity of the modulator for a target or facilitating production of the modulator. In certain embodiments where reduced effector function is desired, the molecule may be engineered to express an aglycosylated form. Substitutions that may result in elimination of one or more variable region framework glycosylation sites to thereby eliminate glycosylation at that site are well known (see e.g. U.S. Pat. Nos. 5,714,350 and 6,350,861). Conversely, enhanced effector functions or improved binding may be imparted to the Fc containing molecule by engineering in one or more additional glycosylation sites.

Other embodiments include an Fc variant that has an altered glycosylation composition, such as a hypofucosylated antibody having reduced amounts of fucosyl residues or an antibody having increased bisecting GlcNAc structures. Such altered glycosylation patterns have been demonstrated to increase the ADCC ability of antibodies. Engineered glycoforms may be generated by any method known to one skilled in the art, for example by using engineered or variant expression strains, by co-expression with one or more enzymes (for example N-acetylglucosaminyltransferase III (GnTI11)), by expressing a molecule comprising an Fc region in various organisms or cell lines from various organisms or by modifying carbohydrate(s) after the molecule comprising Fc region has been expressed (see, for example, WO 2012/117002).

e. Additional Processing

The site-specific antibodies or conjugates may be differentially modified during or after production, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Various post-translational modifications also encompassed by the invention include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression. Moreover, the modulators may also be modified with a detectable label, such as an enzymatic, fluorescent, radioisotopic or affinity label to allow for detection and isolation of the modulator.

6. Site-Specific Antibody Characteristics

No matter how obtained or which of the aforementioned forms the site-specific conjugate takes, various embodiments of the disclosed antibodies may exhibit certain characteristics. In selected embodiments, antibody-producing cells (e.g., hybridomas or yeast colonies) may be selected, cloned and further screened for favorable properties including, for example, robust growth, high antibody production and, as discussed in more detail below, desirable site-specific antibody characteristics. In other cases characteristics of the antibody may be imparted or influenced by selecting a particular antigen (e.g., a specific DLL3 isoform) or immunoreactive fragment of the target antigen for inoculation of the animal. In still other embodiments the selected antibodies may be engineered as described above to enhance or refine immunochemical characteristics such as affinity or pharmacokinetics.

a. Neutralizing Antibodies

In certain embodiments, the conjugates will comprise "neutralizing" antibodies or derivatives or fragments thereof. That is, the present invention may comprise antibody molecules that bind specific domains, motifs or epitopes and are capable of blocking, reducing or inhibiting the biological activity of, for example, DLL3. More generally the term "neutralizing antibody" refers to an antibody that binds to or interacts with a target molecule or ligand and prevents binding or association of the target molecule to a binding partner such as a receptor or substrate, thereby interrupting a biological response that otherwise would result from the interaction of the molecules.

It will be appreciated that competitive binding assays known in the art may be used to assess the binding and specificity of an antibody or immunologically functional fragment or derivative thereof. With regard to the instant invention an antibody or fragment will be held to inhibit or reduce binding of DLL3 to a binding partner or substrate when an excess of antibody reduces the quantity of binding partner bound to DLL3 by at least about 20%, 30%, 40%, 50%, 60%, 70%, 80%, 85%, 90%, 95%, 97%, 99% or more as measured, for example, by Notch receptor activity or in an in vitro competitive binding assay. In the case of antibodies to DLL3 for example, a neutralizing antibody or antagonist will preferably alter Notch receptor activity by at least about 20%, 30%, 40%, 50%, 60%, 70%, 80%, 85%, 90%, 95%, 97%, 99% or more. It will be appreciated that this modified activity may be measured directly using art-recognized techniques or may be measured by the impact the altered activity has downstream (e.g., oncogenesis, cell survival or activation or suppression of Notch responsive genes). Preferably, the ability of an antibody to neutralize DLL3 activity is assessed by inhibition of DLL3 binding to a Notch receptor or by assessing its ability to relieve DLL3 mediated repression of Notch signaling.

b. Internalizing Antibodies

There is evidence that a substantial portion of expressed DLL3 protein remains associated with the tumorigenic cell surface, thereby allowing for localization and internalization of the disclosed site-specific conjugates. In preferred embodiments such modulators will be associated with, or conjugated to, one or more drugs through engineered free cysteine site(s) that kill the cell upon internalization. In particularly preferred embodiments the site-specific conjugates will comprise an internalizing ADC.

As used herein, a modulator that "internalizes" is one that is taken up (along with any payload) by the cell upon binding to an associated antigen or receptor. As will be appreciated, the internalizing antibody may, in select embodiments, comprise antibody fragments and derivatives thereof, as well as antibody conjugates comprising a DAR of approximately 2. Internalization may occur in vitro or in vivo. For therapeutic applications, internalization will preferably occur in vivo in a subject in need thereof. The number of site-specific antibody conjugates internalized may be sufficient or adequate to kill an antigen-expressing cell, especially an antigen-expressing cancer stem cell. Depending on the potency of the payload or site-specific antibody conjugate as a whole, in some instances, the uptake of a single engineered antibody molecule into the cell is sufficient to kill the target cell to which the antibody binds. For example, certain drugs are so highly potent that the internalization of a few molecules of the toxin conjugated to the antibody is sufficient to kill the tumor cell. Whether an antibody internalizes upon binding to a mammalian cell can be determined by various art-recognized assays including those described in the Examples below. Methods of detecting whether an antibody internalizes into a cell are also described in U.S. Pat. No. 7,619,068 which is incorporated herein by reference in its entirety.

c. Depleting Antibodies

In other embodiments the site-specific conjugate will comprise depleting antibodies or derivatives or fragments thereof. The term "depleting" antibody refers to an antibody that preferably binds to or associates with an antigen on or near the cell surface and induces, promotes or causes the death or elimination of the cell (e.g., by CDC, ADCC or introduction of a cytotoxic agent). In preferred embodiments, the selected depleting antibodies will be associated or conjugated to a drug.

Preferably a depleting antibody will be able to remove, incapacitate, eliminate or kill at least 20%, 30%, 40%, 50%, 60%, 70%, 80%, 85%, 90%, 95%, 97%, or 99% of DLL3 expressing cells in a defined cell population. In some embodiments the cell population may comprise enriched, sectioned, purified or isolated tumor perpetuating cells. In other embodiments the cell population may comprise whole tumor samples or heterogeneous tumor extracts that comprise cancer stem cells. Those skilled in the art will appreciate that standard biochemical techniques may be used to monitor and quantify the depletion of tumorigenic cells or tumor perpetuating cells in accordance with the teachings herein.

d. Binning and Epitope Mapping

It will further be appreciated the disclosed site-specific antibody conjugates will associate with, or bind to, discrete epitopes or immunogenic determinants presented by the selected target or fragment thereof. In certain embodiments, epitope or immunogenic determinants include chemically active surface groupings of molecules such as amino acids, sugar side chains, phosphoryl groups, or sulfonyl groups, and, in certain embodiments, may have specific three-dimensional structural characteristics, and/or specific charge characteristics. Thus, as used herein the term "epitope" includes any protein determinant capable of specific binding to an immunoglobulin or T-cell receptor or otherwise interacting with a molecule. In certain embodiments, an antibody is said to specifically bind (or immunospecifically bind or react) an antigen when it preferentially recognizes its target antigen in a complex mixture of proteins and/or macromolecules. In preferred embodiments, an antibody is said to specifically bind an antigen when the equilibrium dissociation constant ($K_D$) is less than or equal to $10^{-6}$M or less than or equal to $10^{-7}$M, more preferably when the equilibrium dissociation constant is less than or equal to $10^{-8}$M, and even more preferably when the dissociation constant is less than or equal to $10^{-9}$M More directly the term "epitope" is used in its common biochemical sense and refers to that portion of the target antigen capable of being recognized and specifically bound by a particular antibody modulator. When the antigen is a polypeptide such as DLL3, epitopes may generally be formed from both contiguous amino acids and noncontiguous amino acids juxtaposed by tertiary folding of a protein ("conformational epitopes"). In such conformational epitopes the points of interaction occur across amino acid residues on the protein that are linearly separated from one another. Epitopes formed from contiguous amino acids (sometimes referred to as "linear" or "continuous" epitopes) are typically retained upon protein denaturing, whereas epitopes formed by tertiary folding are typically lost upon protein denaturing. In any event an antibody epitope typically includes at least 3, and more usually, at least 5 or 8-10 amino acids in a unique spatial conformation.

In this respect it will be appreciated that, in certain embodiments, an epitope may be associated with, or reside in, one or more regions, domains or motifs of, for example, the DLL3 protein. As discussed in more detail herein the extracellular region of the DLL3 protein comprises a series of generally recognized domains including six EGF-like domains and a DSL domain. For the purposes of the instant disclosure the term "domain" will be used in accordance with its generally accepted meaning and will be held to refer to an identifiable or definable conserved structural entity within a protein that exhibits a distinctive secondary structure content. In many cases, homologous domains with common functions will usually show sequence similarities and be found in a number of disparate proteins (e.g., EGF-like domains are reportedly found in at least 471 different proteins). Similarly, the art-recognized term "motif" will be used in accordance with its common meaning and shall generally refer to a short, conserved region of a protein that is typically ten to twenty contiguous amino acid residues. As discussed throughout, selected embodiments comprise site-specific antibodies that associate with or bind to an epitope within specific regions, domains or motifs of DLL3.

As discussed in more detail in PCT/US14/17810 particularly preferred epitopes of human DLL3 bound by exemplary site-specific antibody conjugates are set forth in Table 3 immediately below.

TABLE 3

| Antibody Clone | Epitope | SEQ ID NO: |
|---|---|---|
| SC16.23 | Q93, P94, G95, A96, P97 | 3 |
| SC16.34 | G203, R205, P206 | 4 |
| SC16.56 | G203, R205, P206 | 4 |

Following a similar line of reasoning epitopes of the SEZ6 antigen were determined for selected antibodies. In this respect, and as set forth in PCT/US2013/027476 which is incorporated herein as to the same, site-specific anti-SEZ6 conjugates of the invention may comprise an antibody that specifically binds to an epitope on a SEZ6 protein wherein the epitope comprises amino acid residues selected from the group consisting of (i) residues R762, L764, Q777, 1779, D781 and Q782; (ii) residues R342 and K389 and (iii) residues T352, 5353 and H375.

In any event once a desired epitope on an antigen is determined, it is possible to generate antibodies to that epitope, e.g., by immunizing with a peptide comprising the epitope using techniques described in the present invention. Alternatively, during the discovery process, the generation and characterization of antibodies may elucidate information about desirable epitopes located in specific domains or motifs. From this information, it is then possible to competitively screen antibodies for binding to the same epitope. An approach to achieve this is to conduct competition studies to find antibodies that competitively bind with one another, i.e. the antibodies compete for binding to the antigen. A high throughput process for binning antibodies based upon their cross-competition is described in WO 03/48731. Other methods of binning or domain level or epitope mapping comprising antibody competition or antigen fragment expression on yeast are well known in the art.

As used herein, the term "binning" refers to methods used to group or classify antibodies based on their antigen binding characteristics and competition. While the techniques are useful for defining and categorizing modulators of the instant invention, the bins do not always directly correlate with epitopes and such initial determinations of epitope binding may be further refined and confirmed by other art-recognized methodology as described herein. However it will be appreciated that empirical assignment of antibody modulators to individual bins provides information that may be indicative of the therapeutic potential of the disclosed modulators.

More specifically, one can determine whether a selected reference antibody (or fragment thereof) binds to the same epitope or cross competes for binding with a second test antibody (i.e., is in the same bin) by using methods known in the art and set forth in the Examples herein. In one embodiment, a reference antibody modulator is associated with DLL3 antigen under saturating conditions and then the ability of a secondary or test antibody modulator to bind to DLL3 is determined using standard immunochemical techniques. If the test antibody is able to substantially bind to DLL3 at the same time as the reference anti-DLL3 antibody, then the secondary or test antibody binds to a different epitope than the primary or reference antibody. However, if the test antibody is not able to substantially bind to DLL3 at the same time, then the test antibody binds to the same epitope, an overlapping epitope, or an epitope that is in close proximity (at least sterically) to the epitope bound by the primary antibody. That is, the test antibody competes for antigen binding and is in the same bin as the reference antibody.

The term "compete" or "competing antibody" when used in the context of the disclosed antibodies means competition between antibodies as determined by an assay in which a test antibody or immunologically functional fragment under test prevents or inhibits specific binding of a reference antibody to a common antigen. Typically, such an assay involves the use of purified antigen (e.g., DLL3 or a domain or fragment thereof) bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess and/or allowed to bind first. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the Examples herein. Usually, when a competing antibody is present in excess, it will inhibit specific binding of a reference antibody to a common antigen by at least 30%, 40%, 45%, 50%, 55%, 60%, 65%, 70% or 75%. In some instance, binding is inhibited by at least 80%, 85%, 90%, 95%, or 97% or more.

Conversely, when the reference antibody is bound it will preferably inhibit binding of a subsequently added test antibody (i.e., a DLL3 modulator) by at least 30%, 40%, 45%, 50%, 55%, 60%, 65%, 70% or 75%. In some instance, binding of the test antibody is inhibited by at least 80%, 85%, 90%, 95%, or 97% or more.

With regard to the instant invention, and as set forth in PCT/US14/17810 which is incorporated herein as to the anti-DLL3 antibody bins, it has been determined (via surface plasmon resonance or bio-layer interferometry) that the extracellular domain of DLL3 defines at least nine bins by competitive binding termed "bin A" to "bin I" herein. Given the resolution provided by modulator binning techniques, it is believed that these nine bins comprise the majority of the bins that are present in the extracellular region of the DLL3 protein.

In this respect, and as known in the art the desired binning or competitive binding data can be obtained using solid phase direct or indirect radioimmunoassay (RIA), solid phase direct or indirect enzyme immunoassay (EIA or ELISA), sandwich competition assay, a Biacore™ 2000 system (i.e., surface plasmon resonance—GE Healthcare), a ForteBio® Analyzer (i.e., bio-layer interferometry—ForteBio, Inc.) or flow cytometric methodology. The term "surface plasmon resonance," as used herein, refers to an optical phenomenon that allows for the analysis of real-time specific interactions by detection of alterations in protein concentrations within a biosensor matrix. The term "bio-layer interferometry" refers to an optical analytical technique that analyzes the interference pattern of white light reflected from two surfaces: a layer of immobilized protein on a biosensor tip, and an internal reference layer. Any change in the number of molecules bound to the biosensor tip causes a shift in the interference pattern that can be measured in real-time. In particularly preferred embodiments the analysis (whether surface plasmon resonance, bio-layer interferometry or flow cytometry) is performed using a Biacore or ForteBio instrument or a flow cytometer (e.g., FACSAria II) as known in the art.

In order to further characterize the epitopes that the disclosed DLL3 antibody modulators associate with or bind to, domain-level epitope mapping may be performed using a modification of the protocol described by Cochran et al. (J Immunol Methods. 287 (1-2):147-158 (2004) which is incorporated herein by reference). Briefly, individual domains of DLL3 comprising specific amino acid sequences were expressed on the surface of yeast and binding by each DLL3 antibody was determined through flow cytometry.

Other compatible epitope mapping techniques include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety). In other embodiments Modification-Assisted Profiling (MAP), also known as Antigen Structure-based Antibody Profiling (ASAP) provides a method that categorizes large numbers of monoclonal antibodies (mAbs) directed against the same antigen according to the similarities of the binding profile of each antibody to chemically or enzymatically modified antigen surfaces (U.S.P.N. 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. It will be appreciated that MAP may be used to sort the hDLL3 antibody modulators of the invention into groups of antibodies binding different epitopes Agents useful for altering the structure of the immobilized antigen include enzymes such as proteolytic enzymes (e.g., trypsin, endoproteinase Glu-C, endoproteinase Asp-N, chymotrypsin, etc.). Agents useful for altering the structure of the immobilized antigen may also be chemical agents, such as, succinimidyl esters and their derivatives, primary amine-containing compounds, hydrazines and carbohydrazines, free amino acids, etc.

The antigen protein may be immobilized on either biosensor chip surfaces or polystyrene beads. The latter can be processed with, for example, an assay such as multiplex LUMINEX™ detection assay (Luminex Corp.). Because of the capacity of LUMINEX to handle multiplex analysis with up to 100 different types of beads, LUMINEX provides almost unlimited antigen surfaces with various modifications, resulting in improved resolution in antibody epitope profiling over a biosensor assay.

e. Binding Affinity

Besides epitope specificity the disclosed site-specific antibodies may be characterized using physical characteristics such as, for example, binding affinities. In this regard the present invention further encompasses the use of antibodies that have a high binding affinity for one or more DLL3 isoforms or, in the case of pan-antibodies, more than one member of the DLL family. As used herein, the term "high affinity" for an IgG antibody refers to an antibody having a $K_D$ of $10^{-8}$M or less, more preferably $10^{-9}$M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$M or less, even more preferably $10^{-9}$M or less.

The term "$K_D$", as used herein, is intended to refer to the dissociation constant of a particular antibody-antigen interaction. An antibody of the invention is said to immunospecifically bind its target antigen when the dissociation constant $K_D$ ($k_{off}/k_{on}$) is $\leq 10^{-7}$M. The antibody specifically binds antigen with high affinity when the $K_D$ is $\leq 5\times10^{-9}$M, and with very high affinity when the $K_D$ is $\leq 5\times10^{-10}$M. In one embodiment of the invention, the antibody has a $K_D$ of $\leq 10^{-9}$M and an off-rate of about $1\times10^{-4}$/sec. In one embodiment of the invention, the off-rate is $<1\times10^{-5}$/sec. In other embodiments of the invention, the antibodies will bind to DLL3 with a $K_D$ of between about $10^{-7}$M and $10^{-10}$ M, and in yet another embodiment it will bind with a $K_D \leq 2\times10^{-10}$ M. Still other selected embodiments of the present invention comprise antibodies that have a disassociation constant or $K_D$ ($k_{off}/k_{on}$) of less than $10^{-2}$M, less than $5\times10^{-2}$M, less than $10^{-3}$M, less than $5\times10^{-3}$M, less than $10^{-4}$M, less than $5\times10^{-4}$M, less than $10^{-5}$M, less than $5\times10^{-5}$M, less than $10^{-6}$M, less than $5\times10^{-6}$M, less than $10^{-7}$M, less than $5\times10^{-7}$M, less than $10^{-8}$M, less than $5\times10^{-8}$M, less than $10^{-9}$M, less than $5\times10^{-9}$M, less than $10^{-10}$M, less than $5\times10^{-10}$ M, less than $10^{-11}$M, less than $5\times10^{-11}$M, less than $10^{-12}$M, less than $5\times10^{-12}$M, less than $10^{-13}$M, less than $5\times10^{-13}$M, less than $10^{-14}$M, less than $5\times10^{-14}$M, less than $10^{-15}$M or less than $5\times10^{-15}$M.

In specific embodiments, an antibody of the invention that immunospecifically binds to DLL3 has an association rate constant or $k_{on}$ (or $k_a$) rate (DLL3 (Ab)+antigen (Ag)$^k{}_{on}$←Ab-Ag) of at least $10^5$ M$^{-1}$ s$^{-1}$, at least $2\times10^5$ M$^{-1}$ s$^{-1}$, at least $5\times10^5$ M$^{-1}$ s$^{-1}$, at least $10^6$ M$^{-1}$ s$^{-1}$, at least $5\times10^6$ M$^{-1}$ s$^{-1}$, at least $10^7$ M$^{-1}$ s$^{-1}$, at least $5\times10^7$ M$^{-1}$ s$^{-1}$, or at least $10^8$ M$^{-1}$ s$^{-1}$.

In another embodiment, an antibody of the invention that immunospecifically binds to DLL3 has a disassociation rate constant or $k_{off}$ (or $k_d$) rate (DLL3 (Ab)+antigen (Ag)$^k{}_{off}$←Ab-Ag) of less than $10^{-1}$ s$^{-1}$, less than $5\times10^{-1}$ s$^{-1}$, less than $10^{-2}$ s$^{-1}$, less than $5\times10^{-2}$ s$^{-1}$, less than $10^{-3}$ s$^{-1}$, less than $5\times10^{-3}$ s$^{-1}$, less than $10^4$ s$^{-1}$, less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5\times10^{-6}$ s$^{-1}$ less than $10^{-7}$ s$^{-1}$, less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$ or less than $10^{-10}$ s$^{-1}$.

In other selected embodiments of the present invention anti-DLL3 antibodies will have an affinity constant or $K_a$ ($k_{on}/k_{off}$) of at least $10^2$M$^{-1}$, at least $5\times10^2$M$^{-1}$, at least $10^3$M$^{-1}$, at least $5\times10^3$M$^{-1}$, at least $10^4$M$^{-1}$, at least $5\times10^4$M$^{-1}$, at least $10^5$M$^{-1}$, at least $5\times10^5$M$^{-1}$, at least $10^6$M$^{-1}$, at least $5\times10^6$M$^{-1}$, at least $10^7$M$^{-1}$, at least $5\times10^7$M$^{-1}$, at least $10^8$M$^{-1}$, at least $5\times10^8$M$^{-1}$, at least $10^9$M$^{-1}$, at least $5\times10^9$M$^{-1}$, at least $10^{10}$M$^{-1}$, at least $5\times10^{10}$M$^{-1}$, at least $10^{11}$M$^{-1}$, at least $5\times10^{11}$M$^{-1}$, at least $10^{12}$M$^{-1}$, at least $5\times10^{12}$M$^{-1}$, at least $10^{13}$M$^{-1}$, at least $5\times10^{13}$M$^{-1}$, at least $10^{14}$M$^{-1}$, at least $5\times10^{14}$M$^{-1}$, at least $10^{15}$M$^{-1}$ or at least $5\times10^{15}$M$^{-1}$.

Besides the aforementioned modulator characteristics antibodies of the instant invention may further be characterized using additional physical characteristics including, for example, thermal stability (i.e, melting temperature; Tm), and isoelectric points. (See, e.g., Bjellqvist et al., 1993, Electrophoresis 14:1023; Vermeer et al., 2000, Biophys. J. 78:394-404; Vermeer et al., 2000, Biophys. J. 79: 2150-2154 each of which is incorporated herein by reference).

IV. Site-Specific Conjugates

It will be appreciated that site-specific conjugates of the instant invention comprise a site-specific antibody (e.g., anti-DLL3, anti-SEZ6, anti-CD324) covalently linked (preferably through a linker moiety) to one or more drug payload (s) via unpaired cysteines. As discussed herein the site-specific conjugates of the instant invention may be used to provide cytotoxins or other payloads at the target location (e.g., tumorigenic cells). This is advantageously achieved by the disclosed site-specific ADCs which direct the bound payload to the target site in a relatively unreactive, non-toxic state before releasing and activating the drug payload. As discussed herein this targeted release of the payload is largely achieved through the stable site-specific conjugation of the payloads via one or more free cysteines and the relatively homogeneous composition of the ADC preparations which minimize over-conjugated toxic species. Coupled with drug linkers that are designed to largely release the payload once it has been delivered to the tumor site, the conjugates of the instant invention can substantially reduce undesirable non-specific toxicity. This advantageously provides for relatively high levels of the active cytotoxin at the tumor site while minimizing exposure of non-targeted cells and tissue thereby providing an enhanced therapeutic index when compared with conventional drug conjugates.

It will be appreciated that, while preferred embodiments of the invention comprise payloads of therapeutic moieties (e.g., cytotoxins), other payloads such as diagnostic agents and biocompatible modifiers may benefit from the targeted release provided by the disclosed conjugates. Accordingly, any disclosure directed to exemplary therapeutic payloads is also applicable to payloads comprising diagnostic agents or biocompatible modifiers as discussed herein unless otherwise dictated by context. In this regard the term "engineered conjugate" or "site-specific conjugate" or simply "conjugate" will be used broadly and held to mean any site-specific construct comprising a biologically active or detectable molecule or drug associated with the disclosed targeting moiety through one or more free cysteines. As used herein the terms "drug" or "payload" may be used interchangeably unless otherwise dictated by context and will mean a biologically active or detectable molecule or drug. In this respect it will be understood that such conjugates may, in addition to the specifically disclosed engineered conjugates may comprise peptides, polypeptides, proteins, prodrugs which are metabolized to an active agent in vivo, polymers, nucleic acid molecules, small molecules, binding agents, mimetic agents, synthetic drugs, inorganic molecules, organic molecules and radioisotopes. Moreover, as indicated above the selected payload may be covalently or non-covalently associated with, or linked to, the modulator and exhibit various stoichiometric molar ratios depending, at least in part, on the method used to effect the conjugation.

Essentially any payload that may be linked to a cysteine residue in a conventional antibody using art-recognized techniques may be associated with unpaired cysteines of the engineered constructs of the instant invention using the novel techniques disclosed herein.

More specifically, once the disclosed site-specific antibodies of the invention have been generated and/or fabricated and selected according to the teachings herein they may be linked with, fused to, conjugated to, or otherwise associated with one or more pharmaceutically active or diagnostic moieties or biocompatible modifiers as described below. In this regard it will be appreciated that, unless otherwise dictated by context, the site-specific conjugates of the instant invention may be represented by the formula:

Ab-[L-D]$n$ or a pharmaceutically acceptable salt thereof wherein
 a) Ab comprises an antibody comprising one or more unpaired cysteines;
 b) L comprises an optional linker;
 c) D comprises a drug; and
 d) n is an integer from about 1 to about 8.

Those of skill in the art will appreciate that site-specific conjugates according to the aforementioned formula may be fabricated using a number of different linkers and drugs and that fabrication or conjunction methodology will vary depending on the selection of components. As such, any drug or drug linker compound that reacts with a thiol on the reactive cysteine(s) of the site-specific antibody is compatible with the teachings herein. Similarly, any reaction conditions that allow for site-specific conjugation of the selected drug to the engineered antibody are within the scope of the present invention. Notwithstanding the foregoing, particularly preferred embodiments of the instant invention comprise selective conjugation of the drug or drug linker using stabilization agents in combination with mild reducing agents as described herein and set forth in the Examples below. Such reaction conditions tend to provide more homogeneous preparations with less non-specific conjugation and contaminants and correspondingly less toxicity.

Exemplary payloads compatible with the teachings herein are listed below:

1. Therapeutic Agents

As indicated the site specific antibodies of the invention may be conjugated, linked or fused to or otherwise associated with a pharmaceutically active moiety which is a therapeutic moiety or a drug such as an anti-cancer agent including, but not limited to, cytotoxic agents, cytostatic agents, anti-angiogenic agents, debulking agents, chemotherapeutic agents, radiotherapeutic agents, targeted anti-cancer agents, biological response modifiers, cancer vaccines, cytokines, hormone therapies, anti-metastatic agents and immunotherapeutic agents.

Preferred exemplary anti-cancer agents (including homologs and derivatives thereof) comprise 1-dehydrotestosterone, anthramycins, actinomycin D, bleomycin, colchicin, cyclophosphamide, cytochalasin B, dactinomycin (formerly actinomycin), dihydroxy anthracin, dione, emetine, epirubicin, ethidium bromide, etoposide, glucocorticoids, gramicidin D, lidocaine, maytansinoids such as DM-1 and DM-4 (Immunogen), mithramycin, mitomycin, mitoxantrone, paclitaxel, procaine, propranolol, puromycin, tenoposide, tetracaine and pharmaceutically acceptable salts or solvates, acids or derivatives of any of the above.

Additional compatible cytotoxins comprise dolastatins and auristatins, including monomethyl auristatin E (MMAE) and monomethyl auristatin F (MMAF) (Seattle Genetics), amanitins such as alpha-amanitin, beta-amanitin, gamma-amanitin or epsilon-amanitin (Heidelberg Pharma), DNA minor groove binding agents such as duocarmycin derivatives (Syntarga), alkylating agents, mechlorethamine, thioepa, chlorambucil, melphalan, carmustine (BCNU), lomustine (CCNU), cyclothosphamide, busulfan, dibromomannitol, streptozotocin, mitomycin C and cisdichlorodiamine platinum (II) (DDP) cisplatin, splicing inhibitors such as meayamycin analogs or derivatives (e.g., FR901464 as set forth in U.S. Pat. No. 7,825,267), tubular binding agents such as epothilone analogs and paclitaxel and DNA damaging agents such as calicheamicins and esperamicins, antimetabolites such as methotrexate, 6-mercaptopurine, 6-thioguanine, cytarabine, and 5-fluorouracil decarbazine, anti-mitotic agents such as vinblastine and vincristine and anthracyclines such as daunorubicin (formerly daunomycin) and doxorubicin and pharmaceutically acceptable salts or solvates, acids or derivatives of any of the above.

Furthermore, in one embodiment the antibodies of the instant invention may be associated with anti-CD3 binding molecules to recruit cytotoxic T-cells and have them target tumorigenic cells (BiTE technology; see e.g., Fuhrmann et. al. (2010) Annual Meeting of AACR Abstract No. 5625).

In further embodiments ADCs of the invention may comprise therapeutic radioisotopes conjugated using appropriate linkers. Exemplary radioisotopes that may be compatible with such embodiments include, but are not limited to, iodine ($^{131}$I, $^{125}$I, $^{123}$I, $^{121}$I) carbon ($^{14}$C), copper ($^{62}$Cu, $^{64}$Cu, $^{67}$Cu), sulfur ($^{35}$S), tritium ($^{3}$H), indium ($^{115}$In, $^{113}$In, $^{112}$In, $^{111}$In), bismuth ($^{212}$Bi, $^{213}$Bi), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, $^{117}$Sn, $^{225}$Ac, $^{76}$Br, and $^{211}$At. Other radionuclides are also available as diagnostic and therapeutic agents, especially those in the energy range of 60 to 4,000 keV.

Antibodies of the present invention may also be conjugated to biological response modifiers. For example, in particularly preferred embodiments the drug moiety can be a polypeptide possessing a desired biological activity. Such proteins may include, for example, a toxin such as abrin, ricin A, Onconase (or another cytotoxic RNase), *pseudomonas* exotoxin, cholera toxin, diphtheria toxin; an apoptotic agent such as tumor necrosis factor e.g. TNF-α or TNF-β, α-interferon, β-interferon, nerve growth factor, platelet derived growth factor, tissue plasminogen activator, AIM I (WO 97/33899), AIM II (WO 97/34911), Fas Ligand (Takahashi et al., 1994, PMID: 7826947), and VEGI (WO 99/23105), a thrombotic agent, an anti-angiogenic agent, e.g., angiostatin or endostatin, a lymphokine, for example, interleukin-1 (IL-1), interleukin-2 (IL-2), interleukin-6 (IL-6), granulocyte macrophage colony stimulating factor (GM-CSF), and granulocyte colony stimulating factor (G-CSF), or a growth factor e.g., growth hormone (GH).

2. Diagnostic or Detection Agents

In other preferred embodiments, site-specific antibodies of the present invention, or fragments or derivatives thereof, are conjugated to a diagnostic or detectable agent, marker or reporter which may be, for example, a biological molecule (e.g., a peptide or nucleotide), a small molecule, fluorophore, or radioisotope. Labeled antibodies can be useful for monitoring the development or progression of a hyperproliferative disorder or as part of a clinical testing procedure to determine the efficacy of a particular therapy including the disclosed antibodies (i.e. theragnostics) or to determine a future course of treatment. Such markers or reporters may also be useful in purifying the selected antibody, for use in antibody analytics (e.g., epitope binding or antibody binning), separating or isolating tumorigenic cells or in preclinical procedures or toxicology studies.

Such diagnosis analysis and/or detection can be accomplished by coupling the modulator to detectable substances including, but not limited to, various enzymes comprising for example horseradish peroxidase, alkaline phosphatase, beta-galactosidase, or acetylcholinesterase; prosthetic groups, such as but not limited to streptavidinlbiotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Ph, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabeled or conjugated to specific radioisotopes. In such embodiments appropriate detection methodology is well known in the art and readily available from numerous commercial sources.

As indicated above, in other embodiments the site-specific antibodies or fragments thereof can be fused or conjugated to marker sequences or compounds, such as a peptide or fluorophore to facilitate purification or diagnostic or analytic procedures such as immunohistochemistry, biolayer interferometry, surface plasmon resonance, flow cytometry, competitive ELISA, FACs, etc. In preferred embodiments, the marker comprises a his-tag such as that provided by the pQE vector (Qiagen), among others, many of which are commercially available. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (U.S. Pat. No. 4,703,004).

3. Biocompatible Modifiers

In selected embodiments engineered antibodies of the invention may be conjugated with biocompatible modifiers that may be used to adjust, alter, improve or moderate antibody characteristics as desired. For example, antibodies or fusion constructs with increased in vivo half-lives can be generated by attaching relatively high molecular weight polymer molecules such as commercially available polyethylene glycol (PEG) or similar biocompatible polymers. Those skilled in the art will appreciate that PEG may be obtained in many different molecular weights and molecular configurations that can be selected to impart specific properties to the antibody (e.g. the half-life may be tailored). PEG can be attached to antibodies or antibody fragments or derivatives with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity may be used. The degree of conjugation can be closely monitored by SDS-PAGE and mass spectrometry to ensure optimal conjugation of PEG molecules to antibody molecules. Unreacted PEG can be separated from antibody-PEG conjugates by, e.g., size exclusion or ion-exchange chromatography. In a similar manner, the disclosed antibodies can be conjugated to albumin in order to make the antibody or antibody fragment more stable in vivo or have a longer half-life in vivo. The techniques are well known in the art, see e.g., WO 93/15199, WO 93/15200, and WO 01/77137; and EP 0 413, 622. Other biocompatible conjugates are evident to those of ordinary skill and may readily be identified in accordance with the teachings herein.

4. Linker Compounds

As with the aforementioned payloads numerous linker compounds are compatible with the instant invention and may be successfully used in combination with the teachings herein to provide the disclosed anti-DLL3 site-specific conjugates. In a broad sense the linkers merely need to covalently bind with the reactive thiol provided by the free cysteine and the selected drug compound. However, in other embodiments compatible linkers may covalently bind the selected drug at any accessible site including any substituents. Accordingly, any linker that reacts with the free cysteine(s) of the engineered antibody and may be used to provide the relatively stable site-specific conjugates of the instant invention is compatible with the teachings herein.

With regard to effectively binding to the selectively reduced free cysteine a number of art-recognized compounds take advantage of the good nucleophilicity of thiols and thus are available for use as part of a compatible linker. Free cysteine conjugation reactions include, but are not limited to, thiol-maleimide, thiol-halogeno (acyl halide), thiol-ene, thiol-yne, thiol-vinylsulfone, thiol-bisulfone, thiol-thiosulfonate, thiol-pyridyl disulfide and thiol-parafluoro reactions. As further discussed herein and shown in the Examples below, thiol-maleimide bioconjugation is one of the most widely used approaches due to its fast reaction rates and mild conjugation conditions. One issue with this approach is possibility of the retro-Michael reaction and loss or transfer of the maleimido-linked payload from the antibody or other target protein to other proteins in the plasma, such as, for example, human serum albumin. However, the use of selective reduction and site-specific antibodies as set forth herein may be used to stabilize the conjugate and reduce this undesired transfer. Thiol-acyl halide reactions provide bioconjugates that cannot undergo retro-Michael reaction and therefore are more stable. However, the thiol-halide reactions in general have slower reaction rates compared to maleimide-based conjugations and are thus not as efficient. Thiol-pyridyl disulfide reaction is another popular bioconjugation route. The pyridyl disulfide undergoes fast exchange with free thiol resulting in the mixed disulfide and release of pyridine-2-thione. Mixed disulfides can be cleaved in the reductive cell environment releasing the payload. Other approaches gaining more attention in bioconjugation are thiol-vinylsulfone and thiol-bisulfone reactions, each of which are compatible with the teachings herein and expressly included within the scope of the invention.

With regard to compatible linkers the compounds incorporated into the disclosed ADCs are preferably stable extracellularly, prevent aggregation of ADC molecules and keep the ADC freely soluble in aqueous media and in a monomeric state. Before transport or delivery into a cell, the antibody-drug conjugate is preferably stable and remains intact, i.e. the antibody remains linked to the drug moiety.

While the linkers are stable outside the target cell they are designed to be cleaved or degraded at some efficacious rate inside the cell. Accordingly an effective linker will: (i) maintain the specific binding properties of the antibody; (ii) allow intracellular delivery of the conjugate or drug moiety; (iii) remain stable and intact, i.e. not cleaved or degraded, until the conjugate has been delivered or transported to its targeted site; and (iv) maintain a cytotoxic, cell-killing effect or a cytostatic effect of the drug moiety. As discussed in more detail in the appended Examples stability of the ADC may be measured by standard analytical techniques such as mass spectroscopy, hydrophobic interaction chromatography (HIC), HPLC, and the separation/analysis technique LC/MS. As set forth above covalent attachment of the antibody and the drug moiety requires the linker to have two reactive functional groups, i.e. bivalency in a reactive sense. Bivalent linker reagents which are useful to attach two or more functional or biologically active moieties, such as MMAE and site-specific antibodies are known, and methods have been described to provide their resulting conjugates.

Linkers compatible with the present invention may broadly be classified as cleavable and non-cleavable linkers. Cleavable linkers, which may include acid-labile linkers, protease cleavable linkers and disulfide linkers, take advantage of internalization by the target cell and cleavage in the endosomal-lysosomal pathway. Release and activation of the cytotoxin relies on endosome/lysosome acidic compartments that facilitate cleavage of acid-labile chemical linkages such as hydrazone or oxime. If a lysosomal-specific protease cleavage site is engineered into the linker the cytotoxins will be released in proximity to their intracellular targets. Alternatively, linkers containing mixed disulfides provide an approach by which cytotoxic payloads are released intracellularly as they are selectively cleaved in the reducing environment of the cell, but not in the oxygen-rich environment in the bloodstream. By way of contrast, compatible non-cleavable linkers containing amide linked polyethyleneglycol or alkyl spacers liberate toxic payloads during lysosomal degradation of the antibody-drug conjugate within the target cell. In some respects the selection of linker will depend on the particular drug used in the site-specific conjugate.

Accordingly, certain embodiments of the invention comprise a linker that is cleavable by a cleaving agent that is present in the intracellular environment (e.g., within a lysosome or endosome or caveolae). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, each of which is known to hydrolyze dipeptide drug derivatives resulting in the release of active drug inside target cells. Exemplary peptidyl linkers that are cleavable by the thiol-dependent protease Cathepsin-B are peptides comprising Phe-Leu since cathepsin-B has been found to be highly expressed in cancerous tissue. Other examples of such linkers are described, for example, in U.S. Pat. No. 6,214,345 which incorporated herein by reference as to such linkers. In a specific preferred embodiment, the peptidyl linker cleavable by an intracellular protease is a Val-Cit linker, a Val-Ala linker or a Phe-Lys linker such as is described in U.S. Pat. No. 6,214,345. One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, oxime, semicarbazone, thiosemicarbazone, cis-aconitic amide, orthoester, acetal, ketal, or the like) can be used (See, e.g., U.S. Pat. Nos. 5,122,368; 5,824,805; 5,622,929). Such linkers are relatively stable under neutral pH conditions, such as those in the blood, but are unstable at below pH 5.5 or 5.0, the approximate pH of the lysosome.

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio) butyrate) and SHPT (N-succinimidyl-oxycarbonyl-alpha-methyl-alpha-(2-pyridyl-dithio) toluene). In yet other specific embodiments, the linker is a malonate linker (Johnson et al., 1995, *Anticancer Res.* 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

In particularly preferred embodiments (set forth in U.S.P.N. 2011/0256157 which is incorporated herein as to the linkers) compatible peptidyl linkers will comprise:

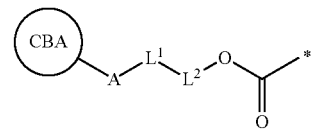

where the asterisk indicates the point of attachment to the drug, CBA is the site-specific antibody, $L^1$ is a linker, A is a connecting group connecting $L^1$ to an unpaired cysteine on the site specific antibody, $L^2$ is a covalent bond or together with —OC(=O)— forms a self-immolative linker, and $L^1$ or $L^2$ is a cleavable linker.

$L^1$ is preferably the cleavable linker, and may be referred to as a trigger for activation of the linker for cleavage.

The nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidising conditions may also find use in the present invention.

$L^1$ may comprise a contiguous sequence of amino acids. The amino acid sequence may be the target substrate for enzymatic cleavage, thereby allowing release of the drug.

In one embodiment, $L^1$ is cleavable by the action of an enzyme. In one embodiment, the enzyme is an esterase or a peptidase.

In one embodiment, $L^1$ comprises a dipeptide. The dipeptide may be represented as —NH—$X_1$—$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$—$X_2$— in dipeptide, —NH—$X_1$—$X_2$—CO—, is selected from:
-Phe-Lys-, -Val-Ala-, -Val-Lys-, -Ala-Lys-, -Val-Cit-, -Phe-Cit-, -Leu-Cit-, -Ile-Cit-, -Phe-Arg- and -Trp-Cit- where Cit is citrulline.

Preferably, the group —$X_1$—$X_2$— in dipeptide, —NH—$X_1$—$X_2$—CO—, is selected from:
-Phe-Lys-, -Val-Ala-, -Val-Lys-, -Ala-Lys-, and -Val-Cit-.

Most preferably, the group —$X_1$—$X_2$— in dipeptide, —NH—$X_1$—$X_2$—CO—, is -Phe-Lys- or -Val-Ala-.

In one embodiment, $L^2$ is present and together with —C(=O)O— forms a self-immolative linker.

In one embodiment, $L^2$ is a substrate for enzymatic activity, thereby allowing release of the drug.

In one embodiment, where $L^1$ is cleavable by the action of an enzyme and $L^2$ is present, the enzyme cleaves the bond between $L^1$ and $L^2$.

$L^1$ and $L^2$, where present, may be connected by a bond selected from:
—C(=O)NH—, —C(=O)O—, —NHC(=O)—, —OC(=O)—, —OC(=O)O—, —NHC(=O)O—, —OC(=O)NH—, and —NHC(=O)NH—.

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxyl group of $L^1$ that connects to $L^2$ may be derived from a hydroxyl group of an amino acid side chain, for example a serine amino acid side chain.

The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids; and (iv) all enantiomers, diastereomers, isomerically enriched, isotopically labelled (e.g. $^2$H, $^3$H, $^{14}$C, $^{15}$N), protected forms, and racemic mixtures thereof.

In one embodiment, —C(=O)O— and $L^2$ together form the group:

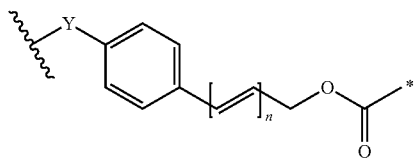

where the asterisk indicates the point of attachment to the drug or cytotoxic agent position, the wavy line indicates the point of attachment to the linker $L^1$, Y is —N(H)—, —O—, —C(=O)N(H)— or —C(=O)O—, and n is 0 to 3. The phenylene ring is optionally substituted with one, two or three substituents as described herein. In one embodiment, the phenylene group is optionally substituted with halo, $NO_2$, R or OR.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

In another particularly preferred embodiments the linker may include a self-immolative linker and the dipeptide together form the group —NH-Val-Ala-CO—NH-PABC-, which is illustrated below:

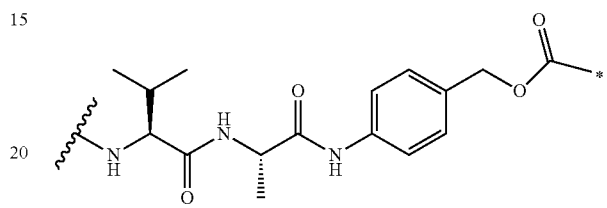

where the asterisk indicates the point of attachment to the selected cytotoxic moiety, and the wavy line indicates the point of attachment to the remaining portion of the linker (e.g., the spacer-antibody binding segments) which may be conjugated to the antibody. Upon enzymatic cleavage of the dipeptide the self-immolative linker will allow for clean release of the protected compound (i.e., the cytotoxin) when a remote site is activated, proceeding along the lines shown below:

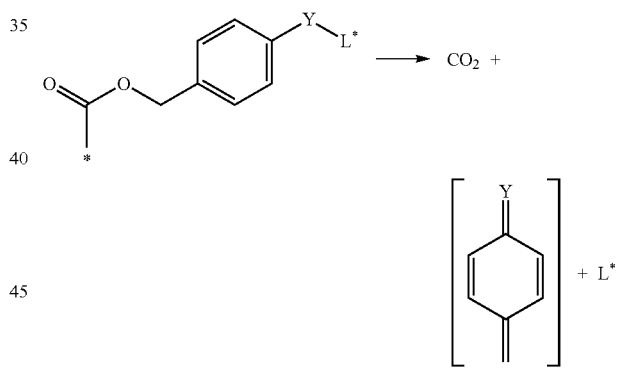

where L* is the activated form of the remaining portion of the linker comprising the now cleaved peptidyl unit. The clean release of the drug ensures they will maintain the desired toxic activity.

In one embodiment, A is a covalent bond. Thus, $L^1$ and the cell binding agent are directly connected. For example, where $L^1$ comprises a contiguous amino acid sequence, the N-terminus of the sequence may connect directly to the free cysteine.

In another embodiment, A is a spacer group. Thus, $L^1$ and the cell binding agent are indirectly connected.

$L^1$ and A may be connected by a bond selected from:
—C(=O)NH—, —C(=O)O—, —NHC(=O)—, —OC(=O)—, —OC(=O)O—, —NHC(=O)O—, —OC(=O)NH—, and —NHC(=O)NH—.

As will be discussed in more detail below and set forth in Examples 10-13 below the drug linkers of the instant invention will be linked to reactive thiol nucleophiles on free cysteines. To this end the free cysteines site-specific antibodies may be made reactive for conjugation with linker reagents by treatment with various reducing agent such as DTT or TCEP or mild reducing agents as set forth herein.

Preferably, the linker contains an electrophilic functional group for reaction with a nucleophilic functional group on the modulator. Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) maleimide groups (ii) activated disulfides, (iii) active esters such as NHS (N-hydroxysuccinimide) esters, HOBt (N-hydroxybenzotriazole) esters, haloformates, and acid halides; (iv) alkyl and benzyl halides such as haloacetamides; and (v) aldehydes, ketones, carboxyl, and, some of which are exemplified as follows:

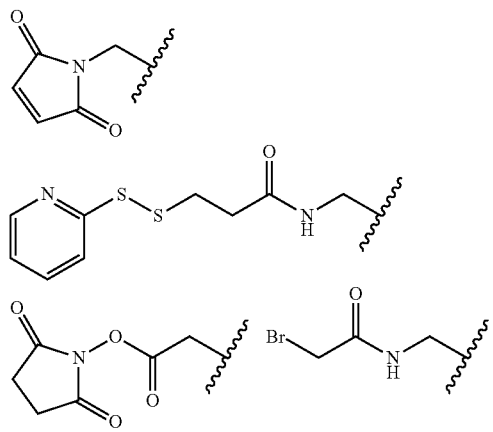

In particularly preferred embodiments the connection between the site-specific antibody and the drug-linker moiety is through a thiol residue of a free cysteine of the engineered antibody and a terminal maleimide group of present on the linker. In such embodiments, the connection between the cell binding agent and the drug-linker is:

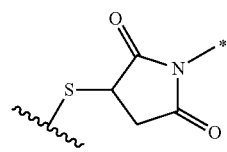 [SMILES: *SC1CC(=O)N(C)C1=O]

where the asterisk indicates the point of attachment to the remaining portion of drug-linker and the wavy line indicates the point of attachment to the remaining portion of the engineered antibody. In this embodiment, the S atom is preferably derived from the free cysteine antibody. With regard to other compatible linkers the binding moiety comprises a terminal iodoacetamide that may be reacted with activated thiols to provide the desired site-specific conjugate. The preferred conjugation procedure for this linker is slightly different from the preferred conjugation procedure for the maleimide binding group comprising selective reduction found in the other embodiments and set forth in the Examples below. In any event one skilled in the art could readily conjugate each of the disclosed drug-linker compounds with a compatible anti-DLL3 site-specific antibody in view of the instant disclosure.

5. Conjugation

As discussed above, the conjugate preparations provided by the instant invention exhibit enhanced stability and substantial homogeneity due, at least in part, to the provision of engineered free cysteine site(s) and/or the novel conjugation procedures set forth herein. Unlike conventional conjugation methodology that fully or partially reduces each of the intrachain or interchain antibody disulfide bonds to provide conjugation sites, the present invention advantageously provides for the selective reduction of certain prepared free cysteine sites and direction of the drug-linker to the same. The conjugation specificity promoted by the engineered sites and attendant selective reduction allows for a high percentage of site directed conjugation at the desired positions. Significantly some of these conjugation sites, such as those present in the terminal region of the light chain constant region, are typically difficult to conjugate effectively as they cross-react with other free cysteines. However, through molecular engineering and selective reduction of the resulting free cysteines efficient conjugation rates may be obtained which considerably reduces unwanted high-DAR contaminants and non-specific toxicity. More generally the engineered constructs and disclosed novel conjugation methods comprising selective reduction apparently provide ADC preparations having improved pharmacokinetics and/or pharmacodynamics and, potentially, an improved therapeutic index.

In this respect the site-specific constructs present free cysteine(s), which when reduced comprise thiol groups that are nucleophilic and capable of reacting to form covalent bonds with electrophilic groups on linker moieties such as those disclosed immediately above. Preferred antibodies of the instant invention will have reducible unpaired interchain or intrachain cysteines, i.e. cysteines providing such nucleophilic groups. Thus, in certain embodiments the reaction of free sulfhydryl groups of the reduced unpaired cysteines and the terminal maleimido or haloacetamide groups of the disclosed drug-linkers will provide the desired conjugation. In such cases, and as set forth in Examples 10 and 11 below, the free cysteines of the antibodies may be made reactive for conjugation with linker reagents by treatment with a reducing agent such as dithiothreitol (DTT) or (tris (2-carboxyethyl)phosphine (TCEP). Each free cysteine will thus present, theoretically, a reactive thiol nucleophile. While such reagents are compatible it will be appreciated that conjugation of the site-specific antibodies may be effected using various reactions, conditions and reagents known to those skilled in the art.

Conversely, the present inventors have discovered that the free cysteines of the engineered antibodies may be selectively reduced to provide enhanced site-directed conjugation and a reduction in unwanted, potentially toxic contaminants. More specifically "stabilizing agents" such as arginine have been found to modulate intra- and inter-molecular interactions in proteins and may be used, in conjunction with selected reducing agents (preferably relatively mild), to selectively reduce the free cysteines and to facilitate site-specific conjugation as set forth herein. As used herein the terms "selective reduction" or "selectively reducing" may be used interchangeably and shall mean the reduction of free cysteine(s) without substantially disrupting native disulfide bonds present in the engineered antibody. In selected embodiments this may be effected by certain reducing agents. In other preferred embodiments selective reduction of an engineered construct will comprise the use of stabilization agents in combination with reducing agents (including mild reducing agents). It will be appreciated that the term "selective conjugation" shall mean the conjugation of an engineered antibody that has been selectively reduced with a cytotoxin as described herein. In this respect, and as demonstrated in Examples 12-13, the use of such stabilizing agents in combination with reducing agents can markedly improve the efficiency of site-specific conjugation as determined by extent of conjugation on the heavy and light antibody chains and DAR distribution of the preparation.

While not wishing to be bound by any particular theory, such stabilizing agents may act to modulate the electrostatic microenvironment and/or modulate conformational changes at the desired conjugation site, thereby allowing relatively mild reducing agents (which do not materially reduce intact native disulfide bonds) to facilitate conjugation at the desired free cysteine site. Such agents (e.g., certain amino acids) are known to form salt bridges (via hydrogen bonding and electrostatic interactions) and may modulate protein-protein interactions in such a way as to impart a stabilizing effect which may cause favorable conformation changes and/or may reduce unfavorable protein-protein interactions. Moreover, such agents may act to inhibit the formation of undesired intramolecular (and intermolecular) cysteine-cysteine bonds after reduction thus facilitating the desired conjugation reaction wherein the engineered site-specific cysteine is bound to the drug (preferably via a linker). Since the reaction conditions do not provide for the significant reduction of intact native disulfide bonds the conjugation reaction is naturally driven to the relatively few reactive thiols on the free cysteines (e.g., preferably 2 free thiols). As alluded to this considerably reduces the levels of non-specific conjugation and corresponding impurities in conjugate preparations fabricated as set forth herein.

In selected embodiments stabilizing agents compatible with the present invention will generally comprise compounds with at least one amine moiety having a basic pKa. In certain embodiments the amine moiety will comprise a primary amine while in other preferred embodiments the amine moiety will comprise a secondary amine. In still other preferred embodiments the amine moiety will comprise a tertiary amine. In other selected embodiments the amine moiety will comprise an amino acid while in other compatible embodiments the amine moiety will comprise an amino acid side chain. In yet other embodiments the amine moiety will comprise a proteinogenic amino acid. In still other embodiments the amine moiety comprises a non-proteinogenic amino acid. In particularly preferred embodiments, compatible stabilizing agents may comprise arginine, lysine, proline and cysteine. In addition compatible stabilizing agents may include guanidine and nitrogen containing heterocycles with basic pKa.

In certain embodiments compatible stabilizing agents comprise compounds with at least one amine moiety having a pKa of greater than about 7.5, in other embodiments the subject amine moiety will have a pKa of greater than about 8.0, in yet other embodiments the amine moiety will have a pKa greater than about 8.5 and in still other embodiments the stabilizing agent will comprise an amine moiety having a pKa of greater than about 9.0. Other preferred embodiments will comprise stabilizing agents where the amine moiety will have a pKa of greater than about 9.5 while certain other embodiments will comprise stabilizing agents exhibiting at least one amine moiety having a pKa of greater than about 10.0. In still other preferred embodiments the stabilizing agent will comprise a compound having the amine moiety with a pKa of greater than about 10.5, in other embodiments the stabilizing agent will comprise a compound having a amine moiety with a pKa greater than about 11.0, while in still other embodiments the stabilizing agent will comprise a amine moiety with a pKa greater than about 11.5. In yet other embodiments the stabilizing agent will comprise a compound having an amine moiety with a pKa greater than about 12.0, while in still other embodiments the stabilizing agent will comprise an amine moiety with a pKa greater than about 12.5. Those of skill in the art will understand that relevant pKa's may readily be calculated or determined using standard techniques and used to determine the applicability of using a selected compound as a stabilizing agent.

The disclosed stabilizing agents are shown to be particularly effective at targeting conjugation to free site-specific cysteines when combined with certain reducing agents. For the purposes of the instant invention, compatible reducing agents may include any compound that produces a reduced free site-specific cysteine for conjugation without significantly disrupting the engineered antibody native disulfide bonds. Under such conditions, provided by the combination of selected stabilizing and reducing agents, the activated drug linker is largely limited to binding to the desired free site-specific cysteine site. Relatively mild reducing agents or reducing agents used at relatively low concentrations to provide mild conditions are particularly preferred. As used herein the terms "mild reducing agent" or "mild reducing conditions" shall be held to mean any agent or state brought about by a reducing agent (optionally in the presence of stabilizing agents) that provides thiols at the free cysteine site(s) without substantially disrupting native disulfide bonds present in the engineered antibody. That is, mild reducing agents or conditions are able to effectively reduce free cysteine(s) (provide a thiol) without significantly disrupting the protein's native disulfide bonds. The desired reducing conditions may be provided by a number of sulfhydryl-based compounds that establish the appropriate environment for selective conjugation. In preferred embodiments mild reducing agents may comprise compounds having one or more free thiols while in particularly preferred embodiments mild reducing agents will comprise compounds having a single free thiol. Non-limiting examples of reducing agents compatible with the instant invention comprise glutathione, n-acetyl cysteine, cysteine, 2-aminoethane-1-thiol and 2-hydroxyethane-1-thiol.

It will be appreciated that selective reduction process set forth above is particularly effective at targeted conjugation to the free cysteine. In this respect the extent of conjugation to the desired target site (defined here as "conjugation efficiency") in site-specific antibodies may be determined by various art-accepted techniques. The efficiency of the site-specific conjugation of a drug to an antibody may be determined by assessing the percentage of conjugation on the target conjugation site (in this invention the free cysteine on the c-terminus of the light chain) relative to all other conjugated sites. In certain embodiments, the method herein provides for efficiently conjugating a drug to an antibody comprising free cysteines. In some embodiments, the conjugation efficiency is at least 5%, at least 10%, at least 15%, at least 20%, at least 25%, at least 30%, at least 35%, at least 40%, at least 45%, at least 50%, at least 55%, at least 60%, at least 70%, at least 75%, at least 80%, at least 85%, at least 90%, at least 95%, at least 98% or more as measured by the percentage of target conjugation relative to all other conjugation sites.

It will further be appreciated that the engineered antibodies capable of conjugation may contain free cysteine residues that comprise sulfhydryl groups that are blocked or capped as the antibody is produced or stored. Such caps include proteins, peptides, ions and other materials that interact with the sulfhydryl group and prevent or inhibit conjugate formation. In some cases the unconjugated engineered antibody may comprise free cysteines that bind other free cysteines on the same or different antibodies. As discussed in the Examples such cross-reactivity may lead to various contaminants during the fabrication procedure. In some embodiments, the engineered antibodies may require uncapping prior to a conjugation reaction. In specific embodiments, antibodies herein are uncapped and display a free sulfhydryl group capable of conjugation. In specific embodiments, antibodies herein are subjected to an uncapping reaction that does not disturb or rearrange the naturally occurring disulfide bonds. It will be appreciated that in most cases the uncapping reactions will occur during the normal reduction reactions (reduction or selective reduction).

6. DAR Distribution and Purification

One of the advantages of the present invention is the ability to generate relatively homogeneous conjugate preparations comprising a narrowly tailored DAR distribution. In this regard the disclosed constructs and/or selective conjugation provides for homogeneity of the ADC species within a sample in terms of the stoichiometric ratio between the drug and the engineered antibody. As briefly discussed above the term "drug to antibody ratio" or "DAR" refers to the molar ratio of drug to site-specific antibody. In some embodiments a conjugate preparation may be substantially homogeneous with respect to its DAR distribution, meaning that within the preparation is a predominant species of site-specific ADC with a particular DAR (e.g., a DAR of 2 or 4) that is also uniform with respect to the site of loading (i.e., on the free cysteines). In certain embodiments of the invention it is possible to achieve the desired homogeneity through the use of site-specific antibodies or selective combination. In other preferred embodiments the desired homogeneity may be achieved through the use of site-specific constructs in combination with selective reduction. In yet other particularly preferred embodiments the preparations may be further purified using analytical or preparative chromatography techniques. In each of these embodiments the homogeneity of the ADC sample can be analyzed using various techniques known in the art including but not limited to SDS-PAGE, HPLC (e.g. size exclusion HPLC, RP-HPLC, HIC-HPLC etc.) or capillary electrophoresis.

With regard to the purification of ADC preparations it will be appreciated that standard pharmaceutical preparative methods may be employed to obtain the desired purity. As demonstrated in the Examples below liquid chromatography methods such as reverse phase (RP) and hydrophobic interaction chromatography (HIC) may separate compounds in the mixture by drug loading value. In some cases, mixed-mode chromatography (MMC) may also be used to isolate species with a specific drug load. More generally, once insoluble contaminants are removed the modulator preparation may be further purified using standard techniques such as, for example, hydroxylapatite chromatography, gel electrophoresis, dialysis, and affinity chromatography, with affinity chromatography of particular interest. In this regard protein A can be used to purify antibodies that are based on human IgG1, IgG2 or IgG4 heavy chains while protein G is recommended for all mouse isotypes and for human IgG3. Other techniques for protein purification such as fractionation on an ion-exchange column, ethanol precipitation, chromatography on silica, chromatography on heparin, sepharose chromatography on an anion or cation exchange resin (such as a polyaspartic acid column), chromatofocusing, SDS-PAGE and ammonium sulfate precipitation are also available depending on the antibody or conjugate to be recovered.

In this regard the disclosed site-specific conjugates and preparations thereof may comprise drug and antibody moieties in various stoichiometric molar ratios depending on the configuration of the engineered construct and, at least in part, on the method used to effect conjugation. Depending on how many and which interchain and intrachain disulfide bonds are disrupted theoretical drug loading may be relatively high though practical limitations such as free cysteine cross reactivity would limit the generation of homogeneous preparations comprising such DAR due to aggregates and other contaminants. That is, higher drug loading, e.g. >6, may cause aggregation, insolubility, toxicity, or loss of cellular permeability of certain antibody-drug conjugates. In view of such concerns practical drug loading provided by the instant invention may range from 1 to 8 drugs per engineered conjugate, i.e. where 1, 2, 3, 4, 5, 6, 7, or 8 drugs are covalently attached to each site specific antibody (e.g., for IgG1, other antibodies may have different loading capacity depending the number of disulfide bonds). Preferably the DAR of compositions of the instant invention will be approximately 2, 4 or 6 and in particularly preferred embodiments the DAR will comprise approximately 2.

Despite the relatively high level of homogeneity provided by the instant invention the disclosed compositions actually comprise a mixture engineered conjugates with a range of drugs compounds, from 1 to 8 (in the case of a IgG1). As such, the disclosed ADC compositions include mixtures of conjugates where most of the constituent antibodies are covalently linked to one or more drug moieties and (despite the conjugate specificity of selective reduction) where the drug moieties may be attached to the antibody by various thiol groups. That is, following conjugation ADC compositions of the invention will comprise a mixture of conjugates with different drug loads (e.g., from 1 to 8 drugs per IgG1 antibody) at various concentrations (along with certain reaction contaminants primarily caused by free cysteine cross reactivity). Using selective reduction and post-fabrication purification the conjugate compositions may be driven to the point where they largely contain a single predominant desired ADC species (e.g., with a drug loading of 2) with relatively low levels of other ADC species (e.g., with a drug loading of 1, 4, 6, etc.). The average DAR value represents the weighted average of drug loading for the composition as a whole (i.e., all the ADC species taken together). Due to inherent uncertainty in the quantification methodology employed and the difficulty in completely removing the non-predominant ADC species in a commercial setting, acceptable DAR values or specifications are often presented as an average, a range or distribution (i.e., an average DAR of 2+/−0.5). Preferably compositions comprising a measured average DAR within the range (i.e., 1.5 to 2.5) would be used in a pharmaceutical setting.

Thus, in certain preferred embodiments the present invention will comprise compositions having an average DAR of 1, 2, 3, 4, 5, 6, 7 or 8 each +/−0.5. In other preferred embodiments the present invention will comprise an average DAR of 2, 4, 6 or 8+/−0.5. Finally, in selected preferred embodiments the present invention will comprise an average DAR of 2+/−0.5. It will be appreciated that the range or deviation may be less than 0.4 in certain preferred embodiments. Thus, in other embodiments the compositions will comprise an average DAR of 1, 2, 3, 4, 5, 6, 7 or 8 each +/−0.3, an average DAR of 2, 4, 6 or 8+/−0.3, even more preferably an average DAR of 2 or 4+/−0.3 or even an average DAR of 2+/−0.3. In other embodiments IgG1 conjugate compositions will preferably comprise a composition with an average DAR of 1, 2, 3, 4, 5, 6, 7 or 8 each +/−0.4 and relatively low levels (i.e., less than 30%) of non-predominant ADC species. In other preferred embodiments the ADC composition will comprise an average DAR of 2, 4, 6 or 8 each +/−0.4 with relatively low levels (<30%) of non-predominant ADC species. In particularly preferred embodiments the ADC composition will comprise an average DAR of 2+/−0.4 with relatively low levels (<30%) of non-predominant ADC species. In yet other embodiments the predominant ADC species (e.g., DAR of 2) will be present at a concentration of greater than 70%, a concentration of greater than 75%, a concentration of greater that 80%, a concentration of greater than 85%, a concentration of greater than 90%, a concentration of greater than 93%, a concentration of greater than 95% or even a concentration of greater than 97% when measured against other DAR species.

As detailed in the Examples below the distribution of drugs per antibody in preparations of ADC from conjugation reactions may be characterized by conventional means such as UV-Vis spectrophotometry, reverse phase HPLC, HIC, mass spectroscopy, ELISA, and electrophoresis. The quantitative distribution of ADC in terms of drugs per antibody may also be determined. By ELISA, the averaged value of the drugs per antibody in a particular preparation of ADC may be determined. However, the distribution of drug per antibody values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. residues.

V. Pharmaceutical Preparations and Therapeutic Uses

1. Formulations and Routes of Administration

Depending on the form of the selected site-specific conjugate, the mode of intended delivery, the disease being treated or monitored and numerous other variables, compositions of the invention may be formulated as desired using art-recognized techniques. In some embodiments, the therapeutic compositions of the invention may be administered neat or with a minimum of additional components while others may optionally be formulated to contain suitable pharmaceutically acceptable carriers comprising excipients and auxiliaries that are well known in the art (see, e.g., Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, $7^{th}$ ed., Lippencott Williams and Wilkins (2004); Kibbe et al., *Handbook of Pharmaceutical Excipients*, $3^{rd}$ ed., Pharmaceutical Press (2000)). Various pharmaceutically acceptable carriers, which include vehicles, adjuvants, and diluents, are readily available from numerous commercial sources. Moreover, an assortment of pharmaceutically acceptable auxiliary substances, such as pH adjusting and buffering agents, tonicity adjusting agents, stabilizers, wetting agents and the like, are also available. Certain non-limiting exemplary carriers include saline, buffered saline, dextrose, water, glycerol, ethanol, and combinations thereof.

More particularly it will be appreciated that, in some embodiments, the therapeutic compositions of the invention may be administered neat or with a minimum of additional components. Conversely the site-specific ADCs of the present invention may optionally be formulated to contain suitable pharmaceutically acceptable carriers comprising excipients and auxiliaries that are well known in the art and are relatively inert substances that facilitate administration of the conjugate or which aid processing of the active compounds into preparations that are pharmaceutically optimized for delivery to the site of action. For example, an excipient can give form or consistency or act as a diluent to improve the pharmacokinetics or stability of the ADC. Suitable excipients or additives include, but are not limited to, stabilizing agents, wetting and emulsifying agents, salts for varying osmolarity, encapsulating agents, buffers, and skin penetration enhancers. In certain preferred embodiments the pharmaceutical compositions may be provided in a lyophilized form and reconstituted in, for example, buffered saline prior to administration. Such reconstituted compositions are preferably administered intravenously.

Disclosed ADCs for systemic administration may be formulated for enteral, parenteral or topical administration. Indeed, all three types of formulation may be used simultaneously to achieve systemic administration of the active ingredient. Excipients as well as formulations for parenteral and nonparenteral drug delivery are set forth in Remington, *The Science and Practice of Pharmacy 20th Ed.* Mack Publishing (2000). Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, hexylsubstituted poly(lactide), sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

Suitable formulations for enteral administration include hard or soft gelatin capsules, pills, tablets, including coated tablets, elixirs, suspensions, syrups or inhalations and controlled release forms thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection.

Compatible formulations for parenteral administration (e.g., intravenous injection) will comprise ADC concentrations of from about 10 µg/ml to about 100 mg/ml. In certain selected embodiments ADC concentrations will comprise 20 µg/ml, 40 µg/ml, 60 µg/ml, 80 µg/ml, 100 µg/ml, 200 µg/ml, 300, µg/ml, 400 µg/ml, 500 µg/ml, 600 µg/ml, 700 µg/ml, 800 µg/ml, 900 µg/ml or 1 mg/ml. In other preferred embodiments ADC concentrations will comprise 2 mg/ml, 3 mg/ml, 4 mg/ml, 5 mg/ml, 6 mg/ml, 8 mg/ml, 10 mg/ml, 12 mg/ml, 14 mg/ml, 16 mg/ml, 18 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml or 100 mg/ml.

In general the compounds and compositions of the invention, comprising site-specific ADCs may be administered in vivo, to a subject in need thereof, by various routes, including, but not limited to, oral, intravenous, intra-arterial, subcutaneous, parenteral, intranasal, intramuscular, intracranial, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen. In particularly preferred embodiments the compounds of the instant invention will be delivered intravenously.

2. Dosages

Similarly, the particular dosage regimen, i.e., dose, timing and repetition, will depend on the particular individual and that individual's medical history, as well as empirical considerations such as pharmacokinetics (e.g., half-life, clearance rate, etc.). Frequency of administration may be determined and adjusted over the course of therapy, and is based on reducing the number of proliferative or tumorigenic cells, maintaining the reduction of such neoplastic cells, reducing the proliferation of neoplastic cells, or delaying the development of metastasis. In other embodiments the dosage administered may be adjusted or attenuated to manage potential side effects and/or toxicity. Alternatively, sustained continuous release formulations of a subject therapeutic composition may be appropriate.

It will be appreciated by one of skill in the art that appropriate dosages of the conjugate compound, and compositions comprising the conjugate compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action that achieve the desired effect without causing substantial harmful or deleterious side-effects.

In general, the site-specific ADCs of the invention may be administered in various ranges. These include about 5 µg/kg body weight to about 100 mg/kg body weight per dose; about 50 µg/kg body weight to about 5 mg/kg body weight per dose; about 100 µg/kg body weight to about 10 mg/kg body weight per dose. Other ranges include about 100 µg/kg body weight to about 20 mg/kg body weight per dose and about 0.5 mg/kg body weight to about 20 mg/kg body weight per dose. In certain embodiments, the dosage is at least about 100 µg/kg body weight, at least about 250 µg/kg body weight, at least about 750 µg/kg body weight, at least about 3 mg/kg body weight, at least about 5 mg/kg body weight, at least about 10 mg/kg body weight.

In selected embodiments the site-specific ADCs will be administered (preferably intravenously) at approximately 10, 20, 30, 40, 50, 60, 70, 80, 90 or 100 µg/kg body weight per dose. Other embodiments will comprise the administration of ADCs at about 200, 300, 400, 500, 600, 700, 800, 900, 1000, 1100, 1200, 1300, 1400, 1500, 1600, 1700, 1800, 1900 or 2000 µg/kg body weight per dose. In other preferred embodiments the disclosed conjugates will be administered at 2.5, 3, 3.5, 4, 4.5, 5, 5.5, 6, 6.5, 7, 7.58, 9 or 10 mg/kg. In still other embodiments the conjugates may be administered at 12, 14, 16, 18 or 20 mg/kg body weight per dose. In yet other embodiments the conjugates may be administered at 25, 30, 35, 40, 45, 50, 55, 60, 65, 70, 75, 80, 90 or 100 mg/kg body weight per dose. With the teachings herein one of skill in the art could readily determine appropriate dosages for various site-specific ADCs based on preclinical animal studies, clinical observations and standard medical and biochemical techniques and measurements. In particularly preferred embodiments such conjugate dosages will be administered intravenously over a period of time. Moreover, such dosages may be administered multiple times over a defined course of treatment.

Other dosing regimens may be predicated on Body Surface Area (BSA) calculations as disclosed in U.S. Pat. No. 7,744,877. As is well known, the BSA is calculated using the patient's height and weight and provides a measure of a subject's size as represented by the surface area of his or her body. In certain embodiments, the conjugates may be administered in dosages from 1 mg/m$^2$ to 800 mg/m$^2$, from 50 mg/m$^2$ to 500 mg/m$^2$ and at dosages of 100 mg/m$^2$, 150 mg/m$^2$, 200 mg/m$^2$, 250 mg/m$^2$, 300 mg/m$^2$, 350 mg/m$^2$, 400 mg/m$^2$ or 450 mg/m$^2$. It will also be appreciated that art recognized and empirical techniques may be used to determine appropriate dosage.

In any event, DLL3 ADCs are preferably administered as needed to subjects in need thereof. Determination of the frequency of administration may be made by persons skilled in the art, such as an attending physician based on considerations of the condition being treated, age of the subject being treated, severity of the condition being treated, general state of health of the subject being treated and the like. Generally, an effective dose of the DLL3 conjugate is administered to a subject one or more times. More particularly, an effective dose of the ADC is administered to the subject once a month, more than once a month, or less than once a month. In certain embodiments, the effective dose of the DLL3 ADC may be administered multiple times, including for periods of at least a month, at least six months, at least a year, at least two years or a period of several years. In yet other embodiments, several days (2, 3, 4, 5, 6 or 7), several weeks (1, 2, 3, 4, 5, 6, 7 or 8) or several months (1, 2, 3, 4, 5, 6, 7 or 8) or even a year or several years may lapse between administration of the disclosed modulators.

In certain preferred embodiments the course of treatment involving conjugated modulators will comprise multiple doses of the selected drug product over a period of weeks or months. More specifically, conjugated modulators of the instant invention may administered once every day, every two days, every four days, every week, every ten days, every two weeks, every three weeks, every month, every six weeks, every two months, every ten weeks or every three months. In this regard it will be appreciated that the dosages may be altered or the interval may be adjusted based on patient response and clinical practices.

Dosages and regimens may also be determined empirically for the disclosed therapeutic compositions in individuals who have been given one or more administration(s). For example, individuals may be given incremental dosages of a therapeutic composition produced as described herein. In selected embodiments the dosage may be gradually increased or reduced or attenuated based respectively on empirically determined or observed side effects or toxicity. To assess efficacy of the selected composition, a marker of the specific disease, disorder or condition can be followed as described previously. For cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

3. Combination Therapies

In accordance with the instant invention combination therapies may be particularly useful in decreasing or inhibiting unwanted neoplastic cell proliferation, decreasing the occurrence of cancer, decreasing or preventing the recurrence of cancer, or decreasing or preventing the spread or metastasis of cancer. In such cases the ADCs of the instant invention may function as sensitizing or chemosensitizing agents by removing the CSCs that would otherwise prop up and perpetuate the tumor mass and thereby allow for more effective use of current standard of care debulking or anti-cancer agents. That is, the disclosed ADCs may, in certain embodiments provide an enhanced effect (e.g., additive or synergistic in nature) that potentiates the mode of action of another administered therapeutic agent. In the context of the instant invention "combination therapy" shall be interpreted broadly and merely refers to the administration of a site-specific ADC and one or more anti-cancer agents that include, but are not limited to, cytotoxic agents, cytostatic agents, anti-angiogenic agents, debulking agents, chemotherapeutic agents, radiotherapy and radiotherapeutic agents, targeted anti-cancer agents (including both monoclonal antibodies and small molecule entities), BRMs, therapeutic antibodies, cancer vaccines, cytokines, hormone therapies, radiation therapy and anti-metastatic agents and immunotherapeutic agents, including both specific and non-specific approaches.

There is no requirement for the combined results to be additive of the effects observed when each treatment (e.g., ADC and anti-cancer agent) is conducted separately. Although at least additive effects are generally desirable, any increased anti-tumor effect above one of the single therapies is beneficial. Furthermore, the invention does not require the combined treatment to exhibit synergistic effects. However, those skilled in the art will appreciate that with certain selected combinations that comprise preferred embodiments, synergism may be observed.

In practicing combination therapy, the conjugate and anti-cancer agent may be administered to the subject simultaneously, either in a single composition, or as two or more distinct compositions using the same or different administration routes. Alternatively, the ADC may precede, or follow, the anti-cancer agent treatment by, e.g., intervals ranging from minutes to weeks. The time period between each delivery is such that the anti-cancer agent and conjugate are able to exert a combined effect on the tumor. In at least one embodiment, both the anti-cancer agent and the ADC are administered within about 5 minutes to about two weeks of each other. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the ADC and the anti-cancer agent.

The combination therapy may be administered once, twice or at least for a period of time until the condition is treated, palliated or cured. In some embodiments, the combination therapy is administered multiple times, for example, from three times daily to once every six months. The administering may be on a schedule such as three times daily, twice daily, once daily, once every two days, once every three days, once weekly, once every two weeks, once every month, once every two months, once every three months, once every six months or may be administered continuously via a minipump. The combination therapy may be administered via any route, as noted previously. The combination therapy may be administered at a site distant from the site of the tumor.

In one embodiment a site-specific ADC is administered in combination with one or more anti-cancer agents for a short treatment cycle to a subject in need thereof. The invention also contemplates discontinuous administration or daily doses divided into several partial administrations. The conjugate and anti-cancer agent may be administered interchangeably, on alternate days or weeks; or a sequence of antibody treatments may be given, followed by one or more treatments of anti-cancer agent therapy. In any event, as will be understood by those of ordinary skill in the art, the appropriate doses of chemotherapeutic agents and the disclosed conjugates will be generally around those already employed in clinical therapies wherein the chemotherapeutics are administered alone or in combination with other chemotherapeutics.

In another preferred embodiment the site-specific conjugates of the instant invention may be used in maintenance therapy to reduce or eliminate the chance of tumor recurrence following the initial presentation of the disease. Preferably the disorder will have been treated and the initial tumor mass eliminated, reduced or otherwise ameliorated so the patient is asymptomatic or in remission. At such time the subject may be administered pharmaceutically effective amounts of the disclosed conjugates one or more times even though there is little or no indication of disease using standard diagnostic procedures. In some embodiments, the ADCs will be administered on a regular schedule over a period of time, such as weekly, every two weeks, monthly, every six weeks, every two months, every three months every six months or annually. Given the teachings herein, one skilled in the art could readily determine favorable dosages and dosing regimens to reduce the potential of disease recurrence. Moreover such treatments could be continued for a period of weeks, months, years or even indefinitely depending on the patient response and clinical and diagnostic parameters.

In yet another preferred embodiment the ADCs of the present invention may be used to prophylactically or as an adjuvant therapy to prevent or reduce the possibility of tumor metastasis following a debulking procedure. As used in the instant disclosure a "debulking procedure" is defined broadly and shall mean any procedure, technique or method that eliminates, reduces, treats or ameliorates a tumor or tumor proliferation. Exemplary debulking procedures include, but are not limited to, surgery, radiation treatments (i.e., beam radiation), chemotherapy, immunotherapy or ablation. At appropriate times readily determined by one skilled in the art in view of the instant disclosure the disclosed ADCs may be administered as suggested by clinical, diagnostic or theragnostic procedures to reduce tumor metastasis. The conjugates may be administered one or more times at pharmaceutically effective dosages as determined using standard techniques. Preferably the dosing regimen will be accompanied by appropriate diagnostic or monitoring techniques that allow it to be modified.

Yet other embodiments of the invention comprise administering the disclosed conjugates to subjects that are asymptomatic but at risk of developing a proliferative disorder. That is, the conjugates of the instant invention may be used in a truly preventative sense and given to patients that have been examined or tested and have one or more noted risk factors (e.g., genomic indications, family history, in vivo or in vitro test results, etc.) but have not developed neoplasia. In such cases those skilled in the art would be able to determine an effective dosing regimen through empirical observation or through accepted clinical practices.

4. Anti-Cancer Agents

The term "anti-cancer agent" or "anti-proliferative agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents. It will be appreciated that, in selected embodiments as discussed above, such anti-cancer agents may comprise conjugates and may be associated with the disclosed site-specific antibodies prior to administration. More specifically, in certain embodiments selected anti-cancer agents will be linked to the unpaired cysteines of the engineered antibodies to provide engineered conjugates as set forth herein. Accordingly, such engineered conjugates are expressly contemplated as being within the scope of the instant invention. In other embodiments the disclosed anti-cancer agents will be given in combination with site-specific conjugates comprising a different therapeutic agent as set forth above.

As used herein the term "cytotoxic agent" means a substance that is toxic to the cells and decreases or inhibits the function of cells and/or causes destruction of cells. In certain embodiments the substance is a naturally occurring molecule derived from a living organism. Examples of cytotoxic agents include, but are not limited to, small molecule toxins or enzymatically active toxins of bacteria (e.g., Diptheria toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca mericana* proteins (PAPI, PAPII, and PAP-S), *Momordica charantia* inhibitor, curcin, crotin, *saponaria officinalis* inhibitor, gelonin, mitegellin, restrictocin, phenomycin, neomycin, and the tricothecenes) or animals, (e.g., cytotoxic RNases, such as extracellular pancreatic RNases; DNase I, including fragments and/or variants thereof).

For the purposes of the instant invention a "chemotherapeutic agent" comprises a chemical compound that non-specifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in regimens such as CHOP or FOLFIRI.

Examples of anti-cancer agents that may be used in combination with the site-specific constructs of the present invention (either as a component of a site specific conjugate or in an unconjugated state) include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; antimetabolites, erlotinib, vemurafenib, crizotinib, sorafenib, ibrutinib, enzalutamide, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, Oreg.), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11), topoisomerase inhibitor RFS 2000; difluorometlhylornithine; retinoids; capecitabine; combretastatin; leucovorin; oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts, acids or derivatives of any of the above.

Particularly preferred anti-cancer agents comprise commercially or clinically available compounds such as erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7, 9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®). Additional commercially or clinically available anti-cancer agents comprise oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); vinorelbine (NAVELBINE®); capecitabine (XELODA®, Roche), tamoxifen (including NOLVADEX®; tamoxifen citrate, FARESTON® (toremifine citrate) MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca).

In other embodiments the site-specific conjugates of the instant invention may be used in combination with any one of a number of antibodies (or immunotherapeutic agents) presently in clinical trials or commercially available. To this end the disclosed conjugates may be used in combination with an antibody selected from the group consisting of abagovomab, adecatumumab, afutuzumab, alemtuzumab, altumomab, amatuximab, anatomomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, ramucirumab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49, 3F8 and combinations thereof.

Still other particularly preferred embodiments will comprise the use of antibodies in testing or approved for cancer therapy including, but not limited to, rituximab, trastuzumab, gemtuzumab ozogamcin, alemtuzumab, ibritumomab tiuxetan, tositumomab, bevacizumab, cetuximab, panitumumab, ramucirumab, ofatumumab, ipilimumab and brentuximab vedotin. Those skilled in the art will be able to readily identify additional anti-cancer agents that are compatible with the teachings herein.

5. Radiotherapy

The present invention also provides for the combination of site-specific conjugates with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed conjugates may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

VI. Indications

It will be appreciated that the ADCs of the instant invention may be used to treat, prevent, manage or inhibit the occurrence or recurrence of any proliferative disorder. Accordingly, whether administered alone or in combination with an anti-cancer agent or radiotherapy, the ADCs of the invention are particularly useful for generally treating neoplastic conditions in patients or subjects which may include benign or malignant tumors (e.g., adrenal, liver, kidney, bladder, breast, gastric, ovarian, colorectal, prostate, pancreatic, lung, thyroid, hepatic, cervical, endometrial, esophageal and uterine carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic, immunologic disorders and disorders caused by pathogens. Particularly, key targets for treatment are neoplastic conditions comprising solid tumors, although hematologic malignancies are within the scope of the invention.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

More specifically, neoplastic conditions subject to treatment in accordance with the instant invention may be selected from the group including, but not limited to, adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma).

In certain preferred embodiments the proliferative disorder will comprise a solid tumor including, but not limited to, adrenal, liver, kidney, bladder, breast, gastric, ovarian, cervical, uterine, esophageal, colorectal, prostate, pancreatic, lung (both small cell and non-small cell), thyroid, carcinomas, sarcomas, glioblastomas and various head and neck tumors. In other preferred embodiments, and as shown in the Examples below, the disclosed ADCs are especially effective at treating small cell lung cancer (SCLC) and non-small cell lung cancer (NSCLC) (e.g., squamous cell non-small cell lung cancer or squamous cell small cell lung cancer). In one embodiment, the lung cancer is refractory, relapsed or resistant to a platinum based agent (e.g., carboplatin, cisplatin, oxaliplatin, topotecan) and/or a taxane (e.g., docetaxel, paclitaxel, larotaxel or cabazitaxel).

In particularly preferred embodiments the disclosed ADCs may be used to treat small cell lung cancer. With regard to such embodiments the conjugated modulators may be administered to patients exhibiting limited stage disease. In other embodiments the disclosed ADCs will be administered to patients exhibiting extensive stage disease. In other preferred embodiments the disclosed ADCs will be administered to refractory patients (i.e., those who recur during or shortly after completing a course of initial therapy) or recurrent small cell lung cancer patients. Still other embodiments comprise the administration of the disclosed ADCs to sensitive patients (i.e., those whose relapse is longer than 2-3 months after primary therapy. In each case it will be appreciated that compatible ADCs may be used in combination with other anti-cancer agents depending the selected dosing regimen and the clinical diagnosis.

As discussed above the disclosed ADCs may further be used to prevent, treat or diagnose tumors with neuroendocrine features or phenotypes including neuroendocrine tumors. True or canonical neuroendocrine tumors (NETs) arising from the dispersed endocrine system are relatively rare, with an incidence of 2-5 per 100,000 people, but highly aggressive. Neuroendocrine tumors occur in the kidney, genitourinary tract (bladder, prostate, ovary, cervix, and endometrium), gastrointestinal tract (colon, stomach), thyroid (medullary thyroid cancer), and lung (small cell lung carcinoma and large cell neuroendocrine carcinoma). These tumors may secrete several hormones including serotonin and/or chromogranin A that can cause debilitating symptoms known as carcinoid syndrome. Such tumors can be denoted by positive immunohistochemical markers such as neuron-specific enolase (NSE, also known as gamma enolase, gene symbol=ENO2), CD56 (or NCAM1), chromogranin A (CHGA), and synaptophysin (SYP) or by genes known to exhibit elevated expression such as ASCL1. Unfortunately traditional chemotherapies have not been particularly effective in treating NETs and liver metastasis is a common outcome.

While the disclosed ADCs may be advantageously used to treat neuroendocrine tumors they may also be used to treat, prevent or diagnose pseudo neuroendocrine tumors (pNETs) that genotypically or phenotypically mimic, resemble or exhibit common traits with canonical neuroendocrine tumors. Pseudo neuroendocrine tumors or tumors with neuroendocrine features are tumors that arise from cells of the diffuse neuroendocrine system or from cells in which a neuroendocrine differentiation cascade has been aberrantly reactivated during the oncogenic process. Such pNETs commonly share certain phenotypic or biochemical characteristics with traditionally defined neuroendocrine tumors, including the ability to produce subsets of biologically active amines, neurotransmitters, and peptide hormones. Histologically, such tumors (NETs and pNETs) share a common appearance often showing densely connected small cells with minimal cytoplasm of bland cytopathology and round to oval stippled nuclei. For the purposes of the instant invention commonly expressed histological markers or genetic markers that may be used to define neuroendocrine and pseudo neuroendocrine tumors include, but are not limited to, chromogranin A, CD56, synaptophysin, PGP9.5, ASCL1 and neuron-specific enolase (NSE).

Accordingly the ADCs of the instant invention may beneficially be used to treat both pseudo neuroendocrine tumors and canonical neuroendocrine tumors. In this regard the ADCs may be used as described herein to treat neuroendocrine tumors (both NET and pNET) arising in the kidney, genitourinary tract (bladder, prostate, ovary, cervix, and endometrium), gastrointestinal tract (colon, stomach), thyroid (medullary thyroid cancer), and lung (small cell lung carcinoma and large cell neuroendocrine carcinoma). Moreover, the ADCs of the instant invention may be used to treat tumors expressing one or more markers selected from the group consisting of NSE, CD56, synaptophysin, chromogranin A, ASCL1 and PGP9.5 (UCHL1). That is, the present invention may be used to treat a subject suffering from a tumor that is $NSE^+$ or $CD56^+$ or $PGP9.5^+$ or $ASCL1^+$ or $SYP^+$ or $CHGA^+$ or some combination thereof.

With regard to hematologic malignancies it will be further be appreciated that the compounds and methods of the present invention may be particularly effective in treating a variety of B-cell lymphomas, including low grade/NHL follicular cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Waldenstrom's Macroglobulinemia, lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas. See, Gaidono et al., "Lymphomas", IN CANCER: PRINCIPLES & PRACTICE OF ONCOLOGY, Vol. 2: 2131-2145 (DeVita et al., eds., 5.sup.th ed. 1997). It should be clear to those of skill in the art that these lymphomas will often have different names due to changing systems of classification, and that patients having lymphomas classified under different names may also benefit from the combined therapeutic regimens of the present invention.

The present invention also provides for a preventative or prophylactic treatment of subjects who present with benign or precancerous tumors. Beyond being a DLL3 associated disorder it is not believed that any particular type of tumor or proliferative disorder should be excluded from treatment using the present invention. However, the type of tumor cells may be relevant to the use of the invention in combination with secondary therapeutic agents, particularly chemotherapeutic agents and targeted anti-cancer agents.

Preferably the "subject" or "patient" to be treated will be human although, as used herein, the terms are expressly held to comprise any species including all mammals. Accordingly the subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

VII. Diagnostics and Screening

1. Diagnostics

The invention provides in vitro and in vivo methods for detecting, diagnosing or monitoring proliferative disorders and methods of screening cells from a patient to identify tumor cells including tumorigenic cells. Such methods include identifying an individual having cancer for treatment or monitoring progression of a cancer, comprising contacting the patient or a sample obtained from a patient (either in vivo or in vitro) with an antibody as described herein and detecting presence or absence, or level of association, of the antibody to bound or free target molecules in the sample. In some embodiments the antibody will comprise a detectable label or reporter molecule as described herein.

In some embodiments, the association of the antibody with particular cells in the sample can denote that the sample may contain tumorigenic cells, thereby indicating that the individual having cancer may be effectively treated with an antibody as described herein.

Samples can be analyzed by numerous assays, for example, radioimmunoassays, enzyme immunoassays (e.g. ELISA), competitive-binding assays, fluorescent immunoassays, immunoblot assays, Western Blot analysis and flow cytometry assays. Compatible in vivo theragnostic or diagnostic assays can comprise art recognized imaging or monitoring techniques, for example, magnetic resonance imaging, computerized tomography (e.g. CAT scan), positron tomography (e.g., PET scan), radiography, ultrasound, etc., as would be known by those skilled in the art.

In a particularly preferred embodiment the antibodies of the instant invention may be used to detect and quantify levels of a particular determinant (e.g., SEZ6, DLL3 or CD324) in a patient sample (e.g., plasma or blood) which may, in turn, be used to detect, diagnose or monitor proliferative disorders that are associated with the relevant determinant. In related embodiments the antibodies of the instant invention may be used to detect, monitor and/or quantify circulating tumor cells either in vivo or in vitro (WO 2012/0128801). In still other embodiments the circulating tumor cells may comprise tumorigenic cells.

In certain embodiments of the invention, the tumorigenic cells in a subject or a sample from a subject may be assessed or characterized using the disclosed antibodies prior to therapy or regimen to establish a baseline. In other examples, the tumorigenic cells can be assessed from a sample that is derived from a subject that was treated.

2. Screening

In certain embodiments, the antibodies can be used to screen samples in order to identify compounds or agents (e.g., drugs for the treatment of proliferative diseases) that alter a function or activity of tumor cells by interacting with a determinant. In one embodiment, a system or method includes tumor cells expressing a certain determinant (e.g. SEZ6, DLL3 or CD324) and a compound or agent (e.g., drug), wherein the cells and compound or agent are in contact with each other. In such embodiments the subject cells may have been identified, monitored and/or enriched using the disclosed antibodies.

In yet another embodiment, a method includes contacting, directly or indirectly, tumor cells with a test agent or compound and determining if the test agent or compound modulates an activity or function of the determinant-associated tumor cells for example, changes in cell morphology or viability, expression of a marker, differentiation or de-differentiation, cell respiration, mitochondrial activity, membrane integrity, maturation, proliferation, viability, apoptosis or cell death. One example of a direct interaction is physical interaction, while an indirect interaction includes, for example, the action of a composition upon an intermediary molecule that, in turn, acts upon the referenced entity (e.g., cell or cell culture).

Screening methods include high throughput screening, which can include arrays of cells (e.g., microarrays) positioned or placed, optionally at pre-determined locations, for example, on a culture dish, tube, flask, roller bottle or plate. High-throughput robotic or manual handling methods can probe chemical interactions and determine levels of expression of many genes in a short period of time. Techniques have been developed that utilize molecular signals, for example via fluorophores or microarrays and automated analyses that process information at a very rapid rate. Libraries that can be screened include, for example, small molecule libraries, phage display libraries, fully human antibody yeast display libraries (Adimab, LLC), siRNA libraries, and adenoviral transfection vectors.

VIII. Articles of Manufacture

Pharmaceutical packs and kits comprising one or more containers, comprising one or more doses of a site-specific ADC are also provided. In certain embodiments, a unit dosage is provided wherein the unit dosage contains a predetermined amount of a composition comprising, for example, an anti-DLL3 conjugate, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in certain embodiments, the conjugate composition may be provided as a lyophilized powder that may be reconstituted upon addition of an appropriate liquid, for example, sterile water or saline solution. In certain preferred embodiments, the composition comprises one or more substances that inhibit protein aggregation, including, but not limited to, sucrose and arginine. Any label on, or associated with, the container(s) indicates that the enclosed conjugate composition is used for treating the neoplastic disease condition of choice.

The present invention also provides kits for producing single-dose or multi-dose administration units of site-specific conjugates and, optionally, one or more anti-cancer agents. The kit comprises a container and a label or package insert on or associated with the container. Suitable containers include, for example, bottles, vials, syringes, etc. The containers may be formed from a variety of materials such as glass or plastic and contain a pharmaceutically effective amount of the disclosed conjugates in a conjugated or unconjugated form. In other preferred embodiments the container(s) comprise a sterile access port (for example the container may be an intravenous solution bag or a vial having a stopper pierceable by a hypodermic injection needle). Such kits will generally contain in a suitable container a pharmaceutically acceptable formulation of the engineered conjugate and, optionally, one or more anti-cancer agents in the same or different containers. The kits may also contain other pharmaceutically acceptable formulations, either for diagnosis or combined therapy. For example, in addition to the DLL3 conjugates of the invention such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents.

More specifically the kits may have a single container that contains the disclosed ADCs, with or without additional components, or they may have distinct containers for each desired agent. Where combined therapeutics are provided for conjugation, a single solution may be pre-mixed, either in a molar equivalent combination, or with one component in excess of the other. Alternatively, the conjugates and any optional anti-cancer agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous or saline solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody conjugate and any optional components to an animal or patient, e.g., one or more needles, I.V. bags or syringes, or even an eye dropper, pipette, or other such like apparatus, from which the formulation may be injected or introduced into the animal or applied to a diseased area of the body. The kits of the present invention will also typically include a means for containing the vials, or such like, and other component in close confinement for commercial sale, such as, e.g., injection or blow-molded plastic containers into which the desired vials and other apparatus are placed and retained. Any label or package insert indicates that the engineered conjugate composition is used for treating cancer, for example small cell lung cancer.

In other preferred embodiments the conjugates of the instant invention may be used in conjunction with, or comprise, diagnostic or therapeutic devices useful in the prevention or treatment of proliferative disorders. For example, in on preferred embodiment the compounds and compositions of the instant invention may be combined with certain diagnostic devices or instruments that may be used to detect, monitor, quantify or profile cells or marker compounds involved in the etiology or manifestation of proliferative disorders. For selected embodiments the marker compounds may comprise NSE, CD56, synaptophysin, chromogranin A, and PGP9.5.

In particularly preferred embodiments the devices may be used to detect, monitor and/or quantify circulating tumor cells either in vivo or in vitro (see, for example, WO 2012/0128801 which is incorporated herein by reference). In still other preferred embodiments, and as discussed above, circulating tumor cells may comprise cancer stem cells.

IX. Miscellaneous

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In addition, ranges provided in the specification and appended claims include both end points and all points between the end points. Therefore, a range of 2.0 to 3.0 includes 2.0, 3.0, and all points between 2.0 and 3.0.

Generally, nomenclature used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Abbas et al., Cellular and Molecular Immunology, 6*th* ed., W.B. Saunders Company (2010); Sambrook J. & Russell D. *Molecular Cloning: A Laboratory Manual,* 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology,* Wiley, John & Sons, Inc. (2002); Harlow and Lane *Using Antibodies: A Laboratory Manual,* Cold Spring Harbor Laboratory Press, Cold Spring Harbor, N.Y. (1998); and Coligan et al., *Short Protocols in Protein Science,* Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art. Moreover, any section headings used herein are for organizational purposes only and are not to be construed as limiting the subject matter described.

As used herein, tumor cell types are abbreviated as follows: adenocarcinoma (Adeno), adrenal (AD), breast (BR), estrogen receptor positive breast (BR-ER+), estrogen receptor negative breast (BR-ER−), progesterone receptor positive breast (BR-PR+), progesterone receptor negative breast (BR-PR−), ERb2/Neu positive breast (BR-ERB2/Neu+), Her2 positive breast (BR-Her2+), claudin-low breast (BR-CLDN-lo), triple-negative breast cancer (BR-TNBC), colorectal (CR), endometrial (EM), gastric (GA), head and neck (FIN), kidney (KDY), large cell neuroendocrine (LC-NEC), liver (LIV), lymph node (LN), lung (LU), lung-carcinoid (LU-CAR), lung-spindle cell (LU-SPC), melanoma (MEL), non-small cell lung (NSCLC), ovarian (OV), ovarian serous (OV-S), ovarian papillary serous (OV-PS), ovarian malignant mixed mesodermal tumor (OV-MMMT), ovarian mucinous (OV-MUC), ovarian clear cell (OV-CC), neuroendocrine tumor (NET), pancreatic (PA), prostate (PR), squamous cell (SCC), small cell lung (SCLC) and tumors derived from skin (SK).

X. References

Unless The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference, regardless of whether the phrase "incorporated by reference" is or is not used in relation to the particular reference. The foregoing detailed description and the examples that follow have been given for clarity of understanding only. No unnecessary limitations are to be understood therefrom. The invention is not limited to the exact details shown and described. Variations obvious to one skilled in the art are included in the invention defined by the claims. Any section headings used herein are for organizational purposes only and are not to be construed as limiting the subject matter described.

XI. Sequence Listing Summary

Appended to the instant application is a sequence listing comprising a number of nucleic acid and amino acid sequences. The following Table 4 provides a summary of the included sequences.

TABLE 4

| SEQ ID NO. | Description |
|---|---|
| 1 | SEZ6 isoform 1 mRNA sequence |
| 2 | SEZ6 isoform 2 mRNA sequence |
| 3 | SEZ6 isoform 1 protein sequence |
| 4 | SEZ6 isoform 2 protein sequence |
| 5 | cDNA sequence of human SEZ6 ORF |
| 6 | Human SEZ6 protein |
| 7 | cDNA sequence of a commercial SEZ6 clone (BC146292) |
| 8 | Human SEZ6-Fc ORF |
| 9 | Human SEZ6-Fc protein |
| 10 | cDNA sequence of mouse SEZ6 ORF |
| 11 | Mouse SEZ6 protein |
| 12 | cDNA sequence of rat SEZ6 ORF |
| 13 | Rat SEZ6 protein |
| 14 | cDNA sequence of cynomolgus SEZ6 ORF |
| 15 | Cynomolgus SEZ6 protein |
| 16 | cDNA sequence of human SEZ6L ECD |
| 17 | Human SEZ6L ECD protein |
| 18 | cDNA sequence of human SEZ6L2 ECD |
| 19 | Human SEZ6L2 ECD protein |
| 20 | SC17.1 VL protein |
| 21 | SC17.1 VH protein |
| 22-169 | Additional murine VL and VH proteins as in SEQ ID NOs 20-21 |
| 170 | hSC17.16 VL protein |
| 171 | hSC17.16 VH protein |
| 172-199 | Additional humanized VL and VH proteins as in SEQ ID NOs 170-171 |
| 200 | Asn-Pro-Thr-Tyr (motif on the SEZ6 C-terminal cytoplasmic domain) |
| 201 | 9-Histidine Tag |
| 202-219 | Reserved |
| 220 | SC17.1 VL nucleic acid |
| 221 | SC17.1 VH nucleic acid |
| 222-369 | Additional murine VL and VH nucleic acids as in SEQ ID NOs 220-221 |
| 370 | hSC17.16 VL nucleic acid |

TABLE 4-continued

| SEQ ID NO. | Description |
|---|---|
| 371 | hSC17.16 VH nucleic acid |
| 372-399 | Additional humanized VL and VH nucleic acids as in SEQ ID NOs 270-271 |
| 400 | hSC17.200 full length light chain amino acid sequence |
| 401 | hSC17.200 full length heavy chain amino acid sequence |
| 402 | hSC17.200vL1 full length light chain amino acid sequence |
| 403 | Kappa constant region protein |
| 404 | IgG1 constant region protein |
| 405 | hSC17.16 CDRL1 |
| 406 | hSC17.16 CDRL2 |
| 407 | hSC17.16 CDRL3 |
| 408 | hSC17.16 CDRH1 |
| 409 | hSC17.16 CDRH2 |
| 410 | hSC17.16 CDRH3 |
| 411 | hSC17.17 CDRL1 |
| 412 | hSC17.17 CDRL2 |
| 413 | hSC17.17 CDRL3 |
| 414 | hSC17.17 CDRH1 |
| 415 | hSC17.17 CDRH2 |
| 416 | hSC17.17 CDRH3 |
| 417 | hSC17.24 CDRL1 |
| 418 | hSC17.24 CDRL2 |
| 419 | hSC17.24 CDRL3 |
| 420 | hSC17.24 CDRH1 |
| 421 | hSC17.24 CDRH2 |
| 422 | hSC17.24 CDRH3 |
| 423 | hSC17.28 CDRL1 |
| 424 | hSC17.28 CDRL2 |
| 425 | hSC17.28 CDRL3 |
| 426 | hSC17.28 CDRH1 |
| 427 | hSC17.28 CDRH2 |
| 428 | hSC17.28 CDRH3 |
| 429 | hSC17.34 CDRL1 |
| 430 | hSC17.34 CDRL2 |
| 431 | hSC17.34 CDRL3 |
| 432 | hSC17.34 CDRH1 |
| 433 | hSC17.34 CDRH2 |
| 434 | hSC17.34 CDRH3 |
| 435 | hSC17.46 CDRL1 |
| 436 | hSC17.46 CDRL2 |
| 437 | hSC17.46 CDRL3 |
| 438 | hSC17.46 CDRH1 |
| 439 | hSC17.46 CDRH2 |
| 440 | hSC17.46 CDRH1 |
| 441 | hSC17.151 CDRL1 |
| 442 | hSC17.151 CDRL2 |
| 443 | hSC17.151 CDRL3 |
| 444 | hSC17.151 CDRH1 |
| 445 | hSC17.151 CDRH2 |
| 446 | hSC17.151 CDRH3 |
| 447 | hSC17.155 and hSC17.155vH1-6 CDRL1 |
| 448 | hSC17.155 and hSC17.155vH1-6 CDRL2 |
| 449 | hSC17.155 and hSC17.155vH1-6 CDRL3 |
| 450 | hSC17.155 and hSC17.155vH1, vH2 and vH4-6 CDRH1 |
| 451 | hSC17.155 and hSC17.155vH1-3 CDRH2 |
| 452 | hSC17.155 and hSC17.155vH1-6 CDRH3 |
| 453 | hSC17.156 CDRL1 |
| 454 | hSC17.156 CDRL2 |
| 455 | hSC17.156 CDRL3 |
| 456 | hSC17.156 CDRH1 |
| 457 | hSC17.156 CDRH2 |
| 458 | hSC17.156 CDRH3 |
| 459 | hSC17.161 and hSC17.161vL1 CDRL1 |
| 460 | hSC17.161 and hSC17.161vL1 CDRL2 |
| 461 | hSC17.161 and hSC17.161vL1 CDRL3 |
| 462 | hSC17.161 and hSC17.161vL1 CDRH1 |
| 463 | hSC17.161 and hSC17.161vL1 CDRH2 |
| 464 | hSC17.161 and hSC17.161vL1 CDRH3 |
| 465 | hSC17.200 CDRL1 |
| 466 | hSC17.200 and hSC17.200vL1 CDRL2 |
| 467 | hSC17.200 and hSC17.200vL1 CDRL3 |
| 468 | hSC17.200 and hSC17.200vL1 CDRH1 |
| 469 | hSC17.200 and hSC17.200vL1 CDRH2 |
| 470 | hSC17.200 and hSC17.200vL1 CDRH3 |
| 471 | hSC17.155vH1 FR1 |
| 472 | hSC17.155vH2 FR1 |
| 473 | hSC17.155vH3 CDRH1 |
| 474 | hSC17.155vH4 CDRH2 |
| 475 | hSC17.155vH5 CDRH2 |
| 476 | hSC17.155vH6 CDRH2 |
| 477 | hSC17.161vH1 FR1 |
| 478 | hSC17.161vH1 FR2 |
| 479 | hSC17.161vH1 FR3 |
| 480 | hSC17.200vL1 CDRL1 |
| 481-499 | Reserved |
| 500 | C220S IgG1 heavy constant region protein |
| 501 | C220A IgG1 heavy constant region protein |
| 502 | C214A Kappa light chain constant region protein |
| 503 | C214S Kappa light chain constant region protein |
| 504 | Lambda light chain constant region protein |
| 505 | C214A Lambda light chain constant region protein |
| 506 | C214S Lambda light chain constant region protein |
| 507 | SC16.56 ss1 and ss2 full length light chain protein |
| 508 | SC16.56 ss3 and ss4 full length heavy chain protein |
| 509 | SC16.56 ss1 full length heavy chain protein |
| 510 | SC16.56 ss2 full length heavy chain protein |
| 511 | SC16.56 ss3 full length light chain protein |
| 512 | SC16.56 ss4 full length light chain protein |
| 513 | SC17.200 ss1 and ss2 full length light chain protein |
| 514 | SC17.200 ss3 and ss4 full length heavy chain protein |
| 515 | SC17.200 ss1 full length heavy chain protein |
| 516 | SC17.200 ss2 full length heavy chain protein |
| 517 | SC17.200 ss3 full length light chain protein |
| 518 | SC17.200 ss4 full length light chain protein |
| 519 | hSC16.13 light chain variable region protein |
| 520 | hSC16.15 light chain variable region protein |
| 521 | hSC16.25 light chain variable region protein |
| 522 | hSC16.34 light chain variable region protein |
| 523 | hSC16.56 light chain variable region protein |
| 524 | hSC16.13 heavy chain variable region protein |
| 525 | hSC16.15 heavy chain variable region protein |
| 526 | hSC16.25 heavy chain variable region protein |
| 527 | hSC16.34 heavy chain variable region protein |
| 528 | hSC16.56 heavy chain variable region protein |
| 529 | SC10.17 light chain variable region protein |
| 530 | SC10.17 heavy chain variable region protein |
| 531 | hSC10.17 light chain variable region protein |
| 532 | hSC10.17 heavy chain variable region protein |
| 533 | SC10.17 light chain variable region nucleic acid |
| 534 | SC10.17 heavy chain variable region nucleic acid |
| 535 | hSC10.17 light chain variable region nucleic acid |
| 536 | hSC10.17 heavy chain variable region nucleic acid |
| 537 | SC17.17 ss1 and ss2 full length light chain protein |
| 538 | SC17.17 ss3 and ss4 full length heavy chain protein |
| 539 | SC17.17 ss1 full length heavy chain protein |
| 540 | SC17.17 ss2 full length heavy chain protein |
| 541 | SC17.17 ss3 full length light chain protein |
| 542 | SC17.17 ss4 full length light chain protein |
| 543 | SC10.17 ss3 full length heavy chain protein |
| 544 | SC10.17 ss3 full length light chain protein |

EXAMPLES

The present invention, thus generally described, will be understood more readily by reference to the following Examples, which are provided by way of illustration and are not intended to be limiting of the instant invention. The Examples are not intended to represent that the experiments below are all or the only experiments performed.

Example 1

Generation of Anti-DLL3 Antibodies

Anti-DLL3 murine antibodies were produced as follows. In a first immunization campaign, three mice (one from each of the following strains: Balb/c, CD-1, FVB) were inoculated with human DLL3-fc protein (hDLL3-Fc) emulsified with an equal volume of TiterMax® or alum adjuvant. The hDLL3-Fc fusion construct was purchased from Adipogen International (Catalog No. AG-40A-0113). An initial immunization was performed with an emulsion of 10 µg hDLL3-Fc per mouse in TiterMax. Mice were then boosted biweekly with 5 µg hDLL3-Fc per mouse in alum adjuvant. The final injection prior to fusion was with 5 µg hDLL3-Fc per mouse in PBS.

In a second immunization campaign six mice (two each of the following strains: Balb/c, CD-1, FVB), were inoculated with human DLL3-His protein (hDLL3-His), emulsified with an equal volume of TiterMax® or alum adjuvant. Recombinant hDLL3-His protein was purified from the supernatants of CHO-S cells engineered to overexpress hDLL3-His. The initial immunization was with an emulsion of 10 µg hDLL3-His per mouse in TiterMax. Mice were then boosted biweekly with 5 µg hDLL3-His per mouse in alum adjuvant. The final injection was with $2 \times 10^5$ HEK-293T cells engineered to overexpress hDLL3.

Solid-phase ELISA assays were used to screen mouse sera for mouse IgG antibodies specific for human DLL3. A positive signal above background was indicative of antibodies specific for DLL3. Briefly, 96 well plates (VWR International, Cat. #610744) were coated with recombinant DLL3-His at 0.5 µg/ml in ELISA coating buffer overnight. After washing with PBS containing 0.02% (v/v) Tween 20, the wells were blocked with 3% (w/v) BSA in PBS, 200 µL/well for 1 hour at room temperature (RT). Mouse serum was titrated (1:100, 1:200, 1:400, and 1:800) and added to the DLL3 coated plates at 50 µL/well and incubated at RT for 1 hour. The plates are washed and then incubated with 50 µL/well HRP-labeled goat anti-mouse IgG diluted 1:10,000 in 3% BSA-PBS or 2% FCS in PBS for 1 hour at RT. Again the plates were washed and 40 µL/well of a TMB substrate solution (Thermo Scientific 34028) was added for 15 minutes at RT. After developing, an equal volume of 2N $H_2SO_4$ was added to stop substrate development and the plates were analyzed by spectrophotometer at OD 450.

Sera-positive immunized mice were sacrificed and draining lymph nodes (popliteal, inguinal, and medial iliac) were dissected and used as a source for antibody producing cells. Cell suspensions of B cells (approximately $229 \times 10^6$ cells from the hDLL3-Fc immunized mice, and $510 \times 10^6$ cells from the hDLL3-His immunized mice) were fused with non-secreting P3x63Ag8.653 myeloma cells at a ratio of 1:1 by electro cell fusion using a model BTX Hybrimmune System (BTX Harvard Apparatus). Cells were re-suspended in hybridoma selection medium consisting of DMEM medium supplemented with azaserine, 15% fetal clone I serum, 10% BM Condimed (Roche Applied Sciences), 1 mM nonessential amino acids, 1 mM HEPES, 100 IU penicillin-streptomycin, and 50 µM 2-mercaptoethanol, and were cultured in four T225 flasks in 100 mL selection medium per flask. The flasks were placed in a humidified 37° C. incubator containing 5% $CO_2$ and 95% air for six to seven days.

On day six or seven after the fusions the hybridoma library cells were collected from the flasks and plated at one cell per well (using the FACSAria I cell sorter) in 200 µL of supplemented hybridoma selection medium (as described above) into 64 Falcon 96-well plates, and 48 96-well plates for the hDLL3-His immunization campaign. The rest of the library was stored in liquid nitrogen.

The hybridomas were cultured for 10 days and the supernatants were screened for antibodies specific to hDLL3 using flow cytometry performed as follows. $1 \times 10^5$ per well of HEK-293T cells engineered to overexpress human DLL3, mouse DLL3 (pre-stained with dye), or cynomolgus DLL3 (pre-stained with Dylight800) were incubated for 30 minutes with 25 µL hybridoma supernatant. Cells were washed with PBS/2% FCS and then incubated with 25 µL per sample DyeLight 649 labeled goat-anti-mouse IgG, Fc fragment specific secondary diluted 1:300 in PBS/2% FCS. After a 15 minute incubation cells were washed twice with PBS/2% FCS and re-suspended in PBS/2% FCS with DAPI and analyzed by flow cytometry for fluorescence exceeding that of cells stained with an isotype control antibody. Remaining unused hybridoma library cells were frozen in liquid nitrogen for future library testing and screening.

The hDLL3-His immunization campaign yielded approximately 50 murine anti-hDLL3 antibodies and the hDLL3-Fc immunization campaign yielded approximately 90 murine anti-hDLL3 antibodies.

Example 2

Sequencing of Anti-DLL3 Antibodies

Based on the foregoing, a number of exemplary distinct monoclonal antibodies that bind immobilized human DLL3 or h293-hDLL3 cells with apparently high affinity were selected for sequencing and further analysis. Sequence analysis of the light chain variable regions and heavy chain variable regions from selected monoclonal antibodies generated in Example 1 confirmed that many had novel complementarity determining regions and often displayed novel VDJ arrangements.

Initially selected hybridoma cells expressing the desired antibodies were lysed in Trizol® reagent (Trizol® Plus RNA Purification System, Life Technologies) to prepare the RNA encoding the antibodies. Between $10^4$ and $10^5$ cells were re-suspended in 1 mL Trizol and shaken vigorously after addition of 200 µL chloroform. Samples were then centrifuged at 4° C. for 10 minutes and the aqueous phase was transferred to a fresh microfuge tube and an equal volume of 70% ethanol was added. The sample was loaded on an RNeasy Mini spin column, placed in a 2 mL collection tube and processed according to the manufacturer's instructions. Total RNA was extracted by elution, directly to the spin column membrane with 100 µL RNase-free water. The quality of the RNA preparations was determined by fractionating 3 µL in a 1% agarose gel before being stored at −80° C. until used.

The variable region of the Ig heavy chain of each hybridoma was amplified using a 5' primer mix comprising 32 mouse specific leader sequence primers designed to target the complete mouse $V_H$ repertoire in combination with a 3' mouse Cγ primer specific for all mouse Ig isotypes. Similarly, a primer mix containing thirty two 5' Vκ leader sequences designed to amplify each of the Vκ mouse families was used in combination with a single reverse primer specific to the mouse kappa constant region in order to amplify and sequence the kappa light chain. For antibodies containing a lambda light chain, amplification was performed using three 5' $V_L$ leader sequences in combination with one reverse primer specific to the mouse lambda constant region. The $V_H$ and $V_L$ transcripts were amplified from 100 ng total RNA using the Qiagen One Step RT-PCR kit as follows. A total of eight RT-PCR reactions were run for each hybridoma, four for the Vκ light chain and four for the Vγ heavy chain. PCR reaction mixtures included 3 µL of RNA, 0.5 µL of 100 µM of either heavy chain or kappa light chain primers (custom synthesized by Integrated Data Technologies), 5 µL of 5×RT-PCR buffer, 1 µL dNTPs, 1 µL of enzyme mix containing reverse transcriptase and DNA polymerase, and 0.4 µL of ribonuclease inhibitor RNasin (1 unit). The thermal cycler program was RT step 50° C. for 30 minutes, 95° C. for 15 minutes followed by 30 cycles of (95° C. for 30 seconds, 48° C. for 30 seconds, 72° C. for 1 minute). There was then a final incubation at 72° C. for 10 minutes.

The extracted PCR products were sequenced using the same specific variable region primers as described above for the amplification of the variable regions. To prepare the PCR products for direct DNA sequencing, they were purified using the QIAquick™ PCR Purification Kit (Qiagen) according to the manufacturer's protocol. The DNA was eluted from the spin column using 50 µL of sterile water and then sequenced directly from both strands (MCLAB).

Selected nucleotide sequences were analyzed using the IMGT sequence analysis tool (http://www.imgt.org/IMGT-medical/sequence_analysis.html) to identify germline V, D and J gene members with the highest sequence homology. These derived sequences were compared to known germline DNA sequences of the Ig V- and J-regions by alignment of $V_H$ and $V_L$ genes to the mouse germline database using a proprietary antibody sequence database.

The derived sequences of the murine heavy and light chain variable regions are provided in the appended sequence listing and, in an annotated form, PCT/US14/17810 which is incorporated herein by reference with respect to such sequences.

Example 3

Generation of Humanized Anti-DLL3 Antibodies

Certain murine antibodies generated as per Example 1 (termed SC16.13, SC16.15, SC16.25, SC16.34 and SC16.56) were used to derive humanized antibodies comprising murine CDRs grafted into a human acceptor antibody. In preferred embodiments the humanized heavy and light chain variable regions described in the instant Example may be incorporated in the disclosed site-specific conjugates as described below.

In this respect the murine antibodies were humanized with the assistance of a proprietary computer-aided CDR-grafting method (Abysis Database, UCL Business) and standard molecular engineering techniques as follows. Total RNA was extracted from the hybridomas and amplified as set forth in Example 2. Data regarding V, D and J gene segments of the $V_H$ and $V_L$ chains of the murine antibodies was obtained from the derived nucleic acid sequences. Human framework regions were selected and/or designed based on the highest homology between the framework sequences and CDR canonical structures of human germline antibody sequences, and the framework sequences and CDRs of the selected murine antibodies. For the purpose of the analysis the assignment of amino acids to each of the CDR domains was done in accordance with Kabat et al. numbering. Once the human receptor variable region frameworks are selected and combined with murine CDRs, the integrated heavy and light chain variable region sequences are generated synthetically (Integrated DNA Technologies) comprising appropriate restriction sites.

The humanized variable regions are then expressed as components of engineered full length heavy and light chains to provide the site-specific antibodies as described herein. More specifically, humanized anti-DLL3 engineered antibodies were generated using art-recognized techniques as follows. Primer sets specific to the leader sequence of the $V_H$ and $V_L$ chain of the antibody were designed using the following restriction sites: AgeI and XhoI for the $V_H$ fragments, and XmaI and DraIII for the $V_L$ fragments. PCR products were purified with a Qiaquick PCR purification kit (Qiagen), followed by digestion with restriction enzymes AgeI and XhoI for the $V_H$ fragments and XmaI and DraIII for the $V_L$ fragments. The $V_H$ and $V_L$ digested PCR products were purified and ligated, respectively, into a human IgG1 heavy chain constant region expression vector or a kappa $C_L$ human light chain constant region expression vector. As discussed in detail below the heavy and/or light chain constant regions may be engineered to present site-specific conjugation sites on the assembled antibody.

The ligation reactions were performed as follows in a total volume of 10 µL with 200 U T4-DNA Ligase (New England Biolabs), 7.5 µL of digested and purified gene-specific PCR product and 25 ng linearized vector DNA. Competent *E. coli* DH10B bacteria (Life Technologies) were transformed via heat shock at 42° C. with 3 µL ligation product and plated onto ampicillin plates at a concentration of 100 µg/mL. Following purification and digestion of the amplified ligation products, the $V_H$ fragment was cloned into the AgeI-XhoI restriction sites of the pEE6.4HuIgG1 expression vector (Lonza) and the $V_L$ fragment was cloned into the XmaI-DraIII restriction sites of the pEE12.4Hu-Kappa expression vector (Lonza) where either the HuIgG1 and/or Hu-Kappa expression vector may comprise either a native or an engineered constant region.

The humanized antibodies were expressed by co-transfection of HEK-293T cells with pEE6.4HuIgG1 and pEE12.4Hu-Kappa expression vectors. Prior to transfection the HEK-293T cells were cultured in 150 mm plates under standard conditions in Dulbecco's Modified Eagle's Medium (DMEM) supplemented with 10% heat inactivated FCS, 100 µg/mL streptomycin and 100 U/mL penicillin G. For transient transfections cells were grown to 80% confluency. 12.5 µg each of pEE6.4HuIgG1 and pEE12.4Hu-Kappa vector DNA were added to 50 µL HEK-293T transfection reagent in 1.5 mL Opti-MEM. The mix was incubated for 30 minutes at room temperature and plated. Supernatants were harvested three to six days after transfection. Culture supernatants containing recombinant humanized antibodies were cleared from cell debris by centrifugation at 800×g for 10 minutes and stored at 4° C. Recombinant humanized antibodies were purified by Mab-Select SuRe Protein A affinity chromatography (GE Life Sciences). For larger scale antibody expression, CHO-S cells were transiently transfected in 1 L volumes, seeded at 2.2e6 cells per mL Polyethylenimine (PEI) was used as a transfection reagent. After 7-10 days of antibody expression, culture supernatants containing recombinant antibodies were cleared from cell debris by centrifugation and purified by MabSelect SuRe Protein A affinity chromatography.

The genetic composition for the selected human acceptor variable regions are shown in Table 5 immediately below for each of the humanized DLL3 antibodies. The sequences depicted in Table 5 correspond to the annotated heavy and light chain sequences set forth in FIGS. 2A and 2B for the subject clones. Note that the complementarity determining regions and framework regions set forth in FIGS. 2A and 2B are defined as per Kabat et al. (supra) using a proprietary version of the Abysis database (Abysis Database, UCL Business).

More specifically, the entries in Table 5 below correspond to the contiguous variable region sequences set forth SEQ ID NOS: 519 and 524 (hSC16.13), SEQ ID NOS: 520 and 525 (hSC16.15), SEQ ID NOS: 521 and 526 (hSC16.25), SEQ ID NOS: 522 and 527 (hSC16.34) and SEQ ID NOS:

523 and 528 (hSC16.56). Besides the genetic composition Table 5 shows that, in these selected embodiments, no framework changes or back mutations were necessary to maintain the favorable binding properties of the selected antibodies. Of course, in other CDR grafted constructs it will be appreciated that such framework changes or back mutations may be desirable and as such, are expressly contemplated as being within the scope of the instant invention.

TABLE 5

| mAb | human VH | human JH | FW changes | human VK | human JK | FW changes |
|---|---|---|---|---|---|---|
| hSC16.13 | IGHV2-5*01 | JH6 | None | IGKV1-39*01 | JK1 | None |
| hSC16.15 | IGHV1-46*01 | JH4 | None | IGKV1-13*02 | JK4 | None |
| hSC16.25 | IGHV2-5*01 | JH6 | None | IGKV6-21*01 | JK2 | None |
| hSC16.34 | IGHV1-3*02 | JH4 | None | IGKV1-27*01 | JK1 | None |
| hSC16.56 | IGHV1-18*01 | JH4 | None | IGKV3-15*01 | JK2 | None |

Though no residues were altered in the framework regions, in one of humanized clones (hSC16.13) mutations were introduced into heavy chain CDR2 to address stability concerns. The binding affinity of the antibody with the modified CDR was evaluated to ensure that it was equivalent to either the corresponding murine antibody.

Following humanization of all selected antibodies by CDR grafting, the resulting light and heavy chain variable region amino acid sequences were analyzed to determine their homology with regard to the murine donor and human acceptor light and heavy chain variable regions. The results, shown in Table 6 immediately below, reveal that the humanized constructs consistently exhibited a higher homology with respect to the human acceptor sequences than with the murine donor sequences. More particularly, the murine heavy and light chain variable regions show a similar overall percentage homology to a closest match of human germline genes (85%-93%) compared with the homology of the humanized antibodies and the donor hybridoma protein sequences (74%-83%).

TABLE 6

| mAb | Homology to Human (CDR acceptor) | Homology to Murine Parent (CDR donor) |
|---|---|---|
| hSC16.13 HC | 93% | 81% |
| hSC16.13 LC | 87% | 77% |
| hSC16.15 HC | 85% | 83% |
| hSC16.15 LC | 85% | 83% |
| hSC16.25 HC | 91% | 83% |
| hSC16.25 LC | 85% | 79% |
| hSC16.34 HC | 87% | 79% |
| hSC16.34 LC | 85% | 81% |
| hSC16.56 HC | 87% | 74% |
| hSC16.56 LC | 87% | 76% |

Upon testing each of the derived humanized constructs exhibited favorable binding characteristics roughly comparable to those shown by the murine parent antibodies.

Example 4

Generation and Humanization of Anti-SEZ6 Antibodies

A SEZ6 antigen was generated by fusing the ECD portion of the human SEZ6 protein to a human IgG2 Fc domain using standard molecular techniques. A more detailed description of the production of the SEZ6 antigen is provided in PCT/US2013/0027391, which is incorporated herein by reference as to the same. Following inoculation of six female mice antibody producing hybridomas were generated substantially as set forth in Example 1. The hybridomas were screened as previously discussed and genetic material obtained from those of interest. Sequences of the heavy and light chain variable regions of the anti-SEZ6 antibodies were determined substantially as set forth in Example 2.

A number of anti-SEZ6 murine antibodies were humanized using similar techniques to those set out in the previous Example. Human frameworks for heavy and light chains were selected based on sequence and structure similarity with respect to functional human germline genes. In this regard structural similarity was evaluated by comparing the mouse canonical CDR structure to human candidates with the same canonical structures as described in Chothia et al. (supra).

More particularly eleven murine antibodies SC17.16, SC17.17, SC17.24, SC17.28, SC17.34, SC17.46, SC17.151, SC17.155, SC17.156, SC17.161 and SC17.200 were humanized with the assistance of a computer-aided CDR-grafting analysis (Abysis Database, UCL Business Plc.) and standard molecular engineering techniques to provide hSC17.16, hSC17.17, hSC17.24, hSC17.28, hSC17.34, hSC17.46, hSC17.151, hSC17.155, hSC17.156, hSC17.161 and hSC17.200 modulators. The human framework regions of the variable regions were selected based on their highest sequence homology to the subject mouse framework sequence and its canonical structure. For the purposes of the humanization analysis, the assignment of amino acids to each of the CDR domains is in accordance with Kabat et al. numbering (supra).

From the nucleotide sequence information, data regarding V, D and J gene segments of the heavy and light chains of subject murine antibodies were obtained. Based on the sequence data new primer sets specific to the leader sequence of the Ig $V_H$ and $V_K$ light chain of the antibodies were designed for cloning of the recombinant monoclonal antibody. Subsequently the V-(D)-J sequences were aligned with mouse Ig germ line sequences. The resulting genetic arrangements for each of the eleven humanized constructs are shown in Table 7 immediately below.

TABLE 7

| mAb | human VH | human DH | human JH | FW changes | human VK | human JK | FW changes |
|---|---|---|---|---|---|---|---|
| hSC17.16 | IGHV1-2 | IGHD3-16 | JH5 | None | IGKV-O2 | JK1 | none |
| hSC17.17 | IGHV1-2 | IGHD4-11 | JH4 | none | IGKV-L6 | JK2 | none |
| hSC17.24 | VH1-f | IGHD5-12 | JH4 | 48I, 73K | VKB3 | JK1 | none |

TABLE 7-continued

| mAb | human VH | human DH | human JH | FW changes | human VK | human JK | FW changes |
|---|---|---|---|---|---|---|---|
| hSC17.28 | IGHV1-2 | IGHD3-16 | JH4 | none | IGKV-A10 | JK4 | none |
| hSC17.34 | IGHV1-3 | IGHD3-10 | JH4 | 71V | IGKV-L1 | JK1 | 71Y |
| hSC17.46 | IGHV1-2 | IGHD4-23 | JH4 | 48I, 69L | IGKV-L11 | JK1 | 87F |
| hSC17.151 | IGHV1-46 | IGHD1-14 | JH4 | none | VKL6 | JK2 | none |
| hSC17.155 | IGHV1-46 | IGHD2-2 | JH4 | none | VKB3 | JK1 | none |
| hSC17.156 | IGHV2-26 | IGHD4-17 | JH4 | none | VKO1 | JK4 | none |
| hSC17.161 | IGHV1-2 | IGHD1-14 | JH4 | none | VKB3 | JK2 | none |
| hSC17.200 | IGHV5-51 | IGHD4-17 | JH4 | none | IGKV-L6 | JK4 | none |

The humanized antibodies listed in Table 7 correspond to the annotated light and heavy chain variable region sequences set forth in FIGS. 3A and 3B (SEQ ID NOS: 170-199). The corresponding nucleic acid sequences of the light and heavy chain variable regions are set forth in the appended sequence listing. Table 7 further demonstrates that very few framework changes were necessary to maintain the favorable properties of the binding modulators. In this respect framework changes or back mutations were only made in three of the heavy chain variable regions and only two framework modifications were undertaken in the light chain variable regions.

Note that, for some humanized light and heavy chain variable regions (e.g. hSC17.200, hSC17.155 and hSC17.161), conservative amino acid mutations were introduced in the CDRs to address stability concerns while maintaining antigen binding. In each case, the binding affinity of the antibodies with modified CDR's was found to be equivalent to either the corresponding chimeric or murine antibody. The sequences of nine exemplary humanized variant chains (light and heavy) are listed at the end of FIGS. 3A and 3B (SEQ ID NOS: 192-199) where they retain the designation of the humanized parent chain with notation to indicate they have been altered (e.g. hSC17.200vL1, hSC17.155vH1-6 and hSC17.161vH1).

Following humanization of all selected antibodies by CDR grafting, the resulting light and heavy chain variable region amino acid sequences were analyzed to determine their homology with regard to the murine donor and human acceptor light and heavy chain variable regions. The results, shown in Table 8 below, reveal that the humanized constructs consistently exhibited a higher homology with respect to the human acceptor sequences than with the murine donor sequences. More specifically, the humanized heavy and light chain variable regions generally show a higher percentage homology to a closest match of human germline genes (84%-95%) as compared to the homology of the humanized variable region sequences and the donor hybridoma protein sequences (74%-89%).

TABLE 8

| mAb | Homology to Human (CDR acceptor) | Homology to Murine Parent (CDR donor) |
|---|---|---|
| hSC17.16 HC | 91% | 80% |
| hSC17.16 LC | 86% | 85% |
| hSC17.17 HC | 93% | 80% |
| hSC17.17 LC | 87% | 77% |
| hSC17.24 HC | 86% | 79% |
| hSC17.24 LC | 93% | 89% |
| hSC17.28 HC | 89% | 77% |
| hSC17.28 LC | 92% | 78% |
| hSC17.34 HC | 85% | 83% |
| hSC17.34 LC | 84% | 86% |
| hSC17.46 HC | 85% | 83% |
| hSC17.46 LC | 84% | 80% |
| hSC17.151 HC | 90% | 79% |
| hSC17.151 LC | 87% | 80% |
| hSC17.155 HC | 90% | 80% |
| hSC17.155 LC | 95% | 87% |
| hSC17.156 HC | 89% | 79% |
| hSC17.156 LC | 86% | 93% |
| hSC17.161 HC | 89% | 86% |
| hSC17.161 LC | 93% | 87% |
| hSC17.200 HC | 90% | 74% |
| hSC17.200 LC | 88% | 82% |

Upon testing each of the humanized constructs exhibited favorable binding characteristics roughly comparable to those shown by the murine parent antibodies (Data not shown).

Example 5

Generation of Humanized Anti-CD324 Antibodies

Anti-CD324 humanized antibodies were generated substantially as set forth in Examples 1-3 above. A more detailed description of the production of the CD324 antigen and corresponding antibodies is provided in PCT/US2013/25356, which is incorporated herein by reference as to the same. Following inoculation of six female mice antibody producing hybridomas were generated substantially as set forth in Example 1. The hybridomas were screened as previously discussed and genetic material obtained from those of interest. Sequences of the heavy and light chain variable regions of the anti-SEZ6 antibodies were determined substantially as set forth in Example 2.

FIG. 4 shows the contiguous amino acid sequences of the light (SEQ ID NO: 529) and heavy (SEQ ID NO: 530) chain variable regions of an exemplary anti-CD324 murine antibody, SC10.17. Nucleic acid sequences corresponding to the murine heavy and light chains are provided in the sequence listing appended hereto (SEQ ID NOS: 531 and 532). Sequences of SC10.17 and other compatible light and heavy chain variable regions from anti-CD324 antibodies are shown in PCT/US2013/25356 which is incorporated herein as to these sequences.

The SC10.17 anti-CD324 murine antibody was humanized, substantially as set forth in Example 3 above using standard molecular engineering techniques. Using Kabat numbering, FIG. 4 denotes the CDRs and framework regions, as determined using the Abysis Database, of the heavy and light chains of the murine parent antibody and the derived humanized construct. A review of FIG. 4 shows the murine heavy and light CDRs were transferred to the human acceptor molecule with only minor alterations in the CDRs. More particularly FIG. 4 shows amino acid sequences of the light (SEQ ID NO: 531) and heavy (SEQ ID NO: 532) chains of an exemplary humanized anti-CD324 antibody, termed hSC10.17. As with the parent murine antibody corresponding nucleic acid sequences are set forth in the appended sequence listing (SEQ ID NOS: 535 and 536). The light and heavy chain variable regions of hSC10.17 exhibited higher homology with the light and heavy chain variable regions of the human acceptor sequence compared to the murine donor sequence (data not shown).

Example 6

Fabrication of Site-Specific Anti-DLL3 Antibodies

Four engineered human IgG1/kappa anti-DLL3 site-specific antibodies were constructed. Two of the four engineered antibodies comprised a native light chain constant regions and had mutations in the heavy chain, wherein cysteine 220 (C220) in the upper hinge region of the heavy chain, which forms an interchain disulfide bond with cysteine 214 in the light chain, was either substituted with serine (C220S) or removed (C220Δ). The remaining two engineered antibodies comprised a native heavy chain constant regions and a mutated light chain, wherein cysteine 214 of the light chain was either substituted with serine (C214S) or removed (C214Δ). When assembled the heavy and light chains form antibodies comprising two free cysteines that are suitable for conjugation to a therapeutic agent. Amino acid sequences for the heavy and light antibody chains for each of the exemplary hSC16.56 constructs are shown in FIGS. 5A and 5B while Table 9 immediately below summarizes the alterations. With regard to FIGS. 5A and 5B the reactive (or free) cysteine is underlined as is the mutated residue (in ss1 and ss4) at position 220 for the heavy chain and position 214 for the light chain. Unless otherwise noted, all numbering of constant region residues is in accordance with the EU numbering scheme as set forth in Kabat et al.

TABLE 9

| Designation | Antibody Component | Alteration | Const. Reg. SEQ ID NO: | SC16.56 SEQ ID NO: |
|---|---|---|---|---|
| ss1 | Heavy Chain | C220S | 500 | 509 |
| | Light Chain | WT | 403 | 507 |
| ss2 | Heavy Chain | C220Δ | 501 | 510 |
| | Light Chain | WT | 403 | 507 |
| ss3 | Heavy Chain | WT | 404 | 508 |
| | Light Chain | C214Δ | 502 | 511 |
| ss4 | Heavy Chain | WT | 404 | 508 |
| | Light Chain | C214S | 503 | 512 |

The engineered antibodies were generated as follows.

An expression vector encoding the humanized anti-DLL3 antibody hSC16.56 light chain (SEQ ID NO: 507) or heavy chain (SEQ ID NO: 508) derived as set forth in Example 3 were used as a template for PCR amplification and site directed mutagenesis. Site directed mutagenesis was performed using the Quick-Change® system (Agilent Technologies) according to the manufacturer's instructions.

For the two heavy chain mutants, the vector encoding the mutant C220S or C220Δ heavy chain of hSC16.56 was co-transfected with the native IgG1 kappa light chain of hSC16.56 in CHO-S cells and expressed using a mammalian transient expression system. The engineered anti-DLL3 site-specific antibodies containing the C220S or C220Δ mutants were termed hSC16.56ss1 (SEQ ID NOS: 509 and 507) or hSC16.56ss2 (SEQ ID NOS: 510 and 507) respectively.

For the two light chain mutants, the vector encoding the mutant C214S or C214Δ light chain of hSC16.56 was co-transfected with the native IgG1 heavy chain of hSC16.56 in CHO-S cells and expressed using a mammalian transient expression system. The engineered antibodies were purified using protein A chromatography (MabSelect SuRe) and stored in appropriate buffer. The engineered anti-DLL3 site-specific antibodies containing the C214S or C214Δ mutants were termed hSC16.56ss3 (SEQ ID NOS: 508 and 511) or hSC16.56ss4 (SEQ ID NOS: 508 and 512) respectively.

The engineered anti-DLL3 antibodies were characterized by SDS-PAGE to confirm that the correct mutants had been generated. SDS-PAGE was conducted on a pre-cast 10% Tris-Glycine mini gel from life technologies in the presence and absence of a reducing agent such as DTT (dithiothreitol). Following electrophoresis, the gels were stained with a colloidal coomassie solution (data not shown).

Band patterns of the two heavy chain (HC) mutants, hSC16.56ss1 (C220S) and hSC16.56ss2 (C220Δ) and the two light chain (LC) mutants, hSC16.56ss3 (C214S) and hSC16.56ss4 (C214Δ) were observed. Under reducing conditions, for each antibody, two bands corresponding to the free LCs and free HCs, were observed. This pattern is typical of IgG molecules in reducing conditions. Under non-reducing conditions, the four engineered antibodies (hSC16.56ss1-hSC16.56ss4) exhibited band patterns that were different from native IgG molecules, indicative of the absence of a disulfide bond between the HC and LC. All four mutants exhibited a band around 98 kD corresponding to the HC-HC dimer. The mutants with a deletion or mutation on the LC (hSC16.56ss3 and hSC16.56ss4) exhibited a single band around 24 kD corresponding to a free LC. The engineered antibodies containing a deletion or mutation on the heavy chain (hSC16.56ss1 and hSC16.56ss2) had a faint band corresponding to the free LC and a predominant band around 48 kD that corresponded to a LC-LC dimer. The formation of some amount of LC-LC species is expected with the ss1 and ss2 constructs due to the free cysteines on the c-terminus of each light chain.

Example 7

Fabrication of Site-Specific Anti-SEZ6 Antibodies

Four engineered human IgG1/kappa anti-SEZ6 site-specific antibodies were constructed substantially as set forth in Example 6 using the humanized antibody hSC17.200 as a starting point. Two of the four engineered antibodies comprised a native light chain constant regions and had mutations in the heavy chain, wherein cysteine 220 (C220) in the upper hinge region of the heavy chain, which forms an interchain disulfide bond with cysteine 214 in the light chain, was either substituted with serine (C220S) or removed (C220Δ). The remaining two engineered antibodies comprised a native heavy chain constant regions and a mutated light chain, wherein cysteine 214 of the light chain was either substituted with serine (C214S) or removed (C214Δ). When assembled the heavy and light chains form antibodies comprising two free cysteines that are suitable for conjugation to a therapeutic agent. Amino acid sequences for the heavy and light antibody chains for each of the exemplary hSC17.200 constructs are shown in FIGS. 6A and 6B while Table 10 immediately below summarizes the alterations. With regard to FIGS. 6A and 6B the reactive cysteine is underlined as is the mutated residue (in ss1 and ss4) at position 220 for the heavy chain and position 214 for the light chain. Unless otherwise noted, all numbering of constant region residues is in accordance with the EU numbering scheme as set forth in Kabat et al.

TABLE 10

| Designation | Antibody Component | Alteration | Const. Reg. SEQ ID NO: | SC17.200 SEQ ID NO: |
|---|---|---|---|---|
| ss1 | Heavy Chain | C220S | 500 | 515 |
|  | Light Chain | WT | 403 | 513 |
| ss2 | Heavy Chain | C220Δ | 501 | 516 |
|  | Light Chain | WT | 403 | 513 |
| ss3 | Heavy Chain | WT | 404 | 514 |
|  | Light Chain | C214Δ | 502 | 517 |
| ss4 | Heavy Chain | WT | 404 | 514 |
|  | Light Chain | C214S | 503 | 518 |

Expression vectors comprising the heavy and light chains of site-specific engineered hSC17.200 antibodies were introduced into CHO or 293 cells which where then used to produce the site-specific antibodies as describe herein.

In addition to hSC17.200 site-specific antibodies hSC17.17 antibodies may be produced and expressed in substantially the same manner. Exemplary hSC17.17 site-specific antibodies would be as summarized in Table 11 set forth immediately below with the full length heavy and light chain amino acid sequences included in the appended sequence listing as indicated.

TABLE 11

| Designation | Antibody Component | Alteration | Const. Reg. SEQ ID NO: | SC17.17 SEQ ID NO: |
|---|---|---|---|---|
| ss1 | Heavy Chain | C220S | 500 | 539 |
|  | Light Chain | WT | 403 | 537 |
| ss2 | Heavy Chain | C220Δ | 501 | 540 |
|  | Light Chain | WT | 403 | 537 |
| ss3 | Heavy Chain | WT | 404 | 538 |
|  | Light Chain | C214Δ | 502 | 541 |
| ss4 | Heavy Chain | WT | 404 | 538 |
|  | Light Chain | C214S | 503 | 542 |

Example 8

Fabrication of Site-Specific Anti-CD324 Antibodies

Four engineered human IgG1/kappa anti-CD324 site-specific antibodies were constructed. Two of the four engineered antibodies comprised a native light chain and had mutations in the heavy chain, wherein cysteine 220 (C220) in the upper hinge region of the heavy chain, which forms an interchain disulfide bond with cysteine 214 in the light chain, was either substituted with serine (C220S) or removed (C220Δ). The remaining two engineered antibodies comprised a native heavy chain and a mutated light chain, wherein cysteine 214 of the light chain was either substituted with serine (C214S, see FIG. 7) or removed (C214Δ). The engineered antibodies were generated as follows.

Expression vectors encoding humanized anti-CD324 hSC17.10 antibody light chain or heavy chain comprising appropriate variable regions (SEQ ID NOS: 531 and 532) were used as templates for PCR amplification and site directed mutagenesis. Site directed mutagenesis was performed using the Quick-Change® system (Agilent Technologies) according to the manufacturer's instructions.

For the two heavy chain mutants, the vector encoding the mutant C220S or C220Δ heavy chain of hSC10.17 was co-transfected with the native IgG1 kappa light chain of hSC10.17 in CHO-S cells and expressed using a mammalian transient expression system. The engineered anti-CD324 site-specific antibodies containing the C220S or C220Δ mutants were termed SC10.17ss1 or SC10.17ss2 respectively.

For the two light chain mutants, the vector encoding the mutant C214S or C214Δ light chain of hSC10.17 was co-transfected with the native IgG1 heavy chain of hSC10.17 in CHO-S cells and expressed using a mammalian transient expression system. The engineered antibodies were purified using protein A chromatography (MabSelectSure protein A resin) and stored in appropriate buffer. The engineered anti-CD324 site-specific antibodies containing the C214S or C214Δ mutants were termed SC10.17ss3 or SC10.17ss4 respectively.

The amino acid sequence of the entire native heavy chain of hSC10.17ss3 is shown in FIG. 7 as SEQ ID NO: 543 while the amino acid sequence of the entire engineered light chain is shown in the same figure as SEQ ID NO: 544. The C214S (Kabat numbering) position in the kappa light chain is denoted by an * as is the free cysteine at position 220 of the heavy chain (again EU index of Kabat numbering).

Example 9

Site-Specific Constructs Retain Binding Characteristics

Site-specific anti-DLL3 antibodies fabricated as set forth in the previous Examples were screened by an ELISA assay to determine whether they bound to DLL3 purified protein. The parental native antibody was used as a control and run alongside the site-specific anti-DLL3 antibody. Binding of the antibodies to DLL3 was detected with a monoclonal antibody (mAb) reporter antibody conjugated to horseradish peroxidase (HRP), (Southern Biotech, Cat. No. SB9052-05), which binds to an epitope present on human IgG1 molecules. HRP reacts with its substrate tetramethyl benzidine (TMB). The amount of hydrolyzed TMB is directly proportional to the amount of test antibody bound to DLL3.

ELISA plates were coated with 1 μg/ml purified DLL3 in PBS and incubated overnight at 4° C. Excess protein was removed by washing and the wells were blocked with 2% (w/v) BSA in PBS with 0.05% tween 20 (PBST), 200 μL/well for 1 hour at room temperature. After washing, 100 μL/well serially diluted antibody or ADC were added in PBST for 1 hour at room temperature. The plates were washed again and 0.5 ug/ml of 100 μL/well of the appropriate reporter antibody was added in PBST for 1 hour at room temperature. After another washing, plates were developed by the addition of 100 μL/well of the TMB substrate solution (Thermo Scientific) for 15 minutes at room temperature. An equal volume of 2 M $H_2SO_4$ was added to stop substrate development. The samples were then analyzed by spectrophotometer at OD 450.

Figure 8:
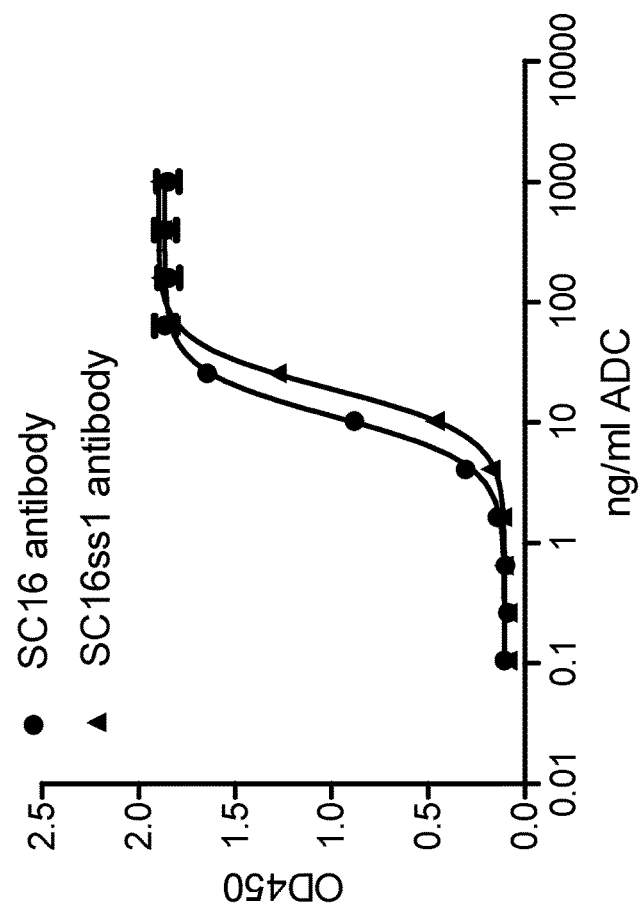
FIG. 8 shows the binding properties of native and site-specific constructs fabricated as set forth herein.

The results of the ELISAs are shown in FIG. 8 as a binding curve. A review of the data demonstrates that engineering of the heavy chain CH1 domain to provide a free cysteine on the light chain constant region did not adversely impact the binding of the antibodies to the target antigen. Similar assays (data not shown) conducted with various site-specific constructs shows that engineering of the light chain constant region or the CH1 region to provide free cysteines has little impact on the binding characteristics of the resulting antibody or ADC.

Example 10

Conjugation of Site-Specific Anti-SEZ6 ADC

Site-specific antibody conjugation was undertaken in which engineered anti-SEZ6 antibodies such as those described in Example 7 were conjugated to thiol reactive monomethyl auristatin E via a val cit linker (vcMMAE, see e.g., U.S. Pat. No. 7,659,241). The site-specific conjugation gives rise to a population of ADCs having reduced heterogeneity and complexity of species. As discussed above a homologous population of ADCs comprising a homogeneous composition can have a favorable impact on stability, pharmacokinetics, aggregation and ultimately safety profile.

More specifically an engineered human IgG1/kappa anti-SEZ6 antibody was constructed, wherein the cysteine in the upper hinge region of the heavy chain (C220), which forms an interchain disulfide bond with the light chain, was substituted with serine (C220S) resulting in an antibody (hSC17.200ss1) having two unpaired cysteines to which cytotoxins could be conjugated. The amino acid sequence of the entire engineered heavy chain is shown in FIG. 6A as SEQ ID NO: 515 while the amino acid sequence of the entire light chain is shown in the same figure as SEQ ID NO: 513. The C220S (as per the EU index of Kabat) position in the heavy chain is denoted in bold and underlined as is the free cysteine at position 214 of the kappa light chain (again numbering as per Kabat).

hSC17.200S was conjugated with vcMMAE in three distinct stages; a reduction step, a re-oxidation step and a conjugation step. A schematic diagram of the process can be seen in FIG. 9.

hSC17.200S was fully reduced with a 40 molar equivalent addition of 10 mM DTT in water. The reduction reaction was allowed to proceed overnight (>12 h) at room temperature. The reduced antibody was then buffer exchanged into a Tris pH 7.5 buffer using a 30 kd membrane (Millipore Amicon Ultra) and the equivalent of 10 diavolumes of buffer exchange. The reduced hSC17.200S was then re-oxidized with either a 4.5 molar equivalent addition of 10 mM dehydroascorbic acid (DHAA) in Dimethylacetamide (DMA). The re-oxidation reaction was allowed to proceed at room temperature for 60 minutes. The re-oxidized antibody was then conjugated by the addition of 1.2 moles of vcMMAE per mole of free thiol from a 10 mM stock of vcMMAE in DMA. Additional DMA was added prior to conjugation such that the final concentration of DMA in the reaction mixture was approximately 6% v/v. Conjugation was allowed to proceed for a minimum of 30 minutes before the reaction was quenched with the addition of 1.2 molar excess of N-acetyl cysteine (NAC), from a 10 mM stock solution prepared in water. After a minimum quench time of 20 minutes, the pH was adjusted to 5.5±0.3 with the addition of 4% v/v of 0.5 M acetic acid. Conjugated hSC17.200SvcMMAE was diafiltered into 20 mM histidine chloride pH 6.0 by constant-volume diafiltration using a 10 kDa membrane and a total of 10 diavolumes of buffer exchange prior to sterile filtration and final formulation. The resulting ADC exhibited binding to the SEZ6 antigen comparable to that of the conjugated native SC17.200 antibody and a relatively high percentage of DAR=2 compounds.

Example 11

Conjugation of Site-Specific Antibodies

Site-specific antibodies (hSC16.56ss1 and hSC17.200ss1) fabricated as set forth in Examples 6 and 7 above were completely reduced using DTT or partially reduced using TCEP (tris(2-carboxyethyl)phosphine) prior to conjugation with linker-drug comprising a vcMMAE in order to demonstrate site-specific conjugation.

Again a schematic diagram of the process can be seen in FIG. 9. The target conjugation site for this construct is the unpaired cysteine (C214) on each light chain constant region. Conjugation efficiency (on-target and off-target conjugation) can be monitored using a reverse-phase HPLC (RP-HPLC) assay that can track on-target conjugation on the light chain vs. off-target conjugation on the heavy chain. A hydrophobic interaction chromatography (HIC) assay may be used to monitor the distribution of drug to antibody ratio species (DAR). In this example, the desired product is an ADC that is maximally conjugated on the light chain (on-target) as determined by reverse-phase chromatography and that minimizes over-conjugated (DAR>2) species while maximizing DAR=2 species.

Different preparations of hSC16.56ss1 or hSC17.200ss1 were either completely reduced with a 40 molar equivalent addition of 10 mM DTT or partially reduced with a 2.6 molar equivalent addition of 10 mM TCEP.

Samples reduced with 10 mM DTT were reduced overnight (>12 h) at room temperature prior to buffer exchange into a Tris pH 7.5 buffer using a 30 kDa membrane (Millipore Amicon Ultra) and the equivalent of 10 diavolumes of buffer exchange. The resulting fully reduced preparations were then re-oxidized with 4.0 molar equivalent addition of 10 mM dehydroascorbic acid (DHAA) in dimethylacetamide (DMA). When the free thiol concentrations (number of free thiols per antibody, as measured by Ellman's method) of the samples were between 1.9 and 2.3, the free cysteines of the antibodies were conjugated to MMAE cytotoxins via a maleimido linker for a minimum of 30 minutes at room temperature. The reaction was then quenched with the addition of 1.2 molar excess of N-acetyl-cysteine (NAC) using a 10 mM stock solution prepared in water. After a minimum quench time of 20 minutes, the pH was adjusted to 6.0 with the addition of 0.5 M acetic acid. The various conjugated preparations of antibody-MMAE were then buffer exchanged into 20 mM histidine chloride pH 6.0 by diafiltration using a 30 kDa membrane.

The samples partially reduced with 10 mM TCEP were reduced for a minimum of 90 minutes at room temperature. When the free thiol concentrations of the samples were between 1.9 and 2.3, the partially reduced antibodies were conjugated to MMAE, a gain via a maleimido linker, for a minimum of 30 minutes at room temperature. The reaction was then quenched with the addition of 1.2 molar excess NAC from a 10 mM stock solution prepared in water. After a minimum quench time of 20 minutes, the pH was adjusted to 6.0 with the addition of 0.5 M acetic acid. The preparations of conjugated antibody-MMAE were then buffer exchanged into 20 mM histidine chloride pH 6.0 by diafiltration using a 30 kDa membrane.

Figures 10A, 10B:
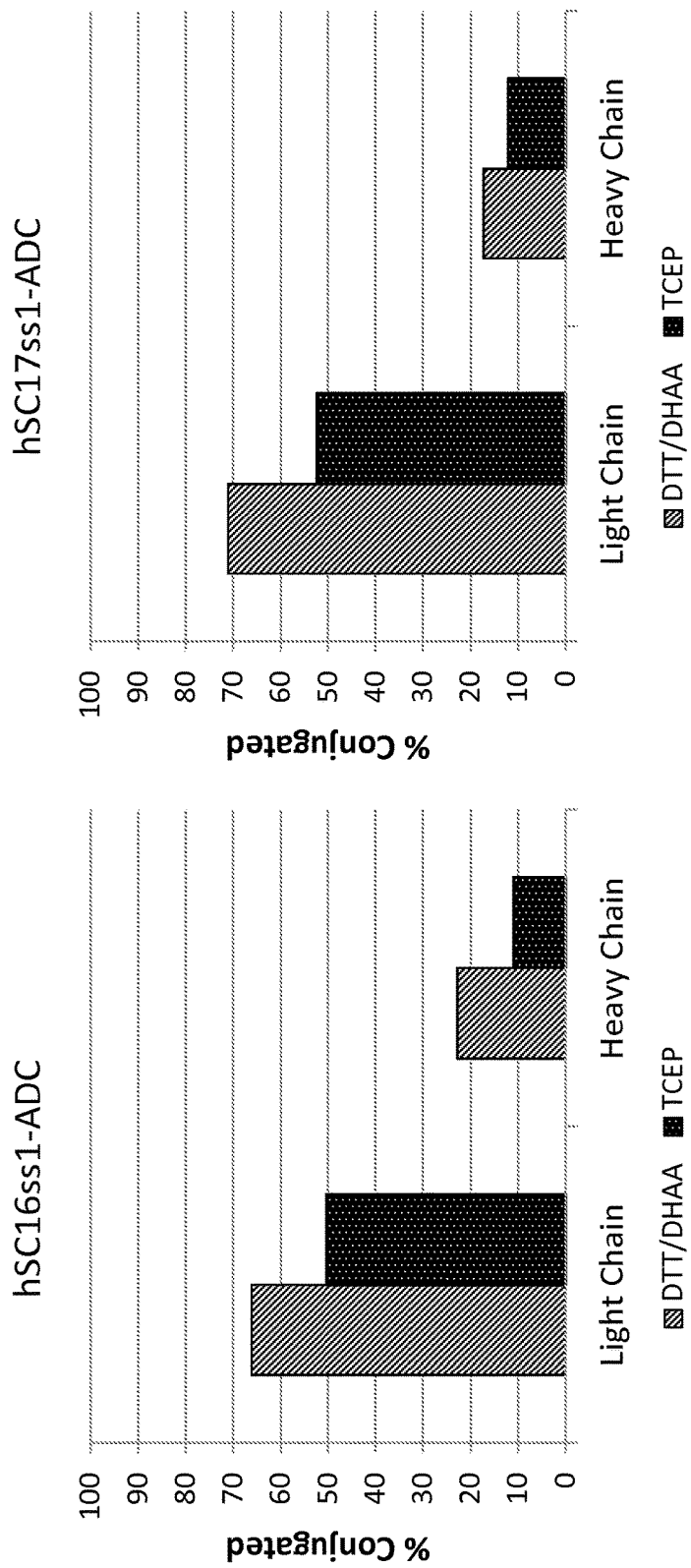
FIGS. 10A and 10B are graphical representations showing the conjugation percentages of site-specific antibody light and heavy chains conjugated using reducing agents as determined using RP-HPLC.

The final antibody-drug preparations (both DTT reduced and TCEP reduced) were analyzed using RP-HPLC to quantify heavy vs. light chain conjugation sites in order to determine the percentage of on-target light-chain conjugation for hSC16.56ss1-MMAE (FIG. 10A) or hSC17.200ss1-MMAE (FIG. 10B). The analysis employed an Aeris WIDE- PORE 3.6 μm C4 column (Phenomenex) with 0.1% v/v TFA in water as mobile phase A, and 0.1% v/v TFA in 90% v/v acetonitrile as mobile phase B. Samples were fully reduced with DTT prior to analysis, then injected onto the column, where a gradient of 30-50% mobile phase B was applied over 10 minutes. UV signal at 214 nm was collected and then used to calculate the extent of heavy and light chain conjugation.

More particularly the distribution of payloads between heavy and light chains in hSC16.56ss1-MMAE and hSC17.200ss1-MMAE conjugated using DTT and TCEP are shown in FIGS. 10A and 10B. Percent conjugation on the heavy and light chains were performed by integrating the area under the RP-HPLC curve of the previously established peaks (light chain, light chain+1 drug, heavy chain, heavy chain+1 drug, heavy chain+2 drugs, etc.) and calculating the % conjugated for each chain separately. As discussed throughout the instant specification selected embodiments of the invention comprise conjugation procedures that favor placement of the payload on the light chain.

The same preparations were also analyzed using HIC to determine the amount of DAR=2 species relative to the unwanted DAR>2 species for hSC16.56ss1-MMAE (FIG. 11A) and hSC17.200ss1-MMAE (FIG. 11B). In this regard HIC was conducted using a PolyPROPYL A 3 μm column (PolyLC) with 1.5M ammonium sulfate and 25 mM potassium phosphate in water as mobile phase A, and 0.25% w/v CHAPS and 25 mM potassium phosphate in water as mobile phase B. Samples were injected directly onto the column, where a gradient of 0-100% mobile phase B was applied over 15 minutes. UV signal at 280 nm was collected, and the chromatogram analyzed for unconjugated antibody and higher DAR species. DAR calculations were performed by integrating the area under the HIC curve of the previously established peaks (DAR=0, DAR=1, DAR=2, DAR=4, etc) and calculating the % of each peak. The resulting DAR distribution in hSC16.56ss1-MMAE and hSC17.200ss1-MMAE conjugated using DTT and TCEP are shown in FIGS. 11A and 11B respectively.

The DAR distributions as determined by HIC of the hSC16 site-specific conjugate preparations indicate that the DTT/DHAA full reduction and reoxidation method results in ~60% DAR=2 species, whereas the typical partial TCEP reduction method results in ~50% DAR=2. The full reduction and reoxidation method also results in higher unwanted DAR>2 species (20-25%) while the partial TCEP reduction method results in 10-15% DAR>2 (FIGS. 11A and 11B). Note that while the TCEP partial reduction had lower levels of DAR>2 species, the DAR=2 percentage is only 50%. Driving up the % DAR=2 species in the TCEP system would result in a corresponding increase in the unwanted DAR>2 species. The increase in high DAR species for the DTT/DHAA full reduction samples can be attributed to higher off-target conjugation on the heavy chain as shown by RP-HPLC (FIGS. 10A and 10B), which is due to non-specific reduction of the hinge region cysteine residues as the driving force for reduction is increased. Thus, while the disclosed site-specific constructs provide improved DAR and less unwanted higher DAR impurities relative to native antibodies, conventional reduction methods generate at least some non-specific conjugates comprising cytotoxic agents on cysteine residues that are different from the intended engineered sites.

Example 12

Conjugation of Engineered Antibodies Using a Selective Reduction Process

In order to further improve the specificity of the conjugation and homogeneity of the final product site-specific antibodies fabricated as set forth in Examples 6 and 7 were selectively reduced using a novel process comprising a stabilizing agent (e.g. L-arginine) and a mild reducing agent (e.g. glutathione) prior to conjugation with linker-drug comprising MMAE. As discussed above, selective conjugation preferentially conjugates the cytotoxin on the free cysteine with a little non-specific conjugation.

Per Examples 6 and 7, the target conjugation site for the hSC16.56ss1 construct is the unpaired cysteine on each light chain. In order to direct conjugation to these engineered sites, preparations of hSC16.56ss1 and hSC17.200ss1 were partially reduced in a buffer containing 1M L-arginine/5 mM glutathione, reduced (GSH)/5 mM EDTA, pH 8.0 for a minimum of one hour at room temperature. Additionally, as controls, each antibody preparation was separately incubated in 1M L-arginine/5 mM EDTA, pH 8.0 and 20 mM Tris/3.2 mM EDTA/5 mM GSH, pH 8.2 buffers for one hour or longer. All preparations were then buffer exchanged into a 20 mM Tris/3.2 mM EDTA, pH 8.2 buffer using a 30 kDa membrane (Millipore Amicon Ultra). The resulting partially reduced preparations (for samples incubated in arginine and glutathione together) had free thiol concentrations between 1.9 and 2.3, and all preparations were then conjugated to MMAE via a maleimido linker for a minimum of 30 minutes at room temperature. The reaction was then quenched with the addition of 1.2 molar excess of NAC using a 10 mM stock solution prepared in water. After a minimum quench time of 20 minutes, the pH was adjusted to 6.0 with the addition of 0.5 M acetic acid. The various conjugated preparations of antibody-MMAE were then diafiltered into 20 mM histidine chloride, pH 6.0 by diafiltration using a 30 kDa membrane.

Figures 12A, 12B:
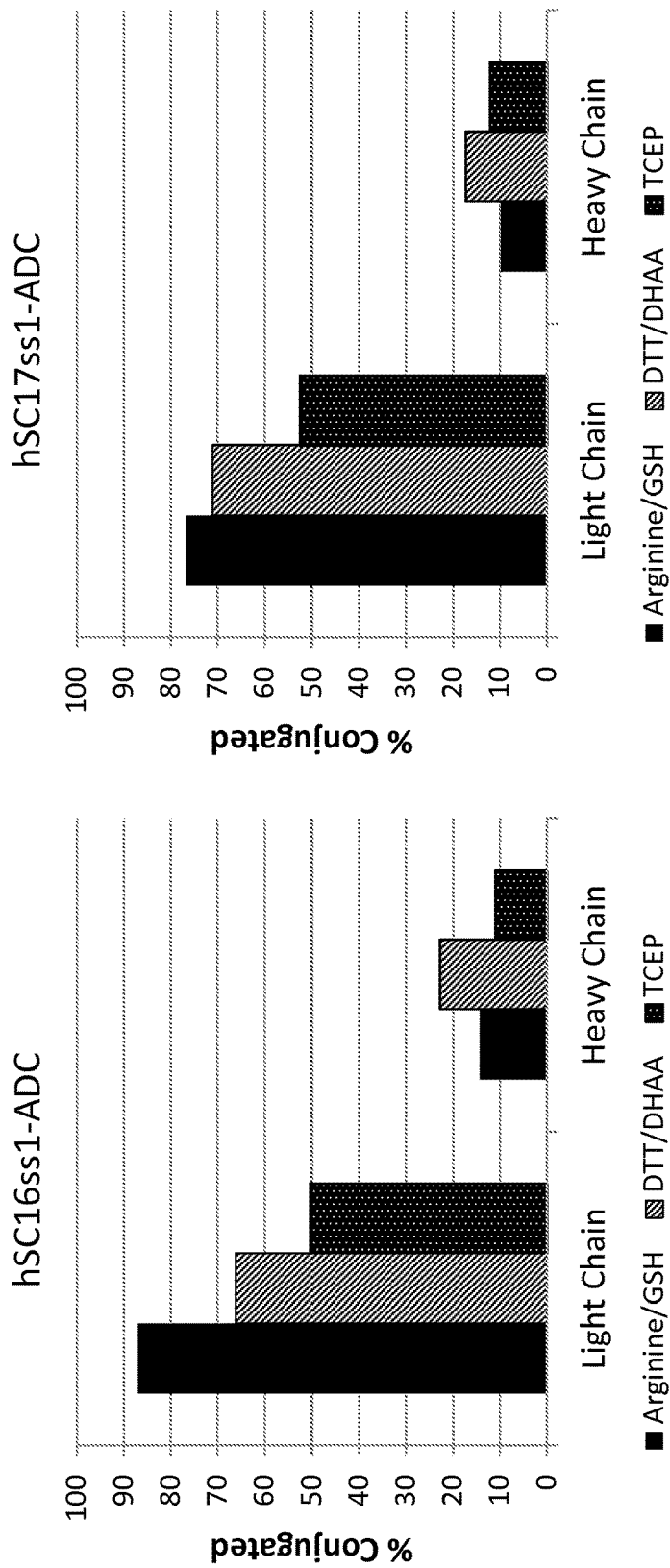
FIGS. 12A and 12B show the conjugation percentages of site-specific antibody light and heavy chains conjugated using stabilizing agents or reducing agents as determined using RP-HPLC.
Figures 14A, 14B:
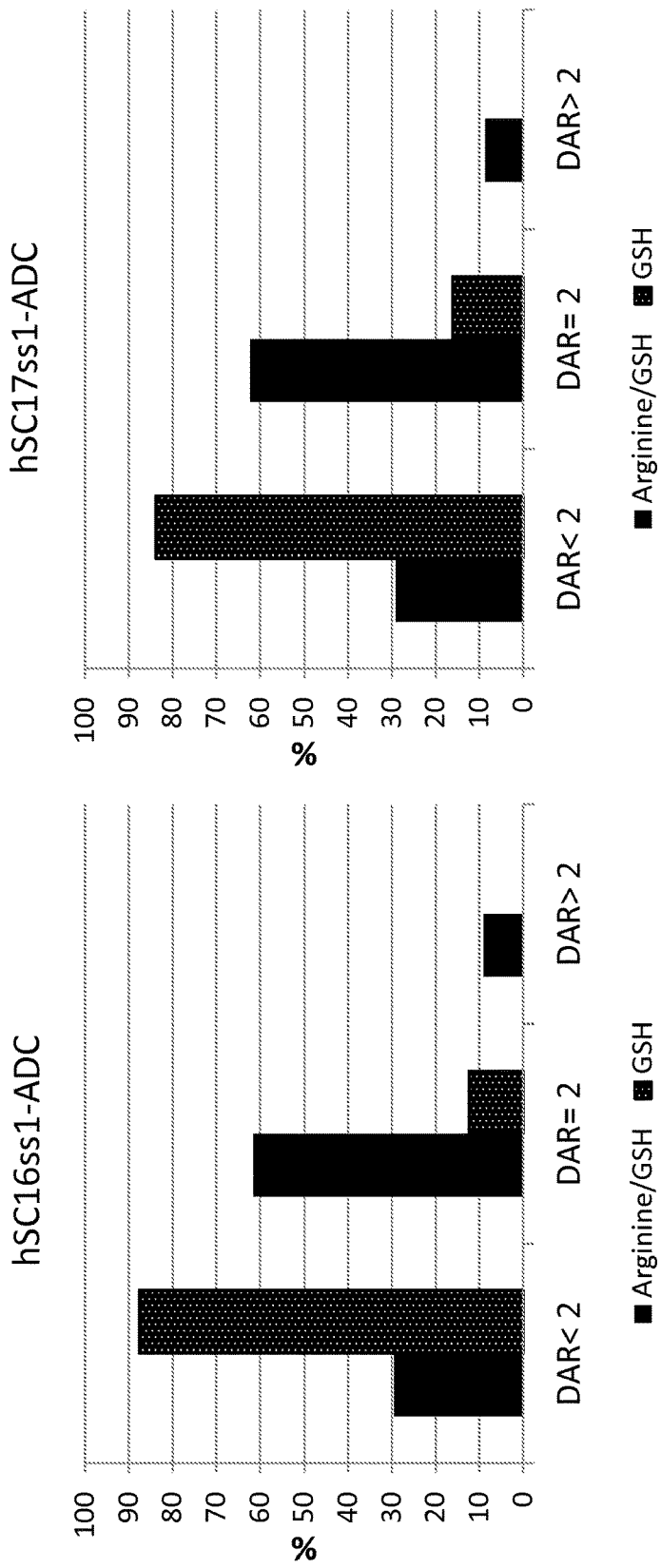
FIGS. 14A and 14B show the DAR distribution of site-specific antibody constructs conjugated using stabilization and/or mild reducing agents as determined using HIC.

The final antibody-drug preparations were analyzed using RP-HPLC as previously discussed to quantify heavy vs. light chain conjugation sites in order to determine the percentage of on-target light-chain conjugation (FIGS. 12A and 12B). The samples were also analyzed using hydrophobic interaction chromatography to determine the amount of DAR=2 species relative to the unwanted DAR>2 species (FIGS. 13A and 13B). For comparative purposes results obtained in the previous Example are included in FIGS. 12 and 13 for DTT/DHAA and TCEP reduced samples. HIC analysis of the EDTA/GSH controls are presented in FIGS. 14A and 14B where they are shown next to the selectively reduced samples.

FIGS. 12 and 13 summarize the HIC DAR distributions and the % conjugated light chain of the antibodies reduced using the selective reduction process compared to standard complete or partial reduction processes (as described in Examples 10 and 11). The benefit of the selective conjugation method in combination with the engineered constructs is readily apparent, resulting in superior selectivity of the desired light chain conjugation site (FIGS. 12A and 12B) and providing an average DAR=2 level of 60-75% while maintaining unwanted DAR>2 species below 10% (FIGS. 13A and 13B). The results shown in FIGS. 12 and 13 demonstrate that selective reduction drives the reaction to provide higher levels of DAR=2 and less of the undesired DAR>2 species than the standard partial or complete reduction procedures. Control procedures shown in FIGS. 14A and 14B demonstrate that the mild reducing agent (e.g. GSH) cannot effect the desired conjugation in the absence of a stabilizing agent (e.g. L-arginine).

These data demonstrate that selective reduction provides advantages over conventional partial and complete reduction conjugation methods. This is particularly true when the novel selective reduction procedures are used in conjunction with antibodies engineered to provide unpaired (or free) cysteine residues. Mild reduction in combination with a stabilizing agent (i.e., selective reduction) produced stable free thiols that were readily conjugated to various linker-drugs, whereas DHAA reoxidation is time sensitive and TCEP reduction was not as successful, particularly for the engineered constructs described herein.

Example 13

Selective Reduction with Different Systems

To further demonstrate the advantages of selective reduction using various combinations of stabilizing agents and reducing agents, hSC16.56ss1 were selectively reduced using different stabilizing agents (e.g. L-lysine) in combination with different mild reducing agents (e.g. N-acetylcysteine or NAC) prior to conjugation.

Figure 15:
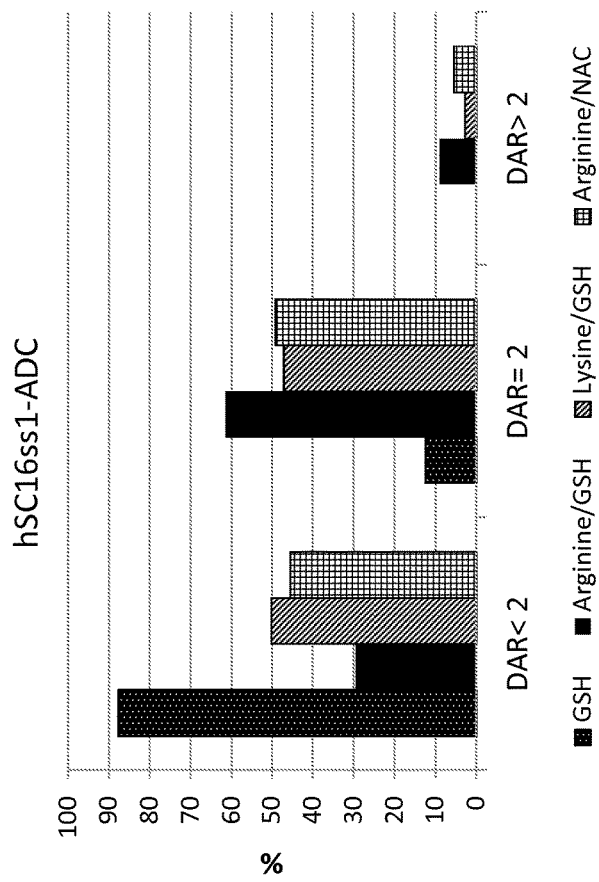
FIG. 15 depicts DAR distribution of site-specific antibody constructs conjugated using various stabilization agents as determined using HIC.

Three preparations each of hSC16.56ss1 were selectively reduced using three different buffer systems: (1) 1M L-arginine/6 mM GSH/5 mM EDTA, pH 8.0, (2) 1M L-arginine/10 mM NAC/5 mM EDTA, pH 8.0, and (3) 1M L-Lysine/5 mM GSH/5 mM EDTA, pH 8.0. Additionally, as controls, the antibody preparations were separately incubated in 20 mM Tris/5 mM EDTA/10 mM NAC, pH 8.0 and 20 mM Tris/3.2 mM EDTA/5 mM GSH, pH 8.2 buffers. All preparations were incubated for a minimum of one hour at room temperature, and then buffer exchanged into a 20 mM Tris/3.2 mM EDTA, pH 8.2 buffer by diafiltration using a 30 kDa membrane (Millipore Amicon Ultra). The resulting selectively reduced preparations, which were found to have free thiol concentrations between 1.7 and 2.4, were then conjugated to MMAE via a maleimido linker. After allowing the conjugation reaction to proceed for a minimum of 30 minutes at room temperature, the reaction was quenched with the addition of 1.2 molar excess of NAC using a 10 mM stock solution. Following a minimum quench time of 20 minutes, the pH was adjusted to 6.0 with the addition of 0.5 M acetic acid. The various conjugated preparations of antibody-MMAE were then buffer exchanged into 20 mM histidine chloride pH 6.0 by diafiltration using a 30 kDa membrane. Final antibody-drug preparations were then analyzed using hydrophobic interaction chromatography to determine DAR distribution (FIG. 15).

DAR distributions as determined by HIC show similar results for the three different selective reduction systems employed (Arg/GSH, Lys/GSH and Arg/NAC). More particularly, DAR=2 levels are 60-65% for the different preparations, and high-DAR species (DAR>2) are maintained below 20% for all selective reduction systems and linker-drug combinations, indicating high selectivity for the engineered cysteine residues in the constant region of the light chain. Again, as previously shown in Example 12, mild reducing agents alone (e.g. GSH or NAC) did not provide sufficient conjugation selectivity while the addition of the stabilizing agent results in significant improvement.

Example 14

Site-Specific Conjugates Retain Binding Characteristics

Site-specific anti-DLL3 ADCs prepared as set forth in the previous Examples are screened to determine whether they bind to DLL3 purified protein. A representative screening assay is an ELISA assay, performed essentially as described below. The ELISAs are used to select engineered antibodies that retain binding characteristics.

The parental non-engineered antibody is used, in conjugated and non-conjugated forms, as a control and run alongside the site-specific anti-DLL3 antibody and anti-DLL3 antibody drug conjugate. Binding of the antibodies to DLL3 is detected with a monoclonal antibody (mAb) reporter antibody conjugated to horseradish peroxidase (HRP), (Southern Biotech, Cat. No. SB9052-05), which binds to an epitope present on human IgG1 molecules. Binding of the ADCs (site-specific or conventional) to DLL3 is detected using an antibody conjugated to horseradish peroxidase (HRP) which binds to the drug or drug linker on the ADC. HRP reacts with its substrate tetramethyl benzidine (TMB). The amount of hydrolyzed TMB is directly proportional to the amount of test article bound to DLL3.

ELISA plates are coated with 1 µg/ml purified DLL3 in PBS and incubated overnight at 4° C. Excess protein is removed by washing and the wells are blocked with 2% (w/v) BSA in PBS with 0.05% tween 20 (PBST), 200 µL/well for 1 hour at room temperature. After washing, 100 µL/well serially diluted antibody or ADC are added in PBST for 1 hour at room temperature. The plates are washed again and 0.5 ug/ml of 100 µL/well of the appropriate reporter antibody is added in PBST for 1 hour at room temperature. After another washing, plates are developed by the addition of 100 µL/well of the TMB substrate solution (Thermo Scientific) for 15 minutes at room temperature. An equal volume of 2 M $H_2SO_4$ is added to stop substrate development. The samples are then analyzed by spectrophotometer at OD 450.

Example 15

In Vitro Cytotoxicity of Site-Specific Conjugates

Assays are performed to demonstrate the ability of site-specific conjugates to effectively kill cells expressing the human DLL3 antigen in vitro. For example, an assay can be used to measure the ability of an anti-DLL3 site-specific conjugate to kill HEK293T cells engineered to express human DLL3. In this assay killing requires binding of the ADC (site-specific or control) to its DLL3 target on the cell surface followed by internalization of ADC. Upon internalization the linker (e.g., a Val-Ala protease cleavable linker as described above) is cleaved and releases the cytotoxin inside the cells leading to cell death. Cell death is measured using CellTiter-Glo reagent that measures ATP content as a surrogate for cell viability.

A representative assay is performed essentially as follows. Cells are plated into 96 well tissue culture treated plates, with 500 cells per well in DMEM supplemented with 10% fetal bovine serum and penicillin/streptomycin (DMEM complete media), one day before the addition of antibody drug conjugates. 24 hours post plating cells are treated with serially diluted SCAb-cytotoxin control or SCAbss1-cytotoxin in DMEM complete media. The cells are cultured for 96 hours post treatment, after which, viable cell numbers are enumerated using Cell Titer Glo® (Promega) as per manufacturer's instructions.

Example 16

Stability of Site-Specific Conjugates in Serum

In order to demonstrate improved stability provided by the site-specific conjugates of the instant invention, selected conjugates are exposed to human serum in vitro for extended periods. Degradation of the ADCs is measured over time. For example, a representative assay is performed essentially as follows.

SCAb ADC and SCAbss1 ADC, each comprising a same cytotoxin, are added to human serum obtained commercially (Bioreclamation) and incubated at 37° C., 5% $CO_2$ for extended periods. Samples are collected at 0, 24, 48, 96 and 168 hours post addition and stability is measured using a sandwich ELISA to measure both total antibody content and ADC levels.

With regard to the measurement of total antibody content the ELISA is configured to detect both conjugated and unconjugated SCAb or SCAbss1 antibodies. This assay employs a pair of anti-idiotypic antibodies which specifically capture and detect SCAb and SCAbss1 with or without conjugated cytotoxins. Mechanically the assay is run using the MSD Technology Platform (Meso Scale Diagnostics, LLC) which uses electrochemiluminescence for increased sensitivity and linearity.

To this end MSD high bind plates are coated overnight at 4° C. with 2 ug/mL capture anti-idiotypic (ID-16) antibody. The next day, plates are washed with PBST (PBS+0.05% Tween20) and blocked with 150 uL 3% BSA in PBST. 25 uL serum samples, along with ADC standard curve are added to the plate and allowed to incubate for 2 hours at room temperature. After incubation, plates are washed with PBST and 25 uL sulfo-tagged detection anti-idiotypic (ID-36) antibody at 0.5 ug/mL is added to each well and incubated for 1 hour at room temperature. Plates are then washed and 150 uL 1×MSD read buffer is added per well and read out with the MSD reader. Data is graphed as a percentage of total ADC initially added into the human serum.

In addition to monitoring the total antibody concentration, ELISA assays are run on the collected samples to determine levels of antibody drug conjugate remaining That is, the assay measures the levels of intact SCAb-cytotoxin and SCAbss1-cytotoxin using the ELISA methodology generally as described immediately above. However, unlike the previous ELISA assay this ELISA quantifies the SCAb or SCAbss1 antibody conjugated to one or more cytotoxin molecules, but cannot determine the number of cytotoxin molecules actually present on the detected ADC. Unlike the total antibody assay, this assay uses a combination of an anti-idiotypic mAb and an anti-cytotoxin specific mAb and does not detect the unconjugated SCAb antibody.

This ELISA assay uses the MSD Technology Platform to generate the data, and a representative assay is performed essentially as follows. MSD standard bind plates are coated overnight at 4° C. with 4 ug/mL anti-cytotoxin specific mAb. The next day, plates are washed with PBST (PBS+0.05% Tween20) and blocked with 150 uL 3% BSA in PBST. 25 uL serum samples, along with ADC standard curve and QC samples are added to the plate and allowed to incubate for 2 hours at room temperature. After incubation, plates are washed with PBST and 25 uL sulfo-tagged detection anti-idiotypic antibody (ID-36) at 0.5 ug/mL is added to each well and incubated for 1 hour at room temperature. Plates are then washed and 150 uL 1×MSD read buffer is added per well and read out with the MSD reader. The data is analyzed to select ADCs showing minimal degradation of the ADC so as to avoid non-specific toxicity resulting from the free cytotoxin and corresponding reduction in the therapeutic index.

Example 17

Albumin Transfer of Site-Specific Conjugates in Serum

With conventional ADCs it has been noted that albumin in serum can leach the conjugated cytotoxin thereby increasing non-specific cytotoxicity. In order to determine the amount of site-specific ADC degradation mediated by albumin transfer, an ELISA assay was developed to measure the amount of albumin-cytotoxin (hAlb-cytotoxin) in serum exposed to SCAb-cytotoxin and SCAbss1-cytotoxin. This ELISA uses an anti-cytotoxin specific mAb to capture hAlb-cytotoxin and an anti-human albumin mAb is used as detection antibody. As free ADC will compete with the hAlb-cytotoxin, serum samples are depleted of the ADC prior to testing. Quantitation is extrapolated from a hAlb-cytotoxin standard curve. Along with the previous Example this assay uses the MSD Technology Platform to generate the data. A representative assay is performed essentially as follows.

Initially the serum samples are inoculated with SCAb-cytotoxin or SCAbss1-cytotoxin to a final concentration of 10 µg along with the relevant controls. As with the previous Example, samples are taken at 0, 24, 48, 96 and 168 hours post addition. MSD standard bind plates are coated overnight at 4° C. with 4 ug/mL anti-cytotoxin specific mAb. The next day, plates are washed with PBST (PBS+0.05% Tween20) and blocked with 25 uL MSD Diluent 2+0.05% Tween-20 for 30 minutes at room temperature. Serum samples are diluted 1:10 in MSD Diluent 2+0.1% Tween-20 (10 uL serum+90 uL diluent) and incubated with 20 uL GE's MabSelect SuRe Protein A resin for 1 hour on vortex shaker. After depletion of intact SCAb-cytotoxin or SCAbss1-cytotoxin by anti-idiotypic antibodies, samples are separated from resin using 96-well 3M filter plate. 25 uL of depleted serum samples are then added to the blocked plate along with an hAlb-6.5 standard curve and incubated for 1 hour at room temperature. After incubation, the plates are washed with PBST and 25 uL of 1 ug/mL sulfo-tagged anti-human albumin mAb (Abcam ab10241) diluted in MSD Diluent 3+0.05% Tween-20 are added. The plates are then incubated for 1 hour, washed with PBST and read out with 150 uL 1×MSD read buffer. The data is analyzed to select ADCs showing minimal albumin transfer rates.

Example 18

Site-Specific Constructs Demonstrate In Vivo Efficacy

In vivo experiments are conducted to confirm the cell killing ability of the site-specific constructs described herein. To this end site-specific DLL3 ADCs prepared as set forth in the previous Examples are tested for in vivo therapeutic effects in immunocompromised NODSCID mice bearing subcutaneous patient-derived xenograft (PDX) small cell lung cancer (SCLC) tumors essentially as follows. Anti-DLL3-cytotoxin conjugates (SCAb-ADC), HIC purified anti-DLL3-cytotoxin conjugates (SCAb-ADCD2), and HIC purified site-specific anti-DLL3-cytotoxin conjugates (SCAbss1-ADCD2) are each tested in three different SCLC models.

SCLC-PDX lines, LU129, LU64, and LU117 are each injected as a dissociated cell inoculum under the skin near the mammary fat pad region, and measured weekly with calipers (ellipsoid volume=$a \times b^2/2$, where a is the long diameter, and b is the short diameter of an ellipse). After tumors grew to an average size of 200 mm³ (range, 100-300 mm³), the mice are randomized into treatment groups (n=5 mice per group) of equal tumor volume averages. Mice are treated with a single dose (100 μL) with either vehicle (5% glucose in sterile water), control human IgG1 ADC (IgG-ADC; 1 mg/kg), or SCAb-ADC preparations (0.75-1.5 mg/kg) via an intraperitoneal injection, with therapeutic effects assessed by weekly tumor volume (with calipers as above) and weight measurements. Endpoint criteria for individual mice or treatment groups includes health assessment (any sign of sickness), weight loss (more than 20% weight loss from study start), and tumor burden (tumor volumes >1000 mm³). Efficacy is monitored by weekly tumor volume measurements (mm³) until groups reach an average of approximately 800-1000 mm³. Tumor volumes are calculated as an average with standard error mean for all mice in treatment group and are plotted versus time (days) since initial treatment. Results of the treatments are depicted as mean tumor volumes with standard error mean (SEM) in 5 mice per treatment group.

DLL3-binding ADCs conjugated using either conventional (SCAb-cytotoxin or SCAb-ADCD2) or site-specific strategies (SCAbss1-ADCD2) with HIC purification (in two preparations) of molecular species containing 2 drug molecules per antibody are evaluated in mice bearing SCLC PDX-LU129, PDX-LU64, or PDX-LU117. The results are analyzed to assess the effect of HIC purification and/or site-specific conjugation of DLL3-binding ADCs on therapeutic effect.

Example 19

Site-Specific Conjugates Demonstrate Reduced Toxicity

In order to further expand the therapeutic index of the disclosed conjugate preparations, studies are run to document their toxicity profile. In particular, these studies are performed to select anti-DLL3 site-specific conjugates that are better tolerated (e.g., no mortality for the same number of doses, reduced incidence of skin toxicity, reduced bone marrow toxicity, reduced severity of lymphoid tissue findings, etc.). Significantly, a reduction in toxicity substantially increases the therapeutic index in that it provides for markedly higher dosing and corresponding higher localized concentrations of the cytotoxin at the tumor site. A representative assay is performed essentially as follows.

The toxicity of DAR2 purified site-specific ADC (SCAbss1-ADCD2) is compared to that of conventional conjugates (SCAb-ADC) or DAR2 purified versions of the same (SCAb-ADCD2). Each of the preparations comprise a same cytotoxin. The studies are conducted using cynomolgus monkeys as a test system. Survival, clinical signs, body weights, food consumption, clinical pathology (hematology, coagulation, clinical chemistry, and urinalysis), toxicokinetics, gross necropsy findings, organ weights, and histopathologic examinations are documented and compared.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. An engineered IgG1 monoclonal antibody comprising one or more unpaired cysteine residues, wherein the engineered antibody binds SEZ6;
   wherein the engineered antibody comprises (i) a cysteine residue at heavy chain position 220 and a deletion of a cysteine residue at light chain position 214, (ii) a cysteine residue at heavy chain position 220 and substitution of a cysteine residue at light chain position 214, (iii) a cysteine residue at light chain position 214 and a deletion of a cysteine residue at heavy chain position 220, or (iv) a cysteine residue at light chain position 214 and a substitution of a cysteine residue at heavy chain position 220;
   wherein the engineered antibody comprises native cysteine residues at heavy chain positions 226 and 229;
   and wherein the engineered antibody comprises (a) three CDRs of a light chain variable region comprising an amino acid sequence set forth as SEQ ID NO: 190 or 192; and three CDRs of a heavy chain variable region comprising an amino acid sequence set forth as SEQ ID NO: 191; or (b) three CDRs of a light chain variable region comprising an amino acid sequence set forth as SEQ ID NO: 172, and three CDRs of a heavy chain variable region comprising an amino acid sequence set forth as SEQ ID NO: 173.

2. The engineered antibody of claim 1 wherein the engineered antibody comprises a humanized antibody or a CDR grafted antibody.

3. The engineered antibody of claim 1 wherein the engineered antibody comprises two light chains, two heavy chains and two unpaired cysteine residues.

4. The engineered antibody of claim 3 wherein each of the two light chains comprises an unpaired cysteine residue at position 214.

5. The engineered antibody of claim 3 wherein each of the two heavy chains comprises an unpaired cysteine residue at position C220.

6. An antibody drug conjugate, comprising an engineered IgG1 monoclonal antibody and a cytotoxic agent, wherein the engineered antibody binds SEZ6;
   wherein the engineered antibody comprises (i) a cysteine residue at heavy chain position 220 and a deletion of a cysteine residue at light chain position 214, (ii) a cysteine residue at heavy chain position 220 and substitution of a cysteine residue at light chain position 214, (iii) a cysteine residue at light chain position 214 and a deletion of a cysteine residue at heavy chain position 220, or (iv) a cysteine residue at light chain position 214 and a substitution of a cysteine residue at heavy chain position 220;
   wherein the engineered antibody comprises native cysteine residues at heavy chain positions 226 and 229;
   wherein the engineered antibody comprises: (a) three CDRs of a light chain variable region comprising an amino acid sequence set forth as SEQ ID NO: 190 or 192, and three CDRs of a heavy chain variable region comprising an amino acid sequence set forth as SEQ ID NO: 191; or (b) three CDRs of a light chain variable region comprising an amino acid sequence set forth as SEQ ID NO: 172, and three CDRs of a heavy chain variable region comprising an amino acid sequence set forth as SEQ ID NO: 173; and
   wherein the antibody is conjugated to the cytotoxic agent via the cysteine residue at light chain position 214 or the cysteine residue at heavy chain position 220.

7. The antibody drug conjugate of claim 6 wherein the engineered antibody comprises a humanized antibody or a CDR grafted antibody.

8. The antibody drug conjugate of claim 6 wherein the engineered antibody comprises two light chains, two heavy chains and two unpaired cysteine residues.

9. The antibody drug conjugate of claim 6, wherein the engineered antibody comprises two light chains and two heavy chains, wherein
   each of the two light chains comprises a cysteine residue at position 214.

10. The antibody drug conjugate of claim 6, wherein the engineered antibody comprises two light chains and two heavy chains, wherein
    each of the two heavy chains comprises a cysteine residue at position C220.

11. A pharmaceutical composition comprising the engineered antibody of claim 1 and a pharmaceutically acceptable carrier.

12. A pharmaceutical composition comprising the antibody drug conjugate of claim 6 and a pharmaceutically acceptable carrier.

13. The engineered antibody of claim 1, comprising
    (a) residues 24-34 of SEQ ID NO: 190 for CDR-L1, residues 50-56 of SEQ ID NO: 190 for CDR-L2, residues 89-97 of SEQ ID NO: 190 for CDR-L3, residues 26-32 of SEQ ID NO: 191 for CDR-H1, residues 52-56 of SEQ ID NO: 191 for CDR-H2, and residues 95-102 of SEQ ID NO: 191 for CDR-H3, wherein the residues are numbered according to Chothia; or
    (b) residues 24-34 of SEQ ID NO: 192 for CDR-L1, residues 50-56 of SEQ ID NO: 192 for CDR-L2, residues 89-97 of SEQ ID NO: 192 for CDR-L3, residues 26-32 of SEQ ID NO: 191 for CDR-H1, residues 52-56 of SEQ ID NO: 191 for CDR-H2, and residues 95-102 of SEQ ID NO: 191 for CDR-H3, wherein the residues are numbered according to Chothia.

14. The engineered antibody of claim 1, comprising
    (a) residues 30-36 of SEQ ID NO: 190 for CDR-L1, residues 46-55 of SEQ ID NO: 190 for CDR-L2, residues 89-96 of SEQ ID NO: 190 for CDR-L3, residues 30-35 of SEQ ID NO: 191 for CDR-H1, residues 47-58 of SEQ ID NO: 191 for CDR-H2, and residues 93-101 of SEQ ID NO: 191 for CDR-H3, wherein the residues are numbered according to MacCallum; or (b) residues 30-36 of SEQ ID NO: 192 for CDR-L1, residues 46-55 of SEQ ID NO: 192 for CDR-L2, residues 89-96 of SEQ ID NO: 192 for CDR-L3, residues 30-35 of SEQ ID NO: 191 for CDR-H1, residues 47-58 of SEQ ID NO: 191 for CDR-H2, and residues 93-101 of SEQ ID NO: 191 for CDR-H3, wherein the residues are numbered according to MacCallum.

15. The engineered antibody of claim 1, comprising
   (a) residues 24-34 of SEQ ID NO: 190 for CDR-L1, residues 50-56 of SEQ ID NO: 190 for CDR-L2, residues 89-97 of SEQ ID NO: 190 for CDR-L3, residues 31-35 of SEQ ID NO: 191 for CDR-H1, residues 50-65 of SEQ ID NO: 191 for CDR-H2, and residues 95-102 of SEQ ID NO: 191 for CDR-H3, wherein the residues are numbered according to Kabat; or
   (b) residues 24-34 of SEQ ID NO: 192 for CDR-L1, residues 50-56 of SEQ ID NO: 192 for CDR-L2, residues 89-97 of SEQ ID NO: 192 for CDR-L3, residues 31-35 of SEQ ID NO: 191 for CDR-H1, residues 50-65 of SEQ ID NO: 191 for CDR-H2, and residues 95-102 of SEQ ID NO: 191 for CDR-H3, wherein the residues are numbered according to Kabat.

16. The engineered antibody of claim 1, wherein the engineered antibody comprises
   (a) a light chain constant region comprising an amino acid sequence set forth as SEQ ID NO: 403 and a heavy chain constant region comprising an amino acid sequence set forth as SEQ ID NO: 500;
   (b) a light chain constant region comprising an amino acid sequence set forth as SEQ ID NO: 403 and a heavy chain constant region comprising an amino acid sequence set forth as SEQ ID NO: 501;
   (c) a light chain constant region comprising an amino acid sequence set forth as SEQ ID NO: 502 and a heavy chain constant region comprising an amino acid sequence set forth as SEQ ID NO: 404; or
   (d) a light chain constant region comprising an amino acid sequence set forth as SEQ ID NO: 503 and a heavy chain constant region comprising an amino acid sequence set forth as SEQ ID NO: 404.

17. The engineered antibody of claim 1, wherein the engineered antibody comprises
   (a) a light chain constant region comprising an amino acid sequence set forth as SEQ ID NO: 504 and a heavy chain constant region comprising an amino acid sequence set forth as SEQ ID NO: 500;
   (b) a light chain constant region comprising an amino acid sequence set forth as SEQ ID NO: 504 and a heavy chain constant region comprising an amino acid sequence set forth as SEQ ID NO: 501;
   (c) a light chain constant region comprising an amino acid sequence set forth as SEQ ID NO: 505 and a heavy chain constant region comprising an amino acid sequence set forth as SEQ ID NO: 404; or
   (d) a light chain constant region comprising an amino acid sequence set forth as SEQ ID NO: 506 and a heavy chain constant region comprising an amino acid sequence set forth as SEQ ID NO: 404.

18. The engineered antibody of claim 1 comprising:
   (a) a light chain variable region comprising an amino acid sequence set forth as SEQ ID NO: 190 and a heavy chain variable region comprising an amino acid sequence set forth as SEQ ID NO: 191;
   (b) a light chain variable region comprising an amino acid sequence set forth as SEQ ID NO: 192 and a heavy chain variable region comprising an amino acid sequence set forth as SEQ ID NO: 191; or
   (c) a light chain variable region comprising an amino acid sequence set forth as SEQ ID NO: 172 and a heavy chain variable region comprising an amino acid sequence set forth as SEQ ID NO: 173.

19. The engineered antibody of claim 1 comprising:
   (a) a light chain comprising an amino acid sequence set forth as SEQ ID NO: 513 and a heavy chain comprising an amino acid sequence set forth as SEQ ID NO: 515;
   (b) a light chain comprising an amino acid sequence set forth as SEQ ID NO: 513 and a heavy chain comprising an amino acid sequence set forth as SEQ ID NO: 516;
   (c) a light chain comprising an amino acid sequence set forth as SEQ ID NO: 517 and a heavy chain comprising an amino acid sequence set forth as SEQ ID NO: 514; or
   (d) a light chain comprising an amino acid sequence set forth as SEQ ID NO: 518 and a heavy chain comprising an amino acid sequence set forth as SEQ ID NO: 514.

20. The engineered antibody of claim 1, wherein the engineered antibody is conjugated to a cytotoxic agent via the cysteine residue at light chain position 214 or the cysteine residue at heavy chain position 220.

21. The engineered antibody of claim 20, wherein the cytotoxic agent is an auristatin, a maytansinoid, a calicheamicin or a radioisotope.

22. The antibody drug conjugate of claim 6, wherein the engineered antibody comprises:
   (a) residues 24-34 of SEQ ID NO: 190 for CDR-L1, residues 50-56 of SEQ ID NO: 190 for CDR-L2, residues 89-97 of SEQ ID NO: 190 for CDR-L3, residues 26-32 of SEQ ID NO: 191 for CDR-H1, residues 52-56 of SEQ ID NO: 191 for CDR-H2, and residues 95-102 of SEQ ID NO: 191 for CDR-H3, wherein the residues are numbered according to Chothia; or
   (b) residues 24-34 of SEQ ID NO: 192 for CDR-L1, residues 50-56 of SEQ ID NO: 192 for CDR-L2, residues 89-97 of SEQ ID NO: 192 for CDR-L3, residues 26-32 of SEQ ID NO: 191 for CDR-H1, residues 52-56 of SEQ ID NO: 191 for CDR-H2, and residues 95-102 of SEQ ID NO: 191 for CDR-H3, wherein the residues are numbered according to Chothia.

23. The antibody drug conjugate of claim 6, wherein the engineered antibody comprises:
   (a) residues 30-36 of SEQ ID NO: 190 for CDR-L1, residues 46-55 of SEQ ID NO: 190 for CDR-L2, residues 89-96 of SEQ ID NO: 190 for CDR-L3, residues 30-35 of SEQ ID NO: 191 for CDR-H1, residues 47-58 of SEQ ID NO: 191 for CDR-H2, and residues 93-101 of SEQ ID NO: 191 for CDR-H3, wherein the residues are numbered according to MacCallum; or
   (b) residues 30-36 of SEQ ID NO: 192 for CDR-L1, residues 46-55 of SEQ ID NO: 192 for CDR-L2, residues 89-96 of SEQ ID NO: 192 for CDR-L3, residues 30-35 of SEQ ID NO: 191 for CDR-H1, residues 47-58 of SEQ ID NO: 191 for CDR-H2, and residues 93-101 of SEQ ID NO: 191 for CDR-H3, wherein the residues are numbered according to MacCallum.

24. The antibody drug conjugate of claim 6, wherein the engineered antibody comprises:
   (a) residues 24-34 of SEQ ID NO: 190 for CDR-L1, residues 50-56 of SEQ ID NO: 190 for CDR-L2, residues 89-97 of SEQ ID NO: 190 for CDR-L3, residues 31-35 of SEQ ID NO: 191 for CDR-H1, residues 50-65 of SEQ ID NO: 191 for CDR-H2, and residues 95-102 of SEQ ID NO: 191 for CDR-H3, wherein the residues are numbered according to Kabat; or (b) residues 24-34 of SEQ ID NO: 192 for CDR-L1, residues 50-56 of SEQ ID NO: 192 for CDR-L2, residues 89-97 of SEQ ID NO: 192 for CDR-L3, residues 31-35 of SEQ ID NO: 191 for CDR-H1, residues 50-65 of SEQ ID NO: 191 for CDR-H2, and residues 95-102 of SEQ ID NO: 191 for CDR-H3, wherein the residues are numbered according to Kabat.

25. The antibody drug conjugate of claim 6, wherein the engineered antibody comprises:
   (a) a light chain constant region comprising an amino acid sequence set forth as SEQ ID NO: 403 and a heavy chain constant region comprising an amino acid sequence set forth as SEQ ID NO: 500;
   (b) a light chain constant region comprising an amino acid sequence set forth as SEQ ID NO: 403 and a heavy chain constant region comprising an amino acid sequence set forth as SEQ ID NO: 501;
   (c) a light chain constant region comprising an amino acid sequence set forth as SEQ ID NO: 502 and a heavy chain constant region comprising an amino acid sequence set forth as SEQ ID NO: 404; or
   (d) a light chain constant region comprising an amino acid sequence set forth as SEQ ID NO: 503 and a heavy chain constant region comprising an amino acid sequence set forth as SEQ ID NO: 404.

26. The antibody drug conjugate of claim 6, wherein the engineered antibody comprises:
   (a) a light chain constant region comprising an amino acid sequence set forth as SEQ ID NO: 504 and a heavy chain constant region comprising an amino acid sequence set forth as SEQ ID NO: 500;
   (b) a light chain constant region comprising an amino acid sequence set forth as SEQ ID NO: 504 and a heavy chain constant region comprising an amino acid sequence set forth as SEQ ID NO: 501;
   (c) a light chain constant region comprising an amino acid sequence set forth as SEQ ID NO: 505 and a heavy chain constant region comprising an amino acid sequence set forth as SEQ ID NO: 404; or
   (d) a light chain constant region comprising an amino acid sequence set forth as SEQ ID NO: 506 and a heavy chain constant region comprising an amino acid sequence set forth as SEQ ID NO: 404.

27. The antibody drug conjugate of claim 6, wherein the engineered antibody comprises:
   (a) a light chain variable region comprising an amino acid sequence set forth as SEQ ID NO: 190 and a heavy chain variable region comprising an amino acid sequence set forth as SEQ ID NO: 191;
   (b) a light chain variable region comprising an amino acid sequence set forth as SEQ ID NO: 192 and a heavy chain variable region comprising an amino acid sequence set forth as SEQ ID NO: 191; or
   (c) a light chain variable region comprising an amino acid sequence set forth as SEQ ID NO: 172 and a heavy chain variable region comprising an amino acid sequence set forth as SEQ ID NO: 173.

28. The antibody drug conjugate of claim 6, wherein the engineered antibody comprises:
   (a) a light chain comprising an amino acid sequence set forth as SEQ ID NO: 513 and a heavy chain comprising an amino acid sequence set forth as SEQ ID NO: 515;
   (b) a light chain comprising an amino acid sequence set forth as SEQ ID NO: 513 and a heavy chain comprising an amino acid sequence set forth as SEQ ID NO: 516;
   (c) a light chain comprising an amino acid sequence set forth as SEQ ID NO: 517 and a heavy chain comprising an amino acid sequence set forth as SEQ ID NO: 514; or
   (d) a light chain comprising an amino acid sequence set forth as SEQ ID NO: 518 and a heavy chain comprising an amino acid sequence set forth as SEQ ID NO: 514.

29. The antibody drug conjugate of claim 6, wherein the cytotoxic agent is an auristatin, a maytansinoid, a calicheamicin or a radioisotope.

30. The antibody drug conjugate of claim 6, wherein the antibody drug conjugate has a drug loading of 2.

31. The pharmaceutical composition of claim 12 comprising an average drug to antibody ratio (DAR) of 2+/−0.4.

32. The pharmaceutical composition of claim 12, wherein the predominant antibody drug conjugate species is present at a concentration of greater than 70%.

33. An engineered IgG1 monoclonal antibody comprising one or more unpaired cysteine residues, wherein the engineered antibody binds SEZ6;
   wherein the engineered antibody comprises (i) a cysteine residue at light chain position 214 and a deletion of a cysteine residue at heavy chain position 220 or (ii) a cysteine residue at light chain position 214 and a substitution of a cysteine residue at heavy chain position 220;
   wherein the engineered antibody comprises native cysteine residues at heavy chain positions 226 and 229;
   and wherein the engineered antibody comprises three CDRs of a light chain variable region comprising an amino acid sequence set forth as SEQ ID NO: 190 and three CDRs of a heavy chain variable region comprising an amino acid sequence set forth as SEQ ID NO: 191.

34. The engineered antibody of claim 33, wherein the engineered antibody comprises a light chain constant region comprising an amino acid sequence set forth as SEQ ID NO: 403 and a heavy chain constant region comprising an amino acid sequence set forth as SEQ ID NO: 500.

35. The engineered antibody of claim 34, wherein the engineered antibody comprises residues 24-34 of SEQ ID NO: 190 for CDR-L1, residues 50-56 of SEQ ID NO: 190 for CDR-L2, residues 89-97 of SEQ ID NO: 190 for CDR-L3, residues 26-32 of SEQ ID NO: 191 for CDR-H1, residues 52-56 of SEQ ID NO: 191 for CDR-H2, and residues 95-102 of SEQ ID NO: 191 for CDR-H3, wherein the residues are numbered according to Chothia.

36. The engineered antibody of claim 34, wherein the engineered antibody comprises residues 30-36 of SEQ ID NO: 190 for CDR-L1, residues 46-55 of SEQ ID NO: 190 for CDR-L2, residues 89-96 of SEQ ID NO: 190 for CDR-L3, residues 30-35 of SEQ ID NO: 191 for CDR-H1, residues 47-58 of SEQ ID NO: 191 for CDR-H2, and residues 93-101 of SEQ ID NO: 191 for CDR-H3, wherein the residues are numbered according to MacCallum.

37. The engineered antibody of claim 34, wherein the engineered antibody comprises residues 24-34 of SEQ ID NO: 190 for CDR-L1, residues 50-56 of SEQ ID NO: 190 for CDR-L2, residues 89-97 of SEQ ID NO: 190 for CDR-L3, residues 31-35 of SEQ ID NO: 191 for CDR-H1, residues 50-65 of SEQ ID NO: 191 for CDR-H2, and residues 95-102 of SEQ ID NO: 191 for CDR-H3, wherein the residues are numbered according to Kabat.

38. An antibody drug conjugate, comprising an engineered IgG1 monoclonal antibody and a cytotoxic agent, wherein the engineered antibody binds SEZ6;
wherein the engineered antibody comprises (i) a cysteine residue at light chain position 214 and a deletion of a cysteine residue at heavy chain position 220, or (ii) a cysteine residue at light chain position 214 and a substitution of a cysteine residue at heavy chain position 220;
wherein the engineered antibody comprises native cysteine residues at heavy chain positions 226 and 229;
wherein the engineered antibody comprises three CDRs of a light chain variable region comprising an amino acid sequence set forth as SEQ ID NO: 190, and three CDRs of a heavy chain variable region comprising an amino acid sequence set forth as SEQ ID NO: 191; and
wherein the antibody is conjugated to the cytotoxic agent via the cysteine residue at light chain position 214.

39. The antibody drug conjugate of claim 38, wherein the engineered antibody comprises a light chain constant region comprising an amino acid sequence set forth as SEQ ID NO: 403 and a heavy chain constant region comprising an amino acid sequence set forth as SEQ ID NO: 500.

40. The antibody drug conjugate of claim 39, wherein the engineered antibody comprises residues 24-34 of SEQ ID NO: 190 for CDR-L1, residues 50-56 of SEQ ID NO: 190 for CDR-L2, residues 89-97 of SEQ ID NO: 190 for CDR-L3, residues 26-32 of SEQ ID NO: 191 for CDR-H1, residues 52-56 of SEQ ID NO: 191 for CDR-H2, and residues 95-102 of SEQ ID NO: 191 for CDR-H3, wherein the residues are numbered according to Chothia.

41. The antibody drug conjugate of claim 39, wherein the engineered antibody comprises residues 30-36 of SEQ ID NO: 190 for CDR-L1, residues 46-55 of SEQ ID NO: 190 for CDR-L2, residues 89-96 of SEQ ID NO: 190 for CDR-L3, residues 30-35 of SEQ ID NO: 191 for CDR-H1, residues 47-58 of SEQ ID NO: 191 for CDR-H2, and residues 93-101 of SEQ ID NO: 191 for CDR-H3, wherein the residues are numbered according to MacCallum.

42. The antibody drug conjugate of claim 39, wherein the engineered antibody comprises residues 24-34 of SEQ ID NO: 190 for CDR-L1, residues 50-56 of SEQ ID NO: 190 for CDR-L2, residues 89-97 of SEQ ID NO: 190 for CDR-L3, residues 31-35 of SEQ ID NO: 191 for CDR-H1, residues 50-65 of SEQ ID NO: 191 for CDR-H2, and residues 95-102 of SEQ ID NO: 191 for CDR-H3, wherein the residues are numbered according to Kabat.

* * * * *

```
                         SEQUENCE LISTING

<160> NUMBER OF SEQ ID NOS: 544

<210> SEQ ID NO 1
<211> LENGTH: 4249
<212> TYPE: DNA
<213> ORGANISM: Homo sapiens
<220> FEATURE:
<221> NAME/KEY: misc_feature
<223> OTHER INFORMATION: SEZ6 isoform 1 mRNA

<400> SEQUENCE: 1
gatccccggc gccgtcgcca ggcgctggcc gtggtgctga ttctgtcagg cgctggcggc        60
ggcagcggcg gtgacggctg cggcccgct ccctctaccc ggccggaccc ggctctgccc       120
ccgcgcccaa gccccaccaa gccccccgcc ctcccgccgc ggtcccagcc cagggcgcgg       180
ccgcaaccag caccatgcgc ccggtagccc tgctgctcct gccctcgctg ctggcgctcc       240
tggctcacgg actctcttta gaggcccaa ccgtggggaa aggacaagcc ccaggcatcg       300
aggagacaga tggcgagctg acagcagccc ccacacctga gcagccagaa cgaggcgtcc       360
actttgtcac aacagccccc accttgaagc tgctcaacca ccacccgctg cttgaggaat       420
tcctacaaga ggggctggaa aagggagatg aggagctgag gccagcactg cccttccagc       480
ctgacccacc tgcacccttc accccaagtc cccttccccg cctggccaac caggacagcc       540
gccctgtctt taccagcccc actccagcca tggctgcggt acccactcag ccccagtcca       600
```

```
aggagggacc ctggagtccg gagtcagagt cccctatgct tcgaatcaca gctcccctac      660
ctccagggcc cagcatggca gtgcccaccc taggcccagg ggagatagcc agcactacac      720
cccccagcag agcctggaca ccaacccaag agggtcctgg agacatggga aggccgtggg      780
ttgcagaggt tgtgtcccag ggcgcaggga tcgggatcca ggggaccatc acctcctcca      840
cagcttcagg agatgatgag gagaccacca ctaccaccac catcatcacc accaccatca      900
ccacagtcca gacaccaggc ccttgtagct ggaatttctc aggcccagag ggctctctgg      960
actcccctac agacctcagc tcccccactg atgttggcct ggactgcttc ttctacatct     1020
ctgtctaccc tggctatggc gtggaaatca aggtccagaa tatcagcctc cgggaagggg     1080
agacagtgac tgtggaaggc ctgggggggc ctgacccact gcccctggcc aaccagtctt     1140
tcctgctgcg gggccaagtc atccgcagcc ccacccacca agcggccctg aggttccaga     1200
gcctcccgcc accggctggc cctggcacct tccatttcca ttaccaagcc tatctcctga     1260
gctgccactt tccccgtcgt ccagcttatg gagatgtgac tgtcaccagc ctccacccag     1320
ggggtagtgc ccgcttccat tgtgccctg gctaccagct gaagggcgcc aggcatctca     1380
cctgtctcaa tgccacccag cccttctggg attcaaagga gcccgtctgc atcgctgctt     1440
gcggcggagt gatccgcaat gccaccaccg ccgcatcgt ctctccaggc ttcccgggca     1500
actacagcaa caacctcacc tgtcactggc tgcttgaggc tcctgagggc agcggctac     1560 acctgcactt tgagaaggtt tccctggcag aggatgatga caggctcatc attcgcaatg     1620
gggacaacgt ggaggcccca ccagtgtatg attcctatga ggtggaatac ctgcccattg     1680
agggcctgct cagctctggc aaacacttct ttgttgagct cagtactgac agcagcgggg     1740
cagctgcagg catggccctg cgctatgagg ccttccagca gggccattgc tatgagccct     1800
ttgtcaaata cggtaacttc agcagcagca caccccaccta ccctgtgggt accactgtgg     1860
agttcagctg cgaccctggc tacaccctgg agcagggctc catcatcatc gagtgtgttg     1920 accccccacga ccccccagtgg aatgagacag agccagcctg ccgagccgtg tgcagcgggg     1980
agatcacaga ctcggctggc gtggtactct ctcccaactg gccagagccc tacggtcgtg     2040
ggcaggattg tatctgggt gtgcatgtgg aagaggacaa gcgcatcatg ctggacatcc     2100
gagtgctgcg cataggccct ggtgatgtgc ttaccttcta tgatggggat gacctgacgg     2160
cccgggttct gggccagtac tcagggcccc gtagccactt caagctcttt acctccatgg     2220
ctgatgtcac cattcagttc cagtcggacc ccgggacctc agtgctgggc taccagcagg     2280
gcttcgtcat ccacttcttt gaggtgcccc gcaatgacac atgtccggag ctgcctgaga     2340
tccccaatgg ctggaagagc ccatcgcagc ctgagctagt gcacggcacc gtggtcactt     2400
accagtgcta ccctggctac caggtagtgg atccagtgt cctcatgtgc cagtgggacc     2460
taacttggag tgaggacctg ccctcatgcc agagggtgac ttcctgccac gatcctggag     2520
atgtggagca cagccgacgc ctcatatcca gccccaagtt tcccgtgggg gccaccgtgc     2580
aatatatctg tgaccagggt tttgtgctga tgggcagctc catcctcacc tgccatgatc     2640
gccaggctgg cagccccaag tggagtgacc gggcccctaa atgtctcctg gaacagctca     2700
agccatgcca tggtctcagt gcccctgaga atggtgcccg aagtcctgag aagcagctac     2760
acccagcagg ggccaccatc cacttctcgt gtgcccctgg ctatgtgctg aagggccagg     2820
ccagcatcaa gtgtgtgcct gggcacccct cgcattggag tgacccccca cccatctgta     2880
gggctgcctc tctggatggg ttctacaaca gtcgcagcct ggatgttgcc aaggcacctg     2940
ctgcctccag caccctggat gctgcccaca ttgcagctgc catcttcttg ccactggtgg     3000
```

```
cgatggtgtt gttggtagga ggtgtatact tctacttctc caggctccag ggaaaaagct    3060
ccctgcagct gccccgcccc cgccccgcc cctacaaccg cattaccata gagtcagcgt    3120
ttgacaatcc aacttacgag actggatctc tttcctttgc aggagacgag agaatatgaa    3180
gtctccatct aggtggggc agtctaggga agtcaactca gacttgcacc acagtccagc    3240
agcaaggctc cttgcttcct gctgtccctc cacctcctgt atataccacc taggaggaga    3300
tgccaccaag ccctcaagaa gttgtgccct tccccgcctg cgatgccac catgcctat     3360 tttcttggtg tcattgccca cttggggccc ttcattgggc ccatgtcagg gggcatctac    3420
ctgtgggaag aacatagctg gagcacaagc atcaacagcc agcatcctga gcctcctcat    3480
gccctggacc agcctggaac acactagcag agcaggagta cctttctcca catgaccacc    3540
atcccgccct ggcatggcaa cctgcagcag gattaacttg accatggtgg gaactgcacc    3600
agggtactcc tcacagcgca tcaccaatgg ccaaaactcc tctcaacggt gacctctggg    3660
tagtcctggc atgccaacat cagcctcttg ggaggtctct agttctctaa agttctggac    3720
agttctgcct cctgccctgt cccagtggag gcagtaattc taggagatcc taaggggttc    3780 aggggggaccc taccccacc tcaggttggg cttccctggg cactcatgct ccacaccaaa    3840
gcaggacacg ccattttcca ctgaccaccc tataccctga ggaaagggag actttcctcc    3900
gatgtttatt tagctgttgc aaacatcttc accctaatag tccctcctcc aattccagcc    3960
acttgtcagg ctctcctctt gaccactgtg ttatgggata aggggagggg gtgggcatat    4020
tctggagagg agcagaggtc caaggaccca ggaatttggc atggaacagg tggtaggaga    4080
gccccaggga gacgcccagg agctggctga aagccacttt gtacatgtaa tgtattatat    4140
ggggtctggg ctccagccag agaacaatct tttatttctg ttgtttcctt attaaaatgg    4200
tgttttggga aaaaaaaaaa aaaaaaaaa aaaaaaaaa aaaaaaaa                   4249

<210> SEQ ID NO 2
<211> LENGTH: 4234
<212> TYPE: DNA
<213> ORGANISM: Homo sapiens
<220> FEATURE:
<221> NAME/KEY: misc_feature
<223> OTHER INFORMATION: SEZ6 isoform 2 mRNA

<400> SEQUENCE: 2
gatccccggc gccgtcgcca ggcgctggcc gtggtgctga ttctgtcagg cgctggcggc      60
ggcagcggcg gtgacggctg cggccccgct ccctctaccc ggccggaccc ggctctgccc     120
ccgcgcccaa gccccaccaa gccccccgcc ctcccgccgc ggtcccagcc cagggcgcgg     180
ccgcaaccag caccatgcgc ccggtagccc tgctgctcct gccctcgctg ctggcgctcc     240
tggctcacgg actctcttta gaggccccaa ccgtggggaa aggacaagcc ccaggcatcg     300
aggagacaga tggcgagctg acagcagccc ccacacctga gcagccagaa cgaggcgtcc     360
actttgtcac aacagccccc accttgaagc tgctcaacca ccaccgctg cttgaggaat     420 tcctacaaga ggggctggaa aagggagatg aggagctgag gccagcactg cccttccagc     480
ctgacccacc tgcacccttc accccaagtc cccttccccg cctggccaac caggacagcc     540
gccctgtctt taccagcccc actccagcca tggctgcggt acccactcag ccccagtcca     600
aggagggacc ctggagtccg gagtcagagt cccctatgct tcgaatcaca gctcccctac     660 ctccaggggcc cagcatggca gtgcccaccc taggcccagg ggagatagcc agcactacac     720
cccccagcag agcctggaca ccaacccaag agggtcctgg agacatggga aggccgtggg     780
```

```
ttgcagaggt tgtgtcccag ggcgcaggga tcgggatcca ggggaccatc acctcctcca      840
cagcttcagg agatgatgag gagaccacca ctaccaccac catcatcacc accaccatca      900
ccacagtcca gacaccaggc ccttgtagct ggaatttctc aggcccagag ggctctctgg      960
actcccctac agacctcagc tcccccactg atgttggcct ggactgcttc ttctacatct     1020
ctgtctaccc tggctatggc gtggaaatca aggtccagaa tatcagcctc cgggaagggg     1080
agacagtgac tgtggaaggc ctggggggcc ctgacccact gccctggcc aaccagtctt      1140 tcctgctgcg gggccaagtc atccgcagcc ccacccacca agcggccctg aggttccaga     1200
gcctcccgcc accggctggc cctggcacct tccatttcca ttaccaagcc tatctcctga     1260
gctgccactt tccccgtcgt ccagcttatg gagatgtgac tgtcaccagc ctccacccag     1320
ggggtagtgc ccgcttccat gtgccactg gctaccagct gaagggcgcc aggcatctca      1380
cctgtctcaa tgccacccag cccttctggg attcaaagga gcccgtctgc atcgctgctt     1440
gcggcggagt gatccgcaat gccaccaccg gccgcatcgt ctctccaggc ttcccgggca     1500
actacagcaa caacctcacc tgtcactggc tgcttgaggc tcctgagggc cagcggctac     1560
acctgcactt tgagaaggtt tccctggcag aggatgatga caggctcatc attcgcaatg     1620
gggacaacgt ggaggcccca ccagtgtatg attcctatga ggtggaatac ctgcccattg     1680
agggcctgct cagctctggc aaacacttct ttgttgagct cagtactgac agcagcgggg     1740
cagctgcagg catggccctg cgctatgagg ccttccagca gggccattgc tatgagccct     1800
ttgtcaaata cggtaacttc agcagcagca cacccaccta ccctgtgggt accactgtgg     1860
agttcagctg cgaccctggc tacaccctgg agcagggctc catcatcatc gagtgtgttg     1920 accccccacga ccccccagtgg aatgagacag agccagcctg ccgagccgtg tgcagcgggg    1980
agatcacaga ctcggctggc gtggtactct ctcccaactg gccagagccc tacggtcgtg     2040
ggcaggattg tatctggggt gtgcatgtgg aagaggacaa gcgcatcatg ctggacatcc     2100
gagtgctgcg cataggccct ggtgatgtgc ttaccttcta tgatgggat gacctgacgg      2160 cccggggttct gggccagtac tcagggcccc gtagccactt caagctcttt acctccatgg     2220
ctgatgtcac cattcagttc cagtcggacc ccgggacctc agtgctgggc taccagcagg     2280
gcttcgtcat ccacttcttt gaggtgcccc gcaatgacac atgtccggag ctgcctgaga     2340
tccccaatgg ctggaagagc ccatcgcagc ctgagctagt gcacggcacc gtggtcactt     2400
accagtgcta ccctggctac caggtagtgg gatccagtgt cctcatgtgc cagtgggacc     2460
taacttggag tgaggacctg ccctcatgcc agagggtgac ttcctgccac gatcctggag     2520
atgtggagca gccgacgc ctcatatcca gccccaagtt tcccgtgggg gccaccgtgc       2580
aatatatctg tgaccaggt tttgtgctga tgggcagctc catcctcacc tgccatgatc      2640
gccaggctgg cagccccaag tggagtgacc gggcccctaa atgtctcctg gaacagctca     2700
agccatgcca tggtctcagt gcccctgaga atggtgcccg aagtcctgag aagcagctac     2760
acccagcagg ggccaccatc cacttctcgt gtgcccctgg ctatgtgctg aagggccagg     2820
ccagcatcaa gtgtgtgcct ggcaccccct cgcattggag tgaccccca cccatctgta      2880 gggctgcctc tctggatggg ttctacaaca gtcgcagcct ggatgttgcc aaggcacctg     2940
ctgcctccag caccctggat gctgcccaca ttgcagctgc catcttcttg ccactggtgg     3000
cgatggtgtt gttggtagga ggtgtatact tctacttctc caggctccag ggaaaaagct     3060
ccctgcagct gccccgcccc cgcccccgcc cctacaaccg cattaccata gagtcagcgt     3120
```

-continued

```
ttgacaatcc aacttacgag actggagaga cgagagaata tgaagtctcc atctaggtgg    3180
gggcagtcta gggaagtcaa ctcagacttg caccacagtc cagcagcaag gctccttgct    3240
tcctgctgtc cctccacctc ctgtatatac cacctaggag gagatgccac caagccctca    3300
agaagttgtg cccttccccg cctgcgatgc ccaccatggc ctatttcctt ggtgtcattg    3360
cccacttggg gcccttcatt gggcccatgt caggggggcat ctacctgtgg gaagaacata    3420
gctggagcac aagcatcaac agccagcatc ctgagcctcc tcatgccctg gaccagcctg    3480
gaacacacta gcagagcagg agtacctttc tccacatgac caccatcccg ccctggcatg    3540
gcaacctgca gcaggattaa cttgaccatg gtgggaactg caccagggta ctcctcacag    3600
cgccatcacc aatggccaaa actcctctca acggtgacct ctgggtagtc ctggcatgcc    3660
aacatcagcc tcttggggagg tctctagttc tctaaagttc tggacagttc tgcctcctgc    3720
cctgtcccag tggaggcagt aattctagga gatcctaagg ggttcagggg gaccctaccc    3780
ccacctcagg ttgggcttcc ctgggcactc atgctccaca ccaaagcagg acacgccatt    3840
ttccactgac cacctatac cctgaggaaa gggagacttt cctccgatgt ttatttagct    3900
gttgcaaaca tcttcaccct aatagtccct cctccaattc cagccacttg tcaggctctc    3960
ctcttgacca ctgtgttatg ggataagggg aggggggtggg catattctgg agaggagcag    4020
aggtccaagg acccaggaat ttggcatgga acaggtggta ggagagcccc agggagacgc    4080
ccaggagctg gctgaaagcc actttgtaca tgtaatgtat tatatggggt ctgggctcca    4140
gccagagaac aatctttttat ttctgttgtt tccttattaa aatggtgttt ttggaaaaaa    4200
aaaaaaaaaa aaaaaaaaaa aaaaaaaaaa aaaa                               4234
```

<210> SEQ ID NO 3
<211> LENGTH: 994
<212> TYPE: PRT
<213> ORGANISM: Homo sapiens
<220> FEATURE:
<221> NAME/KEY: MISC_FEATURE
<223> OTHER INFORMATION: SEZ6 isoform 1 precursor protein
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (20)..(994)
<223> OTHER INFORMATION: Mature protein

<400> SEQUENCE: 3

```
Met Arg Pro Val Ala Leu Leu Leu Pro Ser Leu Leu Ala Leu Leu
1               5                   10                  15

Ala His Gly Leu Ser Leu Glu Ala Pro Thr Val Gly Lys Gly Gln Ala
                20                  25                  30

Pro Gly Ile Glu Glu Thr Asp Gly Glu Leu Thr Ala Ala Pro Thr Pro
            35                  40                  45

Glu Gln Pro Glu Arg Gly Val His Phe Val Thr Thr Ala Pro Thr Leu
        50                  55                  60

Lys Leu Leu Asn His His Pro Leu Leu Glu Glu Phe Leu Gln Glu Gly
65                  70                  75                  80

Leu Glu Lys Gly Asp Glu Glu Leu Arg Pro Ala Leu Pro Phe Gln Pro
                85                  90                  95

Asp Pro Pro Ala Pro Phe Thr Pro Ser Pro Leu Pro Arg Leu Ala Asn
            100                 105                 110

Gln Asp Ser Arg Pro Val Phe Thr Ser Pro Thr Pro Ala Met Ala Ala
```

-continued

```
            115                 120                 125
Val Pro Thr Gln Pro Gln Ser Lys Glu Gly Pro Trp Ser Pro Glu Ser
            130                 135                 140
Glu Ser Pro Met Leu Arg Ile Thr Ala Pro Leu Pro Pro Gly Pro Ser
145                 150                 155                 160
Met Ala Val Pro Thr Leu Gly Pro Gly Glu Ile Ala Ser Thr Thr Pro
                    165                 170                 175
Pro Ser Arg Ala Trp Thr Pro Thr Gln Glu Gly Pro Gly Asp Met Gly
                180                 185                 190
Arg Pro Trp Val Ala Glu Val Ser Gln Gly Ala Gly Ile Gly Ile
            195                 200                 205
Gln Gly Thr Ile Thr Ser Ser Thr Ala Ser Gly Asp Asp Glu Glu Thr
            210                 215                 220
Thr Thr Thr Thr Thr Ile Ile Thr Thr Thr Ile Thr Thr Val Gln Thr
225                 230                 235                 240
Pro Gly Pro Cys Ser Trp Asn Phe Ser Gly Pro Glu Gly Ser Leu Asp
                245                 250                 255
Ser Pro Thr Asp Leu Ser Ser Pro Thr Asp Val Gly Leu Asp Cys Phe
                260                 265                 270
Phe Tyr Ile Ser Val Tyr Pro Gly Tyr Gly Val Glu Ile Lys Val Gln
                275                 280                 285
Asn Ile Ser Leu Arg Glu Gly Glu Thr Val Thr Val Glu Gly Leu Gly
            290                 295                 300
Gly Pro Asp Pro Leu Pro Leu Ala Asn Gln Ser Phe Leu Leu Arg Gly
305                 310                 315                 320
Gln Val Ile Arg Ser Pro Thr His Gln Ala Ala Leu Arg Phe Gln Ser
                325                 330                 335
Leu Pro Pro Pro Ala Gly Pro Gly Thr Phe His Phe His Tyr Gln Ala
                340                 345                 350
Tyr Leu Leu Ser Cys His Phe Pro Arg Arg Pro Ala Tyr Gly Asp Val
                355                 360                 365
Thr Val Thr Ser Leu His Pro Gly Gly Ser Ala Arg Phe His Cys Ala
            370                 375                 380
Thr Gly Tyr Gln Leu Lys Gly Ala Arg His Leu Thr Cys Leu Asn Ala
385                 390                 395                 400
Thr Gln Pro Phe Trp Asp Ser Lys Glu Pro Val Cys Ile Ala Ala Cys
                405                 410                 415
Gly Gly Val Ile Arg Asn Ala Thr Thr Gly Arg Ile Val Ser Pro Gly
                420                 425                 430
Phe Pro Gly Asn Tyr Ser Asn Asn Leu Thr Cys His Trp Leu Leu Glu
                435                 440                 445
Ala Pro Glu Gly Gln Arg Leu His Leu His Phe Glu Lys Val Ser Leu
            450                 455                 460
Ala Glu Asp Asp Asp Arg Leu Ile Ile Arg Asn Gly Asp Asn Val Glu
465                 470                 475                 480
Ala Pro Pro Val Tyr Asp Ser Tyr Glu Val Glu Tyr Leu Pro Ile Glu
                485                 490                 495
Gly Leu Leu Ser Ser Gly Lys His Phe Phe Val Glu Leu Ser Thr Asp
                500                 505                 510
Ser Ser Gly Ala Ala Ala Gly Met Ala Leu Arg Tyr Glu Ala Phe Gln
            515                 520                 525
Gln Gly His Cys Tyr Glu Pro Phe Val Lys Tyr Gly Asn Phe Ser Ser
            530                 535                 540
```

```
Ser Thr Pro Thr Tyr Pro Val Gly Thr Thr Val Glu Phe Ser Cys Asp
545                 550                 555                 560

Pro Gly Tyr Thr Leu Glu Gln Gly Ser Ile Ile Glu Cys Val Asp
            565                 570                 575

Pro His Asp Pro Gln Trp Asn Glu Thr Glu Pro Ala Cys Arg Ala Val
                580                 585                 590

Cys Ser Gly Glu Ile Thr Asp Ser Ala Gly Val Val Leu Ser Pro Asn
            595                 600                 605

Trp Pro Glu Pro Tyr Gly Arg Gly Gln Asp Cys Ile Trp Gly Val His
            610                 615                 620

Val Glu Glu Asp Lys Arg Ile Met Leu Asp Ile Arg Val Leu Arg Ile
625                 630                 635                 640

Gly Pro Gly Asp Val Leu Thr Phe Tyr Asp Gly Asp Asp Leu Thr Ala
                645                 650                 655

Arg Val Leu Gly Gln Tyr Ser Gly Pro Arg Ser His Phe Lys Leu Phe
            660                 665                 670

Thr Ser Met Ala Asp Val Thr Ile Gln Phe Gln Ser Asp Pro Gly Thr
        675                 680                 685

Ser Val Leu Gly Tyr Gln Gln Gly Phe Val Ile His Phe Phe Glu Val
        690                 695                 700

Pro Arg Asn Asp Thr Cys Pro Glu Leu Pro Glu Ile Pro Asn Gly Trp
705                 710                 715                 720

Lys Ser Pro Ser Gln Pro Glu Leu Val His Gly Thr Val Val Thr Tyr
                725                 730                 735

Gln Cys Tyr Pro Gly Tyr Gln Val Val Gly Ser Ser Val Leu Met Cys
            740                 745                 750

Gln Trp Asp Leu Thr Trp Ser Glu Asp Leu Pro Ser Cys Gln Arg Val
            755                 760                 765

Thr Ser Cys His Asp Pro Gly Asp Val Glu His Ser Arg Arg Leu Ile
        770                 775                 780

Ser Ser Pro Lys Phe Pro Val Gly Ala Thr Val Gln Tyr Ile Cys Asp
785                 790                 795                 800

Gln Gly Phe Val Leu Met Gly Ser Ser Ile Leu Thr Cys His Asp Arg
                805                 810                 815

Gln Ala Gly Ser Pro Lys Trp Ser Asp Arg Ala Pro Lys Cys Leu Leu
            820                 825                 830

Glu Gln Leu Lys Pro Cys His Gly Leu Ser Ala Pro Glu Asn Gly Ala
            835                 840                 845

Arg Ser Pro Glu Lys Gln Leu His Pro Ala Gly Ala Thr Ile His Phe
            850                 855                 860

Ser Cys Ala Pro Gly Tyr Val Leu Lys Gly Gln Ala Ser Ile Lys Cys
865                 870                 875                 880

Val Pro Gly His Pro Ser His Trp Ser Asp Pro Pro Ile Cys Arg
                885                 890                 895

Ala Ala Ser Leu Asp Gly Phe Tyr Asn Ser Arg Ser Leu Asp Val Ala
            900                 905                 910

Lys Ala Pro Ala Ala Ser Ser Thr Leu Asp Ala Ala His Ile Ala Ala
            915                 920                 925

Ala Ile Phe Leu Pro Leu Val Ala Met Val Leu Leu Val Gly Gly Val
        930                 935                 940

Tyr Phe Tyr Phe Ser Arg Leu Gln Gly Lys Ser Ser Leu Gln Leu Pro
945                 950                 955                 960
```

Arg Pro Arg Pro Arg Pro Tyr Asn Arg Ile Thr Ile Glu Ser Ala Phe
            965                 970                 975

Asp Asn Pro Thr Tyr Glu Thr Gly Ser Leu Ser Phe Ala Gly Asp Glu
            980                 985                 990

Arg Ile

<210> SEQ ID NO 4
<211> LENGTH: 993
<212> TYPE: PRT
<213> ORGANISM: Homo sapiens
<220> FEATURE:
<221> NAME/KEY: MISC_FEATURE
<223> OTHER INFORMATION: SEZ6 isoform 2 precursor protein
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (20)..(993)
<223> OTHER INFORMATION: Mature protein

<400> SEQUENCE: 4

Met Arg Pro Val Ala Leu Leu Leu Pro Ser Leu Leu Ala Leu Leu
1               5                   10                  15

Ala His Gly Leu Ser Leu Glu Ala Pro Thr Val Gly Lys Gly Gln Ala
                20                  25                  30

Pro Gly Ile Glu Glu Thr Asp Gly Glu Leu Thr Ala Ala Pro Thr Pro
            35                  40                  45

Glu Gln Pro Glu Arg Gly Val His Phe Val Thr Thr Ala Pro Thr Leu
50                  55                  60

Lys Leu Leu Asn His His Pro Leu Leu Glu Glu Phe Leu Gln Glu Gly
65                  70                  75                  80

Leu Glu Lys Gly Asp Glu Leu Arg Pro Ala Leu Pro Phe Gln Pro
                85                  90                  95

Asp Pro Pro Ala Pro Phe Thr Pro Ser Pro Leu Pro Arg Leu Ala Asn
            100                 105                 110

Gln Asp Ser Arg Pro Val Phe Thr Ser Pro Thr Pro Ala Met Ala Ala
            115                 120                 125

Val Pro Thr Gln Pro Gln Ser Lys Glu Gly Pro Trp Ser Pro Glu Ser
130                 135                 140

Glu Ser Pro Met Leu Arg Ile Thr Ala Pro Leu Pro Pro Gly Pro Ser
145                 150                 155                 160

Met Ala Val Pro Thr Leu Gly Pro Gly Glu Ile Ala Ser Thr Thr Pro
                165                 170                 175

Pro Ser Arg Ala Trp Thr Pro Thr Gln Glu Gly Pro Gly Asp Met Gly
            180                 185                 190

Arg Pro Trp Val Ala Glu Val Ser Gln Gly Ala Gly Ile Gly Ile
            195                 200                 205

Gln Gly Thr Ile Thr Ser Ser Thr Ala Ser Gly Asp Asp Glu Thr
            210                 215                 220

Thr Thr Thr Thr Thr Ile Ile Thr Thr Thr Ile Thr Thr Val Gln Thr
225                 230                 235                 240

Pro Gly Pro Cys Ser Trp Asn Phe Ser Gly Pro Glu Gly Ser Leu Asp
            245                 250                 255

Ser Pro Thr Asp Leu Ser Ser Pro Thr Asp Val Gly Leu Asp Cys Phe
            260                 265                 270

Phe Tyr Ile Ser Val Tyr Pro Gly Tyr Gly Val Glu Ile Lys Val Gln

```
            275                 280                 285
Asn Ile Ser Leu Arg Glu Gly Glu Thr Val Thr Val Glu Gly Leu Gly
290                 295                 300

Gly Pro Asp Pro Leu Pro Leu Ala Asn Gln Ser Phe Leu Leu Arg Gly
305                 310                 315                 320

Gln Val Ile Arg Ser Pro Thr His Gln Ala Ala Leu Arg Phe Gln Ser
                325                 330                 335

Leu Pro Pro Pro Ala Gly Pro Gly Thr Phe His Phe His Tyr Gln Ala
                340                 345                 350

Tyr Leu Leu Ser Cys His Phe Pro Arg Arg Pro Ala Tyr Gly Asp Val
                355                 360                 365

Thr Val Thr Ser Leu His Pro Gly Gly Ser Ala Arg Phe His Cys Ala
370                 375                 380

Thr Gly Tyr Gln Leu Lys Gly Ala Arg His Leu Thr Cys Leu Asn Ala
385                 390                 395                 400

Thr Gln Pro Phe Trp Asp Ser Lys Glu Pro Val Cys Ile Ala Ala Cys
                405                 410                 415

Gly Gly Val Ile Arg Asn Ala Thr Thr Gly Arg Ile Val Ser Pro Gly
                420                 425                 430

Phe Pro Gly Asn Tyr Ser Asn Asn Leu Thr Cys His Trp Leu Leu Glu
                435                 440                 445

Ala Pro Glu Gly Gln Arg Leu His Leu His Phe Glu Lys Val Ser Leu
450                 455                 460

Ala Glu Asp Asp Arg Leu Ile Ile Arg Asn Gly Asp Asn Val Glu
465                 470                 475                 480

Ala Pro Pro Val Tyr Asp Ser Tyr Glu Val Glu Tyr Leu Pro Ile Glu
                485                 490                 495

Gly Leu Leu Ser Ser Gly Lys His Phe Phe Val Glu Leu Ser Thr Asp
                500                 505                 510

Ser Ser Gly Ala Ala Ala Gly Met Ala Leu Arg Tyr Glu Ala Phe Gln
                515                 520                 525

Gln Gly His Cys Tyr Glu Pro Phe Val Lys Tyr Gly Asn Phe Ser Ser
                530                 535                 540

Ser Thr Pro Thr Tyr Pro Val Gly Thr Thr Val Glu Phe Ser Cys Asp
545                 550                 555                 560

Pro Gly Tyr Thr Leu Glu Gln Gly Ser Ile Ile Glu Cys Val Asp
                565                 570                 575

Pro His Asp Pro Gln Trp Asn Glu Thr Glu Pro Ala Cys Arg Ala Val
                580                 585                 590

Cys Ser Gly Glu Ile Thr Asp Ser Ala Gly Val Val Leu Ser Pro Asn
                595                 600                 605

Trp Pro Glu Pro Tyr Gly Arg Gly Gln Asp Cys Ile Trp Gly Val His
                610                 615                 620

Val Glu Glu Asp Lys Arg Ile Met Leu Asp Ile Arg Val Leu Arg Ile
625                 630                 635                 640

Gly Pro Gly Asp Val Leu Thr Phe Tyr Asp Gly Asp Leu Thr Ala
                645                 650                 655

Arg Val Leu Gly Gln Tyr Ser Gly Pro Arg Ser His Phe Lys Leu Phe
                660                 665                 670

Thr Ser Met Ala Asp Val Thr Ile Gln Phe Gln Ser Asp Pro Gly Thr
                675                 680                 685

Ser Val Leu Gly Tyr Gln Gln Gly Phe Val Ile His Phe Phe Glu Val
                690                 695                 700
```

```
Pro Arg Asn Asp Thr Cys Pro Glu Leu Pro Glu Ile Pro Asn Gly Trp
705                 710                 715                 720

Lys Ser Pro Ser Gln Pro Glu Leu Val His Gly Thr Val Val Thr Tyr
            725                 730                 735

Gln Cys Tyr Pro Gly Tyr Gln Val Val Gly Ser Ser Val Leu Met Cys
            740                 745                 750

Gln Trp Asp Leu Thr Trp Ser Glu Asp Leu Pro Ser Cys Gln Arg Val
        755                 760                 765

Thr Ser Cys His Asp Pro Gly Asp Val Glu His Ser Arg Arg Leu Ile
    770                 775                 780

Ser Ser Pro Lys Phe Pro Val Gly Ala Thr Val Gln Tyr Ile Cys Asp
785                 790                 795                 800

Gln Gly Phe Val Leu Met Gly Ser Ser Ile Leu Thr Cys His Asp Arg
                805                 810                 815

Gln Ala Gly Ser Pro Lys Trp Ser Asp Arg Ala Pro Lys Cys Leu Leu
            820                 825                 830

Glu Gln Leu Lys Pro Cys His Gly Leu Ser Ala Pro Glu Asn Gly Ala
        835                 840                 845

Arg Ser Pro Glu Lys Gln Leu His Pro Ala Gly Ala Thr Ile His Phe
    850                 855                 860

Ser Cys Ala Pro Gly Tyr Val Leu Lys Gly Gln Ala Ser Ile Lys Cys
865                 870                 875                 880

Val Pro Gly His Pro Ser His Trp Ser Asp Pro Pro Ile Cys Arg
                885                 890                 895

Ala Ala Ser Leu Asp Gly Phe Tyr Asn Ser Arg Ser Leu Asp Val Ala
            900                 905                 910

Lys Ala Pro Ala Ala Ser Ser Thr Leu Asp Ala Ala His Ile Ala Ala
        915                 920                 925

Ala Ile Phe Leu Pro Leu Val Ala Met Val Leu Leu Val Gly Gly Val
    930                 935                 940

Tyr Phe Tyr Phe Ser Arg Leu Gln Gly Lys Ser Ser Leu Gln Leu Pro
945                 950                 955                 960

Arg Pro Arg Pro Arg Pro Tyr Asn Arg Ile Thr Ile Glu Ser Ala Phe
                965                 970                 975

Asp Asn Pro Thr Tyr Glu Thr Gly Glu Thr Arg Glu Tyr Glu Val Ser
            980                 985                 990

Ile
```

```
<210> SEQ ID NO 5
<211> LENGTH: 2925
<212> TYPE: DNA
<213> ORGANISM: Homo sapiens
<220> FEATURE:
<221> NAME/KEY: misc_feature
<223> OTHER INFORMATION: cDNA sequence of hSCRx17 ORF

<400> SEQUENCE: 5
ctgagcctgg aggccccaac cgtggggaaa ggacaagccc caggcatcga ggagacagat      60
ggcgagctga cagcagcccc cacacctgag cagccagaac gaggcgtcca ctttgtcaca     120
acagccccca ccttgaagct gctcaaccac cacccgctgc ttgaggaatt cctacaagag     180
gggctggaaa agggagatga ggagttgagg ccagcactgc ccttccagcc tgacccacct     240
gcacccttca ccccaagtcc ccttcccccgc ctggccaacc aggacagccg ccctgtcttt     300
accagcccca ctccagccat ggctgcggta cccactcagc cccagtccaa ggagggaccc     360
```

```
tggagtccgg agtcagagtc ccctatgctt cgaatcacag ctcccctacc tccagggccc    420
agcatggcag tgcccaccct aggcccaggg gagatagcca gcactacacc ccccagcaga    480
gcctggacac caacccaaga gggtcctgga cacatgggaa ggccgtgggt tgcagaggtt    540
gtgtcccagg gcgcggggat cgggatccag ggaccatcc cctcctccac agcttcagga    600
gatgatgagg agaccaccac taccaccacc atcatcacca ccaccatcac cacagtccag    660
acaccaggcc cttgtagctg gaatttctca ggcccagagg gctctctgga ctcccctaca    720
gacctcagct cccccactga tgttggcctg gactgcttct tctacatctc tgtctaccct    780
ggctatggcg tggaaatcaa ggtccagaat atcagcctcc gggaaggggga gacagtgact    840 gtggaaggcc tggggggggcc cgacccactg cccctggcca accagtcttt cctgctgcgg    900
ggccaagtca tccgcagccc cacccaccaa gcggccctga ggttccagag cctcccgcca    960
ccggctggcc ctggcacctt ccatttccat taccaagcct atctcctgag ctgccacttt   1020
ccccgtcgtc cagcttatgg agatgtgact gtcaccagcc tccacccagg gggtagtgcc   1080
cgcttccatt gtgccactgg ctaccagctg aagggcgcca ggcatctcac ctgtctcaat   1140
gccacccagc ccttctggga ttcaaaggag cccgtctgca tcgctgcttg cggcggagtg   1200
atccgcaatg ccaccaccgg ccgcatcgtc tctccaggct ccccgggcaa ctacagcaac   1260
aacctcacct gtcactggct gcttgaggct cctgagggcc agcggctaca cctgcacttt   1320
gagaaggttt ccctggcaga ggatgatgac aggctcatca ttcgcaatgg ggacaacgtg   1380
gaggccccac cagtgtatga ttcctatgag gtggaatacc tgcccattga gggcctgctc   1440
agctctggca aacacttctt tgttgagctc agtactgaca gcagcgggggc agctgcaggc   1500 atggcccctgc gctatgaggc cttccagcag ggccattgct atgagccctt tgtcaaatac   1560
ggtaacttca gcagcagcac acccacctac cctgtgggta ccactgtgga gttcagctgc   1620
gaccctggct acaccctgga gcagggctcc atcatcatcg agtgtgttga ccccacgac   1680 ccccagtgga atgagacaga gccagcctgc cgagccgtgt gcagcgggga gatcacagac   1740
tcggctggcg tggtactctc tcccaactgg ccagagccct acggtcgtgg gcaggattgt   1800
atctggggtg tgcatgtgga agaggacaag cgcatcatgc tggacatccg agtgctgcgc   1860
ataggccctg gtgatgtgct taccttctat gatggggatg acctgacggc ccgggttctg   1920
ggccagtact cagggcccccg tagccacttc aagctctttta cctccatggc tgatgtcacc   1980
attcagttcc agtcggaccc cggggacctca gtgctgggct accagcaggg cttcgtcatc   2040
cacttctttg aggtgccccg caatgacaca tgtccggagc tgcctgagat ccccaatggc   2100
tggaagagcc catcgcagcc tgagctagtg cacggcaccg tggtcactta ccagtgctac   2160
cctggctacc aggtagtggg atccagtgtc tcatgtgcc agtgggacct aacttggagt   2220
gaggacctgc cctcatgcca gagggtgact tcctgccacg atcctggaga tgtggagcac   2280
agccgacgcc tcatatccag ccccaagttt ccgtggggg ccaccgtgca atatatctgt   2340
gaccagggtt ttgtgctgat gggcagctcc atcctcacct gccatgatcg ccaggctggc   2400
agccccaagt ggagtgaccg ggcccctaaa tgtctcctgg aacagctcaa gccatgccat   2460
ggtctcagtg cccctgagaa tggtgcccga agtcctgaga agcagctaca cccagcaggg   2520
gccaccatcc acttctcgtg tgcccctggc tatgtgctga agggccaggc cagcatcaag   2580
tgtgtgcctg gcacccctc gcattggagt gacccccac ccatctgtag gctgcctct   2640 ctggatgggt tctacaacag tcgcagcctg gatgttgcca aggcacctgc tgcctccagc   2700
```

-continued

```
acctggatg ctgcccacat tgcagctgcc atcttcttgc cactggtggc gatggtgttg   2760
ttggtaggag gtgtatactt ctacttctcc aggctccagg gaaaaagctc cctgcagctg   2820
ccccgccccc gccccgccc ctacaaccgc attaccatag agtcagcgtt tgacaatcca   2880
acttacgaga ctggatctct ttcctttgca ggagacgaga gaata                   2925
```

<210> SEQ ID NO 6
<211> LENGTH: 975
<212> TYPE: PRT
<213> ORGANISM: Homo sapiens
<220> FEATURE:
<221> NAME/KEY: MISC_FEATURE
<223> OTHER INFORMATION: hSCRx17 protein

<400> SEQUENCE: 6

```
Leu Ser Leu Glu Ala Pro Thr Val Gly Lys Gly Gln Ala Pro Gly Ile
1               5                   10                  15

Glu Glu Thr Asp Gly Glu Leu Thr Ala Ala Pro Thr Pro Glu Gln Pro
            20                  25                  30

Glu Arg Gly Val His Phe Val Thr Ala Pro Thr Leu Lys Leu Leu
        35                  40                  45

Asn His His Pro Leu Leu Glu Glu Phe Leu Gln Glu Gly Leu Glu Lys
    50                  55                  60

Gly Asp Glu Glu Leu Arg Pro Ala Leu Pro Phe Gln Pro Asp Pro Pro
65                  70                  75                  80

Ala Pro Phe Thr Pro Ser Pro Leu Pro Arg Leu Ala Asn Gln Asp Ser
                85                  90                  95

Arg Pro Val Phe Thr Ser Pro Thr Pro Ala Met Ala Ala Val Pro Thr
            100                 105                 110

Gln Pro Gln Ser Lys Glu Gly Pro Trp Ser Pro Glu Ser Glu Ser Pro
        115                 120                 125

Met Leu Arg Ile Thr Ala Pro Leu Pro Pro Gly Pro Ser Met Ala Val
    130                 135                 140

Pro Thr Leu Gly Pro Gly Glu Ile Ala Ser Thr Thr Pro Pro Ser Arg
145                 150                 155                 160

Ala Trp Thr Pro Thr Gln Glu Gly Pro Gly Asp Met Gly Arg Pro Trp
                165                 170                 175

Val Ala Glu Val Val Ser Gln Gly Ala Gly Ile Gly Ile Gln Gly Thr
            180                 185                 190

Ile Thr Ser Ser Thr Ala Ser Gly Asp Asp Glu Glu Thr Thr Thr Thr
        195                 200                 205

Thr Thr Ile Ile Thr Thr Thr Ile Thr Thr Val Gln Thr Pro Gly Pro
    210                 215                 220

Cys Ser Trp Asn Phe Ser Gly Pro Glu Gly Ser Leu Asp Ser Pro Thr
225                 230                 235                 240

Asp Leu Ser Ser Pro Thr Asp Val Gly Leu Asp Cys Phe Phe Tyr Ile
                245                 250                 255

Ser Val Tyr Pro Gly Tyr Gly Val Glu Ile Lys Val Gln Asn Ile Ser
            260                 265                 270

Leu Arg Glu Gly Glu Thr Val Thr Val Glu Gly Leu Gly Gly Pro Asp
        275                 280                 285

Pro Leu Pro Leu Ala Asn Gln Ser Phe Leu Leu Arg Gly Gln Val Ile
    290                 295                 300

Arg Ser Pro Thr His Gln Ala Ala Leu Arg Phe Gln Ser Leu Pro Pro
305                 310                 315                 320
```

```
Pro Ala Gly Pro Gly Thr Phe His Phe His Tyr Gln Ala Tyr Leu Leu
            325                 330                 335

Ser Cys His Phe Pro Arg Arg Pro Ala Tyr Gly Asp Val Thr Val Thr
        340                 345                 350

Ser Leu His Pro Gly Gly Ser Ala Arg Phe His Cys Ala Thr Gly Tyr
            355                 360                 365

Gln Leu Lys Gly Ala Arg His Leu Thr Cys Leu Asn Ala Thr Gln Pro
    370                 375                 380

Phe Trp Asp Ser Lys Glu Pro Val Cys Ile Ala Ala Cys Gly Gly Val
385                 390                 395                 400

Ile Arg Asn Ala Thr Thr Gly Arg Ile Val Ser Pro Gly Phe Pro Gly
                405                 410                 415

Asn Tyr Ser Asn Asn Leu Thr Cys His Trp Leu Leu Glu Ala Pro Glu
            420                 425                 430

Gly Gln Arg Leu His Leu His Phe Glu Lys Val Ser Leu Ala Glu Asp
        435                 440                 445

Asp Asp Arg Leu Ile Ile Arg Asn Gly Asp Asn Val Glu Ala Pro Pro
    450                 455                 460

Val Tyr Asp Ser Tyr Glu Val Glu Tyr Leu Pro Ile Glu Gly Leu Leu
465                 470                 475                 480

Ser Ser Gly Lys His Phe Phe Val Glu Leu Ser Thr Asp Ser Ser Gly
                485                 490                 495

Ala Ala Ala Gly Met Ala Leu Arg Tyr Glu Ala Phe Gln Gln Gly His
            500                 505                 510

Cys Tyr Glu Pro Phe Val Lys Tyr Gly Asn Phe Ser Ser Ser Thr Pro
        515                 520                 525

Thr Tyr Pro Val Gly Thr Thr Val Glu Phe Ser Cys Asp Pro Gly Tyr
    530                 535                 540

Thr Leu Glu Gln Gly Ser Ile Ile Glu Cys Val Asp Pro His Asp
545                 550                 555                 560

Pro Gln Trp Asn Glu Thr Glu Pro Ala Cys Arg Ala Val Cys Ser Gly
                565                 570                 575

Glu Ile Thr Asp Ser Ala Gly Val Val Leu Ser Pro Asn Trp Pro Glu
            580                 585                 590

Pro Tyr Gly Arg Gly Gln Asp Cys Ile Trp Gly Val His Val Glu Glu
        595                 600                 605

Asp Lys Arg Ile Met Leu Asp Ile Arg Val Leu Arg Ile Gly Pro Gly
    610                 615                 620

Asp Val Leu Thr Phe Tyr Asp Gly Asp Leu Thr Ala Arg Val Leu
625                 630                 635                 640

Gly Gln Tyr Ser Gly Pro Arg Ser His Phe Lys Leu Phe Thr Ser Met
                645                 650                 655

Ala Asp Val Thr Ile Gln Phe Gln Ser Asp Pro Gly Thr Ser Val Leu
            660                 665                 670

Gly Tyr Gln Gln Gly Phe Val Ile His Phe Phe Glu Val Pro Arg Asn
        675                 680                 685

Asp Thr Cys Pro Glu Leu Pro Glu Ile Pro Asn Gly Trp Lys Ser Pro
    690                 695                 700

Ser Gln Pro Glu Leu Val His Gly Thr Val Thr Tyr Gln Cys Tyr
705                 710                 715                 720

Pro Gly Tyr Gln Val Val Gly Ser Ser Val Leu Met Cys Gln Trp Asp
                725                 730                 735

Leu Thr Trp Ser Glu Asp Leu Pro Ser Cys Gln Arg Val Thr Ser Cys
```

```
                        740                 745                 750
His Asp Pro Gly Asp Val Glu His Ser Arg Arg Leu Ile Ser Ser Pro
            755                 760                 765

Lys Phe Pro Val Gly Ala Thr Val Gln Tyr Ile Cys Asp Gln Gly Phe
        770                 775                 780

Val Leu Met Gly Ser Ser Ile Leu Thr Cys His Asp Arg Gln Ala Gly
785                 790                 795                 800

Ser Pro Lys Trp Ser Asp Arg Ala Pro Lys Cys Leu Leu Glu Gln Leu
                805                 810                 815

Lys Pro Cys His Gly Leu Ser Ala Pro Glu Asn Gly Ala Arg Ser Pro
            820                 825                 830

Glu Lys Gln Leu His Pro Ala Gly Ala Thr Ile His Phe Ser Cys Ala
        835                 840                 845

Pro Gly Tyr Val Leu Lys Gly Gln Ala Ser Ile Lys Cys Val Pro Gly
    850                 855                 860

His Pro Ser His Trp Ser Asp Pro Pro Ile Cys Arg Ala Ala Ser
865                 870                 875                 880

Leu Asp Gly Phe Tyr Asn Ser Arg Ser Leu Asp Val Ala Lys Ala Pro
                885                 890                 895

Ala Ala Ser Ser Thr Leu Asp Ala Ala His Ile Ala Ala Ile Phe
            900                 905                 910

Leu Pro Leu Val Ala Met Val Leu Leu Val Gly Gly Val Tyr Phe Tyr
        915                 920                 925

Phe Ser Arg Leu Gln Gly Lys Ser Ser Leu Gln Leu Pro Arg Pro Arg
    930                 935                 940

Pro Arg Pro Tyr Asn Arg Ile Thr Ile Glu Ser Ala Phe Asp Asn Pro
945                 950                 955                 960

Thr Tyr Glu Thr Gly Ser Leu Ser Phe Ala Gly Asp Glu Arg Ile
                965                 970                 975

<210> SEQ ID NO 7
<211> LENGTH: 994
<212> TYPE: PRT
<213> ORGANISM: Homo sapiens
<220> FEATURE:
<221> NAME/KEY: MISC_FEATURE
<223> OTHER INFORMATION: hSEZ6 BC146292 protein

<400> SEQUENCE: 7

Met Arg Pro Val Ala Leu Leu Leu Pro Ser Leu Ala Leu Leu
1               5                   10                  15

Ala His Gly Leu Ser Leu Glu Ala Pro Thr Val Gly Lys Gly Gln Ala
            20                  25                  30

Pro Gly Ile Glu Glu Thr Asp Gly Glu Leu Thr Ala Ala Pro Thr Pro
        35                  40                  45

Glu Gln Pro Glu Arg Gly Val His Phe Val Thr Thr Ala Pro Thr Leu
    50                  55                  60

Lys Leu Leu Asn His His Pro Leu Leu Glu Glu Phe Leu Gln Glu Gly
65                  70                  75                  80

Leu Glu Lys Gly Asp Glu Glu Leu Arg Pro Ala Leu Pro Phe Gln Pro
                85                  90                  95

Asp Pro Pro Ala Pro Phe Thr Pro Ser Pro Leu Pro Arg Leu Ala Asn
            100                 105                 110

Gln Asp Ser Arg Pro Val Phe Thr Ser Pro Thr Pro Ala Met Ala Ala
        115                 120                 125
```

-continued

Val Pro Thr Gln Pro Gln Ser Lys Glu Gly Pro Trp Ser Pro Glu Ser
    130                 135                 140

Glu Ser Pro Met Leu Arg Ile Thr Ala Pro Leu Pro Pro Gly Pro Ser
145                 150                 155                 160

Met Ala Val Pro Thr Leu Gly Pro Gly Glu Ile Ala Ser Thr Thr Pro
                165                 170                 175

Pro Ser Arg Ala Trp Thr Pro Thr Gln Glu Gly Pro Gly Asp Met Gly
            180                 185                 190

Arg Pro Trp Val Ala Glu Val Val Ser Gln Gly Ala Gly Ile Gly Ile
        195                 200                 205

Gln Gly Thr Ile Thr Ser Ser Thr Ala Ser Gly Asp Asp Glu Glu Thr
    210                 215                 220

Thr Thr Thr Thr Thr Ile Ile Thr Thr Thr Ile Thr Thr Val Gln Thr
225                 230                 235                 240

Pro Gly Pro Cys Ser Trp Asn Phe Ser Gly Pro Gly Ser Leu Asp
                245                 250                 255

Ser Pro Thr Asp Leu Ser Ser Pro Thr Asp Val Gly Leu Asp Cys Phe
            260                 265                 270

Phe Tyr Ile Ser Val Tyr Pro Gly Tyr Gly Val Glu Ile Lys Val Gln
        275                 280                 285

Asn Ile Ser Leu Arg Glu Gly Glu Thr Val Thr Val Glu Gly Leu Gly
    290                 295                 300

Gly Pro Asp Pro Leu Pro Leu Ala Asn Gln Ser Phe Leu Leu Arg Gly
305                 310                 315                 320

Gln Val Ile Arg Ser Pro Thr His Gln Ala Ala Leu Arg Phe Gln Ser
                325                 330                 335

Leu Pro Pro Pro Ala Gly Pro Gly Thr Phe His Phe His Tyr Gln Ala
            340                 345                 350

Tyr Leu Leu Ser Cys His Phe Pro Arg Arg Pro Ala Tyr Gly Asp Val
        355                 360                 365

Thr Val Thr Ser Leu His Pro Gly Gly Ser Ala Arg Phe His Cys Ala
    370                 375                 380

Thr Gly Tyr Gln Leu Lys Gly Ala Arg His Leu Thr Cys Leu Asn Ala
385                 390                 395                 400

Thr Gln Pro Phe Trp Asp Ser Lys Glu Pro Val Cys Ile Gly Glu Cys
                405                 410                 415

Pro Gly Val Ile Arg Asn Ala Thr Thr Gly Arg Ile Val Ser Pro Gly
            420                 425                 430

Phe Pro Gly Asn Tyr Ser Asn Asn Leu Thr Cys His Trp Leu Leu Glu
        435                 440                 445

Ala Pro Glu Gly Gln Arg Leu His Leu His Phe Glu Lys Val Ser Leu
    450                 455                 460

Ala Glu Asp Asp Arg Leu Ile Ile Arg Asn Gly Asp Asn Val Glu
465                 470                 475                 480

Ala Pro Pro Val Tyr Asp Ser Tyr Glu Val Glu Tyr Leu Pro Ile Glu
                485                 490                 495

Gly Leu Leu Ser Ser Gly Lys His Phe Phe Val Glu Leu Ser Thr Asp
            500                 505                 510

Ser Ser Gly Ala Ala Ala Gly Met Ala Leu Arg Tyr Glu Ala Phe Gln
        515                 520                 525

Gln Gly His Cys Tyr Glu Pro Phe Val Lys Tyr Gly Asn Phe Ser Ser
    530                 535                 540

Ser Thr Pro Thr Tyr Pro Val Gly Thr Thr Val Glu Phe Ser Cys Asp

```
                  545                 550                 555                 560
           Pro Gly Tyr Thr Leu Glu Gln Gly Ser Ile Ile Glu Cys Val Asp
                           565                 570                 575
           Pro His Asp Pro Gln Trp Asn Glu Thr Glu Pro Ala Cys Arg Ala Val
                           580                 585                 590
           Cys Ser Gly Glu Ile Thr Asp Ser Ala Gly Val Val Leu Ser Pro Asn
                           595                 600                 605
           Trp Pro Glu Pro Tyr Gly Arg Gly Gln Asp Cys Ile Trp Gly Val His
               610                 615                 620
           Val Glu Glu Asp Lys Arg Ile Met Leu Asp Ile Arg Val Leu Arg Ile
           625                 630                 635                 640
           Gly Pro Gly Asp Val Leu Thr Phe Tyr Asp Gly Asp Leu Thr Ala
                               645                 650                 655
           Arg Val Leu Gly Gln Tyr Ser Gly Pro Arg Ser His Phe Lys Leu Phe
                           660                 665                 670
           Thr Ser Met Ala Asp Val Thr Ile Gln Phe Gln Ser Asp Pro Gly Thr
                           675                 680                 685
           Ser Val Leu Gly Tyr Gln Gln Gly Phe Val Ile His Phe Phe Glu Val
                           690                 695                 700
           Pro Arg Asn Asp Thr Cys Pro Glu Leu Pro Glu Ile Pro Asn Gly Trp
           705                 710                 715                 720
           Lys Ser Pro Ser Gln Pro Glu Leu Val His Gly Thr Val Val Thr Tyr
                               725                 730                 735
           Gln Cys Tyr Pro Gly Tyr Gln Val Val Gly Ser Ser Val Leu Met Cys
                           740                 745                 750
           Gln Trp Asp Leu Thr Trp Ser Glu Asp Leu Pro Ser Cys Gln Arg Val
                           755                 760                 765
           Thr Ser Cys His Asp Pro Gly Asp Val Glu His Ser Arg Arg Leu Ile
                           770                 775                 780
           Ser Ser Pro Lys Phe Pro Val Gly Ala Thr Val Gln Tyr Ile Cys Asp
           785                 790                 795                 800
           Gln Gly Phe Val Leu Met Gly Ser Ser Ile Leu Thr Cys His Asp Arg
                               805                 810                 815
           Gln Ala Gly Ser Pro Lys Trp Ser Asp Arg Ala Pro Lys Cys Leu Leu
                           820                 825                 830
           Glu Gln Leu Lys Pro Cys His Gly Leu Ser Ala Pro Glu Asn Gly Ala
                           835                 840                 845
           Arg Ser Pro Glu Lys Gln Leu His Pro Ala Gly Ala Thr Ile His Phe
           850                 855                 860
           Ser Cys Ala Pro Gly Tyr Val Leu Lys Gly Gln Ala Ser Ile Lys Cys
           865                 870                 875                 880
           Val Pro Gly His Pro Ser His Trp Ser Asp Pro Pro Ile Cys Arg
                               885                 890                 895
           Ala Ala Ser Leu Asp Gly Phe Tyr Asn Ser Arg Ser Leu Asp Val Ala
                               900                 905                 910
           Lys Ala Pro Ala Ala Ser Ser Thr Leu Asp Ala Ala His Ile Ala Ala
                           915                 920                 925
           Ala Ile Phe Leu Pro Leu Val Ala Met Val Leu Leu Val Gly Gly Val
                           930                 935                 940
           Tyr Phe Tyr Phe Ser Arg Leu Gln Gly Lys Ser Ser Leu Gln Leu Pro
           945                 950                 955                 960
           Arg Pro Arg Pro Arg Pro Tyr Asn Arg Ile Thr Ile Glu Ser Ala Phe
                               965                 970                 975
```

Asp Asn Pro Thr Tyr Glu Thr Gly Ser Leu Ser Phe Ala Gly Asp Glu
         980                 985                 990

Arg Ile

<210> SEQ ID NO 8
<211> LENGTH: 3483
<212> TYPE: DNA
<213> ORGANISM: Homo sapiens
<220> FEATURE:
<221> NAME/KEY: misc_feature
<223> OTHER INFORMATION: hSCRx17-Fc ORF

<400> SEQUENCE: 8

| | | | | | |
|---|---|---|---|---|---|
| atggagacag | acacactcct | gctatgggta | ctgctgctct | gggttccgg | gtccactggt | 60 |
| gacggcgcgc | ctggatccct | gagcctggag | gccccaaccg | tggggaaagg | acaagcccca | 120 |
| ggcatcgagg | agacagatgg | cgagctgaca | gcagccccca | cacctgagca | gccagaacga | 180 |
| ggcgtccact | ttgtcacaac | agccccacc | ttgaagctgc | tcaaccacca | cccgctgctt | 240 |
| gaggaattcc | tacaagaggg | gctggaaaag | ggagatgagg | agttgaggcc | agcactgccc | 300 |
| ttccagcctg | acccacctgc | acccttcacc | ccaagtcccc | ttcccgcct | ggccaaccag | 360 |
| gacagccgcc | ctgtctttac | cagccccact | ccagccatgg | ctgcggtacc | cactcagccc | 420 |
| cagtccaagg | agggaccctg | gagtccgag | tcagagtccc | ctatgcttcg | aatcacagct | 480 |
| ccctaccctc | cagggcccag | catggcagtg | cccaccctag | gcccagggga | gatagccagc | 540 |
| actacaccc | ccagcagagc | ctggacacca | acccaagagg | gtcctggaga | catgggaagg | 600 |
| ccgtggggttg | cagaggttgt | gtcccagggc | gcggggatcg | ggatccaggg | gaccatcacc | 660 |
| tcctccacag | cttcaggaga | tgatgaggag | accaccacta | ccaccaccat | catcaccacc | 720 |
| accatcacca | cagtccagac | accaggccct | tgtagctgga | atttctcagg | cccagagggc | 780 |
| tctctggact | ccctacaga | cctcagctcc | ccactgatg | ttggcctgga | ctgcttcttc | 840 |
| tacatctctg | tctaccctgg | ctatggcgtg | gaaatcaagg | tccagaatat | cagcctccgg | 900 |
| gaagggagaa | cagtgactgt | ggaaggcctg | gggggcccg | acccactgcc | cctggccaac | 960 |
| cagtctttcc | tgctgcgggg | ccaagtcatc | cgcagcccca | cccaccaagc | ggccctgagg | 1020 |
| ttccagagcc | tccgccacc | ggctggccct | ggcaccttcc | atttccatta | ccaagcctat | 1080 |
| ctcctgagct | gccactttcc | ccgtcgtcca | gcttatggag | atgtgactgt | caccagcctc | 1140 |
| cacccagggg | gtagtgcccg | cttccattgt | gccactggct | accagctgaa | gggcgccagg | 1200 |
| catctcacct | gtctcaatgc | cacccagccc | ttctgggatt | caaaggagcc | cgtctgcatc | 1260 |
| gctgcttgcg | gcggagtgat | ccgcaatgcc | accaccggcc | gcatcgtctc | tccaggcttc | 1320 |
| ccgggcaact | acagcaacaa | cctcacctgt | cactggctgc | ttgaggctcc | tgagggccag | 1380 |
| cggctacacc | tgcactttga | gaaggtttcc | ctggcagagg | atgatgacag | gctcatcatt | 1440 |
| cgcaatgggg | acaacgtgga | ggccccacca | gtgtatgatt | cctatgaggt | ggaatacctg | 1500 |
| cccattgagg | gcctgctcag | ctctggcaaa | cacttctttg | ttgagctcag | tactgacagc | 1560 |
| agcggggcag | ctgcaggcat | ggccctgcgc | tatgaggcct | tccagcaggg | ccattgctat | 1620 |
| gagccctttg | tcaaatacgg | taacttcagc | agcagcacac | ccacctaccc | tgtgggtacc | 1680 |
| actgtggagt | tcagctgcga | ccctggctac | accctggagc | agggctccat | catcatcgag | 1740 |
| tgtgttgacc | cccacgaccc | ccagtggaat | gagacagagc | cagcctgccg | agccgtgtgc | 1800 |
| agcggggaga | tcacagactc | ggctggcgtg | gtactctctc | ccaactggcc | agagcctac | 1860 |

-continued

| | |
|---|---|
| ggtcgtgggc aggattgtat ctggggtgtg catgtggaag aggacaagcg catcatgctg | 1920 |
| gacatccgag tgctgcgcat aggccctggt gatgtgctta ccttctatga tggggatgac | 1980 |
| ctgacggccc gggttctggg ccagtactca gggccccgta gccacttcaa gctctttacc | 2040 |
| tccatggctg atgtcaccat tcagttccag tcggaccccg ggacctcagt gctgggctac | 2100 |
| cagcagggct tcgtcatcca cttctttgag gtgccccgca atgacacatg tccggagctg | 2160 |
| cctgagatcc ccaatggctg gaagagccca tcgcagcctg agctagtgca cggcaccgtg | 2220 |
| gtcacttacc agtgctaccc tggctaccag gtagtgggat ccagtgtcct catgtgccag | 2280 |
| tgggacctaa cttggagtga ggacctgccc tcatgccaga gggtgacttc ctgccacgat | 2340 |
| cctggagatg tggagcacag ccgacgcctc atatccagcc caagtttcc cgtggggcc | 2400 |
| accgtgcaat atatctgtga ccagggtttt gtgctgatgg gcagctccat cctcacctgc | 2460 |
| catgatcgcc aggctggcag ccccaagtgg agtgaccggg cccctaaatg tctcctggaa | 2520 |
| cagctcaagc catgccatgg tctcagtgcc cctgagaatg gtgcccgaag tcctgagaag | 2580 |
| cagctacacc cagcaggggc caccatccac ttctcgtgtg cccctggcta tgtgctgaag | 2640 |
| ggccaggcca gcatcaagtg tgtgcctggg caccccctcgc attggagtga ccccccaccc | 2700 |
| atctgtaggg ctgcctctct ggatgggttc tacaacagtc gcagcctgga tgttgccaag | 2760 |
| gcacctgctg cctccagcac cctggatgct gcccacctgg ccggccacag atctgtcgag | 2820 |
| tgcccaccgt gccagcacc acctgtggca ggaccgtcag tcttcctctt ccccccaaaa | 2880 |
| cccaaggaca ccctcatgat ctcccggacc cctgaggtca cgtgcgtggt ggtggacgtg | 2940 |
| agccacgaag accccgaggt ccagttcaac tggtacgtgg acggcgtgga ggtgcataat | 3000 |
| gccaagacaa agccacggga ggagcagttc aacagcacgt tccgtgtggt cagcgtcctc | 3060 |
| accgttgtgc accaggactg gctgaacggc aaggagtaca agtgcaaggt ctccaacaaa | 3120 |
| ggcctcccag cccccatcga gaaaaccatc tccaaaacca agggcagcc ccgagaacca | 3180 |
| caggtgtaca ccctgccccc atccagggag gagatgacca gaaccaggt cagcctgacc | 3240 |
| tgcctggtca aaggcttcta ccccagcgac atcgccgtgg agtgggagag caatgggcag | 3300 |
| ccggagaaca actacaagac cacgcctccc atgctggact ccgacggctc cttcttcctc | 3360 |
| tacagcaagc tcaccgtgga caagagcagg tggcagcagg ggaacgtctt ctcatgctcc | 3420 |
| gtgatgcatg aggctctgca caaccactac acgcagaaga gcctctccct gtctccgggt | 3480 |
| tga | 3483 |

<210> SEQ ID NO 9
<211> LENGTH: 1160
<212> TYPE: PRT
<213> ORGANISM: Homo sapiens
<220> FEATURE:
<221> NAME/KEY: MISC_FEATURE
<223> OTHER INFORMATION: hSCRx17-Fc protein

<400> SEQUENCE: 9

Met Glu Thr Asp Thr Leu Leu Leu Trp Val Leu Leu Trp Val Pro
1               5                   10                  15

Gly Ser Thr Gly Asp Gly Ala Pro Gly Ser Leu Ser Leu Glu Ala Pro
            20                  25                  30

Thr Val Gly Lys Gly Gln Ala Pro Gly Ile Glu Glu Thr Asp Gly Glu
        35                  40                  45

Leu Thr Ala Ala Pro Thr Pro Glu Gln Pro Glu Arg Gly Val His Phe
    50                  55                  60

```
Val Thr Thr Ala Pro Thr Leu Lys Leu Leu Asn His His Pro Leu Leu
 65                  70                  75                  80

Glu Glu Phe Leu Gln Glu Gly Leu Glu Lys Gly Asp Glu Glu Leu Arg
             85                  90                  95

Pro Ala Leu Pro Phe Gln Pro Asp Pro Pro Ala Pro Phe Thr Pro Ser
            100                 105                 110

Pro Leu Pro Arg Leu Ala Asn Gln Asp Ser Arg Pro Val Phe Thr Ser
        115                 120                 125

Pro Thr Pro Ala Met Ala Ala Val Pro Thr Gln Pro Gln Ser Lys Glu
    130                 135                 140

Gly Pro Trp Ser Pro Glu Ser Glu Ser Pro Met Leu Arg Ile Thr Ala
145                 150                 155                 160

Pro Leu Pro Pro Gly Pro Ser Met Ala Val Pro Thr Leu Gly Pro Gly
                165                 170                 175

Glu Ile Ala Ser Thr Thr Pro Pro Ser Arg Ala Trp Thr Pro Thr Gln
            180                 185                 190

Glu Gly Pro Gly Asp Met Gly Arg Pro Trp Val Ala Glu Val Val Ser
        195                 200                 205

Gln Gly Ala Gly Ile Gly Ile Gln Gly Thr Ile Thr Ser Ser Thr Ala
    210                 215                 220

Ser Gly Asp Asp Glu Glu Thr Thr Thr Thr Thr Ile Ile Thr Thr
225                 230                 235                 240

Thr Ile Thr Thr Val Gln Thr Pro Gly Pro Cys Ser Trp Asn Phe Ser
                245                 250                 255

Gly Pro Glu Gly Ser Leu Asp Ser Pro Thr Asp Leu Ser Ser Pro Thr
            260                 265                 270

Asp Val Gly Leu Asp Cys Phe Phe Tyr Ile Ser Val Tyr Pro Gly Tyr
        275                 280                 285

Gly Val Glu Ile Lys Val Gln Asn Ile Ser Leu Arg Glu Gly Glu Thr
    290                 295                 300

Val Thr Val Glu Gly Leu Gly Gly Pro Asp Pro Leu Pro Leu Ala Asn
305                 310                 315                 320

Gln Ser Phe Leu Leu Arg Gly Gln Val Ile Arg Ser Pro Thr His Gln
                325                 330                 335

Ala Ala Leu Arg Phe Gln Ser Leu Pro Pro Ala Gly Pro Gly Thr
            340                 345                 350

Phe His Phe His Tyr Gln Ala Tyr Leu Leu Ser Cys His Phe Pro Arg
        355                 360                 365

Arg Pro Ala Tyr Gly Asp Val Thr Val Thr Ser Leu His Pro Gly Gly
    370                 375                 380

Ser Ala Arg Phe His Cys Ala Thr Gly Tyr Gln Leu Lys Gly Ala Arg
385                 390                 395                 400

His Leu Thr Cys Leu Asn Ala Thr Gln Pro Phe Trp Asp Ser Lys Glu
                405                 410                 415

Pro Val Cys Ile Ala Ala Cys Gly Gly Val Ile Arg Asn Ala Thr Thr
            420                 425                 430

Gly Arg Ile Val Ser Pro Gly Phe Pro Gly Asn Tyr Ser Asn Asn Leu
        435                 440                 445

Thr Cys His Trp Leu Leu Glu Ala Pro Glu Gly Gln Arg Leu His Leu
    450                 455                 460

His Phe Glu Lys Val Ser Leu Ala Glu Asp Asp Arg Leu Ile Ile
465                 470                 475                 480

Arg Asn Gly Asp Asn Val Glu Ala Pro Pro Val Tyr Asp Ser Tyr Glu
```

```
                  485                 490                 495
Val Glu Tyr Leu Pro Ile Glu Gly Leu Leu Ser Ser Gly Lys His Phe
                500                 505                 510

Phe Val Glu Leu Ser Thr Asp Ser Ser Gly Ala Ala Ala Gly Met Ala
                515                 520                 525

Leu Arg Tyr Glu Ala Phe Gln Gln Gly His Cys Tyr Glu Pro Phe Val
                530                 535                 540

Lys Tyr Gly Asn Phe Ser Ser Thr Pro Thr Tyr Pro Val Gly Thr
545                 550                 555                 560

Thr Val Glu Phe Ser Cys Asp Pro Gly Tyr Thr Leu Glu Gln Gly Ser
                565                 570                 575

Ile Ile Ile Glu Cys Val Asp Pro His Asp Pro Gln Trp Asn Glu Thr
                580                 585                 590

Glu Pro Ala Cys Arg Ala Val Cys Ser Gly Glu Ile Thr Asp Ser Ala
                595                 600                 605

Gly Val Val Leu Ser Pro Asn Trp Pro Glu Pro Tyr Gly Arg Gly Gln
                610                 615                 620

Asp Cys Ile Trp Gly Val His Val Glu Glu Asp Lys Arg Ile Met Leu
625                 630                 635                 640

Asp Ile Arg Val Leu Arg Ile Gly Pro Gly Asp Val Leu Thr Phe Tyr
                645                 650                 655

Asp Gly Asp Asp Leu Thr Ala Arg Val Leu Gly Gln Tyr Ser Gly Pro
                660                 665                 670

Arg Ser His Phe Lys Leu Phe Thr Ser Met Ala Asp Val Thr Ile Gln
                675                 680                 685

Phe Gln Ser Asp Pro Gly Thr Ser Val Leu Gly Tyr Gln Gln Gly Phe
                690                 695                 700

Val Ile His Phe Phe Glu Val Pro Arg Asn Asp Thr Cys Pro Glu Leu
705                 710                 715                 720

Pro Glu Ile Pro Asn Gly Trp Lys Ser Pro Ser Gln Pro Glu Leu Val
                725                 730                 735

His Gly Thr Val Val Thr Tyr Gln Cys Tyr Pro Gly Tyr Gln Val Val
                740                 745                 750

Gly Ser Ser Val Leu Met Cys Gln Trp Asp Leu Thr Trp Ser Glu Asp
                755                 760                 765

Leu Pro Ser Cys Gln Arg Val Thr Ser Cys His Asp Pro Gly Asp Val
                770                 775                 780

Glu His Ser Arg Arg Leu Ile Ser Ser Pro Lys Phe Pro Val Gly Ala
785                 790                 795                 800

Thr Val Gln Tyr Ile Cys Asp Gln Gly Phe Val Leu Met Gly Ser Ser
                805                 810                 815

Ile Leu Thr Cys His Asp Arg Gln Ala Gly Ser Pro Lys Trp Ser Asp
                820                 825                 830

Arg Ala Pro Lys Cys Leu Leu Glu Gln Leu Lys Pro Cys His Gly Leu
                835                 840                 845

Ser Ala Pro Glu Asn Gly Ala Arg Ser Pro Glu Lys Gln Leu His Pro
850                 855                 860

Ala Gly Ala Thr Ile His Phe Ser Cys Ala Pro Gly Tyr Val Leu Lys
865                 870                 875                 880

Gly Gln Ala Ser Ile Lys Cys Val Pro Gly His Pro Ser His Trp Ser
                885                 890                 895

Asp Pro Pro Pro Ile Cys Arg Ala Ala Ser Leu Asp Gly Phe Tyr Asn
                900                 905                 910
```

Ser Arg Ser Leu Asp Val Ala Lys Ala Pro Ala Ala Ser Ser Thr Leu
        915                 920                 925

Asp Ala Ala His Leu Ala Gly His Arg Ser Val Glu Cys Pro Pro Cys
    930                 935                 940

Pro Ala Pro Val Ala Gly Pro Ser Val Phe Leu Phe Pro Pro Lys
945                 950                 955                 960

Pro Lys Asp Thr Leu Met Ile Ser Arg Thr Pro Glu Val Thr Cys Val
                965                 970                 975

Val Val Asp Val Ser His Glu Asp Pro Glu Val Gln Phe Asn Trp Tyr
            980                 985                 990

Val Asp Gly Val Glu Val His Asn Ala Lys Thr Lys Pro Arg Glu Glu
        995                 1000                1005

Gln Phe Asn Ser Thr Phe Arg Val Val Ser Val Leu Thr Val Val
    1010                1015                1020

His Gln Asp Trp Leu Asn Gly Lys Glu Tyr Lys Cys Lys Val Ser
    1025                1030                1035

Asn Lys Gly Leu Pro Ala Pro Ile Glu Lys Thr Ile Ser Lys Thr
    1040                1045                1050

Lys Gly Gln Pro Arg Glu Pro Gln Val Tyr Thr Leu Pro Pro Ser
    1055                1060                1065

Arg Glu Glu Met Thr Lys Asn Gln Val Ser Leu Thr Cys Leu Val
    1070                1075                1080

Lys Gly Phe Tyr Pro Ser Asp Ile Ala Val Glu Trp Glu Ser Asn
    1085                1090                1095

Gly Gln Pro Glu Asn Asn Tyr Lys Thr Thr Pro Pro Met Leu Asp
    1100                1105                1110

Ser Asp Gly Ser Phe Phe Leu Tyr Ser Lys Leu Thr Val Asp Lys
    1115                1120                1125

Ser Arg Trp Gln Gln Gly Asn Val Phe Ser Cys Ser Val Met His
    1130                1135                1140

Glu Ala Leu His Asn His Tyr Thr Gln Lys Ser Leu Ser Leu Ser
    1145                1150                1155

Pro Gly
    1160

```
<210> SEQ ID NO 10
<211> LENGTH: 2919
<212> TYPE: DNA
<213> ORGANISM: Mus musculus
<220> FEATURE:
<221> NAME/KEY: misc_feature
<223> OTHER INFORMATION: cDNA sequence encoding mature murine SEZ6

<400> SEQUENCE: 10
ctctcctcag aggctccgat cacgggggaa ggtcatgcca cgggcatcag ggagacggat      60
ggggagctga ccgcagcccc tacacctgag cagtcagacc gaggcgtcca cttcgtcacc    120
acagccccta ccctcaagct gctcaaccac cacccacttc tggaagaatt tcttcaagag    180
gggctagaaa gagaggaagc gccgcagcct gcactgccct ccagccgga ctcacctaca    240 cactttactc caagcccct cccccgcctc accaaccagg acaaccgccc cgtctttacc    300
agtccgactc cagccgtggc tgcagcaccc acccagcccc actccaggga gaaaccttgg    360
aacctagaat ccaaaccccc tgagcttttct atcacatcgt cccttcctcc agggccgagt    420
atggcagtgc ccacactgct cccagaggac agacccagta ctacacccc tagccaagca    480
```

```
tggactccaa ctcaggaggg tcctggagac atggacagac cttgggttcc agaggtcatg      540
tctaagacca cagggcttgg tgtcgaggga accattgcca cctccacagc ttcaggggat      600
gacgaagaga ccactaccac catcattacc actactgtca ccacagttca gccaccaggc      660
ccctgtagct ggaatttctc aggcccagag ggctctctgg attccccac ggcccccagc       720 tcaccctctg atgttggcct ggactgtttc tactatatct ctgtctaccc tggatatgga      780
gtagagatca aggtggagaa catcagcctt caggaagggg agaccatcac cgtggagggc      840 ctgggggggcc ccgatccact gcccttggct aaccagtcgt tcctgctgag gggccaggtc     900
atccgcagcc ccacccacca agcagccctg aggttccaga gctcccgct acccgctggg       960 cctggcactt tccatttccg ctaccaagcc tatctcctga gctgccactt tccccgacgt     1020
ccagcgtatg gagatgtgac tgtcaccagt ctccacccag gaggcagcgc ccacttccat     1080
tgtgccactg gctaccagct caagggtgcc aggttcctca cctgtctcaa tgccacccag     1140 ccctttggg attcccaaga gcctgtttgc attgctgctt gtggtggagt gattcggaat      1200
gccaccactg gccgcattgt ctctcctggc ttcccgggga actacagcaa caacctcacc     1260
tgccactggt tgctagaggc tccagagagc cagcggctgc acctgcactt tgaaaaggtc     1320
tccctggcag aagacgacga caggctcatc atccgcaatg gaaataacgt ggaggccccg     1380
ccggtgtacg actcctatga ggtggaatac ctgcccattg agggcctgct cagctctggc     1440
agacacttct tcgtggagtt cagtactgac agcagtgggg cagctgcagg catggccctg     1500
cgctatgagg ccttccagca aggacattgc tatgagccct ttgtcaaata cggcaacttc     1560
agcagcagtg caccgtccta ccctgtgggt acaactgtgg agttcagctg tgaccctggc     1620
tacaccctgg agcagggctc catcatcatc gaatgcgtcg acctccacga ccccagtgg     1680 aatgagacag agccagcctg ccgagccgtg tgcagcgggg agatcacaga ctctgcaggc     1740
gtggtgctct ctccaaactg gccggagcct tatggccgag ggcaggactg catctggggt     1800
gtgcatgtgg aggaggacaa gcgcatcatg ctggacatcc gagtgctgcg cataggctct     1860
ggggatgtac tgaccttcta cgatgggat gacctcacag cccgggtcct gggccaatac     1920
tcagggcccc gtggccactt caagctcttt acctccatgg ccgatgtcac catccagttc     1980
cagtcagacc ctgggacctc ggcgctgggt taccagcaag gatttgtcat ccacttcttt     2040
gaggttcccc gcaacgacac atgtccagag ctacccgaga tccccaacgg ctggaagaac     2100
ccatcacagc ctgagctggt gcacggcacg gtggtcacct atcagtgcta ccctggttac     2160
caggtggtgg gatccagtat tctcatgtgc cagtgggacc taagctggag tgaggacctg     2220
ccttcatgcc agagagtgac atcttgccat gacccagggg atgtggagca cagccgacgc     2280
ctcatatcca gccccaagtt tcccgtggga gcaactgtgc aatatgtctg tgaccagggt     2340
tttgtgctga cggggagtgc cattctcacc tgccatgatc ggcaagcagg cagtcccaag     2400
tggagtgaca gggcccccaa gtgtctcttg gaacaattca gccgtgcca tggcctcagc      2460 gccccggaga atggtgcccg cagccctgag aagcggcttc acccagcagg ggccaccatc     2520
cacttctcct gtgcccctgg ttatgtgctg aagggccagg ccagcatcaa atgcgtgcct     2580
ggacacccct cgcattggag tgacccacca cccatctgta gggctgcctc tctggatggg     2640
ttctacaacg gccgtagcct ggatgttgcc aaggcacctg ccgcctccag tgccctggac     2700
gctgctcacc tggctgctgc catcttccta ccattggtgg ccatggtgtt gctggtggga     2760
ggagtgtacc tctattttc cagattccag gggaaaagtc ccctgcaact tccccgaact     2820
catcctcgcc cctataaccg catcacggta gagtcagcat ttgacaatcc aacttatgag     2880
```
actggatctc tttcctttgc aggagacgag agaatatga        2919

<210> SEQ ID NO 11
<211> LENGTH: 972
<212> TYPE: PRT
<213> ORGANISM: Mus musculus
<220> FEATURE:
<221> NAME/KEY: MISC_FEATURE
<223> OTHER INFORMATION: mSCRx17 protein

<400> SEQUENCE: 11

Leu Ser Ser Glu Ala Pro Ile Thr Gly Glu Gly His Ala Thr Gly Ile
1               5                   10                  15

Arg Glu Thr Asp Gly Glu Leu Thr Ala Ala Pro Thr Pro Glu Gln Ser
            20                  25                  30

Asp Arg Gly Val His Phe Val Thr Thr Ala Pro Thr Leu Lys Leu Leu
        35                  40                  45

Asn His His Pro Leu Leu Glu Glu Phe Leu Gln Glu Gly Leu Glu Arg
    50                  55                  60

Glu Glu Ala Pro Gln Pro Ala Leu Pro Phe Gln Pro Asp Ser Pro Thr
65                  70                  75                  80

His Phe Thr Pro Ser Pro Leu Pro Arg Leu Thr Asn Gln Asp Asn Arg
                85                  90                  95

Pro Val Phe Thr Ser Pro Thr Pro Ala Val Ala Ala Pro Thr Gln
            100                 105                 110

Pro His Ser Arg Glu Lys Pro Trp Asn Leu Glu Ser Lys Pro Pro Glu
        115                 120                 125

Leu Ser Ile Thr Ser Ser Leu Pro Pro Gly Pro Ser Met Ala Val Pro
    130                 135                 140

Thr Leu Leu Pro Glu Asp Arg Pro Ser Thr Thr Pro Pro Ser Gln Ala
145                 150                 155                 160

Trp Thr Pro Thr Gln Glu Gly Pro Gly Asp Met Asp Arg Pro Trp Val
                165                 170                 175

Pro Glu Val Met Ser Lys Thr Thr Gly Leu Gly Val Glu Gly Thr Ile
            180                 185                 190

Ala Thr Ser Thr Ala Ser Gly Asp Asp Glu Thr Thr Thr Thr Ile
        195                 200                 205

Ile Thr Thr Thr Val Thr Thr Val Gln Pro Pro Gly Pro Cys Ser Trp
    210                 215                 220

Asn Phe Ser Gly Pro Glu Gly Ser Leu Asp Ser Pro Thr Ala Pro Ser
225                 230                 235                 240

Ser Pro Ser Asp Val Gly Leu Asp Cys Phe Tyr Tyr Ile Ser Val Tyr
                245                 250                 255

Pro Gly Tyr Gly Val Glu Ile Lys Val Glu Asn Ile Ser Leu Gln Glu
            260                 265                 270

Gly Glu Thr Ile Thr Val Glu Gly Leu Gly Gly Pro Asp Pro Leu Pro
        275                 280                 285

Leu Ala Asn Gln Ser Phe Leu Leu Arg Gly Gln Val Ile Arg Ser Pro
    290                 295                 300

Thr His Gln Ala Ala Leu Arg Phe Gln Ser Leu Pro Leu Pro Ala Gly
305                 310                 315                 320

Pro Gly Thr Phe His Phe Arg Tyr Gln Ala Tyr Leu Leu Ser Cys His
                325                 330                 335

Phe Pro Arg Arg Pro Ala Tyr Gly Asp Val Thr Val Thr Ser Leu His
            340                 345                 350

-continued

Pro Gly Gly Ser Ala His Phe His Cys Ala Thr Gly Tyr Gln Leu Lys
        355                 360                 365

Gly Ala Arg Phe Leu Thr Cys Leu Asn Ala Thr Gln Pro Phe Trp Asp
        370                 375                 380

Ser Gln Glu Pro Val Cys Ile Ala Ala Cys Gly Gly Val Ile Arg Asn
385                 390                 395                 400

Ala Thr Thr Gly Arg Ile Val Ser Pro Gly Phe Pro Gly Asn Tyr Ser
                405                 410                 415

Asn Asn Leu Thr Cys His Trp Leu Leu Glu Ala Pro Glu Ser Gln Arg
                420                 425                 430

Leu His Leu His Phe Glu Lys Val Ser Leu Ala Glu Asp Asp Asp Arg
        435                 440                 445

Leu Ile Ile Arg Asn Gly Asn Asn Val Glu Ala Pro Pro Val Tyr Asp
        450                 455                 460

Ser Tyr Glu Val Glu Tyr Leu Pro Ile Glu Gly Leu Leu Ser Ser Gly
465                 470                 475                 480

Arg His Phe Phe Val Glu Phe Ser Thr Asp Ser Ser Gly Ala Ala Ala
                485                 490                 495

Gly Met Ala Leu Arg Tyr Glu Ala Phe Gln Gln Gly His Cys Tyr Glu
        500                 505                 510

Pro Phe Val Lys Tyr Gly Asn Phe Ser Ser Ser Ala Pro Ser Tyr Pro
        515                 520                 525

Val Gly Thr Thr Val Glu Phe Ser Cys Asp Pro Gly Tyr Thr Leu Glu
        530                 535                 540

Gln Gly Ser Ile Ile Ile Glu Cys Val Asp Leu His Asp Pro Gln Trp
545                 550                 555                 560

Asn Glu Thr Glu Pro Ala Cys Arg Ala Val Cys Ser Gly Glu Ile Thr
                565                 570                 575

Asp Ser Ala Gly Val Val Leu Ser Pro Asn Trp Pro Glu Pro Tyr Gly
                580                 585                 590

Arg Gly Gln Asp Cys Ile Trp Gly Val His Val Glu Glu Asp Lys Arg
        595                 600                 605

Ile Met Leu Asp Ile Arg Val Leu Arg Ile Gly Ser Gly Asp Val Leu
        610                 615                 620

Thr Phe Tyr Asp Gly Asp Asp Leu Thr Ala Arg Val Leu Gly Gln Tyr
625                 630                 635                 640

Ser Gly Pro Arg Gly His Phe Lys Leu Phe Thr Ser Met Ala Asp Val
                645                 650                 655

Thr Ile Gln Phe Gln Ser Asp Pro Gly Thr Ser Ala Leu Gly Tyr Gln
                660                 665                 670

Gln Gly Phe Val Ile His Phe Phe Glu Val Pro Arg Asn Asp Thr Cys
        675                 680                 685

Pro Glu Leu Pro Glu Ile Pro Asn Gly Trp Lys Asn Pro Ser Gln Pro
        690                 695                 700

Glu Leu Val His Gly Thr Val Val Thr Tyr Gln Cys Tyr Pro Gly Tyr
705                 710                 715                 720

Gln Val Val Gly Ser Ser Ile Leu Met Cys Gln Trp Asp Leu Ser Trp
                725                 730                 735

Ser Glu Asp Leu Pro Ser Cys Gln Arg Val Thr Ser Cys His Asp Pro
                740                 745                 750

Gly Asp Val Glu His Ser Arg Arg Leu Ile Ser Ser Pro Lys Phe Pro
        755                 760                 765

Val Gly Ala Thr Val Gln Tyr Val Cys Asp Gln Gly Phe Val Leu Thr
770                 775                 780

Gly Ser Ala Ile Leu Thr Cys His Asp Arg Gln Ala Gly Ser Pro Lys
785                 790                 795                 800

Trp Ser Asp Arg Ala Pro Lys Cys Leu Leu Glu Gln Phe Lys Pro Cys
            805                 810                 815

His Gly Leu Ser Ala Pro Glu Asn Gly Ala Arg Ser Pro Glu Lys Arg
            820                 825                 830

Leu His Pro Ala Gly Ala Thr Ile His Phe Ser Cys Ala Pro Gly Tyr
            835                 840                 845

Val Leu Lys Gly Gln Ala Ser Ile Lys Cys Val Pro Gly His Pro Ser
850                 855                 860

His Trp Ser Asp Pro Pro Ile Cys Arg Ala Ala Ser Leu Asp Gly
865                 870                 875                 880

Phe Tyr Asn Gly Arg Ser Leu Asp Val Ala Lys Ala Pro Ala Ala Ser
            885                 890                 895

Ser Ala Leu Asp Ala Ala His Leu Ala Ala Ala Ile Phe Leu Pro Leu
            900                 905                 910

Val Ala Met Val Leu Leu Val Gly Gly Val Tyr Leu Tyr Phe Ser Arg
915                 920                 925

Phe Gln Gly Lys Ser Pro Leu Gln Leu Pro Arg Thr His Pro Arg Pro
930                 935                 940

Tyr Asn Arg Ile Thr Val Glu Ser Ala Phe Asp Asn Pro Thr Tyr Glu
945                 950                 955                 960

Thr Gly Ser Leu Ser Phe Ala Gly Asp Glu Arg Ile
            965                 970

<210> SEQ ID NO 12
<211> LENGTH: 2919
<212> TYPE: DNA
<213> ORGANISM: Rattus rattus
<220> FEATURE:
<221> NAME/KEY: misc_feature
<223> OTHER INFORMATION: cDNA sequence of rSCRx17 ORF

<400> SEQUENCE: 12

```
ctctcctcag aggctccaat cacgggggaa ggtcaagcca cgggcatcag ggagatggat      60
ggggagctga ccgcagcccc tacacctgag cagtcagacc gaggcgtcca cttcgtcacc     120
acagccccta ccctcaagct actcaaccac cacccacttc tggaggaatt tcttcaagag     180
gggctagaag ggagagagga agctccgagg ccggcactgc ccttccagcc agactcacct     240
acacccttta ctccaagccc ccttccccgc ctcaccaacc aggacaaccg ccctgtcttt     300
accagtccga cgccagctgt agctgcggca cccacgcagc cccactccag aaagaaaccc     360
tggaacccag agtcagagcc cccggagctt tacatcacat ctcccctccc tccagggccg     420
agtatggcag tgcccacact gcacccgag gacagaccca gcactacacc cccagccaa      480 gcatggactc caacccagga gggtcctgga gacatgggca gccttgggt tccagagatc     540 atgtctaaga ccacagggct tggtatcgag gggaccattg ccacctccac agcttcaggg     600
gatgacgaag agaccaccac caccaccatc attccaccg tcaccacaat tcagccacca     660 ggccctgta gctggaattt ctcaggcccg gagggctctc tggattcccc tgcggtcccc     720
agcgtcccct ctgatgttgg cctggactgt ctctactaca tctctgtcta ccctggatat     780
ggagtcgaga tcaaggtgaa gaacatcagc cttcaggaag agagaccat aaccgtggag     840 ggcctggggg ggcctgaccc actgcccttg ctaaccagt ctttcctgct gagggggccag     900
```

```
gtcatccgca gccccaccca ccaggcagcc gtgaggttcc aaagccttcc acttcccgct    960
ggacctggta ctttccattt ccactaccaa gcctatctcc tgagctgcca ctttcctcgg   1020
cgtccagctt atggagatgt gactgtcacc agcctccacc caggaggcag cgcccgcttc   1080
cactgtgcca ctggctacca gctaaagggt gccaggttcc tcacctgtct caatgccacc   1140
cagccctttt gggattccca agagcctgtc tgcattgctg cttgtggagg agtgattcgg   1200
aatgccacca ctggccgcat tgtctctcct ggctttcccg gaactacag caacaacctc   1260
acctgccact ggctgctaga agcccccgag agccagcggc tgcacctgca ctttgaaaag   1320
gtctccctgg cagaagatga cgacaggctc atcatccgta acgggaataa cgtggaggcc   1380
ccgccagtgt atgactccta tgaggtggag tacctgccca ttgagggcct gctcagttct   1440
ggcagacact tcttcgtgga gttcagtact gacagcagcg gggcagccgc aggcatggca   1500
ctgcgctatg aggccttcca gcaaggacat tgctatgagc cctttgtcaa atacggtaac   1560
ttcagcagca gcgcaccgtc ctaccctgtg ggtacgactg tggagttcag ctgtgaccct   1620
ggctacaccc tggagcaggg ttccatcatc atcgaatgcg tcgacctccg tgaccccag   1680
tggaatgaga cagaaccagc ctgccgagcc gtgtgcagcg gggagatcac agactctgca   1740
ggcgtggtgc tctctccaaa ctggccggag ccttatggcc gagggcagga ctgcatctgg   1800
ggtgtgcatg tggaggagga caagcgcatc atgctggaca tccgagtgct gcgcataggc   1860
tctggggatg tactgacctt ctacgatggg gatgacctga cagcccgggt cctgggccaa   1920
tactcagggc cccgtggcca cttcaagctc tttacctcca tggctgatgt caccattcag   1980
ttccagtcag accctgggac gtcggcgctg ggttaccagc aaggatttgt catccacttc   2040
tttgaggtgc cccgcaatga cacatgtcca gagcttcccg agatccccaa cggctggaag   2100
aacccatcac agcctgagct ggtgcatggc acggtggtca cctatcagtg ctaccccggt   2160
taccaggtgg tgggatccag tattctcatg tgccagtggg acctgagctg gagtgaggac   2220
ctgccctcat gccagagagt gacatcctgc catgacccag gggatgtgga gcacagccga   2280
cgcctcatat ccagcctcaa gtttcctgtg ggagcaactg tgcagtatat ctgtgaccag   2340
ggttttgtgc tcacgggtag cgccatcctt acttgccatg atcgtcaagc gggcagtccc   2400
aagtggagtg acagggcccc caagtgtctc ttggaacagt tcaaaccatg tcatggcctc   2460
agtgcccctg agaatggtgc ccgcagccct gagaagaggc tccacccagc aggggccacc   2520
attcacttct cctgtgcccc tggttatgtg ctgaagggcc aggccagcat caaatgcgtg   2580
cctggacacc cctcacattg gagtgatcct ccacccatct gtagggctgc ttctctggat   2640
gggttctaca acggccgtag cctggatgtt gccaaggcac ctgccacctc cagtgccctg   2700
gatgctgccc acatggcagc tgccatcttt ctaccattgg tggccatggt gttgctggtg   2760
ggaggagtgt acctctattt ctccagactc cagggaaaaa gtcctctgca gcttcccgga   2820
actcatcctc gccccataa ccgtatcacg gtagagtcag catttgacaa tccaacttat   2880
gagaccggat ctctttcctt tgcaggagac gagagaata                          2919
```

<210> SEQ ID NO 13
<211> LENGTH: 973
<212> TYPE: PRT
<213> ORGANISM: Rattus rattus
<220> FEATURE:
<221> NAME/KEY: MISC_FEATURE
<223> OTHER INFORMATION: rSCRx17 protein

<400> SEQUENCE: 13

```
Leu Ser Ser Glu Ala Pro Ile Thr Gly Glu Gly Gln Ala Thr Gly Ile
1               5                   10                  15

Arg Glu Met Asp Gly Glu Leu Thr Ala Ala Pro Thr Pro Glu Gln Ser
            20                  25                  30

Asp Arg Gly Val His Phe Val Thr Thr Ala Pro Thr Leu Lys Leu Leu
            35                  40                  45

Asn His His Pro Leu Leu Glu Glu Phe Leu Gln Glu Gly Leu Glu Gly
        50                  55                  60

Arg Glu Glu Ala Pro Arg Pro Ala Leu Pro Phe Gln Pro Asp Ser Pro
65                  70                  75                  80

Thr Pro Phe Thr Pro Ser Pro Leu Pro Arg Leu Thr Asn Gln Asp Asn
                85                  90                  95

Arg Pro Val Phe Thr Ser Pro Thr Pro Ala Val Ala Ala Pro Thr
            100                 105                 110

Gln Pro His Ser Arg Lys Lys Pro Trp Asn Pro Glu Ser Glu Pro Pro
        115                 120                 125

Glu Leu Tyr Ile Thr Ser Pro Leu Pro Pro Gly Pro Ser Met Ala Val
        130                 135                 140

Pro Thr Leu His Pro Glu Asp Arg Pro Ser Thr Thr Pro Pro Ser Gln
145                 150                 155                 160

Ala Trp Thr Pro Thr Gln Glu Gly Pro Gly Asp Met Gly Arg Pro Trp
                165                 170                 175

Val Pro Glu Ile Met Ser Lys Thr Thr Gly Leu Gly Ile Glu Gly Thr
                180                 185                 190

Ile Ala Thr Ser Thr Ala Ser Gly Asp Asp Glu Thr Thr Thr Thr
            195                 200                 205

Thr Ile Ile Thr Thr Val Thr Thr Ile Gln Pro Pro Gly Pro Cys Ser
    210                 215                 220

Trp Asn Phe Ser Gly Pro Glu Gly Ser Leu Asp Ser Pro Ala Val Pro
225                 230                 235                 240

Ser Val Pro Ser Asp Val Gly Leu Asp Cys Leu Tyr Tyr Ile Ser Val
            245                 250                 255

Tyr Pro Gly Tyr Gly Val Glu Ile Lys Val Lys Asn Ile Ser Leu Gln
            260                 265                 270

Glu Gly Glu Thr Ile Thr Val Glu Gly Leu Gly Gly Pro Asp Pro Leu
    275                 280                 285

Pro Leu Ala Asn Gln Ser Phe Leu Leu Arg Gly Gln Val Ile Arg Ser
    290                 295                 300

Pro Thr His Gln Ala Ala Val Arg Phe Gln Ser Leu Pro Leu Pro Ala
305                 310                 315                 320

Gly Pro Gly Thr Phe His Phe His Tyr Gln Ala Tyr Leu Leu Ser Cys
            325                 330                 335

His Phe Pro Arg Arg Pro Ala Tyr Gly Asp Val Thr Val Thr Ser Leu
            340                 345                 350

His Pro Gly Gly Ser Ala Arg Phe His Cys Ala Thr Gly Tyr Gln Leu
        355                 360                 365

Lys Gly Ala Arg Phe Leu Thr Cys Leu Asn Ala Thr Gln Pro Phe Trp
    370                 375                 380

Asp Ser Gln Glu Pro Val Cys Ile Ala Ala Cys Gly Gly Val Ile Arg
385                 390                 395                 400

Asn Ala Thr Thr Gly Arg Ile Val Ser Pro Gly Phe Pro Gly Asn Tyr
                405                 410                 415
```

```
Ser Asn Asn Leu Thr Cys His Trp Leu Leu Glu Ala Pro Glu Ser Gln
            420                 425                 430

Arg Leu His Leu His Phe Glu Lys Val Ser Leu Ala Glu Asp Asp Asp
        435                 440                 445

Arg Leu Ile Ile Arg Asn Gly Asn Asn Val Glu Ala Pro Pro Val Tyr
    450                 455                 460

Asp Ser Tyr Glu Val Glu Tyr Leu Pro Ile Glu Gly Leu Leu Ser Ser
465                 470                 475                 480

Gly Arg His Phe Phe Val Glu Phe Ser Thr Asp Ser Ser Gly Ala Ala
                485                 490                 495

Ala Gly Met Ala Leu Arg Tyr Glu Ala Phe Gln Gln Gly His Cys Tyr
            500                 505                 510

Glu Pro Phe Val Lys Tyr Gly Asn Phe Ser Ser Ser Ala Pro Ser Tyr
        515                 520                 525

Pro Val Gly Thr Thr Val Glu Phe Ser Cys Asp Pro Gly Tyr Thr Leu
    530                 535                 540

Glu Gln Gly Ser Ile Ile Ile Glu Cys Val Asp Leu Arg Asp Pro Gln
545                 550                 555                 560

Trp Asn Glu Thr Glu Pro Ala Cys Arg Ala Val Cys Ser Gly Glu Ile
                565                 570                 575

Thr Asp Ser Ala Gly Val Val Leu Ser Pro Asn Trp Pro Glu Pro Tyr
            580                 585                 590

Gly Arg Gly Gln Asp Cys Ile Trp Gly Val His Val Glu Glu Asp Lys
        595                 600                 605

Arg Ile Met Leu Asp Ile Arg Val Leu Arg Ile Gly Ser Gly Asp Val
    610                 615                 620

Leu Thr Phe Tyr Asp Gly Asp Asp Leu Thr Ala Arg Val Leu Gly Gln
625                 630                 635                 640

Tyr Ser Gly Pro Arg Gly His Phe Lys Leu Phe Thr Ser Met Ala Asp
                645                 650                 655

Val Thr Ile Gln Phe Gln Ser Asp Pro Gly Thr Ser Ala Leu Gly Tyr
            660                 665                 670

Gln Gln Gly Phe Val Ile His Phe Phe Glu Val Pro Arg Asn Asp Thr
        675                 680                 685

Cys Pro Glu Leu Pro Glu Ile Pro Asn Gly Trp Lys Asn Pro Ser Gln
    690                 695                 700

Pro Glu Leu Val His Gly Thr Val Val Thr Tyr Gln Cys Tyr Pro Gly
705                 710                 715                 720

Tyr Gln Val Val Gly Ser Ser Ile Leu Met Cys Gln Trp Asp Leu Ser
                725                 730                 735

Trp Ser Glu Asp Leu Pro Ser Cys Gln Arg Val Thr Ser Cys His Asp
            740                 745                 750

Pro Gly Asp Val Glu His Ser Arg Arg Leu Ile Ser Ser Leu Lys Phe
        755                 760                 765

Pro Val Gly Ala Thr Val Gln Tyr Ile Cys Asp Gln Gly Phe Val Leu
    770                 775                 780

Thr Gly Ser Ala Ile Leu Thr Cys His Asp Arg Gln Ala Gly Ser Pro
785                 790                 795                 800

Lys Trp Ser Asp Arg Ala Pro Lys Cys Leu Leu Glu Gln Phe Lys Pro
                805                 810                 815

Cys His Gly Leu Ser Ala Pro Glu Asn Gly Ala Arg Ser Pro Glu Lys
            820                 825                 830

Arg Leu His Pro Ala Gly Ala Thr Ile His Phe Ser Cys Ala Pro Gly
```

|     |     |     |     | 835 |     |     |     |     | 840 |     |     |     |     | 845 |
| --- | --- | --- | --- | --- | --- | --- | --- | --- | --- | --- | --- | --- | --- | --- |

Tyr Val Leu Lys Gly Gln Ala Ser Ile Lys Cys Val Pro Gly His Pro
            850                 855                 860

Ser His Trp Ser Asp Pro Pro Ile Cys Arg Ala Ala Ser Leu Asp
865                 870                 875                 880

Gly Phe Tyr Asn Gly Arg Ser Leu Asp Val Ala Lys Ala Pro Ala Thr
                    885                 890                 895

Ser Ser Ala Leu Asp Ala Ala His Met Ala Ala Ile Phe Leu Pro
                900                 905                 910

Leu Val Ala Met Val Leu Leu Val Gly Gly Val Tyr Leu Tyr Phe Ser
            915                 920                 925

Arg Leu Gln Gly Lys Ser Pro Leu Gln Leu Pro Gly Thr His Pro Arg
        930                 935                 940

Pro Tyr Asn Arg Ile Thr Val Glu Ser Ala Phe Asp Asn Pro Thr Tyr
945                 950                 955                 960

Glu Thr Gly Ser Leu Ser Phe Ala Gly Asp Glu Arg Ile
                965                 970

<210> SEQ ID NO 14
<211> LENGTH: 2997
<212> TYPE: DNA
<213> ORGANISM: Macaca fascicularis
<220> FEATURE:
<221> NAME/KEY: misc_feature
<223> OTHER INFORMATION: cDNA sequence of cSCRx17 ORF

<400> SEQUENCE: 14

| | |
|---|---|
| atggagacag acacactcct gctatgggta ctgctgctct gggttccagg ttccactggt | 60 |
| gacggcgcgc cactcagcag cgaagctccc acaatgggca agggacaggc ccccggaatt | 120 |
| gaagaaaccg atggcgaact caccgctgcc cctacccctg agcaacccga aggggagtg | 180 |
| cactttgtga ccaccgctcc caccctgaag ctgctcaatc accaccccct cctggaggag | 240 |
| tttctgcagg aaggcctgga aaaggcgac gaggaactca gacctgccct gcccttccaa | 300 |
| cccgaccctc ctaccccctt tacacctagc cctctcccta gactggccaa ccaagactcc | 360 |
| agacctgtgt tcaccagccc tacacctgct acagctgccg tccctaccca acctcaatcc | 420 |
| aaggagggac cttggagcct cgagagcgag cctcccgtgc tgagaatcac agctcctctc | 480 |
| cctcctggcc cttccatggc tgtccccaca ctcggacctg gcgaaaggcc cagcacaaca | 540 |
| cccccctcca gagcctggac ccctacacaa gaaggccctg gcgacatggg aaggccttgg | 600 |
| gtccctgaag tcgtgagcca aggcgccggc atcggaatcc agggaaccat cgccagctcc | 660 |
| acagccagcg agacgatga ggaaacaacc accacaacca ccatcatcac caccacaatc | 720 |
| acaacagtcc agaccccgg cccttgcagc tggaatttt ccggccctga gggatccctg | 780 |
| gattccccca cagatctgtc ctcccctcct gacgtgggcc tcgactgttt cttctatatc | 840 |
| tccgtgtatc ctggctacgg cgtcgaaatc aaagtccaga acatctccct gagggagggc | 900 |
| gaaacagtca ccgtggaagg actgggcgga cccgctcctc tgcctctcgc caaccaatcc | 960 |
| ttcctcctca ggggccaagt gattagatcc cccacacatc aagctgctct caggttccaa | 1020 |
| agcctccctc ccccgctgg acccggaacc tttcacttcc actaccaagc ctatctcctc | 1080 |
| agctgccatt tcccccacag gcccgcttat ggagatgtca cagtcacctc cctgcatcct | 1140 |
| ggcggctccg ctagattcca ctgcgctacc ggataccaac tcaagggcgc caggcatctg | 1200 |
| acatgtctca atgctaccca gcccttctgg gacagcaagg agcccgtctg cattgccgct | 1260 |

```
tgcggaggcg tcatcagaaa tgccaccacc ggcagaatcg tgagcccogg cttcoctggc    1320
aactactcca acaacctgac atgccactgg ctgctggaag ctcctgaggg ccagagactg    1380
catctgcact tcgagaaggt cagcctggcc gaagatgacg acagactcat catcaggaac    1440
ggcgacaacg tggaggctcc ccccgtctat gattcctacg aggtcgagta cctccccatc    1500
gagggactgc tgtcctccgg caagcatttt ttcgtggagc tgtccacaga ttccagcgga    1560
gctgccgccg aatggctct caggtacgag gctttccaac agggccactg ttacgagccc     1620
tttgtgaagt acggcaactt ctccagctcc gctcctacct accccgtcgg cacaaccgtc    1680
gaatttagct gcgaccctgg atacacactc gagcaaggct ccatcatcat cgagtgtgtc    1740
gaccccacg acccccaatg aacgagaca gagcccgcct gtagggccgt gtgtagcgga      1800
gagattaccg actccgccgg agtggtgctc tcccctaatt ggcctgaacc ctacggcaga    1860
ggacaagatt gtatttgggg cgtccatgtc gaggaggaca agaggattat gctcgacgtg    1920
agggtgctga ggattggacc tggcgacgtg ctcacattct atgacggcga cgatctcacc    1980
gccagagtcc tgggacaata ctccggccct cacagccact tcaagctgtt caccagcatg    2040
gctgacgtga ccatccagtt ccagtccgat cctggaacat ccgtgctggg ataccagcag    2100
ggcttcgtca tccacttctt cgaggtcccc aggaacgaca cctgccccga actgcccgag    2160
attcccaacg gctggaaatc cccctcccaa cctgatctcg tgcacggcac cgtcgtcacc    2220
taccaatgct accctggata ccaagtcgtc ggcagcagcg tgctgatgtg ccaatgggac    2280
ctcacctgga gcgaggatct gccctcctgc cagagagtca cctcctgcca cgatcccggc    2340
gatgtggaac actccaggag gctgattagc tcccccaagt tccctgtcgg agccaccgtg    2400
caatacatct gcgaccaggg ctttgtgctg accggaacca gcatcctcac atgccacgac    2460
aggcaagctg gatcccccaa gtggtccgat agggcccca aatgcctcct ggaacagctg    2520
aagccttgtc atggcctcag cgctcctgaa acggcgcta ggagcccga aaagaggctc      2580
caccctgccg gagccaccat ccacttttcc tgtgccccg gatacgtgct gaagggccag     2640
gcctccatta gtgcgtgcc cggacatcct tcccactggt ccgacccccc tcccatctgt     2700
aaagccgcct ccctggacgg attctataac agcagaagcc tggacgtcgc taaggcccct    2760
gctgcttcct ccacccctgga tgctgctcac atcgctgctg ccatctttct gccccctcgtc   2820
gccatggtgc tgctggtggg aggcgtctac ttctacttct ccaggctgca gggaaagagc    2880
tccctgcaac tgcctaggac aagacccagg ccctacaata ggatcacagt cgagagcgcc    2940
ttcgacaacc ccacatacga gacaggatcc ctgagctttg ccggagacga gagaatt       2997
```

<210> SEQ ID NO 15
<211> LENGTH: 999
<212> TYPE: PRT
<213> ORGANISM: Macaca fascicularis
<220> FEATURE:
<221> NAME/KEY: MISC_FEATURE
<223> OTHER INFORMATION: cSCRx17 protein

<400> SEQUENCE: 15

Met Glu Thr Asp Thr Leu Leu Leu Trp Val Leu Leu Leu Trp Val Pro
1               5                   10                  15

Gly Ser Thr Gly Asp Gly Ala Pro Leu Ser Ser Glu Ala Pro Thr Met
            20                  25                  30

Gly Lys Gly Gln Ala Pro Gly Ile Glu Glu Thr Asp Gly Glu Leu Thr
        35                  40                  45

Ala Ala Pro Thr Pro Glu Gln Pro Glu Arg Gly Val His Phe Val Thr

```
                50              55              60
Thr Ala Pro Thr Leu Lys Leu Leu Asn His His Pro Leu Leu Glu Glu
 65              70              75              80

Phe Leu Gln Glu Gly Leu Glu Lys Gly Asp Glu Leu Arg Pro Ala
                 85              90              95

Leu Pro Phe Gln Pro Asp Pro Thr Pro Phe Thr Pro Ser Pro Leu
                100             105             110

Pro Arg Leu Ala Asn Gln Asp Ser Arg Pro Val Phe Thr Ser Pro Thr
                115             120             125

Pro Ala Thr Ala Ala Val Pro Thr Gln Pro Gln Ser Lys Glu Gly Pro
                130             135             140

Trp Ser Leu Glu Ser Glu Pro Pro Val Leu Arg Ile Thr Ala Pro Leu
145             150             155             160

Pro Pro Gly Pro Ser Met Ala Val Pro Thr Leu Gly Pro Gly Glu Arg
                165             170             175

Pro Ser Thr Thr Pro Pro Ser Arg Ala Trp Thr Pro Thr Gln Glu Gly
                180             185             190

Pro Gly Asp Met Gly Arg Pro Trp Val Pro Glu Val Val Ser Gln Gly
                195             200             205

Ala Gly Ile Gly Ile Gln Gly Thr Ile Ala Ser Ser Thr Ala Ser Gly
                210             215             220

Asp Asp Glu Glu Thr Thr Thr Thr Thr Ile Ile Thr Thr Thr Ile
225             230             235             240

Thr Thr Val Gln Thr Pro Gly Pro Cys Ser Trp Asn Phe Ser Gly Pro
                245             250             255

Glu Gly Ser Leu Asp Ser Pro Thr Asp Leu Ser Ser Pro Pro Asp Val
                260             265             270

Gly Leu Asp Cys Phe Phe Tyr Ile Ser Val Tyr Pro Gly Tyr Gly Val
                275             280             285

Glu Ile Lys Val Gln Asn Ile Ser Leu Arg Glu Gly Glu Thr Val Thr
                290             295             300

Val Glu Gly Leu Gly Gly Pro Ala Pro Leu Pro Leu Ala Asn Gln Ser
305             310             315             320

Phe Leu Leu Arg Gly Gln Val Ile Arg Ser Pro Thr His Gln Ala Ala
                325             330             335

Leu Arg Phe Gln Ser Leu Pro Pro Ala Gly Pro Gly Thr Phe His
                340             345             350

Phe His Tyr Gln Ala Tyr Leu Leu Ser Cys His Phe Pro His Arg Pro
                355             360             365

Ala Tyr Gly Asp Val Thr Val Thr Ser Leu His Pro Gly Gly Ser Ala
                370             375             380

Arg Phe His Cys Ala Thr Gly Tyr Gln Leu Lys Gly Ala Arg His Leu
385             390             395             400

Thr Cys Leu Asn Ala Thr Gln Pro Phe Trp Asp Ser Lys Glu Pro Val
                405             410             415

Cys Ile Ala Ala Cys Gly Gly Val Ile Arg Asn Ala Thr Thr Gly Arg
                420             425             430

Ile Val Ser Pro Gly Phe Pro Gly Asn Tyr Ser Asn Asn Leu Thr Cys
                435             440             445

His Trp Leu Leu Glu Ala Pro Glu Gly Gln Arg Leu His Leu His Phe
                450             455             460

Glu Lys Val Ser Leu Ala Glu Asp Asp Arg Leu Ile Ile Arg Asn
465             470             475             480
```

```
Gly Asp Asn Val Glu Ala Pro Pro Val Tyr Asp Ser Tyr Glu Val Glu
            485                 490                 495

Tyr Leu Pro Ile Glu Gly Leu Leu Ser Ser Gly Lys His Phe Phe Val
            500                 505                 510

Glu Leu Ser Thr Asp Ser Ser Gly Ala Ala Gly Met Ala Leu Arg
            515                 520                 525

Tyr Glu Ala Phe Gln Gln Gly His Cys Tyr Glu Pro Phe Val Lys Tyr
            530                 535                 540

Gly Asn Phe Ser Ser Ser Ala Pro Thr Tyr Pro Val Gly Thr Thr Val
545                 550                 555                 560

Glu Phe Ser Cys Asp Pro Gly Tyr Thr Leu Glu Gln Gly Ser Ile Ile
            565                 570                 575

Ile Glu Cys Val Asp Pro His Asp Pro Gln Trp Asn Glu Thr Glu Pro
            580                 585                 590

Ala Cys Arg Ala Val Cys Ser Gly Glu Ile Thr Asp Ser Ala Gly Val
            595                 600                 605

Val Leu Ser Pro Asn Trp Pro Glu Pro Tyr Gly Arg Gly Gln Asp Cys
            610                 615                 620

Ile Trp Gly Val His Val Glu Glu Asp Lys Arg Ile Met Leu Asp Val
625                 630                 635                 640

Arg Val Leu Arg Ile Gly Pro Gly Asp Val Leu Thr Phe Tyr Asp Gly
            645                 650                 655

Asp Asp Leu Thr Ala Arg Val Leu Gly Gln Tyr Ser Gly Pro His Ser
            660                 665                 670

His Phe Lys Leu Phe Thr Ser Met Ala Asp Val Thr Ile Gln Phe Gln
            675                 680                 685

Ser Asp Pro Gly Thr Ser Val Leu Gly Tyr Gln Gln Gly Phe Val Ile
            690                 695                 700

His Phe Phe Glu Val Pro Arg Asn Asp Thr Cys Pro Glu Leu Pro Glu
705                 710                 715                 720

Ile Pro Asn Gly Trp Lys Ser Pro Ser Gln Pro Asp Leu Val His Gly
            725                 730                 735

Thr Val Val Thr Tyr Gln Cys Tyr Pro Gly Tyr Gln Val Val Gly Ser
            740                 745                 750

Ser Val Leu Met Cys Gln Trp Asp Leu Thr Trp Ser Glu Asp Leu Pro
            755                 760                 765

Ser Cys Gln Arg Val Thr Ser Cys His Asp Pro Gly Asp Val Glu His
            770                 775                 780

Ser Arg Arg Leu Ile Ser Ser Pro Lys Phe Pro Val Gly Ala Thr Val
785                 790                 795                 800

Gln Tyr Ile Cys Asp Gln Gly Phe Val Leu Thr Gly Thr Ser Ile Leu
            805                 810                 815

Thr Cys His Asp Arg Gln Ala Gly Ser Pro Lys Trp Ser Asp Arg Ala
            820                 825                 830

Pro Lys Cys Leu Leu Glu Gln Leu Lys Pro Cys His Gly Leu Ser Ala
            835                 840                 845

Pro Glu Asn Gly Ala Arg Ser Pro Glu Lys Arg Leu His Pro Ala Gly
            850                 855                 860

Ala Thr Ile His Phe Ser Cys Ala Pro Gly Tyr Val Leu Lys Gly Gln
865                 870                 875                 880

Ala Ser Ile Lys Cys Val Pro Gly His Pro Ser His Trp Ser Asp Pro
            885                 890                 895
```

```
Pro Pro Ile Cys Lys Ala Ala Ser Leu Asp Gly Phe Tyr Asn Ser Arg
            900                 905                 910

Ser Leu Asp Val Ala Lys Ala Pro Ala Ala Ser Ser Thr Leu Asp Ala
        915                 920                 925

Ala His Ile Ala Ala Ala Ile Phe Leu Pro Leu Val Ala Met Val Leu
    930                 935                 940

Leu Val Gly Gly Val Tyr Phe Tyr Phe Ser Arg Leu Gln Gly Lys Ser
945                 950                 955                 960

Ser Leu Gln Leu Pro Arg Thr Arg Pro Arg Pro Tyr Asn Arg Ile Thr
                965                 970                 975

Val Glu Ser Ala Phe Asp Asn Pro Thr Tyr Glu Thr Gly Ser Leu Ser
            980                 985                 990

Phe Ala Gly Asp Glu Arg Ile
        995

<210> SEQ ID NO 16
<211> LENGTH: 2781
<212> TYPE: DNA
<213> ORGANISM: Homo sapiens
<220> FEATURE:
<221> NAME/KEY: misc_feature
<223> OTHER INFORMATION: cDNA sequence of human SEZ6L ECD

<400> SEQUENCE: 16
ctcgagaggg atgctctgcc tgagggagat gcttcccctc tcggacctta tctgctgccc      60
agcggagctc ctgagagggg atcccccgga aggagcatc ccgaagaaag agtggtcaca     120
gctcccccta gctccagcca gagcgctgag gtgctgggag aactggtcct cgacggaaca     180
gccccttccg cccatcacga tattcctgcc ctcagccctc tcctccccga ggaagctagg     240
cctaaacacg ccctcccccc taaaagaag ctgccttccc tcaagcaggt caattccgcc     300
aggaagcagc tcagacccaa ggccacctcc gctgctacag tccaagagc tggatcccag     360 cctgccagcc agggactcga tctgctcagc agctccacag aaaaacctgg acctcctggc     420
gatcctgacc ctattgtggc cagcgaagaa gctagcgaag tccctctgtg gctggacagg     480
aaggagtccg ctgtccccac cacacccgct cctctccaga tcagccccctt cacctcccag     540 ccttatgtcg ctcatacact gcctcagagg cctgagcctg gcgaacctgg acctgacatg     600
gctcaggagg ctcctcagga ggacaccagc cctatggccc tgatggataa gggcgagaat     660
gaactgaccg gaagcgccag cgaggaaagc caggagacca ccaccagcac aatcatcacc     720
accaccgtca tcaccaccga acaggccccc gctctgtgtt ccgtgtcctt ttccaacccc     780
gagggctaca ttgacagcag cgattacccc ctgctccctc tcaacaactt cctcgagtgc     840
acctacaatg tgaccgtgta caccggctac ggagtcgaac tccaggtgaa gtccgtgaac     900
ctctccgatg gcgaactgct ctccattagg ggcgtcgatg ccctacact caccgtcctg     960 gctaaccaaa ccctgctcgt cgaaggccag gtgattaggt cccccaccaa caccatctcc    1020
gtctacttca ggaccttca agacgacgga ctgggaacct tccaactgca ttaccaggcc    1080
ttcatgctgt cctgtaattt ccccaggaga cccgactccg agacgtcac cgtcatggat    1140 ctgcactccg gaggcgtggc ccactttcat tgtcacctcg gctacgagct ccagggcgcc    1200
aagatgctga catgcatcaa cgccagcaaa cctcactggt ccagccagga gcctatctgt    1260
agcgctcctt gcggcggagc cgtgcacaat gctacaattg gcagagtgct cagcccttcc    1320
taccctgaaa acaccaacgg ctcccagttc tgcatctgga caatcgaggc ccccgaaggc    1380
caaaagctgc acctgcactt tgagaggctc ctgctccacg acaaagacag gatgaccgtg    1440
```

-continued

```
cactccggcc agaccaataa gtccgccctc ctgtatgaca gcctgcagac agagtccgtc    1500 cctttttgaag gcctgctgtc cgagggcaat accatcagga ttgagttcac atccgaccaa    1560
gccagggctg ctagcacctt caacattagg tttgaggctt tcgaaaaggg acactgctac    1620
gagccctata ttcagaatgg caatttcaca acctccgacc ccacctacaa tatcggcaca    1680
attgtggagt ttacctgcga ccctggacac agcctggagc agggacctgc catcatcgaa    1740
tgcatcaacg tcagggaccc ctactggaac gacacagaac ctctgtgtag ggctatgtgc    1800
ggaggcgaac tgagcgctgt ggctggagtc gtgctctccc ctaactggcc cgaaccctat    1860
gtggagggcg aagattgcat ctggaagatc cacgtcggcg aggaaaaaag gatctttctg    1920
gacatccagt tcctgaatct ctccaacagc gacatcctga ccatctacga cggagatgag    1980
gtcatgcccc acattctggg ccagtatctc ggaaactccg gcccccaaaa gctctactcc    2040 tccaccccg acctcacaat ccaattccac agcgatcctg ctggcctcat ctttggaaag    2100
ggacaaggct ttatcatgaa ttacatcgag gtcagcagaa acgacagctg ctccgacctg    2160
cctgagatcc agaacggatg gaagaccacc tcccacaccg agctcgtcag gggagctagg    2220
atcacatacc agtgcgaccc cggatacgac atcgtcggct ccgataccct gacatgccag    2280
tgggatctga gctggagctc cgaccccccc ttttgtgaga agatcatgta ctgcaccgac    2340
cccggcgaag tcgatcatag caccaggctc atcagcgatc ctgtgctgct cgtcggcaca    2400
accatccaat acacctgtaa ccccggattc gtgctcgaag gatcctccct gctcacctgt    2460
tacagcaggg aaaccggcac ccccatttgg acatccaggc tgcctcactg cgtgtccgaa    2520
gagagcctgg cttgcgataa tcccggcctg cctgagaacg gataccagat tctgtacaaa    2580
aggctgtacc tccccggcga gtccctgacc ttcatgtgct acgaaggatt cgagctcatg    2640
ggcgaagtca ccatcaggtg catcctcggc cagccctccc actggaacgg acctctcccc    2700
gtctgtaagg tcaatcagga ttccttcgag cacgctctgg aagtcgctga ggctgccgcc    2760
gagacaagcc tggaaggcgg c                                              2781
```

<210> SEQ ID NO 17
<211> LENGTH: 964
<212> TYPE: PRT
<213> ORGANISM: Homo sapiens
<220> FEATURE:
<221> NAME/KEY: MISC_FEATURE
<223> OTHER INFORMATION: Human SEZ6L ECD protein

<400> SEQUENCE: 17

```
Met Glu Thr Asp Thr Leu Leu Leu Trp Val Leu Leu Leu Trp Val Pro
1               5                   10                  15

Gly Ser Thr Gly Asp His Gly Ala Pro Leu Glu Arg Asp Ala Leu Pro
            20                  25                  30

Glu Gly Asp Ala Ser Pro Leu Gly Pro Tyr Leu Leu Pro Ser Gly Ala
        35                  40                  45

Pro Glu Arg Gly Ser Pro Gly Lys Glu His Pro Glu Glu Arg Val Val
    50                  55                  60

Thr Ala Pro Pro Ser Ser Ser Gln Ser Ala Glu Val Leu Gly Glu Leu
65                  70                  75                  80

Val Leu Asp Gly Thr Ala Pro Ser Ala His His Asp Ile Pro Ala Leu
                85                  90                  95

Ser Pro Leu Leu Pro Glu Glu Ala Arg Pro Lys His Ala Leu Pro Pro
            100                 105                 110
```

-continued

```
Lys Lys Lys Leu Pro Ser Leu Lys Gln Val Asn Ser Ala Arg Lys Gln
            115                 120                 125
Leu Arg Pro Lys Ala Thr Ser Ala Ala Thr Val Gln Arg Ala Gly Ser
        130                 135                 140
Gln Pro Ala Ser Gln Gly Leu Asp Leu Leu Ser Ser Ser Thr Glu Lys
145                 150                 155                 160
Pro Gly Pro Pro Gly Asp Pro Asp Pro Ile Val Ala Ser Glu Glu Ala
                165                 170                 175
Ser Glu Val Pro Leu Trp Leu Asp Arg Lys Glu Ser Ala Val Pro Thr
            180                 185                 190
Thr Pro Ala Pro Leu Gln Ile Ser Pro Phe Thr Ser Gln Pro Tyr Val
        195                 200                 205
Ala His Thr Leu Pro Gln Arg Pro Glu Pro Gly Glu Pro Gly Pro Asp
    210                 215                 220
Met Ala Gln Glu Ala Pro Gln Glu Asp Thr Ser Pro Met Ala Leu Met
225                 230                 235                 240
Asp Lys Gly Glu Asn Glu Leu Thr Gly Ser Ala Ser Glu Glu Ser Gln
                245                 250                 255
Glu Thr Thr Thr Ser Thr Ile Ile Thr Thr Thr Val Ile Thr Thr Glu
            260                 265                 270
Gln Ala Pro Ala Leu Cys Ser Val Ser Phe Ser Asn Pro Glu Gly Tyr
        275                 280                 285
Ile Asp Ser Ser Asp Tyr Pro Leu Leu Pro Leu Asn Asn Phe Leu Glu
    290                 295                 300
Cys Thr Tyr Asn Val Thr Val Tyr Thr Gly Tyr Gly Val Glu Leu Gln
305                 310                 315                 320
Val Lys Ser Val Asn Leu Ser Asp Gly Glu Leu Leu Ser Ile Arg Gly
                325                 330                 335
Val Asp Gly Pro Thr Leu Thr Val Leu Ala Asn Gln Thr Leu Leu Val
            340                 345                 350
Glu Gly Gln Val Ile Arg Ser Pro Thr Asn Thr Ile Ser Val Tyr Phe
        355                 360                 365
Arg Thr Phe Gln Asp Asp Gly Leu Gly Thr Phe Gln Leu His Tyr Gln
    370                 375                 380
Ala Phe Met Leu Ser Cys Asn Phe Pro Arg Arg Pro Asp Ser Gly Asp
385                 390                 395                 400
Val Thr Val Met Asp Leu His Ser Gly Val Ala His Phe His Cys
                405                 410                 415
His Leu Gly Tyr Glu Leu Gln Gly Ala Lys Met Leu Thr Cys Ile Asn
            420                 425                 430
Ala Ser Lys Pro His Trp Ser Ser Gln Glu Pro Ile Cys Ser Ala Pro
        435                 440                 445
Cys Gly Gly Ala Val His Asn Ala Thr Ile Gly Arg Val Leu Ser Pro
    450                 455                 460
Ser Tyr Pro Glu Asn Thr Asn Gly Ser Gln Phe Cys Ile Trp Thr Ile
465                 470                 475                 480
Glu Ala Pro Glu Gly Gln Lys Leu His Leu His Phe Glu Arg Leu Leu
                485                 490                 495
Leu His Asp Lys Asp Arg Met Thr Val His Ser Gly Gln Thr Asn Lys
            500                 505                 510
Ser Ala Leu Leu Tyr Asp Ser Leu Gln Thr Glu Ser Val Pro Phe Glu
        515                 520                 525
Gly Leu Leu Ser Glu Gly Asn Thr Ile Arg Ile Glu Phe Thr Ser Asp
```

```
              530                 535                 540
Gln Ala Arg Ala Ala Ser Thr Phe Asn Ile Arg Phe Glu Ala Phe Glu
545                 550                 555                 560

Lys Gly His Cys Tyr Glu Pro Tyr Ile Gln Asn Gly Asn Phe Thr Thr
                565                 570                 575

Ser Asp Pro Thr Tyr Asn Ile Gly Thr Ile Val Glu Phe Thr Cys Asp
                580                 585                 590

Pro Gly His Ser Leu Glu Gln Gly Pro Ala Ile Ile Glu Cys Ile Asn
                595                 600                 605

Val Arg Asp Pro Tyr Trp Asn Asp Thr Glu Pro Leu Cys Arg Ala Met
                610                 615                 620

Cys Gly Gly Glu Leu Ser Ala Val Ala Gly Val Val Leu Ser Pro Asn
625                 630                 635                 640

Trp Pro Glu Pro Tyr Val Glu Gly Glu Asp Cys Ile Trp Lys Ile His
                645                 650                 655

Val Gly Glu Glu Lys Arg Ile Phe Leu Asp Ile Gln Phe Leu Asn Leu
                660                 665                 670

Ser Asn Ser Asp Ile Leu Thr Ile Tyr Asp Gly Asp Glu Val Met Pro
                675                 680                 685

His Ile Leu Gly Gln Tyr Leu Gly Asn Ser Gly Pro Gln Lys Leu Tyr
                690                 695                 700

Ser Ser Thr Pro Asp Leu Thr Ile Gln Phe His Ser Asp Pro Ala Gly
705                 710                 715                 720

Leu Ile Phe Gly Lys Gly Gln Gly Phe Ile Met Asn Tyr Ile Glu Val
                725                 730                 735

Ser Arg Asn Asp Ser Cys Ser Asp Leu Pro Glu Ile Gln Asn Gly Trp
                740                 745                 750

Lys Thr Thr Ser His Thr Glu Leu Val Arg Gly Ala Arg Ile Thr Tyr
                755                 760                 765

Gln Cys Asp Pro Gly Tyr Asp Ile Val Gly Ser Asp Thr Leu Thr Cys
                770                 775                 780

Gln Trp Asp Leu Ser Trp Ser Ser Asp Pro Pro Phe Cys Glu Lys Ile
785                 790                 795                 800

Met Tyr Cys Thr Asp Pro Gly Glu Val Asp His Ser Thr Arg Leu Ile
                805                 810                 815

Ser Asp Pro Val Leu Leu Val Gly Thr Thr Ile Gln Tyr Thr Cys Asn
                820                 825                 830

Pro Gly Phe Val Leu Glu Gly Ser Ser Leu Leu Thr Cys Tyr Ser Arg
                835                 840                 845

Glu Thr Gly Thr Pro Ile Trp Thr Ser Arg Leu Pro His Cys Val Ser
850                 855                 860

Glu Glu Ser Leu Ala Cys Asp Asn Pro Gly Leu Pro Glu Asn Gly Tyr
865                 870                 875                 880

Gln Ile Leu Tyr Lys Arg Leu Tyr Leu Pro Gly Glu Ser Leu Thr Phe
                885                 890                 895

Met Cys Tyr Glu Gly Phe Glu Leu Met Gly Glu Val Thr Ile Arg Cys
                900                 905                 910

Ile Leu Gly Gln Pro Ser His Trp Asn Gly Pro Leu Pro Val Cys Lys
                915                 920                 925

Val Asn Gln Asp Ser Phe Glu His Ala Leu Glu Val Ala Glu Ala Ala
                930                 935                 940

Ala Glu Thr Ser Leu Glu Gly Gly Leu Ala Gly His His His His
945                 950                 955                 960
```

His His His His

<210> SEQ ID NO 18
<211> LENGTH: 2487
<212> TYPE: DNA
<213> ORGANISM: Homo sapiens
<220> FEATURE:
<221> NAME/KEY: misc_feature
<223> OTHER INFORMATION: cDNA sequence of human SEZ6L2 ECD

<400> SEQUENCE: 18

| | | | | | |
|---|---|---|---|---|---|
| ctgcctctca | aagaggaaga | gattctcccc | gagcccggat | ccgagacacc | cacagtggct | 60 |
| tccgaagccc | tcgctgaact | gctgcacgga | gccctcctga | aaggggacc | tgaaatgggc | 120 |
| tatctccctg | ctccgacag | agatcccaca | ctcgccacac | ctcctgctgg | acagaccctc | 180 |
| gctgtgcctt | ccctgcccag | agccacagaa | cccggaacag | gccctctcac | aacagctgtg | 240 |
| accctaacg | gcgtcagagg | agctggacct | acagccctg | agctgctgac | acctcctcct | 300 |
| ggcacaaccg | ctcctcctcc | tccttcccct | gctagccctg | accccctct | cggacctgaa | 360 |
| ggaggcgagg | aggagacaac | caccaccatt | attaccacca | ccaccgtgac | aaccacagtg | 420 |
| accagccctg | tcctgtgcaa | caacaacatc | agcgaaggcg | aaggctatgt | ggaatcccct | 480 |
| gacctgggct | cccctgtgtc | cagaacactc | ggcctcctgg | attgcacata | ctccattcac | 540 |
| gtgtaccccg | gctacggaat | cgagattcag | gtgcagaccc | tgaatctgtc | ccaggaggag | 600 |
| gaactgctgg | tgctggctgg | cggaggaagc | cctggcctcg | ctcctagact | cctcgctaac | 660 |
| tcctccatgc | tcggcgaagg | ccaggtcctc | agatccccta | ccaacaggct | gctcctgcac | 720 |
| ttccagagcc | ccagagtgcc | tagaggaggc | ggcttcagga | ttcactacca | ggcctatctc | 780 |
| ctgagctgtg | gattccctcc | cagacccgct | catggcgatg | tctccgtcac | cgacctccac | 840 |
| cccggaggaa | cagccaccttc | ccactgtgat | tccggatacc | agctgcaagg | cgaggagacc | 900 |
| ctgatttgcc | tcaatggcac | caggcccagc | tggaacggag | agacacctag | ctgcatggct | 960 |
| agctgcggcg | gaaccatcca | taatgccacc | ctcggcagga | tcgtcagccc | tgaacctggc | 1020 |
| ggagctgtgg | gacctaacct | cacatgcaga | tgggtgatcg | aagctgctga | aggcaggaga | 1080 |
| ctccacctcc | acttcgagag | ggtgtccctg | gacgaggaca | cgacaggct | catggtcaga | 1140 |
| agcggcggaa | gccctctcag | ccctgtgatt | tacgacagcg | acatggacga | tgtgcctgag | 1200 |
| aggggcctca | tctccgatgc | ccaaagcctg | tacgtggaac | tcctctccga | gaccccgct | 1260 |
| aaccccctcc | tcctgagcct | cagattcgag | gccttcgagg | aggacagatg | tttcgctcct | 1320 |
| tttctggccc | atggcaacgt | gaccacaacc | gaccccgagt | acagaccgg | agctctggct | 1380 |
| accttcagct | gtctgcctgg | ctacgccctc | gaacctcccg | gacctcctaa | tgccatcgaa | 1440 |
| tgtgtggatc | ccaccgaacc | ccattggaac | gacaccgagc | ccgcttgtaa | ggctatgtgc | 1500 |
| ggcgagaac | tcagcgaacc | tgccggagtg | gtcctctccc | ctgattggcc | ccagagctat | 1560 |
| tcccccggac | aagactgtgt | ctgggcgtg | cacgtccagg | aggaaaagag | gatcctcctc | 1620 |
| caggtggaga | ttctgaacgt | cagagaggga | gacatgctga | ccctgttcga | cggagacgga | 1680 |
| ccttccgcca | gagtcctcgc | tcagctgaga | ggccctcagc | ccagaaggag | actgctcagc | 1740 |
| tccggccccg | atctgacact | ccagtttcag | gccccccctg | gcccccctaa | tcctggcctg | 1800 |
| ggacagggct | tcgtgctcca | cttcaaggag | gtccccagga | atgatacatg | ccccgaactg | 1860 |
| cctcctcccg | agtggggatg | gaggacagct | tcccatggcg | acctgatcag | ggaaccgtg | 1920 |
| ctgacatatc | agtgtgaacc | cggctacgag | ctgctgggaa | gcgatatcct | gacctgtcag | 1980 |

```
tgggatctct cctggagcgc tgctccccct gcctgtcaga aaatcatgac ctgcgctgac    2040
cctggagaga tcgctaacgg ccacaggacc gcttccgacg ctggatttcc cgtgggctcc    2100
cacgtgcaat acaggtgcct ccccggatac tccctcgaag gcgctgccat gctgacatgc    2160
tacagcaggg acaccggcac acccaagtgg tccgacaggg tgcccaaatg tgctctgaag    2220
tacgagccct gtctcaatcc cggagtgccc gagaacggat accagaccct gtacaagcac    2280
cactatcagg ccggcgaatc cctgagattc ttctgctacg agggcttcga gctcatcggc    2340
gaggtgacaa ttacctgtgt gcccggccat ccttcccagt ggaccagcca gcccccctct    2400
tgtaaggtcg cctacgaaga gctgctcgac aataggaagc tggaggtcac ccagaccacc    2460
gacccttcca gacaactgga aggcggc                                        2487
```

<210> SEQ ID NO 19
<211> LENGTH: 865
<212> TYPE: PRT
<213> ORGANISM: Homo sapiens
<220> FEATURE:
<221> NAME/KEY: MISC_FEATURE
<223> OTHER INFORMATION: Human SEZ6L2 ECD protein

<400> SEQUENCE: 19

```
Met Glu Thr Asp Thr Leu Leu Trp Val Leu Leu Leu Trp Val Pro
1               5                   10                  15

Gly Ser Thr Gly Asp Gly Ala Pro Leu Pro Lys Glu Glu Glu Ile
                20                  25                  30

Leu Pro Glu Pro Gly Ser Glu Thr Pro Thr Val Ala Ser Glu Ala Leu
            35                  40                  45

Ala Glu Leu Leu His Gly Ala Leu Leu Arg Arg Gly Pro Glu Met Gly
        50                  55                  60

Tyr Leu Pro Gly Ser Asp Arg Asp Pro Thr Leu Ala Thr Pro Pro Ala
65                  70                  75                  80

Gly Gln Thr Leu Ala Val Pro Ser Leu Pro Arg Ala Thr Glu Pro Gly
                85                  90                  95

Thr Gly Pro Leu Thr Thr Ala Val Thr Pro Asn Gly Val Arg Gly Ala
            100                 105                 110

Gly Pro Thr Ala Pro Glu Leu Leu Thr Pro Pro Gly Thr Thr Ala
        115                 120                 125

Pro Pro Pro Ser Pro Ala Ser Pro Gly Pro Pro Leu Gly Pro Glu
        130                 135                 140

Gly Gly Glu Glu Thr Thr Thr Thr Ile Ile Thr Thr Thr Thr Val
145                 150                 155                 160

Thr Thr Thr Val Thr Ser Pro Val Leu Cys Asn Asn Asn Ile Ser Glu
                165                 170                 175

Gly Glu Gly Tyr Val Glu Ser Pro Asp Leu Gly Ser Pro Val Ser Arg
            180                 185                 190

Thr Leu Gly Leu Leu Asp Cys Thr Tyr Ser Ile His Val Tyr Pro Gly
        195                 200                 205

Tyr Gly Ile Glu Ile Gln Val Gln Thr Leu Asn Leu Ser Gln Glu Glu
        210                 215                 220

Glu Leu Leu Val Leu Ala Gly Gly Ser Gly Leu Ala Pro Arg
225                 230                 235                 240

Leu Leu Ala Asn Ser Ser Met Leu Gly Glu Gly Gln Val Leu Arg Ser
                245                 250                 255

Pro Thr Asn Arg Leu Leu Leu His Phe Gln Ser Pro Arg Val Pro Arg
```

```
            260                 265                 270
Gly Gly Gly Phe Arg Ile His Tyr Gln Ala Tyr Leu Leu Ser Cys Gly
            275                 280                 285

Phe Pro Pro Arg Pro Ala His Gly Asp Val Ser Val Thr Asp Leu His
290                 295                 300

Pro Gly Gly Thr Ala Thr Phe His Cys Asp Ser Gly Tyr Gln Leu Gln
305                 310                 315                 320

Gly Glu Glu Thr Leu Ile Cys Leu Asn Gly Thr Arg Pro Ser Trp Asn
                325                 330                 335

Gly Glu Thr Pro Ser Cys Met Ala Ser Cys Gly Gly Thr Ile His Asn
            340                 345                 350

Ala Thr Leu Gly Arg Ile Val Ser Pro Glu Pro Gly Gly Ala Val Gly
            355                 360                 365

Pro Asn Leu Thr Cys Arg Trp Val Ile Glu Ala Ala Glu Gly Arg Arg
370                 375                 380

Leu His Leu His Phe Glu Arg Val Ser Leu Asp Glu Asp Asn Asp Arg
385                 390                 395                 400

Leu Met Val Arg Ser Gly Gly Ser Pro Leu Ser Pro Val Ile Tyr Asp
                405                 410                 415

Ser Asp Met Asp Asp Val Pro Glu Arg Gly Leu Ile Ser Asp Ala Gln
            420                 425                 430

Ser Leu Tyr Val Glu Leu Leu Ser Glu Thr Pro Ala Asn Pro Leu Leu
            435                 440                 445

Leu Ser Leu Arg Phe Glu Ala Phe Glu Glu Asp Arg Cys Phe Ala Pro
450                 455                 460

Phe Leu Ala His Gly Asn Val Thr Thr Thr Asp Pro Glu Tyr Arg Pro
465                 470                 475                 480

Gly Ala Leu Ala Thr Phe Ser Cys Leu Pro Gly Tyr Ala Leu Glu Pro
                485                 490                 495

Pro Gly Pro Pro Asn Ala Ile Glu Cys Val Asp Pro Thr Glu Pro His
            500                 505                 510

Trp Asn Asp Thr Glu Pro Ala Cys Lys Ala Met Cys Gly Gly Glu Leu
            515                 520                 525

Ser Glu Pro Ala Gly Val Val Leu Ser Pro Asp Trp Pro Gln Ser Tyr
530                 535                 540

Ser Pro Gly Gln Asp Cys Val Trp Gly Val His Val Gln Glu Glu Lys
545                 550                 555                 560

Arg Ile Leu Leu Gln Val Glu Ile Leu Asn Val Arg Glu Gly Asp Met
                565                 570                 575

Leu Thr Leu Phe Asp Gly Asp Gly Pro Ser Ala Arg Val Leu Ala Gln
            580                 585                 590

Leu Arg Gly Pro Gln Pro Arg Arg Arg Leu Leu Ser Ser Gly Pro Asp
            595                 600                 605

Leu Thr Leu Gln Phe Gln Ala Pro Pro Gly Pro Pro Asn Pro Gly Leu
610                 615                 620

Gly Gln Gly Phe Val Leu His Phe Lys Glu Val Pro Arg Asn Asp Thr
625                 630                 635                 640

Cys Pro Glu Leu Pro Pro Pro Glu Trp Gly Trp Arg Thr Ala Ser His
                645                 650                 655

Gly Asp Leu Ile Arg Gly Thr Val Leu Thr Tyr Gln Cys Glu Pro Gly
            660                 665                 670

Tyr Glu Leu Leu Gly Ser Asp Ile Leu Thr Cys Gln Trp Asp Leu Ser
            675                 680                 685
```

Trp Ser Ala Pro Pro Ala Cys Gln Lys Ile Met Thr Cys Ala Asp
690                 695                 700

Pro Gly Glu Ile Ala Asn Gly His Arg Thr Ala Ser Asp Ala Gly Phe
705                 710                 715                 720

Pro Val Gly Ser His Val Gln Tyr Arg Cys Leu Pro Gly Tyr Ser Leu
            725                 730                 735

Glu Gly Ala Ala Met Leu Thr Cys Tyr Ser Arg Asp Thr Gly Thr Pro
            740                 745                 750

Lys Trp Ser Asp Arg Val Pro Lys Cys Ala Leu Lys Tyr Glu Pro Cys
            755                 760                 765

Leu Asn Pro Gly Val Pro Glu Asn Gly Tyr Gln Thr Leu Tyr Lys His
            770                 775                 780

His Tyr Gln Ala Gly Glu Ser Leu Arg Phe Phe Cys Tyr Glu Gly Phe
785                 790                 795                 800

Glu Leu Ile Gly Glu Val Thr Ile Thr Cys Val Pro Gly His Pro Ser
            805                 810                 815

Gln Trp Thr Ser Gln Pro Pro Leu Cys Lys Val Ala Tyr Glu Glu Leu
            820                 825                 830

Leu Asp Asn Arg Lys Leu Glu Val Thr Gln Thr Thr Asp Pro Ser Arg
            835                 840                 845

Gln Leu Glu Gly Gly Leu Ala Gly His His His His His His His
            850                 855                 860

His
865

<210> SEQ ID NO 20
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.1 VL

<400> SEQUENCE: 20

Gln Ile Val Leu Thr Gln Ser Pro Ala Leu Met Ser Ala Ser Pro Gly
1               5                   10                  15

Glu Lys Val Ser Leu Thr Cys Ser Ala Asn Ser Thr Val Ser Phe Met
            20                  25                  30

Tyr Trp Tyr Gln Gln Lys Pro Arg Ser Ser Pro Thr Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Ser Pro Ile
                85                  90                  95

Thr Phe Gly Ala Gly Thr Lys Leu Glu Leu Lys
            100                 105

<210> SEQ ID NO 21
<211> LENGTH: 117
<212> TYPE: PRT
<213> ORGANISM: Mus musculus
<220> FEATURE:
<221> NAME/KEY: MISC_FEATURE
<223> OTHER INFORMATION: Murine SC17.1 VH

<400> SEQUENCE: 21

```
Asp Val Gln Leu Gln Asp Ser Gly Pro Gly Leu Val Lys Pro Ser Gln
1               5                   10                  15

Ser Leu Ser Val Thr Cys Thr Val Thr Gly Tyr Ser Ile Thr Trp Gly
            20                  25                  30

Tyr Tyr Trp Asn Trp Ile Arg Gln Phe Pro Gly Asn Lys Leu Glu Trp
            35                  40                  45

Met Gly Asn Ile His Asn Ser Gly Gly Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Thr Thr Asn Trp Asp Tyr Phe Asp Tyr Trp Gly Gln Gly Thr Thr
            100                 105                 110

Leu Thr Val Ser Ser
        115
```

<210> SEQ ID NO 22
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.2 VL

<400> SEQUENCE: 22

```
Asp Ile Val Met Ser Gln Ser Pro Ser Ser Leu Ala Val Ser Val Gly
1               5                   10                  15

Glu Lys Val Thr Met Ser Cys Lys Ser Gln Ser Leu Leu Tyr Ser
            20                  25                  30

Ser Asn Gln Lys Ser Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110
```

<210> SEQ ID NO 23
<211> LENGTH: 117
<212> TYPE: PRT
<213> ORGANISM: Mus musculus
<220> FEATURE:
<221> NAME/KEY: MISC_FEATURE
<223> OTHER INFORMATION: Murine SC17.2 VH

<400> SEQUENCE: 23

```
Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
            35                  40                  45

Gly Tyr Ile Tyr Pro Arg Asp Gly Ser Thr Lys Tyr Asn Glu Glu Phe
    50                  55                  60
```

```
Lys Gly Lys Ala Thr Leu Thr Ala Asp Lys Ser Ser Thr Ala Tyr
 65                  70                  75                  80

Met Gln Leu Asn Ser Leu Thr Ser Glu Asp Ser Ala Val Tyr Phe Cys
                 85                  90                  95

Ala Arg Ser Tyr Ser Asn Tyr Phe Asp Tyr Trp Gly Gln Gly Thr Thr
            100                 105                 110

Leu Thr Val Ser Ser
        115

<210> SEQ ID NO 24
<211> LENGTH: 111
<212> TYPE: PRT
<213> ORGANISM: Mus musculus
<220> FEATURE:
<221> NAME/KEY: MISC_FEATURE
<223> OTHER INFORMATION: Murine SC17.9 VL

<400> SEQUENCE: 24

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
 65                 70                  75                  80

Ile Ser Ser Val Lys Ala Glu Asp Leu Ala Val Tyr Phe Cys Gln Gln
                85                  90                  95

Tyr Tyr Asn Tyr Pro Tyr Thr Phe Gly Gly Gly Thr Lys Leu Lys
            100                 105                 110

<210> SEQ ID NO 25
<211> LENGTH: 119
<212> TYPE: PRT
<213> ORGANISM: Mus musculus
<220> FEATURE:
<221> NAME/KEY: MISC_FEATURE
<223> OTHER INFORMATION: Murine SC17.9 VH

<400> SEQUENCE: 25

Gln Val Gln Leu Gln Gln Pro Gly Ala Glu Ile Val Arg Pro Gly Ala
1               5                   10                  15

Ser Val Lys Leu Ser Cys Lys Ala Ser Gly Tyr Thr Phe Thr Asp Tyr
                20                  25                  30

Trp Met Asn Trp Val Lys Gln Arg Pro Gly Gln Gly Leu Glu Trp Ile
            35                  40                  45

Gly Ala Ile Asp Pro Ser Asp Ser Tyr Thr Ser Tyr Asn Pro Lys Phe
        50                  55                  60

Lys Gly Lys Ala Thr Leu Thr Val Asp Thr Ser Ser Ser Ala Tyr
 65                 70                  75                  80

Met Gln Leu Ser Ser Leu Thr Ser Glu Asp Ser Ala Val Tyr Phe Cys
                85                  90                  95

Ala Arg Arg Gly Thr Pro Gly Lys Pro Leu Val Tyr Trp Gly Gln Gly
            100                 105                 110

Thr Leu Val Thr Val Ser Ala
        115
```

<210> SEQ ID NO 26
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.16 VL

<400> SEQUENCE: 26

Asp Ile Gln Met Thr Gln Ser Pro Ala Ser Leu Ser Val Ser Val Gly
1               5                   10                  15

Glu Thr Val Thr Ile Thr Cys Arg Ala Ser Ala Asn Ile Asn Ser Asn
            20                  25                  30

Leu Val Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Asn Tyr Tyr Cys Gln His Phe Trp Gly Thr Pro Arg
                85                  90                  95

Thr Phe Gly Gly Gly Thr Lys Leu Glu Ile Lys
            100                 105

<210> SEQ ID NO 27
<211> LENGTH: 116
<212> TYPE: PRT
<213> ORGANISM: Mus musculus
<220> FEATURE:
<221> NAME/KEY: MISC_FEATURE
<223> OTHER INFORMATION: Murine SC17.16 VH

<400> SEQUENCE: 27

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met Tyr Trp Val Lys Gln Asn Gln Gly Lys Ser Leu Glu Trp Ile
        35                  40                  45

Gly Glu Ile Asn Pro Asn Asn Gly Gly Thr Ala Tyr Asn Gln Lys Phe
    50                  55                  60

Arg Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Tyr Asp Lys Gly Phe Asp Tyr Trp Gly Gln Gly Thr Thr Leu
            100                 105                 110

Thr Val Ser Ser
        115

<210> SEQ ID NO 28
<211> LENGTH: 111
<212> TYPE: PRT
<213> ORGANISM: Mus musculus
<220> FEATURE:
<221> NAME/KEY: MISC_FEATURE
<223> OTHER INFORMATION: Murine SC17.38 VL

<400> SEQUENCE: 28

```
Asp Ile Val Val Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Phe Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Asp Arg
                85                  90                  95

Lys Val Pro Trp Thr Phe Gly Gly Gly Thr Lys Leu Glu Ile Lys
            100                 105                 110

<210> SEQ ID NO 29
<211> LENGTH: 120
<212> TYPE: PRT
<213> ORGANISM: Mus musculus
<220> FEATURE:
<221> NAME/KEY: MISC_FEATURE
<223> OTHER INFORMATION: Murine SC17.38 VH

<400> SEQUENCE: 29

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Ser
            20                  25                  30

Gly Met Ser Val Gly Trp Val Arg Gln Pro Ser Gly Arg Gly Leu Glu
        35                  40                  45

Trp Leu Ala Pro Ile Trp Trp Asn Gly Asp Lys Tyr Tyr Asn Pro Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Val Thr Ala Asp Thr Ala Thr Tyr Phe
                85                  90                  95

Cys Ala Arg Ile Arg Gln Tyr Tyr Ala Met Asp Tyr Trp Gly Gln
            100                 105                 110

Gly Thr Ser Val Thr Val Ser Ser
            115                 120

<210> SEQ ID NO 30
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.3 VL

<400> SEQUENCE: 30

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60
```

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Thr Phe Gly Gly Gly Thr Lys Leu Glu Ile Lys
            100                 105                 110

<210> SEQ ID NO 31
<211> LENGTH: 118
<212> TYPE: PRT
<213> ORGANISM: Mus musculus
<220> FEATURE:
<221> NAME/KEY: MISC_FEATURE
<223> OTHER INFORMATION: Murine SC17.3 VH

<400> SEQUENCE: 31

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Pro Ser Tyr
                20                  25                  30

Trp Ile His Cys Val Lys Gln Arg Pro Gly Gln Gly Leu Glu Trp Ile
            35                  40                  45

Gly Val Ile Asn Pro Ser Asn Gly Arg Thr Asn Tyr Asn Glu Lys Phe
        50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Val Arg Gly Gly Thr Gly Tyr Thr Met Asp Tyr Trp Gly Gln Gly Thr
            100                 105                 110

Ser Val Thr Val Ser Ser
            115

<210> SEQ ID NO 32
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.4 VL

<400> SEQUENCE: 32

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30

Leu Thr Trp Phe Gln Gln Lys Pro Gly Lys Ser Pro Lys Thr Leu Ile
            35                  40                  45

Tyr Arg Ala Asn Arg Leu Ile Asp Gly Val Pro Ser Arg Phe Ser Gly
        50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Asp Phe Pro Trp
                85                  90                  95

Thr Phe Gly Gly Gly Thr Lys Leu Glu Ile Lys
            100                 105

<210> SEQ ID NO 33
<211> LENGTH: 116

```
<212> TYPE: PRT
<213> ORGANISM: Mus musculus
<220> FEATURE:
<221> NAME/KEY: MISC_FEATURE
<223> OTHER INFORMATION: Murine SC17.4 VH

<400> SEQUENCE: 33
```

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Met His Trp Val Lys Gln Ala Pro Gly Lys Gly Leu Lys Trp Leu
            35                  40                  45

Gly Trp Ile Asn Thr Glu Thr Gly Glu Pro Thr Tyr Ser Glu Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Val Lys Asn Lys Gly Trp Phe Ala Tyr Trp Gly Gln Gly Thr Leu Val
                100                 105                 110

Thr Val Ser Ala
            115

```
<210> SEQ ID NO 34
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.8 VL

<400> SEQUENCE: 34
```

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asp Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Thr Leu Ile Pro Tyr Thr Phe Gly Gly Gly Thr Lys Leu Asp Ile Lys
                100                 105                 110

```
<210> SEQ ID NO 35
<211> LENGTH: 114
<212> TYPE: PRT
<213> ORGANISM: Mus musculus
<220> FEATURE:
<221> NAME/KEY: MISC_FEATURE
<223> OTHER INFORMATION: Murine SC17.8 VH

<400> SEQUENCE: 35
```

Gln Val His Leu Gln Gln Ser Gly Thr Glu Val Met Lys Pro Gly Ala
1               5                   10                  15

Ser Val Lys Ile Ser Cys Lys Ala Thr Gly Tyr Thr Phe Ser Ser Tyr

```
                20                  25                  30
Trp Ile Glu Trp Ile Lys Gln Arg Pro Gly His Gly Leu Glu Trp Ile
            35                  40                  45
Gly Glu Ile Leu Pro Gly Ser Gly Asn Thr Asn Asn Asn Glu Lys Phe
        50                  55                  60
Lys Gly Lys Ala Thr Ile Thr Ala Asp Thr Ser Ser Asn Ile Ala Tyr
65                  70                  75                  80
Ile Gln Leu Ser Ser Leu Thr Ser Glu Asp Ser Ala Val Tyr Tyr Cys
                85                  90                  95
Ala Gly Gly Pro Ala Ala Tyr Trp Gly Gln Gly Thr Leu Val Thr Val
            100                 105                 110
Ser Ala

<210> SEQ ID NO 36
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.10 VL

<400> SEQUENCE: 36

Asp Ile Val Met Ser Gln Ser Pro Ser Ser Leu Ala Val Ser Val Gly
1               5                   10                  15
Glu Lys Val Thr Met Ser Cys Lys Ser Ser Gln Ser Leu Leu Tyr Ser
                20                  25                  30
Ser Asn Gln Lys Asn Tyr Leu Ala Trp Tyr Gln Gln Lys Pro Gly Gln
            35                  40                  45
Ser Pro Lys Leu Leu Ile Tyr Trp Ala Ser Thr Arg Glu Ser Gly Val
        50                  55                  60
Pro Asp Arg Phe Thr Gly Ser Gly Ser Gly Thr Asp Phe Thr Leu Thr
65                  70                  75                  80
Ile Ser Ser Val Lys Thr Glu Asp Leu Ala Leu Tyr Tyr Cys Gln Gln
                85                  90                  95
Tyr Tyr Trp Phe Pro Tyr Thr Phe Gly Gly Gly Thr Lys Leu Glu Ile
            100                 105                 110
Lys

<210> SEQ ID NO 37
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.10 VH

<400> SEQUENCE: 37

Glu Val Gln Leu Gln Gln Ser Gly Ala Glu Leu Val Lys Pro Gly Ala
1               5                   10                  15
Ser Val Lys Leu Ser Cys Thr Ala Ser Gly Phe Asn Ile Lys Asp Thr
                20                  25                  30
Tyr Met His Trp Val Lys Gln Arg Pro Glu Gln Gly Leu Glu Trp Ile
            35                  40                  45
Gly Arg Ile Asp Pro Ala Asn Val Asn Thr Lys Tyr Asp Pro Lys Phe
        50                  55                  60
Gln Gly Lys Ala Thr Ile Thr Ala Asp Thr Ser Ser Asn Thr Ala Tyr
65                  70                  75                  80
```

-continued

```
Leu Gln Leu Ser Ser Leu Thr Ser Glu Asp Thr Ala Val Tyr Tyr Cys
                85                  90                  95

Val Arg Gly Asn Val Tyr Trp Gly Gln Gly Thr Leu Val Thr Val Ser
            100                 105                 110

Ala

<210> SEQ ID NO 38
<211> LENGTH: 108
<212> TYPE: PRT
<213> ORGANISM: Mus musculus
<220> FEATURE:
<221> NAME/KEY: MISC_FEATURE
<223> OTHER INFORMATION: Murine SC17.11 VL

<400> SEQUENCE: 38

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Asp Tyr Pro
                85                  90                  95

Phe Thr Phe Gly Ser Gly Thr Lys Leu Val Ile Lys
            100                 105

<210> SEQ ID NO 39
<211> LENGTH: 122
<212> TYPE: PRT
<213> ORGANISM: Mus musculus
<220> FEATURE:
<221> NAME/KEY: MISC_FEATURE
<223> OTHER INFORMATION: Murine SC17.11 VH

<400> SEQUENCE: 39

Glu Val Gln Leu Gln Gln Ser Gly Pro Glu Leu Val Lys Pro Gly Ala
1               5                   10                  15

Leu Val Met Met Ser Cys Lys Ala Ser Gly Tyr Thr Phe Thr Asp Tyr
            20                  25                  30

Tyr Met His Trp Val Lys Gln Ser His Gly Gln Ser Leu Glu Trp Ile
        35                  40                  45

Gly Glu Val Ile Pro Tyr Asn Asp Glu Thr Phe Tyr Asn Arg Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Ile Tyr Tyr Cys
                85                  90                  95

Ala Arg Arg His Arg Tyr Asp Gly Phe Arg Tyr Ala Ile Asp Tyr Trp
            100                 105                 110

Gly Gln Gly Thr Ser Val Thr Val Ser Ser
        115                 120

<210> SEQ ID NO 40
<211> LENGTH: 112
<212> TYPE: PRT
```

```
<213> ORGANISM: Mus musculus
<220> FEATURE:
<221> NAME/KEY: MISC_FEATURE
<223> OTHER INFORMATION: Murine SC17.14 VL

<400> SEQUENCE: 40

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 41
<211> LENGTH: 118
<212> TYPE: PRT
<213> ORGANISM: Mus musculus
<220> FEATURE:
<221> NAME/KEY: MISC_FEATURE
<223> OTHER INFORMATION: Murine SC17.14 VH

<400> SEQUENCE: 41

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Ile Thr Asp Tyr
            20                  25                  30

Asn Met Asn Trp Val Lys Gln Ser His Gly Lys Ser Leu Glu Trp Ile
        35                  40                  45

Gly Val Ile Asn Pro Tyr Asn Gly Asn Thr Arg Tyr Asn Gln Met Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Thr Arg Trp Gly Thr Thr Val Val Gly Ala Asn Trp Gly Gln Gly Thr
            100                 105                 110

Thr Leu Thr Val Ser Ser
        115

<210> SEQ ID NO 42
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.15 VL

<400> SEQUENCE: 42

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Asn Tyr Met
            20                  25                  30
```

```
Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Val Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asn Asn Pro Pro Thr
                85                  90                  95

Phe Gly Ser Gly Thr Lys Leu Glu Leu Lys
                100                 105

<210> SEQ ID NO 43
<211> LENGTH: 122
<212> TYPE: PRT
<213> ORGANISM: Mus musculus
<220> FEATURE:
<221> NAME/KEY: MISC_FEATURE
<223> OTHER INFORMATION: Murine SC17.15 VH

<400> SEQUENCE: 43

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
            35                  40                  45

Ala Thr Ile Thr Ser Gly Gly Gly Asn Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg Asp Tyr Tyr Gly Ser Ser Tyr Val Met Phe Ala Tyr Trp
                100                 105                 110

Gly Gln Gly Thr Leu Val Thr Val Ser Ala
            115                 120

<210> SEQ ID NO 44
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.17 VL

<400> SEQUENCE: 44

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
            35                  40                  45

Asp Thr Ser Lys Leu Pro Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Thr Pro Pro Thr
                85                  90                  95
```

Phe Gly Ala Gly Thr Lys Leu Glu Leu Lys
            100                 105

<210> SEQ ID NO 45
<211> LENGTH: 120
<212> TYPE: PRT
<213> ORGANISM: Mus musculus
<220> FEATURE:
<221> NAME/KEY: MISC_FEATURE
<223> OTHER INFORMATION: Murine SC17.17 VH

<400> SEQUENCE: 45

Glu Val Gln Leu Gln Gln Ser Gly Pro Glu Val Met Lys Pro Gly Ala
1               5                   10                  15

Ser Val Lys Met Ser Cys Lys Ala Ser Gly Tyr Thr Phe Thr Asp Tyr
                20                  25                  30

Asn Met His Trp Val Lys Gln Asn Gln Gly Lys Ser Leu Glu Trp Ile
            35                  40                  45

Gly Glu Ile Asn Pro Asn Ile Gly Gly Thr Gly Tyr Asn Gln Lys Phe
        50                  55                  60

Lys Gly Lys Ala Thr Leu Thr Val His Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Thr Tyr Ser Tyr Tyr Ser Tyr Glu Phe Ala Tyr Trp Gly Gln
                100                 105                 110

Gly Thr Leu Val Thr Val Ser Ala
            115                 120

<210> SEQ ID NO 46
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.18 VL

<400> SEQUENCE: 46

Asp Ile Gln Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
                20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
        50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Ile Pro Leu
                85                  90                  95

Thr Phe Gly Ala Gly Thr Lys Leu Glu Leu Lys
            100                 105

<210> SEQ ID NO 47
<211> LENGTH: 123
<212> TYPE: PRT
<213> ORGANISM: Mus musculus
<220> FEATURE:
<221> NAME/KEY: MISC_FEATURE
<223> OTHER INFORMATION: Murine SC17.18 VH

<400> SEQUENCE: 47

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Thr Met Gly Val Gly Trp Ile Arg Gln Pro Ser Gly Lys Gly Leu Glu
        35                  40                  45

Trp Leu Ala Asp Ile Trp Trp Asp Asp Ser Lys Tyr Tyr Asn Pro Ser
50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Lys Gly Arg Thr Ala Arg Ala Thr Arg Gly Phe Ala Tyr
            100                 105                 110

Trp Gly His Gly Thr Leu Val Thr Val Ser Ala
            115                 120

<210> SEQ ID NO 48
<211> LENGTH: 109
<212> TYPE: PRT
<213> ORGANISM: Mus musculus
<220> FEATURE:
<221> NAME/KEY: MISC_FEATURE
<223> OTHER INFORMATION: Murine SC17.19 VL

<400> SEQUENCE: 48

Asp Ile Val Leu Thr Gln Ser Pro Ala Ser Leu Ala Val Ser Leu Gly
1               5                   10                  15

Gln Arg Ala Ala Ile Ser Cys Lys Pro Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys His Gln Ile Asn
                85                  90                  95

Asp Asp Pro Trp Thr Phe Gly Gly Gly Thr Lys Leu Lys
            100                 105

<210> SEQ ID NO 49
<211> LENGTH: 121
<212> TYPE: PRT
<213> ORGANISM: Mus musculus
<220> FEATURE:
<221> NAME/KEY: MISC_FEATURE
<223> OTHER INFORMATION: Murine SC17.19 VH

<400> SEQUENCE: 49

Asp Val Gln Leu Gln Glu Ser Gly Pro Gly Leu Val Lys Pro Ser Gln
1               5                   10                  15

Ser Leu Ser Val Thr Cys Thr Val Thr Gly Tyr Ser Ile Thr Ser Ser
            20                  25                  30

Tyr Thr Trp Asn Trp Ile Arg Gln Phe Pro Gly Asn Lys Leu Glu Trp
        35                  40                  45

```
Met Gly Tyr Ile His Tyr Ser Gly Ser Thr Asn Tyr Asn Pro Ser Leu
    50                  55                  60

Arg Ser Arg Ile Ser Ile Thr Arg Asp Thr Ser Lys Asn Gln Phe Phe
65              70                  75                  80

Leu Gln Leu Asn Ser Val Thr Thr Glu Asp Thr Ala Thr Tyr Tyr Cys
                85                  90                  95

Ala Arg Ser Arg Tyr Tyr Tyr Asp Ala Tyr Gly Phe Ala Tyr Trp Gly
                100                 105                 110

Gln Gly Thr Leu Val Thr Val Ser Ala
        115                 120

<210> SEQ ID NO 50
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.22 VL

<400> SEQUENCE: 50

Asp Val Val Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ile
                20                  25                  30

Asn Arg His Thr Tyr Leu Gly Trp Tyr Leu Gln Lys Pro Gly Gln Ser
                35                  40                  45

Leu Lys Leu Leu Ile Tyr Gly Val Ser Asn Arg Phe Ser Gly Val Pro
        50                  55                  60

Asp Arg Phe Ser Gly Ser Gly Ser Gly Thr Asp Phe Thr Leu Lys Ile
65              70                  75                  80

Ser Arg Val Glu Ala Glu Asp Met Gly Val Tyr Tyr Cys Phe Gln Gly
                85                  90                  95

Thr His Val Pro Phe Thr Phe Gly Ser Gly Thr Lys Leu Glu Ile Lys
                100                 105                 110

<210> SEQ ID NO 51
<211> LENGTH: 121
<212> TYPE: PRT
<213> ORGANISM: Mus musculus
<220> FEATURE:
<221> NAME/KEY: MISC_FEATURE
<223> OTHER INFORMATION: Murine SC17.22 VH

<400> SEQUENCE: 51

Gln Ile Gln Met Met Gln Ser Gly Pro Glu Leu Lys Lys Pro Gly Glu
1               5                   10                  15

Thr Val Lys Ile Ser Cys Lys Ala Ser Gly Tyr Ser Phe Thr Asn Tyr
                20                  25                  30

Gly Met Asn Trp Val Lys Gln Ala Pro Gly Lys Gly Leu Lys Trp Met
                35                  40                  45

Gly Trp Ile Asn Thr Tyr Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
65              70                  75                  80

Leu Gln Ile Asn Asn Leu Lys Asn Glu Asp Met Ala Thr Tyr Phe Cys
                85                  90                  95

Thr Arg Gly Tyr Tyr Gly Ser Ser Tyr Asp Ala Leu Asp Tyr Trp Gly
                100                 105                 110
```

```
Gln Gly Thr Ser Val Thr Val Ser Ser
        115                 120

<210> SEQ ID NO 52
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.24 VL

<400> SEQUENCE: 52

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Ser Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 53
<211> LENGTH: 117
<212> TYPE: PRT
<213> ORGANISM: Mus musculus
<220> FEATURE:
<221> NAME/KEY: MISC_FEATURE
<223> OTHER INFORMATION: Murine SC17.24 VH

<400> SEQUENCE: 53

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Ile Tyr Pro Arg Asp Gly Ser Thr Lys Tyr Asn Glu Glu Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Ser Tyr Ser Asn Tyr Phe Asp Tyr Trp Gly Gln Gly Thr Thr
            100                 105                 110

Leu Thr Val Ser Ser
        115

<210> SEQ ID NO 54
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.27 VL
```

```
<400> SEQUENCE: 54

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Glu Ser
                20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ile Gln His Pro Arg Thr Phe Gly Gly Gly Thr Lys Leu Glu Ile Lys
                100                 105                 110

<210> SEQ ID NO 55
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.27 VH

<400> SEQUENCE: 55

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
                20                  25                  30

Glu Met His Trp Val Lys Gln Thr Pro Val His Gly Leu Glu Trp Ile
            35                  40                  45

Gly Gly Ile Asp Pro Glu Thr Gly Gly Thr Ala Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Thr Arg Trp Phe Ser Tyr Trp Gly Pro Gly Thr Leu Val Thr Val Ser
                100                 105                 110

Ala

<210> SEQ ID NO 56
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.28 VL

<400> SEQUENCE: 56

Asp Ile Leu Leu Thr Gln Ser Pro Ala Ile Leu Ser Val Ser Pro Gly
1               5                   10                  15

Glu Gly Val Ser Phe Ser Cys Arg Ala Ser Gln Ser Ile Gly Thr Ser
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60
```

```
Ser Gly Ser Gly Thr Asp Phe Thr Leu Arg Ile Asn Ser Leu Glu Ser
65                  70                  75                  80

Glu Asp Ile Ala Asp Tyr Tyr Cys Gln Gln Ser Asn Ser Trp Pro Leu
                85                  90                  95

Thr Phe Gly Ala Gly Thr Lys Leu Glu Leu Lys
            100                 105
```

<210> SEQ ID NO 57
<211> LENGTH: 117
<212> TYPE: PRT
<213> ORGANISM: Mus musculus
<220> FEATURE:
<221> NAME/KEY: MISC_FEATURE
<223> OTHER INFORMATION: Murine SC17.28 VH

<400> SEQUENCE: 57

```
Gln Val His Leu Pro Gln Ser Arg Pro Glu Leu Val Lys Pro Gly Ala
1               5                   10                  15

Ser Val Lys Ile Ser Cys Lys Ala Ser Gly Tyr Gly Phe Thr Arg Ser
                20                  25                  30

Tyr Ile His Trp Val Lys Gln Arg Pro Gly Gln Gly Leu Glu Trp Ile
            35                  40                  45

Gly Tyr Ile Ser Ser Gly Ser Gly Thr Thr Tyr Asn Gln Lys Phe
50                  55                  60

Lys Gly Lys Ala Ser Leu Thr Ala Asp Asn Pro Ser Ser Thr Ala Tyr
65                  70                  75                  80

Met His Leu Ser Ser Leu Thr Ser Glu Asp Ser Ala Ile Tyr Phe Cys
                85                  90                  95

Ala Arg Gly Gly Val Arg Tyr Phe Asp Val Trp Gly Ala Gly Thr Thr
            100                 105                 110

Val Thr Val Ser Ser
            115
```

<210> SEQ ID NO 58
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.29 VL

<400> SEQUENCE: 58

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Asp
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105
```

<210> SEQ ID NO 59

-continued

```
<211> LENGTH: 116
<212> TYPE: PRT
<213> ORGANISM: Mus musculus
<220> FEATURE:
<221> NAME/KEY: MISC_FEATURE
<223> OTHER INFORMATION: Murine SC17.29 VH

<400> SEQUENCE: 59
```

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gly Lys Ser Leu Glu Trp Ile
        35                  40                  45

Gly Glu Ile Asn Pro His Asn Gly Gly Thr Gly Tyr Asn Gln Lys Phe
50                  55                  60

Lys Gly Lys Ala Thr Leu Thr Val Asp Lys Ser Ser Thr Ser Tyr
65                  70                  75                  80

Met Glu Leu Arg Ser Leu Thr Ser Glu Asp Ser Ala Val Tyr Tyr Cys
                85                  90                  95

Ala Gly Gly Tyr Pro Ala Phe Asp Tyr Trp Gly Gln Gly Thr Thr Leu
            100                 105                 110

Thr Val Ser Ser
        115

```
<210> SEQ ID NO 60
<211> LENGTH: 108
<212> TYPE: PRT
<213> ORGANISM: Mus musculus
<220> FEATURE:
<221> NAME/KEY: MISC_FEATURE
<223> OTHER INFORMATION: Murine SC17.30 VL

<400> SEQUENCE: 60
```

Glu Asn Val Leu Thr Gln Ser Pro Ala Ile Val Ser Ala Ser Pro Gly
1               5                   10                  15

Glu Lys Val Thr Met Thr Cys Arg Ala Ser Ser Ser Val Ile Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
50                  55                  60

Gly Ser Ala Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Leu Lys
            100                 105

```
<210> SEQ ID NO 61
<211> LENGTH: 124
<212> TYPE: PRT
<213> ORGANISM: Mus musculus
<220> FEATURE:
<221> NAME/KEY: MISC_FEATURE
<223> OTHER INFORMATION: Murine SC17.30 VH

<400> SEQUENCE: 61
```

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
            35                  40                  45

Ala Asn Ile Asn Tyr Asp Gly Ser Ser Thr Tyr Tyr Leu Asp Ser Leu
 50                  55                  60

Lys Ser Arg Phe Ile Ile Ser Arg Asp Asn Ala Lys Asn Ile Leu Tyr
 65                  70                  75                  80

Leu Gln Met Ser Ser Leu Lys Ser Glu Asp Thr Ala Thr Tyr Tyr Cys
                85                  90                  95

Ala Arg Asp Asp Tyr Tyr Gly Ser Ser Pro Ser Tyr Trp Tyr Phe Asp
            100                 105                 110

Val Trp Gly Ala Gly Thr Thr Val Thr Val Ser Ser
            115                 120

<210> SEQ ID NO 62
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.32 VL

<400> SEQUENCE: 62

Asp Ile Gln Met Thr Gln Ser Pro Ala Ser Leu Ser Ala Ser Val Gly
 1               5                  10                  15

Glu Thr Val Thr Met Thr Cys Arg Ala Ser Gly Asn Ile His Asn Tyr
            20                  25                  30

Leu Val Trp Tyr Gln Gln Lys Gln Gly Lys Ser Pro Gln Leu Leu Val
            35                  40                  45

Tyr Asn Ala Lys Thr Leu Ala Asp Gly Val Pro Ser Arg Phe Ser Gly
 50                  55                  60

Ser Gly Ser Gly Thr Gln Tyr Ser Leu Lys Ile Asn Ser Leu Gln Pro
 65                  70                  75                  80

Glu Asp Phe Gly Ser Tyr Tyr Cys Gln His Phe Trp Ser Thr Pro Pro
                85                  90                  95

Thr Phe Gly Gly Gly Thr Lys Leu Glu Ile Lys
            100                 105

<210> SEQ ID NO 63
<211> LENGTH: 119
<212> TYPE: PRT
<213> ORGANISM: Mus musculus
<220> FEATURE:
<221> NAME/KEY: MISC_FEATURE
<223> OTHER INFORMATION: Murine SC17.32 VH

<400> SEQUENCE: 63

Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Thr Phe Ser Asn Tyr
            20                  25                  30

Trp Met Ser Trp Val Arg Gln Ser Pro Glu Lys Gly Leu Glu Trp Val
            35                  40                  45

Ala Glu Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Ser Ser
 65                  70                  75                  80

Val Phe Leu Gln Met Asn Asn Leu Arg Thr Glu Asp Thr Gly Ile Tyr
                85                  90                  95

Tyr Cys Thr Arg His Tyr Tyr Ala Met Asp Tyr Trp Gly Gln Gly
            100                 105                 110

Thr Ser Val Thr Val Ser Ser
        115

<210> SEQ ID NO 64
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.34 VL

<400> SEQUENCE: 64

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Pro
                85                  90                  95

Thr Phe Gly Gly Gly Thr Lys Leu Glu Ile Lys
            100                 105

<210> SEQ ID NO 65
<211> LENGTH: 118
<212> TYPE: PRT
<213> ORGANISM: Mus musculus
<220> FEATURE:
<221> NAME/KEY: MISC_FEATURE
<223> OTHER INFORMATION: Murine SC17.34 VH

<400> SEQUENCE: 65

Glu Val Gln Leu Gln Gln Ser Gly Pro Glu Leu Val Lys Pro Gly Ser
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Arg Leu Glu Trp Ile
        35                  40                  45

Gly Tyr Ile Tyr Pro Asp Asn Gly Gly Ala Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ser Arg Ser Ile Thr Thr Ala Trp Phe Ala Tyr Trp Gly Gln Gly Thr
            100                 105                 110

Leu Val Thr Val Ser Ala
        115

<210> SEQ ID NO 66
<211> LENGTH: 108

<212> TYPE: PRT
<213> ORGANISM: Mus musculus
<220> FEATURE:
<221> NAME/KEY: MISC_FEATURE
<223> OTHER INFORMATION: Murine SC17.35 VL

<400> SEQUENCE: 66

Glu Asn Val Leu Thr Gln Ser Pro Ala Ile Met Ser Ala Ser Pro Gly
1               5                   10                  15

Glu Lys Val Thr Leu Thr Cys Arg Ala Ser Ser Ser Met Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Ala Tyr Pro
                85                  90                  95

Phe Thr Phe Gly Ser Gly Thr Lys Leu Glu Ile Lys
            100                 105

<210> SEQ ID NO 67
<211> LENGTH: 121
<212> TYPE: PRT
<213> ORGANISM: Mus musculus
<220> FEATURE:
<221> NAME/KEY: MISC_FEATURE
<223> OTHER INFORMATION: Murine SC17.35 VH

<400> SEQUENCE: 67

Glu Val Gln Leu Gln Gln Ser Gly Pro Glu Leu Val Lys Pro Gly Ala
1               5                   10                  15

Leu Val Lys Met Ser Cys Lys Ala Ser Gly Tyr Thr Phe Thr Asp Tyr
            20                  25                  30

Tyr Ile His Trp Val Lys Gln Ser His Gly Lys Ser Leu Glu Trp Ile
        35                  40                  45

Gly Glu Ile Asn Pro Tyr Asn Gly Glu Thr Phe Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Gly Trp Tyr Leu Thr Gly Tyr Ala Met Asp Tyr Trp Gly
            100                 105                 110

Gln Gly Thr Ser Val Thr Val Ser Ser
        115                 120

<210> SEQ ID NO 68
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.36 VL

<400> SEQUENCE: 68

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met

```
                20              25              30
Tyr Trp Tyr Gln Gln Lys Pro Arg Ser Ser Pro Lys Pro Trp Ile Tyr
            35              40              45

Leu Thr Ser Asn Leu Ala Ser Gly Val Pro Ala Arg Phe Ser Gly Ser
    50              55              60

Gly Ser Gly Thr Ser Tyr Ser Leu Thr Ile Ser Ser Met Glu Ala Glu
65              70              75              80

Asp Ala Ala Thr Tyr Tyr Cys Gln Gln Trp Ser Ser Asn Pro Pro Thr
                85              90              95

Phe Gly Gly Gly Thr Lys Leu Glu Ile Lys
            100             105

<210> SEQ ID NO 69
<211> LENGTH: 120
<212> TYPE: PRT
<213> ORGANISM: Mus musculus
<220> FEATURE:
<221> NAME/KEY: MISC_FEATURE
<223> OTHER INFORMATION: Murine SC17.36 VH

<400> SEQUENCE: 69

Glu Val Gln Leu Gln Glu Ser Gly Pro Ser Leu Val Lys Pro Ser Gln
1               5               10              15

Ser Gln Ser Leu Thr Cys Ser Val Thr Gly Asp Ser Ile Thr Ser Asp
            20              25              30

Tyr Trp Asn Trp Ile Arg Lys Phe Pro Gly Lys Lys Val Glu Tyr Met
            35              40              45

Gly Tyr Ile Asn Tyr Ser Gly Ser Thr Tyr Tyr Asn Pro Ser Leu Lys
    50              55              60

Ser Arg Ile Ser Ile Thr Arg Asp Thr Ser Lys Asn Gln Tyr Tyr Leu
65              70              75              80

Gln Leu Asn Ser Val Thr Ser Glu Asp Thr Ala Thr Tyr Tyr Cys Ala
                85              90              95

Arg Thr Ser Tyr Tyr Asn Lys Phe Leu Pro Phe Ala Tyr Trp Gly Gln
            100             105             110

Gly Thr Leu Val Thr Val Ser Ala
            115             120

<210> SEQ ID NO 70
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.39 VL

<400> SEQUENCE: 70

Asp Val Leu Met Thr Gln Thr Pro Leu Ser Leu Pro Val Ser Leu Gly
1               5               10              15

Asp Gln Ala Ser Ile Ser Cys Arg Ser Ser Gln Ser Leu Val His Arg
            20              25              30

Asn Gly Asn Thr Tyr Phe His Trp Tyr Leu Gln Lys Pro Gly Gln Ser
            35              40              45

Pro Lys Leu Leu Ile Tyr Lys Val Ser Asn Arg Phe Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Leu Gly Val Tyr Phe Cys Ser Gln Ser
```

85                  90                  95
Thr Tyr Val Pro Trp Thr Phe Gly Gly Gly Thr Lys Leu Glu Ile Lys
            100                 105                 110

<210> SEQ ID NO 71
<211> LENGTH: 117
<212> TYPE: PRT
<213> ORGANISM: Mus musculus
<220> FEATURE:
<221> NAME/KEY: MISC_FEATURE
<223> OTHER INFORMATION: Murine SC17.39 VH

<400> SEQUENCE: 71

Glu Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Tyr
            20                  25                  30

Gly Met His Trp Val Arg Gln Ala Pro Glu Lys Gly Leu Glu Trp Val
        35                  40                  45

Ala Tyr Ile Ser Ser Asn Asp Gly Thr Ile Tyr Tyr Ala Asp Thr Val
    50                  55                  60

Arg Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Pro Ser Asn Trp Val Phe Asp Tyr Trp Gly Gln Gly Thr Thr
            100                 105                 110

Leu Thr Val Ser Ser
        115

<210> SEQ ID NO 72
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.40 VL

<400> SEQUENCE: 72

Asp Val Val Met Thr Gln Thr Pro Leu Ser Arg Pro Val Thr Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Phe Thr Phe Gly Ser Gly Thr Lys Leu Glu Ile Lys
            100                 105                 110

<210> SEQ ID NO 73
<211> LENGTH: 116
<212> TYPE: PRT
<213> ORGANISM: Mus musculus
<220> FEATURE:
<221> NAME/KEY: MISC_FEATURE
<223> OTHER INFORMATION: Murine SC17.40 VH

<400> SEQUENCE: 73

Gln Val Gln Leu Gln Gln Pro Gly Ala Glu Ile Val Arg Pro Gly Ala
1               5                   10                  15

Ser Val Lys Leu Ser Cys Lys Ala Ser Gly Tyr Thr Phe Thr Asp Tyr
            20                  25                  30

Trp Met Asn Trp Val Lys Gln Arg Pro Gly Gln Gly Leu Glu Trp Ile
        35                  40                  45

Gly Thr Ile Asp Pro Ser Asp Ser Tyr Thr Arg Tyr Asn Gln Lys Phe
    50                  55                  60

Lys Gly Lys Ala Thr Leu Thr Val Asp Thr Ser Phe Ser Ser Ala Tyr
65                  70                  75                  80

Met Gln Leu Ser Ser Leu Thr Ser Glu Asp Ser Ala Val Tyr Phe Cys
                85                  90                  95

Ala Ser Gly Gly Arg Gly Phe Gly Tyr Trp Gly Gln Gly Thr Pro Val
            100                 105                 110

Thr Val Ser Val
            115

<210> SEQ ID NO 74
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.41 VL

<400> SEQUENCE: 74

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Thr Arg Phe Ser Gly Ser
    50                  55                  60

Gly Ser Gly Thr Ser Tyr Ser Leu Thr Ile Ser Ser Met Gly Ala Glu
65                  70                  75                  80

Asp Ala Ala Thr Tyr Tyr Cys Gln Gln Trp Asn Thr Asn Pro Pro Thr
                85                  90                  95

Phe Gly Ala Gly Thr Lys Leu Glu Leu Lys
            100                 105

<210> SEQ ID NO 75
<211> LENGTH: 121
<212> TYPE: PRT
<213> ORGANISM: Mus musculus
<220> FEATURE:
<221> NAME/KEY: MISC_FEATURE
<223> OTHER INFORMATION: Murine SC17.41 VH

<400> SEQUENCE: 75

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

-continued

Ala Thr Ile Ser Ser Gly Gly Asn Thr Tyr Tyr Pro Asp Ser Val
    50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg Arg Asp Tyr Tyr Gly Thr Ser Tyr Val Met Phe Ala Tyr Trp
                100                 105                 110

Gly Gln Gly Thr Leu Val Thr Val Ser
                115                 120

<210> SEQ ID NO 76
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.42 VL

<400> SEQUENCE: 76

Glu Asn Val Leu Thr Gln Ser Pro Ala Ile Met Ser Ala Ser Pro Gly
 1               5                  10                  15

Glu Lys Val Thr Met Thr Cys Ser Ala Ser Ser Ser Val Asn Tyr Met
                20                  25                  30

Tyr Trp Tyr Gln Gln Lys Ser Ser Thr Ser Pro Lys Leu Trp Ile Tyr
                35                  40                  45

Asp Thr Ser Lys Leu Thr Ser Gly Val Pro Gly Arg Phe Ser Gly Ser
 50                  55                  60

Gly Ser Gly Asn Ser Tyr Ser Leu Thr Ile Ser Asn Met Glu Ala Glu
 65                  70                  75                  80

Asp Val Ala Thr Tyr Tyr Cys Phe Gln Gly Ser Gly Tyr Pro Leu Thr
                 85                  90                  95

Phe Gly Ser Gly Thr Lys Leu Glu Ile Lys
                100                 105

<210> SEQ ID NO 77
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.42 VH

<400> SEQUENCE: 77

Asp Val Lys Leu Val Glu Ser Gly Gly Gly Leu Val Arg Pro Gly Gly
 1               5                  10                  15

Ser Leu Lys Leu Ser Cys Ala Ala Ser Gly Phe Thr Phe Ser Arg Tyr
                20                  25                  30

Thr Met Ser Trp Val Arg Gln Thr Pro Glu Lys Arg Leu Glu Trp Ala
                35                  40                  45

Ala Thr Ile Asn Ser Gly Gly Ser Asn Thr Tyr Tyr Pro Asp Ser Val
    50                  55                  60

Lys Gly Arg Phe Thr Ile Ser Arg Asp Asn Ala Lys Asn Thr Leu Phe
 65                  70                  75                  80

Leu Gln Met Ser Ser Leu Lys Ser Glu Asp Thr Ala Met Tyr Tyr Cys
                 85                  90                  95

Thr Asn Gly Asn His Trp Gly Gln Gly Thr Thr Leu Thr Val Ser Ser
                100                 105                 110

```
<210> SEQ ID NO 78
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.45 VL

<400> SEQUENCE: 78
```

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Val Asn Tyr Met
            20                  25                  30

Tyr Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Ser Leu Thr Ile Ser Asn Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ser Gly Thr Lys Leu Glu Ile Lys
            100                 105

```
<210> SEQ ID NO 79
<211> LENGTH: 114
<212> TYPE: PRT
<213> ORGANISM: Mus musculus
<220> FEATURE:
<221> NAME/KEY: MISC_FEATURE
<223> OTHER INFORMATION: Murine SC17.45 VH

<400> SEQUENCE: 79
```

Gln Val Gln Leu Gln Gln Pro Gly Ser Val Leu Val Arg Pro Gly Asp
1               5                   10                  15

Ser Val Lys Leu Ser Cys Lys Ala Ser Gly Tyr Thr Phe Thr Ser Tyr
            20                  25                  30

Trp Met His Trp Val Lys Gln Ser Pro Gly Gln Gly Leu Glu Trp Ile
        35                  40                  45

Gly Glu Ile His Pro Ser Gly Ser Thr Asn Tyr Asn Glu Lys Phe
    50                  55                  60

Lys Gly Lys Ala Thr Leu Thr Val Asp Thr Ser Ser Ser Thr Ala Tyr
65                  70                  75                  80

Val Asp Leu Ser Ser Leu Thr Ser Glu Asp Ser Ala Val Tyr Tyr Cys
                85                  90                  95

Val Gly Gly His Tyr Asp Tyr Trp Gly Gln Gly Thr Thr Leu Thr Val
            100                 105                 110

Ser Ser

```
<210> SEQ ID NO 80
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.46 VL

<400> SEQUENCE: 80
```

Ser Phe Val Met Thr Gln Thr Pro Lys Phe Leu Leu Val Ser Ala Gly

```
                1               5                       10                      15
            Asp Arg Val Thr Ile Thr Cys Lys Ala Ser Gln Ser Val Asn Asn Asp
                                20                      25                      30

Val Ala Trp Tyr Gln Gln Lys Pro Gly Gln Ser Pro Lys Leu Leu Ile
                        35                      40                      45

Tyr Tyr Ala Ser Asn Arg Tyr Thr Gly Val Pro Asp Arg Phe Thr Gly
                    50                      55                      60

Ser Gly Tyr Gly Thr Asp Phe Thr Phe Thr Ile Ser Thr Val Gln Ala
            65                      70                      75                      80

Glu Asp Leu Ala Val Tyr Phe Cys Gln Gln Asp Tyr Ser Ser Pro Arg
                                85                      90                      95

Thr Phe Gly Gly Gly Thr Lys Leu Glu Ile Lys
                            100                     105
```

<210> SEQ ID NO 81
<211> LENGTH: 119
<212> TYPE: PRT
<213> ORGANISM: Mus musculus
<220> FEATURE:
<221> NAME/KEY: MISC_FEATURE
<223> OTHER INFORMATION: Murine SC17.46 VH

<400> SEQUENCE: 81

```
            Gln Val Gln Leu Gln Gln Pro Gly Ala Glu Leu Val Lys Pro Gly Ala
            1               5                       10                      15

Ser Met Lys Leu Ser Cys Lys Ala Ser Gly Tyr Thr Phe Thr Ser Tyr
                                20                      25                      30

Trp Ile Asn Trp Val Lys Gln Arg Pro Gly Gln Gly Leu Glu Trp Ile
                        35                      40                      45

Gly Asn Ile Phe Pro Asp Thr Thr Thr Asn Tyr Asn Glu Lys Phe
                    50                      55                      60

Lys Ser Lys Ala Thr Leu Thr Val Asp Thr Ser Ser Ser Thr Ala Tyr
            65                      70                      75                      80

Met Gln Leu Ser Ser Leu Thr Ser Asp Asp Ser Ala Val Tyr Tyr Cys
                                85                      90                      95

Ala Arg Glu Tyr Tyr Asp Gly Thr Tyr Asp Ala Met Asp Tyr Trp Gly
                            100                     105                     110

Gln Gly Thr Ser Val Thr Val
                    115
```

<210> SEQ ID NO 82
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.47 VL

<400> SEQUENCE: 82

```
            Gln Ile Val Leu Thr Gln Ser Pro Ala Ile Met Ser Ala Ser Pro Gly
            1               5                       10                      15

Glu Lys Val Ser Met Thr Cys Ser Ala Ser Ser Ser Val Ser Tyr Met
                                20                      25                      30

His Trp Tyr Gln Gln Lys Ser Gly Thr Ser Pro Lys Arg Trp Ile Tyr
                        35                      40                      45

Asp Thr Ser Lys Leu Ala Ser Gly Val Pro Ala Arg Phe Ser Gly Ser
                    50                      55                      60

Gly Ser Gly Ser Ser Tyr Ser Leu Thr Ile Ser Ser Met Glu Ala Glu
```

```
                 65                  70                  75                  80
Asp Ala Ala Thr Tyr Tyr Cys Gln Gln Trp Ser Ser Thr Pro Pro Thr
                 85                  90                  95

Phe Gly Gly Gly Thr Lys Leu Glu Ile Lys
                100                 105

<210> SEQ ID NO 83
<211> LENGTH: 119
<212> TYPE: PRT
<213> ORGANISM: Mus musculus
<220> FEATURE:
<221> NAME/KEY: MISC_FEATURE
<223> OTHER INFORMATION: Murine SC17.47 VH

<400> SEQUENCE: 83

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
                 20                  25                  30

Tyr Met Arg Trp Val Lys Gln Ser Pro Glu Lys Ser Leu Glu Trp Ile
             35                  40                  45

Gly Glu Ile Asn Pro Ser Thr Gly Gly Thr Thr Tyr Asn Gln Asn Phe
         50                  55                  60

Lys Ala Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                 85                  90                  95

Ala Arg Gly Gly Tyr Phe Leu Tyr Tyr Phe Asp Tyr Trp Gly Gln Gly
                100                 105                 110

Thr Thr Leu Thr Val Ser Ser
            115

<210> SEQ ID NO 84
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.49 VL

<400> SEQUENCE: 84

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Glu Ser
                 20                  25                  30

Asp Gly Lys Thr Tyr Leu Asn Trp Leu Leu Gln Arg Pro Gly Gln Ser
             35                  40                  45

Pro Lys Arg Leu Ile Tyr Leu Val Ser Lys Leu Asp Ser Gly Val Pro
     50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                 85                  90                  95

Ile Gln His Pro Arg Thr Phe Gly Gly Gly Thr Lys Leu Glu Ile Lys
                100                 105                 110

<210> SEQ ID NO 85
<211> LENGTH: 113
<212> TYPE: PRT
```

```
<213> ORGANISM: Mus musculus
<220> FEATURE:
<221> NAME/KEY: MISC_FEATURE
<223> OTHER INFORMATION: Murine SC17.49 VH

<400> SEQUENCE: 85

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Gly Ile Asp Pro Glu Thr Gly Thr Ala Tyr Asn Gln Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Thr Arg Trp Phe Ser Tyr Trp Gly Pro Gly Thr Leu Val Thr Val Ser
            100                 105                 110

Ala

<210> SEQ ID NO 86
<211> LENGTH: 111
<212> TYPE: PRT
<213> ORGANISM: Mus musculus
<220> FEATURE:
<221> NAME/KEY: MISC_FEATURE
<223> OTHER INFORMATION: Murine SC17.50 VL

<400> SEQUENCE: 86

Asp Ile Val Leu Thr Gln Ser Pro Ala Ser Leu Ala Ala Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Trp Thr Phe Gly Gly Gly Thr Lys Leu Glu Ile Lys
            100                 105                 110

<210> SEQ ID NO 87
<211> LENGTH: 121
<212> TYPE: PRT
<213> ORGANISM: Mus musculus
<220> FEATURE:
<221> NAME/KEY: MISC_FEATURE
<223> OTHER INFORMATION: Murine SC17.50 VH

<400> SEQUENCE: 87

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30
```

Gly Met His Trp Val Arg Gln Ala Pro Glu Lys Gly Leu Glu Trp Val
         35                  40                  45

Ala Tyr Ile Ser Ser Gly Ser Arg Thr Ile Tyr Tyr Ala Asp Thr Val
 50                  55                  60

Lys Gly Arg Phe Thr Ile Ser Arg Asp Asn Ala Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Val Tyr Tyr Gly Ser Thr Tyr Gly Tyr Phe Asp Val Trp Gly
                100                 105                 110

Thr Gly Thr Thr Val Thr Val Ser Ser
            115                 120

<210> SEQ ID NO 88
<211> LENGTH: 111
<212> TYPE: PRT
<213> ORGANISM: Mus musculus
<220> FEATURE:
<221> NAME/KEY: MISC_FEATURE
<223> OTHER INFORMATION: Murine SC17.53 VL

<400> SEQUENCE: 88

Asp Ile Val Leu Thr Gln Ser Pro Ala Ser Leu Ala Ala Ser Leu Gly
 1               5                  10                  15

Gln Arg Ala Thr Ile Ser Cys Arg Ala Ser Gln Ser Val Ser Thr Ser
                 20                  25                  30

Ser Tyr Ser Tyr Met His Trp Tyr Gln Gln Lys Pro Gly His Pro Pro
             35                  40                  45

Lys Leu Leu Ile Arg Tyr Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Thr Ala Thr Tyr Tyr Cys Gln His Ser Trp
                 85                  90                  95

Glu Ile Pro Tyr Thr Phe Gly Gly Gly Thr Lys Leu Glu Ile Lys
                100                 105                 110

<210> SEQ ID NO 89
<211> LENGTH: 119
<212> TYPE: PRT
<213> ORGANISM: Mus musculus
<220> FEATURE:
<221> NAME/KEY: MISC_FEATURE
<223> OTHER INFORMATION: Murine SC17.53 VH

<400> SEQUENCE: 89

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Thr Asp Tyr
                 20                  25                  30

Asn Met His Trp Val Lys Gln Ser His Gly Lys Arg Leu Glu Trp Ile
             35                  40                  45

Gly Tyr Ile His Pro Tyr Asn Gly Gly Ser Gly Tyr Asn Gln Lys Phe
 50                  55                  60

Lys Arg Lys Ala Thr Leu Thr Val Asp Asn Ser Ser Asn Thr Thr Tyr
 65                  70                  75                  80

Met Glu Leu Arg Ser Leu Thr Ser Glu Asp Ser Ala Val Tyr Tyr Cys
                 85                  90                  95

```
Ala Arg Ser Tyr Asp Tyr Asp Thr Trp Phe Gly Tyr Trp Gly Gln Gly
            100                 105                 110

Thr Leu Val Thr Val Arg Ala
        115
```

<210> SEQ ID NO 90
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.54 VL

<400> SEQUENCE: 90

```
Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Leu Tyr Tyr Cys Trp Gln Gly
                85                  90                  95

Thr His Phe Pro Trp Thr Phe Gly Gly Gly Thr Lys Leu Glu Ile Lys
            100                 105                 110
```

<210> SEQ ID NO 91
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.54 VH

<400> SEQUENCE: 91

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Ile Asn Trp Val Arg Gln Ser Pro Glu Lys Gly Leu Glu Trp Val
        35                  40                  45

Ala Glu Ile Arg Met Lys Ser Asn Asn Tyr Ala Thr His Tyr Ala Glu
    50                  55                  60

Ser Val Lys Gly Arg Phe Thr Ile Ser Arg Asp Asp Ser Lys Ser Cys
65                  70                  75                  80

Val Tyr Leu Gln Met Asn Asn Leu Arg Pro Glu Asp Thr Gly Ile Tyr
                85                  90                  95

Tyr Cys Thr Arg Gly Gly Tyr Trp Gly Gln Gly Thr Thr Leu Thr Val
            100                 105                 110

Ser
```

<210> SEQ ID NO 92
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.56 VL

<400> SEQUENCE: 92

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Phe Cys Gln Gln
                85                  90                  95

Tyr Tyr Asn Tyr Pro Tyr Thr Phe Gly Gly Gly Thr Lys Leu Glu Ile
            100                 105                 110

Lys

<210> SEQ ID NO 93
<211> LENGTH: 116
<212> TYPE: PRT
<213> ORGANISM: Mus musculus
<220> FEATURE:
<221> NAME/KEY: MISC_FEATURE
<223> OTHER INFORMATION: Murine SC17.56 VH

<400> SEQUENCE: 93

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Ala Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Ser
65                  70                  75                  80

Leu Gln Ile Ile Asn Leu Lys Asn Glu Asp Thr Ala Thr Tyr Phe Cys
                85                  90                  95

Ala Arg Ile Gly Asp Ser Ser Pro Ser Asp Tyr Trp Gly Gln Gly Thr
            100                 105                 110

Thr Leu Thr Val
        115

<210> SEQ ID NO 94
<211> LENGTH: 108
<212> TYPE: PRT
<213> ORGANISM: Mus musculus
<220> FEATURE:
<221> NAME/KEY: MISC_FEATURE
<223> OTHER INFORMATION: Murine SC17.57 VL

<400> SEQUENCE: 94

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

```
Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Pro Arg Phe Ser
 50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Gly Gly Thr Lys Leu Glu Ile Lys
            100                 105
```

<210> SEQ ID NO 95
<211> LENGTH: 121
<212> TYPE: PRT
<213> ORGANISM: Mus musculus
<220> FEATURE:
<221> NAME/KEY: MISC_FEATURE
<223> OTHER INFORMATION: Murine SC17.57 VH

<400> SEQUENCE: 95

```
Gln Ile Gln Leu Val Gln Ser Gly Pro Glu Leu Lys Lys Pro Gly Glu
1               5                   10                  15

Thr Val Lys Ile Ser Cys Lys Ala Ser Asp Tyr Thr Phe Thr Asp Phe
                20                  25                  30

Ser Ile His Trp Val Arg Gln Ser Pro Gly Lys Gly Leu Lys Trp Met
            35                  40                  45

Gly Trp Ile Asn Thr Glu Thr Gly Glu Pro Thr Val Ala Glu Asp Phe
 50                 55                  60

Lys Gly Arg Phe Ala Phe Ser Leu Glu Thr Ser Ala Ser Thr Ala Phe
65                  70                  75                  80

Leu Gln Ile Tyr Asn Leu Lys Asn Glu Asp Ser Ala Thr Tyr Phe Cys
                85                  90                  95

Ala Arg Gly Arg Tyr Tyr Gly His Asp Tyr Ala Met Asp Tyr Trp Gly
                100                 105                 110

Gln Gly Thr Ser Val Thr Val Ser Ser
        115                 120
```

<210> SEQ ID NO 96
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.59 VL

<400> SEQUENCE: 96

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Leu His Asn Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Asp Gly Val Pro Ser Arg Phe Ser Gly
 50                 55                  60

Ser Gly Ser Gly Thr Gln Tyr Ser Leu Lys Ile Asn Ser Leu Gln Pro
65                  70                  75                  80

Glu Asp Phe Gly Thr Tyr Phe Cys Gln His Phe Trp Ser Ile Pro Pro
                85                  90                  95
```

```
Thr Phe Gly Gly Gly Thr Lys Leu Glu Ile Lys
            100                 105

<210> SEQ ID NO 97
<211> LENGTH: 119
<212> TYPE: PRT
<213> ORGANISM: Mus musculus
<220> FEATURE:
<221> NAME/KEY: MISC_FEATURE
<223> OTHER INFORMATION: Murine SC17.59 VH

<400> SEQUENCE: 97

Glu Val Lys Leu Glu Glu Ser Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
            35                  40                  45

Ala Glu Ile Arg Leu Lys Ser Asn Asn Tyr Ala Thr His Tyr Ala Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Leu Trp Asp Phe Ala Met Asp Tyr Trp Gly Gln Gly
            100                 105                 110

Thr Ser Val Thr Val Ser Ser
        115

<210> SEQ ID NO 98
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.61 VL

<400> SEQUENCE: 98

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Ile
            20                  25                  30

Tyr Trp Tyr Gln Gln Lys Pro Gly Ser Ser Pro Lys Pro Trp Ile Tyr
            35                  40                  45

Arg Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Trp Thr
                85                  90                  95

Phe Gly Gly Gly Thr Lys Leu Glu Ile Lys
            100                 105

<210> SEQ ID NO 99
<211> LENGTH: 125
<212> TYPE: PRT
<213> ORGANISM: Mus musculus
<220> FEATURE:
<221> NAME/KEY: MISC_FEATURE
<223> OTHER INFORMATION: Murine SC17.61 VH
```

<400> SEQUENCE: 99

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala Gln Ile Trp Trp Asp Asp Tyr Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Ala Arg Ile Gly Tyr Tyr Ser Gly Ser Ser Arg Cys Trp Tyr Phe
            100                 105                 110

Asp Val Trp Gly Thr Gly Ser Thr Val Thr Val Ser Ser
        115                 120                 125

<210> SEQ ID NO 100
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.63 VL

<400> SEQUENCE: 100

Ser Ile Val Met Thr Gln Thr Pro Lys Phe Leu Leu Val Ser Ala Gly
1               5                   10                  15

Asp Arg Val Ala Ile Thr Cys Lys Ala Ser Gln Ser Val Ser Asn Asp
            20                  25                  30

Val Ala Trp Tyr Gln Gln Lys Pro Gly Gln Ser Pro Thr Leu Leu Ile
        35                  40                  45

Ser Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Gly Tyr Ser Ser Pro Phe
                85                  90                  95

Thr Phe Gly Gly Gly Thr Lys Leu Glu Ile Lys
            100                 105

<210> SEQ ID NO 101
<211> LENGTH: 116
<212> TYPE: PRT
<213> ORGANISM: Mus musculus
<220> FEATURE:
<221> NAME/KEY: MISC_FEATURE
<223> OTHER INFORMATION: Murine SC17.63 VH

<400> SEQUENCE: 101

Gln Val Gln Leu Gln Gln Ser Asp Ala Glu Leu Val Lys Pro Gly Ala
1               5                   10                  15

Ser Val Lys Ile Ser Cys Lys Ala Ala Gly Tyr Thr Phe Thr Asp Leu
            20                  25                  30

Thr Ile His Trp Val Lys Gln Arg Pro Glu Gln Gly Leu Glu Trp Ile
        35                  40                  45

Gly Tyr Ile Tyr Pro Gly Asp Ser Asn Thr Lys Tyr Asn Glu Lys Phe

```
                 50                  55                  60
Lys Gly Lys Ala Thr Leu Thr Ala Asp Lys Ser Ser Thr Ala Tyr
 65                  70                  75                  80

Met Gln Leu Asn Ser Leu Thr Ser Glu Asp Ser Val Val Tyr Phe Cys
                     85                  90                  95

Ala Arg Met Ile Thr Pro Tyr Tyr Phe Asp Tyr Trp Gly Gln Gly Thr
                100                 105                 110

Thr Leu Thr Val
            115

<210> SEQ ID NO 102
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.71 VL

<400> SEQUENCE: 102

Asp Ile Gln Met Thr Gln Ser Pro Ala Ser Leu Ser Ala Ser Val Gly
 1               5                  10                  15

Glu Thr Val Thr Ile Ala Cys Arg Ala Ser Gly Asn Ile His Asn Tyr
                20                  25                  30

Leu Thr Trp Tyr Gln Gln Arg Gln Gly Lys Ser Pro Gln Leu Leu Val
             35                  40                  45

Tyr Asn Ala Lys Thr Leu Ala Val Gly Val Pro Ser Arg Phe Ser Gly
 50                  55                  60

Ser Gly Ser Gly Thr Gln Tyr Ser Leu Lys Ile Asn Ser Leu Gln Pro
 65                  70                  75                  80

Glu Asp Phe Gly Ser Tyr Tyr Cys Gln His Phe Trp Asn Thr Pro Pro
                 85                  90                  95

Thr Phe Gly Gly Gly Thr Lys Leu Glu Ile Lys
                100                 105

<210> SEQ ID NO 103
<211> LENGTH: 119
<212> TYPE: PRT
<213> ORGANISM: Mus musculus
<220> FEATURE:
<221> NAME/KEY: MISC_FEATURE
<223> OTHER INFORMATION: Murine SC17.71 VH

<400> SEQUENCE: 103

Glu Val Lys Leu Glu Glu Ser Gly Gly Gly Leu Val Gln Pro Gly Gly
 1               5                  10                  15

Ser Met Lys Leu Ser Cys Val Ala Ser Gly Ile Ile Phe Ser Asn Tyr
                20                  25                  30

Trp Met Asn Trp Val Arg Gln Ser Pro Glu Lys Gly Leu Glu Trp Val
             35                  40                  45

Ala Glu Ile Arg Leu Lys Ser Asn Asn Tyr Ser Thr His Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Thr Arg His Tyr Tyr Tyr Ala Met Asp Tyr Trp Gly Gln Gly
                100                 105                 110

Thr Ser Val Thr Val Ser Ser
```

115

<210> SEQ ID NO 104
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.72 VL

<400> SEQUENCE: 104

```
Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Lys Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys
            100                 105
```

<210> SEQ ID NO 105
<211> LENGTH: 119
<212> TYPE: PRT
<213> ORGANISM: Mus musculus
<220> FEATURE:
<221> NAME/KEY: MISC_FEATURE
<223> OTHER INFORMATION: Murine SC17.72 VH

<400> SEQUENCE: 105

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Ala Ile Asn Ser Asn Gly Gly Ser Thr Tyr Tyr Pro Asp Thr Val
50                  55                  60

Lys Gly Arg Leu Thr Ile Ser Arg Asp Asn Gly Lys Asn Thr Leu Tyr
65                  70                  75                  80

Leu Gln Met Ser Ser Leu Arg Ser Glu Asp Thr Ala Leu Tyr Tyr Cys
                85                  90                  95

Val Arg Asp Asp Gly Tyr Tyr Val Phe Phe Ala Tyr Trp Gly Gln Gly
            100                 105                 110

Thr Leu Val Thr Val Ser Ala
        115
```

<210> SEQ ID NO 106
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.74 VL

<400> SEQUENCE: 106

```
Asp Ile Gln Met Thr Gln Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
                35                  40                  45

Ser Gly Ala Thr Ser Leu Glu Thr Gly Val Pro Ser Arg Phe Ser Gly
50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Pro
                85                  90                  95

Thr Phe Gly Ala Gly Thr Lys Leu Glu Leu Lys
            100                 105
```

<210> SEQ ID NO 107
<211> LENGTH: 119
<212> TYPE: PRT
<213> ORGANISM: Mus musculus
<220> FEATURE:
<221> NAME/KEY: MISC_FEATURE
<223> OTHER INFORMATION: Murine SC17.74 VH

<400> SEQUENCE: 107

```
Gln Val Gln Leu Lys Gln Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Asp Trp Val Arg Gln Ser Pro Gly Lys Gly Leu Glu Trp Leu
                35                  40                  45

Gly Val Ile Trp Gly Gly Ser Thr Asn Tyr Asn Ser Ala Leu Lys
50                  55                  60

Ser Arg Leu Ser Ile Thr Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Ser Gly Asp Tyr Asp Gly Ser Leu Trp Phe Ala Tyr Trp Gly Gln Gly
            100                 105                 110

Thr Leu Val Thr Val Ser Ala
        115
```

<210> SEQ ID NO 108
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.76 VL

<400> SEQUENCE: 108

```
Asp Ile Val Ile Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
                35                  40                  45

Pro Gln Leu Leu Ile Tyr Leu Met Ser Thr Arg Ala Ser Gly Val Ser
50                  55                  60
```

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Val Glu Tyr Pro Arg Thr Phe Gly Gly Gly Thr Lys Leu Glu Ile Lys
            100                 105                 110

<210> SEQ ID NO 109
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.76 VH

<400> SEQUENCE: 109

Glu Val Gln Leu Val Glu Ser Gly Gly Asp Leu Val Lys Pro Gly Gly
1               5                   10                  15

Ser Leu Lys Leu Ser Cys Val Ala Ser Gly Phe Thr Phe Ser Ser Tyr
                20                  25                  30

Gly Met Ser Trp Val Arg Gln Thr Pro Asp Lys Arg Leu Glu Trp Val
            35                  40                  45

Ala Thr Ile Ser Ser Gly Gly Thr Phe Thr Tyr Tyr Pro Asp Ser Val
        50                  55                  60

Lys Gly Arg Phe Thr Val Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ser Arg His Gly Trp Gly Trp Gly Gln Gly Thr Leu Val Thr Val Ser
            100                 105                 110

Ala

<210> SEQ ID NO 110
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.77 VL

<400> SEQUENCE: 110

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro Gln Leu Leu Val
            35                  40                  45

Tyr Asn Ala Lys Ala Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ile Pro Pro
                85                  90                  95

Thr Phe Gly Gly Gly Thr Lys Leu Glu Ile Lys
            100                 105

<210> SEQ ID NO 111
<211> LENGTH: 119

```
<212> TYPE: PRT
<213> ORGANISM: Mus musculus
<220> FEATURE:
<221> NAME/KEY: MISC_FEATURE
<223> OTHER INFORMATION: Murine SC17.77 VH

<400> SEQUENCE: 111

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Ala Ile Tyr
                85                  90                  95

Tyr Cys Thr Arg His Tyr Asp Tyr Ala Met Asp Tyr Trp Gly Gln Gly
            100                 105                 110

Thr Ser Val Thr Val Ser Ser
            115

<210> SEQ ID NO 112
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.79 VL

<400> SEQUENCE: 112

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Arg Ile Asn Ser Leu Gln Pro
65                  70                  75                  80

Glu Asp Phe Gly Ser Tyr Tyr Cys Gln His Phe Trp Ser Thr Pro Pro
                85                  90                  95

Thr Phe Gly Gly Gly Thr Lys Val Glu Ile Lys
            100                 105

<210> SEQ ID NO 113
<211> LENGTH: 119
<212> TYPE: PRT
<213> ORGANISM: Mus musculus
<220> FEATURE:
<221> NAME/KEY: MISC_FEATURE
<223> OTHER INFORMATION: Murine SC17.79 VH

<400> SEQUENCE: 113

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Tyr
```

```
                20                  25                  30
Trp Met Asn Trp Val Arg Gln Ser Pro Glu Lys Gly Leu Glu Leu Val
                35                  40                  45

Ala Glu Ile Arg Leu Ile Ser Asn Asn Tyr Ala Thr His Tyr Ala Glu
         50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Thr Arg His Tyr Tyr Tyr Ala Leu Asp Tyr Trp Gly Gln Gly
                100                 105                 110

Thr Ser Val Thr Val Ser Ser
            115

<210> SEQ ID NO 114
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.81 VL

<400> SEQUENCE: 114

Asp Ile Val Met Ser Gln Ser Pro Ser Ser Leu Thr Val Ser Val Gly
 1               5                  10                  15

Glu Lys Val Thr Leu Ser Cys Lys Ser Ser Gln Ser Leu Leu Tyr Ser
                20                  25                  30

Thr Asn Gln Lys Ile Tyr Leu Ala Trp Tyr Gln Gln Lys Pro Gly Gln
                35                  40                  45

Ser Pro Lys Leu Leu Ile Tyr Trp Ala Ser Thr Arg Glu Ser Gly Val
         50                  55                  60

Pro Asp Arg Phe Thr Gly Ser Gly Ser Gly Thr Asp Phe Thr Leu Ala
 65                  70                  75                  80

Ile Ser Asn Val Lys Ala Glu Asp Leu Ala Val Tyr Tyr Cys Gln Gln
                 85                  90                  95

Tyr Tyr Ser Tyr Pro Tyr Thr Phe Gly Gly Gly Thr Lys Leu Glu Ile
                100                 105                 110

Lys

<210> SEQ ID NO 115
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.81 VH

<400> SEQUENCE: 115

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Asn Asp Thr
                20                  25                  30

Tyr Tyr His Trp Leu Lys Gln Arg Pro Glu Gln Gly Leu Glu Trp Ile
                35                  40                  45

Gly Arg Ile Asp Pro Ala Asn Val Asn Thr Lys Tyr Asp Pro Lys Phe
         50                  55                  60

Gln Gly Lys Ala Thr Leu Thr Ala Asp Thr Ser Ser Asn Thr Ala Tyr
 65                  70                  75                  80
```

Leu Gln Leu Ser Ser Leu Thr Ser Glu Asp Thr Ala Val Tyr Tyr Cys
                    85                  90                  95

Gly Arg Gly Asn Ala Tyr Trp Gly Gln Gly Thr Leu Val Thr Val Ser
                100                 105                 110

Ala

<210> SEQ ID NO 116
<211> LENGTH: 104
<212> TYPE: PRT
<213> ORGANISM: Mus musculus
<220> FEATURE:
<221> NAME/KEY: MISC_FEATURE
<223> OTHER INFORMATION: Murine SC17.82 VL

<400> SEQUENCE: 116

Gln Ile Val Leu Thr Gln Ser Pro Ala Ile Met Ser Ala Ser Leu Gly
1               5                   10                  15

Glu Glu Ile Thr Leu Thr Cys Ser Ala Ser Ser Ser Val Ser Tyr Met
                20                  25                  30

His Trp Tyr Gln Gln Lys Ser Gly Thr Ser Pro Lys Leu Leu Ile Tyr
            35                  40                  45

Ser Thr Ser Asn Leu Ala Ser Gly Val Pro Ser Arg Phe Ser Gly Ser
50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Ser Phe Thr Phe Gly
                85                  90                  95

Ser Gly Thr Lys Leu Glu Ile Lys
                100

<210> SEQ ID NO 117
<211> LENGTH: 120
<212> TYPE: PRT
<213> ORGANISM: Mus musculus
<220> FEATURE:
<221> NAME/KEY: MISC_FEATURE
<223> OTHER INFORMATION: Murine SC17.82 VH

<400> SEQUENCE: 117

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Ser
                20                  25                  30

Tyr Met Asn Trp Val Lys Gln Ser His Gly Lys Ser Leu Glu Trp Ile
            35                  40                  45

Gly Arg Val Asn Pro Asn Asn Gly Gly Ala Ser Tyr Asn His Lys Phe
50                  55                  60

Lys Gly Lys Ala Thr Leu Thr Val Asp Lys Ser Leu Ser Thr Ala Tyr
65                  70                  75                  80

Met Arg Leu Asn Ser Leu Thr Ser Glu Asp Ser Ala Val Tyr Tyr Cys
                85                  90                  95

Ser Arg Ser Gly Asp Leu Tyr Tyr Ala Met Asp Tyr Trp Gly Gln
                100                 105                 110

Gly Thr Ser Val Thr Val Ser Ser
            115                 120

<210> SEQ ID NO 118
<211> LENGTH: 106

```
<212> TYPE: PRT
<213> ORGANISM: Mus musculus
<220> FEATURE:
<221> NAME/KEY: MISC_FEATURE
<223> OTHER INFORMATION: Murine SC17.84 VL

<400> SEQUENCE: 118
```

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Trp Ser Ser Thr Pro Pro Thr
                85                  90                  95

Phe Gly Gly Gly Thr Lys Leu Glu Ile Lys
            100                 105

```
<210> SEQ ID NO 119
<211> LENGTH: 117
<212> TYPE: PRT
<213> ORGANISM: Mus musculus
<220> FEATURE:
<221> NAME/KEY: MISC_FEATURE
<223> OTHER INFORMATION: Murine SC17.84 VH

<400> SEQUENCE: 119
```

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Ile Phe Thr Asp Tyr
            20                  25                  30

Asn Met His Trp Val Lys Gln Asn Gln Gly Lys Ser Leu Glu Trp Ile
        35                  40                  45

Gly Glu Val Asn Pro Asn Thr Gly Gly Ile Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Asp Gly Asn Tyr Cys Phe Asp Tyr Trp Gly Gln Gly Thr Thr
            100                 105                 110

Leu Thr Val Ser Ser
        115

```
<210> SEQ ID NO 120
<211> LENGTH: 111
<212> TYPE: PRT
<213> ORGANISM: Mus musculus
<220> FEATURE:
<221> NAME/KEY: MISC_FEATURE
<223> OTHER INFORMATION: Murine SC17.85 VL

<400> SEQUENCE: 120
```

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser

```
            20                  25                  30
Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Glu Arg Phe Ser Ser Ser Gly Ser Gly Ser Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu His Pro Thr Phe Gly Gly Gly Thr Lys Leu Glu Ile Lys
            100                 105                 110

<210> SEQ ID NO 121
<211> LENGTH: 120
<212> TYPE: PRT
<213> ORGANISM: Mus musculus
<220> FEATURE:
<221> NAME/KEY: MISC_FEATURE
<223> OTHER INFORMATION: Murine SC17.85 VH

<400> SEQUENCE: 121

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Ser Thr Gly Gly Thr Tyr Thr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Val Gly Gln Ser Tyr Ser Asp Tyr Val Ser Phe Ala Tyr Trp Gly Gln
            100                 105                 110

Gly Thr Gln Val Thr Val Ser Ala
        115                 120

<210> SEQ ID NO 122
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.87 VL

<400> SEQUENCE: 122

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
```

```
                    85                  90                  95

Thr His Val Pro Pro Met Phe Gly Gly Gly Thr Arg Leu Glu Ile Lys
            100                 105                 110

<210> SEQ ID NO 123
<211> LENGTH: 115
<212> TYPE: PRT
<213> ORGANISM: Mus musculus
<220> FEATURE:
<221> NAME/KEY: MISC_FEATURE
<223> OTHER INFORMATION: Murine SC17.87 VH

<400> SEQUENCE: 123

Glu Val Gln Leu Gln Gln Ser Gly Ala Glu Leu Leu Lys Pro Gly Ala
1               5                   10                  15

Ser Val Lys Leu Ser Cys Thr Ala Ser Gly Leu Asn Ile Lys Asp Tyr
            20                  25                  30

Tyr Ile His Trp Val Tyr Gln Arg Pro Glu Gln Gly Leu Glu Trp Ile
        35                  40                  45

Gly Arg Ile Asp Pro Glu Ser Asp Asn Thr Leu Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Asn Thr Pro Phe Ala Tyr Trp Gly Gln Gly Thr Leu Val Thr
            100                 105                 110

Val Ser Thr
        115

<210> SEQ ID NO 124
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.89 VL

<400> SEQUENCE: 124

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 125
<211> LENGTH: 120
<212> TYPE: PRT
<213> ORGANISM: Mus musculus
<220> FEATURE:
<221> NAME/KEY: MISC_FEATURE
```

<223> OTHER INFORMATION: Murine SC17.89 VH

<400> SEQUENCE: 125

Gln Val Gln Leu Gln Gln Ser Gly Ala Glu Leu Val Arg Pro Gly Thr
1               5                   10                  15

Ser Val Lys Val Ser Cys Lys Thr Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Val Lys Ala Thr Leu Thr Ala Asp Lys Ser Ser Thr Ala Tyr
65                  70                  75                  80

Met Gln Leu Thr Ser Leu Thr Ser Asp Asp Ser Ala Val Tyr Phe Cys
                85                  90                  95

Thr Arg Arg Asp Gly Tyr Phe Phe Pro Trp Phe Ala Tyr Trp Gly Gln
            100                 105                 110

Gly Thr Leu Val Thr Val Ser Ala
        115                 120

<210> SEQ ID NO 126
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.90 VL

<400> SEQUENCE: 126

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Lys Ser Gly Val
    50                  55                  60

Pro Asp Arg Phe Thr Gly Ser Gly Ser Gly Asp Phe Thr Leu Thr
65                  70                  75                  80

Ile Ser Ser Val Lys Ala Glu Asp Leu Ala Val Tyr Tyr Cys His Gln
                85                  90                  95

Tyr Tyr Ser Tyr Pro Leu Thr Phe Ala Ala Gly Thr Lys Leu Glu Leu
            100                 105                 110

Lys

<210> SEQ ID NO 127
<211> LENGTH: 115
<212> TYPE: PRT
<213> ORGANISM: Mus musculus
<220> FEATURE:
<221> NAME/KEY: MISC_FEATURE
<223> OTHER INFORMATION: Murine SC17.90 VH

<400> SEQUENCE: 127

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Glu Ile His Pro Asn Asn Gly Ser Thr Asn Tyr Asn Glu Lys Phe
 50                  55                  60

Lys Gly Lys Ala Thr Leu Thr Val Asp Thr Ser Ser Ser Thr Ala Tyr
 65                  70                  75                  80

Val Asp Leu Ser Ser Leu Thr Ser Glu Asp Ser Ala Val Tyr Tyr Cys
                 85                  90                  95

Ala Arg Trp Thr Leu Phe Thr Tyr Trp Gly Gln Gly Thr Leu Val Thr
                100                 105                 110

Val Ser Ala
        115

<210> SEQ ID NO 128
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.91 VL

<400> SEQUENCE: 128

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                 20                  25                  30

Asn Gly Asn Thr Tyr Leu Leu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Ala Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Ile Lys
                100                 105                 110

<210> SEQ ID NO 129
<211> LENGTH: 117
<212> TYPE: PRT
<213> ORGANISM: Mus musculus
<220> FEATURE:
<221> NAME/KEY: MISC_FEATURE
<223> OTHER INFORMATION: Murine SC17.91 VH

<400> SEQUENCE: 129

Glu Val Gln Leu Val Glu Ser Gly Gly Gly Leu Val Lys Pro Gly Gly
 1               5                  10                  15

Ser Arg Lys Leu Ser Cys Ala Ala Ser Gly Phe Thr Phe Ser Asp Tyr
                 20                  25                  30

Gly Met His Trp Val Arg Gln Ala Pro Glu Lys Gly Leu Glu Trp Val
            35                  40                  45

Ala Tyr Ile Ser Arg Gly Ser Ser Thr Ile His Tyr Ala Asp Thr Val
 50                  55                  60

Lys Gly Arg Phe Thr Ile Ser Arg Asp Asn Ala Lys Asn Thr Leu Phe
 65                  70                  75                  80

Leu Gln Met Thr Ser Leu Arg Ser Glu Asp Thr Ala Met Tyr Tyr Cys
                 85                  90                  95

```
Ala Arg Pro Phe Asn Trp Tyr Phe Asp Val Trp Gly Ala Gly Thr Thr
                100                 105                 110
Val Thr Val Ser Ser
            115

<210> SEQ ID NO 130
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.93 VL

<400> SEQUENCE: 130

Asp Ile Val Met Ser Gln Ser Pro Ser Ser Leu Ala Val Ser Val Gly
1               5                   10                  15

Glu Lys Val Thr Met Thr Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Lys Ala Glu Asp Leu Ala Ile Tyr Tyr Cys Gln Gln
                85                  90                  95

Tyr Tyr Arg Tyr Pro Leu Thr Phe Gly Ala Gly Thr Lys Leu Glu Leu
                100                 105                 110

Lys

<210> SEQ ID NO 131
<211> LENGTH: 121
<212> TYPE: PRT
<213> ORGANISM: Mus musculus
<220> FEATURE:
<221> NAME/KEY: MISC_FEATURE
<223> OTHER INFORMATION: Murine SC17.93 VH

<400> SEQUENCE: 131

Gln Val Gln Leu Gln Gln Pro Gly Ala Glu Leu Val Lys Pro Gly Ala
1               5                   10                  15

Ser Val Met Leu Ser Cys Lys Ala Ser Gly Tyr Thr Phe Thr Ser Tyr
            20                  25                  30

Trp Val His Trp Val Lys Gln Arg Pro Gly Gln Gly Leu Glu Trp Ile
        35                  40                  45

Gly Val Ile Asn Pro Arg Asn Gly Arg Asn Asn Tyr Asn Glu Lys Phe
    50                  55                  60

Lys Thr Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Glu Asp Tyr Asp Gly Gly Asp Tyr Ala Met Asp Tyr Trp Gly
                100                 105                 110

Gln Gly Thr Ser Val Thr Val Ser Ser
            115                 120

<210> SEQ ID NO 132
<211> LENGTH: 107
<212> TYPE: PRT
```

```
<213> ORGANISM: Mus musculus
<220> FEATURE:
<221> NAME/KEY: MISC_FEATURE
<223> OTHER INFORMATION: Murine SC17.95 VL

<400> SEQUENCE: 132

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Thr Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105

<210> SEQ ID NO 133
<211> LENGTH: 121
<212> TYPE: PRT
<213> ORGANISM: Mus musculus
<220> FEATURE:
<221> NAME/KEY: MISC_FEATURE
<223> OTHER INFORMATION: Murine SC17.95 VH

<400> SEQUENCE: 133

Glu Val Glu Leu Gln Gln Ser Gly Pro Glu Leu Val Lys Pro Gly Ala
1               5                   10                  15

Ser Val Lys Ile Ser Cys Lys Thr Ser Gly Asn Thr Tyr Thr Glu Tyr
            20                  25                  30

Thr Met Gln Trp Val Lys Leu Ser His Gly Lys Ser Leu Glu Trp Ile
        35                  40                  45

Gly Gly Ile Asn Pro Asn Asn Gly Ile Thr Ser Tyr Asn Gln Lys Phe
50                  55                  60

Lys Gly Lys Ala Thr Leu Thr Val Asp Lys Ser Ser Ser Thr Ala Tyr
65                  70                  75                  80

Met Glu Leu Arg Ser Leu Lys Ser Glu Asp Ser Ala Val Tyr Tyr Cys
                85                  90                  95

Ala Arg Ala Gly Leu Gly Asn Tyr Val Trp Ala Met Asp Tyr Trp Gly
            100                 105                 110

Gln Gly Ala Ser Val Thr Val Ser Ser
        115                 120

<210> SEQ ID NO 134
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.97 VL

<400> SEQUENCE: 134

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Asn
            20                  25                  30
```

Asn Gly Asn Thr Tyr Leu His Trp Tyr Leu Gln Lys Pro Gly Gln Ser
            35                  40                  45

Pro Asn Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Ile Val Glu Ala Glu Asp Leu Gly Leu Tyr Phe Cys Ser Gln Ser
                85                  90                  95

Thr His Val Pro Arg Thr Phe Gly Gly Gly Thr Lys Leu Glu Ile Lys
                100                 105                 110

<210> SEQ ID NO 135
<211> LENGTH: 119
<212> TYPE: PRT
<213> ORGANISM: Mus musculus
<220> FEATURE:
<221> NAME/KEY: MISC_FEATURE
<223> OTHER INFORMATION: Murine SC17.97 VH

<400> SEQUENCE: 135

Gln Val Gln Leu Pro Gln Ser Gly Ala Glu Leu Ala Lys Pro Gly Ala
 1               5                  10                  15

Ser Val Lys Ile Ser Cys Lys Ala Ser Gly Phe Thr Phe Thr Ser Tyr
                20                  25                  30

Trp Met His Trp Val Lys Gln Arg Pro Gly Gln Gly Leu Glu Trp Ile
            35                  40                  45

Gly Tyr Ile Asn Pro Ser Thr Asp Tyr Thr Glu Tyr Asn Gln Lys Phe
 50                  55                  60

Lys Asp Lys Ala Thr Leu Thr Ala Asp Lys Ser Ser Ser Thr Ala Tyr
 65                  70                  75                  80

Met Gln Leu Gly Ser Leu Thr Ser Glu Asp Ser Ala Val Tyr Tyr Cys
                85                  90                  95

Ala Arg Ser Ser Tyr Gly Ser Ser Pro Phe Asp Tyr Trp Gly Gln Gly
                100                 105                 110

Ser Thr Leu Thr Val Ser Ser
            115

<210> SEQ ID NO 136
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.99 VL

<400> SEQUENCE: 136

Asp Ile Val Met Ser Gln Ser Pro Ser Ser Leu Ala Val Ser Val Gly
 1               5                  10                  15

Glu Lys Val Thr Met Asn Cys Glu Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Asp Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Arg Ala Glu Asp Pro Ala Val Tyr Tyr Cys Gln Gln
                85                  90                  95

```
Tyr Tyr Ser Tyr Pro Leu Thr Phe Gly Ala Gly Thr Lys Leu Glu Leu
            100                 105                 110

Arg

<210> SEQ ID NO 137
<211> LENGTH: 116
<212> TYPE: PRT
<213> ORGANISM: Mus musculus
<220> FEATURE:
<221> NAME/KEY: MISC_FEATURE
<223> OTHER INFORMATION: Murine SC17.99 VH

<400> SEQUENCE: 137

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Ala Tyr Leu Gln Met Asn Ser Leu Arg Ala Glu Asp Thr Gly Ile Tyr
                85                  90                  95

Tyr Cys Val Ser Thr Gly Thr Ser Tyr Trp Gly Gln Gly Thr Leu Val
            100                 105                 110

Thr Val Ser Ala
        115

<210> SEQ ID NO 138
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.102 VL

<400> SEQUENCE: 138

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Pro Arg Phe Ser Gly Arg
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln His Trp Ser Ser Asn Pro Pro Thr
                85                  90                  95

Phe Gly Ala Gly Thr Lys Leu Glu Met Lys
            100                 105

<210> SEQ ID NO 139
<211> LENGTH: 116
<212> TYPE: PRT
<213> ORGANISM: Mus musculus
<220> FEATURE:
```

<221> NAME/KEY: MISC_FEATURE
<223> OTHER INFORMATION: Murine SC17.102 VH

<400> SEQUENCE: 139

Glu Val Gln Leu Gln Gln Ser Gly Pro Glu Leu Met Lys Pro Gly Ala
1               5                   10                  15

Ser Val Lys Met Ser Cys Lys Ala Ser Gly Asp Thr Phe Thr Asp Tyr
            20                  25                  30

Asn Ile His Trp Val Lys Gln Asn Gly Lys Ser Leu Glu Trp Ile
        35                  40                  45

Gly Glu Val Asn Pro Asn Ile Gly Gly Ile Gly Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Met Gly Arg Trp Tyr Phe Asp Val Trp Gly Ala Gly Thr Thr Val
            100                 105                 110

Thr Val Ser Ser
            115

<210> SEQ ID NO 140
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.114 VL

<400> SEQUENCE: 140

Asp Val Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

<210> SEQ ID NO 141
<211> LENGTH: 115
<212> TYPE: PRT
<213> ORGANISM: Mus musculus
<220> FEATURE:
<221> NAME/KEY: MISC_FEATURE
<223> OTHER INFORMATION: Murine SC17.114 VH

<400> SEQUENCE: 141

Glu Val Gln Leu Gln Gln Ser Gly Pro Glu Met Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met His Trp Val Lys Gln Ser His Gly Lys Ser Leu Glu Trp Ile

```
            35                  40                  45
Gly Arg Val Asn Thr Asn Asn Gly Gly Thr Ser Tyr Asp Gln Lys Phe
         50                  55                  60
Glu Gly Lys Ala Thr Leu Thr Val Asp Lys Ser Ser Thr Ala Tyr
 65                  70                  75                  80
Met Glu Leu Asn Ser Leu Thr Ser Glu Asp Ser Ala Val Tyr Tyr Cys
                 85                  90                  95
Val Ile Pro Ala Trp Phe Ala Tyr Trp Gly Gln Gly Thr Leu Val Thr
                100                 105                 110
Val Ser Ala
        115
```

<210> SEQ ID NO 142
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.115 VL

<400> SEQUENCE: 142

```
Asp Ile Val Met Thr Gln Ser Pro Leu Ser Leu Pro Val Ser Leu Gly
 1               5                  10                  15
Asp Gln Ala Ser Ile Ser Cys Arg Ser Ser Gln Ser Leu Val His Ser
                20                  25                  30
Asn Gly Asn Thr Tyr Leu His Trp Tyr Leu Gln Lys Pro Gly Gln Ser
            35                  40                  45
Pro Lys Leu Leu Ile Tyr Arg Val Ser Asn Arg Phe Ser Gly Val Pro
 50                  55                  60
Asp Arg Phe Ser Gly Ser Gly Ser Gly Thr Asp Phe Thr Leu Thr Ile
 65                  70                  75                  80
Ser Arg Val Glu Ala Glu Asp Leu Gly Val Tyr Phe Cys Ser Gln Ser
                 85                  90                  95
Thr His Leu Pro Arg Thr Phe Gly Gly Gly Thr Lys Leu Glu Ile Lys
                100                 105                 110
```

<210> SEQ ID NO 143
<211> LENGTH: 114
<212> TYPE: PRT
<213> ORGANISM: Mus musculus
<220> FEATURE:
<221> NAME/KEY: MISC_FEATURE
<223> OTHER INFORMATION: Murine SC17.115 VH

<400> SEQUENCE: 143

```
Gln Val Gln Leu Gln Gln Ser Gly Ser Val Leu Val Arg Pro Gly Ala
 1               5                  10                  15
Ser Val Lys Leu Ser Cys Lys Ala Ser Gly Tyr Thr Phe Thr Ser Tyr
                20                  25                  30
Trp Met His Trp Val Lys Gln Arg Pro Gly Gln Gly Leu Glu Trp Ile
            35                  40                  45
Gly Glu Ile His Pro Asn Ser Gly Asn Thr Asn Tyr Asn Glu Lys Phe
 50                  55                  60
Lys Gly Lys Ala Thr Leu Thr Val Asp Thr Ser Ser Ser Thr Ala Tyr
 65                  70                  75                  80
Val Asp Leu Ser Ser Leu Thr Ser Glu Asp Ser Ala Val Tyr Tyr Cys
                 85                  90                  95
Ala Gly Gly Asn Tyr Asp Tyr Trp Gly Gln Gly Thr Thr Leu Thr Val
```

Ser Ser

<210> SEQ ID NO 144
<211> LENGTH: 111
<212> TYPE: PRT
<213> ORGANISM: Mus musculus
<220> FEATURE:
<221> NAME/KEY: MISC_FEATURE
<223> OTHER INFORMATION: Murine SC17.120 VL

<400> SEQUENCE: 144

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Val Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Asp Glu Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 145
<211> LENGTH: 117
<212> TYPE: PRT
<213> ORGANISM: Mus musculus
<220> FEATURE:
<221> NAME/KEY: MISC_FEATURE
<223> OTHER INFORMATION: Murine SC17.120 VH

<400> SEQUENCE: 145

Glu Val Gln Leu Glu Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Phe Tyr Pro Gly Asn Ser Gly Thr Tyr Tyr Asn Gln Lys Phe
    50                  55                  60

Lys Asp Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Ser Arg Ser Gly Ser Gly Arg Phe Ala Tyr Trp Gly Gln Gly Thr Leu
            100                 105                 110

Val Thr Val Ser Ala
        115

<210> SEQ ID NO 146
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.121 VL

<400> SEQUENCE: 146

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Ser Asn Thr Pro Pro Thr
                85                  90                  95

Phe Gly Ser Val Thr Lys Leu Glu Ile Lys
            100                 105

<210> SEQ ID NO 147
<211> LENGTH: 116
<212> TYPE: PRT
<213> ORGANISM: Mus musculus
<220> FEATURE:
<221> NAME/KEY: MISC_FEATURE
<223> OTHER INFORMATION: Murine SC17.121 VH

<400> SEQUENCE: 147

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp His
            20                  25                  30

Asn Ile His Trp Val Lys Gln His Gln Gly Lys Ser Leu Glu Trp Ile
        35                  40                  45

Gly Glu Ile Asn Pro Asn Thr Gly Gly Thr Gly Tyr Asn Gln Lys Phe
    50                  55                  60

Gln Gly Lys Ala Thr Met Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Val Arg Gly Leu Tyr Phe Phe Asp Tyr Trp Gly Gln Gly Thr Thr Leu
            100                 105                 110

Thr Val Ser Ser
        115

<210> SEQ ID NO 148
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.122 VL

<400> SEQUENCE: 148

Asp Ile Val Ile Thr Gln Asp Asp Leu Ser Asn Pro Val Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

```
Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Val Glu Tyr Pro Arg Thr Phe Gly Gly Gly Thr Lys Leu Glu Ile Lys
            100                 105                 110
```

<210> SEQ ID NO 149
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.122 VH

<400> SEQUENCE: 149

```
Glu Val His Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
                20                  25                  30

Gly Met Ser Trp Val Arg Gln Thr Pro Asp Lys Arg Leu Glu Trp Val
            35                  40                  45

Ala Thr Ile Ser Ser Gly Gly Thr Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ser Arg His Gly Trp Gly Trp Gly Gln Gly Thr Leu Val Thr Val Ser
            100                 105                 110

Ala
```

<210> SEQ ID NO 150
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.140 VL

<400> SEQUENCE: 150

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Thr Pro Pro Thr
                85                  90                  95

Phe Gly Ser Gly Thr Lys Leu Glu Ile Lys
            100                 105
```

```
<210> SEQ ID NO 151
<211> LENGTH: 120
<212> TYPE: PRT
<213> ORGANISM: Mus musculus
<220> FEATURE:
<221> NAME/KEY: MISC_FEATURE
<223> OTHER INFORMATION: Murine SC17.140 VH

<400> SEQUENCE: 151
```

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gly Lys Ser Leu Glu Trp Ile
        35                  40                  45

Gly Glu Ile Asn Pro Asn Thr Gly Thr Gly Tyr Asn Gln Lys Phe
    50                  55                  60

Lys Gly Lys Ala Thr Leu Thr Val Asp Lys Phe Ser Ser Thr Ala Phe
65                  70                  75                  80

Ile Glu Leu Arg Ser Leu Thr Ser Glu Asp Ser Ala Ile Tyr Tyr Cys
                85                  90                  95

Thr Arg Gly Gly Tyr Asp His Tyr Trp Tyr Phe Asp Val Trp Gly Ala
            100                 105                 110

Gly Thr Thr Val Thr Val Ser Ser
        115                 120

```
<210> SEQ ID NO 152
<211> LENGTH: 111
<212> TYPE: PRT
<213> ORGANISM: Mus musculus
<220> FEATURE:
<221> NAME/KEY: MISC_FEATURE
<223> OTHER INFORMATION: Murine SC17.151 VL

<400> SEQUENCE: 152
```

Asp Ile Val Leu Thr Gln Phe Pro Ala Ser Leu Ala Val Ser Leu Gly
1               5                   10                  15

Gln Arg Ala Thr Ile Pro Cys Arg Ala Ser Glu Ser Val Asp Ser Tyr
            20                  25                  30

Gly Asn Ser Phe Met His Trp Phe Gln Gln Lys Pro Gly Gln Pro Pro
        35                  40                  45

Lys Leu Leu Ile Tyr Arg Ala Ser Asn Leu Glu Ser Glu Ile Pro Ala
    50                  55                  60

Arg Phe Ser Gly Ser Gly Ser Gly Thr Asp Phe Thr Leu Thr Ile Asn
65                  70                  75                  80

Pro Val Glu Ala Asp Asp Val Ala Thr Tyr Tyr Cys Gln Gln Ser His
                85                  90                  95

Glu Asp Pro Tyr Thr Phe Gly Gly Thr Lys Met Glu Ile Lys
            100                 105                 110

```
<210> SEQ ID NO 153
<211> LENGTH: 117
<212> TYPE: PRT
<213> ORGANISM: Mus musculus
<220> FEATURE:
<221> NAME/KEY: MISC_FEATURE
<223> OTHER INFORMATION: Murine SC17.151 VH

<400> SEQUENCE: 153
```

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Lys Asn Asp Thr Thr Tyr Asn Gln Lys Phe
    50                  55                  60

Lys Gly Lys Ala Lys Leu Thr Ala Val Thr Ser Ala Ser Thr Leu Tyr
65                  70                  75                  80

Met Glu Leu Ser Ser Leu Thr Asn Glu Asp Ser Ala Val Tyr Tyr Cys
                85                  90                  95

Thr Arg Ser Gly Lys Gly Tyr Phe Ala Tyr Trp Gly Gln Gly Thr Leu
            100                 105                 110

Val Thr Val Ser Ala
        115

<210> SEQ ID NO 154
<211> LENGTH: 112
<212> TYPE: PRT
<213> ORGANISM: Mus musculus
<220> FEATURE:
<221> NAME/KEY: MISC_FEATURE
<223> OTHER INFORMATION: Murine SC17.156 VL

<400> SEQUENCE: 154

Asp Val Val Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 155
<211> LENGTH: 118
<212> TYPE: PRT
<213> ORGANISM: Mus musculus
<220> FEATURE:
<221> NAME/KEY: MISC_FEATURE
<223> OTHER INFORMATION: Murine SC17.156 VH

<400> SEQUENCE: 155

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Lys Thr Ser Gly Lys Gly Leu Glu
        35                  40                  45

Trp Leu Ala His Ile Phe Trp Asp Asp Lys Trp Tyr Asn Pro Ser
    50                  55                  60

Leu Lys Ser Arg Leu Thr Ile Ser Lys Ala Thr Ser Ser Asn Gln Val
65                  70                  75                  80

```
Phe Leu Ile Leu Thr Ser Val Asp Thr Ala Asp Thr Ala Thr Tyr Tyr
                85                  90                  95

Cys Ala Thr Phe Tyr Gly Leu Tyr Phe Ala Tyr Trp Gly Gln Gly Thr
            100                 105                 110

Thr Leu Thr Val Ser Ser
        115

<210> SEQ ID NO 156
<211> LENGTH: 113
<212> TYPE: PRT
<213> ORGANISM: Mus musculus
<220> FEATURE:
<221> NAME/KEY: MISC_FEATURE
<223> OTHER INFORMATION: Murine SC17.161 VL

<400> SEQUENCE: 156

Asp Ile Val Met Ser Gln Ser Pro Ser Ser Leu Ala Val Ser Val Gly
 1               5                  10                  15

Glu Lys Val Thr Met Asn Cys Glu Ser Ser Gln Ser Leu Leu Tyr Asn
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Asp Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Arg Ala Asp Asp Pro Ala Val Tyr Tyr Cys Gln Gln
                85                  90                  95

Tyr Phe Asn Tyr Pro Leu Thr Phe Gly Ala Gly Thr Lys Leu Glu Leu
            100                 105                 110

Lys

<210> SEQ ID NO 157
<211> LENGTH: 116
<212> TYPE: PRT
<213> ORGANISM: Mus musculus
<220> FEATURE:
<221> NAME/KEY: MISC_FEATURE
<223> OTHER INFORMATION: Murine SC17.161 VH

<400> SEQUENCE: 157

Glu Val Lys Leu Glu Glu Ser Gly Gly Gly Leu Val Gln Pro Gly Gly
 1               5                  10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
            35                  40                  45

Ala Glu Ile Arg Ser Lys Pro Asn Asn His Ala Thr Tyr Tyr Ala Glu
 50                  55                  60

Ser Val Lys Gly Arg Phe Thr Ile Ser Arg Asp Ser Lys Ser Ser
 65                  70                  75                  80

Ala Tyr Leu Gln Met Asn Ser Leu Arg Ala Glu Asp Thr Gly Ile Tyr
                85                  90                  95

Tyr Cys Val Ser Thr Gly Thr Ser Tyr Trp Gly Gln Gly Thr Leu Val
            100                 105                 110

Thr Val Ser Ala
        115
```

```
<210> SEQ ID NO 158
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.166 VL

<400> SEQUENCE: 158

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Trp Ser Ser Thr Pro Pro Thr
                85                  90                  95

Phe Gly Gly Gly Thr Lys Leu Glu Ile Lys
            100                 105

<210> SEQ ID NO 159
<211> LENGTH: 117
<212> TYPE: PRT
<213> ORGANISM: Mus musculus
<220> FEATURE:
<221> NAME/KEY: MISC_FEATURE
<223> OTHER INFORMATION: Murine SC17.166 VH

<400> SEQUENCE: 159

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Ile Phe Thr Asp Tyr
            20                  25                  30

Asn Met His Trp Val Lys Gln Asn Gly Lys Ser Leu Glu Trp Ile
        35                  40                  45

Gly Glu Val Asn Pro Asn Thr Gly Gly Ile Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Asp Gly Asn Tyr Cys Phe Asp Tyr Trp Gly Gln Gly Thr Thr
            100                 105                 110

Leu Thr Val Ser Ser
        115

<210> SEQ ID NO 160
<211> LENGTH: 107
<212> TYPE: PRT
<213> ORGANISM: Mus musculus
<220> FEATURE:
<221> NAME/KEY: MISC_FEATURE
<223> OTHER INFORMATION: Murine SC17.187 VL

<400> SEQUENCE: 160

Asp Ile Lys Met Thr Gln Ser Pro Ser Ser Met Tyr Ala Ser Leu Gly
```

```
            1               5                  10                 15
         Glu Arg Val Thr Leu Thr Cys Lys Ala Ser Gln Asp Ile Asn Ser Tyr
                         20                 25                 30

Leu Ser Trp Phe Gln Gln Lys Pro Gly Lys Ser Pro Glu Thr Leu Ile
                         35                 40                 45

Tyr Arg Ala Asn Arg Leu Ile Asp Gly Val Pro Ser Arg Phe Ser Gly
                         50                 55                 60

Ser Gly Ser Gly Gln Asp Tyr Ser Leu Thr Ile Ser Ser Leu Glu Tyr
         65                 70                 75                 80

Glu Asp Met Gly Ile Tyr Tyr Cys Leu Gln Tyr Asp Glu Phe Pro Pro
                         85                 90                 95

Thr Phe Gly Gly Gly Thr Lys Leu Glu Ile Lys
                         100                105

<210> SEQ ID NO 161
<211> LENGTH: 118
<212> TYPE: PRT
<213> ORGANISM: Mus musculus
<220> FEATURE:
<221> NAME/KEY: MISC_FEATURE
<223> OTHER INFORMATION: Murine SC17.187 VH

<400> SEQUENCE: 161

Glu Val His Leu Gln Gln Ser Gly Pro Glu Leu Val Asn Pro Gly Ser
         1               5                  10                 15

Ser Val Lys Ile Ser Cys Lys Ala Ala Gly Tyr Thr Phe Thr Asp Tyr
                         20                 25                 30

Asn Met Asp Trp Val Lys Gln Ser His Gly Lys Arg Leu Glu Trp Ile
                         35                 40                 45

Gly Asn Ile Tyr Pro Asn Asn Gly Gly Ala Gly Tyr Asn Gln Asn Phe
                         50                 55                 60

Lys Asp Lys Ala Thr Leu Thr Val Asp Lys Ser Ser Ser Thr Ala Tyr
         65                 70                 75                 80

Met Glu Leu Arg Ser Leu Thr Ser Glu Asp Ser Ala Val Tyr Tyr Cys
                         85                 90                 95

Ala Arg Ser Ile Thr Ala Ala Trp Phe Ala Tyr Trp Gly Gln Gly Thr
                         100                105                110

Leu Val Thr Val Ser Ala
                         115

<210> SEQ ID NO 162
<211> LENGTH: 106
<212> TYPE: PRT
<213> ORGANISM: Mus musculus
<220> FEATURE:
<221> NAME/KEY: MISC_FEATURE
<223> OTHER INFORMATION: Murine SC17.191 VL

<400> SEQUENCE: 162

Gln Ile Val Leu Thr Gln Ser Pro Ala Ile Met Ser Ala Ser Pro Gly
         1               5                  10                 15

Glu Lys Val Thr Met Thr Cys Ser Ala Ser Ser Ser Val Ser Tyr Met
                         20                 25                 30

His Trp Tyr Gln Gln Lys Ser Gly Thr Ser Pro Lys Arg Trp Ile Tyr
                         35                 40                 45

Asp Thr Ser Lys Leu Ala Ser Gly Val Pro Ala Arg Phe Thr Gly Ser
                         50                 55                 60

Gly Ser Gly Thr Ser Tyr Ser Leu Thr Ile Ser Ser Met Glu Ala Glu
```

```
                65                  70                  75                  80
Asp Ala Ala Thr Tyr Tyr Cys Gln Gln Trp Ser Ser Pro Pro Thr
                    85                  90                  95

Phe Gly Ala Gly Thr Lys Leu Glu Leu Lys
                100                 105

<210> SEQ ID NO 163
<211> LENGTH: 120
<212> TYPE: PRT
<213> ORGANISM: Mus musculus
<220> FEATURE:
<221> NAME/KEY: MISC_FEATURE
<223> OTHER INFORMATION: Murine SC17.191 VH

<400> SEQUENCE: 163

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
                20                  25                  30

Asn Met His Trp Val Lys Gln Asn Gln Gly Lys Ser Leu Glu Trp Ile
            35                  40                  45

Gly Glu Ile Asn Pro Asn Thr Gly Gly Thr Gly Tyr Asn Gln Lys Phe
        50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ile Pro Ser Leu Arg Arg Tyr Tyr Phe Asp Tyr Trp Gly Gln
                100                 105                 110

Gly Thr Thr Leu Thr Val Ser Ser
            115                 120

<210> SEQ ID NO 164
<211> LENGTH: 111
<212> TYPE: PRT
<213> ORGANISM: Mus musculus
<220> FEATURE:
<221> NAME/KEY: MISC_FEATURE
<223> OTHER INFORMATION: Murine SC17.193 VL

<400> SEQUENCE: 164

Asp Leu Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ser Thr Ser
                20                  25                  30

Gly Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Thr Thr Tyr Tyr Cys Gln His Ser Arg
                85                  90                  95

Glu Leu Pro Tyr Thr Phe Gly Gly Gly Thr Lys Leu Glu Ile Lys
                100                 105                 110

<210> SEQ ID NO 165
<211> LENGTH: 122
<212> TYPE: PRT
```

```
<213> ORGANISM: Mus musculus
<220> FEATURE:
<221> NAME/KEY: MISC_FEATURE
<223> OTHER INFORMATION: Murine SC17.193 VH

<400> SEQUENCE: 165

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ile Thr Tyr
            20                  25                  30

Gly Ile Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Asn Val Asp Thr Ala Asp Thr Ala Thr Tyr Tyr
                85                  90                  95

Cys Ala Arg Met Val Tyr Tyr Asp Tyr Asp Gly Phe Ala Tyr Trp
            100                 105                 110

Gly Gln Gly Thr Leu Val Thr Val Ser Ala
        115                 120

<210> SEQ ID NO 166
<211> LENGTH: 111
<212> TYPE: PRT
<213> ORGANISM: Mus musculus
<220> FEATURE:
<221> NAME/KEY: MISC_FEATURE
<223> OTHER INFORMATION: Murine SC17.199 VL

<400> SEQUENCE: 166

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Pro Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 167
<211> LENGTH: 116
<212> TYPE: PRT
<213> ORGANISM: Mus musculus
<220> FEATURE:
<221> NAME/KEY: MISC_FEATURE
<223> OTHER INFORMATION: Murine SC17.199 VH

<400> SEQUENCE: 167

Glu Val Gln Leu Gln Gln Ser Gly Thr Val Leu Ala Arg Pro Gly Ala
1               5                   10                  15

Ser Val Arg Met Ser Cys Lys Ala Ser Gly Tyr Thr Phe Thr Ser Tyr
            20                  25                  30
```

Trp Met His Trp Val Lys Gln Arg Pro Gly Gln Gly Leu Glu Trp Ile
            35                  40                  45

Gly Ala Ile Tyr Pro Gly Asn Ser Asp Thr Ser Tyr Asn His Lys Phe
        50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Ser Gly Thr Gly Trp Phe Ala Tyr Trp Gly Gln Gly Thr Leu
            100                 105                 110

Val Thr Val Ser
        115

<210> SEQ ID NO 168
<211> LENGTH: 111
<212> TYPE: PRT
<213> ORGANISM: Mus musculus
<220> FEATURE:
<221> NAME/KEY: MISC_FEATURE
<223> OTHER INFORMATION: Murine SC17.200 VL

<400> SEQUENCE: 168

Asp Ile Val Leu Thr Gln Ser Pro Ala Ser Leu Ala Val Ser Leu Gly
1               5                   10                  15

Gln Arg Ala Thr Ile Phe Cys Arg Ala Ser Gln Ser Val Asp Tyr Asn
            20                  25                  30

Gly Ile Ser Tyr Met His Trp Phe Gln Gln Lys Pro Gly Gln Pro Pro
        35                  40                  45

Lys Leu Leu Ile Tyr Ala Ala Ser Asn Val Gln Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Phe Tyr Cys Gln Gln Ser Ile
                85                  90                  95

Glu Asp Pro Pro Thr Phe Gly Gly Gly Thr Lys Leu Glu Ile Lys
            100                 105                 110

<210> SEQ ID NO 169
<211> LENGTH: 115
<212> TYPE: PRT
<213> ORGANISM: Mus musculus
<220> FEATURE:
<221> NAME/KEY: MISC_FEATURE
<223> OTHER INFORMATION: Murine SC17. VH
<220> FEATURE:
<221> NAME/KEY: MISC_FEATURE
<223> OTHER INFORMATION: Murine SC17.200 VH

<400> SEQUENCE: 169

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile Asn Trp Val Lys Gln Arg Pro Gly Gln Gly Leu Glu Trp Ile
        35                  40                  45

Gly Arg Ile Tyr Pro Gly Glu Gly Asp Thr Asn Tyr Ser Gly Asn Phe
    50                  55                  60

Glu Gly Lys Ala Thr Leu Thr Ala Asp Lys Ser Ser Thr Thr Ala Tyr
65                  70                  75                  80

```
Met Gln Leu Ser Ser Leu Thr Ser Val Asp Ser Ala Val Tyr Phe Cys
                85                  90                  95

Thr Arg Gly Leu Val Met Asp Tyr Trp Gly Gln Gly Thr Ala Leu Thr
            100                 105                 110

Val Ser Ser
        115

<210> SEQ ID NO 170
<211> LENGTH: 107
<212> TYPE: PRT
<213> ORGANISM: Artificial Sequence
<220> FEATURE:
<223> OTHER INFORMATION: Humanized hSC17.16 VL

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Asn Ile Asn Ser Asn
            20                  25                  30

Leu Val Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Gly Thr Pro Arg
                85                  90                  95

Thr Phe Gly Gly Gly Thr Lys Leu Glu Ile Lys
            100                 105

<210> SEQ ID NO 171
<211> LENGTH: 116
<212> TYPE: PRT
<213> ORGANISM: Artificial Sequence
<220> FEATURE:
<223> OTHER INFORMATION: Humanized hSC17.16 VH

<400> SEQUENCE: 171

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Tyr Trp Val Arg Gln Ala Pro Gly Gln Gly Leu Glu Trp Met
        35                  40                  45

Gly Glu Ile Asn Pro Asn Asn Gly Gly Thr Ala Tyr Asn Gln Lys Phe
    50                  55                  60

Arg Gly Lys Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Asp Lys Gly Phe Asp Tyr Trp Gly Gln Gly Thr Thr Val
            100                 105                 110

Thr Val Ser Ser
        115

<210> SEQ ID NO 172
<211> LENGTH: 106
<212> TYPE: PRT
```

<213> ORGANISM: Artificial Sequence
<220> FEATURE:
<223> OTHER INFORMATION: Humanized hSC17.17 VL

<400> SEQUENCE: 172

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Pro Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Thr Pro Pro Thr
                85                  90                  95

Phe Gly Gln Gly Thr Lys Leu Glu Ile Lys
            100                 105
```

<210> SEQ ID NO 173
<211> LENGTH: 120
<212> TYPE: PRT
<213> ORGANISM: Artificial Sequence
<220> FEATURE:
<223> OTHER INFORMATION: Humanized hSC17.17 VH

<400> SEQUENCE: 173

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ile Gly Gly Thr Gly Tyr Asn Gln Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Thr Tyr Ser Tyr Tyr Ser Tyr Glu Phe Ala Tyr Trp Gly Gln
            100                 105                 110

Gly Thr Leu Val Thr Val Ser Ser
        115                 120
```

<210> SEQ ID NO 174
<211> LENGTH: 112
<212> TYPE: PRT
<213> ORGANISM: Artificial Sequence
<220> FEATURE:
<223> OTHER INFORMATION: Humanized hSC17.24 VL

<400> SEQUENCE: 174

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Ser Tyr Leu Ala Trp Tyr Gln Gln Lys Pro Gly Gln
        35                  40                  45
```

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Arg Thr Phe Gly Gly Gly Thr Lys Val Glu Ile Lys
            100                 105                 110

<210> SEQ ID NO 175
<211> LENGTH: 117
<212> TYPE: PRT
<213> ORGANISM: Artificial Sequence
<220> FEATURE:
<223> OTHER INFORMATION: Humanized hSC17.24 VH

<400> SEQUENCE: 175

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp His
                20                  25                  30

Thr Ile His Trp Val Arg Gln Ala Pro Gly Lys Gly Leu Glu Trp Ile
            35                  40                  45

Gly Tyr Ile Tyr Pro Arg Asp Gly Ser Thr Lys Tyr Asn Glu Glu Phe
        50                  55                  60

Lys Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Ser Asn Tyr Phe Asp Tyr Trp Gly Gln Gly Thr Thr
            100                 105                 110

Val Thr Val Ser Ser
            115

<210> SEQ ID NO 176
<211> LENGTH: 107
<212> TYPE: PRT
<213> ORGANISM: Artificial Sequence
<220> FEATURE:
<223> OTHER INFORMATION: Humanized hSC17.28 VL

<400> SEQUENCE: 176

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Ser
                20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Ser Trp Pro Leu
                85                  90                  95

Thr Phe Gly Gln Gly Thr Lys Leu Glu Ile Lys
            100                 105

<210> SEQ ID NO 177
<211> LENGTH: 117
<212> TYPE: PRT
<213> ORGANISM: Artificial Sequence
<220> FEATURE:
<223> OTHER INFORMATION: Humanized hSC17.28 VH

<400> SEQUENCE: 177

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Ser
            20                  25                  30

Tyr Ile His Trp Val Arg Gln Ala Pro Gly Gln Gly Leu Glu Trp Met
        35                  40                  45

Gly Tyr Ile Ser Ser Gly Ser Gly Thr Thr Tyr Asn Gln Lys Phe
    50                  55                  60

Lys Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Val Arg Tyr Phe Asp Val Trp Gly Gln Gly Thr Thr
            100                 105                 110

Val Thr Val Ser Ser
        115
```

<210> SEQ ID NO 178
<211> LENGTH: 107
<212> TYPE: PRT
<213> ORGANISM: Artificial Sequence
<220> FEATURE:
<223> OTHER INFORMATION: Humanized hSC17.34 VL

<400> SEQUENCE: 178

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Pro
                85                  90                  95

Thr Phe Gly Gln Gly Thr Lys Leu Glu Ile Lys
            100                 105
```

<210> SEQ ID NO 179
<211> LENGTH: 118
<212> TYPE: PRT
<213> ORGANISM: Artificial Sequence
<220> FEATURE:
<223> OTHER INFORMATION: Humanized hSC17.34 VH

<400> SEQUENCE: 179

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

```
Asn Met Asp Trp Val Arg Gln Ala Pro Gly Gln Arg Leu Glu Trp Ile
         35                  40                  45

Gly Tyr Ile Tyr Pro Asp Asn Gly Ala Gly Tyr Asn Gln Lys Phe
     50                  55                  60

Lys Gly Arg Val Thr Ile Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ser Arg Ser Ile Thr Thr Ala Trp Phe Ala Tyr Trp Gly Gln Gly Thr
            100                 105                 110

Leu Val Thr Val Ser Ser
            115

<210> SEQ ID NO 180
<211> LENGTH: 107
<212> TYPE: PRT
<213> ORGANISM: Artificial Sequence
<220> FEATURE:
<223> OTHER INFORMATION: Humanized hSC17.46 VL

<400> SEQUENCE: 180

Ala Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Asn Asn Asp
             20                  25                  30

Val Ala Trp Tyr Gln Gln Lys Pro Gly Lys Ala Pro Lys Leu Leu Ile
         35                  40                  45

Tyr Tyr Ala Ser Asn Arg Tyr Thr Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Asp Tyr Ser Ser Pro Arg
                 85                  90                  95

Thr Phe Gly Gln Gly Thr Lys Leu Glu Ile Lys
            100                 105

<210> SEQ ID NO 181
<211> LENGTH: 121
<212> TYPE: PRT
<213> ORGANISM: Artificial Sequence
<220> FEATURE:
<223> OTHER INFORMATION: Humanized hSC17.46 VH

<400> SEQUENCE: 181

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Trp Ile Asn Trp Val Arg Gln Ala Pro Gly Gln Gly Leu Glu Trp Ile
         35                  40                  45

Gly Asn Ile Phe Pro Asp Thr Thr Thr Asn Tyr Asn Glu Lys Phe
     50                  55                  60

Lys Gly Arg Val Thr Leu Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Tyr Tyr Asp Gly Thr Tyr Asp Ala Met Asp Tyr Trp Gly
```

Gln Gly Thr Leu Val Thr Val Ser Ser
          115                 120

<210> SEQ ID NO 182
<211> LENGTH: 111
<212> TYPE: PRT
<213> ORGANISM: Artificial Sequence
<220> FEATURE:
<223> OTHER INFORMATION: Humanized hSC17.151 VL

<400> SEQUENCE: 182

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Ser Tyr
            20                  25                  30

Gly Asn Ser Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser His
                85                  90                  95

Glu Asp Pro Tyr Thr Phe Gly Gln Gly Thr Lys Leu Glu Ile Lys
            100                 105                 110

<210> SEQ ID NO 183
<211> LENGTH: 117
<212> TYPE: PRT
<213> ORGANISM: Artificial Sequence
<220> FEATURE:
<223> OTHER INFORMATION: Humanized hSC17.151 VH

<400> SEQUENCE: 183

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Ala Ile Tyr Pro Gly Lys Ser Asp Thr Thr Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Lys Gly Tyr Phe Ala Tyr Trp Gly Gln Gly Thr Leu
            100                 105                 110

Val Thr Val Ser Ser
        115

<210> SEQ ID NO 184
<211> LENGTH: 113
<212> TYPE: PRT
<213> ORGANISM: Artificial Sequence
<220> FEATURE:
<223> OTHER INFORMATION: Humanized hSC17.155 VL

<400> SEQUENCE: 184

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Lys Pro Gly Gln
        35                  40                  45

Pro Pro Lys Leu Leu Ile Tyr Trp Ala Ser Thr Arg Lys Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Tyr Pro Leu Thr Phe Gly Gln Gly Thr Lys Leu Glu Ile
                100                 105                 110

Lys
```

<210> SEQ ID NO 185
<211> LENGTH: 113
<212> TYPE: PRT
<213> ORGANISM: Artificial Sequence
<220> FEATURE:
<223> OTHER INFORMATION: Humanized hSC17.155 VH

<400> SEQUENCE: 185

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Trp Met His Trp Val Arg Gln Ala Pro Gly Gln Gly Leu Glu Trp Met
        35                  40                  45

Gly Glu Ile His Pro Asn Asn Gly Ser Thr Asn Tyr Asn Glu Lys Phe
50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Thr Leu Phe Thr Tyr Trp Gly Gln Gly Thr Leu Val Thr
                100                 105                 110

Val
```

<210> SEQ ID NO 186
<211> LENGTH: 112
<212> TYPE: PRT
<213> ORGANISM: Artificial Sequence
<220> FEATURE:
<223> OTHER INFORMATION: Humanized hSC17.156 VL

<400> SEQUENCE: 186

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 187
<211> LENGTH: 118
<212> TYPE: PRT
<213> ORGANISM: Artificial Sequence
<220> FEATURE:
<223> OTHER INFORMATION: Humanized hSC17.156 VH

<400> SEQUENCE: 187

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Phe Trp Asp Asp Lys Trp Tyr Asn Pro Ser
50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Thr Phe Tyr Gly Leu Tyr Phe Ala Tyr Trp Gly Gln Gly Thr
            100                 105                 110

Leu Val Thr Val Ser Ser
        115

<210> SEQ ID NO 188
<211> LENGTH: 113
<212> TYPE: PRT
<213> ORGANISM: Artificial Sequence
<220> FEATURE:
<223> OTHER INFORMATION: Humanized hSC17.161 VL

<400> SEQUENCE: 188

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Tyr Asn
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Asn Tyr Pro Leu Thr Phe Gly Gln Gly Thr Lys Leu Glu Ile
            100                 105                 110

Lys

<210> SEQ ID NO 189
<211> LENGTH: 116

<212> TYPE: PRT
<213> ORGANISM: Artificial Sequence
<220> FEATURE:
<223> OTHER INFORMATION: Humanized hSC17.161 VH

<400> SEQUENCE: 189

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asp Ala
            20                  25                  30

Trp Met Asp Trp Val Arg Gln Ala Pro Gly Gln Arg Leu Glu Trp Met
        35                  40                  45

Gly Glu Ile Arg Ser Lys Pro Asn Asn His Ala Thr Tyr Tyr Ala Glu
    50                  55                  60

Ser Val Lys Gly Arg Val Thr Ile Thr Arg Asp Thr Ser Ala Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Thr Gly Thr Ser Tyr Trp Gly Gln Gly Thr Leu Val
            100                 105                 110

Thr Val Ser Ser
        115

<210> SEQ ID NO 190
<211> LENGTH: 111
<212> TYPE: PRT
<213> ORGANISM: Artificial Sequence
<220> FEATURE:
<223> OTHER INFORMATION: Humanized hSC17.200 VL

<400> SEQUENCE: 190

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Tyr Asn
            20                  25                  30

Gly Ile Ser Tyr Met His Trp Tyr Gln Gln Lys Pro Gly Gln Ala Pro
        35                  40                  45

Arg Leu Leu Ile Tyr Ala Ala Ser Asn Val Gln Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Ile
                85                  90                  95

Glu Asp Pro Pro Thr Phe Gly Gly Gly Thr Lys Val Glu Ile Lys
            100                 105                 110

<210> SEQ ID NO 191
<211> LENGTH: 115
<212> TYPE: PRT
<213> ORGANISM: Artificial Sequence
<220> FEATURE:
<223> OTHER INFORMATION: Humanized hSC17.200 VH

<400> SEQUENCE: 191

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Ser
            20                  25                  30

Trp Ile Asn Trp Val Arg Gln Met Pro Gly Lys Gly Leu Glu Trp Met

```
                    35                  40                  45

Gly Arg Ile Tyr Pro Gly Glu Gly Asp Thr Asn Tyr Ser Gly Asn Phe
             50                  55                  60

Glu Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Thr Arg Gly Leu Val Met Asp Tyr Trp Gly Gln Gly Thr Leu Val Thr
            100                 105                 110

Val Ser Ser
        115

<210> SEQ ID NO 192
<211> LENGTH: 111
<212> TYPE: PRT
<213> ORGANISM: Artificial Sequence
<220> FEATURE:
<223> OTHER INFORMATION: Humanized hSC17.200 VL

<400> SEQUENCE: 192

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asp Tyr Asp
             20                  25                  30

Gly Ile Ser Tyr Met His Trp Tyr Gln Gln Lys Pro Gly Gln Ala Pro
             35                  40                  45

Arg Leu Leu Ile Tyr Ala Ala Ser Asn Val Gln Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Ser Ile
                 85                  90                  95

Glu Asp Pro Pro Thr Phe Gly Gly Gly Thr Lys Val Glu Ile Lys
            100                 105                 110

<210> SEQ ID NO 193
<211> LENGTH: 113
<212> TYPE: PRT
<213> ORGANISM: Artificial Sequence
<220> FEATURE:
<223> OTHER INFORMATION: Humanized hSC17.155 VH1

<400> SEQUENCE: 193

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asp Ser Tyr
             20                  25                  30

Trp Met His Trp Val Arg Gln Ala Pro Gly Gln Gly Leu Glu Trp Met
             35                  40                  45

Gly Glu Ile His Pro Asn Asn Gly Ser Thr Asn Tyr Asn Glu Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Trp Thr Leu Phe Thr Tyr Trp Gly Gln Gly Thr Leu Val Thr
            100                 105                 110
```

Val

<210> SEQ ID NO 194
<211> LENGTH: 113
<212> TYPE: PRT
<213> ORGANISM: Artificial Sequence
<220> FEATURE:
<223> OTHER INFORMATION: Humanized hSC17.155 VH2

<400> SEQUENCE: 194

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile His Pro Asn Asn Gly Ser Thr Asn Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Thr Leu Phe Thr Tyr Trp Gly Gln Gly Thr Leu Val Thr
            100                 105                 110

Val

<210> SEQ ID NO 195
<211> LENGTH: 113
<212> TYPE: PRT
<213> ORGANISM: Artificial Sequence
<220> FEATURE:
<223> OTHER INFORMATION: Humanized hSC17.155 VH3

<400> SEQUENCE: 195

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Tyr Tyr
            20                  25                  30

Trp Met His Trp Val Arg Gln Ala Pro Gly Gln Gly Leu Glu Trp Met
        35                  40                  45

Gly Glu Ile His Pro Asn Asn Gly Ser Thr Asn Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Thr Leu Phe Thr Tyr Trp Gly Gln Gly Thr Leu Val Thr
            100                 105                 110

Val

<210> SEQ ID NO 196
<211> LENGTH: 113
<212> TYPE: PRT
<213> ORGANISM: Artificial Sequence
<220> FEATURE:
<223> OTHER INFORMATION: Humanized hSC17.155 VH4

<400> SEQUENCE: 196

Gln Val Gln Leu Val Gln Ser Gly Ala Glu Val Lys Lys Pro Gly Ala

-continued

```
                1               5                      10                          15
            Ser Val Lys Val Ser Cys Lys Ala Ser Gly Tyr Thr Phe Asn Ser Tyr
                            20                      25                      30

Trp Met His Trp Val Arg Gln Ala Pro Gly Gln Gly Leu Glu Trp Met
                        35                      40                      45

Gly Glu Ile His Pro Asn Asp Gly Ser Thr Asn Tyr Asn Glu Lys Phe
                    50                      55                      60

Lys Gly Arg Val Thr Met Thr Arg Asp Thr Ser Thr Ser Thr Val Tyr
            65                      70                      75                      80

Met Glu Leu Ser Ser Leu Arg Ser Glu Asp Thr Ala Val Tyr Tyr Cys
                                85                      90                      95

Ala Arg Trp Thr Leu Phe Thr Tyr Trp Gly Gln Gly Thr Leu Val Thr
                            100                     105                     110

Val
```

<210> SEQ ID NO 197
<211> LENGTH: 113
<212> TYPE: PRT
<213> ORGANISM: Artificial Sequence
<220> FEATURE:
<223> OTHER INFORMATION: Humanized hSC17.155 VH5

<400> SEQUENCE: 197

```
            Gln Val Gln Leu Val Gln Ser Gly Ala Glu Val Lys Lys Pro Gly Ala
            1               5                      10                          15

Ser Val Lys Val Ser Cys Lys Ala Ser Gly Tyr Thr Phe Asn Ser Tyr
                            20                      25                      30

Trp Met His Trp Val Arg Gln Ala Pro Gly Gln Gly Leu Glu Trp Met
                        35                      40                      45

Gly Glu Ile His Pro Asn Gly Ser Thr Asn Tyr Asn Glu Lys Phe
                    50                      55                      60

Lys Gly Arg Val Thr Met Thr Arg Asp Thr Ser Thr Ser Thr Val Tyr
            65                      70                      75                      80

Met Glu Leu Ser Ser Leu Arg Ser Glu Asp Thr Ala Val Tyr Tyr Cys
                                85                      90                      95

Ala Arg Trp Thr Leu Phe Thr Tyr Trp Gly Gln Gly Thr Leu Val Thr
                            100                     105                     110

Val
```

<210> SEQ ID NO 198
<211> LENGTH: 113
<212> TYPE: PRT
<213> ORGANISM: Artificial Sequence
<220> FEATURE:
<223> OTHER INFORMATION: Humanized hSC17.155 VH6

<400> SEQUENCE: 198

```
            Gln Val Gln Leu Val Gln Ser Gly Ala Glu Val Lys Lys Pro Gly Ala
            1               5                      10                          15

Ser Val Lys Val Ser Cys Lys Ala Ser Gly Tyr Thr Phe Asn Ser Tyr
                            20                      25                      30

Trp Met His Trp Val Arg Gln Ala Pro Gly Gln Gly Leu Glu Trp Met
                        35                      40                      45

Gly Glu Ile His Pro Asn Ser Gly Ser Thr Asn Tyr Asn Glu Lys Phe
                    50                      55                      60

Lys Gly Arg Val Thr Met Thr Arg Asp Thr Ser Thr Ser Thr Val Tyr
            65                      70                      75                      80
```

```
Met Glu Leu Ser Ser Leu Arg Ser Glu Asp Thr Ala Val Tyr Tyr Cys
            85                  90                  95

Ala Arg Trp Thr Leu Phe Thr Tyr Trp Gly Gln Gly Thr Leu Val Thr
            100                 105                 110

Val

<210> SEQ ID NO 199
<211> LENGTH: 116
<212> TYPE: PRT
<213> ORGANISM: Artificial Sequence
<220> FEATURE:
<223> OTHER INFORMATION: Humanized hSC17.161 VH1

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
            35                  40                  45

Gly Glu Ile Arg Ser Lys Pro Asn Asn His Ala Thr Tyr Tyr Ala Glu
50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Ala Arg Thr Gly Thr Ser Tyr Trp Gly Gln Gly Thr Leu Val
            100                 105                 110

Thr Val Ser Ser
        115

<210> SEQ ID NO 200
<211> LENGTH: 4
<212> TYPE: PRT
<213> ORGANISM: Homo sapiens
<220> FEATURE:
<221> NAME/KEY: MISC_FEATURE
<223> OTHER INFORMATION: C-terminal cytoplasmic domain motif

<400> SEQUENCE: 200

Asn Pro Thr Tyr
1

<210> SEQ ID NO 201
<211> LENGTH: 9
<212> TYPE: PRT
<213> ORGANISM: Artificial Sequence
<220> FEATURE:
<223> OTHER INFORMATION: His tag

<400> SEQUENCE: 201

His His His His His His His His His
1               5

<210> SEQ ID NO 202

<400> SEQUENCE: 202

000

<210> SEQ ID NO 203
```

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

<210> SEQ ID NO 215
<400> SEQUENCE: 215

000

<210> SEQ ID NO 216
<400> SEQUENCE: 216

000

<210> SEQ ID NO 217
<400> SEQUENCE: 217

000

<210> SEQ ID NO 218
<400> SEQUENCE: 218

000

<210> SEQ ID NO 219
<400> SEQUENCE: 219

000

<210> SEQ ID NO 220
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.1 VL

<400> SEQUENCE: 220

```
caaattgttc tcacccagtc tccagcactc atgtctgcat ctccagggga aaaggtctcc    60
ctgacctgca gtgccaactc aactgtaagt tcatgtact ggtaccagca gaagccaaga   120
tcctccccca caccctggat ttatctcaca tccaacctgg cttctggagt ccctgctcgc   180
ttcagtggca gtgggtctgg gacctcttac tctcttacaa tcagcagcat ggaggctgaa   240
gatgctgcca cttattactg ccagcagtgg agtagtaact cacccatcac gttcggtgct   300
gggaccaagc tggagctgaa a                                             321
```

<210> SEQ ID NO 221
<211> LENGTH: 351
<212> TYPE: DNA
<213> ORGANISM: Mus musculus
<220> FEATURE:
<221> NAME/KEY: misc_feature
<223> OTHER INFORMATION: Murine SC17.1 VH

<400> SEQUENCE: 221

```
gatgtgcagc ttcaggactc aggacctggc ctggtgaaac cttctcagtc tctgtccgtc    60
acctgcactg tcactggcta ctccatcacc tggggttatt actggaactg gatccggcag   120
tttccaggaa acaaactgga gtggatgggt aacatacaca acagtggtgg cactaactac   180
aacccatctc tcaagagtcg aatctctatc actcgagaca catccaagaa ccagttcttc   240
```

```
ctgcagttga attctgtgac tactgaggac acagccacat attactgtgc aaccacaaac    300
tgggactact tgactactg gggccaaggc accactctca cagtctcctc a              351

<210> SEQ ID NO 222
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.2 VL

<400> SEQUENCE: 222
gacattgtga tgtcacagtc tccatcctcc ctggctgtgt cagttggaga aaggtcact     60 atgagctgca agtccagtca gagcctttta tatagtagca atcaaaagag ctacttggcc    120
tggtaccagc agaaaccagg gcagtctcct aaactgttaa tctactgggc atccactagg    180
gaatctgggg tccctgaccg cttcacaggc agtggatcag ggacagattt cactctcacc    240
atcagcagtg tgcaggctga agacctggcc gtttattact gcaagcaatc ttataatctt    300
cggacgttcg gtggaggcac caagctggaa atcaaa                              336

<210> SEQ ID NO 223
<211> LENGTH: 351
<212> TYPE: DNA
<213> ORGANISM: Mus musculus
<220> FEATURE:
<221> NAME/KEY: misc_feature
<223> OTHER INFORMATION: Murine SC17.2 VH

<400> SEQUENCE: 223
caggttcagc tgcagcagtc tgacgctgag ttggtgaaac ctggagcttc agtgaagata    60
tcctgcaagg tttctggcta caccttcact gaccatacta ttcactggat gaagcagagg    120
cctgaacagg gcctggaatg gattggatat atttatccta gagatggtag tactaagtac    180
aatgaggagt tcaagggcaa ggccacattg actgcagaca aatcctccag cacagcctac    240
atgcagctca acagcctgac atctgaggac tctgcagtct atttctgtgc aagatcatat    300
agtaactact tgactactg gggccaaggc accactctca cagtctcctc a              351

<210> SEQ ID NO 224
<211> LENGTH: 333
<212> TYPE: DNA
<213> ORGANISM: Mus musculus
<220> FEATURE:
<221> NAME/KEY: misc_feature
<223> OTHER INFORMATION: Murine SC17.9 VL

<400> SEQUENCE: 224
gacattgtga tgtcacagtc tccatcctcc ctagctgtgt cagttggaga aaggttact     60 atgagctgca agtccagtca gagcctttta tatagtagca atcaaaagaa ctacttggcc    120
tggtaccagc agaaaccagg gcagtctcct aaactgctga tttactgggc atccactagg    180
gaatctgggg tccctgatcg cttcacaggc agtggatctg ggacagattt cactctcacc    240
atcagcagtg tgaaggctga agacctggca gtttatttct gtcagcaata ttataactat    300
ccgtacacgt tcggaggggg gaccaagctg aaa                                 333

<210> SEQ ID NO 225
<211> LENGTH: 357
<212> TYPE: DNA
<213> ORGANISM: Mus musculus
```

```
<220> FEATURE:
<221> NAME/KEY: misc_feature
<223> OTHER INFORMATION: Murine SC17.9 VH

<400> SEQUENCE: 225
caggtccaac tgcagcaacc tggggctgaa attgtgaggc ctggggcttc agtgaagctg      60
tcctgcaagg cttctggcta cacctttacc gactattgga tgaactgggt aaaacagagg     120
cctggacaag gccttgagtg gatcggagca attgatcctt ctgatagtta tactagctac     180
aatccaaaat tcaagggcaa ggccacattg actgtagaca cctcctccag ctcagcctac     240
atgcagctca gcagcctgac atctgaggac tctgcggtct atttctgtgc aagaagagga     300 accccctggta aaccccttgt ttactgggc caagggactc tggtcactgt ctctgca        357

<210> SEQ ID NO 226
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.16 VL

<400> SEQUENCE: 226
gacatccaga tgactcagtc tccagcctcc ctatctgtat ctgtgggaga aactgtcacc      60
atcacatgtc gagcaagtgc gaatattaac agtaatttag tatggtatca gcagaaacag     120
ggaaaatctc ctcagctcct ggtctatgct gcaacaaact agcggatgg tgtgccatca     180 cggttcagtg gcagtggatc aggcacacag tattccctca agatcaacag cctgcagtct     240
gaagattttg ggaattacta ctgtcaacat ttttggggta ctcctcggac gttcggtgga     300
ggcaccaagc tggaaatcaa a                                              321

<210> SEQ ID NO 227
<211> LENGTH: 348
<212> TYPE: DNA
<213> ORGANISM: Mus musculus
<220> FEATURE:
<221> NAME/KEY: misc_feature
<223> OTHER INFORMATION: Murine SC17.16 VH

<400> SEQUENCE: 227
gaggtccagc tgcaacagtc tggacctgag ctaatgaagc ctggggcttc agtgaagatg      60
tcctgcaagg cttctggata cacattcact gactacaaca tgtactgggt gaagcagaac     120
caaggaaaga gcctagagtg gataggagaa attaatccta acaatggtgg tactgcctac     180
aaccagaagt tcagaggcaa ggccacgttg actgtagaca gtcctccag cacagcctac     240 atggagctcc gcagcctgac atctgaggac tctgcagtct attactgtgc aagatatgat     300
aaggggtttg actactgggg ccaaggcacc actctcacag tctcctca                 348

<210> SEQ ID NO 228
<211> LENGTH: 333
<212> TYPE: DNA
<213> ORGANISM: Mus musculus
<220> FEATURE:
<221> NAME/KEY: misc_feature
<223> OTHER INFORMATION: Murine SC17.38 VL

<400> SEQUENCE: 228
gacattgtgg tcacccaatc tccagcttct ttggctgtgt ctctggggca gagagccacc      60
atctcctgca gagccagtga aagtgttgaa tattatggca aagtttaat gcagtggttc     120
```

```
caacagaaac caggacagcc acccaaactc ctcatctatg ctgcatccaa cgtagaatct    180
ggggtccctg ccaggtttag tggcagtggg tctgggacag acttcagcct caacatccat    240
cctgtggagg aggatgatat tgcaatgtat ttctgtcagc aagataggaa ggttccttgg    300
acgttcggtg gaggcaccaa gctggaaatc aaa                                 333
```

<210> SEQ ID NO 229
<211> LENGTH: 360
<212> TYPE: DNA
<213> ORGANISM: Mus musculus
<220> FEATURE:
<221> NAME/KEY: misc_feature
<223> OTHER INFORMATION: Murine SC17.38 VH

<400> SEQUENCE: 229

```
caggttactc tgaaagagtc tggccctggg atattgcagc cctcccagac cctcagtcta     60
acttgttctt tctctgggtt ttcactgaac acatctggta tgagtgtagg ctgggttcgt    120
cagccttcag ggaggggtct ggaatggctg gcccccattt ggtggaatgg tgataagtac    180
tataacccag ccctgaaaag ccggctcaca atctccaagg atacctccaa caaccaggtt    240
ttcctcaaga tcgccagtgt ggtcactgca gatactgcca catacttctg tgctcgaata    300
cggcaatatt actatgctat ggactactgg ggtcaaggaa cctcagtcac cgtctcctca    360
```

<210> SEQ ID NO 230
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.3 VL

<400> SEQUENCE: 230

```
gacattgtga tgtcacagtc tccatcctcc ctagctgtgt cagttggaga aaggttact     60 atgagctgca agtccagtca gagccttta tatagtagca tcaaaagaa ctacttggcc    120 tggtaccagc agaaaccagg gcagtctcct aaactgctga tttactgggc atccactagg    180
gaatctgggg tccctgatcg cttcacaggc agtggatctg gacagatttt cactctcacc    240
atcagcagtg tgaaggctga agacctggca gtttattact gtcagcaata ttatagctat    300
ccgacgttcg gtggaggcac caagctggaa atcaaa                              336
```

<210> SEQ ID NO 231
<211> LENGTH: 354
<212> TYPE: DNA
<213> ORGANISM: Mus musculus
<220> FEATURE:
<221> NAME/KEY: misc_feature
<223> OTHER INFORMATION: Murine SC17.3 VH

<400> SEQUENCE: 231

```
caggtccaac tgcagcagcc tggggctgag cttgtgaagc ctggggcttc agtgaagctg     60
tcctgcaagg cttctggcta caccttcccc agctactgga tacactgtgt gaagcagagg    120
cctggacaag gccttgagtg gattggagtg attaatccta gcaacggtcg tactaactac    180
aatgagaagt tcaagaacaa ggccacactg actgtagaca atcctccag cacagcctac    240 atgcaactca gcagcctgac atctgaggac tctgcggtct attactgtgt cagggggggg    300
acgggctata ctatggacta ctggggtcaa ggaacctcag tcaccgtctc ctca          354
```

<210> SEQ ID NO 232

```
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.4 VL

<400> SEQUENCE: 232
gacatcaaga tgacccagtc tccatcttcc atgtatgcct ctctaggaga gagagtcact      60
atcacttgca aggcgagtca ggacattaat agctatttaa cctggttcca gcagaaacca     120
gggaaatctc ctaagaccct gatctatcgt gcaaacagat tgatagatgg ggtcccatca     180
aggttcagtg gcagtggatc tgggcaagat tattctctca ccatcagcag cctggattat     240
gaagatatgg gaatttatta ttgtctacag tatgatgact ttccgtggac gttcggtgga     300
ggcaccaagc tggaaatcaa a                                               321

<210> SEQ ID NO 233
<211> LENGTH: 348
<212> TYPE: DNA
<213> ORGANISM: Mus musculus
<220> FEATURE:
<221> NAME/KEY: misc_feature
<223> OTHER INFORMATION: Murine SC17.4 VH

<400> SEQUENCE: 233
cagatccagt tggtgcagtc tggacctgag ctgaagaagc ctggagagac agtcaagatc      60
tcctgcaagg cttctggtta taccttcaca gactattcaa tgcactgggt gaagcaggct     120
ccaggaaagg gtttaaagtg gctgggctgg ataaacactg agactggcga gccaacatat     180
tcagaagact caagggacg gtttgccttc tctttggaaa cctctgccag cactgcctat     240
ttgcagatca acaacctcaa aaatgaagac acggctactt atttctgtgt taaaaataag     300
ggctggtttg cttattgggg ccaagggact ctggtcactg tctctgca                  348

<210> SEQ ID NO 234
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.8 VL

<400> SEQUENCE: 234
gatgttgtga tgacccaaac tccactctcc ctgcctgtca gtcttggaga tcaagcctcc      60
atctcttgca gatctagtca gagccttgta cacagtaatg gagacaccta tttacattgg     120
tacctgcaga agccaggcca gtctccaaaa ctcctgatct acaaagtttc caaccgattt     180
tctggggtcc cagacaggtt cagtggcagt ggatcaggga cagatttcac actcaagatc     240
agcagagtgg aggctgagga tctgggactt tatttctgct ctcaaagtac acttattccg     300
tacacgttcg gaggggggac caagctggac ataaaa                               336

<210> SEQ ID NO 235
<211> LENGTH: 342
<212> TYPE: DNA
<213> ORGANISM: Mus musculus
<220> FEATURE:
<221> NAME/KEY: misc_feature
<223> OTHER INFORMATION: Murine SC17.8 VH

<400> SEQUENCE: 235
caggttcacc tgcagcagtc tggaactgaa gtgatgaagc ctggggcctc agtgaagata      60
```

```
tcctgcaagg ctactggcta cacattcagt agctactgga tagagtggat aaagcagagg    120
cctggacatg gccttgagtg gattggagag attttgcctg gaagtggtaa tactaacaac    180
aatgagaagt tcaagggcaa ggccacaatc actgcagata catcctccaa tatagcctac    240
atacaattaa gcagcctgac atctgaggac tctgccgtct attactgtgc gggaggcccg    300
gcggcttact ggggccaagg gactctggtc actgtctctg ca                      342
```

```
<210> SEQ ID NO 236
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.10 VL

<400> SEQUENCE: 236
gacattgtga tgtcacagtc tccatcctcc ctagctgtgt cagttggaga gaaggttact     60
atgagctgca agtccagtca gagccttta tatagtagca tcaaaagaa ctacttggcc     120 tggtaccagc agaaaccagg gcagtctcct aaactgctga tttactgggc atccactagg    180
gaatctgggg tccctgatcg cttcacaggc agtggatctg gacagattt cactctcacc    240 atcagcagtg tgaagactga agacctggca ctttattact gtcagcaata ttattggttt    300
ccgtacacgt tcggagggg gaccaagctg gaaataaaa                            339
```

```
<210> SEQ ID NO 237
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.10 VH

<400> SEQUENCE: 237
gaggttcagc tgcagcagtc tggggcagaa cttgtgaagc caggggcctc agtcaagttg     60
tcctgcacag cttctggctt caacattaaa gacacctata tgcactgggt gaagcagagg    120
cctgaacagg gcctggagtg gattggaagg attgatcctg cgaatgttaa tactaaatat    180
gacccgaagt tccagggcaa ggccactata acagcagaca catcctccaa cacagcctac    240
ctgcagctca gcagcctgac atctgaggac actgccgtct attactgtgt tagggggaat    300
gtttactggg gccaagggac tctggtcact gtctctgca                           339
```

```
<210> SEQ ID NO 238
<211> LENGTH: 324
<212> TYPE: DNA
<213> ORGANISM: Mus musculus
<220> FEATURE:
<221> NAME/KEY: misc_feature
<223> OTHER INFORMATION: Murine SC17.11 VL

<400> SEQUENCE: 238
gaaaatgtgc tcacccagtc tccagcaatc atgtctgcat ctccagggga aaaggtcacc     60
atgacctgca gggccagctc aagtgtaagt tccagttact tgcactggta ccagcagaag    120
tcaggtgcct cccccaaact ctggatttat agcacatcca acttggcttc tggagtccct    180
gctcgcttca gtggcagtgg gtctgggacc tcttactctc tcacaatcag cagtgtggag    240
gctgaagatg ctgccactta ttactgccag cagtacagtg attacccatt cacgttcggc    300
tcggggacaa agttggtaat aaaa                                           324
```

<210> SEQ ID NO 239
<211> LENGTH: 366
<212> TYPE: DNA
<213> ORGANISM: Mus musculus
<220> FEATURE:
<221> NAME/KEY: misc_feature
<223> OTHER INFORMATION: Murine SC17.11 VH

<400> SEQUENCE: 239

```
gaggtccagc tgcagcagtc tggacctgag ctggtgaaac ctggggcttt agtgatgatg      60
tcctgcaagg cttctggata cacattcact gactactaca tgcactgggt gaagcagagc     120
catggacaga gccttgagtg gattggagag gttattcctt acaatgatga aactttctac     180
aaccggaagt tcaaggacaa ggccacattg actgtagaca atcctctag tacagcctac     240
atggagctcc ggagcctgac atctgaggac tctgcaatct attattgtgc aagaagacat     300
aggtacgacg ggtttcgtta tgctatagac tactggggtc aaggaacctc agtcaccgtc     360
tcctca                                                                366
```

<210> SEQ ID NO 240
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.14 VL

<400> SEQUENCE: 240

```
gatgttttga tgacccaaac tccactctcc ctgcctgtca gtcttggaga tcaagcctcc      60
atctcttgca gatctagtca gagcattgtc catagtaatg aaacaccta tttagagtgg     120
ttcctgcaga accaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
tacacgttcg gaggggggac caagctggaa ataaaa                               336
```

<210> SEQ ID NO 241
<211> LENGTH: 354
<212> TYPE: DNA
<213> ORGANISM: Mus musculus
<220> FEATURE:
<221> NAME/KEY: misc_feature
<223> OTHER INFORMATION: Murine SC17.14 VH

<400> SEQUENCE: 241

```
gaggtccagc tgcaacagtc tggacctgtg ctggtgaagc ctggggcttc agtgaagatg      60
tcctgtaagg cttctggata cacaatcact gactacaata tgaactgggt gaagcagagc     120
catggaaaga gccttgagtg gattggagtt attaatcctt acaacggtaa tactagatat     180
aaccagatgt tcaagggcaa ggccacattg actgttgaca gtcctccag cacagcctac     240
atggagctca acagcctgac atctgaggac tctgcagtct attactgtac aagatggggt     300
actacggtgg taggtgcgaa ctggggccaa ggcaccactc tcacagtctc ctca           354
```

<210> SEQ ID NO 242
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.15 VL

<400> SEQUENCE: 242

| caaattgttc tcacccagtc tccagcactc atgtctgcat ctccagggga gaaggtcacc | 60 |
| atgacctgca gtgccagctc aagtgtaaat tacatgtact ggtaccagca gaagccaaga | 120 |
| tcctccccca aaccctggat ttatctcaca tccaacctgg cttctggagt ccctgttcgc | 180 |
| ttcagtggca gtgggtctgg gacctcttac tctctcacaa tcagcagcat ggaggctgaa | 240 |
| gatgctgcca cttactactg ccagcagtgg agtaataacc acccacgtt cggttctggg | 300 |
| accaagctgg agctgaaa | 318 |

<210> SEQ ID NO 243
<211> LENGTH: 366
<212> TYPE: DNA
<213> ORGANISM: Mus musculus
<220> FEATURE:
<221> NAME/KEY: misc_feature
<223> OTHER INFORMATION: Murine SC17.15 VH

<400> SEQUENCE: 243

| gacgtgaagc tcgtggagtc tgggggaggc ttagtgaagc ttggagggtc cctgaaactc | 60 |
| tcctgtgcag cctctggatt cactttcagt agctatgcca tgtcttgggt tcgccagact | 120 |
| ccggagaaga ggctggagtg ggtcgcaacc attactagtg gtggtggtaa cacctactat | 180 |
| ccagacagtg tgaagggtcg attcaccatc tccagagaca atgccaagaa caccctgtac | 240 |
| ctgcaaatga gcagtttgaa gtctgaggac acggccatgt attactgtgc aagaagggat | 300 |
| tactacggta gtagttacgt tatgtttgct tattggggcc aagggactct ggtcactgtc | 360 |
| tctgca | 366 |

<210> SEQ ID NO 244
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.17 VL

<400> SEQUENCE: 244

| caaattgttc tcacccagtc tccagcaatc atgtctgcat ctccagggga gaaggtcacc | 60 |
| atgacctgca gtgccagctc aagtgtaagt tacatgcact ggtaccagca gaagtcaggc | 120 |
| acctccccca aaagatggat ttatgacaca tccaaactgc cttctggagt ccctgctcgc | 180 |
| ttcagtggca gtgggtctgg gacctcttac tctctcacaa tcagcagcat ggaggctgaa | 240 |
| gatgctgcca cttattactg ccagcagtgg agtagtaccc acccacgtt cggtgctggg | 300 |
| accaagctgg agctgaaa | 318 |

<210> SEQ ID NO 245
<211> LENGTH: 360
<212> TYPE: DNA
<213> ORGANISM: Mus musculus
<220> FEATURE:
<221> NAME/KEY: misc_feature
<223> OTHER INFORMATION: Murine SC17.17 VH

<400> SEQUENCE: 245

| gaggtccagc tgcaacagtc tggacctgag gtaatgaagc ctggggcttc agtgaagatg | 60 |
| tcctgcaagg cttctggata cacattcact gactacaaca tgcactgggt gaagcagaac | 120 |

```
caaggaaaga gcctagagtg gataggagaa attaatccta acattggtgg tactggctac      180
aaccagaagt tcaaaggcaa ggccacattg actgtacaca agtcctccag cacagcctac      240
atggagctcc gcagcctgac atctgaggac tctgcagtct attactgtgc aagaacctat      300
agttactata gttacgagtt tgcttactgg ggccaaggga ctctggtcac tgtctctgca      360

<210> SEQ ID NO 246
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.18 VL

<400> SEQUENCE: 246
gacatccaga tgacacaatc ttcatcctac ttgtctgtat ctctaggagg cagagtcacc       60
attacttgca aggcaagtga ccacattaat aattggttag cctggtatca gcagaaacca      120
ggaaatgctc ctaggctctt aatatctggt gcaaccagtt tggaaactgg ggttccttca      180
agattcagtg gcagtggatc tggaaaggat tacactctca gcattaccag tcttcagact      240
gaagatgttg ctacttatta ctgtcaacag tattggagta ttccgctcac gttcggtgcg      300
gggaccaagc tggagctgaa a                                                321

<210> SEQ ID NO 247
<211> LENGTH: 369
<212> TYPE: DNA
<213> ORGANISM: Mus musculus
<220> FEATURE:
<221> NAME/KEY: misc_feature
<223> OTHER INFORMATION: Murine SC17.18 VH

<400> SEQUENCE: 247
caggttactc tgaaagagtc tggccctggg atattgcagc cctcccagac cctcagtctg       60
acttgttctt tctctgggtt ttcactgagc acttctacta tgggtgtagg ctggattcgt      120
cagccttcag gaaagggtct agagtggctg gcagacattt ggtgggatga cagtaagtac      180
tataatccat ccctgaagag ccggctcaca atctccaagg atacctccag caaccaggta      240
ttcctcaaga tcaccagtgt ggacactgca gatactgcca cttactactg tgcgcgaaag      300
ggaaggacag ctcgggctac gagagggttt gcttactggg gccacgggac tctggtcact      360
gtctctgca                                                              369

<210> SEQ ID NO 248
<211> LENGTH: 327
<212> TYPE: DNA
<213> ORGANISM: Mus musculus
<220> FEATURE:
<221> NAME/KEY: misc_feature
<223> OTHER INFORMATION: Murine SC17.19 VL

<400> SEQUENCE: 248
gacattgtgc tgacccaatc tccagcttct ttggctgtgt ctctagggca gagggccgcc       60
atctcttgca gcccagcca aagtgttgat tatgatggtg atagttatat gaactggtac      120
caacagaaac caggccagcc acccaaactc ctcatttatg ctgcatccaa tctagaatct      180
gggatcccag ccaggtttag tggcagtggg tctgggacag acttcaccct caacatccat      240
cctgtggagg aggaggatgc tgcaacctat tactgtcacc aaattaatga cgatccgtgg      300
acgttcggtg gaggcaccaa gctgaaa                                          327
```

<210> SEQ ID NO 249
<211> LENGTH: 363
<212> TYPE: DNA
<213> ORGANISM: Mus musculus
<220> FEATURE:
<221> NAME/KEY: misc_feature
<223> OTHER INFORMATION: Murine SC17.19 VH

<400> SEQUENCE: 249

| | | | | | | |
|---|---|---|---|---|---|---|
| gatgtgcagc | ttcaggagtc | aggacctggc | ctggtgaaac | cttctcagtc | tctgtctgtc | 60 |
| acctgcactg | tcactggcta | ctccatcacc | agtagttata | cctggaactg | gatccggcag | 120 |
| tttccaggaa | acaaactgga | gtggatgggc | tacatacatt | acagtggtag | cactaactac | 180 |
| aacccatctc | tcagaagtcg | aatctctatt | actcgagaca | cgtccaagaa | ccagttcttc | 240 |
| ctgcagttga | attctgtgac | tactgaggac | acagccacat | attactgtgc | aagatcccgt | 300 |
| tattactacg | atgcttacgg | gtttgcttac | tggggccaag | ggactctggt | cactgtctct | 360 |
| gca | | | | | | 363 |

<210> SEQ ID NO 250
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.22 VL

<400> SEQUENCE: 250

| | | | | | | |
|---|---|---|---|---|---|---|
| gatgttgtgt | tgacccaaac | tccactctcc | ctgcctgtca | gtcttggaga | tcaagcctcc | 60 |
| atctcttgca | gatctagtca | gagcattgta | cacattaata | gacacaccta | cttaggatgg | 120 |
| tacctgcaga | aaccaggcca | gtcgctaaag | ctcctgatat | atggggtttc | caaccgattt | 180 |
| tctggggtcc | cagacaggtt | cagtggcagt | ggatcaggga | cagatttcac | actcaagatc | 240 |
| agcagagtgg | aggctgagga | tatgggagtt | tattactgct | ttcaaggtac | acatgttcca | 300 |
| ttcacgttcg | gctcggggac | aaagttggaa | ataaaa | | | 336 |

<210> SEQ ID NO 251
<211> LENGTH: 363
<212> TYPE: DNA
<213> ORGANISM: Mus musculus
<220> FEATURE:
<221> NAME/KEY: misc_feature
<223> OTHER INFORMATION: Murine SC17.22 VH

<400> SEQUENCE: 251

| | | | | | | |
|---|---|---|---|---|---|---|
| cagatccaga | tgatgcagtc | tggacctgag | ctgaagaagc | ctggagagac | agtcaagatc | 60 |
| tcctgcaagg | cttctgggta | ttccttcaca | aactatggaa | tgaactgggt | gaagcaggct | 120 |
| ccaggaaagg | gtttaaagtg | gatgggctgg | ataaacacct | acactggaga | gccaacatat | 180 |
| gctgatgact | tcaagggacg | gtttgccttc | tcttttgaaa | cctctgccag | cactgcctat | 240 |
| ttgcagatca | acaacctcaa | aaatgaggac | atggctacat | atttctgtac | aagaggttac | 300 |
| tacggtagta | gctacgatgc | tttggactac | tggggtcaag | gaacctcagt | caccgtctcc | 360 |
| tca | | | | | | 363 |

<210> SEQ ID NO 252
<211> LENGTH: 336
<212> TYPE: DNA
<213> ORGANISM: Mus musculus
<220> FEATURE:

<221> NAME/KEY: misc_feature
<223> OTHER INFORMATION: Murine SC17.24 VL

<400> SEQUENCE: 252

```
gacattgtga tgtcacagtc tccatcctcc ctggctgtgt cagttggaga gaaggtcact    60
atgagctgca agtccagtca gagccttttta tatagtagca tcaaaagag ctacttggcc   120
tggtaccagc agaaaccagg gcagtctcct aaactgttaa tctactgggc atccactagg   180
gaatctgggg tccctgaccg cttcacaggc agtggatcag ggacagattt cactctcacc   240
atcagcagtg tgcaggctga agacctggcc gtttattact gcaagcaatc ttataatctt   300
cggacgttcg gtggaggcac caagctggaa atcaaa                              336
```

<210> SEQ ID NO 253
<211> LENGTH: 351
<212> TYPE: DNA
<213> ORGANISM: Mus musculus
<220> FEATURE:
<221> NAME/KEY: misc_feature
<223> OTHER INFORMATION: Murine SC17.24 VH

<400> SEQUENCE: 253

```
caggttcagc tgcagcagtc tgacgctgag ttggtgaaac ctggagcttc agtgaagata    60
tcctgcaagg tttctggcta caccttcact gaccatacta ttcactggat gaagcagagg   120
cctgaacagg gcctggaatg gattggatat atttatccta gagatggtag tactaagtac   180
aatgaggagt tcaagggcaa ggccacattg actgcagaca atcctccag cacagcctac   240
atgcagctca acagcctgac atctgaggac tctgcagtct atttctgtgc aagatcatat   300
agtaactact ttgactactg gggccaaggc accactctca cagtctcctc a             351
```

<210> SEQ ID NO 254
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.27 VL

<400> SEQUENCE: 254

```
gatgttgtga tgacccagac tccactcact ttgtcggtta ccattggaca accagcctcc    60
atctcttgca gtcaagtca gagcctctta gaaagtgatg gaaagacata tttgaattgg   120
ttgttacaga ggccaggcca gtctccaaag cgcctaatct atctggtgtc taaactggac   180
tctggagtcc ctgacaggtt cacgggcagt ggatcaggga cagatttcac actgaaaatc   240
agcagagtgg aggctgagga tttgggagtt tattattgct ggcaaggtat acaacatcct   300
cggacgttcg gtggaggcac caagctggaa atcaaa                              336
```

<210> SEQ ID NO 255
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.27 VH

<400> SEQUENCE: 255

```
caggttcaac tgcagcagtc tggggctgag ctggtgaggc ctggggcttc agtgacgctg    60
tcctgcaagg cttcgggcta cacatttact gactatgaaa tgcactgggt gaagcagaca   120
cctgtgcatg gcctggaatg gattggaggt attgatcctg aaactggtgg tactgcctac   180
```

```
aatcagaagt tcaagggcaa ggccacactg actgcagaca atcctccag cacagcctac    240 atggagctcc gcagcctgac atctgaggac tctgccgtct acttctgtac aagatggttt    300
tcttactggg gcccagggac tctggtcact gtctctgca                          339
```

<210> SEQ ID NO 256
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.28 VL

<400> SEQUENCE: 256

```
gacatcttgc tgactcagtc tccagccatc ctgtctgtga gtccaggaga aggagtcagt    60
ttctcctgca gggccagtca gagcattggc acaagcatac actggtatca gcaaagaaca    120
aatggttctc caagacttct cataaagtat gcttctgagt ctatctctgg gatcccttct    180
aggtttagtg gcagtgggtc aggacagat tttactcttc gcatcaacag tctggagtct    240
gaagatattg cagattatta ctgtcaacaa agtaatagct ggccactcac gttcggtgct    300
gggaccaagc tggagctgaa a                                             321
```

<210> SEQ ID NO 257
<211> LENGTH: 351
<212> TYPE: DNA
<213> ORGANISM: Mus musculus
<220> FEATURE:
<221> NAME/KEY: misc_feature
<223> OTHER INFORMATION: Murine SC17.28 VH

<400> SEQUENCE: 257

```
caggtccacc tgccgcagtc tagacctgaa ctggtgaagc ctggagcttc agtgaagata    60
tcctgcaagg cttctggcta cggcttcaca cgcagctata tacactgggt gaagcagagg    120
cctggacagg gcctagagtg gattggatat atttcttctg gaagtggtgg tactacctac    180
aatcagaagt ttaagggcaa ggcctcactg actgcagaca atccctccag cactgcctac    240
atgcatctca gtagcctgac atctgaggac tctgcgatct atttctgtgc aagagggggg    300
gtacggtact tcgatgtctg gggcgcaggg accacggtca ccgtctcctc a             351
```

<210> SEQ ID NO 258
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.29 VL

<400> SEQUENCE: 258

```
gacattgtga tgacccagtc tcacaaattc atgtccacat cagtaggaga cagggtcagc    60
atcacctgca aggccagtca ggatgtgggt actgatgtag cctggtatca acagaaacca    120
gggcaatctc ctaaactact gatttactgg gcatccaccc ggcacactgg agtccctgat    180
cgcttcacag gcagtggatc tgggacagat ttcactctca ccattagcaa tgtgcagtct    240
gaagacttgg cagattattt ctgtcagcaa tatagcagct atccgtacac gttcggaggg    300
gggacaaagc tggaaataaa a                                             321
```

<210> SEQ ID NO 259
<211> LENGTH: 348

```
<212> TYPE: DNA
<213> ORGANISM: Mus musculus
<220> FEATURE:
<221> NAME/KEY: misc_feature
<223> OTHER INFORMATION: Murine SC17.29 VH

<400> SEQUENCE: 259
gaggtccagc tgcaacagtc tggacctgag ctaatgaagc tggggcttc  agtgaagatg     60
tcctgcaagg cttctggata cacattcact gactacaaca tgcactgggt gaagcagaac    120
caaggaaaga gcctagagtg gattggagaa attaatcctc acaatggtgg tactggctac    180
aaccagaagt tcaaaggcaa ggccacattg actgtagaca gtcctccag  cacatcctac    240
atggagctcc gcagcctgac atctgaggac tctgcagtct attactgtgc aggcggttac    300
ccggcctttg actactgggg ccaaggcacc actctcacag tctcctca               348

<210> SEQ ID NO 260
<211> LENGTH: 324
<212> TYPE: DNA
<213> ORGANISM: Mus musculus
<220> FEATURE:
<221> NAME/KEY: misc_feature
<223> OTHER INFORMATION: Murine SC17.30 VL

<400> SEQUENCE: 260
gaaaatgtgc tcacccagtc tccagcaatc gtgtctgcat ctccagggga aaaggtcacc     60
atgacctgca gggccagctc aagtgtaatt tccagttact gcactggta  ccagcagaag    120
tcaggtgcct cccccaaact ctggatttat agcacatcca acttggcttc tggagtccct    180
gctcgcttca gtggcagtgc gtctgggacc tcttactctc tcacaatcag cagtgtggag    240
gctgaagatg ctgccactta ttactgccag cagtacagtg gttacccgct cacgttcggt    300
gctgggacca agctggagct gaaa                                            324

<210> SEQ ID NO 261
<211> LENGTH: 372
<212> TYPE: DNA
<213> ORGANISM: Mus musculus
<220> FEATURE:
<221> NAME/KEY: misc_feature
<223> OTHER INFORMATION: Murine SC17.30 VH

<400> SEQUENCE: 261
gaagtgaagc tggtggagtc tgagggaggc ttagtgcagc ctggaagttc catgaaactc     60
tcctgcacag cctctggatt cactttcagt gactattaca tggcttgggt ccgccaggtt    120
ccagaaaagg gtctagaatg ggttgcaaac attaattatg atggtagtag cacttactat    180
ctggactcct tgaagagccg tttcatcatc tcgagagaca tgcaaagaa  cattctatac    240
ctgcaaatga gcagtctgaa gtctgaggac acagccacgt attactgtgc aagagatgat    300
tattacggta gtagcccaag ctactggtac ttcgatgtct ggggcgcagg gaccacggtc    360
accgtctcct ca                                                         372

<210> SEQ ID NO 262
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.32 VL

<400> SEQUENCE: 262
```

```
gacatccaga tgactcagtc tccagcctcc ctatctgcat ctgtgggaga aactgtcacc      60
atgacatgtc gagcaagtgg gaatattcac aattatttag tatggtatca gcagaaacag     120
ggaaaatctc ctcagctcct ggtctataat gcaaaaacct agcagatgg tgtgccatca      180 aggttcagtg gcagtggatc aggaacacaa tattctctca agatcaacag cctgcagcct     240
gaagattttg ggagttatta ctgtcaacat ttttggagta ctcctccgac gttcggtgga     300
ggcaccaagc tggaaatcaa a                                               321
```

<210> SEQ ID NO 263
<211> LENGTH: 357
<212> TYPE: DNA
<213> ORGANISM: Mus musculus
<220> FEATURE:
<221> NAME/KEY: misc_feature
<223> OTHER INFORMATION: Murine SC17.32 VH

<400> SEQUENCE: 263

```
gaagtgaaac ttgaggagtc tggaggaggc ttggtgcaac ctggaggatc catgaaactc      60
tcctgtgttg cctctggatt cactttcagt aactactgga tgagctgggt ccgccagtct     120
ccagagaagg ggcttgagtg ggttgctgaa attagattga aatctaataa ttatgcaaca     180
cattatgcgg agtctgtgaa agggaggttc accatctcaa gagacgattc aaaagtagt      240 gtcttcctgc aaatgaacaa cttaagaact gaagacactg gcatttatta ctgtaccagg     300
cactattact atgctatgga ctactggggt caaggaacct cagtcaccgt ctcctca        357
```

<210> SEQ ID NO 264
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.34 VL

<400> SEQUENCE: 264

```
gacatcaaga tgacccagtc tccatcttcc atgtatgcat ctctaggaga gagagtcact      60
atcacctgca aggcgagtca ggacattaat agctatttaa gctggttcca gcagaaacca     120
gggaaatctc ctaagaccct gatctatcgt gcaaacagat tggtagatgg gtcccatca      180 aggttcagtg gcagtggatc tgggcaagat tattctctca ccatcagtag cctggagtat     240
gaagatatgg gaatttatta ttgtctacag tatgatgagt ttcctccgac gttcggtgga     300
ggcaccaagc tggaaatcaa a                                               321
```

<210> SEQ ID NO 265
<211> LENGTH: 354
<212> TYPE: DNA
<213> ORGANISM: Mus musculus
<220> FEATURE:
<221> NAME/KEY: misc_feature
<223> OTHER INFORMATION: Murine SC17.34 VH

<400> SEQUENCE: 265

```
gaggtccagc tacaacagtc tggacctgag ctggtgaagc ctgggtcttc agtgaagata      60
tcctgcaagg cttctggata cacattcact gactacaaca tggactgggt gaagcagagc     120
catggaaaga gacttgagtg gattggatat atttatcctg acaatggtgg tgctggctac     180
aaccagaagt tcaagggcaa ggccacattg actgtagaca gtcctccag cacagcctac     240 atggagctcc gcagcctgac atctgaggac tctgcagtct attactgttc aagatccatt     300
```

-continued actacggctt ggtttgctta ctggggccaa gggactctgg tcactgtctc tgca    354

<210> SEQ ID NO 266
<211> LENGTH: 324
<212> TYPE: DNA
<213> ORGANISM: Mus musculus
<220> FEATURE:
<221> NAME/KEY: misc_feature
<223> OTHER INFORMATION: Murine SC17.35 VL

<400> SEQUENCE: 266
gaaaatgtgc tcacccagtc tccagcaatc atgtctgcat ctccagggga aaaggtcacc    60
ctgacctgca gggccagctc aagtatgagt tccagttact gcactggta ccagcagaag    120 tcaggtgcct cccccaaact ctggatttat agcacatcca acttggcttc tggagtccct    180
gctcgcttca gtggcagtgg gtctgggacc tcttactctc tcacaatcag cagtgtggag    240
gctgaagatg ctgccactta ttactgccag cagtacagtg cttacccatt cacgttcggc    300
tcggggacaa agttggaaat aaaa    324

<210> SEQ ID NO 267
<211> LENGTH: 363
<212> TYPE: DNA
<213> ORGANISM: Mus musculus
<220> FEATURE:
<221> NAME/KEY: misc_feature
<223> OTHER INFORMATION: Murine SC17.35 VH

<400> SEQUENCE: 267
gaggtccagc tgcagcagtc tggacctgag ctagtgaaac ctggggcttt agtgaagatg    60
tcctgcaagg cttctggata cacattcact gactactaca tacactgggt gaagcagagc    120
catggaaaga gccttgagtg gattggagaa attaatcctt acaatggtga ctttctac    180 aaccagaagt tcaagggcaa ggccacattg actgtagaca atcctctag tacagcctac    240 atggaactcc ggagcctgac atctgaggac tctgcagtct attattgtgc aagaagggga    300
tggtatctaa caggctatgc tatggactac tggggtcaag gaacctcagt caccgtctcc    360
tca    363

<210> SEQ ID NO 268
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.36 VL

<400> SEQUENCE: 268
caaattgttc tcacccagtc tccagcactc atgtctgcat ctccagggga gaaggtcacc    60
atgacctgca gtgccagctc aagtgtaagt tacatgtact ggtaccagca gaagccaaga    120
tcctccccca aacccggat ttatctcaca tccaacctgg cttctggagt ccctgctcgc    180
ttcagtggca gtgggtctgg gacctcttac tctctcacaa tcagcagcat ggaggctgaa    240
gatgctgcca ttattactg ccagcagtgg agtagtaacc cacccacgtt cggaggggg    300 accaagctgg aaataaaa    318

<210> SEQ ID NO 269
<211> LENGTH: 360
<212> TYPE: DNA
<213> ORGANISM: Mus musculus
<220> FEATURE:

<221> NAME/KEY: misc_feature
<223> OTHER INFORMATION: Murine SC17.36 VH

<400> SEQUENCE: 269

```
gaggtgcagc ttcaggagtc aggacctagc ctcgtgaaac cttctcagtc tcagtccctc      60
acctgttctg tcactggcga ctccatcacc agtgattact ggaactggat ccggaaattc     120
ccagggaaga agttgagta catggggtac ataaactaca gtggtagcac ttactacaat      180
ccatctctca aaagtcgaat ctccatcact cgagacacat ccaagaacca gtactacctg    240
cagttgaact ctgtgacttc tgaggacaca gccacatatt actgtgcacg tacctcgtac    300
tataataagt ttctaccatt tgcttactgg ggccaaggga ctctggtcac tgtctctgca    360
```

<210> SEQ ID NO 270
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.39 VL

<400> SEQUENCE: 270

```
gatgttttaa tgacccaaac tccactctcc ctgcctgtca gtcttggaga tcaagcctcc    60
atctcttgca gatctagtca gagtcttgta cacagaaatg gaaacaccta ttttcattgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac atatgttccg   300
tggacgttcg gtggaggcac caagctggaa atcaaa                               336
```

<210> SEQ ID NO 271
<211> LENGTH: 351
<212> TYPE: DNA
<213> ORGANISM: Mus musculus
<220> FEATURE:
<221> NAME/KEY: misc_feature
<223> OTHER INFORMATION: Murine SC17.39 VH

<400> SEQUENCE: 271

```
gaggtgcagc tggtggagtc tgggggaggc ttagtgcagc ctggagggtc ccggaaactc     60
tcctgtgcag cctctggatt cactttcagt agctatggaa tgcactgggt ccgtcaggct   120
ccagagaagg ggctggagtg ggtcgcatat attagtagta cgatggtac catctactat    180 gcagacacag tgaggggccg attccaccatc tccagagaca atgccaagaa caccctgttc  240
ttgcaaatga ccagtctaag gtctgaggac acggccatgt attactgtgc aagaccttct   300
aactgggtct ttgactactg gggccaaggc accactctca cagtctcctc a             351
```

<210> SEQ ID NO 272
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.40 VL

<400> SEQUENCE: 272

```
gatgttgtga tgacccaaac tccactctcc cggcctgtca ctcttggaga tcaagcctcc    60
atctcttgca gatctagtca gagccttgta cacagtaatg gaaacaccta tttcattgg    120 tacctgcaga agccaggcca gtctccaaag ctcctgatct acaaagtttc caaccgattt   180
```

```
tctggggtcc ctgacaggtt cagtggcagt ggatcaggga cagatttcac actcaagatc    240
agcagagtgg aggctgagga tctgggagtt tatttctgct ctcaaaatac acatgttcca    300
ttcacgttcg gctcggggac aaagttggaa ataaaa                              336
```

<210> SEQ ID NO 273
<211> LENGTH: 348
<212> TYPE: DNA
<213> ORGANISM: Mus musculus
<220> FEATURE:
<221> NAME/KEY: misc_feature
<223> OTHER INFORMATION: Murine SC17.40 VH

<400> SEQUENCE: 273

```
caggtccaac tgcagcagcc tggggctgaa attgtgaggc ctggggcttc agtgaagctg     60
tcctgcaagg cttctggcta cacctttacc gactattgga tgaactgggt gaagcagagg    120
cctggacaag ccttgagtg gatcggaaca attgatcctt ctgatagtta tactcgttac    180
aatcaaaagt tcaagggcaa ggccacattg actgtagaca catccttcag ctcagcctac    240
atgcagctca gcagcctgac atctgaggac tctgcggtct atttctgtgc aagtggggga    300
cgggggtttg gttactgggg ccaagggact ccggtcactg tctctgta                 348
```

<210> SEQ ID NO 274
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.41 VL

<400> SEQUENCE: 274

```
caaattgttc tcacccagtc tccagcactc atgtctgcat ctccagggga gaaggtcacc     60
atgacctgca gtgccagctc aagtgtaagt tacatgtact ggtaccagca gaagccaaga    120
tcctccccca aaccctggat ttatctcaca tccaacctgg cttctggagt ccctactcgc    180
ttcagtggca gtgggtctgg gacctcttac tctctcacaa tcagcagcat ggggctgaa     240 gatgctgcca cttattactg ccagcagtgg aatactaacc cacccacgtt cggtgctggg    300
accaagctgg agctgaaa                                                  318
```

<210> SEQ ID NO 275
<211> LENGTH: 363
<212> TYPE: DNA
<213> ORGANISM: Mus musculus
<220> FEATURE:
<221> NAME/KEY: misc_feature
<223> OTHER INFORMATION: Murine SC17.41 VH

<400> SEQUENCE: 275

```
gacgtgaagc tcgtggagtc tggggaggc ttagtgaagc ttggagggtc cctgaaactc      60
tcctgtgcag cctctggatt cactttcagt agctatgcca tgtcttgggt tcgccagact    120
ccggagaaga ggctggagtg ggtcgcaacc attagtagtg gtggtggtaa cacctactat    180
ccagacagtg tgaagggtcg attcaccatc tccagagaca atgccaagaa caccctgtac    240
ctgcaaatga gcagtttgaa gtctgaggac acggccatgt attactgtgc aagaagggat    300
tactacggta ctagctacgt tatgtttgct tactggggcc aagggactct ggtcactgtc    360
tct                                                                  363
```

<210> SEQ ID NO 276
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.42 VL

<400> SEQUENCE: 276

```
gaaaatgttc tcacccagtc tccagcaatc atgtctgcat ctccagggga aaaggtcacc      60
atgacctgta gtgccagctc aagtgtaaat tacatgtact ggtaccagca gaagtcaagc     120
acctccccca aactctggat ttatgacaca tccaaactga cttctggagt cccaggtcgc     180
ttcagtggca gtgggtctgg aaactcttac tctctcacga tcagcaacat ggaggctgaa     240
gatgttgcca cttattactg ttttcagggg agtgggtacc cactcacgtt cggctcgggg     300
acaaaattgg aaataaaa                                                   318
```

<210> SEQ ID NO 277
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.42 VH

<400> SEQUENCE: 277

```
gacgtgaagc tggtggagtc ggggggaggc ttagtgaggc ctggagggtc cctgaaactc      60
tcctgtgcag cctctggatt cactttcagt agatatacca tgtcttgggt tcgccagaca     120
ccggagaaga ggctggagtg ggccgcaacc attaatagtg gtggtagtaa cacctactat     180
ccagacagtg tgaagggccg attcaccatc tccagagaca tgccaagaa cacccctgttc    240
ctgcaaatga gcagtctgaa gtctgaggac acagccatgt attactgtac aaatggtaac     300
cactggggcc aaggcaccac tctcacagtc tcctca                               336
```

<210> SEQ ID NO 278
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.45 VL

<400> SEQUENCE: 278

```
gaaaatgttc tcacccagtc tccagcaatc atgtctgcat ctccagggga aaaggtcacc      60
atgacctgta gtgccagctc aagtgtaaat tacatgtact ggtaccagca gaagtcaagc     120
acctccccca aactctggat ttatgacaca tccaaactga cttctggagt cccaggtcgc     180
ttcagtggca gtgggtctgg aaactcttac tctctcacga tcagcaacat ggaggctgaa     240
gatgttgcca cttattactg ttttcagggg agtgggtacc cactcacgtt cggctcgggg     300
acaaaattgg aaataaaa                                                   318
```

<210> SEQ ID NO 279
<211> LENGTH: 342
<212> TYPE: DNA
<213> ORGANISM: Mus musculus
<220> FEATURE:
<221> NAME/KEY: misc_feature
<223> OTHER INFORMATION: Murine SC17.45 VH

<400> SEQUENCE: 279

```
caggtgcaac tgcagcagcc tgggtctgtg ctggtgaggc ctggagattc agtgaagctg      60
tcgtgcaagg cttctggcta cacattcacc agctactgga tgcactgggt gaagcagagc     120
cctggacaag gccttgagtg gattggagag attcatcctc atagtggtag tactaactac     180
aatgagaagt tcaagggcaa ggccacactg actgtagaca catcctccag cacagcctac     240
gtggatctca gcagcctgac atctgaggac tctgcggtct attactgtgt aggtggtcac     300
tacgactact ggggccaagg caccactctc acagtctcct ca                        342

<210> SEQ ID NO 280
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.46 VL

<400> SEQUENCE: 280
agttttgtga tgacccaaac tcccaaattc ctgcttgtat cagcaggaga cagggttacc      60
ataacctgca aggccagtca gagtgtgaat aatgatgtag cttggtacca acagaagcca     120
gggcagtctc ctaaactgct gatatactat gcatccaatc gctacactgg agtccctgat     180
cgcttcactg gcagtggata tgggacggat ttcactttca ccatcagcac tgtgcaggct     240
gaagacctgg cagtttattt ctgtcagcag gattatagct ctcctcggac gttcggtgga     300
ggcaccaagc tggaaatcaa a                                                321

<210> SEQ ID NO 281
<211> LENGTH: 357
<212> TYPE: DNA
<213> ORGANISM: Mus musculus
<220> FEATURE:
<221> NAME/KEY: misc_feature
<223> OTHER INFORMATION: Murine SC17.46 VH

<400> SEQUENCE: 281
caggtccaac tgcagcagcc tggtgctgag cttgtgaagc ctggggcctc aatgaagctg      60
tcctgcaagg cttctggcta cactttcacc agctactgga taaactgggt gaagcagagg     120
cctggacaag gccttgagtg gattggaaat atttttcctg atactactac tactaactac     180
aatgagaagt tcaagagcaa ggccacactg actgtagaca catcctccag cacagcctat     240
atgcagctca gcagcctgac atctgacgac tctgcggtct attattgtgc aagggagtac     300
tacgatggta cctacgatgc tatggattac tggggtcaag aacctcagt caccgtc        357

<210> SEQ ID NO 282
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.47 VL

<400> SEQUENCE: 282
caaattgttc tcacccagtc tccagcaatc atgtctgcat ctccagggga gaaggtctcc      60
atgacctgca gtgccagctc aagtgtaagt tacatgcact ggtaccagca gaagtcaggc     120
acctccccca aaagatggat ttatgacaca tccaaactgg cttctggagt ccctgctcgc     180
ttcagtggca gtgggtctgg gtcctcttac tctctcacaa tcagcagcat ggaggctgaa     240
gatgctgcca cttattactg ccagcagtgg agtagcaccc ccccacgtt cggagggggg     300
```
accaagctgg aaataaaa 318

<210> SEQ ID NO 283
<211> LENGTH: 357
<212> TYPE: DNA
<213> ORGANISM: Mus musculus
<220> FEATURE:
<221> NAME/KEY: misc_feature
<223> OTHER INFORMATION: Murine SC17.47 VH

<400> SEQUENCE: 283
gaggtccagc tgcagcagtc tggacctgag ctggtgaagc ctggggcttc agtgaagata 60
tcctgcaagg cttctggtta tcattcact gactactaca tgcgctgggt gaagcaaagt 120
cctgaaaaga gccttgagtg gattggagag attaatccta gcactggtgg tactacctac 180
aaccagaact tcaaggccaa ggccacattg actgtagaca atcctccag cacagcctac 240 atgcagctca agagcctgac atctgaggac tctgcagtct attactgtgc aagaggggt 300 tacttcttgt actactttga ctactggggc caaggcacca ctctcacagt ctcctca 357

<210> SEQ ID NO 284
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.49 VL

<400> SEQUENCE: 284
gatgttgtga tgacccagac tccactcact ttgtcggtta ccattggaca accagcctcc 60
atctcttgca gtcaagtca gagcctctta aaagtgatg aaagacata tttgaattgg 120 ttgttacaga ggccaggcca gtctccaaag cgcctaatct atctggtgtc taaactggac 180
tctggagtcc ctgacaggtt cacgggcagt ggatcaggga cagatttcac actgaaaatc 240
agcagagtgg aggctgagga tttgggagtt tattattgct ggcaaggtat acaacatcct 300
cggacgttcg gtggaggcac caagctggaa atcaaa 336

<210> SEQ ID NO 285
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.49 VH

<400> SEQUENCE: 285
caggttcaac tgcagcagtc tggggctgag ctggtgaggc ctggggcttc agtgacgctg 60
tcctgcaagg cttcgggcta cacatttact gactatgaaa tgcactgggt gaagcagaca 120
cctgtgcatg gcctggaatg gattggaggt attgatcctg aaactggtgg tactgcctac 180
aatcagaagt tcaagggcaa ggccacactg actgcagaca atcctccag cacagcctac 240 atggagctcc gcagcctgac atctgaggac tctgccgtct acttctgtac aagatggttt 300
tcttactggg gccagggac tctggtcact gtctctgca 339

<210> SEQ ID NO 286
<211> LENGTH: 333
<212> TYPE: DNA
<213> ORGANISM: Mus musculus
<220> FEATURE:
<221> NAME/KEY: misc_feature
<223> OTHER INFORMATION: Murine SC17.50 VL

<400> SEQUENCE: 286

```
gacattgtgc tgacacagtc tcctgcttcc ttagctgcat ctctggggca gagggccacc      60
atctcatgca gggccagcca aagtgtcagt acatctagct atagttatat gcactggtac     120
caacagaaac caggacagcc acccaaactc ctcatcaagt atgcatccaa cctagaatct     180
ggggtccctg ccaggttcag tggcagtggg tctgggacag acttcaccct caacatccat     240
cctgtggagg aggaggatac tgcaacatat tactgtcagc acagttggga gattccgtgg     300
acgttcggtg gaggcaccaa gctggaaatc aaa                                  333
```

<210> SEQ ID NO 287
<211> LENGTH: 363
<212> TYPE: DNA
<213> ORGANISM: Mus musculus
<220> FEATURE:
<221> NAME/KEY: misc_feature
<223> OTHER INFORMATION: Murine SC17.50 VH

<400> SEQUENCE: 287

```
gaggtgcagc tggtggagtc tgggggaggc ttagtgaagc ctggagggtc cctgaaactc      60
tcctgtgcag cctctggatt cactttcagt gactatggaa tgcactgggt tcgtcaggct     120
ccagagaagg ggctggagtg ggttgcatac attagtagtg gcagtagaac catctactat     180
gcagacacag tgaagggccg attcaccatc tccagagaca tgccaagaa caccctgttc      240 ctgcaaatga ccagtctgag gtctgaggac acggccatgt attactgtgc aaggggtttac    300 tacggaagta cctacgggta tttcgatgtc tggggcacag gaccacggt caccgtctcc      360 tca                                                                   363
```

<210> SEQ ID NO 288
<211> LENGTH: 333
<212> TYPE: DNA
<213> ORGANISM: Mus musculus
<220> FEATURE:
<221> NAME/KEY: misc_feature
<223> OTHER INFORMATION: Murine SC17.53 VL

<400> SEQUENCE: 288

```
gacattgtgc tgacacagtc tcctgcttcc ttagctgcat ctctggggca gagggccacc      60
atctcatgca gggccagtca aagtgtcagt acatctagct atagttatat gcactggtac     120
caacagaagc caggacatcc acccaaactc ctcatcaggt atgcatccaa cctagagtct     180
ggggtccctg ccaggttcag tggcagtggg tctgggacag acttcaccct caacatccat     240
cctgtggagg aggaggatac tgcaacatat tactgtcagc acagttggga gattccgtac     300
acgttcggag gggggaccaa gctggaaata aaa                                  333
```

<210> SEQ ID NO 289
<211> LENGTH: 357
<212> TYPE: DNA
<213> ORGANISM: Mus musculus
<220> FEATURE:
<221> NAME/KEY: misc_feature
<223> OTHER INFORMATION: Murine SC17.53 VH

<400> SEQUENCE: 289

```
gaggtccagc ttcagcagtc aggacctgag ctggtgaaac ctggggcctc agtgaagata      60
tcctgcaagg cttctggata cacattcact gactacaaca tgcactgggt gaagcagagc     120
catggaaagc gccttgagtg gattggatat attcatcctt acaatggtgg tagtggctac     180
```

```
aaccagaagt tcaagaggaa ggccacattg actgtagaca attcctccaa cacaacctac    240
atggagctcc gcagcctgac atctgaggac tctgcagtct attactgtgc aagatcttat    300
gattacgaca cctggtttgg ttactggggc caagggactc tggtcactgt ccgtgca       357
```

<210> SEQ ID NO 290
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.54 VL

<400> SEQUENCE: 290

```
gatgttgtgc tgacccagac tccactcact ttgtcggtta ccattggaca accagcctcc     60
atctcttgca agtcaagtca gagcctctta tatagtgatg gaaagacata tttgaattgg    120
ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggactt tattattgct ggcaaggtac acattttccg    300
tggacgttcg gtggaggcac caagctggaa atcaaa                              336
```

<210> SEQ ID NO 291
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.54 VH

<400> SEQUENCE: 291

```
gaagtgaaac ttgaggagtc tggaggaggc ttggtgcaac ctggaggatc catgaaactc     60
tcctgtgttg cctctggatt cactttcagt aactactgga taaactgggt ccgccagtct    120
ccagagaagg ggcttgagtg ggttgctgaa atcagaatga atctaataa ttatgcaaca     180 cattatgcgg agtctgtgaa agggaggttc accatctcaa gagatgattc caaaagttgt    240
gtctacctgc aaatgaacaa cttaagacct gaagacactg gcatttatta ctgtaccagg    300
gggggctact ggggccaagg caccactctc accgtctcc                           339
```

<210> SEQ ID NO 292
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.56 VL

<400> SEQUENCE: 292

```
gacattgtga tgtcacagtc tccatcctcc ctagctgtgt cagttggaga gaaggttact     60
atgagctgca gtccagtca gagccttta tatagtagca tcaaaagaa ctacttggcc       120 tggtaccagc agaaaccagg gcagtctcct aaactgctga tttactgggc atccactagg    180
gaatctgggg tccctgatcg cttcacaggc agtggatctg ggacagattt cactctcacc    240
atcagcagtg tgaaggctga agacctggca gtttatttct gtcagcaata ttataactat    300
ccgtacacgt tcggaggggg gaccaagctg gaaataaaa                           339
```

<210> SEQ ID NO 293
<211> LENGTH: 348

```
<212> TYPE: DNA
<213> ORGANISM: Mus musculus
<220> FEATURE:
<221> NAME/KEY: misc_feature
<223> OTHER INFORMATION: Murine SC17.56 VH

<400> SEQUENCE: 293
cagatccagt tggtgcagtc tggacctgaa ctgaagaagc tggagagac agtcaagatc      60
tcctgcaagg cttctgggta taccttcaca aactatggaa tgaactgggt gaagcaggct     120
ccaggaaagg gtttaaagtg gatggcctgg ataaacacct acactggaga gccaacatat    180
gctgatgact tcaagggacg gtttgccttc tctttggaaa cctctgccag cactgcctct    240
ttgcagatca tcaacctcaa aaatgaggac acggctacat atttctgtgc aaggatcggc    300
gatagtagtc cctctgacta ctggggccag ggcaccactc tcacagtc                 348

<210> SEQ ID NO 294
<211> LENGTH: 324
<212> TYPE: DNA
<213> ORGANISM: Mus musculus
<220> FEATURE:
<221> NAME/KEY: misc_feature
<223> OTHER INFORMATION: Murine SC17.57 VL

<400> SEQUENCE: 294
caaattgttc tcacccagtc tccagcaatc atgtctgcat ctctagggga acgggtcacc     60
atgacctgca ctgccagctc aagtgtaagt tccagttact tgcactggta ccagcagaag    120
ccaggatcct cccccaaact ctggatttat agcacatcca acctggcttc tggagtccca    180
cctcgcttca gtggcagtgg gtctgggacc tcttactctc tcacaatcag cagcatggag    240
gctgaagatg ctgccactta ttactgccac cagtatcatc gttccccacc gacgttcggt    300
ggaggcacca agctggaaat caaa                                           324

<210> SEQ ID NO 295
<211> LENGTH: 363
<212> TYPE: DNA
<213> ORGANISM: Mus musculus
<220> FEATURE:
<221> NAME/KEY: misc_feature
<223> OTHER INFORMATION: Murine SC17.57 VH

<400> SEQUENCE: 295
cagatccagt tggtgcagtc tggacctgaa ctgaagaagc tggagagac agtcaagatc      60
tcctgcaagg cttctgatta taccttcaca gacttttcaa tacactgggt gaggcagtct    120
ccaggaaagg gtttaaagtg gatgggctgg ataaacactg agactggtga gccaacagtt    180
gcagaagact tcaagggacg gtttgccttc tctttggaga cctctgccag cactgccttt    240
ttgcagatct acaacctcaa aaatgaggac tcggcaacat atttctgtgc taggggcgt     300
tactacggcc atgactatgc tatggactac tggggtcaag gaacctcagt caccgtctcc    360
tca                                                                  363

<210> SEQ ID NO 296
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.59 VL

<400> SEQUENCE: 296
```

```
gacatccaga tgactcagtc tccagcctcc ctatctgcat ctgtgggaga aactgtcacc    60
atcacatgtc gagcaagtgg gaatcttcac aattatttag catggtatca gcagaaacag   120
ggaaaatctc ctcagctcct ggtctataat gcaaaaacct agcagatggg tgtgccatca   180
aggttcagtg gcagtggatc aggaacacaa tattctctca agatcaacag cctgcagcct   240
gaagattttg ggacttattt ctgtcaacat ttttggagta ttcctcccac gttcgggggg   300
gggaccaagc tggaaataaa a                                              321
```

<210> SEQ ID NO 297
<211> LENGTH: 357
<212> TYPE: DNA
<213> ORGANISM: Mus musculus
<220> FEATURE:
<221> NAME/KEY: misc_feature
<223> OTHER INFORMATION: Murine SC17.59 VH

<400> SEQUENCE: 297

```
gaagtgaagc ttgaggagtc tggaggaggc ttggtgcaac ctgggggatc catgaaactc    60
tcctgtgttg cctctggatt cactttcagt aactattgga tgaactgggt ccgccagtct   120
ccagagaagg ggcttgagtg ggttgctgaa attagattga aatctaataa ttatgcaaca   180
cattatgcgg agtctgtgaa agggaggttc accatctcaa gagatgattc aaaagtagt   240 gtctacctgc aaatgaacaa cttaagagct gaagacactg gcatttatta ctgtaccaga   300
ctctgggact ttgctatgga ctactgggt caaggaacct cagtcaccgt ctcctca     357
```

<210> SEQ ID NO 298
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.61 VL

<400> SEQUENCE: 298

```
caaattgttc tcacccagtc tccagcaatc atgtctgcat ctccagggga aaggtcacc    60 atatcctgca gtgccagctc aagtgtaagt tacatatact ggtaccagca gaagccagga   120
tcctccccca aaccctggat ttatcgcaca tccaacctgg cttctggagt ccctgctcgc   180
ttcagtggca gtgggtctgg gacctcttac tctctcacaa tcagcagcat ggaggctgaa   240
gatgctgcca cttattactg ccagcagtat catagttacc cgtggacgtt cggtggaggc   300
accaagctgg aaatcaaa                                                  318
```

<210> SEQ ID NO 299
<211> LENGTH: 375
<212> TYPE: DNA
<213> ORGANISM: Mus musculus
<220> FEATURE:
<221> NAME/KEY: misc_feature
<223> OTHER INFORMATION: Murine SC17.61 VH

<400> SEQUENCE: 299

```
caggttactc tgaaagagtc tggccctggg atattgcagc cctcccagac cctcagtctg    60
acttgttctt tctctgggtt ttcactgagc acttttggta tgggtgtagg ctggattcgt   120
cagccttcag ggaagggtct ggagtggctg gcacagattt ggtgggatga ttataagtac   180
tataacccag ccctgaagag tcggctcaca atctccaagg atacctccaa aaaccaggta   240
ttcctcaaga tcgccaatgt ggacactgca gatactgcca catactactg tgctcgaatc   300
```

```
ggatattact ccggtagtag ccgttgctgg tacttcgatg tctggggcac agggagcacg      360
gtcaccgtct cctca                                                       375

<210> SEQ ID NO 300
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.63 VL

<400> SEQUENCE: 300
agtattgtga tgacccagac tcccaaattc ctgcttgtat cagcaggaga cagggttgcc       60
ataacctgca aggccagtca gagtgtgagt aatgatgtag cttggtacca acagaagcca      120
gggcagtctc ctacactgct gatatcctat gcatccaatc gctacactgg agtccctgat      180
cgcttcactg gcagtggata tgggacggat ttcactttca ccatcagcac tgtgcaggct      240
gaagacctgg cagtttattt ctgtcagcag ggttatagct ctccgttcac gttcggaggg      300
gggaccaagc tggaaataaa a                                                321

<210> SEQ ID NO 301
<211> LENGTH: 348
<212> TYPE: DNA
<213> ORGANISM: Mus musculus
<220> FEATURE:
<221> NAME/KEY: misc_feature
<223> OTHER INFORMATION: Murine SC17.63 VH

<400> SEQUENCE: 301
caggttcagc tgcaacagtc tgacgctgag ttggtgaaac ctggggcttc agtgaagata       60
tcctgcaagg ctgctggcta caccttcact gaccttacta ttcactgggt gaaacagagg      120
cctgaacagg gcctggagtg gattggatat atttatcctg agatagtaa tactaagtac      180 aatgagaagt tcaagggcaa ggccacattg actgcagata atcctccag cactgcctat      240 atgcagctca acagcctgac atctgaggat tctgtagtgt atttctgtgc aagaatgatt      300
actccttact actttgacta ctggggccaa ggcaccactc tcacagtc                   348

<210> SEQ ID NO 302
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.71 VL

<400> SEQUENCE: 302
gacatccaga tgactcagtc tccagcctcc ctatctgcct ctgtgggaga aactgtcacc       60
atcgcatgtc gagcaagtgg gaatattcac aattatttaa catggtatca gcagagacag      120
ggaaaatctc ctcagctcct ggtctataat gcaaaaacct tagcagttgg tgtgccatca      180
aggttcagtg gcagtggctc aggaacacaa tattctctca agatcaacag cctgcagcct      240
gaagattttg ggagttatta ctgtcaacat ttttggaata ctcctccgac gttcggtgga      300
ggcaccaagc tggaaatcaa a                                                321

<210> SEQ ID NO 303
<211> LENGTH: 357
<212> TYPE: DNA
<213> ORGANISM: Mus musculus
<220> FEATURE:
```

```
<221> NAME/KEY: misc_feature
<223> OTHER INFORMATION: Murine SC17.71 VH

<400> SEQUENCE: 303
gaagtgaagc ttgaggagtc tggaggaggc ttggtgcaac ctggaggatc catgaaactc      60
tcctgtgttg cctctggaat catttttcagt aactactgga tgaattgggt ccgccagtct    120
ccagagaagg ggcttgagtg ggttgctgaa attagattga aatctaataa ttattcaaca     180
cattatgcgg agtctgtgaa agggaggttc accatctcaa gagatgattc caaaagtagt    240
gtctacctgc aaatgaacaa cttaagagct gaagacactg gcatttatta ctgtaccagg     300
cactattact atgctatgga ctactggggt caaggaacct cagtcaccgt ctcctca        357

<210> SEQ ID NO 304
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.72 VL

<400> SEQUENCE: 304
gatatccaga tgacacagac tacatcctcc ctgtctgcct ctctgggaga cagagtcacc      60
atcagttgca gtgcaagtca gggcattagc aattatttaa actggtatca gcagaaacca    120
gatggaactg ttaaactcct gatctattac acatcaagtt tacactcagg agtcccatca    180
aagttcagtg gcagtgggtc tgggacagat tattctctca ccatcagcaa cctggaacct    240
gaagatatcg ccacttacta ttgtcagcag tatagtaagc ttccgtacac gttcggaggg    300
gggaccaagc tggaaataaa a                                               321

<210> SEQ ID NO 305
<211> LENGTH: 357
<212> TYPE: DNA
<213> ORGANISM: Mus musculus
<220> FEATURE:
<221> NAME/KEY: misc_feature
<223> OTHER INFORMATION: Murine SC17.72 VH

<400> SEQUENCE: 305
gaggtgcagc tggtggagtc tgggggaggc ttagtgaagc ctggagggtc cctgaaactc      60
tcctgtgcag cctctggatt cactttcagt agctatggca tgtcttgggt tcgccagact    120
ccggagaaga ggctggagtg ggtcgcagcc attaatagta atggtggtag cacctactat    180
ccagacactg tgaagggccg actcaccatc tccagagaca atgcaagaa caccctgtac     240 ctgcaaatga gcagtctgag gtctgaggac acagccttgt attactgtgt aagggatgat    300
ggttactacg ttttctttgc ttactggggc caagggactc tggtcactgt ctctgca        357

<210> SEQ ID NO 306
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.74 VL

<400> SEQUENCE: 306
gacatccaga tgacacaatc ttcatcctac ttgtctgtat ctctaggagg cagagtcacc      60
attacttgca aggcaagtga ccacattaat aattggttag cctggtatca gcagaaacca    120
ggaaatgctc ctaggctctt aatatctggt gcaaccagtt tggaaactgg ggttccttca    180
```

| | |
|---|---|
| agattcagtg gcagtggatc tggaaaggat tacactctca gcattaccag tcttcagact | 240 |
| gaagatgttg ctacttatta ctgtcaacag tattggagta ctcctcccac gttcggtgct | 300 |
| gggaccaagc tggagctgaa a | 321 |

<210> SEQ ID NO 307
<211> LENGTH: 357
<212> TYPE: DNA
<213> ORGANISM: Mus musculus
<220> FEATURE:
<221> NAME/KEY: misc_feature
<223> OTHER INFORMATION: Murine SC17.74 VH

<400> SEQUENCE: 307

| | |
|---|---|
| caggtgcagc tgaagcagtc aggacctggc ctagtggcgc cctcacagag cctgtccatc | 60 |
| acatgcactg tctctggttt ctcattaacc agctatggtg tagactgggt tcgccagtct | 120 |
| ccaggaaagg gtctggagtg gctgggagtg atatggggtg gtggaagcac aaattataat | 180 |
| tcagctctca aatccagact gagcatcacc aaggacaact ccaagagcca gttttctta | 240 |
| aaaatgaaca gtctgcaaac tgatgacaca gccatgtact actgtgccag tggagactac | 300 |
| gatggtagcc tctggtttgc ttactggggc caagggactc tggtcactgt ctctgca | 357 |

<210> SEQ ID NO 308
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.76 VL

<400> SEQUENCE: 308

| | |
|---|---|
| gatattgtga taacccagga tgaactctcc aatcctgtca cttctggaga atcagtttcc | 60 |
| atctcctgca ggtctagtaa gagtctccta tataaggatg gaagacata cttgaattgg | 120 |
| tttctgcaga gaccaggaca atctcctcag ctcctgatct atttgatgtc cacccgtgca | 180 |
| tcaggagtct cagaccggtt tagtggcagt gggtcaggaa cagatttcac cctggaaatc | 240 |
| agtagagtga aggctgagga tgtgggtgtg tattactgtc aacaacttgt agagtatcct | 300 |
| cggacgttcg gtggaggcac caagctggaa atcaaa | 336 |

<210> SEQ ID NO 309
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.76 VH

<400> SEQUENCE: 309

| | |
|---|---|
| gaggtgcagc tggtggagtc tgggggagac ttagtgaagc ctggagggtc cctgaaactc | 60 |
| tcctgtgtag cctctggatt cactttcagt agctatggca tgtcttgggt tcgccagact | 120 |
| ccagacaaga ggctggagtg ggtcgcaacc attagtagtg gtggtacttt cacctactat | 180 |
| ccagacagtg tgaaggggcg attcaccgtc tccagagaca atgccaagaa caccctgtac | 240 |
| ctgcaaatga gcagtctgaa gtctgaggac acagccatgt attactgttc aagacatggg | 300 |
| tggggctggg gccaagggac tctggtcact gtctctgca | 339 |

<210> SEQ ID NO 310
<211> LENGTH: 321

```
<212> TYPE: DNA
<213> ORGANISM: Mus musculus
<220> FEATURE:
<221> NAME/KEY: misc_feature
<223> OTHER INFORMATION: Murine SC17.77 VL

<400> SEQUENCE: 310
gacatccaga tgactcagtc tccagcctcc ctatctgcat ctgtgggaga aactgtcacc      60
atcacatgtc gagcaagtgg gaatattcac aattatttag catggtatca gcagaaacag     120
ggaaaatctc ctcagctcct ggtctataat gcaaaagcct tagcagatgg tgtgccatca     180
aggttcagtg gcagtggatc aggaacacaa tattctctca agatcaacag cctgcagcct     240
gaagattttg ggagttatta ctgtcaacat ttttggagta ttcctccgac gttcggtgga     300
ggcaccaagc tggaaatcaa a                                               321

<210> SEQ ID NO 311
<211> LENGTH: 357
<212> TYPE: DNA
<213> ORGANISM: Mus musculus
<220> FEATURE:
<221> NAME/KEY: misc_feature
<223> OTHER INFORMATION: Murine SC17.77 VH

<400> SEQUENCE: 311
gaagtgaagc ttgaggagtc tggaggaggc ttggtgcaac ctggaggatc catgaaactc      60
tcctgtgttg cctctggatt cactttcagt aactactgga tgaactgggt ccgccagtct     120
ccagagaagg ggcttgagtg ggttgctgaa attagattga atctaataa ttatgcaaca      180 cattatgcgg agtctgtgaa agggaggttc accatctcaa gagatgattc caaaagtagt     240
gtctacctgc aaatgaacaa cttaagagtt gaagacactg ccatttatta ctgtaccagg     300
cactatgact atgctatgga ctactgggt caaggaacct cagtcaccgt ctcctca        357

<210> SEQ ID NO 312
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.79 VL

<400> SEQUENCE: 312
gacatccaga tgactcagtc tccagcctcc ctatctgcat ctgtgggaga aactgtcacc      60
atcacatgtc gagcaagtgg gaatattcac aattatttag catggtatca gcagaaacag     120
ggaaaatctc ctcagctcct ggtctataat gcaaaaacct tagcagatgg tgtgccatca     180
aggttcagtg gcagtggatc aggaacacaa tattctctca ggatcaacag cctgcagcct     240
gaagattttg ggagttatta ctgtcaacat ttttggagta ctcctccgac gttcggtgga     300
ggcaccaagg tggaaatcaa a                                               321

<210> SEQ ID NO 313
<211> LENGTH: 357
<212> TYPE: DNA
<213> ORGANISM: Mus musculus
<220> FEATURE:
<221> NAME/KEY: misc_feature
<223> OTHER INFORMATION: Murine SC17.79 VH

<400> SEQUENCE: 313
gaagtgaagc ttgaggagtc tggaggaggc ttggtacaac ctggaggatc catgaaactc      60
```

```
tcctgtgttg cctctggatt cactttcagt gactactgga tgaactgggt ccgccagtct    120
ccagagaagg ggcttgagtt ggttgctgaa attagattga tatctaataa ttatgcaaca    180
cattatgcgg agtctgtgaa agggaggttc accatctcaa gagatgattc caaaagtagt    240
gtctacctgc aaatgaacaa cttaagagct gaagacactg gcatttatta ctgtaccagg    300
cactattact atgctttgga ctactggggt caaggaacct cagtcaccgt ctcctca       357
```

<210> SEQ ID NO 314
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.81 VL

<400> SEQUENCE: 314

```
gacattgtga tgtcacagtc tccatcctcc ctaactgtgt cagttggaga aaggttact     60 ttgagctgca agtccagtca gagccttta tatagtacca atcaaaagat ctacttggcc    120
tggtaccagc agaaaccagg gcagtctcct aaactgctga tttactgggc atccactagg    180
gaatctgggg tccctgatcg cttcacaggc agtggatctg gacagattt cactctcgcc    240 atcagcaatg tgaaggctga agacctggca gtttattact gtcagcaata ttatagctat    300
ccgtacacgt tcggagggg gaccaagctg gaaataaaa                            339
```

<210> SEQ ID NO 315
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.81 VH

<400> SEQUENCE: 315

```
gaggttcagc tgcagcagtc tggggcagag cttgtgaagc caggggcctc agtcaagttg    60
tcctgcacag cttctggctt caacattaat gacacctatt accattggtt gaagcagagg   120
cctgaacagg gcctggagtg gattggaagg attgatcctg cgaatgttaa tactaaaatat  180 gaccccgaagt tccagggcaa ggccacttta acagcagaca catcctccaa cacagcctac   240
ctgcagctca gcagcctgac atctgaggac actgccgtct attactgtgg tagggggaat   300
gcttactggg gccaagggac tctggtcact gtctctgca                            339
```

<210> SEQ ID NO 316
<211> LENGTH: 312
<212> TYPE: DNA
<213> ORGANISM: Mus musculus
<220> FEATURE:
<221> NAME/KEY: misc_feature
<223> OTHER INFORMATION: Murine SC17.82 VL

<400> SEQUENCE: 316

```
caaattgttc tcacccagtc tccagcaatc atgtctgcat ctctagggga ggagatcacc    60
ctaacctgca gtgccagttc gagtgtaagt tacatgcact ggtaccagca gaagtcaggc   120
acttctccca aactcttgat ttatagcaca tccaacctgg cttctggagt ccttctcgc    180 ttcagtggca gtgggtctgg gaccttttat tctctcacaa tcagcagtgt ggaggctgaa   240
gatgctgccg attattactg ccatcagtgg agtagtttca cgttcggctc ggggacaaag   300
ttggaaataa aa                                                        312
```

<210> SEQ ID NO 317
<211> LENGTH: 360
<212> TYPE: DNA
<213> ORGANISM: Mus musculus
<220> FEATURE:
<221> NAME/KEY: misc_feature
<223> OTHER INFORMATION: Murine SC17.82 VH

<400> SEQUENCE: 317

```
gaggtccagc tgcaacagtc tggacctgag ctggtgaagc ctggggcttc agtgaagatg      60
tcctgtaagg cttctggata cacattcact gactcctaca tgaactgggt gaagcagagt     120
catggaaaga gccttgagtg gattggacgt gttaatccta acaatggtgg tgctagctac     180
aaccacaagt tcaagggcaa ggccacattg acagtagaca atccctcag cacagcctac      240
atgcgcctca acagcctgac atctgaggac tctgcggtct attactgttc aagatctgga     300
gacctttatt actatgctat ggactactgg ggtcaaggaa cctcagtcac cgtctcctca     360
```

<210> SEQ ID NO 318
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.84 VL

<400> SEQUENCE: 318

```
caaattgttc tcacccagtc tccagcaatc atgtctgcat ctccagggga aaggtcacc      60
atgacctgca gtgccagctc aagtataagt tacatgcact ggtaccagca gaagtcaggc    120
acctccccca aaagatggat ttatgacaca tccaaactgg cttctggagt ccctgctcgc    180
ttcagtggca gtgggtctgg gacctcttac tctctcacaa tcagcaacat ggaggctgaa    240
gatgctgcca cttattactg ccagcagtgg agtagtaccc cacccacgtt cggaggggg    300
accaagctgg aaataaaa                                                  318
```

<210> SEQ ID NO 319
<211> LENGTH: 351
<212> TYPE: DNA
<213> ORGANISM: Mus musculus
<220> FEATURE:
<221> NAME/KEY: misc_feature
<223> OTHER INFORMATION: Murine SC17.84 VH

<400> SEQUENCE: 319

```
gaggtccagt tgcaacagtc tggacctgag ctaatgaagc ctggggcttc agtgaagatg      60
tcctgcaagg cttctggata tatttact gactacaaca tgcactgggt gaagcagaac       120
caaggaaaga gcctagagtg gataggagaa gttaatccta acactggtgg tattggctac    180
aatcagaaat tcaaaggcaa ggccacattg actgtagaca gtcctccag cacagcctac     240
atggacctcc gcagcctgac atctgaggac tctgcagtct attactgtgc aagagatggc    300
aattattgct ttgactactg ggccaaggc accactctca cagtctcctc a              351
```

<210> SEQ ID NO 320
<211> LENGTH: 333
<212> TYPE: DNA
<213> ORGANISM: Mus musculus
<220> FEATURE:
<221> NAME/KEY: misc_feature
<223> OTHER INFORMATION: Murine SC17.85 VL

<400> SEQUENCE: 320

```
gatattgtga tgacgcaggc tgcattctcc aatccagtca ctcttggaac atcagcttcc      60
atctcctgca ggtctagtaa gagtctccta catagtaatg gcatcactta tttgtattgg     120
tatctgcaga agccaggcca gtctcctcag ctcctgattt atcagatgtc caaccttgcc     180
tcaggagtcc cagagaggtt cagtagcagt gggtcaggat ctgatttcac actgagaatc     240
agcagagtgg aggctgagga tgtgggtgtt tattactgtg ctcaaaatct agaacatccg     300
acgttcggtg gaggcaccaa gctggaaatc aaa                                  333
```

<210> SEQ ID NO 321
<211> LENGTH: 360
<212> TYPE: DNA
<213> ORGANISM: Mus musculus
<220> FEATURE:
<221> NAME/KEY: misc_feature
<223> OTHER INFORMATION: Murine SC17.85 VH

<400> SEQUENCE: 321

```
gaggtgcagc tggtggagtc tgggggagac ttagtgaagc ctggagggtc cctgaaactc      60
tcctgtgcag cctctggatt cactttcagt aactatggca tgtcttgggt tcgccagact     120
ccagacaaga ggctggagtg gtcgcaacc attagtactg gtggtactta cacctactat     180
ccagacagtg tgaaggggcg attcaccatc tccagagaca atgccaagaa caccctgtac     240
ctgcaaatga gcagtctgaa gtctgaggac acagccatgt attactgtgt aggacagtcc     300
tatagtgact acgtctcgtt tgcttattgg ggccaaggga ctcaggtcac tgtctctgca     360
```

<210> SEQ ID NO 322
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.87 VL

<400> SEQUENCE: 322

```
gatgttgtga tgacccaaac tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct ccaaagtttc caaccgattt     180
tctggggtcc cagacaggtt cagtggcagt ggatcaggga cagatttcac tctcaagatc     240
agcagagtgg aggctgaaga tctgggagtt tatttctgct ctcaaagtac acatgttcct     300
cccatgttcg gaggggggac caggctggaa ataaaa                               336
```

<210> SEQ ID NO 323
<211> LENGTH: 345
<212> TYPE: DNA
<213> ORGANISM: Mus musculus
<220> FEATURE:
<221> NAME/KEY: misc_feature
<223> OTHER INFORMATION: Murine SC17.87 VH

<400> SEQUENCE: 323

```
gaggttcagc tgcagcagtc tggggctgag cttctgaagc caggggcctc agtcaagttg      60
tcctgcacag cttctggcct caacattaaa gactactata tacactgggt gtaccagagg     120
cctgaacagg gcctggagtg gattggaagg attgatcctg agagtgataa tactttatat     180
gacccgaagt tccagggcaa ggccagtata acagcagaca catcctccaa cacagcctac     240
ctgcagctca gcagcctgac atctgaggac actgccgtct attactgtac tactaatacc     300
```

```
cctttttgctt actggggcca agggactctg gtcactgtct ctaca            345
```

<210> SEQ ID NO 324
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.89 VL

<400> SEQUENCE: 324

```
gatgttttga tgacccaaac tccactctcc ctgcctgtca gtcttggaga tcaagcctcc   60
atctcttgca gatctagtca gagcattgta catagtaatg gaaacaccta tttagaatgg  120
tacctgcaga aaccaggcca gtctccaaag ctcctgatct acaaagtttc caaccgattt  180
tctggggtcc cagacaggtt cagtggcagt ggatcaggga cagatttcac actcaagatc  240
agtagagtgg aggctgagga tctgggagtt tattattgct ttcaaggttc acatgttcca  300
ttcacgttcg gctcggggac aaagttggaa ataaaa                            336
```

<210> SEQ ID NO 325
<211> LENGTH: 360
<212> TYPE: DNA
<213> ORGANISM: Mus musculus
<220> FEATURE:
<221> NAME/KEY: misc_feature
<223> OTHER INFORMATION: Murine SC17.89 VH

<400> SEQUENCE: 325

```
caggtccagt tgcaacagtc tggagctgaa ctggtaaggc ctgggacttc agtgaaggtg   60
tcctgcaaga cttctggata cgccttcact aattacttga tagagtgggt aaagcagagg  120
cctggacagg gccttgagtg gattggggtg attaatcctg aagtggtgg tactaactac   180
aatgagaagt tcaaggtcaa ggcaacactg actgcagaca atcctccag cactgcctac   240
atgcagctca ccagcctgac atctgatgac tctgcggtct atttctgtac aagaagggat  300
ggttacttct ttccctggtt tgcttactgg ggccaaggga ctctggtcac tgtctctgca  360
```

<210> SEQ ID NO 326
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.90 VL

<400> SEQUENCE: 326

```
gacattgtga tgtcacagtc tccatcctcc ctagctgtgt cagttggaga gaaggttact   60
atgagctgca gtccagtca gagccttta tatagtagca tcaaaagaa ctacttggcc   120
tggtaccagc agaaaccagg gcagtctcct aaactgctga tttactgggc atccactagg  180
aaatctgggg tccctgatcg cttcacaggc agtggatctg ggacagattt cactctcacc  240
atcagcagtg tgaaggctga agacctggca gtttattact gtcatcaata ttatagctat  300
ccgctcacgt tcgctgctgg gaccaagctg gagctgaaa                         339
```

<210> SEQ ID NO 327
<211> LENGTH: 345
<212> TYPE: DNA
<213> ORGANISM: Mus musculus
<220> FEATURE:
<221> NAME/KEY: misc_feature
<223> OTHER INFORMATION: Murine SC17.90 VH

<400> SEQUENCE: 327

| caggtgcaac tgcagcagcc tgggtctgtg ctggtgaggc tggagcttc agtgaagctg | 60 |
| tcctgcaagg cttctggcta cacattcacc agctactgga tgcactgggt gaagcagagg | 120 |
| cctggacaag gccttgagtg gattggagag attcatccta ataatggtag tactaactac | 180 |
| aatgagaagt tcaagggcaa ggccacactg actgtagaca catcctccag cacagcctac | 240 |
| gtggatctca gcagcctgac atctgaggac tctgcggtct attactgtgc aagatggact | 300 |
| ttgtttactt actggggcca aggactctg gtcactgtct ctgca | 345 |

<210> SEQ ID NO 328
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.91 VL

<400> SEQUENCE: 328

| gatgttgtga tgacccaaac tccactctcc ctgcctgtca gtcttggaga tcaagcctcc | 60 |
| atctcttgca gatctagtca gagccttgta cacagtaatg gaaacaccta tttactttgg | 120 |
| tacctgcaga agccaggcca gtctccaaag ctcctgatct acaaagtttc caaccgattt | 180 |
| tctggggtcc cagacaggtt cagtggcagt ggatcaggga cagatttcgc actcaagatc | 240 |
| agcagagtgg aggctgagga tctgggagtt tatttctgct ctcaaagtac acatgttccg | 300 |
| tggacgttcg gtggaggcac caagctggaa atcaaa | 336 |

<210> SEQ ID NO 329
<211> LENGTH: 351
<212> TYPE: DNA
<213> ORGANISM: Mus musculus
<220> FEATURE:
<221> NAME/KEY: misc_feature
<223> OTHER INFORMATION: Murine SC17.91 VH

<400> SEQUENCE: 329

| gaggtgcagc tggtggagtc tggggggaggc ttagtgaagc ctggagggtc ccggaaactc | 60 |
| tcctgtgcag cctctggatt cactttcagt gactatggaa tgcactgggt ccgtcaggct | 120 |
| ccagagaagg ggctggagtg ggttgcatac attagtcgtg gcagtagtac catccactat | 180 |
| gcagacacag tgaagggccg attcaccatc tccagagaca atgccaagaa caccctgttc | 240 |
| ctgcaaatga ccagtctaag gtctgaggac acagccatgt attactgtgc aaggcctttc | 300 |
| aactggtact cgatgtctg gggcgcaggg acaacggtca ccgtctcctc a | 351 |

<210> SEQ ID NO 330
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.93 VL

<400> SEQUENCE: 330

| gacattgtga tgtcacagtc tccatcctcc ctagctgtgt cagttggaga gaaggttact | 60 |
| atgacctgca gtccagtca gagccttta tatagtagca atcaaaagaa ctacttggcc | 120 |
| tggtaccagc agaaaccagg gcagtctcct aaactactaa tttactgggc atccactagg | 180 |

```
gaatctgggg tccctgatcg cttcataggc agtggctctg ggacagattt cactctcacc    240
atcagcagtg tgaaggctga agacctggca atttattact gtcagcaata ttatcgctat    300
ccgctcacgt tcggtgctgg gaccaaactg gagctgaaa                            339
```

<210> SEQ ID NO 331
<211> LENGTH: 363
<212> TYPE: DNA
<213> ORGANISM: Mus musculus
<220> FEATURE:
<221> NAME/KEY: misc_feature
<223> OTHER INFORMATION: Murine SC17.93 VH

<400> SEQUENCE: 331

```
caggtccaac tgcagcagcc tggggctgag cttgtgaagc ctggggcttc agtgatgctg     60
tcctgcaagg cttctggcta caccttcacc agctactggg tacactgggt gaagcagagg    120
cctggacaag ccttgagtg gattggagtg attaatccta gaaacggtcg taacaattac    180
aatgagaagt tcaagaccaa ggccacactg actgtagaca atcatccag cacagcctac    240 atgcaactca gcagcccgac atctgaggac tctgcggtct attactgtgc acgagaggat    300
tacgacgggg gggactatgc tatggactac tggggtcaag aacctcagt caccgtctcc    360 tca                                                                   363
```

<210> SEQ ID NO 332
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.95 VL

<400> SEQUENCE: 332

```
gatatccaga tgacacagac tacatcctcc ctgtcggcct ctctgggaga cagggtcacc     60
atcagttgca gtgcaagtca gggcattaac aattatttaa actggtatca gcagaaacca    120
gatggaactg ttacactcct gatctattac acatcaagtt tacactcagg agtcccatcc    180
aggttcagtg gcagtgggtc tgggacagat tattctctca ccatcagcaa cctggaacct    240
gaagatattg ccacttacta ttgtcagcag tatagtaagc ttccgtggac gttcggtgga    300
ggcaccaagc tggaaatcaa a                                               321
```

<210> SEQ ID NO 333
<211> LENGTH: 363
<212> TYPE: DNA
<213> ORGANISM: Mus musculus
<220> FEATURE:
<221> NAME/KEY: misc_feature
<223> OTHER INFORMATION: Murine SC17.95 VH

<400> SEQUENCE: 333

```
gaggtcgagc tgcaacagtc tggacctgag ctggtgaagc cgggggcttc agtgaagata    60
tcctgcaaga cttccggaaa cacatacact gaatacacca tgcagtgggt gaagctgagc    120
catggaaaga gccttgagtg gattggaggt attaatccta acaatggtat tactagttac    180
aaccagaagt tcaagggcaa ggccacattg actgtagaca gtcctccag cacagcctac    240 atggagctcc gcagcctgaa atctgaggat tctgcagtct attactgtgc aagagcggga    300
cttggtaact acgtttgggc tatggactac tggggtcaag agcctcagt caccgtctcc    360 tca                                                                   363
```

<210> SEQ ID NO 334
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.97 VL

<400> SEQUENCE: 334

```
gatgttgtga tgacccaaac tccactctcc ctgcctgtca gtcttggaga tcaagcctcc      60
atctcttgca gatctagtca gagccttgta cacaataatg gaaacaccta tttacattgg     120
tacctgcaga agccaggcca gtctccaaac ctcctgatct acaaagtttc caaccgattt     180
tctggggtcc cagacaggtt cagtggcagt ggatcaggga cagatttcac actcaagatc     240
agcatagtgg aggctgagga tctgggactt tatttctgct ctcaaagtac acatgttcct     300
cggacgttcg gtggaggcac caagctggaa atcaaa                               336
```

<210> SEQ ID NO 335
<211> LENGTH: 357
<212> TYPE: DNA
<213> ORGANISM: Mus musculus
<220> FEATURE:
<221> NAME/KEY: misc_feature
<223> OTHER INFORMATION: Murine SC17.97 VH

<400> SEQUENCE: 335

```
caggtccagc ttccgcagtc tggggctgaa ctggcaaaac ctggggcctc agtgaaaatc      60
tcctgcaagg cttctggctt caccttact tcctactgga tgcactgggt aaaacagagg      120
cctggacagg gtctggaatg gattggatac attaatccta gcactgatta tactgagtac     180
aatcagaagt tcaaggacaa ggccacattg actgcagaca atcctccag cacagcctac      240
atgcaactgg gcagcctgac atctgaggac tctgcagtct attactgtgc aagatcttcc     300
tacggtagta gccccttga ttattggggc caaggctcca ctctcacagt ctcctca        357
```

<210> SEQ ID NO 336
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.99 VL

<400> SEQUENCE: 336

```
gacattgtga tgtcacagtc tccatcctcc ctagctgtgt ctgttggaga gaaggttact      60
atgaactgcg agtccagtca gagccttta tatagtagca tcaaaagaa ctacttggcc       120
tggtaccagc agaaaccagg gcagtctcct aaactgctga tttactgggc atccactagg     180
gattctgggg tccctgatcg cttcacaggc agtggatctg ggacagattt cactctcacc     240
atcagcagtg tgagggctga agaccccggca gtttattact gtcagcaata ttatagctat    300
ccgctcacgt tcggtgctgg gaccaagctg gagctgaga                            339
```

<210> SEQ ID NO 337
<211> LENGTH: 348
<212> TYPE: DNA
<213> ORGANISM: Mus musculus
<220> FEATURE:
<221> NAME/KEY: misc_feature
<223> OTHER INFORMATION: Murine SC17.99 VH

<400> SEQUENCE: 337

```
gaagtgaagc ttgaggagtc tggaggaggc ttggtgcaac ctggaggatc catgaaactc    60
tcttgcgctg cctctggatt cacttttagt gacgcctgga tggactgggt ccgccagtct   120
ccagagaagg ggcttgagtg ggttgctgaa ataagaagca aagctaataa tcatgcaaca   180
tactatgctg agtctgtgaa agggaggttc accatctcaa gagatgattc caaaagtagt   240
gcctacctgc aaatgaacag cttaagagct gaagacactg gcatttatta ttgtgtttca   300
acagggactt cttactgggg ccaagggact ctggtcactg tctctgca                348
```

<210> SEQ ID NO 338
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.102 VL

<400> SEQUENCE: 338

```
caaattgttc tcacccagtc tccagcaatc atgtctgcat ctccagggga aaggtcacc     60 atgacctgca gtgccagctc aagtgtaagt tacatgcact ggtaccagca gaagtcaggc   120
acctccccca aaagatggat ttatgacaca tccaaactgg cttctggagt ccctcctcgc   180
ttcagtggcc gtgggtctgg gacctcttac tctctcacaa tcagcagcat ggaggctgaa   240
gatgctgcca cttattactg ccagcattgg agtagtaacc cacccacgtt cggtgctggg   300
accaagctgg agatgaaa                                                 318
```

<210> SEQ ID NO 339
<211> LENGTH: 348
<212> TYPE: DNA
<213> ORGANISM: Mus musculus
<220> FEATURE:
<221> NAME/KEY: misc_feature
<223> OTHER INFORMATION: Murine SC17.102 VH

<400> SEQUENCE: 339

```
gaggtccagc tgcaacagtc tggacctgag ctaatgaagc ctggggcttc agtgaagatg    60
tcctgcaagg cttctggaga cacattcact gactacaaca tacactgggt gaagcagaac   120
caaggaaaga gcctagagtg gataggagaa gttaatccta acattggtgg tattggctat   180
aaccagaagt tcaaaggcaa ggccacattg actgtagaca gtcctccag cacagcctac    240 atggagctcc gcagcctgac atctgaggac tctgcagtct attactgtgc aatggggagg   300
tggtacttcg atgtctgggg cgcagggacc acggtcaccg tctcctca                348
```

<210> SEQ ID NO 340
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.114 VL

<400> SEQUENCE: 340

```
gatgttgtga tgacccagtc tccactctcc ctgcctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acaaagtttc cagccgattt   180
tctggggtcc cagacaggtt cagtggcagt ggatcaggga cagatttcac actcaagatc   240
agcagagtgg aggctgagga tctgggagtt tatttctgct ctcaaagtac acatgttcca   300
```

```
ttcacgttcg gctcggggac aaagttggaa ataaaa                              336
```

<210> SEQ ID NO 341
<211> LENGTH: 345
<212> TYPE: DNA
<213> ORGANISM: Mus musculus
<220> FEATURE:
<221> NAME/KEY: misc_feature
<223> OTHER INFORMATION: Murine SC17.114 VH

<400> SEQUENCE: 341

```
gaggtccagc tgcagcagtc tggacctgag atggtgaagc ctggggcttc agtgaagata    60
tcctgcaagg cttctggata cacattcact gactactaca tgcactgggt gaaacagagc   120
catggaaaga gccttgagtg gattggacgt gttaatacta caatggtgg aactagctac    180
gaccagaagt tcgagggcaa ggccacattg actgttgaca aatcttccag cacagcctac   240
atggagctca acagcctgac atctgaggac tctgcggtct attactgtgt aatccctgcc   300
tggtttgctt actggggcca agggactctg gtcactgtct ctgca                   345
```

<210> SEQ ID NO 342
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.115 VL

<400> SEQUENCE: 342

```
gatattgtga tgacccagtc tccactctcc ctgcctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acagagtttc caaccgattt   180
tctggggtcc cagacaggtt cagtggcagt ggatcaggga cagatttcac actcacgatc   240
agcagagtgg aggctgagga tctgggagtt tatttctgct ctcaaagtac acatcttcct   300
cggacgttcg gtggaggcac caagctggag atcaaa                              336
```

<210> SEQ ID NO 343
<211> LENGTH: 342
<212> TYPE: DNA
<213> ORGANISM: Mus musculus
<220> FEATURE:
<221> NAME/KEY: misc_feature
<223> OTHER INFORMATION: Murine SC17.115 VH

<400> SEQUENCE: 343

```
caggtgcaac tgcagcagtc tgggtctgtg ctggtgaggc ctggagcttc agtgaagctg    60
tcctgcaagg cttctggcta cacattcacc agctactgga tgcactgggt gaagcagagg   120
cctggacaag gccttgagtg gattggagag attcatccta atagtgggaa tactaattac   180
aatgagaagt tcaagggcaa ggccacactg actgtagaca catcctccag cacagcctac   240
gtggatctca gcagcctgac atctgaggac tctgcggtct attattgtgc aggtggtaac   300
tacgactact ggggccaagg caccactctc acagtctcct ca                      342
```

<210> SEQ ID NO 344
<211> LENGTH: 333
<212> TYPE: DNA
<213> ORGANISM: Mus musculus
<220> FEATURE:
<221> NAME/KEY: misc_feature
<223> OTHER INFORMATION: Murine SC17.120 VL

<400> SEQUENCE: 344

```
gacattgtgc tgacccaatc tccagcttct ttggctgtat ctctagggca gagggccacc    60
atatcctgca gagccagtga aagtgttgat agttatggca atagttttat gcactggtac   120
cagcagaaac caggacagcc acccaaagtc ctcatctatc gtgcatccaa cctagaatct   180
gggatccctg ccaggttcag tggcagtggg tctaggacag acttcaccct caccattaat   240
cctgtggagg atgaagatgt tgcaacctat tactgtcagc aaagtaatga ggatccgtac   300
acgttcgggg gggggaccaa gctggaaata aaa                                333
```

<210> SEQ ID NO 345
<211> LENGTH: 351
<212> TYPE: DNA
<213> ORGANISM: Mus musculus
<220> FEATURE:
<221> NAME/KEY: misc_feature
<223> OTHER INFORMATION: Murine SC17.120 VH

<400> SEQUENCE: 345

```
gaggttcagc tcgagcagtc tggggactgtg ctggcaaggc ctggggcttc agtgaagatg    60
tcctgcaagg cttctggcta cacctttacc agctactgga tgcactgggt gaaacagagg   120
cctggacagg gtctggaatg gattggcgct ttttatcctg aaacagtgg tacttattac    180
aaccaaaaat tcaaggacaa ggccaaactg actgcagtca catctgccag cactgcctac   240
atggagctca gcagcctgac aaatgaggac tctgcggtct attactgttc aagatcaggg   300
tcaggaaggt ttgcttactg gggccaaggg actctggtca ctgtctctgc a            351
```

<210> SEQ ID NO 346
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.121 VL

<400> SEQUENCE: 346

```
caaattgttc tcacccagtc tccagcaatc atgtctgcat ctccagggga aaggtcacc    60
atgacctgca gtgccagctc aagtgtgagt tacatgcact ggtaccagca gaagtcaggc   120
acctccccca aaagatggat ttatgacaca tccaaactgg cttctggagt ccctgctcgc   180
ttcagtggca gtgggtctgg gacctcttac tctctcacaa tcagcagcat ggagactgaa   240
gatgctgcca cttattactg ccagcagtgg agtaataccc acccacgtt cggctcggtg    300
acaaagttgg aaataaaa                                                 318
```

<210> SEQ ID NO 347
<211> LENGTH: 348
<212> TYPE: DNA
<213> ORGANISM: Mus musculus
<220> FEATURE:
<221> NAME/KEY: misc_feature
<223> OTHER INFORMATION: Murine SC17.121 VH

<400> SEQUENCE: 347

```
gaggtccagc tgcaacagtc tggacctgag ctaatgaagc ctggggcttc agtgaagatg    60
tcctgcaagg cttctggata cacattcact gaccacaaca tacactgggt gaaacagcac   120
caaggaaaga gcctagagtg gataggagaa attaatccta acactggtgg tactggctac   180
```

```
aaccagaagt tccaaggcaa ggccacaatg actgtagaca agtcctccag cacagcctac    240
atggaactcc gcagcctgac atctgaggac tctgcagtct attactgtgt tagaggactg    300
tacttctttg actactgggg ccaaggcacc actctcacag tctcctca                 348
```

<210> SEQ ID NO 348
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.122 VL

<400> SEQUENCE: 348

```
gatattgtga taacccagga tgatctctcc aatcctgtca cttctggaga atcagtttcc    60
atctcctgca ggtctagtaa gagtctccta tataaggatg gaagacataa cttgaattgg   120
tttctgcaga gaccaggaca atctcctcag ctcctgatct atttgatgtc acccgtgca    180 tcaggagtct cagaccggtt tagtggcagt gggtcaggaa cagatttcac cctggaaatc   240
agtagagtga aggctgagga tgtgggtgtg tattactgtc aacaacttgt agagtatcct   300
cggacgttcg gtggaggcac caagctggaa atcaaa                             336
```

<210> SEQ ID NO 349
<211> LENGTH: 339
<212> TYPE: DNA
<213> ORGANISM: Mus musculus
<220> FEATURE:
<221> NAME/KEY: misc_feature
<223> OTHER INFORMATION: Murine SC17.122 VH

<400> SEQUENCE: 349

```
gaggtgcacc tggtggagtc tgggggagac ttagtgaagc ctggagggtc cctgaaactc    60
tcctgtgcag cctctggatt cactttcagt agctatggca tgtcttgggt tcgccagact   120
ccagacaaga ggctggagtg ggtcgcaacc attagtagtg gtggtactta cacctactat   180
ccagacagtg tgaaggggcg attcaccatc tccagagaca atgccaagaa caccctgtat   240
ctgcaaatga gcagtctgaa gtctgaggac acagccatgt attactgttc aagacatggg   300
tggggctggg gccaagggac tctggtcact gtctctgca                          339
```

<210> SEQ ID NO 350
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.140 VL

<400> SEQUENCE: 350

```
caaattgttc tcacccagtc tccagcaatc atgtctgcat ctccagggga aaggtcacc     60 atgacctgca gtgccagctc aagtgttagt tacatgcact ggtaccagca gaagtcaggc   120
acctccccca aaagatggat ttatgacaca tccaaactgg cttctggagt ccctgctcgc   180
ttcagtggca gtgggtctgg gacctcttac tctctcacaa tcagcagcat ggaggctgaa   240
gatgctgcca cttattactg ccagcagtgg agtagtaccc cacccacgtt cggctcgggg   300
acaaagttgg aaataaaa                                                 318
```

<210> SEQ ID NO 351
<211> LENGTH: 360
<212> TYPE: DNA

<213> ORGANISM: Mus musculus
<220> FEATURE:
<221> NAME/KEY: misc_feature
<223> OTHER INFORMATION: Murine SC17.140 VH

<400> SEQUENCE: 351

```
gaggtccagc tgcaacagtc tggacctgag ctaatgaagc tggggcttc  agtgaagatg      60
tcctgcaagg cttctggata cacattcact gactacaaca tgcactgggt gaagcagaac     120
caaggaaaga gcctagagtg gataggagaa attaatccca acactggtgg tactggctac     180
aaccagaagt tcaaaggcaa ggccacattg actgtagaca gttttccag  cacagccttc     240
attgagctcc gcagcctgac atctgaggac tctgcaatct attactgtac aagagggggt     300
tacgaccact attggtactt cgatgtctgg ggcgcaggga ccacggtcac cgtctcctca     360
```

<210> SEQ ID NO 352
<211> LENGTH: 333
<212> TYPE: DNA
<213> ORGANISM: Mus musculus
<220> FEATURE:
<221> NAME/KEY: misc_feature
<223> OTHER INFORMATION: Murine SC17.151 VL

<400> SEQUENCE: 352

```
gacattgtgc tgacccaatt tccagcttct ttggctgtgt ctctagggca gagggccacc      60
atacctgca  gagccagtga aagtgttgat agttatggca atagttttat gcactggttc     120
cagcagaaac caggacagcc acccaaactc ctcatctatc gtgcatccaa cctagaatct     180
gagatccctg ccaggttcag tggcagtggg tctgggacag acttcaccct caccattaat     240
cctgtggagg ctgatgatgt tgcaacctat tactgtcagc aaagtcatga ggatccgtac     300
acgttcggag gggggaccaa gatggaaata aaa                                  333
```

<210> SEQ ID NO 353
<211> LENGTH: 351
<212> TYPE: DNA
<213> ORGANISM: Mus musculus
<220> FEATURE:
<221> NAME/KEY: misc_feature
<223> OTHER INFORMATION: Murine SC17.151 VH

<400> SEQUENCE: 353

```
gaggttcagc tgcagcagtc tgggactgtg ctggcaaggc tggggcttc  agtgaagatg      60
tcctgcaagg cttctggcta tacctttacc agctactgga tgcactgggt aaaacagagg     120
cctggacagg tctggaatg  gattggcgct atttatcctg aaagaatga  tactacctac     180
aaccagaagt tcaagggcaa ggccaaactg actgcagtca catctgccag cactttatac     240
atggagctca gcagcctgac aaatgaggac tctgcggtct attactgtac aagatctgga     300
aagggttact tgcttactg  ggccaaggg  actctggtca ctgtctctgc a               351
```

<210> SEQ ID NO 354
<211> LENGTH: 336
<212> TYPE: DNA
<213> ORGANISM: Mus musculus
<220> FEATURE:
<221> NAME/KEY: misc_feature
<223> OTHER INFORMATION: Murine SC17.156 VL

<400> SEQUENCE: 354

```
gatgttgtga tgacccagtc tccactctcc ctgcctgtca gtcttggaga tcaagcctcc      60
atctcttgca gatctagtca gagcattgta catagtaatg gaaacaccta tttagaatgg     120
```

```
tacctgcaga aaccaggcca gtctccaaag ctcctgatct acaaagtttc aaccgattt      180 tctggggtcc cagacaggtt cagtggcagt ggatcaggga cagatttcac actcaagatc    240
agcagagtgg aggctgagga tctgggagtt tattactgct ttcaaggttc acatgttcct    300
ccgacgttcg gtggaggcac caaactggaa atcaaa                              336
```

<210> SEQ ID NO 355  
<211> LENGTH: 354  
<212> TYPE: DNA  
<213> ORGANISM: Mus musculus  
<220> FEATURE:  
<221> NAME/KEY: misc_feature  
<223> OTHER INFORMATION: Murine SC17.156 VH

<400> SEQUENCE: 355

```
caggttactc tgaaagagtc tggccctggg atattgcagc cctcccagac cctcagtctg     60
acttgttctt tctctgggtt ttcactgagc acttctggta tgggtgtgag ctggattcgt    120
aagacttcag gaaagggtct ggaatggctg gcacacattt tctgggatga tgacaagtgg    180
tataatccat ccctgaagag ccggctcaca atctccaagg ctacctccag caaccaggta    240
ttcctcatac tcaccagtgt ggatactgcc gatactgcca catactactg tgctaccttc    300
tatggtctct actttgccta ctggggccaa ggcaccactc tcacagtctc ctca          354
```

<210> SEQ ID NO 356  
<211> LENGTH: 339  
<212> TYPE: DNA  
<213> ORGANISM: Mus musculus  
<220> FEATURE:  
<221> NAME/KEY: misc_feature  
<223> OTHER INFORMATION: Murine SC17.161 VL

<400> SEQUENCE: 356

```
gacattgtga tgtcacagtc tccatcctcc ctagctgtgt ctgttggaga gaaggttact     60
atgaactgcg agtccagtca gagccttta tataatagca tcaaaagaa ctacttggcc      120 tggtaccagc agaaaccagg gcagtctcct aaactgctga tttactgggc atccactagg   180
gattctgggg tccctgatcg cttcacaggc agtggatctg ggacagattt cactctcacc   240
atcagcagtg tgagggctga tgacccggca gtttattact gtcagcaata ttttaactat  300
ccgctcacgt tcggtgctgg gaccaagctg gagctgaaa                           339
```

<210> SEQ ID NO 357  
<211> LENGTH: 348  
<212> TYPE: DNA  
<213> ORGANISM: Mus musculus  
<220> FEATURE:  
<221> NAME/KEY: misc_feature  
<223> OTHER INFORMATION: Murine SC17.161 VH

<400> SEQUENCE: 357

```
gaagtgaagc ttgaggagtc tggaggaggc ttggtgcaac ctggaggatc catgaaactc     60
tcttgcgctg cctctggatt cacttttagt gacgcctgga tggactgggt ccgccagtct   120
ccagagaagg ggcttgagtg ggttgctgaa ataagaagca aacctaataa tcatgcaaca   180
tactatgctg agtctgtgaa agggaggttc accatctcaa gagatgattc caaaagtagt   240
gcctacctgc aaatgaacag cttaagagct gaagacactg gcatttatta ctgtgtttca   300
acagggactt cttactgggg ccaagggact ctggtcactg tctctgca                348
```

<210> SEQ ID NO 358
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.166 VL

<400> SEQUENCE: 358

| | | | | | |
|---|---|---|---|---|---|
| caaattgttc | tcacccagtc | tccagcaatc | atgtctgcat | ctccagggga | gaaggtcacc | 60 |
| atgacctgca | gtgccagctc | aagtataagt | tacatgcact | ggtaccagca | gaagtcaggc | 120 |
| acctccccca | aaagatggat | ttatgacaca | tccaaactgg | cttctggagt | ccctgctcgc | 180 |
| ttcagtggca | gtgggtctgg | gacctcttac | tctctcacaa | tcagcaacat | ggaggctgaa | 240 |
| gatgctgcca | cttattactg | ccagcagtgg | agtagtaccc | cacccacgtt | cggagggggg | 300 |
| accaagctgg | aaataaaa | | | | | 318 |

<210> SEQ ID NO 359
<211> LENGTH: 351
<212> TYPE: DNA
<213> ORGANISM: Mus musculus
<220> FEATURE:
<221> NAME/KEY: misc_feature
<223> OTHER INFORMATION: Murine SC17.166 VH

<400> SEQUENCE: 359

| | | | | | |
|---|---|---|---|---|---|
| gaggtccagt | tgcaacagtc | tggacctgag | ctaatgaagc | ctggggcttc | agtgaagatg | 60 |
| tcctgcaagg | cttctggata | tatatttact | gactacaaca | tgcactgggt | gaagcagaac | 120 |
| caaggaaaga | gcctagagtg | gataggagaa | gttaatccta | cactggtgg | tattggctac | 180 |
| aatcagaaat | tcaaaggcaa | ggccacattg | actgtagaca | gtcctccag | cacagcctac | 240 |
| atggacctcc | gcagcctgac | atctgaggac | tctgcagtct | attactgtgc | aagagatggc | 300 |
| aattattgct | ttgactactg | gggccaaggc | accactctca | cagtctcctc | a | 351 |

<210> SEQ ID NO 360
<211> LENGTH: 321
<212> TYPE: DNA
<213> ORGANISM: Mus musculus
<220> FEATURE:
<221> NAME/KEY: misc_feature
<223> OTHER INFORMATION: Murine SC17.187 VL

<400> SEQUENCE: 360

| | | | | | |
|---|---|---|---|---|---|
| gacatcaaga | tgacccagtc | tccatcttcc | atgtatgcat | ctctaggaga | gagagtcact | 60 |
| ctcacttgca | aggcgagtca | ggacattaat | agctatttaa | gctggttcca | gcagaaacca | 120 |
| gggaaatctc | ctgagaccct | gatctatcgt | gcaaacagat | tgatagatgg | ggtcccatca | 180 |
| aggttcagtg | gcagtggatc | tgggcaagat | tattctctca | ccatcagcag | cctggagtat | 240 |
| gaagatatgg | ggatttatta | ttgtctacag | tatgatgagt | ttcctccgac | gttcggtgga | 300 |
| ggcaccaagc | tggaaatcaa | a | | | | 321 |

<210> SEQ ID NO 361
<211> LENGTH: 354
<212> TYPE: DNA
<213> ORGANISM: Mus musculus
<220> FEATURE:
<221> NAME/KEY: misc_feature
<223> OTHER INFORMATION: Murine SC17.187 VH

<400> SEQUENCE: 361

```
gaggtccacc tacaacagtc tggacctgaa ctggtgaacc ctgggtcttc agtgaagata    60
tcctgcaagg ctgctggata cacattcact gactacaaca tggactgggt gaagcagagc   120
catggaaaga gacttgagtg gattggaaat atttatccta acaatggtgg tgctggatac   180
aaccagaact tcaaggacaa ggccacattg actgtagaca gtcctccag cacagcctac    240 atggagctcc gcagcctgac atctgaggac tctgcagtct attactgtgc aagatccatt   300
actgcggctt ggtttgctta ctggggccaa gggactctgg tcactgtctc tgca          354
```

<210> SEQ ID NO 362
<211> LENGTH: 318
<212> TYPE: DNA
<213> ORGANISM: Mus musculus
<220> FEATURE:
<221> NAME/KEY: misc_feature
<223> OTHER INFORMATION: Murine SC17.191 VL

<400> SEQUENCE: 362

```
caaattgttc tcacccagtc tccagcaatc atgtctgcat ctccagggga gaaggtcacc    60
atgacctgca gtgccagctc aagtgtaagt tacatgcact ggtaccagca gaagtcaggc   120
acctccccca aaagatggat ttatgacaca tccaaactgg cttctggagt ccctgctcgc   180
ttcactggca gtgggtctgg gacctcttac tctctcacaa tcagcagcat ggaggctgaa   240
gatgctgcca cttattactg ccagcagtgg agtagtagcc cacccacgtt cggtgctggg   300
accaagctgg aactgaaa                                                 318
```

<210> SEQ ID NO 363
<211> LENGTH: 360
<212> TYPE: DNA
<213> ORGANISM: Mus musculus
<220> FEATURE:
<221> NAME/KEY: misc_feature
<223> OTHER INFORMATION: Murine SC17.191 VH

<400> SEQUENCE: 363

```
gaggtccagc tgcaacagtc tggacctgag ctaatgaagc ctggggcttc agtgaagatg    60
tcctgcaagg cttctggata cacattcact gactacaaca tgcactgggt gaagcagaac   120
caaggaaaga gcctagagtg gataggagaa attaatccta cactggtgg tactggctac   180 aaccagaagt tcaaagacaa ggccacattg actgtagaca gtcctccag cacagcctac    240 atggagctcc gcagcctgac atctgaggac tctgcagtct attactgtgc aagaattccc   300
tccctgagac gatactactt tgactactgg ggccaaggca ccactctcac agtctcctca   360
```

<210> SEQ ID NO 364
<211> LENGTH: 333
<212> TYPE: DNA
<213> ORGANISM: Mus musculus
<220> FEATURE:
<221> NAME/KEY: misc_feature
<223> OTHER INFORMATION: Murine SC17.193 VL

<400> SEQUENCE: 364

```
gaccttgtgc tgacacagtc tcctgcttcc ttagctgtat ctctggggca gagggccacc    60
atctcatgca gggccagcga aagtgtcagt acatctggct atagttatat gcactggtac   120
caacagaaac caggacagcc acccaaactc ctcatctatc ttgcatccaa cctcgaatct   180 gggtccctg ccaggttcag tggcagtggg tctgggacag acttcaccct caacatccat    240
cctgtggagg aggaggatgc tacaacctat tactgtcagc acagtaggga gcttccgtac   300
```

```
acgttcggag gggggaccaa gctggaaata aaa                               333
```

<210> SEQ ID NO 365
<211> LENGTH: 366
<212> TYPE: DNA
<213> ORGANISM: Mus musculus
<220> FEATURE:
<221> NAME/KEY: misc_feature
<223> OTHER INFORMATION: Murine SC17.193 VH

<400> SEQUENCE: 365

```
caggttactc tgaaagagtc tggccctggg atattgcagc cctcccagac cctcagtctg    60
acttgttctt tctctgggtt ttcactgatc acttatggta taggagtagg ctggattcgt   120
cagccttcag ggaagggtct ggagtggctg gcacacattt ggtggaatga taataagtac   180
tataacacag ccctgaagag ccggctcaca atctccaagg atacctccaa caaccaggta   240
ttcctcaaga tcgccaatgt ggacactgca gatactgcca catactactg tgctcgaatg   300
gtctactatg attacgacgg ggggtttgct tactggggcc aagggactct ggtcactgtc   360
tctgca                                                              366
```

<210> SEQ ID NO 366
<211> LENGTH: 333
<212> TYPE: DNA
<213> ORGANISM: Mus musculus
<220> FEATURE:
<221> NAME/KEY: misc_feature
<223> OTHER INFORMATION: Murine SC17.199 VL

<400> SEQUENCE: 366

```
gacattgtgc tgacccaatc tccagcttct ttggctgtgt ctctagggca gagggccacc    60
atatcctgca gagccagtga aagtgttgat agttatggca atagtttat gcactggtac    120 cagcagaaac caggacagcc acccaaaccc ctcatttatc gtgcatccaa cctagaatct   180
gggatccctg ccagattcag tggcagtggg tctaggacag acttcaccct caccattaat   240
cctgtggagg ctgatgatgt tgcaacctat tactgtcagc aaagtaatga ggatccgtac   300
acgttcggag gggggaccaa gctggaaata aaa                                333
```

<210> SEQ ID NO 367
<211> LENGTH: 348
<212> TYPE: DNA
<213> ORGANISM: Mus musculus
<220> FEATURE:
<221> NAME/KEY: misc_feature
<223> OTHER INFORMATION: Murine SC17.199 VH

<400> SEQUENCE: 367

```
gaggtgcagc tgcagcagtc tgggactgtg ctggcaaggc ctggggcttc agtaaggatg    60
tcctgcaagg cttctggcta cacctttacc agctactgga tgcactgggt aaaacaaagg   120
cctggacagg gtctggaatg gattggcgct atttatcctg gaaatagtga tactagctac   180
aaccataagt tcaagggcaa ggccaaactg actgcagtca catctgccag cactgcctac   240
atggagctca gcagcctgac aaatgaggac tctgcggtct attactgtac aagatctggg   300
acgggctggt tgcttactg ggggccaaggg actctggtca ctgtctct                348
```

<210> SEQ ID NO 368
<211> LENGTH: 333
<212> TYPE: DNA
<213> ORGANISM: Mus musculus
<220> FEATURE:

<221> NAME/KEY: misc_feature
<223> OTHER INFORMATION: Murine SC17.200 VL

<400> SEQUENCE: 368

| | | | | | |
|---|---|---|---|---|---|
| gacattgtgc | tgacccaatc | tccagcttct | ttggctgtgt | ctctaggaca | gagagccact | 60 |
| atcttctgca | gagccagcca | gagtgtcgat | tataatggaa | ttagttatat | gcactggttc | 120 |
| caacaaaaac | caggacagcc | acccaaactc | ctcatctatg | ctgcatccaa | cgttcaatct | 180 |
| gggatccctg | ccaggttcag | tggcagtggg | tctgggacag | acttcaccct | caacatccat | 240 |
| cctgtggagg | aggaagatgc | tgcaacccttt | tactgtcagc | aaagtattga | ggatcctccg | 300 |
| acgttcggtg | gaggcaccaa | gctggaaatc | aaa | | | 333 |

<210> SEQ ID NO 369
<211> LENGTH: 345
<212> TYPE: DNA
<213> ORGANISM: Mus musculus
<220> FEATURE:
<221> NAME/KEY: misc_feature
<223> OTHER INFORMATION: Murine SC17.200 VH

<400> SEQUENCE: 369

| | | | | | |
|---|---|---|---|---|---|
| caggtccagc | tgcagcagtc | tggacctgag | ctggtgaaac | ctggggcctc | agtgaagatt | 60 |
| tcctgcaaag | cttctggcta | cgcattcagt | agttcttgga | ttaactgggt | gaagcagagg | 120 |
| cctggacagg | tcttgagtg | gattggacgg | atttatcctg | agaaggtga | tactaactac | 180 |
| agtgggaatt | tcgagggcaa | ggccacactg | actgcagaca | aatcctccac | cacagcctac | 240 |
| atgcagctca | gcagtctgac | ctctgtggac | tctgcggtct | atttctgtac | aagaggacta | 300 |
| gtcatggact | actggggcca | aggcaccgct | ctcacagtct | cctca | | 345 |

<210> SEQ ID NO 370
<211> LENGTH: 321
<212> TYPE: DNA
<213> ORGANISM: Artificial Sequence
<220> FEATURE:
<223> OTHER INFORMATION: Humanized hSC17.16 VL

<400> SEQUENCE: 370

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtgc | gaacattaac | agcaatttag | tttggtatca | gcagaaacca | 120 |
| gggaaagccc | ctaagctcct | gatctatgct | gcaaccaatt | tggcagatgg | ggtcccatca | 180 |
| aggttcagtg | gcagtggatc | tgggacagat | ttcactctca | ccatcagcag | tctgcaacct | 240 |
| gaagattttg | caacttacta | ctgtcaacat | ttttgggta | ctcctcggac | gttcggtgga | 300 |
| ggcaccaagc | tggaaatcaa | a | | | | 321 |

<210> SEQ ID NO 371
<211> LENGTH: 348
<212> TYPE: DNA
<213> ORGANISM: Artificial Sequence
<220> FEATURE:
<223> OTHER INFORMATION: Humanized hSC17.16 VH

<400> SEQUENCE: 371

| | | | | | |
|---|---|---|---|---|---|
| caggtgcagc | tggtgcagtc | tggggctgag | gtgaagaagc | ctggggcctc | agtgaaggtc | 60 |
| tcctgcaagg | cttctggata | caccttcacc | gactacaata | tgtactgggt | gcgacaggcc | 120 |
| cctggacaag | gcttgagtg | gatgggagag | atcaacccta | caatggtgg | cacagcctat | 180 |
| aatcagaagt | ttaggggcaa | ggtcaccatg | accagggaca | cgtccatcag | cacagcctac | 240 |

-continued

```
atggagctga gcaggctgag atctgacgac acggccgtgt attactgtgc gagatatgat    300
aaggggtttg actactgggg ccaaggcacc actgtcacag tctcctca                 348
```

<210> SEQ ID NO 372
<211> LENGTH: 318
<212> TYPE: DNA
<213> ORGANISM: Artificial Sequence
<220> FEATURE:
<223> OTHER INFORMATION: Humanized hSC17.17 VL

<400> SEQUENCE: 372

```
gaaattgtgt tgacacagtc tccagccacc ctgtctttgt ctccagggga aagagccacc     60
ctctcctgca gtgccagtag cagtgttagc tacatgcatt ggtaccaaca gaaacctggc    120
caggctccca ggctcctcat ctatgataca tccaaattgc ccagtggcat cccagccagg    180
ttcagtggca gtgggtctgg gacagacttc actctcacca tcagcagcct agagcctgaa    240
gattttgcag tttattactg tcagcagtgg agtagtaccc cacccacgtt cggtcagggg    300
accaagctgg agattaaa                                                  318
```

<210> SEQ ID NO 373
<211> LENGTH: 360
<212> TYPE: DNA
<213> ORGANISM: Artificial Sequence
<220> FEATURE:
<223> OTHER INFORMATION: Humanized hSC17.17 VH

<400> SEQUENCE: 373

```
caggtgcagc tggtgcagtc tggggctgag gtgaagaagc ctggggcctc agtgaaggtc     60
tcctgcaagg cttctggata caccttcacc gactacaata tgcactgggt gcgacaggcc    120
cctggacaag gcttgagtg gatgggagag atcaaccctct acattggtgg cacaggctat    180
aaccagaagt ttaagggcag ggtcaccatg accaggaca cgtccatcag cacagcctac    240
atggagctga gcaggctgag atctgacgac acggccgtgt attactgtgc gagaacctat    300
agttactata gttacgagtt tgcttactgg ggccaaggga ctctggtcac tgtctcttca    360
```

<210> SEQ ID NO 374
<211> LENGTH: 336
<212> TYPE: DNA
<213> ORGANISM: Artificial Sequence
<220> FEATURE:
<223> OTHER INFORMATION: Humanized hSC17.24 VL

<400> SEQUENCE: 374

```
gacatcgtga tgacccagtc tccagactcc ctggctgtgt ctctgggcga gagggccacc     60
atcaactgca gtccagcca gagtcttctc tacagctcca accagaagag ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtaagcaatc ttataatctt    300
cggacgttcg gtggaggcac caaggtggaa atcaaa                              336
```

<210> SEQ ID NO 375
<211> LENGTH: 351
<212> TYPE: DNA
<213> ORGANISM: Artificial Sequence
<220> FEATURE:
<223> OTHER INFORMATION: Humanized hSC17.24 VH

<400> SEQUENCE: 375

```
gaagtgcagc tggtgcagtc tggggctgag gtgaagaagc ctggggccac cgtgaagata    60
tcctgcaagg tgtctggata caccttcaca gaccacacta tacactgggt gcgacaggcc   120
cctggaaagg ggcttgagtg gattggatac atctaccctc gtgatggtag cacaaaatac   180
aacgaggagt tcaaaggcag agtcaccatc accgccgaca cgtccacgga cacagcctac   240
atggagctga gcagcctgag atctgaggac acggccgtgt attactgtgc gagatcatat   300
agtaactact ttgactactg gggccaaggc accactgtca cagtctcctc a            351
```

<210> SEQ ID NO 376
<211> LENGTH: 321
<212> TYPE: DNA
<213> ORGANISM: Artificial Sequence
<220> FEATURE:
<223> OTHER INFORMATION: Humanized hSC17.28 VL

<400> SEQUENCE: 376

```
gaaattgtgc tgactcagtc tccagacttt cagtctgtga ctccaaagga gaaagtcacc    60
atcacctgcc gggccagtca gagcattggt actagcatac actggtacca gcagaaacca   120
gatcagtctc caaagctcct catcaagtat gcttccgagt ccatctcagg ggtcccctcg   180
aggttcagtg gcagtggatc tgggacagat ttcaccctca ccatcaatag cctggaagct   240
gaagatgctg caacgtatta ctgtcagcaa agtaatagct ggccactcac gttcggtcaa   300
gggaccaagc tggagataaa a                                              321
```

<210> SEQ ID NO 377
<211> LENGTH: 351
<212> TYPE: DNA
<213> ORGANISM: Artificial Sequence
<220> FEATURE:
<223> OTHER INFORMATION: Humanized hSC17.28 VH

<400> SEQUENCE: 377

```
caggtgcagc tggtgcagtc tggggctgag gtgaagaagc ctggggcctc agtgaaggtc    60
tcctgcaagg cttctggata caccttcacc agaagctata tccactgggt gcgacaggcc   120
cctggacaag ggcttgagtg gatgggatac atcagcagtg gcagtggtgg cacaacctat   180
aaccagaagt ttaagggcag ggtcaccagt accaggggaca cgtccatcag cacagcctac   240
atggagctga gcaggctgag atctgacgac acggccgtgt attactgtgc gagaggggggg   300
gtacggtact cgatgtctg gggccaaggg accacggtca ccgtctcctc a              351
```

<210> SEQ ID NO 378
<211> LENGTH: 321
<212> TYPE: DNA
<213> ORGANISM: Artificial Sequence
<220> FEATURE:
<223> OTHER INFORMATION: Humanized hSC17.34 VL

<400> SEQUENCE: 378

```
gacatccaga tgacccagtc tccatcctca ctgtctgcat ctgtaggaga cagagtcacc    60
atcacttgta aggcgagtca ggacattaat agttatttat cctggtttca gcagaaacca   120
gggaaagccc ctaagtccct gatctataga gcaaacagat tggtagatgg ggtcccatca   180
aggttcagcg gcagtggatc tgggacagat tacactctca ccatcagcag cctgcagcct   240
gaagattttg caacttatta ctgcctacag tatgatgagt ttcctccgac gttcggtcag   300
ggcaccaagc tggaaatcaa a                                              321
```

<210> SEQ ID NO 379
<211> LENGTH: 354
<212> TYPE: DNA
<213> ORGANISM: Artificial Sequence
<220> FEATURE:
<223> OTHER INFORMATION: Humanized hSC17.34 VL

<400> SEQUENCE: 379

```
caggtccagc ttgtgcagtc tggggctgag gtgaagaagc ctggggcctc agtgaaggtt    60
tcctgcaagg cttctggata caccttcact gactataata tggattgggt gcgccaggcc   120
cccggacaaa ggcttgagtg gattggatac atctaccctg acaatggtgg cgcaggatat   180
aatcagaagt tcaagggcag agtcaccatt accgtggaca catccgcgag cacagcctac   240
atggagctga gcagcctgag atctgaagac acggctgtgt attactgttc aagatccatt   300
actacggctt ggtttgctta ctggggccaa gggactctgg tcactgtctc ttca          354
```

<210> SEQ ID NO 380
<211> LENGTH: 321
<212> TYPE: DNA
<213> ORGANISM: Artificial Sequence
<220> FEATURE:
<223> OTHER INFORMATION: Humanized hSC17.46 VL

<400> SEQUENCE: 380

```
gccatccaga tgacccagtc tccatcctcc ctgtctgcat ctgtaggaga cagagtcacc    60
atcacttgca aggcaagtca gagcgttaat aatgatgtag cctggtatca gcagaaacca   120
gggaaagccc ctaagctcct gatctattat gcatccaatc gatatactgg ggtcccatca   180
aggttcagcg gcagtggatc tggcacagat ttcactctca ccatcagcag cctgcagcct   240
gaagattttg caacttattt ctgtcagcag gattatagct ctcctcggac gttcggtcag   300
gggaccaagc tggaaataaa g                                              321
```

<210> SEQ ID NO 381
<211> LENGTH: 363
<212> TYPE: DNA
<213> ORGANISM: Artificial Sequence
<220> FEATURE:
<223> OTHER INFORMATION: Humanized hSC17.46 VH

<400> SEQUENCE: 381

```
caggtgcagc tggtgcagtc tggggctgag gtgaagaagc ctggggcctc agtgaaggtc    60
tcctgcaagg cttctggata caccttcacc agctactgga tcaactgggt gcgacaggcc   120
cctggacaag gcttgagtg gattggaaac atcttccctg acactactac cacaaactat   180
aacgagaagt ttaagggcag ggtcaccctg accaggacag cgtccatcag cacagcctac   240
atggagctga gcaggctgag atctgacgac acggccgtgt attactgtgc gagagagtac   300
tacgatggta cctacgatgc tatggattac tggggtcaag gaaccctagt caccgtctcc   360
tca                                                                  363
```

<210> SEQ ID NO 382
<211> LENGTH: 333
<212> TYPE: DNA
<213> ORGANISM: Artificial Sequence
<220> FEATURE:
<223> OTHER INFORMATION: Humanized hSC17.151 VL

<400> SEQUENCE: 382

```
gagatcgtgc tgacccagag ccctgctaca ctgtccctgt cccctggaga gagggccaca    60
ctctcctgca gggcttccga gtccgtggat tcctacggca actccttcat gcactggtac   120
cagcagaaac ccggccaggc cctaggctg ctgatctaca gggcctccaa cctggagtcc    180
ggcatccctg ctaggttctc cggatccggc tccggcaccg actttaccct gaccatctcc   240
tccctggagc ccgaggactt cgccgtgtac tactgccagc agtcccacga ggaccectac   300 accttcggcc agggcaccaa gctggagatc aag                                333
```

<210> SEQ ID NO 383
<211> LENGTH: 351
<212> TYPE: DNA
<213> ORGANISM: Artificial Sequence
<220> FEATURE:
<223> OTHER INFORMATION: Humanized hSC17.151 VH

<400> SEQUENCE: 383

```
caggtccagc tggtgcagag cggcgctgag gtgaagaagc ctggcgccag cgtgaaggtg    60
tcctgcaaag ccagcggcta caccttcacc tcctactgga tgcattgggt gaggcaggct   120
cctggccaag gactggagtg gatgggcgcc atctaccccg gcaagtccga caccacctac   180
aaccagaagt tcaagggcag ggtgaccatg acacgggaca cctccacctc caccgtgtac   240
atggagctgt cctccctgag gtccgaggac accgccgtgt actactgcgc caggtccggc   300
aagggctatt tcgcctactg gggccagggc acactggtga ccgtgtcctc c             351
```

<210> SEQ ID NO 384
<211> LENGTH: 339
<212> TYPE: DNA
<213> ORGANISM: Artificial Sequence
<220> FEATURE:
<223> OTHER INFORMATION: Humanized hSC17.155 VL

<400> SEQUENCE: 384

```
gacatcgtga cccagtc tccagactcc ctggctgtgt ctctgggcga gagggccacc       60
atcaactgca gtccagcca gagtttatta tacagctcca accaaaagaa ctacttagct    120
tggtaccagc agaaaccagg acagcctcct aagctgctca tttactgggc atctacccgg   180
aaatccgggg tccctgaccg attcagtggc agcgggtctg ggacagattt cactctcacc   240
atcagcagcc tgcaggctga agatgtggca gtttattact gtcatcaata ttatagctat   300
ccgctcacgt tcggtcaagg caccaagctg gaaatcaaa                          339
```

<210> SEQ ID NO 385
<211> LENGTH: 339
<212> TYPE: DNA
<213> ORGANISM: Artificial Sequence
<220> FEATURE:
<223> OTHER INFORMATION: Humanized hSC17.155 VH

<400> SEQUENCE: 385

```
caggtgcagc tggtgcagtc tggggctgag gtgaagaagc ctggggcctc agtgaaggtt    60
tcctgcaagg catctggata caccttcaac agctactgga tgcactgggt gcgacaggcc   120
cctggacaag gcttgagtg gatgggagaa atccacccta ataatggtag cacaaactac    180
aacgagaagt tcaagggcag agtcaccatg accagggaca cgtccacgag cacagtctac   240
atggagctga gcagcctgag atctgaggac acggccgtgt attactgtgc gagatggact   300
ttgtttactt actggggcca aggactctg gtcactgtc                            339
```

<210> SEQ ID NO 386
<211> LENGTH: 336
<212> TYPE: DNA
<213> ORGANISM: Artificial Sequence
<220> FEATURE:
<223> OTHER INFORMATION: Humanized hSC17.156 VL

<400> SEQUENCE: 386

| | | |
|---|---|---|
| gacatcgtga tgacccagac ccctctgtcc ctgcctgtga cccctggaga acccgccagc | 60 |
| atctcctgca ggtcctccca gtccatcgtg cactccaacg gcaacaccta cctggagtgg | 120 |
| tacctgcaga agcccggaca gtcccccag ctgctgatct acaaggtgtc caataggttt | 180 |
| tccggagtgc ccgacaggtt ctccggatcc ggatccggca ccgacttcac cctgaagatc | 240 |
| tccagggtgg aggccgagga cgtgggagtg tactactgct ccagggcag ccacgtgccc | 300 |
| cctacattcg gaggcggcac caagctggag atcaag | 336 |

<210> SEQ ID NO 387
<211> LENGTH: 354
<212> TYPE: DNA
<213> ORGANISM: Artificial Sequence
<220> FEATURE:
<223> OTHER INFORMATION: Humanized hSC17.156 VH

<400> SEQUENCE: 387

| | | |
|---|---|---|
| caggtcaccc tgaaggagtc cggccccgtg ctggtgaaac ccaccgagac cctcaccctg | 60 |
| acctgcaccg tctccggctt ctccctgtcc acctccggca tgggagtgtc ctggatcagg | 120 |
| cagccccctg gaaaggctct ggagtggctg gcccacatct ctgggacga cgacaagtgg | 180 |
| tacaacccct ccctgaagtc caggctgacc atctccaagg acacctccaa gtcccaggtg | 240 |
| gtgctgacca tgaccaacat ggaccccgtg gacaccgcca cctactactg cgctaccttc | 300 |
| tacggcctgt acttcgccta ctggggccag ggaaccctgg tgaccgtgtc ctcc | 354 |

<210> SEQ ID NO 388
<211> LENGTH: 339
<212> TYPE: DNA
<213> ORGANISM: Artificial Sequence
<220> FEATURE:
<223> OTHER INFORMATION: Humanized hSC17.161 VL

<400> SEQUENCE: 388

| | | |
|---|---|---|
| gacatcgtga tgacccagtc ccccgattcc ctggctgtga gcctgggaga gagggccacc | 60 |
| atcaactgcg agtcctccca gtccctgctg tacaactcca accagaagaa ctacctggcc | 120 |
| tggtaccagc agaagcccgg acagcccccc aagctgctga tctactgggc ttccacaagg | 180 |
| gagtccggag tgcccgatcg gttcagcgga tccggatccg gcaccgactt caccctcacc | 240 |
| atcagctccc tgcaagccga ggacgtggcc gtgtactact gccagcagta cttcaactac | 300 |
| cctctgacct tcggccaggg caccaagctg gagatcaag | 339 |

<210> SEQ ID NO 389
<211> LENGTH: 348
<212> TYPE: DNA
<213> ORGANISM: Artificial Sequence
<220> FEATURE:
<223> OTHER INFORMATION: Humanized hSC17.161 VH

<400> SEQUENCE: 389

| | | |
|---|---|---|
| caggtgcagc tggtccagtc cggagctgag gtgaagaagc ccggcgcctc cgtgaaggtg | 60 |
| tcctgcaagg ccagcggctt caccttctcc gatgcctgga tggactgggt gaggcaggct | 120 |

```
cctggccaaa ggctggagtg gatgggcgag atcaggtcca agcccaacaa ccacgccacc    180
tactacgccg agagcgtgaa gggcagggtg accatcacaa gggatacatc cgcctccacc    240
gcctacatgg agctgtcctc cctgaggtcc gaggacaccg ccgtgtacta ctgtgccagg    300
accggaacct cctactgggg ccagggcaca ctggtgaccg tgtcctcc                 348
```

<210> SEQ ID NO 390
<211> LENGTH: 333
<212> TYPE: DNA
<213> ORGANISM: Artificial Sequence
<220> FEATURE:
<223> OTHER INFORMATION: Humanized hSC17.200 VL

<400> SEQUENCE: 390

```
gaaattgtgt tgacacagtc tccagccacc ctgtctttgt ctccagggga aagagccacc    60
ctctcctgca gggccagtca gagtgttgac tataatggaa ttagctacat gcactggtac   120
caacagaaac ctggccaggc tcccaggctc ctcatctatg ctgcatccaa cgtgcagagt   180
ggcatcccag ccaggttcag tggcagtggg tctgggacag acttcactct caccatcagc   240
agcctagagc ctgaagattt tgcagtttat tactgtcagc agagtattga ggatcctccg   300
acgttcggtg aggcaccaa ggtggaaatc aaa                                  333
```

<210> SEQ ID NO 391
<211> LENGTH: 345
<212> TYPE: DNA
<213> ORGANISM: Artificial Sequence
<220> FEATURE:
<223> OTHER INFORMATION: Humanized hSC17.200 VH

<400> SEQUENCE: 391

```
gaggtgcagc tggtgcagtc tggagcagag gtgaaaaagc ccggggagtc tctgaagatc    60
tcctgtaagg gttctggata cagctttacc agctcctgga tcaactgggt gcgccagatg   120
cccgggaaag gcctggagtg gatggggaga atctatcctg gtgagggtga taccaactac   180
agcgggaact tcgaaggcca ggtcaccatc tcagccgaca gtccatcag caccgcctac   240 ctgcagtgga gcagcctgaa ggcctcggac accgccatgt attactgtac aagaggacta   300
gtcatggact actggggcca aggcacccett gtcacagtct cgagc                   345
```

<210> SEQ ID NO 392
<211> LENGTH: 333
<212> TYPE: DNA
<213> ORGANISM: Artificial Sequence
<220> FEATURE:
<223> OTHER INFORMATION: Humanized hSC17.200 VL1

<400> SEQUENCE: 392

```
gaaattgtgt tgacacagtc tccagccacc ctgtctttgt ctccagggga aagagccacc    60
ctctcctgca gggccagtca gagtgttgac tatgatggaa ttagctacat gcactggtac   120
caacagaaac ctggccaggc tcccaggctc ctcatctatg ctgcatccaa cgtgcagagt   180
ggcatcccag ccaggttcag tggcagtggg tctgggacag acttcactct caccatcagc   240
agcctagagc ctgaagattt tgcagtttat tactgtcagc agagtattga ggatcctccg   300
acgttcggtg aggcaccaa ggtggaaatc aaa                                  333
```

<210> SEQ ID NO 393
<211> LENGTH: 339
<212> TYPE: DNA
<213> ORGANISM: Artificial Sequence -continued

```
<220> FEATURE:
<223> OTHER INFORMATION: Humanized hSC17.155 VH1

<400> SEQUENCE: 393
caggtgcagc tggtgcagtc tggggctgag gtgaagaagc ctggggcctc agtgaaggtt    60
tcctgcaagg catctggata caccttcgac agctactgga tgcactgggt gcgacaggcc   120
cctggacaag ggcttgagtg gatgggagaa atccacccta ataatggtag cacaaactac   180
aacgagaagt tcaagggcag agtcaccatg accagggaca cgtccacgag cacagtctac   240
atggagctga gcagcctgag atctgaggac acggccgtgt attactgtgc gagatggact   300
ttgtttactt actggggcca aggactctg gtcactgtc                           339

<210> SEQ ID NO 394
<211> LENGTH: 339
<212> TYPE: DNA
<213> ORGANISM: Artificial Sequence
<220> FEATURE:
<223> OTHER INFORMATION: Humanized hSC17.155 VH2

<400> SEQUENCE: 394
caggtgcagc tggtgcagtc tggggctgag gtgaagaagc ctggggcctc agtgaaggtt    60
tcctgcaagg catctggata caccttcacc agctactgga tgcactgggt gcgacaggcc   120
cctggacaag ggcttgagtg gatgggagaa atccacccta ataatggtag cacaaactac   180
aacgagaagt tcaagggcag agtcaccatg accagggaca cgtccacgag cacagtctac   240
atggagctga gcagcctgag atctgaggac acggccgtgt attactgtgc gagatggact   300
ttgtttactt actggggcca aggactctg gtcactgtc                           339

<210> SEQ ID NO 395
<211> LENGTH: 339
<212> TYPE: DNA
<213> ORGANISM: Artificial Sequence
<220> FEATURE:
<223> OTHER INFORMATION: Humanized hSC17.155 VH3

<400> SEQUENCE: 395
caggtgcagc tggtgcagtc tggggctgag gtgaagaagc ctggggcctc agtgaaggtt    60
tcctgcaagg catctggata caccttcaac tactactgga tgcactgggt gcgacaggcc   120
cctggacaag ggcttgagtg gatgggagaa atccacccta ataatggtag cacaaactac   180
aacgagaagt tcaagggcag agtcaccatg accagggaca cgtccacgag cacagtctac   240
atggagctga gcagcctgag atctgaggac acggccgtgt attactgtgc gagatggact   300
ttgtttactt actggggcca aggactctg gtcactgtc                           339

<210> SEQ ID NO 396
<211> LENGTH: 339
<212> TYPE: DNA
<213> ORGANISM: Artificial Sequence
<220> FEATURE:
<223> OTHER INFORMATION: Humanized hSC17.155 VH4

<400> SEQUENCE: 396
caggtgcagc tggtgcagtc tggggctgag gtgaagaagc ctggggcctc agtgaaggtt    60
tcctgcaagg catctggata caccttcaac agctactgga tgcactgggt gcgacaggcc   120
cctggacaag ggcttgagtg gatgggagaa atccacccta atgatggtag cacaaactac   180
aacgagaagt tcaagggcag agtcaccatg accagggaca cgtccacgag cacagtctac   240
```

```
atggagctga gcagcctgag atctgaggac acggccgtgt attactgtgc gagatggact    300
ttgtttactt actggggcca agggactctg gtcactgtc                            339

<210> SEQ ID NO 397
<211> LENGTH: 339
<212> TYPE: DNA
<213> ORGANISM: Artificial Sequence
<220> FEATURE:
<223> OTHER INFORMATION: Humanized hSC17.155 VH5

<400> SEQUENCE: 397
caggtgcagc tggtgcagtc tggggctgag gtgaagaagc ctggggcctc agtgaaggtt    60
tcctgcaagg catctggata caccttcaac agctactgga tgcactgggt gcgacaggcc    120
cctggacaag gcttgagtg gatgggagaa atccacccta atggtggtag cacaaactac     180
aacgagaagt tcaagggcag agtcaccatg accagggaca cgtccacgag cacagtctac    240
atggagctga gcagcctgag atctgaggac acggccgtgt attactgtgc gagatggact    300
ttgtttactt actggggcca agggactctg gtcactgtc                            339

<210> SEQ ID NO 398
<211> LENGTH: 339
<212> TYPE: DNA
<213> ORGANISM: Artificial Sequence
<220> FEATURE:
<223> OTHER INFORMATION: Humanized hSC17.155 VH6

<400> SEQUENCE: 398
caggtgcagc tggtgcagtc tggggctgag gtgaagaagc ctggggcctc agtgaaggtt    60
tcctgcaagg catctggata caccttcaac agctactgga tgcactgggt gcgacaggcc    120
cctggacaag gcttgagtg gatgggagaa atccacccta atagtggtag cacaaactac     180
aacgagaagt tcaagggcag agtcaccatg accagggaca cgtccacgag cacagtctac    240
atggagctga gcagcctgag atctgaggac acggccgtgt attactgtgc gagatggact    300
ttgtttactt actggggcca agggactctg gtcactgtc                            339

<210> SEQ ID NO 399
<211> LENGTH: 348
<212> TYPE: DNA
<213> ORGANISM: Artificial Sequence
<220> FEATURE:
<223> OTHER INFORMATION: Humanized hSC17.161 VH1

<400> SEQUENCE: 399
gaggtgcagc tggtggaatc cggaggcggc ctggtgcaac tggaggatcc ctcaggctg     60 tcctgtgccg cttccggatt caccttctcc gatgcctgga tggactgggt gaggcaggcc    120
cctggcaaag gactggaatg ggtgggcgag atcaggtcca aacccaacaa ccacgccacc    180
tactacgccg agtccgtgaa gggcaggttc accatctcca gggacgactc caagaactcc    240
ctgtacctgc agatgaactc cctgaagacc gaggacaccg ccgtgtacta ctgcgctagg    300
accggcacct cctattgggg acagggcacc ctggtgaccg tgtcctcc                  348

<210> SEQ ID NO 400
<211> LENGTH: 218
<212> TYPE: PRT
<213> ORGANISM: Artificial Sequence
<220> FEATURE:
<223> OTHER INFORMATION: Humanized hSC17.200 light chain

<400> SEQUENCE: 400
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Tyr Asn
            20                  25                  30

Gly Ile Ser Tyr Met His Trp Tyr Gln Gln Lys Pro Gly Gln Ala Pro
        35                  40                  45

Arg Leu Leu Ile Tyr Ala Ala Ser Asn Val Gln Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Ile
                85                  90                  95

Glu Asp Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 401
<211> LENGTH: 444
<212> TYPE: PRT
<213> ORGANISM: Artificial Sequence
<220> FEATURE:
<223> OTHER INFORMATION: Humanized hSC17.200 heavy chain

<400> SEQUENCE: 401

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Ser
            20                  25                  30

Trp Ile Asn Trp Val Arg Gln Met Pro Gly Lys Gly Leu Glu Trp Met
        35                  40                  45

Gly Arg Ile Tyr Pro Gly Glu Gly Asp Thr Asn Tyr Ser Gly Asn Phe
    50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gly Leu Val Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140
```

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 402
<211> LENGTH: 218
<212> TYPE: PRT
<213> ORGANISM: Artificial Sequence
<220> FEATURE:
<223> OTHER INFORMATION: Humanized hSC17.200vL1 light chain

<400> SEQUENCE: 402

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Tyr Asp
            20                  25                  30

Gly Ile Ser Tyr Met His Trp Tyr Gln Gln Lys Pro Gly Gln Ala Pro
        35                  40                  45

Arg Leu Leu Ile Tyr Ala Ala Ser Asn Val Gln Ser Gly Ile Pro Ala
50                  55                  60

```
Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Ser Ile
                 85                  90                  95

Glu Asp Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 403
<211> LENGTH: 107
<212> TYPE: PRT
<213> ORGANISM: Homo sapiens
<220> FEATURE:
<221> NAME/KEY: MISC_FEATURE
<223> OTHER INFORMATION: Kappa light chain constant region

<400> SEQUENCE: 403

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 404
<211> LENGTH: 329
<212> TYPE: PRT
<213> ORGANISM: Homo sapiens
<220> FEATURE:
<221> NAME/KEY: MISC_FEATURE
<223> OTHER INFORMATION: IgG1 heavy chain constant region

<400> SEQUENCE: 404

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 405
<211> LENGTH: 11
<212> TYPE: PRT
<213> ORGANISM: Mus musculus
<220> FEATURE:
<221> NAME/KEY: MISC_FEATURE
<223> OTHER INFORMATION: hSC17.16 CDRL1

<400> SEQUENCE: 405

Arg Ala Ser Ala Asn Ile Asn Ser Asn Leu Val
1               5                   10

<210> SEQ ID NO 406
<211> LENGTH: 7
<212> TYPE: PRT
<213> ORGANISM: Mus musculus
<220> FEATURE:
<221> NAME/KEY: MISC_FEATURE
```

<223> OTHER INFORMATION: hSC17.16 CDRL2

<400> SEQUENCE: 406

Ala Ala Thr Asn Leu Ala Asp
1               5

<210> SEQ ID NO 407
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC17.16 CDRL3

<400> SEQUENCE: 407

Gln His Phe Trp Gly Thr Pro Arg Thr
1               5

<210> SEQ ID NO 408
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC17.16 CDRH1

<400> SEQUENCE: 408

Asp Tyr Asn Met Tyr
1               5

<210> SEQ ID NO 409
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.16 CDRH2

<400> SEQUENCE: 409

Glu Ile Asn Pro Asn Asn Gly Gly Thr Ala Tyr Asn Gln Lys Phe Arg
1               5                   10                  15

Gly

<210> SEQ ID NO 410
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC17.16 CDRH3

<400> SEQUENCE: 410

Tyr Asp Lys Gly Phe Asp Tyr
1               5

<210> SEQ ID NO 411
<211> LENGTH: 10
<212> TYPE: PRT
<213> ORGANISM: Mus musculus
<220> FEATURE:
<221> NAME/KEY: MISC_FEATURE
<223> OTHER INFORMATION: hSC17.17 CDRL1

<400> SEQUENCE: 411

Ser Ala Ser Ser Ser Val Ser Tyr Met His
1               5                   10

<210> SEQ ID NO 412
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC17.17 CDRL2

<400> SEQUENCE: 412

Asp Thr Ser Lys Leu Pro Ser
1               5

<210> SEQ ID NO 413
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC17.17 CDRL3

<400> SEQUENCE: 413

Gln Gln Trp Ser Ser Thr Pro Pro Thr
1               5

<210> SEQ ID NO 414
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC17.17 CDRH1

<400> SEQUENCE: 414

Asp Tyr Asn Met His
1               5

<210> SEQ ID NO 415
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.17 CDRH2

<400> SEQUENCE: 415

Glu Ile Asn Pro Asn Ile Gly Gly Thr Gly Tyr Asn Gln Lys Phe Lys
1               5                   10                  15

Gly

<210> SEQ ID NO 416
<211> LENGTH: 11
<212> TYPE: PRT
<213> ORGANISM: Mus musculus
<220> FEATURE:
<221> NAME/KEY: MISC_FEATURE
<223> OTHER INFORMATION: hSC17.17 CDRH3

<400> SEQUENCE: 416

Thr Tyr Ser Tyr Tyr Ser Tyr Glu Phe Ala Tyr
1               5                   10

<210> SEQ ID NO 417
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.24 CDRL1

<400> SEQUENCE: 417

Lys Ser Ser Gln Ser Leu Leu Tyr Ser Ser Asn Gln Lys Ser Tyr Leu
1               5                   10                  15
Ala

<210> SEQ ID NO 418
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC17.24 CDRL2

<400> SEQUENCE: 418

Trp Ala Ser Thr Arg Glu Ser
1               5

<210> SEQ ID NO 419
<211> LENGTH: 8
<212> TYPE: PRT
<213> ORGANISM: Mus musculus
<220> FEATURE:
<221> NAME/KEY: MISC_FEATURE
<223> OTHER INFORMATION: hSC17.24 CDRL3

<400> SEQUENCE: 419

Lys Gln Ser Tyr Asn Leu Arg Thr
1               5

<210> SEQ ID NO 420
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC17.24 CDRH1

<400> SEQUENCE: 420

Asp His Thr Ile His
1               5

<210> SEQ ID NO 421
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.24 CDRH2

<400> SEQUENCE: 421

Tyr Ile Tyr Pro Arg Asp Gly Ser Thr Lys Tyr Asn Glu Glu Phe Lys
1               5                   10                  15
Gly

<210> SEQ ID NO 422
<211> LENGTH: 8
<212> TYPE: PRT
<213> ORGANISM: Mus musculus
<220> FEATURE:
<221> NAME/KEY: MISC_FEATURE
<223> OTHER INFORMATION: hSC17.24 CDRH3

<400> SEQUENCE: 422

Ser Tyr Ser Asn Tyr Phe Asp Tyr

-continued

<210> SEQ ID NO 423
<211> LENGTH: 11
<212> TYPE: PRT
<213> ORGANISM: Mus musculus
<220> FEATURE:
<221> NAME/KEY: MISC_FEATURE
<223> OTHER INFORMATION: hSC17.28 CDRL1

<400> SEQUENCE: 423

Arg Ala Ser Gln Ser Ile Gly Thr Ser Ile His
1               5                   10

<210> SEQ ID NO 424
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC17.28 CDRL2

<400> SEQUENCE: 424

Tyr Ala Ser Glu Ser Ile Ser
1               5

<210> SEQ ID NO 425
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC17.28 CDRL3

<400> SEQUENCE: 425

Gln Gln Ser Asn Ser Trp Pro Leu Thr
1               5

<210> SEQ ID NO 426
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC17.28 CDRH1

<400> SEQUENCE: 426

Arg Ser Tyr Ile His
1               5

<210> SEQ ID NO 427
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.28 CDRH2

<400> SEQUENCE: 427

Tyr Ile Ser Ser Gly Ser Gly Gly Thr Thr Tyr Asn Gln Lys Phe Lys
1               5                   10                  15

Gly

<210> SEQ ID NO 428
<211> LENGTH: 8
<212> TYPE: PRT
<213> ORGANISM: Mus musculus

```
<220> FEATURE:
<221> NAME/KEY: MISC_FEATURE
<223> OTHER INFORMATION: hSC17.28 CDRH3

<400> SEQUENCE: 428

Gly Gly Val Arg Tyr Phe Asp Val
1               5

<210> SEQ ID NO 429
<211> LENGTH: 11
<212> TYPE: PRT
<213> ORGANISM: Mus musculus
<220> FEATURE:
<221> NAME/KEY: MISC_FEATURE
<223> OTHER INFORMATION: hSC17.34 CDRL1

<400> SEQUENCE: 429

Lys Ala Ser Gln Asp Ile Asn Ser Tyr Leu Ser
1               5                   10

<210> SEQ ID NO 430
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC17.34 CDRL2

<400> SEQUENCE: 430

Arg Ala Asn Arg Leu Val Asp
1               5

<210> SEQ ID NO 431
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC17.34 CDRL3

<400> SEQUENCE: 431

Leu Gln Tyr Asp Glu Phe Pro Pro Thr
1               5

<210> SEQ ID NO 432
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC17.34 CDRH1

<400> SEQUENCE: 432

Asp Tyr Asn Met Asp
1               5

<210> SEQ ID NO 433
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.34 CDRH2

<400> SEQUENCE: 433

Tyr Ile Tyr Pro Asp Asn Gly Gly Ala Gly Tyr Asn Gln Lys Phe Lys
1               5                   10                  15
```

Gly

<210> SEQ ID NO 434
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC17.34 CDRH3

<400> SEQUENCE: 434

Ser Ile Thr Thr Ala Trp Phe Ala Tyr
1               5

<210> SEQ ID NO 435
<211> LENGTH: 11
<212> TYPE: PRT
<213> ORGANISM: Mus musculus
<220> FEATURE:
<221> NAME/KEY: MISC_FEATURE
<223> OTHER INFORMATION: hSC17.46 CDRL1

<400> SEQUENCE: 435

Lys Ala Ser Gln Ser Val Asn Asn Asp Val Ala
1               5                   10

<210> SEQ ID NO 436
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC17.46 CDRL2

<400> SEQUENCE: 436

Tyr Ala Ser Asn Arg Tyr Thr
1               5

<210> SEQ ID NO 437
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC17.46 CDRL3

<400> SEQUENCE: 437

Gln Gln Asp Tyr Ser Ser Pro Arg Thr
1               5

<210> SEQ ID NO 438
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC17.46 CDRH1

<400> SEQUENCE: 438

Ser Tyr Trp Ile Asn
1               5

<210> SEQ ID NO 439
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.46 CDRH2

<400> SEQUENCE: 439

Asn Ile Phe Pro Asp Thr Thr Thr Thr Asn Tyr Asn Glu Lys Phe Lys
1               5                   10                  15
Gly

<210> SEQ ID NO 440
<211> LENGTH: 12
<212> TYPE: PRT
<213> ORGANISM: Mus musculus
<220> FEATURE:
<221> NAME/KEY: MISC_FEATURE
<223> OTHER INFORMATION: hSC17.46 CDRH3

<400> SEQUENCE: 440

Glu Tyr Tyr Asp Gly Thr Tyr Asp Ala Met Asp Tyr
1               5                   10

<210> SEQ ID NO 441
<211> LENGTH: 15
<212> TYPE: PRT
<213> ORGANISM: Mus musculus
<220> FEATURE:
<221> NAME/KEY: MISC_FEATURE
<223> OTHER INFORMATION: hSC17.151 CDRL1

<400> SEQUENCE: 441

Arg Ala Ser Glu Ser Val Asp Ser Tyr Gly Asn Ser Phe Met His
1               5                   10                  15

<210> SEQ ID NO 442
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC17.151 CDRL2

<400> SEQUENCE: 442

Arg Ala Ser Asn Leu Glu Ser
1               5

<210> SEQ ID NO 443
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC17.151 CDRL3

<400> SEQUENCE: 443

Gln Gln Ser His Glu Asp Pro Tyr Thr
1               5

<210> SEQ ID NO 444
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC17.151 CDRH1

<400> SEQUENCE: 444

Ser Tyr Trp Met His
1               5

```
<210> SEQ ID NO 445
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.151 CDRH2

<400> SEQUENCE: 445

Ala Ile Tyr Pro Gly Lys Ser Asp Thr Thr Tyr Asn Gln Lys Phe Lys
1               5                   10                  15

Gly

<210> SEQ ID NO 446
<211> LENGTH: 8
<212> TYPE: PRT
<213> ORGANISM: Mus musculus
<220> FEATURE:
<221> NAME/KEY: MISC_FEATURE
<223> OTHER INFORMATION: hSC17.151 CDRH3

<400> SEQUENCE: 446

Ser Gly Lys Gly Tyr Phe Ala Tyr
1               5

<210> SEQ ID NO 447
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.155 and hSC17.155vH1-6 CDRL1

<400> SEQUENCE: 447

Lys Ser Ser Gln Ser Leu Leu Tyr Ser Ser Asn Gln Lys Asn Tyr Leu
1               5                   10                  15

Ala

<210> SEQ ID NO 448
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC17.155 and hSC17.155vH1-6 CDRL2

<400> SEQUENCE: 448

Trp Ala Ser Thr Arg Lys Ser
1               5

<210> SEQ ID NO 449
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC17.155 and hSC17.155vH1-6 CDRL3

<400> SEQUENCE: 449

His Gln Tyr Tyr Ser Tyr Pro Leu Thr
1               5

<210> SEQ ID NO 450
<211> LENGTH: 5
<212> TYPE: PRT
<213> ORGANISM: Mus musculus
```

```
<220> FEATURE:
<221> NAME/KEY: MISC_FEATURE
<223> OTHER INFORMATION: hSC17.155 and hSC17.155vH1, vH2 and vH4-6 CDRH1

<400> SEQUENCE: 450

Ser Tyr Trp Met His
1               5

<210> SEQ ID NO 451
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.155 and hSC17.155vH1-3 CDRH2

<400> SEQUENCE: 451

Glu Ile His Pro Asn Asn Gly Ser Thr Asn Tyr Asn Glu Lys Phe Lys
1               5                   10                  15

Gly

<210> SEQ ID NO 452
<211> LENGTH: 6
<212> TYPE: PRT
<213> ORGANISM: Mus musculus
<220> FEATURE:
<221> NAME/KEY: MISC_FEATURE
<223> OTHER INFORMATION: hSC17.155 and hSC17.155vH1-6 CDRH3

<400> SEQUENCE: 452

Trp Thr Leu Phe Thr Tyr
1               5

<210> SEQ ID NO 453
<211> LENGTH: 16
<212> TYPE: PRT
<213> ORGANISM: Mus musculus
<220> FEATURE:
<221> NAME/KEY: MISC_FEATURE
<223> OTHER INFORMATION: hSC17.156 CDRL1

<400> SEQUENCE: 453

Arg Ser Ser Gln Ser Ile Val His Ser Asn Gly Asn Thr Tyr Leu Glu
1               5                   10                  15

<210> SEQ ID NO 454
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC17.156 CDRL2

<400> SEQUENCE: 454

Lys Val Ser Asn Arg Phe Ser
1               5

<210> SEQ ID NO 455
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC17.156 CDRL3

<400> SEQUENCE: 455

Phe Gln Gly Ser His Val Pro Pro Thr
```

-continued

```
<210> SEQ ID NO 456
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC17.156 CDRH1

<400> SEQUENCE: 456

Thr Ser Gly Met Gly Val Ser
1               5

<210> SEQ ID NO 457
<211> LENGTH: 16
<212> TYPE: PRT
<213> ORGANISM: Mus musculus
<220> FEATURE:
<221> NAME/KEY: MISC_FEATURE
<223> OTHER INFORMATION: hSC17.156 CDRH2

<400> SEQUENCE: 457

His Ile Phe Trp Asp Asp Asp Lys Trp Tyr Asn Pro Ser Leu Lys Ser
1               5                   10                  15

<210> SEQ ID NO 458
<211> LENGTH: 8
<212> TYPE: PRT
<213> ORGANISM: Mus musculus
<220> FEATURE:
<221> NAME/KEY: MISC_FEATURE
<223> OTHER INFORMATION: hSC17.156 CDRH3

<400> SEQUENCE: 458

Phe Tyr Gly Leu Tyr Phe Ala Tyr
1               5

<210> SEQ ID NO 459
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.161 and hSC17.161vL1 CDRL1

<400> SEQUENCE: 459

Glu Ser Ser Gln Ser Leu Leu Tyr Asn Ser Asn Gln Lys Asn Tyr Leu
1               5                   10                  15
Ala

<210> SEQ ID NO 460
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC17.161 and hSC17.161vL1 CDRL2

<400> SEQUENCE: 460

Trp Ala Ser Thr Arg Glu Ser
1               5

<210> SEQ ID NO 461
<211> LENGTH: 9
<212> TYPE: PRT
<213> ORGANISM: Mus musculus
```

```
<220> FEATURE:
<221> NAME/KEY: MISC_FEATURE
<223> OTHER INFORMATION: hSC17.161 and hSC17.161vL1 CDRL3

<400> SEQUENCE: 461

Gln Gln Tyr Phe Asn Tyr Pro Leu Thr
1               5

<210> SEQ ID NO 462
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC17.161 and hSC17.161vL1 CDRH1

<400> SEQUENCE: 462

Asp Ala Trp Met Asp
1               5

<210> SEQ ID NO 463
<211> LENGTH: 19
<212> TYPE: PRT
<213> ORGANISM: Mus musculus
<220> FEATURE:
<221> NAME/KEY: MISC_FEATURE
<223> OTHER INFORMATION: hSC17.161 and hSC17.161vL1 CDRH2

<400> SEQUENCE: 463

Glu Ile Arg Ser Lys Pro Asn Asn His Ala Thr Tyr Tyr Ala Glu Ser
1               5                   10                  15

Val Lys Gly

<210> SEQ ID NO 464
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC17.161 and hSC17.161vL1 CDRH3

<400> SEQUENCE: 464

Thr Gly Thr Ser Tyr
1               5

<210> SEQ ID NO 465
<211> LENGTH: 15
<212> TYPE: PRT
<213> ORGANISM: Mus musculus
<220> FEATURE:
<221> NAME/KEY: MISC_FEATURE
<223> OTHER INFORMATION: hSC17.200 CDRL1

<400> SEQUENCE: 465

Arg Ala Ser Gln Ser Val Asp Tyr Asn Gly Ile Ser Tyr Met His
1               5                   10                  15

<210> SEQ ID NO 466
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC17.200 and hSC17.200vL1 CDRL2

<400> SEQUENCE: 466

Ala Ala Ser Asn Val Gln Ser
```

```
<210> SEQ ID NO 467
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC17.200 and hSC17.200vL1 CDRL3

<400> SEQUENCE: 467

Gln Gln Ser Ile Glu Asp Pro Pro Thr
1               5

<210> SEQ ID NO 468
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC17.200 and hSC17.200vL1 CDRH1

<400> SEQUENCE: 468

Ser Ser Trp Ile Asn
1               5

<210> SEQ ID NO 469
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.200 and hSC17.200vL1 CDRH2

<400> SEQUENCE: 469

Arg Ile Tyr Pro Gly Glu Gly Asp Thr Asn Tyr Ser Gly Asn Phe Glu
1               5                   10                  15

Gly

<210> SEQ ID NO 470
<211> LENGTH: 6
<212> TYPE: PRT
<213> ORGANISM: Mus musculus
<220> FEATURE:
<221> NAME/KEY: MISC_FEATURE
<223> OTHER INFORMATION: hSC17.200 and hSC17.200vL1 CDRH3

<400> SEQUENCE: 470

Gly Leu Val Met Asp Tyr
1               5

<210> SEQ ID NO 471
<211> LENGTH: 30
<212> TYPE: PRT
<213> ORGANISM: Homo sapiens
<220> FEATURE:
<221> NAME/KEY: MISC_FEATURE
<223> OTHER INFORMATION: hSC17.155vH1 FR1

<400> SEQUENCE: 471

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp
            20                  25                  30

<210> SEQ ID NO 472
```

```
<211> LENGTH: 30
<212> TYPE: PRT
<213> ORGANISM: Homo sapiens
<220> FEATURE:
<221> NAME/KEY: MISC_FEATURE
<223> OTHER INFORMATION: hSC17.155vH2 FR1

<400> SEQUENCE: 472

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 473
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC17.155vH3 CDRH1

<400> SEQUENCE: 473

Tyr Tyr Trp Met His
1               5

<210> SEQ ID NO 474
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.155vH4 CDRH2

<400> SEQUENCE: 474

Glu Ile His Pro Asn Asp Gly Ser Thr Asn Tyr Asn Glu Lys Phe Lys
1               5                   10                  15

Gly

<210> SEQ ID NO 475
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.155vH5 CDRH2

<400> SEQUENCE: 475

Glu Ile His Pro Asn Gly Gly Ser Thr Asn Tyr Asn Glu Lys Phe Lys
1               5                   10                  15

Gly

<210> SEQ ID NO 476
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC17.155vH6 CDRH2

<400> SEQUENCE: 476

Glu Ile His Pro Asn Ser Gly Ser Thr Asn Tyr Asn Glu Lys Phe Lys
1               5                   10                  15

Gly

<210> SEQ ID NO 477
```

```
<211> LENGTH: 30
<212> TYPE: PRT
<213> ORGANISM: Homo sapiens
<220> FEATURE:
<221> NAME/KEY: MISC_FEATURE
<223> OTHER INFORMATION: hSC17.161vH1 FR1

<400> SEQUENCE: 477

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 478
<211> LENGTH: 14
<212> TYPE: PRT
<213> ORGANISM: Homo sapiens
<220> FEATURE:
<221> NAME/KEY: MISC_FEATURE
<223> OTHER INFORMATION: hSC17.161vH1 FR2

<400> SEQUENCE: 478

Trp Val Arg Gln Ala Pro Gly Lys Gly Leu Glu Trp Val Gly
1               5                   10

<210> SEQ ID NO 479
<211> LENGTH: 32
<212> TYPE: PRT
<213> ORGANISM: Homo sapiens
<220> FEATURE:
<221> NAME/KEY: MISC_FEATURE
<223> OTHER INFORMATION: hSC17.161vH1 FR3

<400> SEQUENCE: 479

Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys Ala Arg
            20                  25                  30

<210> SEQ ID NO 480
<211> LENGTH: 15
<212> TYPE: PRT
<213> ORGANISM: Mus musculus
<220> FEATURE:
<221> NAME/KEY: MISC_FEATURE
<223> OTHER INFORMATION: hSC17.200vL1 CDRL1

<400> SEQUENCE: 480

Arg Ala Ser Gln Ser Val Asp Tyr Asp Gly Ile Ser Tyr Met His
1               5                   10                  15

<210> SEQ ID NO 481

<400> SEQUENCE: 481

000

<210> SEQ ID NO 482

<400> SEQUENCE: 482

000

<210> SEQ ID NO 483

<400> SEQUENCE: 483
```

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500
<211> LENGTH: 329
<212> TYPE: PRT
<213> ORGANISM: Homo sapiens
<220> FEATURE:
<221> NAME/KEY: MISC_FEATURE
<223> OTHER INFORMATION: C220S IgG1 heavy constant region

<400> SEQUENCE: 500

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 501
<211> LENGTH: 328
<212> TYPE: PRT
<213> ORGANISM: Homo sapiens
<220> FEATURE:
<221> NAME/KEY: MISC_FEATURE
<223> OTHER INFORMATION: C220delta IgG1 heavy constant region

<400> SEQUENCE: 501

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205
```

Ala Leu Pro Ala Pro Ile Glu Lys Thr Ile Ser Lys Ala Lys Gly Gln
            210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 502
<211> LENGTH: 106
<212> TYPE: PRT
<213> ORGANISM: Homo sapiens
<220> FEATURE:
<221> NAME/KEY: MISC_FEATURE
<223> OTHER INFORMATION: C214delta Kappa light chain constant region

<400> SEQUENCE: 502

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu
            100                 105

<210> SEQ ID NO 503
<211> LENGTH: 107
<212> TYPE: PRT
<213> ORGANISM: Homo sapiens
<220> FEATURE:
<221> NAME/KEY: MISC_FEATURE
<223> OTHER INFORMATION: C214S Kappa light chain constant region

<400> SEQUENCE: 503

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Ser
            100                 105

<210> SEQ ID NO 504
<211> LENGTH: 105
<212> TYPE: PRT
<213> ORGANISM: Homo sapiens
<220> FEATURE:
<221> NAME/KEY: MISC_FEATURE
<223> OTHER INFORMATION: Lambda light chain constant region

<400> SEQUENCE: 504

Gln Pro Lys Ala Asn Pro Thr Val Thr Leu Phe Pro Pro Ser Ser Glu
 1               5                  10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Gly Ser Pro Val
            35                  40                  45

Lys Ala Gly Val Glu Thr Thr Lys Pro Ser Lys Gln Ser Asn Asn Lys
50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105

<210> SEQ ID NO 505
<211> LENGTH: 104
<212> TYPE: PRT
<213> ORGANISM: Homo sapiens
<220> FEATURE:
<221> NAME/KEY: MISC_FEATURE
<223> OTHER INFORMATION: C214delta Lambda light chain constant region

<400> SEQUENCE: 505

Gln Pro Lys Ala Asn Pro Thr Val Thr Leu Phe Pro Pro Ser Ser Glu
 1               5                  10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Gly Ser Pro Val
            35                  40                  45

Lys Ala Gly Val Glu Thr Thr Lys Pro Ser Lys Gln Ser Asn Asn Lys
50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Ser
            100

<210> SEQ ID NO 506
<211> LENGTH: 105
<212> TYPE: PRT
<213> ORGANISM: Homo sapiens
```

<220> FEATURE:
<221> NAME/KEY: MISC_FEATURE
<223> OTHER INFORMATION: C214S Lambda light chain constant region

<400> SEQUENCE: 506

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Thr Lys Pro Ser Lys Gln Ser Asn Asn Lys
50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Ser Ser
            100                 105

<210> SEQ ID NO 507
<211> LENGTH: 214
<212> TYPE: PRT
<213> ORGANISM: Mus musculus
<220> FEATURE:
<221> NAME/KEY: MISC_FEATURE
<223> OTHER INFORMATION: SC16.56 ss1 and ss2 full length light chain

<400> SEQUENCE: 507

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
            20                  25                  30

Val Val Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Tyr Thr Ser Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 508
<211> LENGTH: 447
<212> TYPE: PRT
<213> ORGANISM: Mus musculus
<220> FEATURE:
<221> NAME/KEY: MISC_FEATURE
<223> OTHER INFORMATION: SC16.56 ss3 and ss4 full length heavy chain

<400> SEQUENCE: 508

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ile Gly Asp Ser Ser Pro Ser Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
```

```
                355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
                435                 440                 445

<210> SEQ ID NO 509
<211> LENGTH: 447
<212> TYPE: PRT
<213> ORGANISM: Mus musculus
<220> FEATURE:
<221> NAME/KEY: MISC_FEATURE
<223> OTHER INFORMATION: SC16.56 ss1 full length heavy chain

<400> SEQUENCE: 509

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Gly Met Asn Trp Val Arg Gln Ala Pro Gly Gln Gly Leu Glu Trp Met
        35                  40                  45
Gly Trp Ile Asn Thr Tyr Thr Gly Glu Pro Thr Tyr Ala Asp Asp Phe
    50                  55                  60
Lys Gly Arg Val Thr Met Thr Thr Asp Thr Ser Thr Ser Thr Ala Tyr
65                  70                  75                  80
Met Glu Leu Arg Ser Leu Arg Ser Asp Thr Ala Val Tyr Tyr Cys
                85                  90                  95
Ala Arg Ile Gly Asp Ser Ser Pro Ser Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Ser Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 510
<211> LENGTH: 446
<212> TYPE: PRT
<213> ORGANISM: Mus musculus
<220> FEATURE:
<221> NAME/KEY: MISC_FEATURE
<223> OTHER INFORMATION: SC16.56 ss2 full length heavy chain

<400> SEQUENCE: 510

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ile Gly Asp Ser Ser Pro Ser Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190
```

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Asp Glu Leu Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly
    435                 440                 445

<210> SEQ ID NO 511
<211> LENGTH: 213
<212> TYPE: PRT
<213> ORGANISM: Mus musculus
<220> FEATURE:
<221> NAME/KEY: MISC_FEATURE
<223> OTHER INFORMATION: SC16.56 ss3 full length light chain

<400> SEQUENCE: 511

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
            20                  25                  30

Val Val Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Tyr Thr Ser Pro Trp
            85                  90                  95

Thr Phe Gly Gln Gly Thr Lys Leu Glu Ile Lys Arg Thr Val Ala Ala

```
                100             105             110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
        210

<210> SEQ ID NO 512
<211> LENGTH: 214
<212> TYPE: PRT
<213> ORGANISM: Mus musculus
<220> FEATURE:
<221> NAME/KEY: MISC_FEATURE
<223> OTHER INFORMATION: SC16.56 ss4 full length light chain

<400> SEQUENCE: 512

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
            20                  25                  30

Val Val Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Tyr Thr Ser Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser
        210

<210> SEQ ID NO 513
<211> LENGTH: 218
```

```
<212> TYPE: PRT
<213> ORGANISM: Mus musculus
<220> FEATURE:
<221> NAME/KEY: MISC_FEATURE
<223> OTHER INFORMATION: SC17.200 ss1 and ss2 full length light chain

<400> SEQUENCE: 513
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Tyr Asn
            20                  25                  30

Gly Ile Ser Tyr Met His Trp Tyr Gln Gln Lys Pro Gly Gln Ala Pro
        35                  40                  45

Arg Leu Leu Ile Tyr Ala Ala Ser Asn Val Gln Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Ile
                85                  90                  95

Glu Asp Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

```
<210> SEQ ID NO 514
<211> LENGTH: 444
<212> TYPE: PRT
<213> ORGANISM: Mus musculus
<220> FEATURE:
<221> NAME/KEY: MISC_FEATURE
<223> OTHER INFORMATION: SC17.200 ss3 and ss4 full length heavy chain

<400> SEQUENCE: 514
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Ser
            20                  25                  30

Trp Ile Asn Trp Val Arg Gln Met Pro Gly Lys Gly Leu Glu Trp Met
        35                  40                  45

Gly Arg Ile Tyr Pro Gly Glu Gly Asp Thr Asn Tyr Ser Gly Asn Phe
    50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

```
Thr Arg Gly Leu Val Met Asp Tyr Trp Gly Gln Gly Thr Leu Val Thr
                100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 515
<211> LENGTH: 444
<212> TYPE: PRT
<213> ORGANISM: Mus musculus
<220> FEATURE:
<221> NAME/KEY: MISC_FEATURE
<223> OTHER INFORMATION: SC17.200 ss1 full length heavy chain

<400> SEQUENCE: 515

Glu Val Gln Leu Val Gln Ser Gly Ala Glu Val Lys Lys Pro Gly Glu
1               5                   10                  15
```

-continued

Ser Leu Lys Ile Ser Cys Lys Gly Ser Gly Tyr Ser Phe Thr Ser Ser
                20                  25                  30

Trp Ile Asn Trp Val Arg Gln Met Pro Gly Lys Gly Leu Glu Trp Met
            35                  40                  45

Gly Arg Ile Tyr Pro Gly Glu Gly Asp Thr Asn Tyr Ser Gly Asn Phe
50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gly Leu Val Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Ser Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 516
<211> LENGTH: 443
<212> TYPE: PRT
<213> ORGANISM: Mus musculus
<220> FEATURE:
<221> NAME/KEY: MISC_FEATURE
<223> OTHER INFORMATION: SC17.200 ss2 full length heavy chain

<400> SEQUENCE: 516

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Ser
            20                  25                  30

Trp Ile Asn Trp Val Arg Gln Met Pro Gly Lys Gly Leu Glu Trp Met
        35                  40                  45

Gly Arg Ile Tyr Pro Gly Glu Gly Asp Thr Asn Tyr Ser Gly Asn Phe
    50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gly Leu Val Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

```
Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
            435                 440

<210> SEQ ID NO 517
<211> LENGTH: 217
<212> TYPE: PRT
<213> ORGANISM: Mus musculus
<220> FEATURE:
<221> NAME/KEY: MISC_FEATURE
<223> OTHER INFORMATION: SC17.200 ss3 full length light chain

<400> SEQUENCE: 517

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Tyr Asn
            20                  25                  30

Gly Ile Ser Tyr Met His Trp Tyr Gln Gln Lys Pro Gly Gln Ala Pro
        35                  40                  45

Arg Leu Leu Ile Tyr Ala Ala Ser Asn Val Gln Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Ile
                85                  90                  95

Glu Asp Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu
    210                 215

<210> SEQ ID NO 518
<211> LENGTH: 218
<212> TYPE: PRT
<213> ORGANISM: Mus musculus
<220> FEATURE:
<221> NAME/KEY: MISC_FEATURE
```

<223> OTHER INFORMATION: SC17.200 ss4 full length light chain

<400> SEQUENCE: 518

| Glu | Ile | Val | Leu | Thr | Gln | Ser | Pro | Ala | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Arg | Ala | Ser | Gln | Ser | Val | Asp | Tyr | Asn |
| | | | 20 | | | | | 25 | | | | | 30 | | |

| Gly | Ile | Ser | Tyr | Met | His | Trp | Tyr | Gln | Gln | Lys | Pro | Gly | Gln | Ala | Pro |
| | | 35 | | | | | 40 | | | | | 45 | | | |

| Arg | Leu | Leu | Ile | Tyr | Ala | Ala | Ser | Asn | Val | Gln | Ser | Gly | Ile | Pro | Ala |
| | 50 | | | | | 55 | | | | | 60 | | | | |

| Arg | Phe | Ser | Gly | Ser | Gly | Ser | Gly | Thr | Asp | Phe | Thr | Leu | Thr | Ile | Ser |
| 65 | | | | | 70 | | | | | 75 | | | | | 80 |

| Ser | Leu | Glu | Pro | Glu | Asp | Phe | Ala | Val | Tyr | Tyr | Cys | Gln | Gln | Ser | Ile |
| | | | | 85 | | | | | 90 | | | | | 95 | |

| Glu | Asp | Pro | Pro | Thr | Phe | Gly | Gly | Gly | Thr | Lys | Val | Glu | Ile | Lys | Arg |
| | | | 100 | | | | | 105 | | | | | 110 | | |

| Thr | Val | Ala | Ala | Pro | Ser | Val | Phe | Ile | Phe | Pro | Pro | Ser | Asp | Glu | Gln |
| | | | 115 | | | | | 120 | | | | | 125 | | |

| Leu | Lys | Ser | Gly | Thr | Ala | Ser | Val | Val | Cys | Leu | Leu | Asn | Asn | Phe | Tyr |
| | 130 | | | | | 135 | | | | | 140 | | | | |

| Pro | Arg | Glu | Ala | Lys | Val | Gln | Trp | Lys | Val | Asp | Asn | Ala | Leu | Gln | Ser |
| 145 | | | | | 150 | | | | | 155 | | | | | 160 |

| Gly | Asn | Ser | Gln | Glu | Ser | Val | Thr | Glu | Gln | Asp | Ser | Lys | Asp | Ser | Thr |
| | | | | 165 | | | | | 170 | | | | | 175 | |

| Tyr | Ser | Leu | Ser | Ser | Thr | Leu | Thr | Leu | Ser | Lys | Ala | Asp | Tyr | Glu | Lys |
| | | | 180 | | | | | 185 | | | | | 190 | | |

| His | Lys | Val | Tyr | Ala | Cys | Glu | Val | Thr | His | Gln | Gly | Leu | Ser | Ser | Pro |
| | | | 195 | | | | | 200 | | | | | 205 | | |

| Val | Thr | Lys | Ser | Phe | Asn | Arg | Gly | Glu | Ser |
| | 210 | | | | | 215 | | | |

<210> SEQ ID NO 519
<211> LENGTH: 106
<212> TYPE: PRT
<213> ORGANISM: Artificial Sequence
<220> FEATURE:
<223> OTHER INFORMATION: hSC16.13 light chain variable region

<400> SEQUENCE: 519

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Ser | Ala | Ser | Ser | Val | Ser | Tyr | Met |
| | | | 20 | | | | | 25 | | | | | 30 | |

| Tyr | Trp | Tyr | Gln | Gln | Lys | Pro | Gly | Lys | Ala | Pro | Lys | Leu | Leu | Ile | Tyr |
| | | | 35 | | | | | 40 | | | | | 45 | | |

| Leu | Thr | Ser | Asn | Leu | Ala | Ser | Gly | Val | Pro | Ser | Arg | Phe | Ser | Gly | Ser |
| | 50 | | | | | 55 | | | | | 60 | | | | |

| Gly | Ser | Gly | Thr | Asp | Phe | Thr | Leu | Thr | Ile | Ser | Ser | Leu | Gln | Pro | Glu |
| 65 | | | | | 70 | | | | | 75 | | | | | 80 |

| Asp | Phe | Ala | Thr | Tyr | Tyr | Cys | Gln | Gln | Trp | Arg | Ser | Asn | Pro | Phe | Thr |
| | | | | 85 | | | | | 90 | | | | | 95 | |

| Phe | Gly | Gln | Gly | Thr | Lys | Leu | Glu | Ile | Lys |
| | | | 100 | | | | | 105 | |

<210> SEQ ID NO 520

```
<211> LENGTH: 107
<212> TYPE: PRT
<213> ORGANISM: Artificial Sequence
<220> FEATURE:
<223> OTHER INFORMATION: hSC16.15 light chain variable region

<400> SEQUENCE: 520

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Asn Ile Tyr Tyr Asn
            20                  25                  30

Leu Ala Trp Tyr Gln Gln Lys Pro Gly Lys Ala Pro Lys Leu Leu Ile
        35                  40                  45

Tyr Thr Ala Asn Ser Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Lys Gln Ala Tyr Asp Val Pro Pro
                85                  90                  95

Thr Phe Gly Gly Gly Thr Lys Leu Glu Ile Lys
            100                 105

<210> SEQ ID NO 521
<211> LENGTH: 106
<212> TYPE: PRT
<213> ORGANISM: Artificial Sequence
<220> FEATURE:
<223> OTHER INFORMATION: hSC16.25 light chain variable region

<400> SEQUENCE: 521

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Val Ser Tyr Met
            20                  25                  30

His Trp Tyr Gln Gln Lys Pro Asp Gln Ser Pro Lys Leu Leu Ile Lys
        35                  40                  45

Asp Ser Ser Lys Leu Ala Ser Gly Val Pro Ser Arg Phe Ser Gly Ser
    50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Ile Lys
            100                 105

<210> SEQ ID NO 522
<211> LENGTH: 107
<212> TYPE: PRT
<213> ORGANISM: Artificial Sequence
<220> FEATURE:
<223> OTHER INFORMATION: hSC16.34 light chain variable region

<400> SEQUENCE: 522

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Val Pro Lys Leu Leu Ile
        35                  40                  45
```

Tyr Tyr Ala Ser Asn Arg Tyr Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Asp Tyr Ser Ser Pro Trp
                85                  90                  95

Thr Phe Gly Gly Gly Thr Lys Val Glu Ile Lys
            100                 105

<210> SEQ ID NO 523
<211> LENGTH: 107
<212> TYPE: PRT
<213> ORGANISM: Artificial Sequence
<220> FEATURE:
<223> OTHER INFORMATION: hSC16.56 light chain variable region

<400> SEQUENCE: 523

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
                20                  25                  30

Val Val Trp Tyr Gln Gln Lys Pro Gly Gln Ala Pro Arg Leu Leu Ile
            35                  40                  45

Tyr Tyr Ala Ser Asn Arg Tyr Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Tyr Thr Ser Pro Trp
                85                  90                  95

Thr Phe Gly Gln Gly Thr Lys Leu Glu Ile Lys
            100                 105

<210> SEQ ID NO 524
<211> LENGTH: 124
<212> TYPE: PRT
<213> ORGANISM: Artificial Sequence
<220> FEATURE:
<223> OTHER INFORMATION: hSC16.13 heavy chain variable region

<400> SEQUENCE: 524

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Gly Trp Ile Arg Gln Pro Pro Gly Lys Ala Leu Glu
            35                  40                  45

Trp Leu Ala His Ile Trp Trp Asp Asp Val Lys Arg Tyr Ser Pro Ser
        50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Val Ser Phe Asn Asp Val Val Ser Ala Met Asp
                100                 105                 110

Tyr Trp Gly Gln Gly Thr Leu Val Thr Val Ser Ser
            115                 120

<210> SEQ ID NO 525

```
<211> LENGTH: 117
<212> TYPE: PRT
<213> ORGANISM: Artificial Sequence
<220> FEATURE:
<223> OTHER INFORMATION: hSC16.15 heavy chain variable region

<400> SEQUENCE: 525
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Trp Ile His Trp Ile Arg Gln Ala Pro Gly Gln Gly Leu Glu Trp Met
        35                  40                  45

Gly Tyr Ile Asn Pro Thr Thr Val Tyr Thr Glu Phe Asn Gln Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Asn Phe Phe Asp Tyr Trp Gly Gln Gly Thr Thr
            100                 105                 110

Val Thr Val Ser Ser
        115

```
<210> SEQ ID NO 526
<211> LENGTH: 124
<212> TYPE: PRT
<213> ORGANISM: Artificial Sequence
<220> FEATURE:
<223> OTHER INFORMATION: hSC16.25 heavy chain variable region

<400> SEQUENCE: 526
```

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Thr Asp Ile Trp Trp Asp Asp Asn Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Val Asn Tyr Tyr Asp Pro Tyr Tyr Ala Met Asp
            100                 105                 110

Tyr Trp Gly Gln Gly Thr Leu Val Thr Val Ser Ser
        115                 120

```
<210> SEQ ID NO 527
<211> LENGTH: 118
<212> TYPE: PRT
<213> ORGANISM: Artificial Sequence
<220> FEATURE:
<223> OTHER INFORMATION: hSC16.34 heavy chain variable region

<400> SEQUENCE: 527
```

Gln Val Gln Leu Val Gln Ser Gly Ala Glu Val Lys Lys Pro Gly Ala
1               5                   10                  15

-continued

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Arg Leu Glu Trp Met
        35                  40                  45

Gly Trp Ile Asn Thr Tyr Thr Gly Asp Pro Thr Tyr Ala Asp Asp Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Gly Gly Asn Ser Pro Ser Asp Tyr Trp Gly Gln Gly Thr
            100                 105                 110

Thr Val Thr Val Ser Ser
            115

<210> SEQ ID NO 528
<211> LENGTH: 118
<212> TYPE: PRT
<213> ORGANISM: Artificial Sequence
<220> FEATURE:
<223> OTHER INFORMATION: hSC16.56 heavy chain variable region

<400> SEQUENCE: 528

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ile Gly Asp Ser Ser Pro Ser Asp Tyr Trp Gly Gln Gly Thr
            100                 105                 110

Leu Val Thr Val Ser Ser
            115

<210> SEQ ID NO 529
<211> LENGTH: 112
<212> TYPE: PRT
<213> ORGANISM: Mus musculus
<220> FEATURE:
<221> NAME/KEY: MISC_FEATURE
<223> OTHER INFORMATION: SC10.17 light chain variable region

<400> SEQUENCE: 529

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asp Gly Asn Thr Tyr Leu Glu Trp Tyr Leu Arg Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Leu Gly Val Tyr Tyr Cys Phe Gln Gly
                    85                  90                  95

Ser His Ala Pro Trp Thr Phe Gly Gly Gly Thr Lys Leu Glu Ile Lys
                100                 105                 110

<210> SEQ ID NO 530
<211> LENGTH: 120
<212> TYPE: PRT
<213> ORGANISM: Mus musculus
<220> FEATURE:
<221> NAME/KEY: MISC_FEATURE
<223> OTHER INFORMATION: SC10.17 heavy chain variable region

<400> SEQUENCE: 530

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Tyr
                20                  25                  30

Gly Met His Trp Val Arg Gln Ala Pro Glu Thr Gly Leu Glu Trp Val
            35                  40                  45

Ala Tyr Ile Thr Thr Arg Ser Ser Thr Ile Tyr Tyr Ala Ala Thr Val
        50                  55                  60

Lys Gly Arg Phe Thr Ile Ser Arg Asp Asn Ala Arg Asn Thr Leu Phe
65                  70                  75                  80

Leu Gln Met Thr Ser Leu Arg Ser Glu Asp Thr Ala Met Tyr Tyr Cys
                85                  90                  95

Thr Arg Glu Pro Leu Thr Gly Tyr Tyr Ala Met Asp Tyr Trp Gly Gln
                100                 105                 110

Gly Thr Ser Val Thr Val Ser Ser
            115                 120

<210> SEQ ID NO 531
<211> LENGTH: 112
<212> TYPE: PRT
<213> ORGANISM: Artificial Sequence
<220> FEATURE:
<223> OTHER INFORMATION: hSC10.17 light chain variable region

<400> SEQUENCE: 531

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
                20                  25                  30

Asp Gly Asn Thr Tyr Leu Glu Trp Tyr Gln Gln Arg Pro Gly Gln Ser
            35                  40                  45

Pro Arg Arg Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ala Pro Trp Thr Phe Gly Gly Gly Thr Lys Val Glu Ile Lys
                100                 105                 110

<210> SEQ ID NO 532
<211> LENGTH: 120
<212> TYPE: PRT
<213> ORGANISM: Artificial Sequence
```

<220> FEATURE:
<223> OTHER INFORMATION: hSC10.17 heavy chain variable region

<400> SEQUENCE: 532

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Tyr Ile Thr Thr Arg Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Glu Pro Leu Thr Gly Tyr Tyr Ala Met Asp Tyr Trp Gly Gln
            100                 105                 110

Gly Thr Ser Val Thr Val Ser Ser
        115                 120

<210> SEQ ID NO 533
<211> LENGTH: 337
<212> TYPE: DNA
<213> ORGANISM: Mus musculus
<220> FEATURE:
<221> NAME/KEY: misc_feature
<223> OTHER INFORMATION: SC10.17 light chain variable region

<400> SEQUENCE: 533
gatgttttga tgacccaaac tccactctcc ctgcctgtca gtcttggaga tcaagcctcc      60
atctcttgca gatctagtca gagcattgta catagtgatg aaacaccta tttagaatgg     120 tacctgcgga aaccaggcca gtctccaaga ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgctccg    300
tggacgttcg gtggaggcac caagctggaa atcaaac                              337

<210> SEQ ID NO 534
<211> LENGTH: 360
<212> TYPE: DNA
<213> ORGANISM: Mus musculus
<220> FEATURE:
<221> NAME/KEY: misc_feature
<223> OTHER INFORMATION: SC10.17 heavy chain variable region

<400> SEQUENCE: 534
gatgtgcagc tggtggagtc tgggggaggc ttagtgcagc ctggagggtc ccggaaactc      60
tcctgtgcag cctctggatt cactttcagt agctacggaa tgcactgggt tcgtcaggct    120
ccagagacgg ggctggagtg ggtcgcatac attactactc gcagtagtac catctactat    180
gcagccacag tgaagggccg attcaccatc tccagagaca atgccaggaa caccctgttc    240
ctgcaaatga ccagtctaag gtctgaggac acggccatgt attactgtac tagagaaccc    300
ctaactggat actatgctat ggactactgg ggtcaaggaa cctcagtcac cgtctcctca    360

<210> SEQ ID NO 535
<211> LENGTH: 337
<212> TYPE: DNA

<213> ORGANISM: Artificial Sequence
<220> FEATURE:
<223> OTHER INFORMATION: hSC10.17 light chain variable region

<400> SEQUENCE: 535

```
gatgttgtga tgactcagtc tccactctcc ctgcccgtca cccttggaca gccggcctcc     60
atctcctgca ggtctagtca agcatcgta cacagtgatg aaacaccta cttggaatgg    120
tatcagcaga ggccaggcca atctccaagg cgcctaattt ataaggtttc taaccggttc   180
tctggggtcc cagacagatt cagcggcagt gggtcaggca ctgatttcac actgaaaatc   240
agcagggtgg aggctgagga tgttggggtt tattactgct ttcaaggttc acatgctccg   300
tggacgttcg gtggaggcac caaggtggaa atcaaac                             337
```

<210> SEQ ID NO 536
<211> LENGTH: 361
<212> TYPE: DNA
<213> ORGANISM: Artificial Sequence
<220> FEATURE:
<223> OTHER INFORMATION: hSC10.17 heavy chain variable region

<400> SEQUENCE: 536

```
gaggtgcagc tggtggagtc tgggggaggc ttggtacagc ctggggggtc cctgagactc     60
tcctgtgcag cctctggatt caccttcagt agctatggca tgcactgggt ccgccaggct    120
ccagggaagg ggctggagtg ggttgcatac attactacta gaagtagtac catatactac   180
gcagactctg tgaagggccg attcaccatc tccagagaca atgccaagaa ctcactgtat   240
ctgcaaatga acagcctgag agccgaggac acggctgtgt attactgtac tagagaaccc   300
ctaactggat actatgctat ggactactgg ggtcaaggaa cctcagtcac cgtctcctca   360
g                                                                  361
```

<210> SEQ ID NO 537
<211> LENGTH: 213
<212> TYPE: PRT
<213> ORGANISM: Mus musculus
<220> FEATURE:
<221> NAME/KEY: MISC_FEATURE
<223> OTHER INFORMATION: SC17.17 ss1 and ss2 full length light chain

<400> SEQUENCE: 537

```
Glu Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Ser Val Ser Tyr Met
             20                  25                  30

His Trp Tyr Gln Gln Lys Pro Gly Gln Ala Pro Arg Leu Leu Ile Tyr
         35                  40                  45

Asp Thr Ser Lys Leu Pro Ser Gly Ile Pro Ala Arg Phe Ser Gly Ser
     50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Trp Ser Ser Thr Pro Pro Thr
                 85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140
```

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
                195                 200                 205

Asn Arg Gly Glu Cys
        210

<210> SEQ ID NO 538
<211> LENGTH: 449
<212> TYPE: PRT
<213> ORGANISM: Mus musculus
<220> FEATURE:
<221> NAME/KEY: MISC_FEATURE
<223> OTHER INFORMATION: SC17.17 ss3 and ss4 full length heavy chain

<400> SEQUENCE: 538

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Met
            35                  40                  45

Gly Glu Ile Asn Pro Asn Ile Gly Gly Thr Gly Tyr Asn Gln Lys Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Thr Tyr Ser Tyr Tyr Ser Tyr Glu Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
```

```
                    275                 280                 285
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 539
<211> LENGTH: 449
<212> TYPE: PRT
<213> ORGANISM: Mus musculus
<220> FEATURE:
<221> NAME/KEY: MISC_FEATURE
<223> OTHER INFORMATION: SC17.17 ss1 full length heavy chain

<400> SEQUENCE: 539

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ile Gly Gly Thr Gly Tyr Asn Gln Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Thr Tyr Ser Tyr Tyr Ser Tyr Glu Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180                 185                 190
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Ser Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 540
<211> LENGTH: 448
<212> TYPE: PRT
<213> ORGANISM: Mus musculus
<220> FEATURE:
<221> NAME/KEY: MISC_FEATURE
<223> OTHER INFORMATION: SC17.17 ss2 full length heavy chain

<400> SEQUENCE: 540

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ile Gly Gly Thr Gly Tyr Asn Gln Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
```

85                  90                  95
Ala Arg Thr Tyr Ser Tyr Tyr Ser Tyr Glu Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 541
<211> LENGTH: 212
<212> TYPE: PRT
<213> ORGANISM: Mus musculus
<220> FEATURE:
<221> NAME/KEY: MISC_FEATURE
<223> OTHER INFORMATION: SC17.17 ss3 full length light chain

<400> SEQUENCE: 541

-continued

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

His Trp Tyr Gln Gln Lys Pro Gly Gln Ala Pro Arg Leu Leu Ile Tyr
            35                  40                  45

Asp Thr Ser Lys Leu Pro Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Thr Pro Pro Thr
                85                  90                  95

Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu
    210

<210> SEQ ID NO 542
<211> LENGTH: 213
<212> TYPE: PRT
<213> ORGANISM: Mus musculus
<220> FEATURE:
<221> NAME/KEY: MISC_FEATURE
<223> OTHER INFORMATION: SC17.17 ss4 full length light chain

<400> SEQUENCE: 542

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

His Trp Tyr Gln Gln Lys Pro Gly Gln Ala Pro Arg Leu Leu Ile Tyr
            35                  40                  45

Asp Thr Ser Lys Leu Pro Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Thr Pro Pro Thr
                85                  90                  95

Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Ser
            210

<210> SEQ ID NO 543
<211> LENGTH: 449
<212> TYPE: PRT
<213> ORGANISM: Mus musculus
<220> FEATURE:
<221> NAME/KEY: MISC_FEATURE
<223> OTHER INFORMATION: SC10.17ss3 full length heavy chain

<400> SEQUENCE: 543

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Tyr Ile Thr Thr Arg Ser Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Thr Arg Glu Pro Leu Thr Gly Tyr Tyr Ala Met Asp Tyr Trp Gly Gln
            100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His

```
                275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly

<210> SEQ ID NO 544
<211> LENGTH: 219
<212> TYPE: PRT
<213> ORGANISM: Mus musculus
<220> FEATURE:
<221> NAME/KEY: MISC_FEATURE
<223> OTHER INFORMATION: SC10.17ss3 full length light chain

<400> SEQUENCE: 544

Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Ile Val His Ser
                20                  25                  30
Asp Gly Asn Thr Tyr Leu Glu Trp Tyr Gln Gln Arg Pro Gly Gln Ser
                35                  40                  45
Pro Arg Arg Leu Ile Tyr Lys Val Ser Asn Arg Phe Ser Gly Val Pro
                50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Ala Pro Trp Thr Phe Gly Gly Gly Thr Lys Val Glu Ile Lys
                100                 105                 110
Arg Thr Val Ala Ala Pro Ser Val Phe Ile Phe Pro Pro Ser Asp Glu
                115                 120                 125
Gln Leu Lys Ser Gly Thr Ala Ser Val Val Cys Leu Leu Asn Asn Phe
                130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
```

-continued

```
              180                 185                 190
Lys His Lys Val Tyr Ala Cys Glu Val Thr His Gln Gly Leu Ser Ser
        195                 200                 205

Pro Val Thr Lys Ser Phe Asn Arg Gly Glu Ser
    210                 215
```

UNITED STATES PATENT AND TRADEMARK OFFICE
CERTIFICATE OF CORRECTION

| | | |
|---|---|---|
| PATENT NO. | : 10,035,853 B2 | Page 1 of 1 |
| APPLICATION NO. | : 15/056490 | |
| DATED | : July 31, 2018 | |
| INVENTOR(S) | : Arathoon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 5 days.

Signed and Sealed this
Eighteenth Day of June, 2019

Andrei Iancu
*Director of the United States Patent and Trademark Office*